US006912470B2

(12) United States Patent
Farnet et al.

(10) Patent No.: US 6,912,470 B2
(45) Date of Patent: Jun. 28, 2005

(54) GENES AND PROTEINS INVOLVED IN THE BIOSYNTHESIS OF ENEDIYNE RING STRUCTURES

(75) Inventors: Chris M. Farnet, Outremont (CA); Alfredo Staffa, Saint-Laurent (CA); Emmanuel Zazopoulos, Montreal (CA)

(73) Assignee: Ecopia Biosciences, Inc., Saint-Laurent (CA)

( * ) Notice: Subject to any disclaimer, the term of this patent is extended or adjusted under 35 U.S.C. 154(b) by 0 days.

(21) Appl. No.: 10/152,886

(22) Filed: May 21, 2002

(65) Prior Publication Data

US 2003/0064491 A1 Apr. 3, 2003

Related U.S. Application Data

(60) Provisional application No. 60/334,604, filed on Dec. 3, 2001, and provisional application No. 60/291,959, filed on May 21, 2001.

(51) Int. Cl.$^7$ .......................... G06F 19/00; C12N 15/30; C07K 14/00
(52) U.S. Cl. .......................... 702/20; 530/350; 536/23.7
(58) Field of Search .......................... 702/20; 536/23.7; 530/350

(56) References Cited

U.S. PATENT DOCUMENTS

| 4,259,319 | A | 3/1981 | Umezawa et al. |
| 4,946,778 | A | 8/1990 | Ladner et al. |
| 6,361,974 | B1 | 3/2002 | Short et al. |
| 6,372,497 | B1 | 4/2002 | Stemmer |
| 6,733,998 | B1 * | 5/2004 | Thorson .................... 435/71.1 |

FOREIGN PATENT DOCUMENTS

| CA | 2430684 A1 | 10/2002 |
| WO | WO 00/37608 | 6/2000 |
| WO | WO 00/40596 | 7/2000 |

OTHER PUBLICATIONS

Thorson, J.S. et al., Bioorganic Chemistry (1999), vol. 27, pp. 172–188, "Enediyne Biosynthesis and Self-Resistance: A Progress Report".
Takeyama H. et al., (1997) Microbiology, vol. 143 pp. 2725–2731 "Expression of the elcosanpentaenoic acid synthesis gene cluster from Sherwanella sp. In a transgenic marinecyanobacterium, Synechococcus sp.".
Hopwood DA, (1997) Chemical Reviews, vol. 97, pp. 2465–2497 "Genetic Contributions to Understanding Polyketide Synthesis".
Katz L.(1997) Chemical Reviews, vol. 97 (7), pp. 2557–2575 "Manipulation of Modular Polyketide Synthases".
Kakavas S. et al. (1997) Journal of Bacteriology, vol. 179 No. 23, pp. 7515–7522 "Identification and Characterization of the Niddamycin Polyketide Synthase Genes from Streptomyces caelestis".
Morita N. et al. (2000) Biochem. Soc. Trans., vol. 28(6), pp. 943–945 "Biosynthesis of fatty acids in the decosahexaenoic acid–producing bacterium Moritella marina strain MP–1".
Thompson J.D. et al. (1997) Nucleic Acids Research, vol. 25 No. 24, pp. 4876–4882 "The CLUSTAL_X windows interface: flexible strategies for multiple sequence alignment aided by quality analysis tools".
Serre L. et al. (1995) J. Biol. Chem., vol. 270, pp. 12961–12964 "The Escherichia coli Malonyl–CoA:Acyl Carrier Protein Transacylase at 1.5–A Resolution".
Breton R. et al. (1996) Structure, vol. 4(8), pp. 905–915 "The structure of a complex human 17beta–hydroxysteroid dehydrogenase with estradiol and NADP+ identifies two-principal targets for the design of inhibitors".
Fritsche K. et al. (1999) FEBS Letters, vol. 462(3), pp. 249–253 "Isolation and characterization of a calenidc acid producing (8,11)–linoleoyl desaturase".
Desanti, C. L. (2000) 262 pp. Ph.D dissertation, Ohio State Univ., Colombus OH, pp. 33–103 "The molecular biology of the Streptomyces snp Locus".
Gish et al. (1993) Nature Genetics, vol. 3, pp. 266–272 "Identification of protein coding regions by database similarity".
Eddy S.R. (1998) Bioinformatics, vol. 14 No. 9, pp. 755–763 "Profile hidden Markov models".
Bailey T.L. et al. (1997) J. Steroid Biochem Mol Biol., vol. 62 No. 1, pp. 29–44 "An Artificial Intelligence Approach to Motif Discovery in Protein Sequences: Application to Steroid Dehydrogenases".
Nabban C. and Tallman M.S. (2002) Clin Lymphoma, Mar;2 Suppl 1:S19–23 "Early phase I/II Trials with Gemtuzumab Ozogamicin (Mylotarg(r)) in Acute Myleloid Leukemia".
Liu W. et al. (2000) Antimicrobial Agents and Chemotherapy, vol. 44 No. 2, pp 382–392 "Genes for Production of the Enediyne Antitumor Antibiotic C–1027 in Streptomyces globisporus Are Clustered with the CagA Gene That Encodes the C–1027 Apoprotein".
Hensens, O.D. et al. (1989) J. Am. Chem Soc., vol. 111, pp. 3295–3299 "Biosynthesis of NCS Chrom A, the Chromophore of the Antitumor Antibiotic Neocarzinostatin".
Lam K.S. et al. (1993) J. Am. Chem. Soc., vol. 115, pp 12340–12345 "Biosynthesis of Esperamicin A1, an Enediyne Antitumor Antitbiotic".

(Continued)

Primary Examiner—John S. Brusca
(74) Attorney, Agent, or Firm—Pandiscio & Pandiscio

(57) ABSTRACT

Five protein families cooperate to form the warhead structure that characterizes enediyne compounds, both chromoprotein enediynes and non-chromoprotein enediynes. The protein families include a polyketide synthase and thioesterase protein which form a polyketide synthase catalytic complex involved in warhead formation in enediynes. Genes encoding a member of each of the five protein families are found in all enediyne biosynthetic loci. The genes and proteins may be used in genetic engineering applications to design new enediyne compounds and in methods to identify new enediyne biosynthetic loci.

14 Claims, 38 Drawing Sheets

OTHER PUBLICATIONS

Tokiwa Y. et al. (1992) J. Am. Chem Soc., vol. 114, pp. 4107–4110 "Biosynthesis of Dynemicin A, a 3–Ene–1.5–diyne Antitumor Antibiotic".

Samy T.S. et al. (1983) J. Biol. Chem., vol. 258 No. 1, pp. 183–191 "Primary Structure of Macromycin, an Antitumor Antibiotic Protein".

Seow K.T. et al. (1997) J. Bacteriol., vol. 179 No. 23, pp. 7360–7368 "A Study of Iterative Type II Polyketide Synthases, using Bacterial Genes Cloned from Soil DNA: a Means to Access and Use Genes from Uncultured Microorganisms".

Gluzman Y. (1981) Cell., vol. 23, pp. 175–182 "SV40–Transformed Simian Cells Support the Replication of Early SV40 Mutants".

Caldwell, R.C. & Joyce G.F. (1992) PCR Methods Applic., vol. 2, pp. 28–33 "Randomization of Genes by PCR Mutagenesis".

Rejdhaar–Olson J.F. and Sauer R.T. (1988) Science, vol. 241, pp. 53–57 "Combinatorial Cassette Mutagenesis as a Probe of the Informational Content of Protein Sequences".

Kholer G. and Milstein C. (1975) Nature, vol. 256, pp. 495–497 "Continuous cultures of fused cells secreting antibody of predefined specificity".

Kozbor D. et al. (1983) Immunology Today, vol. 4 No. 3, pp. 72–79 "The production of monoclonal antibodies from human lymphocytes".

Wood T. and Mahailngeshawara B. (1988) Methods in Enzymology, vol. 160, pp. 87–116 "Methods for Measuring Cellulase Activities".

Altschul S. et al. (1990) J. Mol. Biol. vol. 215, pp. 403–410 "Basic Local Alignment Search Tool".

Pearson W. and Lipman D. (1988) Proc. Natl. Acad. Sci. USA, vol. 85, pp. 2444–2448 "Improved tools for biological sequence comparison".

Brutlag D. L. et al. (1990) Comp. App. Biosci., vol. 6 No. 3, pp. 237–245 "Improved sensitivity of biological sequence database searches".

Vandre D.D. et al. (1982) Biochemistry, vol. 21, pp. 5089–5096 "Largomycin: Preparation, Properties, and Structure".

Yamashita T. et al.(1979) J. Antibiot., vol. 32(4), pp. 330–339 "Studies on auromomycin".

Fleishmann R. et al. (1995) Science, vol. 269, pp. 496–512 "Whole–Genome Random Sequencing and Assembly of Haemophilus influenza Rd".

Van Roey P. and Beerman T.A. (1989) Proc Natl Acad USA, vol. 86(17), pp. 6587–6591 "Crystal structure analysis of auromomycin apoprotein (macromycin) shows importance of protein side to chains to chromophore binding selectivity".

Thompson J.D. et al. (1994) Nucleic Acids Res., vol. 22(2), pp. 4673–4680 "CLUSTAL W:improving the sensitivity of progressive multiple sequence alignment through sequence weighting, position–specific gap penalties and weight matrix choice".

Higgins D. et al. (1996) Methods Enzymol., vol. 266, pp. 382–402 "Using CLUSTAL for Multiple Sequence Alignments".

Higgins D. and Sharp P. M. (1988) Gene, vol. 73 pp. 237–244 "CLUSTAL: a package for performing multiple sequence alignment on a microcomputer".

Metz J. G. et al. (2001) Science, vol. 293, pp. 290–293 "Production of Polyunsaturated Fatty Acids by Polyketide Synthases in Both Prokaryotes and Eukaryotes".

Kelley et al. (2000) J. Mol. Biol. vol. 299 pp. 499–520 "Enhanced genome annotation using structural profiles in the program 3D–PSSM".

Reuter K. et al. (1999)The EMBO Journal, vol. 18 No. 23, pp. 6823–6831 "Crystal structure of the surfactin synthetase–activating enzyme Sfp: a prototype of the 4'–phosphopantetheinyl transferase superfamily".

Quadri L.E. et al. (1998) Biochemistry, vol. 37(6), 1585–1595 "Characterization of Sfp, a *Bacillus subtillis* phosphopantetheinyl transferase for peptidyl carrier protein domains in peptide synthetases".

Fitchtischerer et al., 2000, Eur. J. Biochem., vol. 267, 2666–2671 "A novel function of yeast fatty acid synthase".

Benning M.M. et al. (1998) J. Biol. Chem., vol. 273 No. 50, pp. 33572–33579 "The Three–dimensional Structure of 4–Hydroxybenzol–CoA Thioesterase from *Pseudomonas* sp. Strain CBS–3*".

Nakai K. et al. (1999) Trends Biochem. Sci., vol. 24(1), pp. 34–36 "PSORT: a pogram for detecting sorting signals in proteins and predicting their subcellar localization".

Kennedy J. et al. (1999) Science, vol. 284(5418), pp. 1368–1372 "Modulation of polyketide synthase activity by accessory proteins during lovastatin biosynthesis".

Greenstein M. et al. (1986) Antimicrob. Agents Chemotherap., vol. 29 No. 5, pp. 861–866 "Light–Dependent Activity of the Antitumor Antibiotics Ravidomycin and Desacetylravidomycin".

Biggins J. et al. (2000) Proc. Natl. Acad. Sci. USA, vol. 97 No. 25, 13537–13542 "A continuous assay for DNA cleavage: The application of "break lights" to enediynes, iron–dependent agents, andiucleases".

Stryer L. (1998) Biochemistry, 3rd edition, W.H. Freeman and Co., New York, pp. 752–754.

Christensen S.D. et al., 12th International Symposium on the Biology of Actinomycetes, Aug. 5–9, 2001 Vancouver, Canada.

* cited by examiner

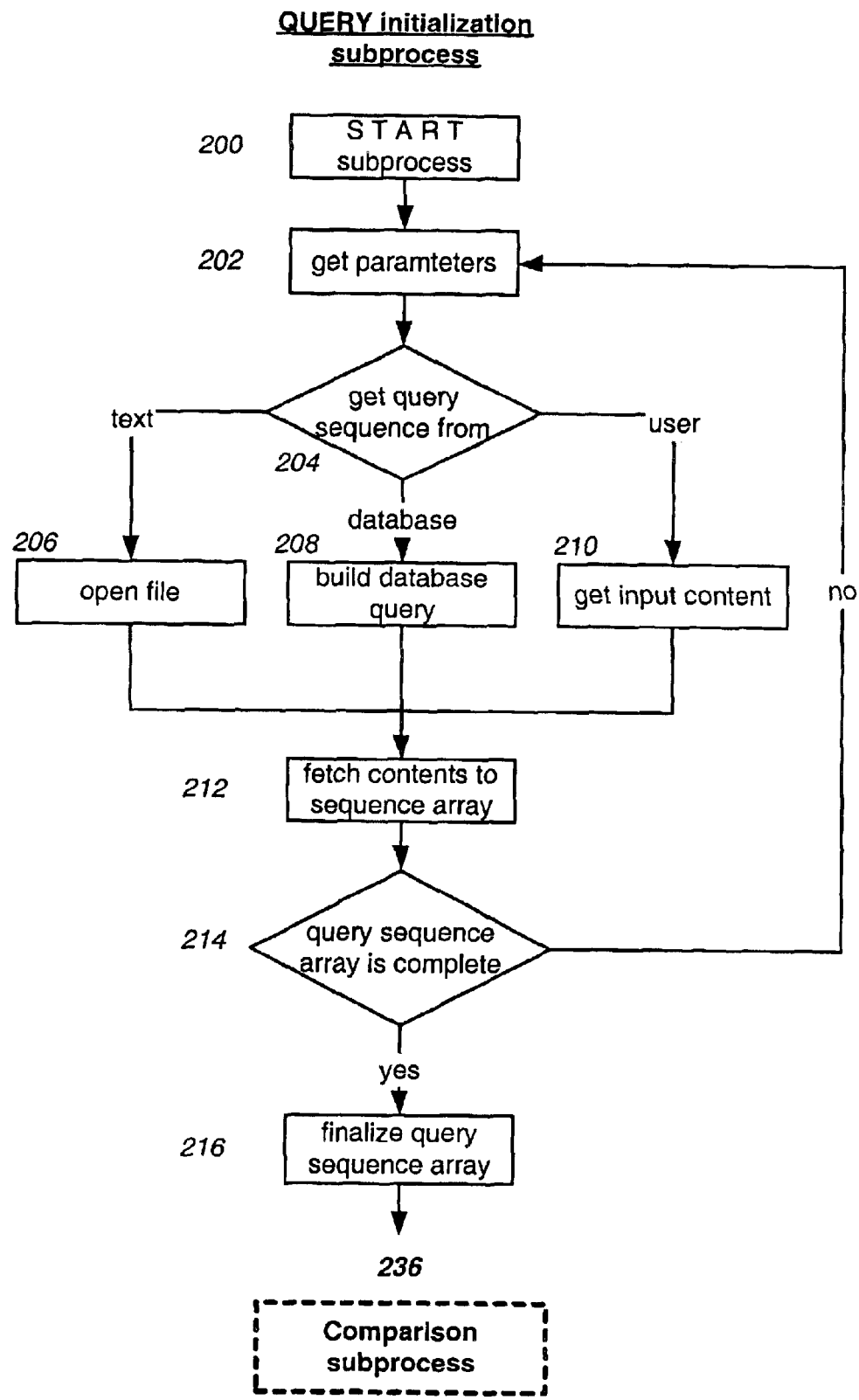
Figure 2-A

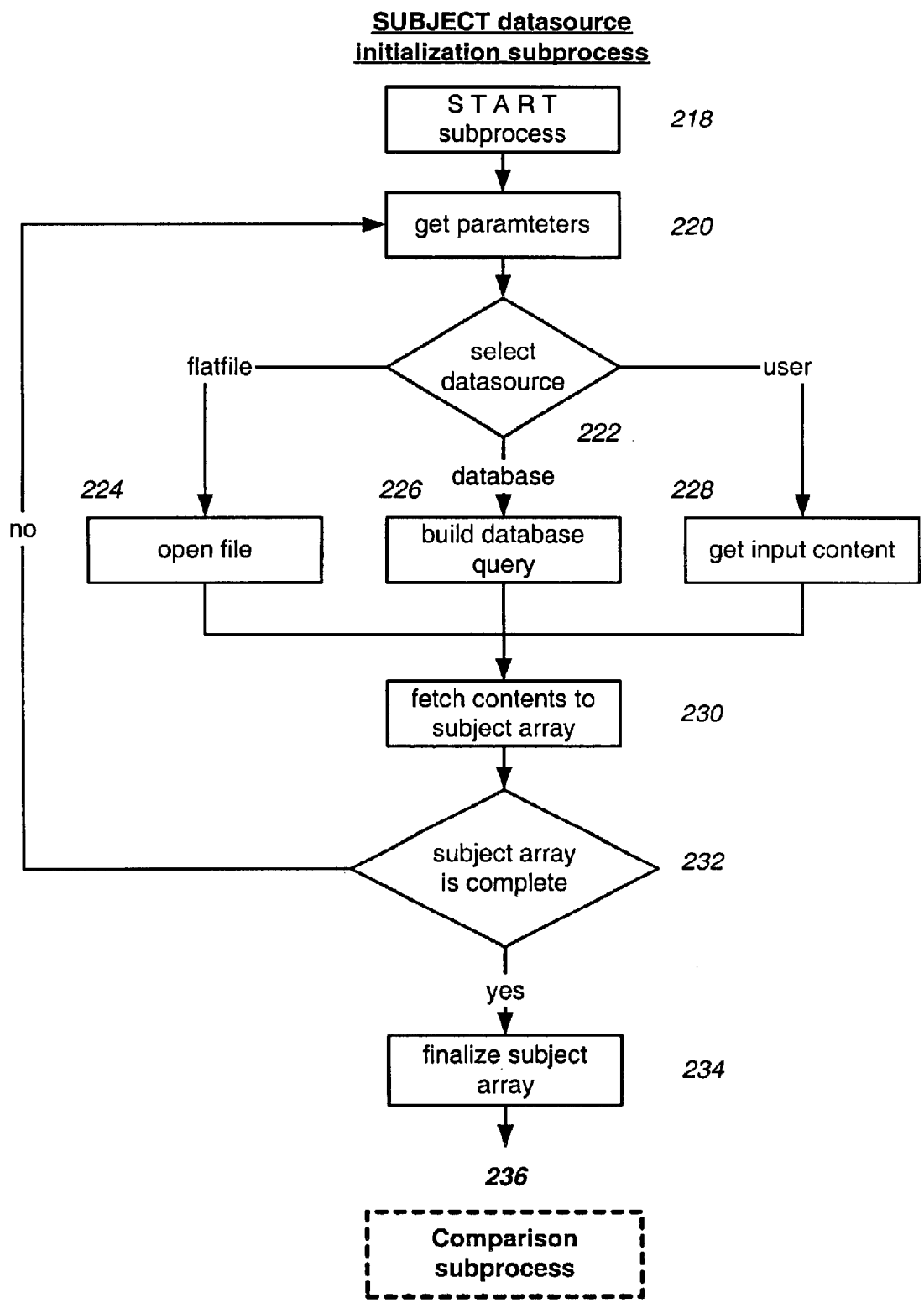
Figure 2-B

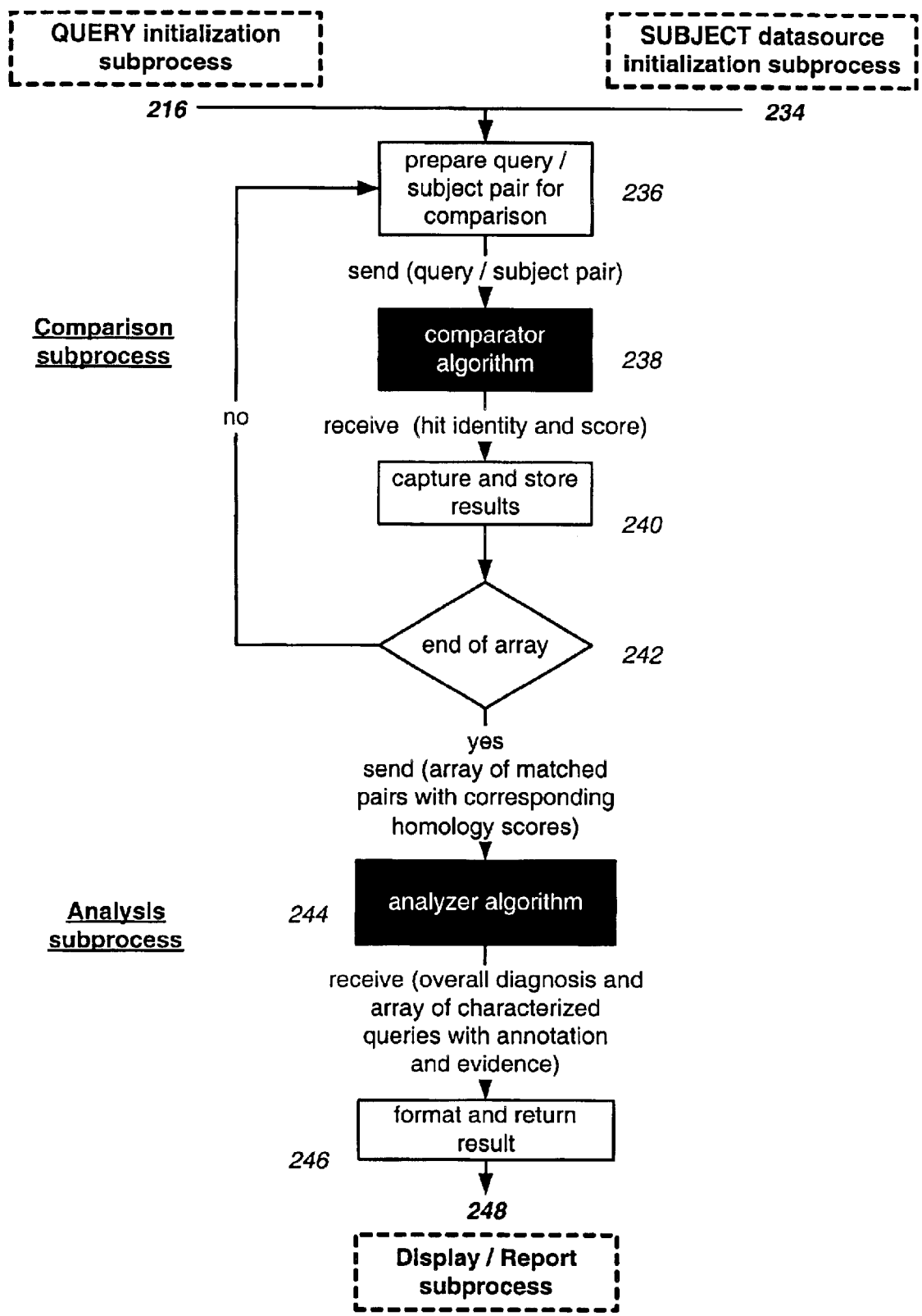
Figure 2-C

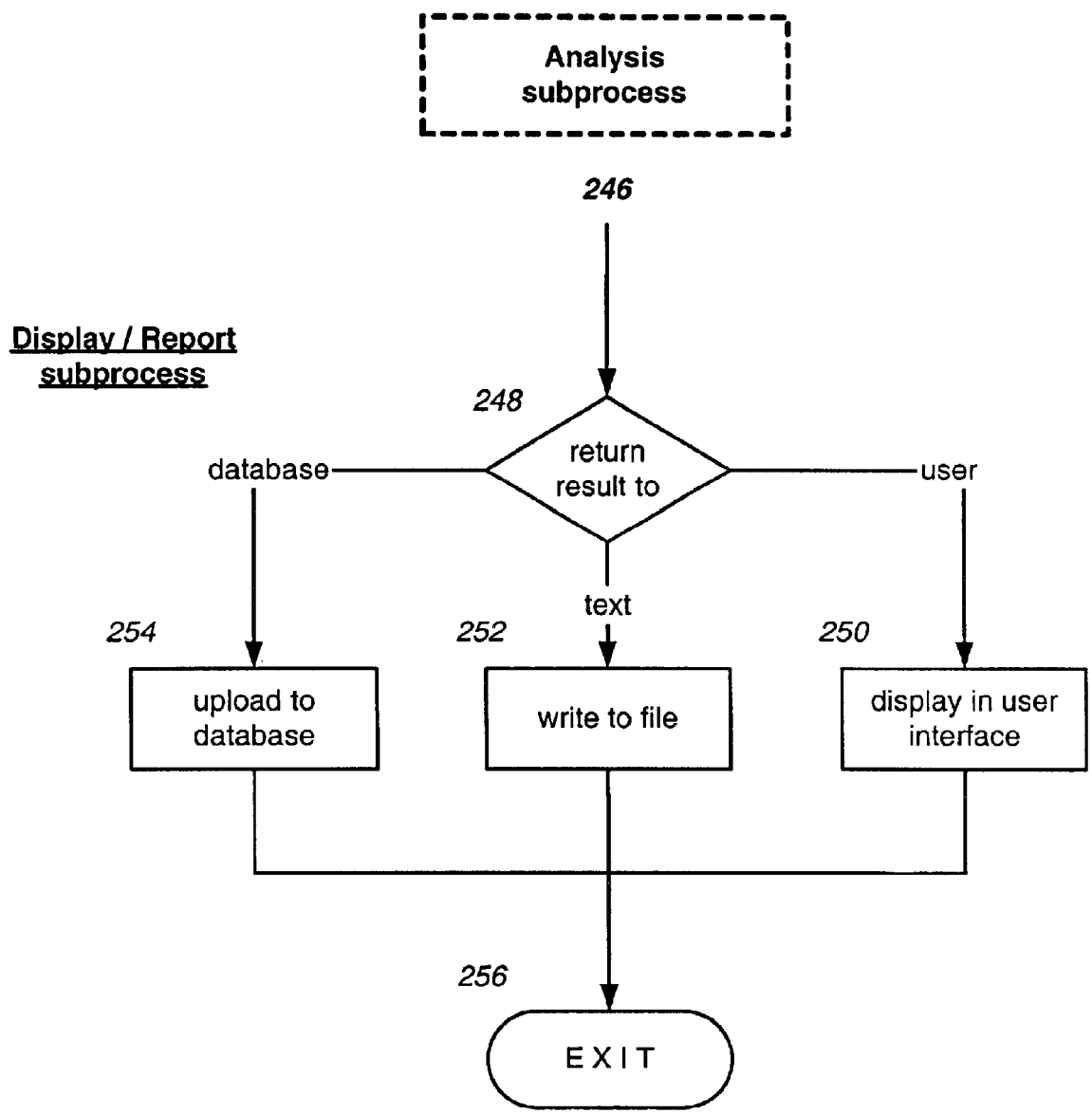
Figure 2-D

Figure 6
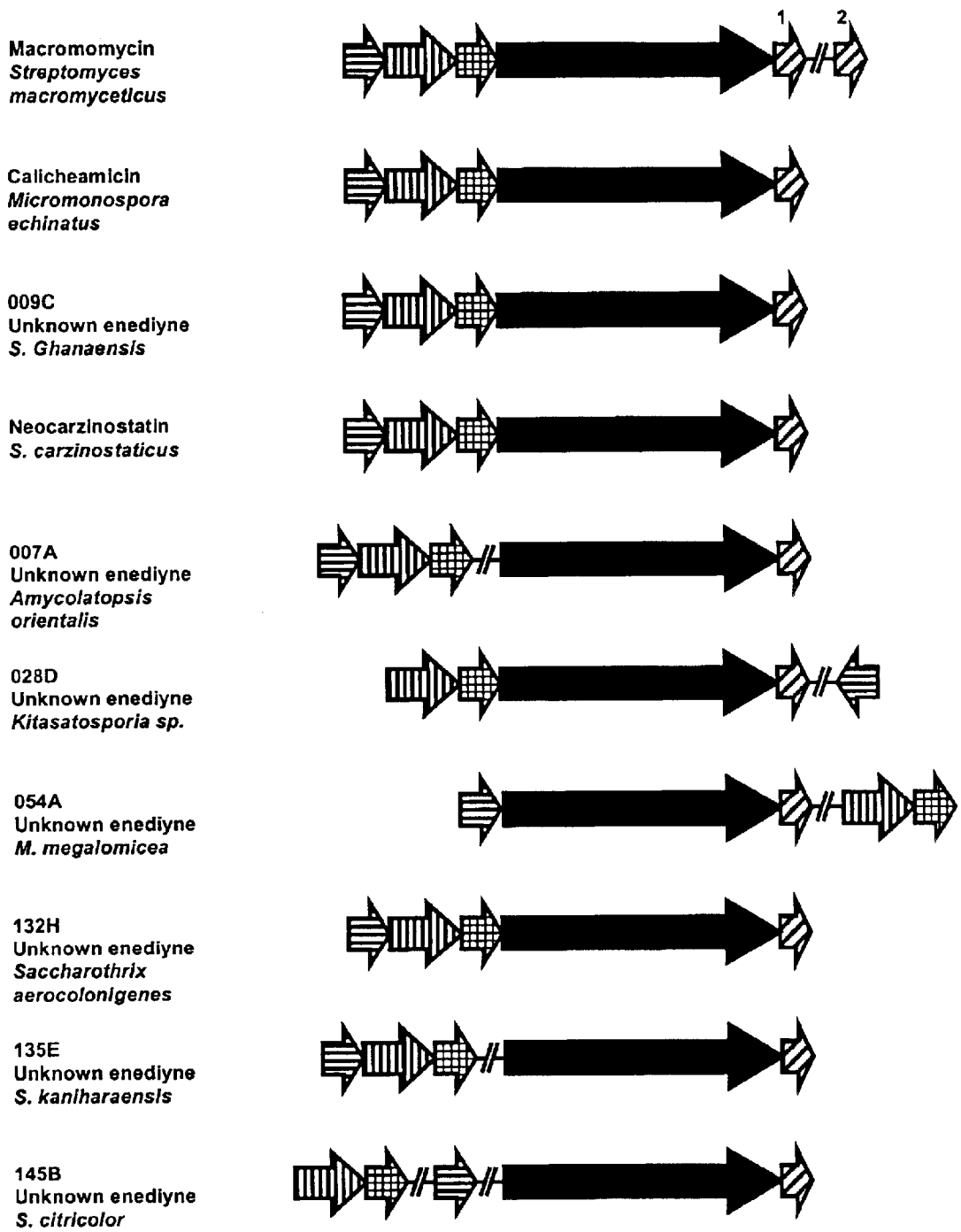

Figure 8A

```
                              >> KS
PKSE|MACR    ----------------VTRIAIVGIAARYPDATSHRELWENAVAGRRAFRRLPDVRMRL  43
PKSE|CALI    ----------------MSRIAVVGLACRFPDAAGPGQLWENALAGRRAFRRLPEERMRA  43
PKSE|009C    ----------------MTRIAIVGMACRYPDATDPKELWDNAVAGRRAFRRLPDVRMNL  43
PKSE|NEOC    ----------------MTRIAIVGMACRYPDATSPAELWANAIAGRRAFRRLPEERIRL  43
PKSE|007A    --------------MSVERISIVGIGLRYPDAGSPEELWENVLAGRRAFRRLPDERMNR  45
PKSE|028D    VSDGAGRPARDGGQPTGRGRIAVVGMACRYPDADSPEQLWQNVLAGRRAFRRLPDVRMRA  60
PKSE|054A    ----------------MTRIAVVGMACRYPDATSPRELWENALAGRRAFRRLPDVRMRL  43
PKSE|132H    ----------VRHGDDADPIAVGMACRYPDADDPQQLWQMVLDQRQAFRRIPPERLDL  49
PKSE|135E    ---------------VSGQRVAIVGIGLRYPDANSPIELWENVLSGRRAFRRLPDERMNH  45
PKSE|145B    ---------MGGEYMSSERIAIVGIGLRYPDANSASELWDNVLSGRRAFRRLPDERMNQ  50
                           :::**:. *:***  .  :**  .: *:****:*  *:

PKSE|MACR    EDYWDADPTTPDRFYARNAAVLEGYSFDRIAHRIAGSTYRSTDLTHWLALETASSALADA 103
PKSE|CALI    ADYWSPDPAAPDRYYAGNAAVIEGYEFDRVGFKVSGSTYRSTDLTHWLALDMAAQALADA 103
PKSE|009C    DDYWDADPTTPDTFYARNAAVIEGYEFDRIAHKIAGSTFRSTDLTHWLALDTAGRALADA 103
PKSE|NEOC    EDYWDADPSTPDTFYARNAAVLEGYSFDRVTHRIAGSTFRSTDMTHWLALDTAGRALADA 103
PKSE|007A    EDYYSPDPKAPDRFYAQKAAVLRDYEFDRIKYKVAGSTFRSTDTTHWLALDVAAQALADA 105
PKSE|028D    EDYYSPDPAAPDRFYSAKAAVIEGFEFDRVRHRVAGSTFRATDMTHWLALDTAARALEDA 120
PKSE|054A    DDYWDADPAAPDKFYARNAAVIEGYEFDRIAYKIAGSTFRSTDMTHWLALDVAASALADA 103
PKSE|132H    ADYFDADRTAADRIYSSMAALIEGWEFDRAAFRIPGPSYRATDPAHWLALETAGRALSDA 109
PKSE|135E    ADYWSPDRAAPDRFYATKAAVLRDFEFDRIAYSVAGSTYRSTDLTHWLALDTAARALADA 105
PKSE|145B    ADYWSADRSAPDRYYATKAAVLRDYSFDRIRYSVAGSTYRATDLTHWLALDVAAEALADA 110
             **:..*  :.*  *:  **::..:.***  .  :.*.::*:** :*****:  *.  ** **

PKSE|MACR    GFAAGEGLPKERTGVIVGNTLTGEFSRANVMRLRWPYVRRVLAAALK-AEDWEDEKLADF 162
PKSE|CALI    GFPEGDGLPRERTAVVVGNTLTGEFTRAGMMRLRWPYVRRVVGAALG-EQGWDDDRVAAF 162
PKSE|009C    GFPGGEGLPRERTGVVVGNTLTGEFSRANVMRLRWPYVRRVMAAALKDEQDWDEDRIARF 163
PKSE|NEOC    GFPAGEGLPHERTGVVMGNTLTGEFTRANVMRLRWPYVRRVMAAALAGQQDWDEARVTAF 163
PKSE|007A    GFPEGEGLPKPATGVVIGNSLTGEFSRANIMRLRWPYVRRTVAAALA-ERGWADGDTAEF 164
PKSE|028D    GFPFGEGLADANTGVVIGNTLTGEFSRANLMRLRWPYVRRTVGAALR-EQGWGDTELGAF 179
PKSE|054A    GFPMGDGLPRERTGVVVGNSLTGEFSRANQLRLRWPYVRRMVAAALK-EQDWDDDQLGTF 162
PKSE|132H    GWPGADGLARDKVAVVFGNSLTGEVTRATTMRLRWPYVRHALTAALA-EAEISTEQAGLL 168
PKSE|135E    GFPGGSGLPGQTTGVVVGNSLTGEFSRANIMRLRWPYVRRTVAAALA-GKGWSESAAAEF 164
PKSE|145B    GFPDGSGLPRQTTGVVVGNSLTGEFSRANVMRLRWPYVRRTVAAALV-GQGWSQGDIAVF 169
             *:.  ..**.     ..*:.*****.:**   :********: :  ***

PKSE|MACR    LEGVEGAYKQPFPAIDEDTLAGGLSNTIAGRICNYFDLNGGGYTVDGACSSSLLSVTTAA 222
PKSE|CALI    LADLERSYKAPFAEITEDSLAGGLSNTIAGRICNHFDLHGGGYTVDGACASSLLSVVTAC 222
PKSE|009C    LDDVETAYKEPFPAIDEDTLAGGLANTIAGRICNHFDLNGGGYTVDGACSSSLLSVTTAG 223
PKSE|NEOC    LEEVETSYKAPFPPVDEDTLAGGLSNTIAGRICNHFDLNGGGYTVDGACSSSLLSVTTAG 223
PKSE|007A    LHDLEAQYKAPFPEIDEDTLAGGLANTIAGRVCNFFDFGGGGFTVDGACSSSLLSVVTAA 224
PKSE|028D    LDGLEGRYKSAFPPIGEDTLAGGLANTIAGRICNHFDFKGGGFTVDGACSSSLLSVSTAC 239
PKSE|054A    LDEFEATFKSPFPQVDEDTLAGALSNTIAGRICNHFDFKGGGYTVDGACSSSLLSVATAG 222
PKSE|132H    LGRAEAHYLAPFPAVGDETLAGALSNTIAGRICNYFDLHGGGYTVDGACSSALLAVVTAC 228
PKSE|135E    LEELEQAYKAPFPPIDEDSLAGGLANTIAGRICNHFDLRGGGYTVDGACSSSLLSVITAA 224
PKSE|145B    LQDLEPQYKAPFPPIDEDSLAGGLANTIAGRICNHFDLRGGGYTVDGACSSSLLSVVTAA 229
             *   *   :  .*. :  :::***.*:******:**.**:  ***:*****:.*:**:* **

PKSE|MACR    TGLVNGDLDVAVAGGVDLSIDPPFEIIGPAKTGALAKREMRLYDRGSNGFWPGEGCGMVVL 282
PKSE|CALI    RSLTDLDVDVAVAGGVDLSIDPPFEMVGFAKTGALAGDEMRVYDRRSNGFWPGEGCGMVVL 282
PKSE|009C    TALINGDIDVAVAGGVDLSIDPPFEIIGPAKTGALAKGEMRLYDRGSNGFWPGEGCGMIVL 283
PKSE|NEOC    TALVNGDLDVAVAGGVDLSIDPPFEIIGPAKTGALARGEMKLYDKGSNGFWPGEGCGVVVL 283
PKSE|007A    NALSEGDLDVAIAGGVDLSIDPPFEVIGPAKTGALAKREMKVYDADSNGFWPGEGSGMLVL 284
PKSE|028D    DALLGGRMDVAVAGGVDLSIDPPFEVIGPAKTGALATAEMRVYDKGSNGFWPGEGCGMVVL 299
PKSE|054A    KTLIDGDVDVAVAGGVDLSIDPPFEIIGPAKTGALARGEMRVYDRSANGFWPGEGCGMVVL 282
PKSE|132H    RSLRDGSADVVLAGGVDLSVDPPELVGFAKTGALTAGPMRVYDERSDGFIPGEGCGVVVL 288
PKSE|135E    RSLADGDLDVALAGGVDLSIDPPFEVIGPAKTGALATGEMKVYDRDSNGFWPGEGSGMLVL 284
PKSE|145B    KALADGELEVAVAGGVDLSIDPPFEVIGPAKTGALATGEMKVYDRDSNGFWPGEGSGMLVL 289
                  *    :*.:*******:****.****   *::**  ::** ****.*::**
```

Figure 8B

```
PKSE|MACR    MREEDALASGHRIYASVAGWGISSDGQGGITRPEVSGYQLAMRRAYERAGFGADTVPLFE 342
PKSE|CALI    MRERDALAQGRRIYASVAGWGVSSDGRGGITRPEAAGYRLALRRAYQRAGFGVDTVPLFE 342
PKSE|009C    MREEDALAAGHRIYATIAGWGVSSDGQGGITRPEVSGYQLALRRAYERAGFGIETVGLFE 343
PKSE|NEOC    MREEDAIARGHRIYATVAGWGVSSDGQGGITRPEVDGYRLALERAYARAGFGIETVPLFE 343
PKSE|007A    MREEDAIAQGKRIYATIGGWGVSSDGKGGITRPEASGHRLALKRAYDKAGYGVETVSYFE 344
PKSE|028D    MRDEDARAQGRFRYATIPGWGYSSDGRGGITRPEASGHRLALTRAYRAAGFGIETVGYFE 359
PKSE|054A    MREVDAVAAGHRIYATLTGWGISSDGKGGITRPEVGGYRLALRRAYQRSGFGIETVGLFE 342
PKSE|132H    MRASDARAAGARVYAEITGWGLSSDGNGGITRPEKQGQLLALRRAYAMAGVDPAEVRLIE 348
PKSE|135E    MREEDALAASRRIYASIAGWGVSSDGKGGITRPEAGGHRLALARAYRQAGYGVETVSYFE 344
PKSE|145B    MREEDALAQGRRIYASITGWGVSSDGKGGITRPEAGGHRLALDRAYRRAGYGVETVSYFE 349
             **  ** *  .  **  : *** ****.*******   **: ***  :*  .  *  :*
```

Figure 8C

```
PKSE|MACR    G GTGTEVGDATELTAIMGARAEADPKAPLAAISSIKGMIG TKAAAGVAGLIKAAMAVD  402
PKSE|CALI    G GTGTAVGDGTELRALGEERRAADPDADPAAIGSIKGMIG TKAAAGVAGLIKAVLAVH  402
PKSE|009C    G GTGTAVGDTTELTALSDARRRADPDAPAAAITSIKGMIG TKAAAGVAGLIKAAMAVN  403
PKSE|NEOC    G GTGTAVGDATELAALIKARSAADPQAPVAAIGSIKGMIG TKAAAGVAGLIKAALAVD  403
PKSE|007A    G GTGTALGDATEIEALSTARRDADPLAERAALSTIKGNIG TKAAAGVAGLIKATLAVY  404
PKSE|028D    G GTGTAVGDATELRAFSEARRAAG-ATAPAALSTVKGNFG TKAAAGVAGLLKAILAVR  418
PKSE|054A    G GTGTSVGDTTELTALSAARTAAGGAGLPAAVGSIKAMIG TKAAAGVAGLIKAAMAVH  402
PKSE|132H    G GTGTAVGDETELSALAELRGGAR---EQAVVGSIKANIG TKAASGVAGLIKAVLSIA  405
PKSE|135E    G GTGTALGDATEIEALSSARRAADPVARPAALGTVKGNFG TKAAAGVAGLIKAALAVH  404
PKSE|145B    G GTGTALGDATEIEALSSARRAADPTARPAALGTVKGNFG TKAAAGVAGLIKAALAVH  409
              *  ****  :**  **:   *:        *   *     *.:  ::*.  : *   ****:*****;**  :::

PKSE|MACR    AAMLPPAIGCVDPHDLLTGEQSNLRVLRKAEAWPKDAPLRAAVTAMGFGGINTHVVVDKA  462
PKSE|CALI    HQVVPPTVGCVEPHPELAADRPALRAVRRAEPWPAGAAQRAGVTAMGFGGINTHLVVDGP  462
PKSE|009C    HQVLPPSIGTIDPHALLTDDNATLKALRKAEPWPTGAPRRAGVTAMGFGGINTHVVLDEP  463
PKSE|NEOC    NQTLPPSIGTSDPHELLTEPGANLKALRKAETWPRELPRRAGITAMGFGGINTHVVLDEP  463
PKSE|007A    HQVIPPATGHFEPHESLVGDSARMYVPAEAGLWPSDQPVRAGVSAMGFGGINSHVTVTEA  464
PKSE|028D    HQVIPPATSHVDPHPELTGPAPALRVPDRAELWPAGAPIRAGISSMGFGGINAHVVVEHA  478
PKSE|054A    QEVLPPAVGCVDPHEVLTGTSPALRVLRKAEAWPTDVPVRAGVTAMGFGGINTHIVLENP  462
PKSE|132H    SGVLPPVTGCERPHHVLTARETPLRVLTEAQPWPAG-PRLAGVSSFGFGGINAHVALRDP  464
PKSE|135E    HQVIPPGTGHHDPHPGLLGDDAALYVPGRAELWPADSPVRAGVSAMGFGGINTHVAVTAA  464
PKSE|145B    HQVIPPATGHYDPHPGLLGETAAMYVPRQAGLWPADQPVRAGVSAMGFGGINTHIALTQA  469
              :**    .   **   *      . :. *   **     *.::::*****:*:..

KS <<           >> AT
PKSE|MACR    VP-KRRPAPSRRATTLAASLQDAELLLLDGESPQALAARLTEVAAFAAQVSYAQVGDLAA  521
PKSE|CALI    TR-PRRRSLDRRTQQLARSVQDAELLLVDADTRDELRDRLDDLRTVVAGLAFAELGDLAT  521
PKSE|009C    AG-RRRTAPSRRSATLAHTPQDCELLVLDGESPKALHARLTEVAAFVAQVSYGQVADLAA  522
PKSE|NEOC    SG-RRRPASVRRLTPLADSMQDSELLLFEGASARELSHRLSEVADYTVRLSYGEIADLAA  522
PKSE|007A    PGAARRKELDERTRSLVAGRQDSELLLLDADDAASLRGKVTGLLEVVPKLSFAELADLAG  524
PKSE|028D    DG-VRRTAVPAVAHRLVASRQDAELLLLDGADPAELHAKATRLAAFAAQLSYAEIGDLAA  537
PKSE|054A    RP-RRRVPLDTRTRALAASIQDAELLAVDAASAPELVQRLTRLVDFVGSVSYAQLADLGA  521
PKSE|132H    VT-ALPRTVSTPIRPHHRPAPRTDAFVLAGSDAAELRATLERIAELAPRLSEAELHDLAC  523
PKSE|135E    PAAPRRTALDADTGRLVAGRQDAELLLLEARDRDGLRAEAARLLDLVPRLAQAELADLAG  524
PKSE|145B    PGTARREALDERITRLVAGRQDAELLLLLDGADQAALRAELVRLLDLVPRLAQAELADLAG  529
                                  :    :..    *    :    ::  .:: **.

PKSE|MACR    ----TLQRELRDLPYRAAAVVTSPEDADLRLRQLAGTVE-AGTTSLFAPDGRTFLGRTGD  576
PKSE|CALI    ----NLHRSQRGRAYRAAVVARSPEEADRALGLAARALAPEGAGTLVDPARGVFVGRVT-  576
PKSE|009C    ----TLQRELRGLSHRAAVVVTSPEDAERRLTHLADLLQ-TGETSYTAADGRGFLGRAT-  576
PKSE|NEOC    ----TLQRELRGLPHRAAAVVTSPDDAENRLRHLADLLD-RGETEHWAADGRTLLGKAT-  576
PKSE|007A    ----TLSAELSGKPVRAAVVAAGPDDAERKLAKLLDLLG-EGEPEVFSAKEGIFAGSRS-  578
PKSE|028D    ----ALQRDLADRPLRAAVLADSPEQAAQRFTGLAQLLD-SGARSLLSPAQGVFLGSAG-  591
PKSE|054A    ----TLHGELRDLPYRAAVVATSPEDAERRLRQLRTAVE-AGETRQFSSDGRSLLGHVN-  575
PKSE|132H    ----QWGRDVAPGEHRVALVASTPRQLAERAVVAARSLE-SAPRGRLVVEDGVFLGTAV-  577
PKSE|135E    GLAAGLADGLTGAPVRAAVVATSPDDAARALERLLGLLA-SGATRALCSGEGVFLGTGR-  582
PKSE|145B    ----TLADRLSDGPVRAAVVASSPDDAVRALERLVALLD-SGTREAFSAGEGIFLGRAR-  583
                *.*  :. * :             :   .           :      : *

PKSE|MACR    GDARIGFLFPG GSGKGTGGGALRRRFTEAAEVYDKAGLPTDGDMV-ATDVAQPRIVTGS  635
PKSE|CALI    RPARVGFLFPG GSGRGWGGGALRRRFTEIDDVYRAAGEPPGDEAAGSTVFAQPRIVTGS  636
PKSE|009C    RPARIGFLFPG GSGHGTVGGALCRRFPEAAEVFARAALPATGDMT-ATNVAQPRIATGS  635
PKSE|NEOC    GRKRIGLLFPG GSGRGTGGGALSRRFPEVAEVLARAGSAAGSDTV-ATEVAQPRIVTGS  635
PKSE|007A    QSPKIGFLFPG GSGQ-GRVGALRKRFAHADDIYRAANLSTGADQV-ATDVAQPRIVTGS  636
PKSE|028D    RAPRIGFLFPG GAGRRGDGGALRRRFTAVRDLYAHLDLPADGDQV-ATDVAQPRIVAAS  650
PKSE|054A    GPGRIGLLFPG GSGRGTSGGALRRRFTEVEETYLRADLPTGGDVV-ATEVAQPRIVTGS  634
PKSE|132H    -AGRVTVLLPG GAPVRAELGALGRDLALTGGELRLDEELAGTR---GTATAQPSIFRAS  633
PKSE|135E    TEPTIAYLFPG GSGR-GAVGAIRRRFAQADEVYRRAGLPTGADQV-DTRVAQPRIVTGS  640
PKSE|145B    SAPRIAYLFPG GSGR-GGVGAIRRRFATAERVFHDFGPPTDDQV-ATQVAQPRIVTGS  641
              :  *;**  *:       **:  :  :.              *   *** *   .*
```

Figure 8D

```
PKSE|MACR    TAGLRVLDALGIEADVAVGHSLGELSALHWAGALDGPTVLEAARVRGAAMAEHSAS-GTM  694
PKSE|CALI    LAGLRALAALDIDATVVVGHSLGELTTLHWAGCLDEDELRELVTLRGEAMARHAPP-GAM  695
PKSE|009C    AAGLRVLDALRLEASVAVGHSLGELSALHWAGALDEETLLQAARVRGRAMAEHSAT-GTM  694
PKSE|NEOC    AAGLRVLDELRVEASVGIGHSLGELSALCWAGALDEDVLIEAAGVRGRAMABHGSS-GTM  694
PKSE|007A    LAGLRVLKSLGIEAATVTGHSLGELTALHWGGALTEREVLKLAKIRGKVMATASDGDGAM  696
PKSE|028D    VAGLRVLDLLGVQADLATGHSLGELTALHWAGAMDEDTVLRAAAARGRIMAAAGDGGGTM  710
PKSE|054A    TAGLRVLHTLGIESSIAVGHSLGELSALHWAGVLDEADLLRIASLRGAAMARHSSS-GMM  693
PKSE|132H    LAALRWLDRLGVVAGAAVGHSLGEIAALVWAGCLSTEDADRLVRERGRVMEDFGPRATGM  693
PKSE|135E    LAALRVLDGLGIRAAAAVGHSLGELTALHWAGALTEDQVLRLATVRGQVMAEVGSGGGAM  700
PKSE|145B    LAALRVLDGLGIRADTAVGHSLGELTALHWAGAMSEEQLVRLATIRGRVMARASHGGGAM  701
             *.**  *   *   : **:***::* *.*  :        ..  *  *   .    *
```

Figure 8E

```
PKSE|MACR  ASLAAAPDAVAPLIDGLPVVISGYNGPQQTVVAGPVDAVESVAQRAGQAGVKCTRLAVSH 754
PKSE|CALI  LGVTAGPEETVALLAGTNAVIAGYNGPRQTVVAGADDIVAEVARRAATAGVNCTRLPVPH 755
PKSE|009C  ASLAAAPERAEELLADLDAVIAGYNGPEQTVIAGSPADIEELQRRAERAEVTCTRLNVSH 754
PKSE|NEOC  ASLGAAPEQAEELIGALSVVVAGYNGPQQTVVSGPVHEVEEVRRRAARSGVTCTPLAVSH 754
PKSE|007A  AAIAATPSVAEGLAEGEEVVIAGYNAPEQTVLSGPAEAIDRVVARARAEGVTAARINVSH 756
PKSE|028D  AALATTPALAEALIVGEPVVVAGLNSPTQTVVSGPVDAVDRVCALAARQGIGVGRVNVSH 770
PKSE|054A  ASLAADPEALDPLLADLPVVVAAYNGPGNTVVAGTDEAVRAACQRAGDAGFTATVLPVSH 753
PKSE|132H  VGIVADVPTAHGLCEGTGMVVACYNGPRSQVLAGARTAIDEVVARAARLGVQTVVLPVTH 753
PKSE|135E  AGLAATPEDGTRLCAGLDVVIAGYNGPRQTVVSGPAAAVDEVCRRAVAEGVTATRLNVSH 760
PKSE|145B  AGLAATPERTTRLSAGQDVVVAGYNGPRQTVVSGPAEAVDEVCRRAAAEGVTATRLNVSH 761
                .: :      *           *::  *.*  *::*.   :    *  .    : *.*

PKSE|MACR  AFHSPLVAPAAESFGEWLAGADFGSVDRRIVSTVTGADLEQDGDLAKLLRQQITDPVLFT 814
PKSE|CALI  AFHSPLMASAAAAFAERLRSRRFGPLLRRVASTVTGAVLPSDTDLPRHLHRQIEAPVRFA 815
PKSE|009C  AFHSPLVAHSAEVFGAWLAEARLGSPSGRVVSTVTGEELTAGTDLAALLTEQITGPVRFT 814
PKSE|NEOC  AFHSPLVASAAESFGNWLKSVDFREPAGRVVSTVTGAELTPGTDLSALLREQITAAVRFT 814
PKSE|007A  AFHSPAVVPAAEAMTGELAAIDFARLDRPVVSTVTGDVLHAAEDLRDLLRDQVVLPVRFR 816
PKSE|028D  AFHSPAVAPAAAGLAEHLAGERFGPVGPGLVSTVTGAPLPADTDVVDLLTRQVVQPVRFT 830
PKSE|054A  AFHSPLVAPAADEFGAALADRQWHPLAGRVISTVTGDLLPPHTDVPALLRRQITDPVLFT 813
PKSE|132H  GFHSPAMADGATEFKPYLQSVGFRAPAARLVSTVLGRTLSAQDDIGELLGQQFTAPVRFW 813
PKSE|135E  AFHSPLVAPAAHAMAERLGEFDFARPVRPVASTVTGALLDPAADLRTLLRDQVARPVRFH 820
PKSE|145B  AFHSPLVEPAAVAMAAELAGFDFREPVRPIASTVTGELLDPAADLRELLRDQVLRPVRFH 821
            .* **  :  .*   :    *        : ***  *   *:     *  *.  .* *

PKSE|MACR  QALEAAAADVDLFIEVGPGRVLSTLAEAGV-DVPAVALNTDDESLRALLQVVGAAYVVGA 873
PKSE|CALI  AALGRAAAEVDLFLEVGPGRVLTGLAREQAPDVPALAVDTDAESLSGLLAAVGAVYALGG 875
PKSE|009C  RAVSEAARHVDLFVEVGPGRVLSGLARATT-GVPAVALNTDDESLRSALAVAGAAFVAGA 873
PKSE|NEOC  EAVRAAAQDVDLFIEVGPGRVLGHLAGTAT-NIPAVSLDTDDESLRSLLQVVGAAFVVGA 873
PKSE|007A  EAAAKVAERSDLVIEVGPGRVLTGLLGTIAPGTPVLSIDTDSLTLAPVLKVAGAAFAFGA 876
PKSE|028D  DALRAMDGQVDLLIEVGPGQILRTLAAEVLPAVPAVATEADALSLAGLLATVATAWTMGA 890
PKSE|054A  QAVGLAAKSVDLFVEVGPGRVLAGLAGRAT-DVPAVSLDTDDESIASLLTVVGSAYVVGA 872
PKSE|132H  QAMDEVLPDTDLFCEAGPGRTLSALVAAGC-PVPVVGVDAGALDDRPLAETVAALFAAGA 872
PKSE|135E  EAAAAATADADLVVEVGPGRVLSGLLAEIAPDRPALAVDTDSSSLGPLLRVAAAAFVLGS 880
PKSE|145B  EAAGVAAVGADLVVEVGPGRVLSGLLAEIAPDPTVLALDTDSASLGALLRVVGAAYVLGA 881
              *   **. *.*** *   *             ..:.  ::.          ...: . *.

AT <<
PKSE|MACR  PLIHERLFRDRLTRPLEIGAEFSFLTSPCEQAPEISLPAGR------------------ 914
PKSE|CALI  PAAYPVLFEDRLTRPFDPHRARTFFASPCEAAPELAGPAPAA----------------- 917
PKSE|009C  PVALERFFEDRLIRPLRVGQEFSFLANPCEQAPREKAPAGRR----------PRPVTP 921
PKSE|NEOC  PVAPERLFRDRLIRPLRIGQELSFLASPCEQAPATTLPVSRRSAQPPAVPADR-EQEPQP 932
PKSE|007A  QLETSTLFPDGRVVRALPADGEFSFLASPCEAAPSIGAVLTRD---------------- 918
PKSE|028D  PVRHERLFADRFTRPLPLDKEFRFFASPCETGGEDFVLEHAG---------------- 932
PKSE|054A  ARIEAALFHGRLIRPLAVGAEFSFFANPCEQAPSVDLPV-R------------------ 912
PKSE|132H  LHDLSPVFTGRPARPIDIWRDRRFLANPCSSVPNAKPIEVVP---------------- 914
PKSE|135E  PVRAAGLFEGRLVRPLPADGAMTFLASPCESAPAIDAARLTP---------------- 922
PKSE|145B  PVRTGALFGDRLIRPLPADGVMSFLANPCEAAPPIGAGLVPQD---------------- 924
            .*  .*   *.:          *::.**.

>> ACP
PKSE|MACR  -------APRTEGAGDGDGGEQAGQAQ---------------GESALEVLRALVAERAE 951
PKSE|CALI  -------VAPVPAPARADDTALPAATG---------------ALELVRHLVAERAE 951
PKSE|009C  AAETPHDAHPAPTPADATTAAEAPTT--EEAPED--------GAGALEVLRVLVAERAE 970
PKSE|NEOC  AAVSPPAAQNSPASNDTSTASTASTAGSERTPQEEESI-----GAKALDVLSALVVERAE 987
PKSE|007A  --------R--VAEPAEAAAGTASESG---------------GSSTLDLLRKLASERVE 952
PKSE|028D  -------ATPATAAAPRPAAAAAPAAG---------------EATSLEVLIRLAAARAE 969
PKSE|054A  -------AAGPVPVAEADAQSAAVVP----------------GETTVDLLRRIAAERAE 948
PKSE|132H  -------IEVVTPGEVAPPAEEIRD------------------PRTVVLELLAEASE 946
PKSE|135E  -------ARP-AVEAATGTATAPAEAG---------------GESTLDLLRRLAAERVE 958
PKSE|145B  -----GGDRG-DGAAGRDEGTTPARIADSGAC----------PDSTLELLRRLAAERVE 967
                                                      . :: :     *
```

Figure 8F

```
                                                                      ACP <<
PKSE|MACR    LPPELVADDSSLLDDLHMSSITVGQIVNQAATRLGIG-AAHVPTNFATATVAQLAEALEE  1010
PKSE|CALI    LPVEVLRDDSRFLDDLHMSSITVGQLVNEAARAMGLS-AVAMPTNFATATVREMAEALEA  1010
PKSE|009C    LPAELVDPDSRLLDDLHMSSITVGQIVNQAASRLGIA-AAQVPTNFATATLAELAEALDT  1029
PKSE|NEOC    LPAHLVDPDSRLLDDLHLSSITVGQIVNQAMAQLGIAPAAQEPTNFATATLAELAEALES  1047
PKSE|007A    LPLEAVTADTHPLDDLHLSSITVGQLVNDVTRALGRP-ALEGMPNFATVCLGELAEMIDE  1011
PKSE|028D    LPAETVDPAANPLDELHLSSITVGQIMNQAAQELGIS-APMVTTAFATSTLSQLADLLDE  1028
PKSE|054A    LPPETVRPDSRLLDDLHLSSITVGQVVNQLAQRLNVP-PAAVPTNFAVATVQELAEALDT  1007
PKSE|132H    LDVASLDPRARLLGDLHLTSLAVTQLVLAAVDAAGRE-RPAAPLALADASIAELIETIEN  1005
PKSE|135E    LPLESVTAATHPMDDLHLSSITVGQIVNDVTRALGLP-ALEATTSFATVGLGELAELIDR  1017
PKSE|145B    LPLDSVTARTHPMDDLHLSSITVGQIVNDVTRALGQP-VLTATPSFATVSLGELADLIDG  1026
              *    :   :  :.:**::*::* *::        :*    :  :: : ::
```

Figure 8G

```
                                        >> domain?
PKSE|MACR    LAGTGGGAAG-SGPLVTGSAVWARPFAVDLDEVPLAVA---APGGENGPWELFTAGSDPF 1066
PKSE|CALI    REREAPHERA---DLVAGVAPWVRTFVVDLVDEPLPAT---DPTEPCGRWQVPAGADHPL 1064
PKSE|009C    LVDTGTTGEP-TTSAVVGAAPWARPPAVDLDEVARPHA---AADGADGDWELFAPQDHPY 1085
PKSE|NEOC    LASTGGPADAGAASPIAGAAPWARPPAVDLDAVARPPA---RPAAVRGTWELFAPAGYGI 1104
PKSE|007A    LAQTAKPADS-NQAEVAGVGPWVRPPAVEYVVAPKPSP-DLATGISTABWTAFAPAGHPL 1069
PKSE|028D    LAQQS-PQDT-RPGAAAGVAPWVRPPRIDLTETPPPAP----AAGPGGRWBVFATDRHPL 1082
PKSE|054A    LAATASADDAVAAPVVAGAAPWARAWRIDLDVAEPPTR---ADAPEDGTWQLFAADDHPL 1064
PKSE|132H    LPAAEAIGEN---EPVAGVASWIRCPAEVPGPVVEPGP---PGGTRRWRIHIHSGQRPDV 1059
PKSE|135E    LAQTAEDGPA-PASEVPGVAPWVRPFAVEHVEAALPAR-TAAPAAATGSWTVYSTPGHPL 1075
PKSE|145B    LADTSQDGAA-AADEVPGVAPWVRPFAVEYMEAALVPRPLPGPQAAAGDWAVYSTPGHPL 1085
                     *  . * * :                                . :

PKSE|MACR    GQQLKAALEGAGVGAG---VVVWLPPACPAEHIAQALDGAKAALAGD---RERRFVLVQH 1120
PKSE|CALI    ADALRRALEAAGVGEG---VLVCLPDEPDEEHLVTAVRGAQAALRQP---PGGRLVVVQP 1118
PKSE|009C    AERLRRELAGAGVGAG---VVAVLPKGCARQEVDRVLAAAHSALAGD---RTRRFVLVQD 1139
PKSE|NEOC    AATLRAALQDAQAGSG---VLVCLPPQCSADGIDLALAAAKRALAAP---KDSRFVLVQH 1158
PKSE|007A    AEPLRAALATAGVGDG---VLLCLNADSASGDVGLFLDAGRAVLAAP---NGTRFVVVQH 1123
PKSE|028D    AGPLAERLTATAPGGG---VLLALPRDCDQRHLGLMLAAARAALDPARRAAGTRLVAVGD 1139
PKSE|054A    ATELLAELHRARLGGG---VLVWLPQDCPEEALEHALRGAQQAARGG---PGTRFVLVDH 1118
PKSE|132H    ADEIRLLFGGSDAGSGDVADLLYLPDPSAQEAVGTLLSAVSSALGSG------RLVVITH 1113
PKSE|135E    AEPLRTALAEAGIGDG---VLLCLPAECGAGDTELFLAAGRAAATAP---GGTRLVVVQH 1129
PKSE|145B    AEPLRAALARAGIGDG---VLLCLPAECGAGEADLFLAAGRAVLAAP---EGTRLVVVQH 1139
              .  :   :   * *   :  *          :  .          *;*  :

domain? <<               >> KR
PKSE|MACR    GRGAAGLAKTLHQEG-HLRTTIVHTPR-------PDADAVRTVVAEVAATARFTEVHYDT 1172
PKSE|CALI    AARAGALAKTARLEGDRLRTTVVTTP--------LDPAAVDRVVADVAATDDFTEAVYDP 1170
PKSE|009C    GRGAAGLAKTLYLEAPHLRTTVVHTP--------AAQDVVERVVAEVAATTRFTEVHYDE 1191
PKSE|NEOC    GRAAAGLVKTLHQEASHLVTTVVDTP--------LTEDTVDRVVAEVSATTRFSEVHYSA 1210
PKSE|007A    GLGASGLAKTLRLEDPSARTTIVDLADLGPVDPEALDAAVSTVVTEVAATTDFSEVRYDT 1183
PKSE|028D    HRGAAGLAKTLHLEAPDIPVTVVTLPLDQELPAPAAEQAAARIAADTAATTGFSEVHYDA 1199
PKSE|054A    GRGGAGLAKTLRLEAPHLRVTVVHLS--------DASGAVERVTAEVAGTVGFVEVDYDA 1170
PKSE|132H    GSGLSGFLRSLRMEHPRLGVTLLRVPP-------GVDGVRAAARHAVVAAGEWRELVVGA 1166
PKSE|135E    RLGATGLAKTLHLEHPSVPTTVVELPDPLAP------EAVGLVVAEAAATTGFTEVRYGP 1183
PKSE|145B    RFGAGGMAKTLHLEHPSVLTTVVELADPAPKG-AALDEAVARVVAEAAATAGPAEVRYRQ 1198
              .: ::   *   .*::   .                .         ..: : *

PKSE|MACR    EGARRVPTLRALPVAPARK-EHVLGSSDVLLVTGGKGITAECALAVAKETGAKLAVLGR 1231
PKSE|CALI    GGRRRVPVLRPLPASDGEPGALPLGPADVLLVTGGKGITAESALMLARESGARLAVLGR 1230
PKSE|009C    AGVRRVPTLRALPVAPQHT-ASPLDASDVLLVTGGKGISAECALAVAQRTGAALAVLGR 1250
PKSE|NEOC    DGVRRVPTLRALPMSPEQQ-DKPLSASDVLLVTGGKGISAECALAIAQDSGTRLAVLGR 1269
PKSE|007A    AGVRTVPKLAALTPAEAEG--TPLDTGDVLLVTGGKGITAESALALAKDSGAKLALLGR 1241
PKSE|028D    DGTRRVPVLRPVPLEPDPG-RQALGPRDVLLVTGGKGITAECALALAGGNGAAIGLIGR 1258
PKSE|054A    DGTRRVPVLRAMSVRPQIS-RPALDDTDVLLVTGGKGITAECALAMATDSGASLALLGR 1229
PKSE|132H    EGVATEPAHRPVWHLSDGE--PPLGERDVLLVTGGKGIGYECAAALARRSGAALALVGR 1224
PKSE|135E    DGRRTVPVLRPLTPTEAPGASPLDEADVLLVTGGKGITAECALAMARDSGAALALIGR 1243
PKSE|145B    DGRRTVPVLRPLQLSPAPAGESPLDARDVLLVTGGKGITAECALAIAKDSGAGLALIGR 1258
              *   *   .:        *. *****       *.* :* .*: ..::;**

PKSE|MACR    SDPAEDKDLGDNLARMADSGVTVAYARADVTDPARVAAAVAELAEKLGPVTALLHGAGRN 1291
PKSE|CALI    SDPTADEALADNLKRLADAASDLRYLRVDVTDAGAVAAAVATVTADWGPVTAVLHGAGQN 1290
PKSE|009C    SDPASDRELADNIERMRAGGARVHYARADVTVPEQVTAAVAELTERLGTITALLHGAGRN 1310
PKSE|NEOC    SDPATDRELADNLKRMEDSGVTMRYARADVTNPEQVRTAVAELRGELGPITGVLHGAGRN 1329
PKSE|007A    SDPADDAELSENLGRMAAAGITYRYERADVTDGRQVADAIGRVQAEFGPVTAVLHGAGRN 1301
PKSE|028D    SDPARDTELADNLARMAAAGMRVHYARADVTKAAVTEITRELGVTGLLHGARDN 1318
PKSE|054A    SAPAEDPELAANLSRMTAAGVTVRYARADVTDPDQVRRAVAELTADLGPVTAVLHGAGRN 1289
PKSE|132H    ADPHADELLRSNVDNLSAAGLRVAYESVDVDADPPAAVEAGVRRLEQRLGPITALMHASGVN 1284
PKSE|135E    ADPAEDAELAANLARMTAAGLRLRYERADVTSAAQTAEAVERLEHALGPVTAVLHGAGRN 1303
PKSE|145B    ADPAADTELAENLARMDAAGLRYRYARADVTSADQVAAAVDLLEAELGPVTAVLHGAGRN 1318
              : *  :  * :  *:   ..    * .**:    .  .:  *.: *.::: .. *  *
```

Figure 8H

```
PKSE|MACR    EPAALTALGIEDFRRTFAPKVDGLRAVLDAVGEGSLKLLVTFGSIIGRAGLRGEAHMATA 1351
PKSE|CALI    TPAALADLDEAALRGVFAAKVDGLRAVLAAVDPARLRLLVTFGSIIGRAGLHGEAHMAAA 1350
PKSE|009C    EPNALARLAPRDFERTFAPKVDGLRTVLDAVDPGNLKLLVTFGSIIGRAGLRGEAHMATA 1370
PKSE|NEOC    EPGPLHALEPEDFRRTFAPKVDGLRTVLEAVDAEELKLLVTFGSIIGRAGLRGEAHMATA 1389
PKSE|007A    EPAALFSLTEESFRKTLAPKIGGLNAVLDAVDKDKIKLLVTFGSIIGRAGLRGEAHMATA 1361
PKSE|028D    EPQSLATLDEDSFRRTLATKIDGVEAVLAAVDTAALRLFVTFGSIIGRAGLRGEADMATA 1378
PKSE|054A    EPAALANLDMGAVRRTFAPKLDGLSATLAAVDPDRLRLLVTLGSIIGRAGLRGEAHMATA 1349
PKSE|132H    EPTRFDPLDDTRFTTHLAPKTIGLRNLLAALEPRRLRLLVTFGMVIGRHGLTGECHMAFA 1344
PKSE|135E    EPAAVTSLTPDDFRRTLAPKTDGLAAVLDAVAPERLKLLITFGSIIGRAGLRGEAHMATA 1363
PKSE|145B    EPAALETLSAEDFRRTLAPKTDGLEAVLAAVEPERLKLLITFGSIIGRAGLRGEAHMATA 1376
                *  . *   . :*.* *: * *:    ::*::*:*M:*** ** **..M* *
```

Figure 8I

```
PKSE|MACR    NEWLADLTEEVARNHPGCRALCMEWSVWSGVGMGEKLSVVETLSREGIVPVSPDHGVEIL 1411
PKSE|CALI    NEALAELTREVAATRPECRAVCLEWSVWSGVGMGERLSVVESLSGSGVTPISPDDGLRVL 1410
PKSE|009C    NEWLADLTEEVARAHPNLRARCMEWSVWSGVGMGEKLSVVESLSREGITPVSPDQGVDIL 1430
PKSE|NEOC    NEWLADLTEEIARTHPQVRARCVEWSVWSGVGMGEKLSVVESLSRQGIVPVSPDQGVEIL 1449
PKSE|007A    NDWMTELTVRFGQEHPRAKAIALEWSVWSGTGMGEKLGVVSALMRDGITPIPTEEGIEIL 1421
PKSE|028D    NDWLTDLTVRFQQDHPHCRCLALEWSVWSGSGMGERLGVLEALVREGIEPIPTEDGVALL 1438
PKSE|054A    NDWLAEATTAFGRRHRHCRSLCLEWSVWSGVGMGERLSVVESLHREGVAALTPDQGVAVL 1409
PKSE|132H    NGALRAEAERLAAELPDCRVLNLDWSVWSGAGMGESLGVLDTLLRLDVTPIPVPEGVELF 1404
PKSE|135E    NDWMTELTLRFAEKHPQARVLAIEWSVWSGAGMGERLGVVEALMREGITPISTEEGIRVL 1423
PKSE|145B    NDWMTELTLRFRRRHPQARAIALEWSVWSGAGMGERLGVVEALIREGITPISTENGIQVL 1438
                :  : .    :   ::****** **** *.*:..*    .: .:.  .*: ::

KR <<      >> DH
PKSE|MACR    LRLISDPDAPVVTVISGRTEGIATVRRDLPQLPLLRFAGTPLVRYHGVELVTEVELNSGT 1471
PKSE|CALI    REVVADDTLPPVVVVTGRTGGVETLRYHRSELPLLRFTERPLVRYDGIELVCEVDLARTT 1470
PKSE|009C    LRLIEDPDAPVVTVVSGRTEGIDTVRRDLPDLPMLRFTGNPLVRYHGVELVTEVELNAGT 1490
PKSE|NEOC    LRLIRDPDAPVVTVVSGRTEGIETVRRDLPPLPLLRFTGTPLVRYHGVELVTEVELNAGT 1509
PKSE|007A    RQVVGDPAAPSVLVVCGRTAGLATLPVEKRELPLTRFVDRAVVHYPGVELITEADLSAGS 1481
PKSE|028D    GRLLATPGTDTALVVMGRAGGLPTLTLEQRELPLLRFLERPQVHYPGIELVADAELTGGG 1498
PKSE|054A    RRLLADPEATGTVVVSGRTQGIDTIGYDRPELPLRRFLEKPLVHYPGVELVAETELNVGT 1469
PKSE|132H    LRLLGTHDLPTTVAVHGRLGGLFTVG---KPLFGGRFLETVPAYCPEVELVADSRLDLDR 1461
PKSE|135E    RELLADPSAGPVLVVSGRAAGLPTLALEQRDLPLARFLERVVTHYPGVELVTEAELSEGS 1483
PKSE|145B    REVLADPSAGPVLVVSGRVGGLPTLTTAHRELPLTRFVERVVVHHPDIELITEAELTEGS 1498
               .::       . .:  **     *:  *:      * **       :**: :   *

PKSE|MACR    DAYLADHLLDGNLLMPAVLGMEAMVQVAHAATGWE--KVPVIEGAKFLRPIVVPPNGATR 1529
PKSE|CALI    DPYLEDHRLDGDLLFPAVLGLEAMAQVATALARHP--GVPVIEEVRFDRPVVVDPDTGTT 1528
PKSE|009C    DPYLSDHLLDGNLLPAVIGMEAMAQVASAVTGRT--GVPVIEDAEFLRPIVVPPSGSTR 1548
PKSE|NEOC    DPYLGDHLLDGNLLPAVMGMEAMVQVAAAATGWP--GTPVIEGARFLRPIVVPPDGSTT 1567
PKSE|007A    DPYLADHLLDGQLLFLAVIGMEAMTQVAKAALAAETLPAPVFSDVEFLRPIIVSPGGSTT 1541
PKSE|028D    DRYLPDHLLDGDLLFPAVLGMEAMTQAATALTGRR--DTPVLEGMEFLRPIVVPVTGATT 1556
PKSE|054A    DLYLADHLLDGNLLFPAVFGMEAMAQVAAAVRGTD--DVPVIERAEFLRPIIVPPYGRGR 1527
PKSE|132H    DAYLRDHRIDGLAVLPAVVGMEAMAQVASALAGRP---LREMTDVTLERPVIVPEDGDRM 1518
PKSE|135E    DPYLTDHQLDGDLLFPAVLGMEAMAQAAAAVSGHQ--GPPMLEAVEFLRPIAVRPGGSTT 1541
PKSE|145B    DPYLTDHRLQGDLLFPAVLGMEAMAQVAAAVSGHQ--GPPLLEDVEFRRPVVVRPGGSTT 1556
             * ** *:  ::   ::.**.:***.*.*  *          :     : **: *

DH <<
PKSE|MACR    IRIAATVTGPDTVDVAVHAEETGFVAEHFRARLRYA-EGAIPDGAPDQVGAGVPAAPLVP 1588
PKSE|CALI    VRVAALVRSEQVIDVVLRSAVTGFAADHFRARLRFAPDETYPAYTAAPAPAELPAVPLDP 1588
PKSE|009C    IRIAAVVTAPDTVDVAVHAEDTGFVAEHPRARLLFT-GAAVPDGPPLQVPDDTPVVPLDP 1607
PKSE|NEOC    IRVAATVTGPDTVDVAVHASDTGPAAEHPRARLVYS-VAGVPDGPPLQTGSDTPEVPLDP 1626
PKSE|007A    IRLAALARDAETVDVVLRSGETGFSADHFRARLSFS-RPDPLG-DTVARDVALPPVPVDP 1599
PKSE|028D    LRTAVLATGPDTVQAVLRSGETGFQADHFRATLRYG-AARPED-EPAPVTDEVPRVPLTP 1614
PKSE|054A    IRVGAVATDDDTVEVAVRSEDTDFVADHFTARLRYG-VGPAPEGPPEQLSDDLGPVSLAP 1586
PKSE|132H    VRVCALRQD-DAVLVVLRSDETRCQVDHFRARFPLT---PVSGATPSEEDFPEGEAGLNG 1574
PKSE|135E    LRTAALVQDTGTVDVVLRTSDTGFAADHFRARLRYL-RPALPD-SPRPAALDLPAVPVDP 1599
PKSE|145B    IRIAALVRAPGTVDVVLRSADTDFAADHFRARLRYP-RPGVPT-TPVPVAFGLPTVPVDP 1614
             :*    .    .: ..::: *   .:** * :             .    . :

>> domain ?
PKSE|MACR    ATDLYGGVLFQGDRFQRLGTFHRAAARHVDADVAIG-APTGWFAPYLPATLLMADPGMRD 1647
PKSE|CALI    ARDLYGDVLFQAGRFRRIKGYRQVAARVAEAEVVTS-DAASWFSAFLPGRLVLGDPGARD 1647
PKSE|009C    ATDLYGGILFQGARFQRLHRFHRAAARHVDAEVAVQQRPEGWFAGFLPGRLLLADPGMRD 1667
PKSE|NEOC    ASDLYGGILFQGSRFQRLRRFHRMAARHVDADVTVR-RPEGWFAGFLPAEMLLADPGMRD 1685
PKSE|007A    TTELYGTVLFQGKRFQRVTGYRRASARHAVAEVATG-AEVDWFAPFLPQEQLLADPGTRD 1658
PKSE|028D    -AQLYGPVLFQGDRFRRLLAYRDLAATHCLAEIDDT-PRTDWFAGYHPGELLLADPGTRD 1672
PKSE|054A    DADLYGGLLFQGSRFQRLRGYRRAAAKCVDAEVAAL-DGVDWFAPFVPDELLLGDPGVRD 1645
PKSE|132H    -DELYGPLFFHTGRFRLVRRFSALAARHCRVRLHAS-EHAPDGLALLGDPSLLGDLASND 1632
PKSE|135E    VTELYGSVLFQGKRFQRLLDYRRAGARHAVAEVSTT-TPAPWFAAYLPQEQLLADPGTRD 1658
PKSE|145B    VTELYGSVLFQGKRFQRLLEYRRAGARHALAEISTT-AQAPWFAAFLPQDQLLADPGTRD 1673
              :***  ::*:  **: :    .*      . :             ::.*  . .*
```

Figure 8J

```
                                                                      domain 7 <<
PKSE|MACR     ALMHGNQVCVPDATLLPSGIERLYPMAAGTDLP-AKVRYCATERYRDGDTYVYDIAVRTE 1706
PKSE|CALI     AFMHGIQVCVPDATLLPEGIDRIWSAGPKLSAT-EAVTMTAREREQHGTAYVYDVVVRDA 1706
PKSE|009C     ALMHGNQVCVPDATLLPSGVERIHALGSGEHVP-DRLRYTAVERSRDGDTYVYDIAVRDE 1726
PKSE|NEOC     ALMHGNQVCVPDATLLPSGVERVHPLGNSGNVP-DQLRYCAVERSRDGDTYVYDIAVRDA 1744
PKSE|007A     AMMHAIQCCVPDATLLPQGIERLYLAEPGEQHP-EYVLLDARERSQDGDSYVYDLDVRNP 1717
PKSE|028D     ALMHSIQACVPDATLLPVSVERLHLAEAAAARTGRLLFLDARERSRDGDSYLYDLDVRDA 1732
PKSE|054A     ALMHGNQVCVPDATLLPMGVDRIHPGAAALSGR-RDLRFCAVERSRDGDTYVYDVALRDP 1704
PKSE|132H     ATVHALQACVPHRRLLPVGCERFAVEPDAG----AAVEVLASERHAGGGEYVWDVVALDR 1688
PKSE|135E     TMMHAIQCCVPDATLLPRGIERLHLAERADQDS-EFIVLDARERSQDGDTYVYDVDVRTP 1717
PKSE|145B     AMMHAIQCCVPDATLLPQSIERLWLADRADQDS-EYVVLDARERSQDGDTYVYDLDVRTP 1732
              : :*. * ***. ***  .:*.            :  * **   *  *::*:
```

Figure 8K

```
                    >> PPTE
PKSE|MACR   DGTVVERWEGLTLHAVRKTDGSGPWVEPLLGSYLERTLEEVLGSHIAVAVEPDAPD--AD 1764
PKSE|CALI   TGAVIEHWMGLRLRAVRPHAPRGSWPPALLGPLLQRRLAEVFPGDIAVAAAPGG------ 1760
PKSE|009C   NGVVVERWDGLTLHAVRKTDGSGPWVAPLLGPYLERSLEDVTGSRIAVAVEPHGDA--PA 1784
PKSE|NEOC   EGTVVERWEGLTLHAVRKTNGSGPWVAPLLGPYLERTLEEVLGAHIAVTVEPHGDN--PA 1802
PKSE|007A   DGKLVERWEGLKLRAVRKRDGEGPWVPSMLGSYLERSVERLLGSSRAIVVEPDPVGV-PV 1776
PKSE|028D   AGSPVEQWEGLLLRAVRKQDGSGPWLPALLGPFLERRVEAALGHRVRCVVLPGGED--AD 1790
PKSE|054A   DGRTVERWEGLRLRAVRRQDGSGPWVAPLLGAYLERTLDDLVGTPVAVTVQPDGPDDGPD 1764
PKSE|132H   DGRRRASWSGLRLRDTGSLPASGPWAAALLSVYLERSVLALVPAPRLTVRIGAG------ 1742
PKSE|135E   DGRVVERWEGLALVAVRKRDGAGPWVPAMLGSYLERGLERVLGGSRAVVVEAAG------ 1771
PKSE|145B   SGTVVERWEGLALVAVRKRGGAGPWVPAMLGSYLERGLERVLGGSRAVVVEPAPD---AA 1789
                 *    * **  *      *.*    .:*.   *:*     :

PKSE|MACR   GSQGSRRAGTAVALQRALGATAEVRYRPDGRPEIDGG-----LQVSAAHGLGVTLGVAA- 1818
PKSE|CALI   -----GPRDSGALLSRALGQPVVVRHRPDGRPEVDLP-----YTVSVAHSAPLDLAVAG- 1809
PKSE|009C   GSVAQRRGFTADAAARALGSPVAVRHRPDGRPELEPDRH---LSVSAAHGLGVTLSAVS- 1840
PKSE|NEOC   GSVAERRALTTIAASRTLGAAVTVRHRPDGRPEVDGG-----WHISASHGLELTVSAVA- 1856
PKSE|007A   ETTPERRAQTALAAGRAVDAPLEIRYRPDGKPEADG------VEVSASHSADLTLAIAG- 1829
PKSE|028D   GSVADRRRRTAEAASWALGRTTEVHHRPDGRPELADG-----RRISSSHAAGVTFTVVAD 1845
PKSE|054A   DHVARRRARTRSAAGQVFGRPVEVRYRPDGRPEVPGG-----QNLSVAHGAGLTLCVSS- 1818
PKSE|132H   ----ERFGGS-------------RSRHAGPADLSG------RECR-SYQNGMVLSVSA- 1776
PKSE|135E   -AEADRRARTADAVARALGAPAELRHRPDGRPELDG------HTVSAAHSDGLTLAVVG- 1823
PKSE|145B   TADQDRRSRTETAVGRALGRPVKLRHRPDGRPELDGGPGLEGRTVSASHDAGLTLAVVG- 1848
                                       :  * :              :  .

PKSE|MACR   -GRTVACEVPAVNVRTEADWTGLLG-EHAALAKLVAKETGEAPDTAATRVWSAAECLKKA 1876
PKSE|CALI   -DGTLACDAPPVAARPADVRRDLVG-RHGAVAALLVAEVGDPPDVAATRVWCAEECLQKA 1867
PKSE|009C   -DTEVACDIEAVSMRSAHEWRGLLG-EHAVAAELVAKETGEAPDTAATRVWGAVECLRKA 1898
PKSE|NEOC   -RAEVACEIEAVSMREPSEWQGLLG-EYAAVAELVARETGEAPDTAATPVWSAVECLRKA 1914
PKSE|007A   AGR-IACDVPTAIERTPEDWAGLLGEDLLAVGELLAADAREPLSVAHTRVWSALPCVRKT 1888
PKSE|028D   AGRPLACDVEQVAERTAEQWAGLLGPDAERLAHLLAAERGEPLSTAATRVWGAVETLRKA 1905
PKSE|054A   -AETVGCDVEPVTGRSAQTWTGLLG-RHTDLARLLAAEAGEEIDVAATRVWTALECLQKA 1876
PKSE|132H   -AARVACDWEAVGRRTDDEWLLLVGSRFEPLIGQLRTMLTEPVTHTAARVWTAVECLSSI 1835
PKSE|135E   QGR-LACEAPTVRPRRAEDWAALLGEAQLPVRDLLVAEAGDDPAVAATRVWCALECLRRS 1882
PKSE|145B   AGR-LACDVESVRERTAEDWDGLLGAGRLALRNLLATEAGEDRAVAGTRVWSALECLRRA 1907
             :.*  .   . *               *:*         : :  : *  *  : :

PPTE <<
PKSE|MACR   GVMAGAPLTLAPRT--RDNWVVFTAGALRIATFVTSLRGALDPAVFAFLTDGADDVPGVK 1934
PKSE|CALI   G-RPEGRLTLLPGA-LPDGWVVLDAGDVRVATRVVAVAGAAAPAVVAVLSGAGR------ 1919
PKSE|009C   GIMAGAPLTVLPRR--KDAWVVFAAGDLRIATFVTALRDALEPAVFAFLTRTPELLEGRS 1972
PKSE|NEOC   GAMAGTPLTVLPQK--KEAWVVFTAGDLRIATFVTALRDALEPAVFAFLTHEPQSAQERG 1956
PKSE|007A   G-DMTQALTVHRVD--PDGWAVLSHGGARIATWVTTVNDRTDPVVFAVLQGEES------ 1939
PKSE|028D   G-HAVAALSLADGSGLPPGWVALRGGAHRIVSFVTALDGAADPVAFTVLTGGAR------ 1958
PKSE|054A   GRRSGDPLVLHPVT--RSGWSVLVSGDVRVATFATTVRDVTEPVVFAVLTEGR------- 1927
PKSE|132H   GYPPGVPLVLGGVY--DEGWVVLRTGSVTLVSTVVPISGADSPVAVAVLVAAPEGGDRG- 1892
PKSE|135E   A-ATGQALALDRVD--GSGWAVLSAGDAAIATWVTTVTDREDPVVFAFLAGKER------ 1933
PKSE|145B   G-ATTQALTLDRVH--PDGWAVLSAGDATVATWVTTVNGRTDPVVFAVLAGKEN------ 1958
             .     *  :      * .: *   :.: ... .    *...:.*

PKSE|MACR   GA--- 1936
PKSE|CALI   -----
PKSE|009C   -----
PKSE|NEOC   QDYVG 1977
PKSE|007A   -----
PKSE|028D   -----
PKSE|054A   -----
PKSE|132H   -----
PKSE|135E   -----
PKSE|145B   -----
```

Figure 9A

```
MACR  939 -------LEVLRALVAERAELP-PELVADDSSL-LDDLHMSSITVGQIVNQAATRLGIG-  988
NEOC  975 -------LDVLSALVVERAELP-AHLVDPDSRL-LDDLHLSSITVGQIVNQAMAQLGIAP 1025
CALI  939 -------LELVRHIVAERAELP-VEVLRDDSRF-LDDLHMSSITVGQLVNEAARAMCLS-  988
1AF8    1 MATLLTTDDLRRALVECAGETDGTDLSGDFLDLRFEDIGYDSLALMETAARLESRYCVSI   60
              ::       **  * .*   : ..      : ::*: .*:::    *:.

MACR      ------AAHVPTNFATATVAQLAEALE 1009
NEOC      ------AAQEPTNFATATLAELAEALE 1046
CALI      ------AVAMPTNFATATVREMAEALE 1009
1AF8      PDDVAGRVDTPRELLDLINGALAEAA- 86
              .  ::    *    :***
```

Figure 9B

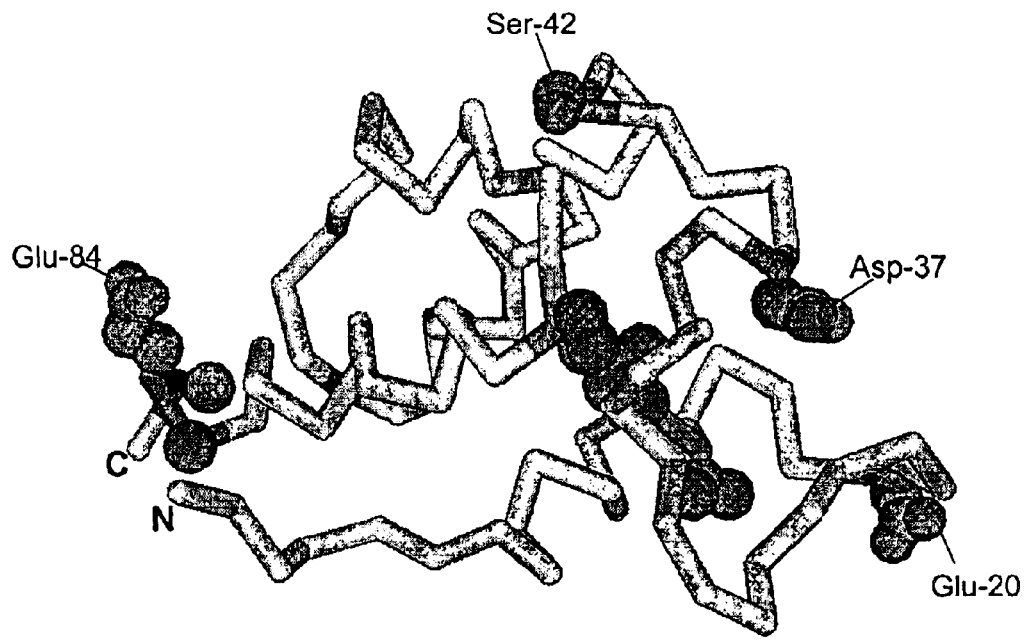

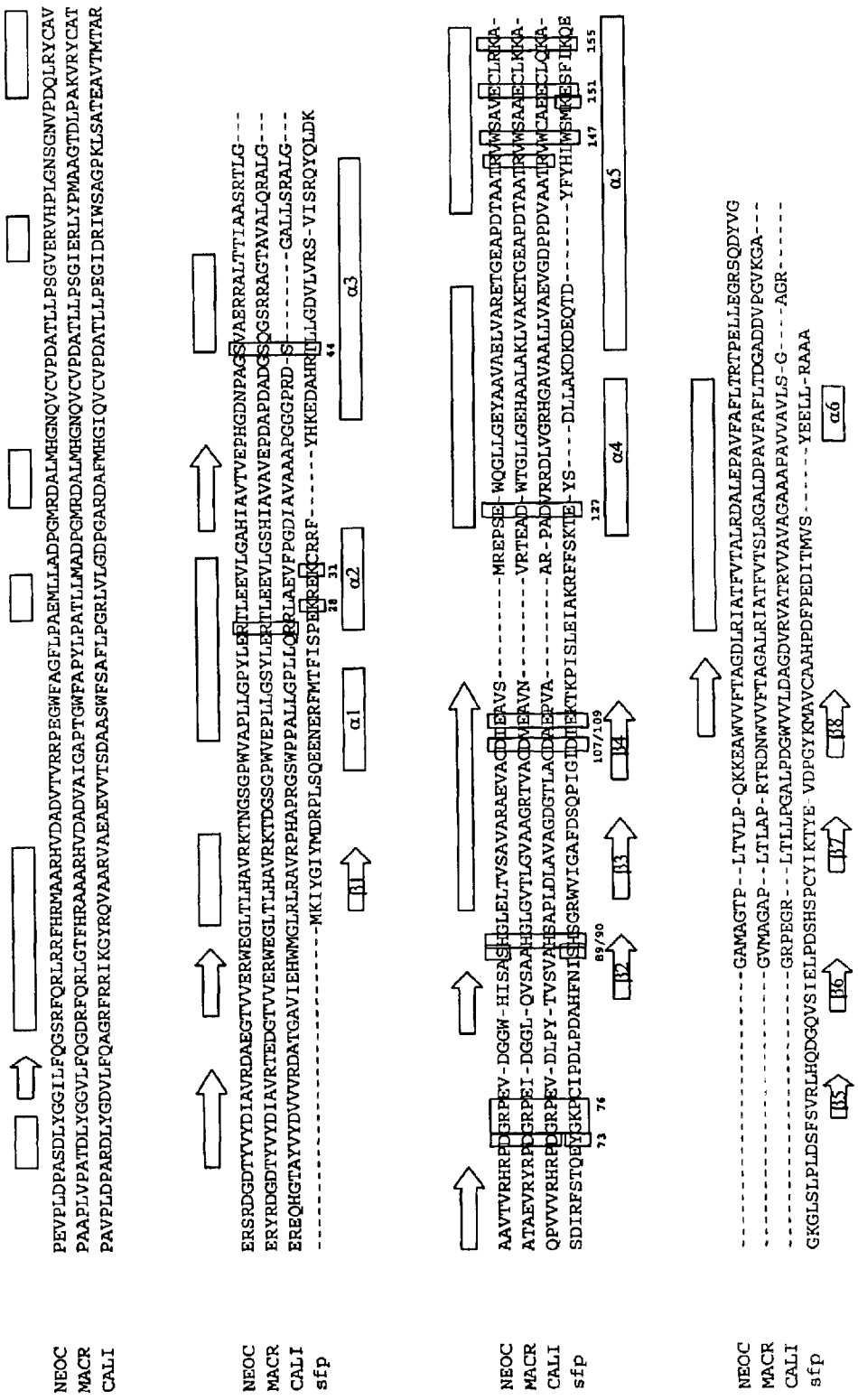

Figure 11

```
                              β1                    α1                   α2
                          --------->    ----------------->       ------...
1BVQ         ------MARSITMQQRIEFGDCPAGIVWYPNYHRWLDAASRNYFIKCGLP---PWRQTV  51
TEBC1|MACR   MSGSADSLGYFEYRHTVAFAETDLAGSADYVNYLQWQA-RCRQLFLRQTAFGTVLDDDLD 59
TEBC2|MACR   -MTTTATTDYFEYRHTVGFEETNLVGNVYYVNYLRWQG-RCRELFLKQKAP-----AVLA  53
TEBC|CALI    ----VSMPRYYEYRHVVGFEETNLVGNVYYVNYLRWQG-RCREMFLYEHAP-----EILD  50
TEBC|009C    -----MAEDYFEYRHTVGFEETNLVGNVYYVNYLRWQG-RCRELFLQQKAP-----EVLA  49
TEBC|NEOC    -----MSDDYFEYRHTVGFEETNLVGNVYYVNYLRWQG-RCRELFLKQKAP-----EVLA  49
TEBC|007A    ------MADYYEILHTVGFEETNLVGNVYYVNYVRWQG-RCREMFLKEKAP-----AVLE  48
TEBC|028D    ----VTGPDYYEYRHLVGFEETNLVGNVYYVNYLRWQG-RCREMFLLEKAP-----EVLA  50
TEBC|054A    ------MEQYYEYRHVVGFEETNIVGNVYYVNYLRWQG-RCREMFLRERAP-----QVLA  48
TEBC|132H    ----VTVARTPDYRHVITLEETNLVGNVYYFTNYLRWQG-HCRERFLMEHAP-----GVLR  50
TEBC|135E    -----VMAGYYEIRHTVGFEETNLVGNVYYVNYLRWQG-RCREMFLKEKAP-----GVLA  49
TEBC|145B    ------MSGYYEIRHTVGFEETNLVGNVYYVNYLRWQG-RCREMFLKEKAP-----GVLA  48
                 : : : : :  .* . :  **  :*       .*:  *:

β2    β3              β4              β5          β6
             ...->  ------>------>  -------------->--------------->-------->
1BVQ         VERGIVGTPIVSCNASFVCTASYDDVLTIETCIKEWRRKSFVQRHSVSRTTPGGDVQLVM 111
TEBC1|MACR   AGHADLRLFTLQVECELFEAVSALDRLAIRMRVAEIGHTQFDLTFDYVKGAGEG-DVPVA 118
TEBC2|MACR   DVQEDLKLFTLKVDCEFFAEITAFDELSIRMRLAEQAQTQLEFTFDYVKVTEDGTETLVA 113
TEBC|CALI    ELRADLKLFTLKAECEFFAELAPFDRLAVRMRLVELTQTQMELGFDYLRLGGDD--LLVA 108
TEBC|009C    EVQDDLKLFTLKVDCEFFAEITAFDELSIRMRLSELGQTQLEFSFDYVKVTG-GAELLVA 108
TEBC|NEOC    DVQDDLKLFTLKVDCEFFAEITAFDELSIRMRLSDFGQTQLEFTFDYVKVDEDGGETLVA 109
TEBC|007A    EVRHDLKLFTLKVDCEFYAEITAFDELSIRLRLEELTQTQIQFTFDYVHLTAEG-ERLVA 107
TEBC|028D    DIRADLKLFTLKVDCEFFAEITAFDELSIRMRLADLTQTQVAFTFDYVKLGPDGTEYLVA 110
TEBC|054A    DLQDDLKLFTLRVDCEFFAEITAFDELAIRMRLLELAQTQVEFGFDYVRLGVAGVETLVA 108
TEBC|132H    ALRGALALVTVSCQCDFFDELFASDTVELRMALQGTSDNRVTMAFDYYRTSG-SVAQLVA 109
TEBC|135E    ELRDDLKLFTLRVDCEFFAEITAFDELAVRMRLEEIAQTQLQFSFDYLRLDGAG-EHLVA 108
TEBC|145B    ELRDDLKLFTLKVDCDFFAEITAFDELSIRMRLEELTQTQIQFSFDYLRLDGGQ-ENLVA 107
               :     :    :  :..:      * :.  :     ..   ..  :        *

β7         β8      α3
             ---------->   --->  -------->
1BVQ         RADEIRVFAMNDGERLRAIEVPADYIELCS-------------------------- 141
TEBC1|MACR   RGRQRVVCLRGPAGAPVPALIPDALAQALAPYAAGTR-------------PLAGRHT-- 162
TEBC2|MACR   RGKQRIACMRGPNTATVPSLIPDALAQALAPYATQNR-------------SLVGRAA-- 157
TEBC|CALI    RGRQRIACMRGPNGRTEPVRVPAGLVRAFAPFRSAT---------------VGQG--- 148
TEBC|009C    RGRQRIACMRGPNTNTVPSRIPEALAHALEPYTAHGR-------------VPTGRAA-- 152
TEBC|NEOC    RGRQRVACMRGPNTNTVPSLVPEALVRALEPYGAQRR-------------VLPGRTA-- 153
TEBC|007A    RGRQRIACMRGPNTATVPSRVPEQLREALAPYAVD------------------GKGE-- 146
TEBC|028D    RGQQRVACMRGPNTDTRPTRVPEPLRLALEPYAVPATAP-----------SLTGTTTVG 158
TEBC|054A    RGTQRVACMRGPNNRTVPARVPEALGRALAPYATGAPVT-----------VAAGRPL-- 154
TEBC|132H    RGSQTIACMSRTEEGTVPVSVPAELRDALSHYAE------------------------ 143
TEBC|135E    RGRQRIACMRGPNTDTVPARVPEELRRALAPYATGPVGA-----------AAAGRPR-- 154
TEBC|145B    RGRQRIACMRGPNTATVPARVPEELRLALAPYAEGPVAARLPAAPTSPGGPVRTGRGR-- 165
             *. :   .           . :*
```

Figure 12A

```
UNBL|MACR  -VSMLRALRRRVLTPNVRETHLDRRGFHVKNPEAKNQLETVGATFLQGYAYAVEARSAAE  59
UNBL|CALI  MPANWRTIRQYALTPGMAQTTFATRGFRARDEPTRERLESVGAHFLTGYGHAVGARGPDE  60
UNBL|009C  VSSVFGALRRRLLTPPVSETTMEVRGFHVKNAEAKKRLEYIGEVFLRGYAYAVEAGSPAE  60
UNBL|NEOC  VSTAFGALRRRLLTPPISETTMKVRGFHVKNTESKKRLEQVGETFLQGYAFAVEAGSSAE  60
UNBL|007A  LGNGWRTIRRRMITPDVSETSLDKRGFHKKSPAAQELLETVGEKFLLGYAHAVEARSVEQ  60
UNBL|028D  MSGGWRAVRRRLLTPSHNETKLSTRGFHLKDDAARTNLETVGGTFLDGYAIAVEARDQDE  60
UNBL|054A  -MKAWRTLRRRVLTPDVSQTLMSVRGFHVKDQAGRERLENVGRYFLTGYAAAAEARTAAE  59
UNBL|132H  ---------VAALGQELDQVDFGRRRFRLRTGPARETLERAGRSFLEGFNAAVAYPADDR  51
UNBL|135E  VPSPLRMLRRRILTPNVAETQLARRGFHVKTPDARELLETVGSRFLEGYAYAMEAGTPAE  60
UNBL|145B  VPSAWRKLRRRILTPSTSETLLEKRGFHRKTPAAQQLLETVGERFLEGYGYAMEARDTGS  60
                 :   :.  :   *  *: :       :  ** * ** *: *

UNBL|MACR  AEEWLETVPRAYRGFAYEGAGMGAVMLDSLTGSK--RLAGFLEGEGARHDYMIWVGVGWA  117
UNBL|CALI  AVGALETVAPDLRGFAYEGAAMGLAVLDGLTGGR--RIARFLAGPAARHVYMVHVGVGWA  118
UNBL|009C  AQERLETVPRDVRGFAYEGAGMGAVVHDALPGHGG-RLQGLLAGQGRHHDYMIYVGIGWA  119
UNBL|NEOC  AEELLETVPRDFRGFAYEGAAMGAVIHDALPGHGG-RLAGLLSGRGRYHDYMIHVGIGWA  119
UNBL|007A  AEEWLEQIPVKYRGFAYEGAGMGYGMLDGLPGGGRRHVERFLDGPGEKHDYIIYVGVGWA  120
UNBL|028D  AHERLERIPVRYRGFAYEGAAMGLAMLDGLPLPGNDRVARFLAGHGAPHDYMVHVGVGWA  120
UNBL|054A  AEVPLEAVAAPYRGFAYEGAAMASAVRDALPGGGR-HVRDLLAGRGDRHVYMAYVGVGWA  118
UNBL|132H  LASEIERIDVPLRGFAYEGAGMACAVLDILTLSGGRNTRALLRGPASDYPHLVHVGVGWA  111
UNBL|135E  AETRLETVPARFRGFAYEGAGMGFAMLDGLPLPGRGRVGEFLAGRGARHNYMVYVGIGWA  120
UNBL|145B  AENLLEGVPIRFRGFAYEGAGMGFAMLDGLPLSGSGSVARFLAGRGADHVYMVYIGVGWA  120
              :*  :    ********.*.  ; * *.        :* *  .  : ::  :*:***

UNBL|MACR  MARLP-KPLWPDVTEIDPVLRWLILDGYGFHQAYFKTDAYVRKPHLTHPFSWKGGDD-TY  175
UNBL|CALI  MARLP-RWRRHAIQPADRLLGWLALDGYGFHQAYFHTRRYVWSHRRDEVLPWPGDPIGRW  177
UNBL|009C  MARLP-KPLWPDISATDPLLRWLALDGYGFHQAYFRTDAYVRNPHLQHPFRWRGGHN-HY  177
UNBL|NEOC  MARLP-RPLWPDIRTTDPLLRWLALDGFGPHQAYFKTSAYVRDPSPPAPFRWNGGHN-HY  177
UNBL|007A  MARLP-RFRWPSAEDFDPLLRWLVLDGYGFHQAYFKTAKYVDGQFQDPDFSWPPGND-GY  178
UNBL|028D  MARLP-RFRWASIAPPDPLLRWLALDGYGFHQAYFRTARYVHQHHRESDFPWPGDGTGRY  179
UNBL|054A  MARLP-RPLWGRLHAPDPLLRWLVLDGYGFHQAYFKTSRYVDGQYRHDRFPWPVEGPADY  177
UNBL|132H  FARLRLRPGWGRAVVRDPLLRWLAWDGYGFHQGFFHTDRVIGGKVVEHGLTE---D----  164
UNBL|135E  MARLP-RFRWPDITGLDPLLRWLVLDGYGFHQAYFRTEQYVHGRHRERSFPWPADDSPGY  179
UNBL|145B  MARLP-RFRWPDIDALDPLLRWLVLDGYGFHQAYFRTARYVHEQYRDPAFPWPAHDSPSY  179
           :***  :       * :* ** **:****.:*:*   :                :

UNBL|MACR  SQRVLDQGIGRALWFVGGTDPDVVAGLIAAYPEHRHGDLYAGSGLACTYAGSADETELKR  235
UNBL|CALI  TGRVVDQGIGRALWFVEGADTDRIADTVDGFPPDRHEDLYSGVALAATYAGGAPPEDLRR  237
UNBL|009C  TANAIDQGIGRALWFVGGTDPDVVSGLIRAYPEHRHGDLYAGAGLACAYAGGAGEDELAH  237
UNBL|NEOC  TANAIDQGIGRALWFVGGTDPDTVAGLIRSYSEPRHADLWAGAGLACAYAGGATEQELAL  237
UNBL|007A  ALRAIDQGIGRALWFICGTDVDLVADTVARFPERRHGDLYAGIGLASTYACGVTGDELLK  238
UNBL|028D  AGHAIDQGVGRALWFIGGTDPAVVADLVDGYQADRHADLWAGVGLAACYAAGATDAELRL  239
UNBL|054A  AARVVDQGVGRATWFVCGTDARRVVQTFDRFAADRRPDLYAGAGLAATYAGGAGAQELTW  237
UNBL|132H  QRAIRDQGVGRSLWFQECADPEAVALRIDDFPRNRRPDLWSGVGLAATYAGGVRADELES  224
UNBL|135E  VSRAIDQGVGRALWFVGGTDPDVVATLIEKFPERRHSDLYGGAGLAAAYAGGVDEAELRA  239
UNBL|145B  AGRAIDQGIGRALWFVGGTDADLVATMIEKFPESRRSDLYSGAGLAATYAGGVDEAELRA  239
               ***:**: **  :*    :    . :    *: **:.* .**. **  ..    :*

UNBL|MACR  FAEHAGKHLPNLAQGSAFASEARVKAGTIIDHTKMASRVLCAGRTPEEASRVCLETRPTG  295
UNBL|CALI  LRERGGAYAPAMAQGSAFAAEARERAGLTTAHTAVATDVFCG-APPAEAAAVTQAALADL  296
UNBL|009C  FAEGAGEHRWALAQGAAFATEARIKAGTVIDHTHLAARVVCG-TTAEKASQVCRDTRPQA  296
UNBL|NEOC  FARQAGEHRWALAQGAAFAAEARVRAGLVSEHTHLASRVVCG-VSVEQASRMCNGLRPSV  296
UNBL|007A  LAEFAGEHRGNLAQGSAFAAEARVRAGLLIPETEVATRAICG-LPAERAAAITQEVRPAT  297
UNBL|028D  LLDRAGPHRPQLAQGAAFAATARIEAGLLTEHABAATAVLCG-LTPQQAAGVCTRARPRP  298
UNBL|054A  LRDAAGPYAADLAQGAAFAAGARVRAGLVVPHNEVATRILCG-LPTQAAAAVTDEARIDL  296
UNBL|132H  LALLAGEYRADLAQGCSFACEARRVSGVVPEHTRLAAPILAG-VTADVAGSWANRAQHAL  283
UNBL|135E  FQDRAGIHRAIVAQGAAFACEARIRAGLLGPHTELAAQVLCG-TDAAAAKVTQDLRPTG  298
UNBL|145B  FWERAGSHRAMVAQGSAFAAEARERAGLPVVHTELATRVFCG-MTPAQAARVTQEVRPAG  298
            .  .* :     :***.:** **  :*    .  :  ...       *.
```

Figure 12B

```
UNBL|MACR    CDGG-AIPAFETWRQEIARQIVVPAYSQKGASA  327
UNBL|CALI    DRDG-PEPAYLVWRQRIAKQFVTLG----RC--   322
UNBL|009C    PDVHGAFPAYEKWRRDIAAQLASSSLVSKGADQ   329
UNBL|NEOC    ASRN-ALPAYENWRRDISARLASESTLRKGADQ   328
UNBL|007A    VVDG-ELPAFETWRQRIAEAILSG----GAGK    324
UNBL|028D    AVDG-PVPAYEVWRQEIADRITDLA---AGAHR   327
UNBL|054A    AAVG-ATPVYEVWRQRIKSTFASTR----RA--   322
UNBL|132H    GPADGTSAQYQQWRAGIRNLWADNME---GQPS   313
UNBL|135E    RSTG-PVPSYETWRQAIADTFTAAR----S---   323
UNBL|145B    PVPG-ALPAYEVWRQAIADRFTNVG----GC--   324
                  .  :        **   *
```

Figure 13A

```
                <Putative N-terminal signal sequence>
UNBV|MACR       MTQNPVSWLRRQAAGIVALVVMVSAPYAVKPDESSAAEKRELAKSFQFEPMSIAMPAGFK  60
UNBV|CALI       -------MFRRQLAGLVALVLLTGMYVLVRQPEANADERRAMAEPYRFTPMSLPMPGGLP  53
UNBV|009C       -VTVAKNWIRRNSPGIVALALMVGTFYGVRLPESSAAEIDKLAKDFSFEPMSIALPAGFE  59
UNBV|NEOC       -VTMAKNWLRRNSPGIVALTLMASVFYVVRLPEPSAADVRESAADFAFEPMTIAMPGGFP  59
UNBV|007A       -MTATLGWLRKQLAGIVALVLMAGLFVVAQLPTVSTAEADTMASKYAFEPLTIALPEAAK  59
UNBV|028D       --MSPRRRFRRLVPGLVTVLVAASMFFVIRSSVAVAGG-DDAAAAYRFKELPIAMPPGYE  57
UNBV|054A       LPSQPVSPLRRLMAPILVLVLAATMFLVARLPSASADTRAEIAGRFAFTELPIELPPGLP  60
UNBV|132H       --VLSAPGFRRFVPKIAAALCCVLAWVLAQPPSVAAEDRARLATRFGFDHHAISPADRDG  58
UNBV|135E       -MPTVLGRIRLQLPGIIAVLAIVTGYFLVLPPTTSAAEQDRMASRFHFTALPIELPPASK  59
UNBV|145B       --VAYRERFRRLIPGLVVIVVATSLFFAVRTSVAVAGG-EQVAKQYGFKEMPIAMPPGYD  57
                  :*            .         :           * :*   .:  .

UNBV|MACR       QQ---TVRKVNKAYKHIEAWISSVGAGVAMNDIDNDGLPNDLCITDPRIDQAVITPAPVP  117
UNBV|CALI       QQ---SIRRVNGAYQHLAAWISSVGAGAAMNDLDGDGLANDLCVTDPRVDRVVVTPAPT-  109
UNBV|009C       RQ---EVRKVNKAYQHIEAWISSVGAGVAVNDLDGDGLANDLCVNDVRIDQAVVTPAPT-  115
UNBV|NEOC       TQ---KIRQVNKAYEHIDAWISSVGAGIALNDMDGDGLSNDLCLTDPRIDQAVVTPAPS-  115
UNBV|007A       SQ---SIRTVNKEYEHIRAWISSVGAAIAVNDLDGDKLANDLCFVDPRSDQVVITPTPG-  115
UNBV|028D       SRPMNTIRKVNPAYEKIRAWISSVGASIAINDVTGHGLADGMCIVDTRTDSVVVTWTPTA  117
UNBV|054A       ER---SIRTVNPKYEHIRSWISSVGASIAVNDLDGQGVANDMCLVDTRSDAVIVTPVPDT  117
UNBV|132H       DR---RMRAVAPVYERIRNWVSSVGAGAGLFAVDGGVVSHDICLVDPRTDTVTVEPAPT-  114
UNBV|135E       HQ---TIRTVNQDYEHIRAWISSVGAAITMTDLRGTGKSGDLCLVDTRTDQVVVTPVPG-  115
UNBV|145B       RQPMNTVRTVNPAYQKIRSWISSVGASIAINDLTGHGVADGMCIVDTRTNSVIVTYTPTA  117
                 :  ;* *   *:::  *:*****.  :    :   . ..:*. *  * : . .*

UNBV|MACR       GRKSATYEPFALDMAPLPKSKYSAPIGCVPGDFNEDGATDLLVYYWGRTPVIFQQKKMAW  177
UNBV|CALI       -AGADRYQPFVLDPAPLPMNPYVAPMGCLPGDLNADGRTDLLVYWWGRTPVVFLAR----  164
UNBV|009C       --RKDAYEPFALDPAPLGTSKTMAPMGCMPGDYNEDGRMDLLVYYWGRTPVLFMNE---G  170
UNBV|NEOC       --RGKAYEPFALDAAPLGISDTMAPMGCVPGDFNEDGAIDLLVYYWGRTPVIFQNE---G  170
UNBV|007A       -KGGDRYAPFALDAAPLPMGKYIAPMGCVPADYNEDGRVDLLAYYWGRTPILPLSK----  170
UNBV|028D       P-EADRFTPFVLDGRPLPMDDTMAPTGCTPGDFNGDGRNDFLVTYWGRTPVLFMAR----  172
UNBV|054A       ---GATYQPFVVDPAPLPMGSTIAPMGCTPGDFNLDGRMDLLVIYWGRTPVVFLQK----  170
UNBV|132H       --TGERYAAFTLKPATLPYAGYVAPMGCLPADLNEDGWQDVVVYWGRSPVLFLRT----  168
UNBV|135E       -SDGTRYAPFALDAAPLPMNEYIAPMGCVAGDFNEDGRTDLLVYYWGRTPVLFLGR----  170
UNBV|145B       R-PADRFTPFVLDAAPLPMDDTMAPTGCTPGDFNGDGRMDLLVTYWGRTPILFMAK----  172
                 .  .*.:.   .*     **  **  .  * **  *.:. :***.*::*

UNBV|MACR       DKKMPPKMECFEPIELVPG--AGGGIYTGPLWNSNAAAVADPDGDGHKDLYIGNYFPESP  235
UNBV|CALI       ADATGLSRAAYHPVELVPGAATGGSRYDGPKWNTNAATLADPDGDGHLDVYIGNYFPDSA  224
UNBV|009C       EKGKPLTADSFTPTELLPG--KPGRTYTGPLWNSNAAAVADFDGDGHDDIYIGNYFPDSP  228
UNBV|NEOC       GRGEPLTASSFTPTELLPG--KPGPRYTGPLWNSNTAAVADFDGDGHDDIYIGNYFPDSA  228
UNBV|007A       PGATKLEPKAYEPVELVPGNNSKNGEYSGPLWNTNAASVGDFDGDGHQDIFIGNYFPDSA  230
UNBV|028D       ADAAAPAAESYVPRELVASE-SLDGRYHGPRWNTDAAYVGDLDGSGHPSIIIGNYFPDSD  231
UNBV|054A       EGATALSNDTYQPVELVPQQRTDDGVYRGPLWNTNAVTVADFDGDGRPDIALFNYFPDSQ  230
UNBV|132H       -PGSAPAAAGFSERELVSP---------PQVWNTNAATTADLDGDGHLDLFFGNYFPDGA  218
UNBV|135E       PDATTLDAHAFQPVELVPGPNETDGKYTGAQWNTNTATVADFDGDGHQDIFIGNYFPNGP  230
UNBV|145B       SDATTPSASSYVPRELVPSQ-SLDGKYHGPRWNTDADYVADLDGSGHPSIVIGNYFPDSD  231
                 :   **:.          **:::    .*:**.*:  .:  :     ****:.

UNBV|MACR       -VLDDTKDG-GVTMNDSMSHAQNGGGGHFFLKTPG--GYKWIP----ADKVVP-EGREKG  286
UNBV|CALI       -VLDDTVHG-GVAMNRSMSNGLNGGEDHVFRWTGGTAGATPSASFAEVPDVFD-TKVSRG  281
UNBV|009C       -VLDPSKDG-DVTMNASLSHAQNGGGGHFFRWTED--GYEKV------DDAIP-QSLNKG  277
UNBV|NEOC       -VLDPSKNG-DVTMNDSLSHAQNGGGGHFFRWTES--GFEKT------DDAIP-QGLNKG  277
UNBV|007A       -VLDDRVSG-GVEMNKSMSHADNAGGKYILRFTGATQGAKPSATFALDDKAIP-ADSQGG  287
UNBV|028D       -VLDPQGIR-NVQMNDSLSSAKNAGGDHVLRFHSSTAGAAPDARFVEEKDAIA-FDASTG  288
UNBV|054A       -VLDPEGLP-NVQMNHSMSHGHNAGGAHVLRWSGATSGDDPTVTY-EEQVALD-PRYATG  286
UNBV|132H       RVLDPTAQQPELVMTDSLSDGHNGGTHRYFRFASATGGSTPDVRYAEAVDPVEGDSRTTG  278
UNBV|135E       -VLNDQVSG-GVVMNHSMSHAQNSGGKYILRRTGGNVGDKLSAGFECSDDAFP-DEAKHG  287
UNBV|145B       -VLDPHGLN-NVVMNNSLSSARNAGGDHVLRWYRSTSGPEPTVSYVEEKDAIP-YSASTG  288
                 **:       : *. *:*  .  *:*    .        *           .     *
```

Figure 13B

```
UNBV|MACR    WTLAASATDVDGDLLPELYLGLDFGSTTLLHNRSTPGELKFVEVKAS-HNGIMPKSKEIG 345
UNBV|CALI    WTLAVAANDLDGDQLPELYVANDFGPDRLLHNRSERGRIAFAPVESPGLPGLTPKSKRLG 341
UNBV|009C    WTLGASAADLDGDGLPEMFLAHDFGTSALLHNTSTPGRLRFSEVKSE-HTATIPKSKELG 336
UNBV|NEOC    WSLGASAADLDGDRLPEIFLAHDFGTSALLHNTSRPGRIEFREVKAV-HSGTVPKSKEIG 336
UNBV|007A    WSLAASATDVDGDNLPELYIGNDFGHDRLLYNKSRPGHVEFAEVKGI-RGPNEPKSKVIG 346
UNBV|028D    WTLAIAGADLTGDALPEVYIANDFGHAHLLHNVSTPGRIRFEEATGE-RTPTTPKSFVLG 347
UNBV|054A    WTLGAASADLDGDLLPELYLANDFGQDRFFHNVSTPGRIRFNLAEGV-RTPLTPKSLVLG 345
UNBV|132H    WTLAAAAQDVDQDGLPELYVANDFSPDQLLVNVSTPGQIRFREAHGE-RHALTPKSKVVG 337
UNBV|135E    WSLASSAIDLDGDQLPELYVANDFGNDRMLHNVSSPGHPKFVTVTGP-RDATTPKSKILG 346
UNBV|145B    WTLAISGADLTGEGLPDLYIANDFGHAHLLYNRSTPGHISFTEAKGE-RTPTTPKSFVLG 347
             *:*. :. *: ; **::::. **.    :: * * *.  *  . .    ***  :*
```

Figure 13C

```
UNBV|MACR    RSSFKGMGIDWADLNGDGILDAFLSNITTSFGIQESNYTFISKAKNLDDLHRKMSDKKAP 405
UNBV|CALI    HDSFKGMGVDFGDIDGDGMFDLYVGNITTSFGIQESNFAFVNTAADTAALRAALWAGEAP 401
UNBV|009C    RSSFKGMGVDFGDLDHDGLYDMFVSNITTSFGIQESNFAFISDAGSRSELQGRFAEGEAP 396
UNBV|NEOC    RSSFKGMGVDFGDLDHDGLYDMFVSNITTSFGIQESNFAFINKAGDKADLRSRFENGEAP 396
UNBV|007A    NDSFKGMGVDFADLDHDGLYDLYVSNITTSWGIEESHFQFMNTAKDTADLRGRLQGGEAP 406
UNBV|028D    KGSFKGMGVDFGDVDGNGSFDMMVSNITVAWGLEESNFLWINQAKDPAEMKRKLTDRIAP 407
UNBV|054A    HDSFKGMGVDFADLHSRGRFDMFVSNITESWGLEESNFVWHNTAASPEAAREQLSRGIAP 405
UNBV|132H    NDSFKGMGASFADLNNDGMPDILVSNITEPYALQESNFAFISTGD-----RDALRRGVAP 392
UNBV|135E    NDSFKGMGVDFGDLDRKGLYDLFVSNITASFGIEESNFQFMNTARDKADLRAQMDDGTAP 406
UNBV|145B    NGSFKGMGVDFGDLGHDGRFDMVVSNITVPWGLEESNFVWINQAKDNADMRRKLSSGVAP 407
             ..******..:.*:  *  *  :.***  .:.::**::  :  ..    :  :   **

UNBV|MACR    WKDESASLNTAWSGWGWDAKMADFDNDGRPEITQATGFVKGKRSRWAQLQELATANDLLV 465
UNBV|CALI    WHDRSAELGLAWSGWSWDVKFGDFTNRGDPAIVQTSGFVKGEVNRWAQLQEAATANDDLL 461
UNBV|009C    YKDKSTGLGLAWSGWGWDVKMGDFDNNGDLEIVQALGFVKGKNNRWPQLQELATANDALV 456
UNBV|NEOC    YRDESTDLGLAWSGWGWDVKMGDFDNNGDLEITQALGFVKGKNNRWPQLQELATSNDALV 456
UNBV|007A    WVDRSAQAGTAWSGWGWDVKIADYDNSGESVITQATGFVKGDVNRWPQLQELATSNDELL 466
UNBV|028D    FTQEAADHGVAWTGWGWDAKMGDFRNSGQQDILQADGFVKGNIDRWPWLQEMAMTNDDLL 467
UNBV|054A    FENRAARRNLAWVGWGWDVKMADFDNSGLEVVQAAGFIKGDINRFNWLQELAMANDLML 465
UNBV|132H    FDDRSEELGLSRSGWSWDVKAADFDNDGAAEVMHATGFIRGTTNRWPQMQEAAMSNDLIL 452
UNBV|135E    FEDRSAAAGTARSGWGWDVKMGDFDNSGQLAIVQATGFVKGGTNRWPQLQELATANDALL 466
UNBV|145B    FTQEAQQYGMAWTGWGWDAKMGDFLNSGDLSVLQADGFVKGNIDRWPWLQEMAMTNDDLL 467
             :  :.:   ..   **.**.*  .*:  *  *    :  ::  **::* .*:  :** * :**  ::

UNBV|MACR    RHPGAWPKVEAGDDLAGDQYLRFWTRN--GGKYDNISPELGLDVPVPTRGIATGDADGDG 523
UNBV|CALI    ANPRWWPKVEQGDDIAGGQHLAFHVRG-ADGRYEDLSHELGLADRVPSRGIATADADGDG 520
UNBV|009C    PNPQWWPNVEHGDDLAGSQRMRFFAKDPDSGRYHNLSVALGIGEPIPTRGIATGDVDGDG 516
UNBV|NEOC    ANPTWWPNVRQGDDLAGSQRMRFFAKDQDTGRYINLSTALGLGDPVPTRGIATGDVDGDG 516
UNBV|007A    KHPYFWPNMVAGDDVGGDHTLHFWAKSS-DGRYTDLAPRLGLAVPVPTRGIATGDADGDG 525
UNBV|028D    SNPKLWPNVGPGDDLAGDETMAFYARTD-SGKFANISKQLGLDVPIPTRGIATADTTGTG 526
UNBV|054A    REPAMWPNAKPGDDISGGNPVAFWVRED-NGRYVNLSPELGLDEDTPSRGISVADPDGDG 524
UNBV|132H    GNPALWPRFTEEDGLSGHDRNTFFTRDG-AGRFADVADLVGVGTDAVSRAFAVGDVDGDG 511
UNBV|135E    DNPWWWPNVKAGDDLAGDQTLRFFVKGT-DGHYSNLAGRLGLAVPVPTRGIATGDAYGNG 525
UNBV|145B    SNPAMWPNVQPGDDIAGDEAIAFYAKTP-DGRYVNISSQLGIAVKTPTRGIATGDTTGTG 526
             . *   **.   *.:.*  .    *  .:   *::  :::  :*:    :*.:.:..* * *

UNBV|MACR    RLDFVVARQWDAPVFYCNLSPAKNDFLGLKLVDDK----------------------- 558
UNBV|CALI    RLDLVVARQWDAPVFYRNDSPDTGSFLTLRLLHEQA--------PAAG---------P-L 562
UNBV|009C    RLDLVVARQWGEPVFLHNVSKSPGAYLGLKLTHPD------------------------ 551
UNBV|NEOC    RLDIAVARQWDEPVFYRNTAPEPGSWLELVFTHPD------------------------ 551
UNBV|007A    KLDFAVARQWEQPIFYRNVSPGTGSYLNLKLVHDKA--------SADG---------P-L 567
UNBV|028D    ALDFAVARQWGPPAFYANQSANLGHDLTLRLYRPATDTATTGTTGAGATAATDATAGPGL 586
UNBV|054A    AQDIAVARQWGAPAYFRNTRGDSDNHLSLRLSRPA--------LAADG-------RTP-- 567
UNBV|132H    RLDFVVANQWAQSTLYRNTSQSSAEFVGLRLRQPADVG------TCAG-----------N 554
UNBV|135E    RLDFAVARQWDAPVFYRNDSPDPGAYLGLRLTYDTP--------DAAG---------P-L 567
UNBV|145B    ALDFAVARQWGPPAFYANTSPNLGDYLNLRLYRPA---------GAGG-------AGQGL 570
             *:..:*.**  .   *       :  * :

UNBV|MACR    ---G-SPVVGAQVRVNFPDGKVLLGRVDGGSGHSGKRSTDVHIGLG-KVSGPVQASISWR 613
UNBV|CALI    AGAG-SPVVGAQVRVTTPDGRVLIDRVDGGSGHSGRRSNEVSLGLD-DVTGPVSVHLTWR 620
UNBV|009C    ---G-SPVVGAEVCVELPDGTKRITRLDGGGGHSGKRSTDVHIGLGKDVRDPVPATITWR 607
UNBV|NEOC    ---G-APVVGAEVRVELPDGSKRVARVDGGGGHSGKRSTDIHIGLGEEAQGEVSGTVTWR 607
UNBV|007A    KAAG-TAAIGAQVTVVTPDGKKYMDRVDGGSGHSGKRSHEIQIGLGK-VTGPVKVCLQWR 625
UNBV|028D    ATTG-TPAYGATVCVTTPDGRKQIGQLDGGGGHGGFRSFDVRFGLGTQSG-PVTVDLAWR 644
UNBV|054A    STTGTSPAYGAHVTITTADGRTQVGQLDGGGGHSGRRSFDVFFGLGDAADRPVSVQLCWR 627
UNBV|132H    SEGADRPAIGATAVVTTPDGTKHSQQVYPANGHNGVNAPDLVFGLGDVRDGPLPVELSWR 614
UNBV|135E    PAPG-SPVIGAQIEVTTPDGRKLIDRVDGGSGHSGKRSHYVHIGLGQGVSGPLPVKLQWR 626
UNBV|145B    VNTG-SPAYGATVRITTPAG-TQISQLDGGGGHGGFRSFDVRFGLGTYHG-PVTADLTWR 627
             .  .. ** :  .  *    ::  ..**.* .: : :**.    :   : **
```

Figure 13D

```
UNBV|MACR    DTTGQVRKQALTLSPGWHSVQLGTEAKEK----  642
UNBV|CALI    DRSGAPHEQELTLAPGRHTLTLGSQAREVSR--  651
UNBV|009C    DRAGEVHEQKLKLTPGWHSIQLGTEAKEK----  636
UNBV|NEOC    DREGDVHEQEVRLAPGRHSFELGSQVKEK----  636
UNBV|007A    DLTGQIRTQEVQLTPGDHTFQLGAQAKEK----  654
UNBV|028D    DNAGGLHTETRQLSAGSHTLMLTDDIQEVAAR-  676
UNBV|054A    DLNGQTHRQTIDLTAGRHDLLLTDRAEELNRR-  659
UNBV|132H    DGCGRRHTATVNVAPGWHRILLHADGTTMVEDK  647
UNBV|135E    DRTGQVHTQTVTLSPGWHSLQLGSQAKEK----  655
UNBV|145B    DAGGTLHQTTKQLSPGTHSLMLTSDVQEVPSR-  659
             *  *   :       ::.*  *  .  *
```

Figure 14A

```
                                                                                      -...
UNBU|MACR   -----MSSHTSAVPPTAAAPTAAAGSPAKSAKPAAPPRHDP---------KVIKALQRF  45
UNBU|CALI   -------------MTQKPAK-------------DPR---------------ITALRRF  17
UNBU|009C   --------------VTMSAPH------------TAARHNP----------KVTTALRRF  23
UNBU|NEOC   --------------VTMSAAQPLS--------QTAGPRHNP---------KVVTALRRF  28
UNBU|007A   ------MTVMAEQTLTAPKSN-----------------------------KTITALRRF  24
UNBU|028D   ------------MTATDISGVATR------AVRPHAAKKQP-------NRDPRYLALRNF  35
UNBU|054A   MTDVKPVEDARGVLTTASPDTAGRNG-GNPVPRQQAGGDRPGVPPRVDSRDPRYMALRNF  59
UNBU|132H   -------------VKTLPRKTKDQ--------GDSAGHRKP---------KDPRSAALRRF  31
UNBU|135E   ------VTDMADKAPTTKQTAHQPAPPEAAARPATASRHEP---------KVVIALRRF  44
UNBU|145B   -----------MSTTAQPRPKGV------AAAATAGPAKP--------KDPRYLALRNF  34
                       *                                          **:.*

1A                         1B
              ................                ..................
UNBU|MACR   AVSISVLNVLGYTVLGFEQGWLWPPFIAVATGYTTEIVLEWISAKGEGRAPRYAGGGRKGL 105
UNBU|CALI   AISITILNIAGYTVLGFEQAWAWPLIALATGYAVELGLEIIGARAERRPPRFRGNGLRGL  77
UNBU|009C   AISISVLNVFGYTVLGFEQPWLWPFVALATGYTVEIALELLGARAEGRAPRFTGGGFKGL  83
UNBU|NEOC   AISISVLNIVGYTVLGFEQPWLWPPFIALATAYTVELTLEAVGARAEKRATRFRGGGFRGL  88
UNBU|007A   AISITIFNIIGYTVLGFEQPYTYPFIALATAYATEILLEIIGARAQGRGVRFRGNGFKGL  84
UNBU|028D   ALSMSVFPNIFGYTLLGFEQPWLWPLICAPFGYVVEIVLELISAWAQQRTPRFRGNGPRGL  95
UNBU|054A   AMSMTVFNILGYTVLGFEQPWTWPFFALAIGYATEILVETVAARATGRSAAYSGNGMWGM 119
UNBU|132H   GLSISVLTIVGHTLLGFEQAYLTPVVAVLVALGTEVLLESVEAASLGRRPRYLGQAG-AV  90
UNBU|135E   AISITVFNILGYTVLGFEQPWTWPLIALATAYTTETALELVGAKVEGRRPRFLGNGLPGM 104
UNBU|145B   AISISVFNIFGYTLLGFEQPWLWPIIAVLTAYACEICFELISAWAQRRAPRFRGNGVRGV  94
             .:*::::.:  *:*:*****  :  *... .   *  .* : *   *   : * .  .:

2                         3
                       .................            ------...
UNBU|MACR   MEFLLPAHITSLAVNMLTYTNDRWWVMMFGVIVAVGTKHVLRAPVKGRMRHYMNPSNFGI 165
UNBU|CALI   VEFLYPAHITALAVNMLLYVNDRVPVMMFAVAVAISGKWLFRVPVNGRLRHFMNPSNFGI 137
UNBU|009C   VEFLFPAHITALAVNMLSYVNDKMWVMVFGVIVAVGTKWVLRAPVKGRMRHFMNPSNFGI 143
UNBU|NEOC   MEFLFPAHITALAVNMLTYVNDQVWVMVFGVVVAVGAKWVLRAPVRGRMRHFMNPSNLGI 148
UNBU|007A   VEFLFPAHITGLALNMLTYVNDQVLVMMFGVVVAVGAKWVLQAPVRGRLRHYMNPSNFGI 144
UNBU|028D   YEFLLPSHITALAANMLLYANDRLLPILLAVFIGVAAKHVLQAPVYGRMRHFMNPSNFGI 155
UNBU|054A   YTFLLPTHITALAANMLLYANDNFWPIGFAVVVAVGQKALLQAPIRGRMRHFMNPSNFGI 179
UNBU|132H   VDFLLPSYIGGLACAMLLYANDRLMPTVLAVVIAVASKYLIRVKVNGRLRHVLNPSNTGI 150
UNBU|135E   LEFLYPSHITGLALNMLTYVNDRLPVMMFGVVPAVSAKWVLRVPVRGRLRHYMNPSNFGI 164
UNBU|145B   YEFLLPAHITALAVNMLTYGNNQLLPVFFGVVVGVGGKHALQAPIAGRMRHFMNPSNFGI 154
             ** *::*  .**  **  * *:.        :.*   ..:.  *  ::.  :  **:** :****  **

3                       4                         5
            ................       ...................       ---------..
UNBU|MACR   MIILVLF-PWASIAPPYHFTEYLTGTTGPGDWILPAVIITLGTMLNAKLTNRMPLIMGWL 224
UNBU|CALI   AVVLLLF-PWISIAPPYQFTEYLEG---PADWIVPAVIVVFGTMLNAKLTGRMWLIAGWL 193
UNBU|009C   AVILVLF-PWASIAPPYHFTEYLDG---GFDWLVPAIIITLGTMLNAKLTERMWLILAWV 199
UNBU|NEOC   AVILLLF-PWASIAPPYHFTEYVDG---GIDWLVPAVILTLGTMLNAKLTERMWLIVAWV 204
UNBU|007A   TIILLVF-PWASIAPPYHFTEQVDS---WVGWLIVGIIIVSGTVLNAMLTQRMWLIGAWL 200
UNBU|028D   TMALVLFGSWISIAPPYEFTENANT---FFRIGIPLIITTAGTVINAMLTKRVPLIVGWL 212
UNBU|054A   TATLLVF-SWVNVAPPYHFTENVPD---MISILIPIVIVTAGTVLNAMLTKKVPLIVGWL 235
UNBU|132H   VVVLLVF-PWVSIAPPYQFTEWTSG---VVDALIPVLLLAAGTMLNAKLTKKIPLILGWV 206
UNBU|135E   AAILVLF-PWASIAPPYHFTEHVNT---PFGWLIVLGILMSGTILNAKLTGRMWLIAGWL 220
UNBU|145B   TMSLLCFGSWFSIAPPYEFTENANT---YFRVMIPLIIATAGTVINALLTKRTPLIVGWL 211
             *: * .*  .:****.***         :   :  ** ::**  ** :   **  .*:
```

Figure 14B

```
                    5                   6
          ..---------   -------------------
UNBU|MACR  VGFALQAIIRGWMFDTSIPAALGMMTGTAFVLFTNYMVTDPGTSPSKKSSQIAFGAGVAA 284
UNBU|CALI  GVFVLQSVVRGLVLDTAILPALATMTGVAFVLFTNYMITDPGTTPSRPLSQFAFGGGVAL 253
UNBU|009C  GGFALQAIVRGLLFDTSIPAALAMMTGVAFVLFTNYMITDPGTTPSSKWGQIAFGGGVAA 259
UNBU|NEOC  GGFAAQAVVRGLLFGTSIPAALAMMTGVAFVLFTNYMITDPGTTPSSKWGQIAFGGGVAA 264
UNBU|007A  ITFALQAIIRGLVFDTAIPGALGMMTGVAFVLYTNYMVTDPGTTPSKPASQILFGSGVAL 260
UNBU|028D  GGFVIQALLRHWIWDVAIFSALGPMSGVAFVLYTNYMITDPGTTPSKGRNQFMFGSSVAM 272
UNBU|054A  GAFIIQALVRHWIWDVSLWGALVPITGVAFVLFTNYMITDPGTTPTAGWMQFMFGASVGM 295
UNBU|132H  GGFVLQAVLRSAFTDLSIVSAVLPITGTAFILFTNYMITDPSTSPSKPRNQVLFGLATAA 266
UNBU|135E  GTFALQAVLRGLVFGTSIPAALGMMTGVAFVLFTNYMITDPGTTPSKPANQVAFGAGVAL 280
UNBU|145B  GAFAIQAFIRHWIWHVALFSALGVMTGVAFVLFTNYMISDPGTTPMKGRAQFVFGSSVAF 271
            *  *:..:*   .   ::  *:  ::*.**:*:****::**.*:*    *. **  ...
```

Figure 14C

```
                                                                            7
                                                         ---------------------
UNBU|MACR    VYGLLMAVNITYGIFFATAIVCGIRGLFLWFLHLQAKQQAAAKTAPVRPVEALVAVPSPA   344
UNBU|CALI    VYGVLTGASIVYGLFFATAIVCLIRGGFLWSLHAVRVA---------ARDGKGTPPAA-    302
UNBU|009C    LYGVLTAMSIAYGLFFATALACAIRGAFLWTADIVAKK---------RAEEALELAAVTR   310
UNBU|NEOC    AYGLLTALSVAYGIFFATALVCGVRGGFLWISDIVSRR---------RTEEALAVAAVG-   314
UNBU|007A    AYGFFMVVHVAYGLFLATALVCLIRGMFLWGLHFSKKA-----------TEKWEAEQAK-   308
UNBU|028D    VYGVLMLFNVVYTLFFATTIVCGLRGAGWWVAHFRNRR-----------KQGGGPVEVP-   320
UNBU|054A    VYGVLMVFNIVYTTFFAVTIVCLLRGLFWWGKWLLERK----------HRDVSLDPAP-   343
UNBU|132H    AYAVLVQLHVVFGLFFALVAVCALRGVGLAILSWRQSVEVP-------AQVAQKHDAVVR   319
UNBU|135E    LYALFMIAHIAYGIFFATALTCLIRGLYLWYVHFRDRG----------HDERQATVLR-   328
UNBU|145B    VYGILMVFNVVYTLFFATTIVCGLRGLGWWAAHLIKRA----------RQADATGAES-   319
               *..:      :.:    *:*. .* :**

UNBU|MACR    PAP-AEAPTVPLAAATEDACAAGTCGHEKCAAARVAAPAAAVPPAAVSPAVPAAASAAAE   403
UNBU|CALI    -------P----------------------GTVDGTVPPAVAR----------------   316
UNBU|009C    SVSRAEAPSG--------------AQPDAAPAQAEAPAPCACPADACSCPAPANTEAAP   355
UNBU|NEOC    -LT-SEKPS-----------------VERTPIEHAETLPCVN----------------   337
UNBU|007A    --------------------------SAEITSLPKPAEK-------------------   321
UNBU|028D    --------------------------SGQSGAPERPMGN-------------------   333
UNBU|054A    --------------------------PPAAVALPTAR---------------------   354
UNBU|132H    --------------------------DRIEEVGVPVFGAN------------------   333
UNBU|135E    --------------------------AAAASAPAAEAS--------------------   340
UNBU|145B    --------------------------SGGTAAQPQQSQV-------------------   332

UNBU|MACR    DACAAGSCQHGKCAAMRAEAAKEKKVAVSL   433
UNBU|CALI    ----------------------EMVRA--   321
UNBU|009C    CACPADACSCP---APANTEADPAKTPVAA  382
UNBU|NEOC    -GCAEGACSCSG--NPKDSEADDRRIVVSA  364
UNBU|007A    ------------------PET--GAVAA--  329
UNBU|028D    -----------------------EAVAA--  338
UNBU|054A    ------------------------------
UNBU|132H    -----------------------GRV----  336
UNBU|135E    ----------------------GKVAAV-  346
UNBU|145B    -----------------------GAVAA--  337
```

GENES AND PROTEINS INVOLVED IN THE BIOSYNTHESIS OF ENEDIYNE RING STRUCTURES

CROSS-REFERENCE TO RELATED APPLICATIONS

This application claims benefit under 35 USC § 119 of provisional applications U.S. Ser. No. 60/291,959 filed on May 21, 2001 and U.S. Ser. No. 60/334,604 filed on Dec. 3, 2001 which are hereby incorporated by reference in their entirety for all purposes.

FIELD OF INVENTION

The present invention relates to the field of microbiology, and more specifically to genes and proteins involved in the production of enediynes.

BACKGROUND

Enediyne natural products are characterized by the presence of the enediyne ring structure also referred to as the warhead. The labile enediyne ring structure undergoes a thermodynamically favorable Bergman cyclization resulting in transient formation of a biradical species. The biradical species is capable of inducing irreversible DNA damage in the cell. This reactivity gives rise to potential biological activity against both bacterial and tumor cell lines. Enediynes have potential as anticancer agents because of their ability to cleave DNA. Calicheamicin is currently in clinical trials as an anticancer agent for acute myeloid leukemia (Nabhan C. and Tallman M S, Clin Lymphoma (2002) March; 2 Suppl 1:S19–23). Enediynes also have utility as anti-infective agents. Accordingly, processes for improving production of existing enediynes or producing novel modified enediynes are of great interest to the pharmaceutical industry.

Enediynes are a structurally diverse group of compounds. Chromoprotein enediynes refer to enediynes associated with a protein conferring stability to the complex under physiological conditions. Non-chromoprotein enediynes refer to enediynes that require no additional stabilization factors. The structure of the chromoprotein enediynes neocarzinostatin and C-1027, and the non-chromoprotein enediynes calicheamicin and dynemicin are shown below with the dodecapolyene backbone forming the warhead structure in each enediyne highlighted in bold.

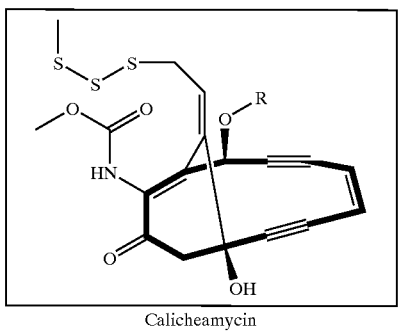
Calicheamycin

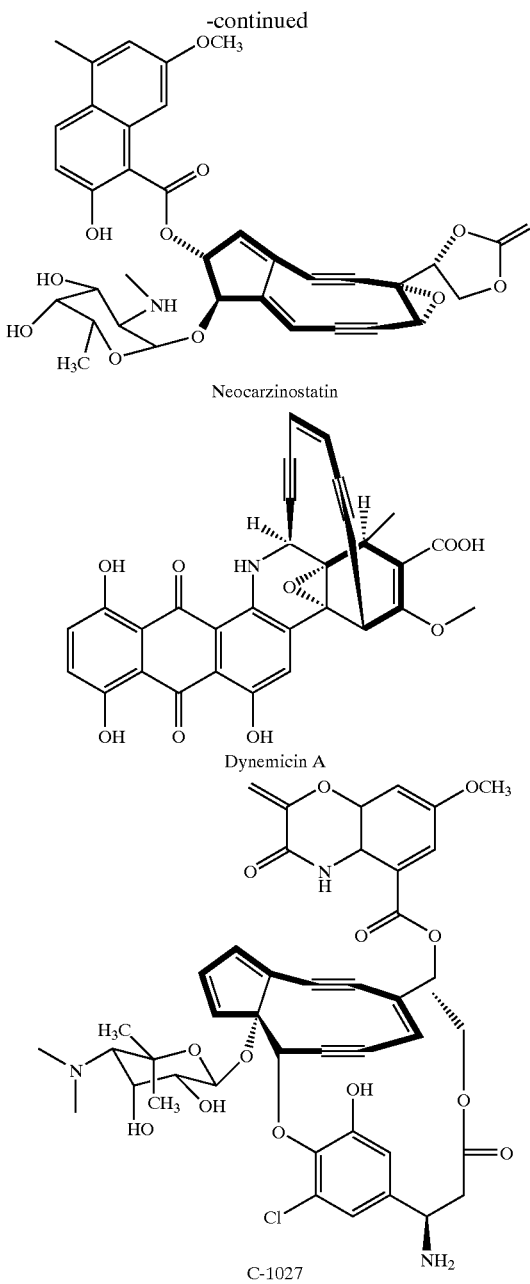
Neocarzinostatin

Dynemicin A

C-1027

Efforts at discovering the genes responsible for synthesis of the warhead structure that characterizes enediynes have been unsuccessful. Genes encoding biosynthetic enzymes for the aryltetrasaccharide of calicheamicin, and for calicheamicin resistance are described in WO 00/37608. Additional genes involved in the biosynthesis of the chromoprotein enediyne C-1027 have been isolated (Liu, et al. *Antimicrobial Agents and Chemotherapy*, vol. 44, pp 382–292 (2000); WO 00/40596). Isotopic incorporation experiments have indicated that the enediyne backbones of esperamicin, dynemicin, and neocarzinostatin are acetate derived (Hansens, O. D. et al. *J. Am. Chem Soc.* 11, vol 111 pp. 3295–3299 (1989); Lam, K. et al. *J. Am. Chem. Soc.* vol. 115, pp 12340–12345 (1993); Tokiwa, Y et al. *J. Am. Chem Soc.* vol. 113 pp. 4107–4110). However, both PCR and DNA probes homologous to type I and type II PKSs have failed to identify the presence of PKS genes associated with biosynthesis of enediynes in known enediyne producing microorganisms (WO 00/40596; W. Liu & B. Shen, Antimicrobial Agents Chemotherapy, vol. 44 No. 2 pp. 382–392 (2000)).

Elucidation of the genes involved in biosynthesis of enediynes, particularly the warhead structure, would provide access to rational engineering of enediyne biosynthesis for novel drug leads and makes it possible to construct over-producing strains by de-regulating the biosynthetic machinery. Elucidation of PKS genes involved in the biosynthesis of enediynes would contribute to the field of combinatorial biosynthesis by expanding the repertoire of PKS genes available for making novel enediynes via combinatorial biosynthesis.

Existing screening methods for identifying enediyne-producing microbes are laborious, time-consuming and have not provided sufficient discrimination to date to detect organisms producing enediyne natural products at low levels. There is a need for improved tools to detect enediyne-producing organisms. There is also a need for tools capable of detecting organisms that produce enediynes at levels that are not detected by traditional culture tests.

SUMMARY OF THE INVENTION

One embodiment of the present invention is an isolated, purified or enriched nucleic acid comprising a sequence selected from the group consisting of: (a) SEQ ID NOS: 2, 14, 24, 34, 44, 54, 64, 74, 84, 94; sequences complementary to SEQ ID NOS: 2, 14, 24, 34, 44, 54, 64, 74, 84, 94; fragments comprising 2000, preferably 3000, more preferably 4000, still more preferably 5000, still more preferably 5600 and most preferably 5750 consecutive nucleotides of SEQ ID NOS: 2, 14, 24, 34, 44, 54, 64, 74, 84, 94; and fragments comprising 2000, preferably 3000, more preferably 4000, still more preferably 5000, still more preferably 5600 and most preferably 5750 consecutive nucleotides of the sequences complementary to SEQ ID NOS: 2, 14, 24, 34, 44, 54, 64, 74, 84, 94; (b) SEQ ID NOS: 4, 6, 16, 26, 36, 46, 56, 66, 76, 86, 96; sequences complementary to SEQ ID NOS: 4, 6, 16, 26, 36, 46, 56, 66, 76, 86, 96; fragments comprising 150, preferably 200, more preferably 250, still more preferably 300, still more preferably 350 and most preferably 400 consecutive nucleotides of the sequences complementary to SEQ ID NOS: 4, 6, 16, 26, 36, 46, 56, 66, 76, 86, 96; and fragments comprising 150, preferably 200, more preferably 250, still more preferably 300, still more preferably 350 and most preferably 400 consecutive nucleotides of the sequences complementary to SEQ ID NOS: 4, 6, 16, 26, 36, 46, 56, 66, 76, 86, 96; (c) SEQ ID NOS: 8, 18, 28, 38, 48, 58, 68, 78, 88, 98; sequences complementary to SEQ ID NOS: 8, 18, 28, 38, 48, 58, 68, 78, 88, 98; fragments comprising 700, preferably 750, more preferably 800, still more preferably 850, still more preferably 900 and most preferably 950 consecutive nucleotides of SEQ ID NOS: 8, 18, 28, 38, 48, 58, 68, 78, 88, 98; and fragments comprising 700, preferably 750, more preferably 800, still more preferably 850, still more preferably 900 and most preferably 950 consecutive nucleotides of the sequences complementary to SEQ ID NOS: 8, 18, 28, 38, 48, 58, 68, 78, 88, 98; (d) SEQ ID NOS: 10, 20, 30, 40, 50, 60, 70, 80, 90, 100; sequences complementary to SEQ ID NOS: 10, 20, 30, 40, 50, 60, 70, 80, 90, 100; fragments comprising 600, preferably 700, more preferably 750, still more preferably 800, still more preferably 850 and most preferably 900 consecutive nucleotides of SEQ ID NOS: 10, 20, 30, 40, 50, 60, 70, 80, 90, 100, and fragments comprising 600, preferably 700, more preferably 750, still more preferably 800, still more preferably 850 and most preferably 900 consecutive nucleotides of SEQ ID NOS: 10, 20, 30, 40, 50, 60, 70, 80, 90, 100, and (e) SEQ ID NOS: 12, 22, 32, 42, 52, 62, 72, 82, 92, 102; sequences complementary to SEQ ID NOS: 12, 22, 32, 42, 52, 62, 72, 82, 92, 102; fragments comprising 700, preferably 750, more preferably 800, still more preferably 850, still more preferably 900 and most preferably 950 consecutive nucleotides of the sequences complementary to SEQ ID NOS: 12, 22, 32, 42, 52, 62, 72, 82, 92, 102; and fragments comprising 700, preferably 750, more preferably 800, still more preferably 850, still more preferably 900 and most preferably 950 consecutive nucleotides of SEQ ID NOS: 12, 22, 32, 42, 52, 62, 72, 82, 92, 102. One aspect of the present invention is an isolated, purified or enriched nucleic acid capable of hybridizing to the nucleic acid of this embodiment under conditions of high stringency. Another aspect of the present invention is an isolated, purified or enriched nucleic acid capable of hybridizing to the nucleic acid of this embodiment under conditions of moderate stringency. Another aspect of the present invention is an isolated, purified or enriched nucleic acid capable of hybridizing to the nucleic acid of this embodiment under low stringency. Another aspect of the present invention is an isolated, purified or enriched nucleic acid having at least 70% homology to the nucleic acid of this embodiment by analysis with BLASTN version 2.0 with the default parameters. Another aspect of the present invention is an isolated, purified or enriched nucleic acid having at least 99% homology to the nucleic acid of this embodiment as determined by analysis with BLASTN version 2.0 with the default parameters.

Another embodiment is an isolated, purified or enriched nucleic acid that encodes an enediyne polyketide synthase protein comprising a polypeptide selected from the group consisting of: (a) SEQ ID NOS: 1, 13, 23, 33, 43, 53, 63, 73, 83, 93; (b) polypeptides having at least 75% homology to a polypeptide of SEQ ID NOS: 1, 13, 23, 33, 43, 53, 63, 73, 83, 93 as determined using the BLASTP algorithm with the default parameters and having the ability to substitute for a polypeptide of SEQ ID NOS: 1, 13, 23, 33, 43, 53, 63, 73, 83 or 93 during synthesis a warhead structure in an enediyne compound; and (c) fragments of the polypeptides of (a) and (b), which fragments have the ability to substitute for a polypeptide of SEQ ID NOS: 1, 13, 23, 33, 43, 53, 63, 73, 83, 93 in the synthesis of the warhead structure in an enediyne compound. In one aspect of this embodiment, the nucleic acid encoding an enediyne polyketide synthase protein may be used in genetic engineering applications to synthesize the warhead structure of an enediyne compound.

Another embodiment is an isolated, purified or enriched nucleic acid that encodes an enediyne polyketide synthase catalytic complex comprising (a) a polypeptide selected from the group consisting of SEQ ID NOS: 1, 13, 23, 33, 43, 53, 63, 73, 83, 93; polypeptides having at least 75% homology to a polypeptide of SEQ ID NOS: 1, 13, 23, 33, 43, 53, 63, 73, 83, 93 as determined using the BLASTP algorithm with the default parameters and having the ability to substitute for a polypeptide of SEQ ID NOS: 1, 13, 23, 33, 43, 53, 63, 73, 83 or 93 during synthesis a warhead structure in an enediyne compound; and fragments thereof, which fragments have the ability to substitute for a polypeptide of SEQ ID NOS: 1, 13, 23, 33, 43, 53, 63, 73, 83, 93 in the synthesis of the warhead structure in an enediyne compound; and (b) a polypeptide selected from the group consisting of SEQ ID NOS: 3, 5, 15, 25, 35, 45, 55, 65, 75, 85, 95; polypeptides having at least 75% homology to a polypeptide of SEQ ID NOS: 3, 5, 15, 25, 35, 45, 55, 65, 75, 85, 95 as determined using the BLASTP algorithm with the default parameters and having the ability to substitute for a polypeptide of SEQ ID NOS: 3, 5, 15, 25, 35, 45, 55, 65, 75, 85, 95 during synthesis of a warhead structure in an enediyne compound; and fragments thereof, which fragments have the ability to substitute for a polypeptide of SEQ ID NOS: 3, 5, 15, 25, 35, 45, 55, 65, 75, 85, 95 in the synthesis of the warhead structure in an enediyne compound. In one aspect of this embodiment, the nucleic acid encoding an enediyne polyketide synthase catalytic complex may be used in genetic engineering application to synthesize the warhead structure of an enediyne compound.

Another embodiment is an isolated, purified or enriched nucleic acid encoding a gene cassette comprising: (a) a nucleic acid encoding an enediyne polyketide synthase catalytic complex as described above, and (b) at least one nucleic acid encoding a polypeptide selected from the group consisting of (i) SEQ ID NOS: 7, 17, 27, 37, 47, 57, 67, 77, 87, 97, polypeptides having at least 75% homology to a polypeptide of SEQ ID NOS: 7, 17, 27, 37, 47, 57, 67, 77, 87, 97 as determined using the BLASTP algorithm with the default parameters and having the ability to substitute for a polypeptide of SEQ ID NOS: 7, 17, 27, 37, 47, 57, 67, 77, 87, 97 during synthesis of a warhead structure in an enediyne compound; and fragments thereof, which fragments have the ability to substitute for a polypeptide of SEQ ID NOS: 7, 17, 27, 37, 47, 57, 67, 77, 87, 97 in the synthesis of the warhead structure in an enediyne compound; (ii) SEQ ID NOS: 9, 19, 29, 39, 49, 59, 69, 79, 89, 99; polypeptides having at least 75% homology to a polypeptide of SEQ ID NOS: 9, 19, 29, 39, 49, 59, 69, 79, 89, 99 as determined using the BLASTP algorithm with the default parameters and having the ability to substitute for a polypeptide of SEQ ID NOS: 9, 19, 29, 39, 49, 59, 69, 79, 89, 99 during synthesis of a warhead structure in an enediyne compound; and fragments thereof, which fragments have the ability to substitute for a polypeptide of SEQ ID NOS: 9, 19, 29, 39, 49, 59, 69, 79, 89, 99 in the synthesis of the warhead structure in an enediyne compound; and (iii) SEQ ID NOS: 11, 21, 31, 41, 51, 61, 71, 81, 91, 101; polypeptides having at least 75% homology to a polypeptide of SEQ ID NOS: 11, 21, 31, 41, 51, 61, 71, 81, 91, 101 as determined using the BLASTP algorithm with the default parameters and having the ability to substitute for a polypeptide of SEQ ID NOS: 11, 21, 31, 41, 51, 61, 71, 81, 91, 101 during synthesis of a warhead structure in an enediyne compound; and fragments thereof, which fragments have the ability to substitute for a polypeptide of SEQ ID NOS: 11, 21, 31, 41, 51, 61, 71, 81, 91, 101 in the synthesis of the warhead structure in an enediyne compound. In one aspect of this embodiment, the nucleic acid encoding the gene cassette may be used in genetic engineering application to synthesize the warhead structure of an enediyne compound.

Another embodiment is an isolated, purified or enriched nucleic acid encoding a gene cassette comprising: (a) a nucleic acid encoding a polypeptide selected from the group consisting of SEQ ID NOS: 1, 13, 23, 33, 43, 53, 63, 73, 83, 93; a polypeptide having at least 75% homology to a polypeptide of SEQ ID NOS: 1, 13, 23, 33, 43, 53, 63, 73, 83, 93 as determined using the BLASTP algorithm with the default parameters and having the ability to substitute for a polypeptide of SEQ ID NOS: 1, 13, 23, 33, 43, 53, 63, 73, 83 or 93 during synthesis a warhead structure in an enediyne compound; or a fragment thereof, which fragment has the ability to substitute for a polypeptide of SEQ ID NOS: 1, 13, 23, 33, 43, 53, 63, 73, 83, 93 in the synthesis of the warhead structure in an enediyne compound; (b) at least one nucleic acid encoding a polypeptide selected from the group consisting of SEQ ID NOS: 3, 5, 15, 25, 35, 45, 55, 65, 75, 85, 95; a polypeptide having at least 75% homology to a polypeptide of SEQ ID NOS: 3, 5, 15, 25, 35, 45, 55, 65, 75, 85, 95 as determined using the BLASTP algorithm with the default parameters and having the ability to substitute for a polypeptide of SEQ ID NOS: 3, 5, 15, 25, 35, 45, 55, 65, 75, 85, 95 during synthesis of a warhead structure in an enediyne compound; or a fragment thereof, which fragment has the ability to substitute for a polypeptide of SEQ ID NOS: 3, 5, 15, 25, 35, 45, 55, 65, 75, 85, 95 in the synthesis of the warhead structure in an enediyne compound; (c) at least one nucleic acid encoding a polypeptide selected from the group consisting of SEQ ID NOS: 7, 17, 27, 37, 47, 57, 67, 77, 87, 97; a polypeptide having at least 75% homology to a polypeptide of SEQ ID NOS: 7, 17, 27, 37, 47, 57, 67, 77, 87, 97 as determined using the BLASTP algorithm with the default parameters and having the ability to substitute for a polypeptide of SEQ ID NOS: 7, 17, 27, 37, 47, 57, 67, 77, 87, 97 during synthesis of a warhead structure in an enediyne compound; and a fragment thereof, which fragment has the ability to substitute for a polypeptide of SEQ ID NOS: 7, 17, 27, 37, 47, 57, 67, 77, 87, 97 in the synthesis of the warhead structure in an enediyne compound; (d) at least one nucleic acid encoding a polypeptide selected from SEQ ID NOS: 9, 19, 29, 39, 49, 59, 69, 79, 89, 99; a polypeptide having at least 75% homology to a polypeptide of SEQ ID NOS: 9, 19, 29, 39, 49, 59, 69, 79, 89, 99 as determined using the BLASTP algorithm with the default parameters and having the ability to substitute for a polypeptide of SEQ ID NOS: 9, 19, 29, 39, 49, 59, 69, 79, 89, 99 during synthesis of a warhead structure in an enediyne compound; and a fragment thereof, which fragment has the ability to substitute for a polypeptide of SEQ ID NOS: 9, 19, 29, 39, 49, 59, 69, 79, 89, 99 in the synthesis of the warhead structure in an enediyne compound; and (e) at least one nucleic acid encoding a polypeptide selected from SEQ ID NOS: 11, 21, 31, 41, 51, 61, 71, 81, 91, 101; a polypeptide having at least 75% homology to a polypeptide of SEQ ID NOS: 11, 21, 31, 41, 51, 61, 71, 81, 91, 101 as determined using the BLASTP algorithm with the default parameters and having the ability to substitute for a polypeptide of SEQ ID NOS: 11, 21, 31, 41, 51, 61, 71, 81, 91, 101 during synthesis of a warhead structure in an enediyne compound; and a fragment thereof, which fragment has the ability to substitute for a polypeptide of SEQ ID NOS: 11, 21, 31, 41, 51, 61, 71, 81, 91, 101 in the synthesis of the warhead structure in an enediyne compound. In one aspect of this embodiment, the nucleic acid encoding the gene cassette may be used in genetic engineering application to synthesize the warhead structure of an enediyne compound.

Another embodiment of the present invention is an isolated or purified polypeptides comprising a sequence selected from the group consisting of: (a) SEQ ID NOS: 1, 13, 23, 33, 43, 53, 63, 73, 83, 93 and fragments comprising 1300, preferably 1450, more preferably 1550, still more preferably 1650, still more preferably 1750 and most preferably 1850 consecutive amino acids of SEQ ID NOS: 1, 13, 23, 33, 43, 53, 63, 73, 83, 93; (b) SEQ ID NOS: 3, 5, 15, 25, 35, 45, 55, 65, 75, 85, 95; and fragments comprising 40, preferably 60, more preferably 80, still more preferably 100, still more preferably 120 and most preferably 130 consecutive amino acids of SEQ ID NOS: 3, 5, 15, 25, 35, 45, 55, 65, 75, 85, 95; (c) SEQ ID NOS: 7, 17, 27, 37, 47, 57, 67, 77, 87, 97; and fragments comprising 220, preferably 240, more preferably 260, still more preferably 280, still more preferably 300 and most preferably 310 consecutive amino acids of SEQ ID NOS: 7, 17, 27, 37, 47, 57, 67, 77, 87, 97; (d) SEQ ID NOS: 9, 19, 29, 39, 49, 59, 69, 79, 89, 99; and fragments comprising 520, preferably 540, more preferably 560, still more preferably 580, still more preferably 600 and most preferably 620 consecutive amino acids of SEQ ID NOS: 9, 19, 29, 39, 49, 59, 69, 79, 89, 99; and (e) SEQ ID NOS: 11, 21, 31, 41, 51, 61, 71, 81, 91, 101; and fragments comprising 220, preferably 240, more preferably 260, still more preferably 280, still more preferably 300 and most preferably 320 consecutive amino acids of SEQ ID NOS: 11, 21, 31, 41, 51, 61, 71, 81, 91 and 101. One aspect of the present invention is an isolated or purified polypeptide having at least 70% homology to the polypeptide of this embodiment by analysis with BLASTP algorithm with the default parameters. Another aspect of the present invention is an isolated or purified polypeptide having at least 99% homology to the polypeptides of this embodiment as determined by analysis with BLASTP algorithm with the default parameters.

Another embodiment is an isolated or purified enediyne polyketide synthase comprising a polypeptide selected from the group consisting of (a) SEQ ID NOS: 1, 13, 23, 33, 43, 53, 63, 73, 83, 93; (b) polypeptides having at least 75% homology to a polypeptide of SEQ ID NOS: 1, 13, 23, 33, 43, 53, 63, 73, 83, 93 as determined using the BLASTP algorithm with the default parameters and having the ability to substitute for a polypeptide of SEQ ID NOS: 1, 13, 23, 33, 43, 53, 63, 73, 83 or 93 during synthesis a warhead structure in an enediyne compound; and (c) fragments of the polypeptides of (a) and (b), which fragments have the ability to substitute for a polypeptide of SEQ ID NOS: 1, 13, 23, 33, 43, 53, 63, 73, 83, 93 in the synthesis of the warhead structure in an enediyne compound. In one aspect of this embodiment, the enediyne polyketide synthase protein may be used in genetic engineering applications to synthesize the warhead structure of an enediyne compound.

Another embodiment is an isolated, purified enediyne polyketide synthase catalytic complex comprising (a) a polypeptide selected from the group consisting of SEQ ID NOS: 1, 13, 23, 33, 43, 53, 63, 73, 83, 93, polypeptides having at least 75% homology to a polypeptide of SEQ ID NOS: 1, 13, 23, 33, 43, 53, 63, 73, 83, 93 as determined using the BLASTP algorithm with the default parameters and having the ability to substitute for a polypeptide of SEQ ID NOS: 1, 13, 23, 33, 43, 53, 63, 73, 83 or 93 during synthesis a warhead structure in an enediyne compound; and fragments thereof, which fragments have the ability to substitute for a polypeptide of SEQ ID NOS: 1, 13, 23, 33, 43, 53, 63, 73, 83, 93 in the synthesis of the warhead structure in an enediyne compound; and (b) a polypeptide selected from the group consisting of SEQ ID NOS: 3, 5, 15, 25, 35, 45, 55, 65, 75, 85, 95; polypeptides having at least 75% homology to a polypeptide of SEQ ID NOS: 3, 5, 15, 25, 35, 45, 55, 65, 75, 85, 95 as determined using the BLASTP algorithm with the default parameters and having the ability to substitute for a polypeptide of SEQ ID NOS: 3, 5, 15, 25, 35, 45, 55, 65, 75, 85, 95 during synthesis of a warhead structure in an enediyne compound; and fragments thereof, which fragments have the ability to substitute for a polypeptide of SEQ ID NOS: 3, 5, 15, 25, 35, 45, 55, 65, 75, 85, 95 in the synthesis of the warhead structure in an enediyne compound. In one aspect of this embodiment, the enediyne polyketide synthase catalytic complex may be used in genetic engineering applications to synthesize the warhead structure of an enediyne compound.

In another embodiment, the invention is a polypeptide selected from the group consisting of: (a) SEQ ID NOS: 7, 17, 27, 37, 47, 57, 67, 77, 87, 97; (b) polypeptides having at least 75% homology to a polypeptide of SEQ ID NOS: 7, 17, 27, 37, 47, 57, 67, 77, 87, 97 as determined using the BLASTP algorithm with the default parameters and having the ability to substitute for a polypeptide of SEQ ID NOS: 7, 17, 27, 37, 47, 57, 67, 77, 87, 97 during synthesis of a warhead structure in an enediyne compound, and (c) fragments of (a) or (b), which fragments have the ability to substitute for a polypeptide of SEQ ID NOS: 7, 17, 27, 37, 47, 57, 67, 77, 87, 97 in the synthesis of the warhead structure in an enediyne compound. In one aspect, the polypeptide of this embodiment may be used with an enediyne polyketide synthase catalytic complex of the invention in genetic engineering applications to synthesize the warhead structure of an enediyne compound.

In another embodiment, the invention is a polypeptide selected from the group consisting of (a) SEQ ID NOS: 9, 19, 29, 39, 49, 59, 69, 79, 89, 99; (b) polypeptides having at least 75% homology to a polypeptide of SEQ ID NOS: 9, 19, 29, 39, 49, 59, 69, 79, 89, 99 as determined using the BLASTP algorithm with the default parameters and having the ability to substitute for a polypeptide of SEQ ID NOS: 9, 19, 29, 39, 49, 59, 69, 79, 89, 99 during synthesis of a warhead structure in an enediyne compound; and (c) fragments of (a) or (b), which fragments have the ability to substitute for a polypeptide of SEQ ID NOS: 9, 19, 29, 39, 49, 59, 69, 79, 89, 99 in the synthesis of the warhead structure in an enediyne compound. In one aspect, the polypeptide of this embodiment may be used with an enediyne polyketide synthase catalytic complex of the invention in genetic engineering applications to synthesize the warhead structure of an enediyne compound.

In another embodiment, the invention is a polypeptide selected from the group consisting of (a) SEQ ID NOS: 11, 21, 31, 41, 51, 61, 71, 81, 91, 101; (b) polypeptides having at least 75% homology to a polypeptide of SEQ ID NOS: 11, 21, 31, 41, 51, 61, 71, 81, 91, 101 as determined using the BLASTP algorithm with the default parameters and having the ability to substitute for a polypeptide of SEQ ID NOS: 11, 21, 31, 41, 51, 61, 71, 81, 91, 101 during synthesis of a warhead structure in an enediyne compound; and (c) fragments of (a) or (b), which fragments have the ability to substitute for a polypeptide of SEQ ID NOS: 11, 21, 31, 41, 51, 61, 71, 81, 91, 101 in the synthesis of the warhead structure in an enediyne compound. In one aspect of this embodiment, the polypeptide of this embodiment may be used with an enediyne polyketide synthase catalytic complex of the invention in genetic engineering applications to synthesize the warhead structure of an enediyne compound.

An enediyne gene cluster may be identified using compositions of the invention such as hybridization probes or PCR primers Hybridization probes or PCR primers according to the invention are derived from protein families associated with the warhead structure characteristic of enediynes. To identify enediyne gene clusters, the hybridization probes or PCR primers are derived from any one or more nucleic acid sequences corresponding to the five protein families designated herein as PKSE, TEBC, UNBL, UNBV and UNBU. The compositions of the invention are used as probes to identify enediyne biosynthetic genes, enediyne gene fragments, enediyne gene clusters, or enediyne producing organisms from samples including potential enediyne producing microorganisms The samples may be in the form of environmental biomass, pure or mixed microbial culture, isolated genomic DNA from pure or mixed microbial culture, genomic DNA libraries from pure or mixed microbial culture. The compositions are used in polymerase chain reaction, and nucleic acid hybridization techniques well known to those skilled in the art.

Environmental samples that harbour microorganisms with the potential to produce enediynes are identified by PCR methods. Nucleic acids contained within the environmental sample are contacted with primers derived from the invention so as to amplify target orthosomycin biosynthetic gene sequences. Environmental samples deemed to be positive by PCR are then pursued to identify and isolate the enediyne gene cluster and the microorganism that contains the target gene sequences. The enediyne gene cluster may be identified by generating genomic DNA libraries (for example, cosmid, BAC, etc.) representative of genomic DNA from the population of various microorganisms contained within the environmental sample, locating genomic DNA clones that contain the target sequences and possibly overlapping clones (for example, by hybridization techniques or PCR), determining the sequence of the desired genomic DNA clones and deducing the ORFs of the enediyne biosynthetic locus. The microorganism that contains the enediyne biosynthetic locus may be identified and isolated, for example, by colony hybridization using nucleic acid probes derived from either the invention or the newly identified enediyne biosynthetic locus. The isolated enediyne biosynthetic locus may be introduced into an appropriate surrogate host to achieve heterologous production of the enediyne compound(s); alternatively, if the microorganism containing the enediyne biosynthetic locus is identified and isolated it may be subjected to fermentation to produce the enediyne compound(s).

A microorganism that harbours an enediyne gene cluster is first identified and isolated as a pure culture, for example, by colony hybridization using nucleic acid probes derived from the invention. Beginning with a pure culture, a genomic DNA library (for example, cosmid, BAC, etc.) representative of genomic DNA from this single species is prepared, genomic DNA clones that contain the target sequences and possibly overlapping clones are located using probes derived from the invention (for example, by hybridization techniques or PCR), the sequence of the desired genomic DNA clones is determined and the ORFs of the enediyne biosynthetic locus are deduced. The microorganism containing the enediyne biosynthetic locus may be subjected to fermentation to produce the enediyne compound(s) or the enediyne biosynthetic locus may be introduced into an appropriate surrogate host to achieve heterologous production of the enediyne compound(s).

An enediyne gene cluster may also be identified in silico using one or more sequences selected from enediyne-specific nucleic acid code, and enediyne-specific polypeptide code as taught by the invention. A query from a set of query sequences stored on computer readable medium is read and compared to a subject selected from the reference sequences of the invention. The level of similarity between said subject and query is determined and queries sequences representing enediyne genes are identified.

Thus another embodiment of the invention is a method of identifying an enediyne biosynthetic gene or gene fragment comprising providing a sample containing genomic DNA, and detecting the presence of a nucleic acid sequence coding for a polypeptide from at least one or the groups consisting of: (a) SEQ ID NOS: 1, 13, 23, 33, 43, 53, 63, 73, 83, 93; and polypeptides having at least 75% homology to a polypeptide of SEQ ID NOS: 1, 13, 23, 33, 43, 53, 63, 73, 83, 93 as determined using the BLASTP algorithm with the default parameters; (b) SEQ ID NOS: 3, 5, 15, 25, 35, 45, 55, 65, 75, 85, 95; and polypeptides having at least 75% homology to a polypeptide of SEQ ID NOS: 3, 5, 15, 25, 35, 45, 55, 65, 75, 85, 95 as determined using the BLASTP algorithm with the default parameters; (c) SEQ ID NOS: 7, 17, 27, 37, 47, 57, 67, 77, 87, 97; and polypeptides having at least 75% homology to a polypeptide of SEQ ID NOS: 7, 17, 27, 37, 47, 57, 67, 77, 87, 97as determined using the BLASTP algorithm with the default parameters; (d) SEQ ID NOS: 9, 19, 29, 39, 49, 59, 69, 79, 89, 99; and polypeptides having at least 75% homology to a polypeptide of SEQ ID NOS: 9, 19, 29, 39, 49, 59, 69, 79, 89, 99 as determined using the BLASTP algorithm with the default parameters; and (e) SEQ ID NOS: 11, 21, 31, 41, 51, 61, 71, 81, 91, 101; and polypeptides having at least 75% homology to a polypeptide of SEQ ID NOS: 11, 21, 31, 41, 51, 61, 71, 81, 91 and 101 as determined using the BLASTP algorithm with the default parameters. One aspect of this embodiment provides detecting a nucleic acid sequence coding a polypeptide from at least two of the above groups (a), (b), (c), (d) and (e). Another aspect of this embodiment provides detecting a nucleic acid sequence coding a polypeptide from at least three of the groups (a), (b), (c), (d) and (e). Another aspect of this embodiment provides detecting a nucleic acid sequence coding a polypeptide from at least four of the groups (a), (b), (c), (d) and (e). Another aspect of this embodiment provides detecting a nucleic acid sequence coding a polypeptide from each of the groups (a), (b), (c), (d) and (e). Another aspect of this embodiment of the invention provide the further step of using the nucleic acid detected to isolate an enediyne gene cluster from the sample containing genomic DNA. Another aspect of this embodiment of the invention comprises identifying an organism containing the nucleic acid sequence detected from the genomic DNA in the sample.

It is understood that the invention, having provided, compositions and methods to identify enediyne biosynthetic gene cluster, further provides enediynes produced by the biosynthetic gene clusters identified.

BRIEF DESCRIPTION OF THE DRAWINGS

FIGS. 2A, 2B, 2C and 2D are flow diagrams of a sequence comparison software that can be employed for the purpose of comparing a query to a subject, wherein the subject is selected from the reference sequences of the invention, wherein FIG. 2A is the query initialization subprocess of the sequence comparison software, FIG. 2B is the subject datasource initialization subprocess of the sequence comparison software, FIG. 2C illustrates the comparison subprocess and the analysis subprocess of the sequence comparison software, and FIG. 2D is the Display/Report subprocess of the sequence comparison software.

FIG. 6 illustrates the 5 genes conserved throughout ten enediyne biosynthetic loci from diverse genera, including both chromoprotein and non-chromoprotein enediyne loci.

FIG. 8 is an amino acid clustal alignment of enediyne polyketide synthase (PKSE) sequences from ten enediyne biosynthetic loci, wherein the sequences aligned are SEQ ID NO: 1 (residues 1–1936) representing the PKSE from *Streptomyces macromycetius* (MACR); SEQ ID NO: 13 (residues 1–1919) representing the PKSE from *Micromonospora echinospora* subsp. *calichensis* (CALI), SEQ ID NO: 23 (residues 1–1956) representing the PKSE from *Streptomyces ghanaensis* (009C), SEQ ID NO: 33 (residues 1–1977) representing the PKSE from *Streptomyces carzinostaticus* subsp. *neocarzinostatius* (NEOC), SEQ ID NO: 43 (residues 1–1939) representing the PKSE from *Amycolatopsis orientalis* ATOC 43491 (007A), SEQ ID NO: 53 (residues 1–1958) representing the PKSE from *Kitasatosporia* sp. (028D), SEQ ID NO: 63 (residues 1–1927) representing the PKSE from *Micromonospora megalomicea* (054A), SEQ ID NO: 73 (residues 1–1892) representing the PKSE from *Saccharothrix aerocolonigenes* (132H), SEQ ID NO: 83 (residues 1–1933) representing the PKSE from *Streptomyces kaniharaenais* (135E) and SEQ ID NO: 93 (residues 1–1958) representing the PKSE from *Streptomyces citricolor* (145B). Approximate domain boundaries are indicated above the alignment. Conserved residues or motifs important for the function of each domain are highlighted in black.

FIG. 9a is an amino acid clustal alignment of acyl carrier protein (ACP) domains in enediyne polyketide synthase (PKSE) proteins, namely SEQ ID NO: 1 (residues 939–1009) of the PKSE of macromomycin from *Streptomyces macromyceticus* (MACR), SEQ ID NO: 33 (residues 975–1046) of the PKSE of neocazinostatin from *Streptomyces carzinostaticus* subsp. *neocarzinostaticus* (NEOC), SEQ ID NO: 13 (residues 939–1009) of calicheamicin from *Micromonospora echinospora* subsp. *calichensis* (CALI), and the publicly available ACP domain of the actinorhodin Type II PKS system (1AF8). FIG. 9b depicts the space-filling side-chains of the conserved residues on the three dimensional structure of the ACP of the actinorhodin Type II PKS system (1AF8).

FIG. 10 is an amino acid clustal alignment sequences of 4'-phosphopantetheinyl transferase (PPTE) domains in enediyne polyketide synthase (PKSE) proteins, namely SEQ ID NO: 33 (residues 1620–1977) of neocazinostatin from *Streptomyces carzinostaticus* subsp. *neocarzinostaticus* (NEOC), SEQ ID NO: 1 (residues 1582–1936) of macromomycin from *Streptoniyces macromyceticus* (MACR), SEQ ID NO: 13 (residues 1582–1919) of calicheamicin from *Micromonospora echinospora* subsp. *calichensis* (CALI) and the publicly available 4'-phosphopantetheinyl transferase of *Bacillus subtilis* (Sfp). Conserved residues are boxed. The known secondary structure of Sfp is shown below the aligned sequences and the predicted secondary structure of the PPTE domain of the PKSE is shown above the aligned sequences wherein the boxes indicate α-helices and the arrows indicate β-sheets.

FIG. 11 is an amino acid clustal alignment of the publicly available 4-hydroxybenzoyl-CoA thioesterase (1BVQ) of *Pseudomonas* sp. strain CBS-3 (superimposed with secondary structure of 1BVQ), and eleven enediyne thioesterase (TEBC) proteins, namely SEQ ID NO: 3 (residues 1–162) and SEQ ID NO: 5 (residues 1–157) both of macromomycin from *Streptomyces macromyceticus* (MACR), SEQ ID NO: 15 (residues 1–148) of calicheamicin from *Micromonospora echinospora* subsp. *calichensis* (CALI), SEQ ID NO: 25 (residues 1–152) from *Streptomyces ghanaensis* (009C), SEQ ID NO: 35 (residues 1–153) of neocazinostatin from *Streptomyces carzinostaticus* subsp. *neocarzinostaticus* (NEOC), SEQ ID NO: 45 (residues 1–146) from *Amycolatopsis orientalis* (007A), SEQ ID NO: 55 (residues 1–158) from *Kitasatosporia* sp. (028D), SEQ ID NO: 65 (residues 1–154) from *Micromonospora megalomicea* (054A), SEQ ID NO: 75 (residues 1–143) from *Saccharothrix aerocolonigenes* (132H), SEQ ID NO: 85 (residues 1–154) from *Streptomyces kaniharaensis* (135E) and SEQ ID NO: 95 (residues 1–165) from *Streptomyces citricolor* (145B) Alpha-helices (α) and beta-sheets (β) are depicted by arrows.

FIG. 12 is an amino acid clustal alignment of ten enediyne UNBL proteins, namely SEQ ID NO: 7 (residues 1–327) of macromomycin from *Streptomyces macromyceticus* (MACR), SEQ ID NO: 17 (residues 1–322) of calicheamicin from *Micromonospora echinospora* subsp. *calichensis* (CALI), SEQ ID NO: 27 (residues 1–329) from *Streptomyces ghanaensis* (009C), SEQ ID NO: 37 (residues 1–328) of neocazinostatin from *Streptomyces carzinostaticus* subsp. *neocarzinostaticus* (NEOC), SEQ ID NO: 47 (residues 1–324) from *Amycolatopsis orientalis* ATCC 43491 (007A), SEQ ID NO: 57 (residues 1–327) of *Kitasatosporia* sp. (028D), SEQ ID NO: 67 (residues 1–322) from *Micromonospora megalomicea* (054A), SEQ ID NO: 77 (residues 1–313) from *Saccharothrix aerocolonigenes* (132H), SEQ ID NO: 87 (residues 1–323) from *Streptomyces kaniharaensis* (135E) and SEQ ID NO: 97 (residues 1–324) from *Streptomyces citricolor* (145B). Areas of high conservation are shown in the bottom line of the alignment.

FIG. 13 is an amino acid clustal alignment of ten enediyne UNBV proteins, namely SEQ ID NO: 9 (residues 1–642) of macromomycin from *Streptomyces macromyceticus* (MACR), SEQ ID NO: 19 (residues 1–651) of calicheamicin from *Micromonospora echinospora* subsp. *calichensis* (CALI), SEQ ID NO: 29 (residues 1–636) from *Streptomyces ghanaensis* (009C), SEQ ID NO: 39 (residues 1–636) of neocazinostatin from *Streptomyces carzinostaticus* subsp. *neocarzinostaticus* (NEOC), SEQ ID NO: 49 (residues 1–654) from *Amycolatopsis orientalis* ATCC 43491 (007A), SEQ ID NO: 59 (residues 1–676) of *Kitasatosporia* sp. (028D), SEQ ID NO: 69 (residues 1–659) from *Micromonospora megalomicea* (054A), SEQ ID NO: 79 (residues 1–647) from *Saccharothrix aerocolonigenes* (132H), SEQ ID NO: 89 (residues 1–655) from *Streptomyces kaniharaensis* (135E) and SEQ ID NO: 99 (1–659) from *Streptomyces citricolor* (145B). The putative N-terminal signal sequence that targets these proteins for secretion is highlighted.

FIG. 14 is an amino acid clustal alignment of enediyne UNBU proteins from ten enedyine biosynthetic loci, namely SEQ ID NO: 11 (residues 1–433) of macromomycin from *Streptomyces macromyceticus* (MACR), SEQ ID NO: 21 (residues 1–321) of calicheamicin from *Micromonospora echinospora* subsp. *calichensis* (CALI), SEQ ID NO: 31

(residues 1–382) from *Streptomyces ghanaensis* (009C), SEQ ID NO: 41 (residues 1–364) of neocazinostatin from *Streptomyces carzinostaticus* subsp. *neocarzinostaticus* (NEOC), SEQ ID NO: 51 (residues 1–329) from *Amycolatopsis orientalis* ATCC 43491 (007A), SEQ ID NO: 61 (residues 1–338) of *Kitasatosporia* sp. (028D), SEQ ID NO: 71 (residues 1–354) from *Micromonospora megalomicea* (054A), SEQ ID NO: 81 (residues 1–336) from *Saccharothrix aerocolonigenes* (132H), SEQ ID NO: 91 (residues 1–346) from *Streptomyces kaniharaensis* (135E) and SEQ ID NO: 101 (residues 1–337) from *Streptomyces citricolor* (145B). The putative transmembrane domains that anchor this family of proteins within the cell membrane are highlighted.

Figure 15:
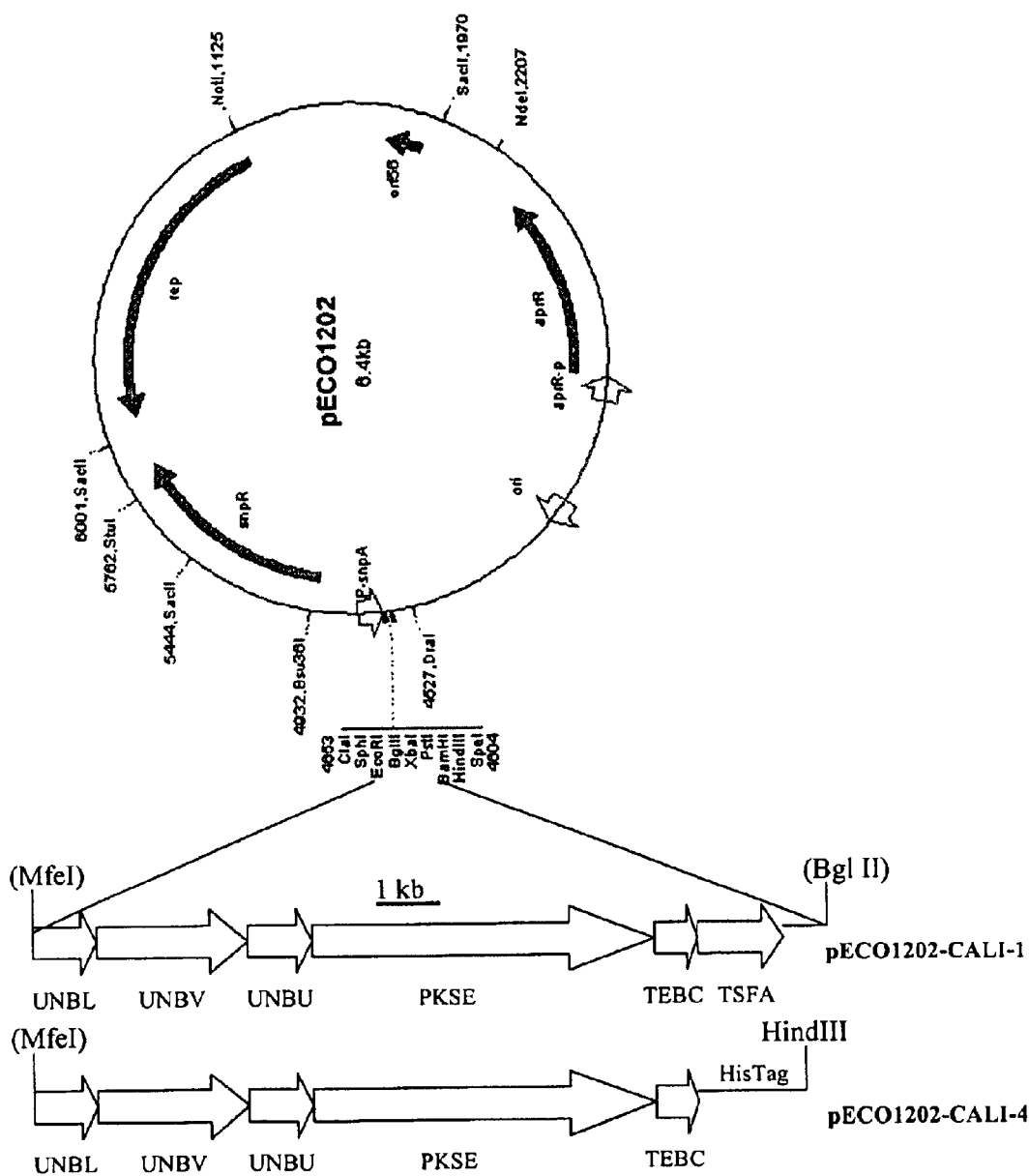

FIG. 15 shows restriction site and functional maps of plasmids pECO1202-CALI-1 and pECO1202-CALI-4 of the invention. The open reading frames of the genes forming an expression cassette according to the invention are shown as arrows pointing in the direction of transcription.

Figure 16:
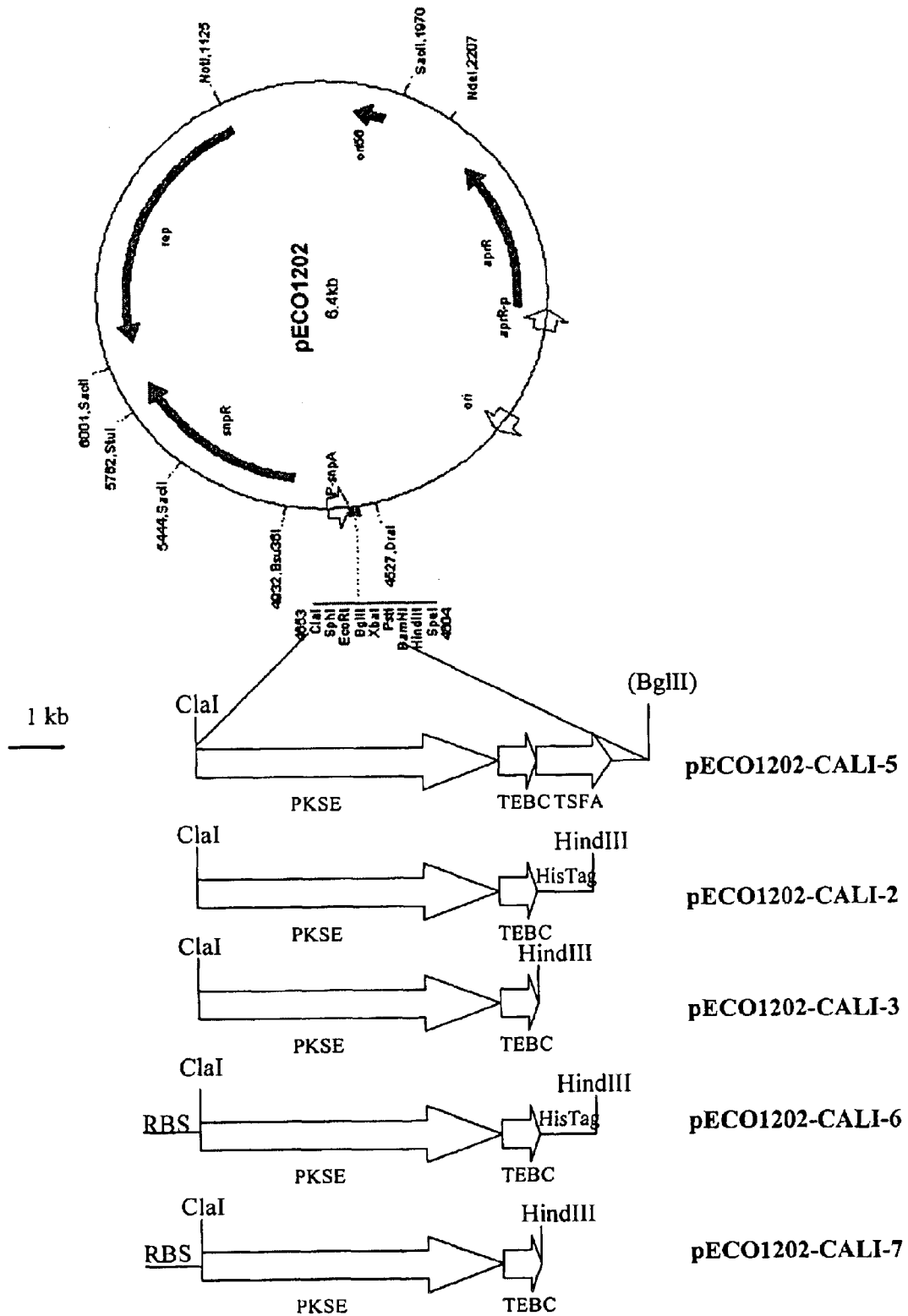

FIG. 16 shows restriction site and functional maps of plasmids pECO1202-CALI-5, pECO1202-CALI-2, pECO1202-CALI-3, pECO1202-CALI-6 and pECO1202-CALI-7. The open reading frames of the genes forming the expression cassette according to the invention are shown as arrows pointing in the direction of transcription.

Figure 17:
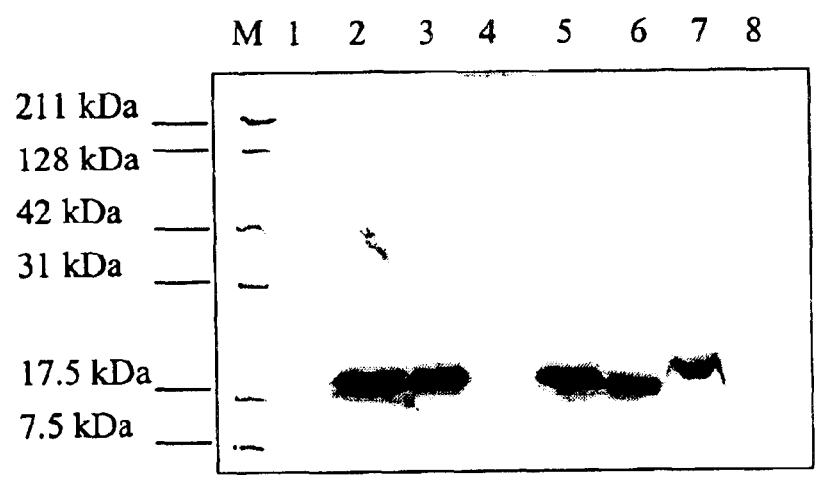

FIG. 17 is an immunoblot analysis of His-tagged TEBC protein in total protein extracts from recombinant *S. lividans* TK24 clones harboring the pECO1202-CALI-2 or the pECO1202-CALI-4 expression vector.

Figure 18:
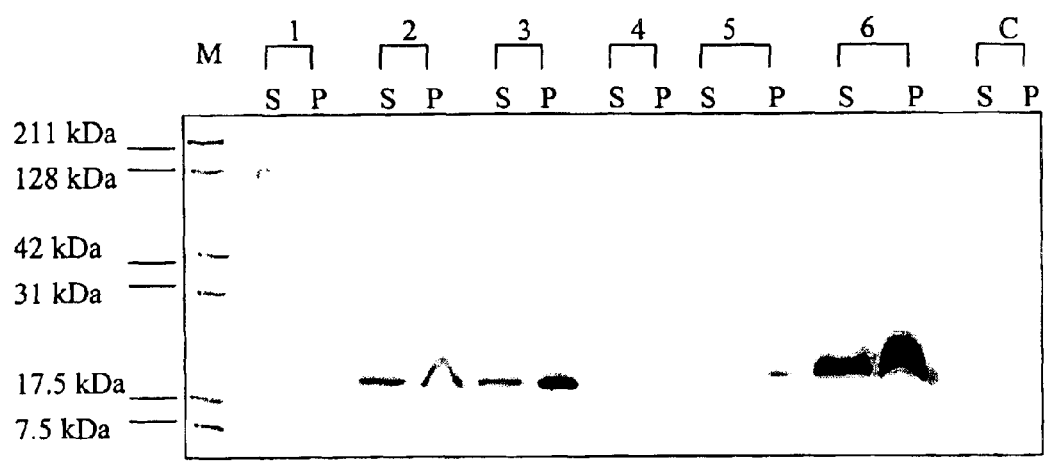

FIG. 18 is an immunoblot analysis of His-tagged TEBC protein in fractionated extracts from recombinant *S. lividans* TK24 clones harboring the pECO1202-CALI-2 expression vector.

DETAILED DESCRIPTION OF THE INVENTION

The invention provides enediyne related compositions. The compositions can be used to produce enediyne-related compounds. The compositions can also be used to identify enediyne natural products, enediyne genes, enediyne gene clusters and enediyne producing organisms. The invention rests on the surprising discovery that all enediynes, including chromoprotein enediynes and non-chromoprotein enediynes, use a conserved set of genes for formation of the warhead structure.

To provide the compositions and methods of the invention, a sample of the microorganism *Streptomyces macromyceticus* was obtained and the biosynthetic locus for the chromoprotein enediyne macromomycin was identified. The gene cluster was identified as the biosynthetic locus for macromomycin from *Streptomyces macromyceticus* NRRL B-5335 (sometimes referred to herein as MACR), firstly by confirming the sequence encoding the apoprotein associated with the chromoprotein, which sequence is disclosed in Samy T S et al., *J. Biol. Chem* (1983) January 10; 258(1) pp. 183–91, and secondly using the genome scanning procedure disclosed in co-pending application U.S. Ser. No. 09/910,813.

A sample of the microorganism *Micromonospora echinospora* subsp. *calichensis* was then obtained and the full biosynthetic locus for the non-chromoprotein enediyne calicheamicin was identified. The gene cluster was identified as the biosynthetic locus for calicheamicin from *Micromonospora echinospora* subsp. *calichensis* NRRL 15839 (sometimes referred to herein as CALI) by comparing the sequence with the partial locus for CALI which was disclosed in WO 00/40596. We were able to overcome the problems encountered in prior attempts to isolate and clone the entire biosynthetic locus by using a shotgun-based approach as described in co-pending application U.S. Ser. No. 09/910,813.

We identified two further enediyne natural products biosynthetic loci from organisms not previously reported to produce enediyne compounds, namely a chromoprotein enediyne from *Streptomyces ghanaensis* NRRL B-12104 (sometimes referred to herein as 009C), and a chromoprotein enediyne from *Amycolatopsis orientalis* ATCC 43491 (sometimes referred to herin as 007A). The presence of an apoprotein encoding gene in 009C and 007A confirms that 009C and 007A produce chromoprotein enediyne compounds.

Comparison of the MACR, CALI, 009C and 007A loci revealed that all loci contain at least one a member of five (5) protein families. The five protein families are referred to throughout the description and figures by reference to a four-letter designation as indicated Table 1.

TABLE 1

Family descriptions

| Families | Function |
|---|---|
| PKSE | unusual polyketide synthase, found only in enediyne biosynthetic loci and involved in warhead formation; believed to act iteratively. |
| TEBC | thioesterase unique to enediyne biosynthetic loci, significant similarity to small (130–150 aa) proteins of the 4-hydroxybenzoyl-CoA thioesterase family in a number of bacteria. |
| UNBL | unique to enediyne biosynthetic loci, these proteins are rich in basic amino acids and contain several conserved or invariant histidine residues. |
| UNBV | unique to enediyne biosynthetic loci, secreted proteins, contain putative cleavable N-terminal signal sequence, believed to be associated with stabilization and/or export of the enediyne chromophore and/or late modifications in the biosynthesis of enediyne chromophores. |
| UNBU | unique to enediyne biosynthetic loci, C-terminal domain homology to bacterial putative ABC transporters and permease transport systems, integral membrane proteins with seven or eight putative membrane-spanning alpha helices, believed to be involved in transport of enediynes and/or intermediates across the cell membrane. |

A member of each of the five protein families was found in each of the more than ten biosynthetic loci for chromoprotein and non-chromoprotein enediynes studied. Two of the five protein families, PKSE and TEBC, form a polyketide synthase catalytic complex involved in formation of the warhead structure that distinguishes enediyne compounds.

The other three protein families conserved throughout chromoprotein and non-chromoprotein enediyne biosynthetic loci are also associated with the warhead structure that characterizes enediyne compounds. Nucleic acid sequences and polypeptide sequences related to these five protein families form the basis for the compositions and methods of the invention.

We have discovered at least one member of each of the protein families PKSE, TEBC, UNBL, UNBV and UNBU in all of the 10 enediyne biosynthetic loci studied, including MACR, CALI, 009C, 007A, an enediyne biosynthetic locus from *Kitasatosporia* sp. (sometimes referred to herein as 028D), an enediyne biosynthetic locus from *Micromonospora megalomicea* (sometimes referred to herein as 054A), an enediyne biosynthetic locus from *Saccharothrix aerocolonigenes* (sometimes referred to herein as 132H), an enediyne biosynthetic locus from *Streptomyces kaniharaensis* (sometimes referred to herein as 135E), an enediyne biosynthetic locus from *Streptomyces citricolor* (sometimes referred to herein as 145B), and the biosynthetic locus for the chromoprotein enediyne neocarzinostatin from *Streptomyces carzinostaticus* (sometimes referred to herein as NEOC).

The protein families PKSE, TEBC, UNBL, UNBV and UNBU of the present invention are associated with warhead formation in enediyne compounds and are found in both chromoprotein and non-chromoprotein enediyne biosynthetic loci. Members of the protein families PKSE, TEBC, UNBL, UNBV and UNBU found within an enediyne biosynthetic loci are necessarily present in a single operon and are therefore not necessarily transcriptionally linked to one another. However, the members of the protein families PKSE, TEBC, UNBL, UNBV and UNBU that are found within a single enediyne biosynthetic locus are functionally linked to one another in that they act in a concerted fashion in the production of an enediyne product. Although expression of functionally linked enediyne specific genes encoding members of the PKSE, TEBC, UNBL, UNBV and UNBU protein families may be under control of distinct transcriptional promoters, they may nonetheless be expressed in a concerted fashion.

Due to high overall sequence conservation between members of the PKSE, TEBC, UNBL, UNBV and UNBU protein families, it is expected that members of the PKSE, TEBC, UNBL, UNBV and UNBU protein families may be exchanged for another member of the same protein family while retaining the ability of the new enediyne biosynthetic system to synthesize the warhead structure of an enediyne compound. Thus, it is contemplated that genes encoding a polypeptide from protein families PKSE, TEBC, UNBL, UNBV and UNBU from two or more different enediyne biosynthetic systems may be combined so as to obtain a full complement of the five-gene enediyne cassette of the invention, wherein one or more genes in the enediyne cassette has inherent or engineered optimal properties.

Representative nucleic acid sequences and polypeptide sequences drawn from each of the ten enediyne loci described herein are provided in the accompanying sequence listing as examples of the compositions of the invention. Referring to the sequence listing, a nucleic acid sequence encoding a member of the PKSE protein family of the invention from the biosynthetic locus for macromomycin from *Streptomyces macromyceticus* (MACR) is provided in SEQ ID NO: 2, with the corresponding deduced polypeptide sequence provided in SEQ ID NO: 1. Nucleic acid sequences encoding two members of the TEBC protein family from MACR are provided in SEQ ID NOS: 4 and 6 with the corresponding deduced polypeptide sequences provided in SEQ ID NOS: 3 and 5 respectively. A nucleic acid sequence encoding a member of the UNBL protein family from MACR is provided in SEQ ID NO: 8 with the corresponding deduced polypeptide sequence provided in SEQ ID NO: 7. A nucleic acid sequence encoding a member of the protein family UNBV from MACR is provided in SEQ ID NO: 10 with the corresponding deduced polypeptide provided in SEQ ID NO: 9. A nucleic acid sequence encoding a member of the protein family UNBU from MACR is provided in SEQ ID NO: 12 with the corresponding deduced polypeptide provided in SEQ ID NO: 11.

A nucleic acid sequence encoding a member of the PKSE protein family of the invention from the biosynthetic locus for calicheamicin from *Micromonospora echinospora* subsp *calichensis* (CALI) is provided in SEQ ID NO: 14, with the corresponding deduced polypeptide sequence provided in SEQ ID NO: 13 A nucleic acid sequence encoding a member of the TEBC protein family from CALI is provided in SEQ ID NO: 16, with the corresponding deduced polypeptide sequence provided in SEQ ID NO: 15. A nucleic acid sequence encoding a member of the UNBL protein family from CALI is provided in SEQ ID NO: 18, with the corresponding deduced polypeptide sequence provided in SEQ ID NO: 17. A nucleic acid sequence encoding a member of the UNBV protein family from CALI is provided in SEQ ID NO: 20, with the corresponding deduced polypeptide sequence provided in SEQ ID NO: 19. A nucleic acid sequence encoding a member of the UNBU protein family from CALI is provided in SEQ ID NO: 22, with the corresponding deduced polypeptide sequence provided in SEQ ID NO: 21.

A nucleic acid sequence encoding a member of the PKSE protein family of the invention from the enediyne biosynthetic locus from *Streptomyces ghanaensis* (009C) is provided in SEQ ID NO: 24, with the corresponding deduced polypeptide sequence provided in SEQ ID NO: 23. A nucleic acid sequence encoding a member of the TEBC protein family from 009C is provided in SEQ ID NO: 26, with the corresponding deduced polypeptide sequence provided in SEQ ID NO: 25. A nucleic acid sequence encoding a member of the UNBL protein family from 009C is provided in SEQ ID NO: 28, with the corresponding deduced polypeptide sequence provided in SEQ ID NO: 27. A nucleic acid sequence encoding a member of the UNBV protein family from 009C is provided in SEQ ID NO: 30, with the corresponding deduced polypeptide sequence provided in SEQ ID NO: 29. A nucleic acid sequence encoding a member of the UNBU protein family from 009C is provided in SEQ ID NO: 32, with the corresponding deduced polypeptide sequence provided in SEQ: ID NO: 31.

A nucleic acid sequence encoding a member of the PKSE protein family of the invention from the biosynthetic locus for neocazinostatin from *Streptomyces carzinostaticus* subsp. *neocarzinostaticus* (NEOC) is provided in SEQ ID NO: 34, with the corresponding deduced polypeptide sequence provided in SEQ ID NO: 33. A nucleic acid sequence encoding a member of the TEBC protein family from NEOC is provided in SEQ ID NO: 36, with the corresponding deduced polypeptide sequence provided in SEQ ID NO: 35. A nucleic acid sequence encoding a member of the UNBL protein family from NEOC is provided in SEQ ID NO: 38, with the corresponding deduced polypeptide sequence provided in SEQ ID NO: 37. A nucleic acid sequence encoding a member of the UNBV protein family from NEOC is provided in SEQ ID NO: 40, with the corresponding deduced polypeptide sequence provided in SEQ ID NO: 39. A nucleic acid sequence encoding a member of the UNBU protein family from NEOC is provided in SEQ ID NO: 42, with the corresponding deduced polypeptide sequence provided in SEQ ID NO: 41.

A nucleic acid sequence encoding a member of the PKSE protein family of the invention from the enediyne biosynthetic locus from *Amycolatopsis orientalis* (007A) is provided in SEQ ID NO: 44, with the corresponding deduced polypeptide sequence provided in SEQ ID NO: 43. A nucleic acid sequence encoding a member of the TEBC protein family from 007A is provided in SEQ ID NO: 46, with the corresponding deduced polypeptide sequence provided in SEQ ID NO: 45. A nucleic acid sequence encoding a member of the UNBL protein family from 007A is provided in SEQ ID NO: 48, with the corresponding deduced polypeptide sequence provided in SEQ ID NO: 47 A nucleic acid sequence encoding a member of the UNBV protein family from 007A is provided in SEQ ID NO: 50, with the corresponding deduced polypeptide sequence provided in SEQ ID NO: 49. A nucleic acid sequence encoding a member of the UNBU protein family from 007A is provided in SEQ ID NO: 52, with the corresponding deduced polypeptide sequence provided in SEQ ID NO: 51.

A nucleic acid sequence encoding a member of the PKSE protein family of the invention from the enediyne biosynthetic locus from *Kitasatosporia* sp. (028D) is provided in SEQ ID NO: 54, with the corresponding deduced polypeptide sequence provided in SEQ ID NO: 53. A nucleic acid sequence encoding a member of the TEBC protein family from 028D is provided in SEQ ID NO: 56, with the corresponding deduced polypeptide sequence provided in SEQ ID NO: 55. A nucleic acid sequence encoding a member of the UNBL protein family from 028D is provided in SEQ ID NO: 58, with the corresponding deduced polypeptide sequence provided in SEQ ID NO: 57. A nucleic acid sequence encoding a member of the UNBV protein family from 028D is provided in SEQ ID NO: 60, with the corresponding deduced polypeptide sequence provided in SEQ ID NO: 59. A nucleic acid sequence encoding a member of the UNBU protein family from 028D is provided in SEQ ID NO: 62, with the corresponding deduced polypeptide sequence provided in SEQ ID NO: 61.

A nucleic acid sequence encoding a member of the PKSE protein family of the invention from the enediyne biosynthetic locus from *Micromonospora megalomicea* (054A) is provided in SEQ ID NO: 64, with the corresponding deduced polypeptide sequence provided in SEQ ID NO: 63. A nucleic acid sequence encoding a member of the TEBC protein family from 054A is provided in SEQ ID NO: 66, with the corresponding deduced polypeptide sequence provided in SEQ ID NO: 65. A nucleic acid sequence encoding a member of the UNBL protein family from 054A is provided in SEQ ID NO: 68, with the corresponding deduced polypeptide sequence provided in SEQ ID NO: 67. A nucleic acid sequence encoding a member of the UNBV protein family from 054A is provided in SEQ ID NO: 70, with the corresponding deduced polypeptide sequence provided in SEQ ID NO: 69. A nucleic acid sequence encoding a member of the UNBU protein family from 054A is provided in SEQ ID NO: 72, with the corresponding deduced polypeptide sequence provided in SEQ ID NO: 71.

A nucleic acid sequence encoding a member of the PKSE protein family of the invention from the enediyne biosynthetic locus from *Saccharothrix aerocolonigenes* (132H) is provided in SEQ ID NO: 74, with the corresponding deduced polypeptide sequence provided in SEQ ID NO: 73. A nucleic acid sequence encoding a member of the TEBC protein family from 132H is provided in SEQ ID NO: 76, with the corresponding deduced polypeptide sequence provided in SEQ ID NO: 75. A nucleic acid sequence encoding a member of the UNBL protein family from 132H is provided in SEQ ID NO: 78, with the corresponding deduced polypeptide sequence provided in SEQ ID NO: 77. A nucleic acid sequence encoding a member of the UNBV protein family from 132H is provided in SEQ ID NO: 80, with the corresponding deduced polypeptide sequence provided in SEQ ID NO: 79. A nucleic acid sequence encoding a member of the UNBU protein family from 132H is provided in SEQ ID NO: 82, with the corresponding deduced polypeptide sequence provided in SEQ ID NO: 81.

A nucleic acid sequence encoding a member of the PKSE protein family of the invention from the enediyne biosynthetic locus from *Streptomyces kaniharaensis* (135E) is provided in SEQ ID NO: 84, with the corresponding deduced polypeptide sequence provided in SEQ ID NO: 83. A nucleic acid sequence encoding a member of the TEBC protein family from 135E is provided in SEQ ID NO: 86, with the corresponding deduced polypeptide sequence provided in SEQ ID NO: 85. A nucleic acid sequence encoding a member of the UNBL protein family from 135E is provided in SEQ ID NO: 88, with the corresponding deduced polypeptide sequence provided in SEQ ID NO: 87. A nucleic acid sequence encoding a member of the UNBV protein family from 135E is provided in SEQ ID NO: 90, with the corresponding deduced polypeptide sequence provided in SEQ ID NO: 89. A nucleic acid sequence encoding a member of the UNBU protein family from 135E is provided in SEQ ID NO: 92, with the corresponding deduced polypeptide sequence provided in SEQ ID NO: 91.

A nucleic acid sequence encoding a member of the PKSE protein family of the invention from the enediyne biosynthetic locus from *Streptomyces citricolor* (145B) is provided in SEQ ID NO: 94, with the corresponding deduced polypeptide sequence provided in SEQ ID NO: 93. A nucleic acid sequence encoding a member of the TEBC protein family from 145B is provided in SEQ ID NO: 96, with the corresponding deduced polypeptide sequence provided in SEQ ID NO: 95. A nucleic acid sequence encoding a member of the UNBL protein family from 145B is provided in SEQ ID NO: 98, with the corresponding deduced polypeptide sequence provided in SEQ ID NO: 97. A nucleic acid sequence encoding a member of the UNBV protein family from 145B is provided in SEQ ID NO: 100, with the corresponding deduced polypeptide sequence provided in SEQ ID NO: 99. A nucleic acid sequence encoding a member of the UNBU protein family from 145B is provided in SEQ ID NO: 102, with the corresponding deduced polypeptide sequence provided in SEQ ID NO: 101.

As used herein, PKSE refers to a family of polyketide synthase proteins that are uniquely associated with enediyne biosynthetic loci and that are involved in synthesis of the warhead structure that characterizes enediyne compounds. Representative members of the protein family PKSE include the polypeptides of SEQ ID NOS: 1, 13, 23, 33, 43, 53, 63, 73, 83, and 93. Other members of protein family PKSE include polypeptides having at least 75%, preferably 80%, more preferably, 85% still more preferably 90% and most preferably 95% or more homology to a polypeptide having the sequence of SEQ ID NOS: 1, 13, 23, 33, 43, 53, 63, 73, 83, 93 as determined using the BLASTP algorithm with the default parameters and having the ability to substitute for another PKSE protein and retaining the ability to act in a concerted fashion with a TEBC protein during synthesis of a warhead structure of an enediyne compound. Other members of the protein family PKSE include fragments, analogs and derivatives of the above polypeptides, which fragments, analogs and derivatives have the ability to substitute for another PKSE protein and retain the ability to act in a concerted fashion with TEBC during synthesis of a warhead structure of an enediyne compound.

TEBC refers to a family of thioesterase proteins unique to enediyne biosynthesis which together with a protein from the protein family PKSE forms an enediyne polyketide catalytic complex and is involved in synthesis of a warhead structure that characterizes enediyne compounds. Representative members of the protein family TEBC include the polypeptides of SEQ ID NOS: 3, 5, 15, 25, 35, 45, 55, 65, 75, 85, and 95. Other members of protein family TEBC include polypeptides having at least 75%, preferably 80%, more preferably, 85% still more preferably 90% and most preferably 95% or more homology to a polypeptide having the sequence of SEQ ID NOS: 3, 5, 15, 25, 35, 45, 55, 65, 75, 85, and 95 as determined using the BLASTP algorithm with the default parameters and retaining the ability to act in a concerted fashion with a protein from the protein family PKSE during synthesis of a warhead structure in an enediyne compound. Other members of the protein family TEBC include fragments, analogs and derivatives of the above polypeptides, which fragments, analogs and derivatives have the ability to substitute for another TEBC protein and retain the ability to act in a concerted fashion with a PKSE protein during formation of a warhead structure in an enediyne compound.

UNBL refers to a family of proteins indicative of enediyne biosynthetic loci and which are rich in basic amino acids and contain several conserved or invariant histidine residues Representative members of the protein family UNBL include the polypeptides of SEQ ID NOS: 7, 17, 27, 37, 47, 57, 67, 77, 87 and 97. Other members of protein family UNBL include polypeptides having at least 75%, preferably 80%, more preferably, 85% still more preferably 90% and most preferably 95% or more homology to a polypeptide having the sequence of SEQ ID NOS: 7, 17, 27, 37, 47, 57, 67, 77, 87 and 97 as determined using the BLASTP algorithm with the default parameters and that are present in a gene cluster associated with the biosynthesis of an enediyne compound. Other members of the protein family UNBL include fragments, analogs and derivatives of the above polypeptides, which fragments, analogs and derivatives have the ability to substitute for another UNBL protein and retain the ability to act in a concerted fashion with genes in an enediyne biosynthetic locus to form a warhead structure of an enediyne compound.

UNBV refers to a family of proteins indicative of enediyne biosynthetic loci and which may contain a cleavable N-terminal signal sequence Representative members of the protein family UNBV include the polypeptides of SEQ ID NOS: 9, 19, 29, 39, 49, 59, 69, 79, 89 and 99. Other members of protein family UNBV include polypeptides having at least 75%, preferably 80%, more preferably, 85% still more preferably 90% and most preferably 95% or more homology to a polypeptide having the sequence of SEQ ID NOS: 9, 19, 29, 39, 49, 59, 69, 79, 89 and 99 as determined using the BLASTP algorithm with the default parameters and that are present in a gene cluster associated with the biosynthesis of an enediyne compound. Other members of the protein family UNBV include fragments, analogs and derivatives of the above polypeptides, which fragments, analogs and derivatives have the ability to substitute for another UNBV protein and retain the ability to act in a concerted fashion with genes in an enediyne biosynthetic locus to form a warhead structure in an enediyne compound.

UNBU refers to a family of membrane proteins indicative of enediyne biosynthetic loci. Representative members of the protein family UNBU include the polypeptides of SEQ ID NOS: 11, 21, 31, 41, 51, 61, 71, 81, 91 and 101. Other members of protein family UNBU include polypeptides having at least 75%, preferably 80%, more preferably, 85% still more preferably 90% and most preferably 95% or more homology to a polypeptide having the sequence of SEQ ID NOS: 11, 21, 31, 41, 51, 61, 71, 81, 91 and 101 as determined using the BLASTP algorithm with the default parameters and that are present in a gene cluster associated with the biosynthesis of an enediyne compound. Other members of the protein family UNBU include fragments, analogs and derivatives of the above polypeptides, which fragments, analogs and derivatives have the ability to substitute for another UNBU protein and retain the ability to act in a concerted fashion with genes in an enediyne biosynthetic locus to form the warhead structure in an enediyne compound.

"Enediyne producer" or "enediyne-producing organism" refers to a microorganism which carries the genetic information necessary to produce an enediyne compound, whether or not the organism is known to produce an enediyne product. The terms apply equally to organisms in which the genetic information to produce an enediyne compound is found in the organism as it exists in its natural environment, and to organisms in which the genetic information is introduced by recombinant techniques. For the sake of particularity, specific organisms contemplated herein include organisms of the family Micromonosporaceae, of which preferred genera include *Micromonospora, Actinoplanes* and *Dactylosporangium*; the family Streptomycetaceae, of which preferred genera include *Streptomyces* and *Kitasatospora*; the family Pseudonocardiaceae, of which preferred genera are *Amycolatopsis* and *Saccharopolyspora*; and the family Actinosynnemataceae, of which preferred genera include *Saccharothrix* and *Actinosynnema*; however the terms are intended to encompass all organisms containing genetic information necessary to produce an enediyne compound.

"Enediyne biosynthetic gene product" refers to any enzyme involved in the biosynthesis of an enediyne, whether a chromoprotein enediyne or a non-chromoprotein enediyne. These gene products are located in any enediyne biosynthetic locus in an organism of the family Micromonosporaceae, of which preferred genera include *Micromonospora, Actinoplanes* and *Dactylosporangium*; the family Streptomycetaceae, of which preferred genera include *Streptomyces* and *Kitasatospora*; the family Pseudonocardiaceae, of which preferred genera are *Amycolatopsis* and *Saccharopolyspora*. For the sake of particularity, the enediyne biosynthetic loci described herein are associated with *Streptomyces macromyceticus, Micromonospora echinospora* subsp. *calichensis, Streptomyces ghanaensis, Streptomyces carzinostaticus* subsp. *neocarzinostaticus, Amycolatopsis orientalis, Kitasatosporia* sp., *Micromonospora megalomicea, Saccharothrix aerocolonigenes, Streptomyces kaniharaensis,* and *Streptomyces citricolor*; however, it should be understood that this term encompasses enediyne biosynthetic enzymes (and genes encoding such enzymes) isolated from any microorganism of the genus *Streptomyces, Micromonospora, Amycolatopsis, Kitesatosporia,* or *Saccharithrix* and furthermore that these genes may have novel homologues in any microorganism, actinomycete or non-actinomycete, that falls within the scope of the claims stated herein Specific embodiments include the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101.

The term "isolated" means that the material is removed from its original environment, e.g. the natural environment if it is naturally occurring. For example, a naturally-occurring polynucleotide or polypeptide present in a living organism is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The term "purified" does not require absolute purity; rather, it is intended as a relative definition. Individual nucleic acids obtained from a library have been conventionally purified to electrophoretic homogeneity. The purified nucleic acids of the present invention have been purified from the remainder of the genomic DNA in the organism by at least $10^4$ to $10^6$ fold. However, the term "purified" also includes nucleic acids which have been purified from the remainder of the genomic DNA or from other sequences in a library or other environment by at least one order of magnitude, preferably two or three orders of magnitude, and more preferably four or five orders of magnitude.

"Recombinant" means that the nucleic acid is adjacent to "backbone" nucleic acid to which it is not adjacent in its natural environment. "Enriched" nucleic acids represent 5% or more of the number of nucleic acid inserts in a population of nucleic acid backbone molecules. "Backbone" molecules include nucleic acids such as expression vectors, self-replicating nucleic acids, viruses, integrating nucleic acids, and other vectors or nucleic acids used to maintain or manipulate a nucleic acid of interest. Preferably, the enriched nucleic acids represent 15% or more, more preferably 50% or more, and most preferably 90% or more, of the number of nucleic acid inserts in the population of recombinant backbone molecules.

"Recombinant polypeptides" or "recombinant proteins" refers to polypeptides or proteins produced by recombinant DNA techniques, i.e. produced from cells transformed by an exogenous DNA construct encoding the desired polypeptide or protein "Synthetic" polypeptides or proteins are those prepared by chemical synthesis.

The term "gene" means the segment of DNA involved in producing a polypeptide chain; it includes regions preceding and following the coding region (leader and trailer) as well as, where applicable, intervening regions (introns) between individual coding segments (exons).

The term "operon" means a transctional gene cassette under the control of a single transcriptional promoter, which gene cassette encodes polypeptides that may act in a concerted fashion to carry out a biochemical pathway and/or cellular process.

A DNA or nucleotide "coding sequence" or "sequence encoding" a particular polypeptide or protein, is a DNA sequence which is transcribed and translated into a polypeptide or protein when placed under the control of appropriate regulatory sequences.

"Oligonucleotide" refers to a nucleic acid, generally of at least 10, preferably 15 and more preferably at least 20 nucleotides, preferably no more than 100 nucleotides, that are hybridizable to a genomic DNA molecule, a cDNA molecule, or an mRNA molecule encoding a gene, mRNA, cDNA or other nucleic acid of interest.

A promoter sequence is "operably linked to" a coding sequence recognized by RNA polymerase which initiates transcription at the promoter and transcribes the coding sequence into mRNA.

"Plasmids" are designated herein by a lower case p followed by capital letters and/or numbers. The starting plasmids herein are commercially available, publicly available on an unrestricted basis, or can be constructed from available plasmids in accord with published procedures. In addition, equivalent plasmids to those described herein are known in the art and will be apparent to the skilled artisan.

"Digestion" of DNA refers to enzymatic cleavage of the DNA with a restriction enzyme that acts only at certain sequences in the DNA. The various restriction enzymes used herein are commercially available and their reaction conditions, cofactors and other requirements were used as would be known to the ordinary skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular enzymes are specified by the manufacturer. Incubation times of about 1 hour at 37° C. are ordinarily used, but may vary in accordance with the suppliers instructions. After digestion, gel electrophoresis may be performed to isolate the desired fragment.

Two deposits have been made with the International Depositary Authority of Canada, Bureau of Microbiology, Health Canada, 1015 Arlington Street, Winnipeg, Manitoba, Canada R3E 3R2 on Apr. 3, 2002. The first deposit is an *E. coli* DH10B strain harbouring a cosmid clone (020CN) of a partial biosynthetic locus for macromomycin from *Streptomyces macromyceticus*, including open reading frames coding for the polypeptides of SEQ ID NOS: 1, 3, 5, 7, 9 and 11, which deposit was assigned deposit accession number IDAC030402-1. The second deposit is an *E. coli* DH10B strain harbouring a cosmid clone (061CR) of a partial biosynthetic locus for calicheamicin from *Micromonospora echinospora* subsp. *calichensis*, including open reading frames coding for the polypeptides of SEQ ID NOS: 13, 15, 17, 19, and 21, which deposit was assigned accession number IDAC 030402-2. The *E. coli* strain deposits are referred to herein as "the deposited strains".

The deposited strains comprise a member from each of the protein families PKSE, TEBC, UNBL, UNBV and UNBU drawn from a chromoprotein enediyne biosynthetic locus (macromomycin) and a member from each of the protein families PKSE, TEBC, UNBL, UNBV and UNBU drawn from a non-chromoprotein enediyne biosynthetic locus (calicheamicin). The sequence of the polynucleotides comprised in the deposited strains, as well as the amino acid sequence of any polypeptide encoded thereby are controlling in the event of any conflict with any description of sequences herein.

The deposit of the deposited strains has been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S C. §112. A license may be required to make, use or sell the deposited strains or nucleic acids therein, and compounds derived therefrom, and no such license is hereby granted.

Representative nucleic acid sequences encoding members of the five protein families are provided in the accompanying sequence listing as SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102. Representative polypeptides representing members of the five protein families are provided in the accompanying sequence listing as SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101.

One aspect of the present invention is an isolated, purified, or enriched nucleic acid comprising one of the sequences of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, the sequences complementary thereto, or a fragment comprising at least 10, 15, 20, 25, 30, 35, 40, 50, 75, 100, 150, 200, 300, 400 or 500 consecutive bases of one of the sequences of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 or the sequences complementary thereto. The isolated, purified or enriched nucleic acids may comprise DNA, including cDNA, genomic DNA, and synthetic DNA. The DNA may be double stranded or single stranded, and if single stranded may be the coding or non-coding (antisense) strand. Alternatively, the isolated, purified or enriched nucleic acids may comprise RNA.

As discussed in more detail below, the isolated, purified or enriched nucleic acids of one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 may be used to prepare one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or fragments comprising at least 5, 10, 15, 20, 25, 30, 35, 40, 50, 75, 100 or 100 consecutive amino acids of one of the polypeptides of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101.

Accordingly, another aspect of the present invention is an isolated, purified or enriched nucleic acid which encodes one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100 or 150 consecutive amino acids of one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101. The coding sequences of these nucleic acids may be identical to one of the coding sequences of one of the nucleic acids of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, or a fragment thereof or may be different coding sequences which encode one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100 or 150 consecutive amino acids of one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 as a result of the redundancy or degeneracy of the genetic code. The genetic code is well known to those of skill in the art and can be obtained, for example, from Stryer, *Biochemistry*, 3$^{rd}$ edition, W. H. Freeman & Co., New York.

The isolated, purified or enriched nucleic acid which encodes one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, may include, but is not limited to: (1) only the coding sequences of one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102; (2) the coding sequences of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 and additional coding sequences, such as leader sequences or proprotein sequences; or (3) the coding sequences of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 and non-coding sequences, such as introns or non-coding sequences 5' and/or 3' of the coding sequence. Thus, as used herein, the term "polynucleotide encoding a polypeptide" encompasses a polynucleotide which includes only coding sequence for the polypeptide as well as a polynucleotide which includes additional coding and/or non-coding sequence.

The invention relates to polynucleotides based on SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 but having polynucleotide changes that are "silent", for example changes which do not alter the amino acid sequence encoded by the polynucleotides of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102. The invention also relates to polynucleotides which have nucleotide changes which result in amino acid substitutions, additions, deletions, fusions and truncations of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101. Such nucleotide changes may be introduced using techniques such as site directed mutagenesis, random chemical mutagenesis, exonuclease III deletion, and other recombinant DNA techniques.

The isolated, purified or enriched nucleic acids of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, the sequences complementary thereto, or a fragment comprising at least 10, 15, 20, 25, 30, 35, 40, 50, 75, 100, 150, 200, 300, 400 or 500 consecutive bases of one of the sequence of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, or the sequences complementary thereto may be used as probes to identify and isolate DNAs encoding the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 respectively.

For example, a genomic DNA library may be constructed from a sample microorganism or a sample containing a microorganism capable of producing an enediyne. The genomic DNA library is then contacted with a probe comprising a coding sequence or a fragment of the coding sequence, encoding one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or a fragment thereof under conditions which permit the probe to specifically hybridize to sequences complementary thereto. In one embodiment, the probe is an oligonucleotide of about 10 to about 30 nucleotides in length designed based on a nucleic acid of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102. Genomic DNA clones which hybridize to the probe are then detected and isolated. Procedures for preparing and identifying DNA clones of interest are disclosed in Ausubel et al., Current Protocols in Molecular Biology, John Wiley 503 Sons, Inc 1997; and Sambrook et al., Molecular Cloning A Laboratory Manual 2d Ed., Cold Spring Harbor Laboratory Press, 1989. In another embodiment, the probe is a restriction fragments or a PCR amplified nucleic acid derived from SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102.

The isolated, purified or enriched nucleic acids of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, the sequences complementary thereto, or a fragment comprising at least 10, 15, 20, 25, 30, 35, 40, 50, 75, 100, 150, 200, 300, 400 or 500 consecutive bases of one of the sequences of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, or the sequences complementary thereto may be used as probes to identify and isolate related nucleic acids. In some embodiments, the related nucleic acids may be genomic DNAs (or cDNAs) from potential enediyne producers. In one embodiment, isolated, purified or enriched nucleic acids of SEQ ID NOS: 2, 14, 24, 34, 44, 54, 64, 74, 84, 94 the sequences complementary thereto, or a fragment comprising at least 10, 15, 20, 25, 30, 35, 40, 50, 75, 100, 150, 200, 300, 400 or 500 consecutive bases of one of the sequences of SEQ ID NOS: 2, 14, 24, 34, 44, 54, 64, 74, 84, 94 or the sequences complementary thereto may be used as probes to identify and isolate related nucleic acids. In such procedures, a nucleic acid sample containing nucleic acids from a potential enediyne-producer is contacted with the probe under conditions which permit the probe to specifically hybridize to related sequences. The nucleic acid sample may be a genomic DNA (or cDNA) library from the potential enediyne-producer. Hybridization of the probe to nucleic acids is then detected using any of the methods known in the art, including those referred to herein.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2×10^7$ cpm (specific activity $4-9×10^8$ cpm/ug) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm–10 C for the oligonucleotide probe where Tm is the melting temperature. The membrane is then exposed to auto-radiographic film for detection of hybridization signals.

By varying the stringency of the hybridization conditions used to identify nucleic acids, such as genomic DNAs or cDNAs, which hybridize to the detectable probe, nucleic acids having different levels of homology to the probe can be identified and isolated. Stringency may be varied by conducting the hybridization at varying temperatures below the melting temperatures of the probes. The melting temperature of the probe may be calculated using the following formulas For oligonucleotide probes between 14 and 70 nucleotides in length the melting temperature (Tm) in degrees Celcius may be calculated using the formula: Tm=81.5+16.6(log [Na+])+0.41(fraction G+C)−(600/N) where N is the length of the oligonucleotide.

If the hybridization is carried out in a solution containing formamide, the melting temperature may be calculated using the equation Tm=81.5+16.6(log [Na+])+0.41(fraction G+C)−(0.63% formamide)−(600/N) where N is the length of the probe.

Prehybridization may be carried out in 6×SSC, 5× Denhardt's reagent, 0.5% SDS, 0.1 mg/ml denatured fragmented salmon sperm DNA or 6×SSC, 5× Denhardt's reagent, 0.5% SDS, 0.1 mg/ml denatured fragmented salmon sperm DNA, 50% formamide. The composition of the SSC and Denhardt's solutions are listed in Sambrook et al., supra.

Hybridization is conducted by adding the detectable probe to the hybridization solutions listed above. Where the probe comprises double stranded DNA, it is denatured by incubating at elevated temperatures and quickly cooling before addition to the hybridization solution. It may also be desirable to similarly denature single stranded probes to eliminate or diminish formation of secondary structures or oligomerization. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the Tm. Preferably, the hybridization is conducted in 6×SSC, for shorter probes. Preferably, the hybridization is conducted in 50% formamide containing solutions, for longer probes.

All the foregoing hybridizations would be considered to be examples of hybridization performed under conditions of high stringency.

Following hybridization, the filter is washed for at least 15 minutes in 2×SSC, 0.1% SDS at room temperature or higher, depending on the desired stringency. The filter is then washed with 0.1×SSC, 0.5% SDS at room temperature (again) for 30 minutes to 1 hour.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1 M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide A specific example of "moderate stringency" hybridization conditions is when the above hybridization is conducted at 30% formamide. A specific example of "low stringency" hybridization conditions is when the above hybridization is conducted at 10% formamide.

Nucleic acids which have hybridized to the probe are identified by autoradiography or other conventional techniques.

For example, the preceding methods may be used to isolate nucleic acids having a sequence with at least 97%, at least 95%, at least 90%, at least 85%, at least 80%, or at least 70% homology to a nucleic acid sequence selected from the group consisting of the sequences of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, fragments comprising at least 10, 15, 20, 25, 30, 35, 40, 50, 75, 100, 150, 200, 300, 400, or 500 consecutive bases thereof, and the sequences complementary thereto. Homology may be measured using BLASTN version 2.0 with the default parameters. For example, the homologous polynucleotides may have a coding sequence which is a naturally occurring allelic variant of one of the coding sequences described herein. Such allelic variant may have a substitution, deletion or addition of one or more nucleotides when compared to the nucleic acids of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, or the sequences complementary thereto.

Additionally, the above procedures may be used to isolate nucleic acids which encode polypeptides having at least 99%, 95%, at least 90%, at least 85%, at least 80%, or at least 70% homology to a polypeptide having the sequence of one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof as determined using the BLASTP version 2.2.2 algorithm with default parameters.

Structural features common to the biosynthesis of all enediyne compounds require one or more proteins selected from a group of 5 specific protein families, namely PKSE, TEBC, UNBL, UNBV and UNBU. Thus, a polypeptide representing a member of any one of these five protein families or a polynucleotide encoding a polypeptide representing a member of any one of these five protein families is considered indicative of an enediyne gene cluster, a enediyne natural product or an enediyne producing organism. It is not necessary that a member of each of the five protein families considered indicative of an enediyne compound be detected to identify an enediyne biosynthetic locus and an enediyne-producing organism. Rather, the presence of at least one, preferably two, more preferably three, still more preferably four, and most preferably five of the protein families PKSE, TEBC, UNBV and UNBU indicates the presence of an enediyne natural product, an enediyne biosynthetic locus or an enediyne producing organism.

To identify an enediyne natural product, an enediyne gene cluster or an enediyne-producing organism, nucleic acids from cultivated microorganisms or from an environmental sample, e.g soil, potentially harboring an organism having the genetic capacity to produce an enediyne compound may be contacted with a probe based on nucleotide sequences coding a member of the five protein families PKSE, TEBC, UNBL, UNBV and UNBU.

In such procedures, nucleic acids are obtained from cultivated microorganisms or from an environmental sample potentially harboring an organism having the genetic capacity to produce an enediyne compound. The nucleic acids are contacted with probes designed based on the teachings and compositions of the invention under conditions which permit the probe to specifically hybridize to any complementary sequences indicative of the presence of a member of the PKSE, TEBC, UNBL, UNBV and UNBU protein families of the invention. The presence of at least one, preferably two, more preferably three, still more preferably 4 or 5 of the PKSE, TEBC, UNBL, UNBV and UNBU protein families indicates the presence of an enediyne gene cluster or an enediyne producing organism Diagnostic nucleic acid sequences encoding members of the PKSE, TEBC, UNBL, UNBV and UNBU protein families for identifying enediyne genes, biosynthetic loci, and microorganisms that harbor such genes or gene clusters may be employed on complex mixtures of microorganisms such as those from environmental samples (e.g., soil). A mixture of microorganisms refers to a heterogeneous population of microorganisms consisting of more than one species or strain. In the absence of amplification outside of its natural habitat, such a mixture of microorganisms is said to be uncultured. A cultured mixture of microorganisms may be obtained by amplification or propagation outside of its natural habitat by in vitro culture using various growth media that provide essential nutrients. However, depending on the growth medium used, the amplification may preferentially result in amplification of a sub-population of the mixture and hence may not be always desirable If desired, a pure culture representing a single species or strain may obtained from either a cultured or uncultured mixture of microorganisms by established microbiological techniques such as serial dilution followed by growth on solid media so as to isolate individual colony forming units.

Enediyne biosynthetic genes and/or enediyne biosynthetic gene clusters may be identified from either a pure culture or cultured or uncultured mixtures of microorganisms employing the diagnostic nucleic acid sequences disclosed in this invention by experimental techniques such as PCR, hybridization, or shotgun sequencing followed by bioinformatic analysis of the sequence data. The identification of one or more members of the protein families PKSE, TEBC, UNBL, UNBV and UNBU or enediyne gene clusters including one or more members of the protein families PKSE, TEBC, UNBL, UNBV and UNBU in a pure culture of a single organism directly distinguishes such an enediyne-producer. The identification of one or more members of the protein families PKSE, TEBC, UNBL, UNBV and UNBU or enediyne gene clusters including one or more members of the protein families PKSE, TEBC, UNBL, UNBV and UNBU in a cultured or uncultured mixture of microorganisms requires further steps to identify and isolate the microorganism(s) that harbor(s) them so as to obtain pure cultures of such microorganisms.

By way of example, the colony lift technique (Ausubel et al., Current Protocols in Molecular Biology, John Wiley 503 Sons, Inc. 1997; and Sambrook et al., Molecular Cloning: A Laboratory Manual 2d Ed., Cold Spring Harbor Laboratory Press, 1989) may be used to to identify microorganisms that harbour enediyne genes and/or enediyne biosynthetic loci from a cultured mixture of microorganisms. In such a procedure, the mixture of microorganisms is grown on an appropriate solid medium. The resulting colony forming units are replicated on a solid matrix such as a nylon membrane. The membrane is contacted with detectable diagnostic nucleic acid sequences, the positive colony forming units are identified, and the corresponding colony forming units on the original medium are identified, purified, and amplified.

Nucleic acids encoding a member of the protein families PKSE, TEBC, UNBL, UNBV and UNBU may be used to survey a number of environmental samples for the presence of organisms that have the potential to produce enediyne compounds, i.e., those organisms that contain enediyne biosynthetic genes and/or an enediyne biosynthetic locus. One protocol for use of a survey to identify polypeptides encoded by DNA isolated from uncultured mixtures of microorganisms is outlined in Seow et al. (1997) J. Bacteriol. Vol. 179 pp. 7360–7368.

Where necessary, conditions which permit the probe to specifically hybridize to complementary sequences from an enediyne-producer may be determined by placing a probe based on a member of the protein families PKSE, TEBC, UNBL, UNBV and UNBU in contact with complementary sequences obtained from an enediyne-producer as well as control sequences which are not from an enediyne-producer. In some analyses, the control sequences may be from organisms related to enediyne-producers. Alternatively, the control sequences are not related to enediyne-producers. Hybridization conditions, such as the salt concentration of the hybridization buffer, the formamide concentration of the hybridization buffer, or the hybridization temperature, may be varied to identify conditions which allow the probe to hybridize specifically to nucleic acids from enediyne-producers.

If the sample contains nucleic acids from enediyne-producers, specific hybridization of the probe to the nucleic acids from the enediyne-producer is then detected. Hybridization may be detected by labeling the probe with a detectable agent such as a radioactive isotope, a fluorescent dye or an enzyme capable of catalyzing the formation of a detectable product. Many methods for using the labeled probes to detect the presenceof nucleic acids in a sample are familiar to those skilled in the art. These include Southern Blots, Northern Blots, colony hybridization procedures, and dot blots.

Another aspect of the present invention is an isolated or purified polypeptide comprising the sequence of one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or fragments comprising at least 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell For example, the expression vector may comprise a promoter, a ribosome binding site for translation initiation and a transcription terminator. The vector may also include appropriate sequences for modulating expression levels, an origin of replication and a selectable marker.

Promoters suitable for expressing the polypeptide or fragment thereof in bacteria include the E. coli lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the α factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donors and acceptor sites, transcriptional termination sequences, and 5' flanking non-transcribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers In addition, the expression vectors preferably contain one or more selectable marker genes to permit selection of host cells containing the vector. Examples of selectable markers that may be used include genes encoding dihydrofolate reductase or genes conferring neomycin resistance for eukaryotic cell culture, genes conferring tetracycline or ampicillin resistance in E coli, and the S. cerevisiae TRP1 gene.

In some embodiments, the nucleic acid encoding one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof is assembled in appropriate phase with a leader sequence capable of directing secretion of the translated polypeptides or fragments thereof. Optionally, the nucleic acid can encode a fusion polypeptide in which one of the polypeptide of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics such as increased stability or simplified purification or detection.

The appropriate DNA sequence may be inserted into the vector by a variety of procedures. In general, the DNA sequence is ligated to the desired position in the vector following digestion of the insert and the vector with appropriate restriction endonucleases. Alternatively, appropriate restriction enzyme sites can be engineered into a DNA sequence by PCR. A variety of cloning techniques are disclosed in Ausbel et al. Current Protocols in Molecular Biology, John Wiley 503 Sons, Inc. 1997 and Sambrook et al., Molecular Cloning: A Laboratory Manual 2d Ed., Cold Spring Harbour Laboratory Press, 1989. Such procedures and others are deemed to be within the scope of those skilled in the art.

The vector may be, for example, in the form of a plasmid, a viral particle, or a phage. Other vectors include derivatives of chromosomal, nonchromosomal and synthetic DNA sequences, viruses, bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook et al., Molecular Cloning: A Laboratory Manual, Second Edition, Cold Spring Harbor, N.Y., (1989).

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and stable in the host cell.

The host cell may be any of the host cells familiar to those skilled in the art, including prokaryotic cells or eukaryotic cells. As representative examples of appropriate hosts, there may be mentioned bacteria cells, such as *E. coli, Streptomyces lividans, Bacillus subtilis, Salmonella typhimurium* and various species within the genera *Pseudomonas, Streptomyces*, and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including electroporation, transformation, transfection, transduction, viral infection, gene guns, or Ti-mediated gene transfer. Where appropriate, the engineenred host cells can be cultured in conventional nutrient media modified as appropriate for activating promoters, selecting transformants or amplifying the genes of the present invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175(1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptide produced by host cells containing the vector may be glycosylated or may be non-glycosylated. Polypeptides of the invention may or may not also include an initial methionine amino acid residue.

Alternatively, the polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polynucleotides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof using mRNAs transcribed form a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The present invention also relates to variants of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Preferably, these nucleotide differences result in amino acid changes with respect to the polypeptides encoded by the nucleic acids from the natural isolates.

For example, variants may be created using error prone PCR. In error prone PCR, DNA amplification is performed under conditions where the fidelity of the DNA polymerase is low, such that a high rate of point mutation is obtained along the entire length of the PCR product. Error prone PCR is described in Leung, D. W., et al., Technique, 1:11–15 (1989) and Caldwell, R. C. & Joyce G. F., PCR Methods Applic., 2:28–33 (1992). Variants may also be created using site directed mutagenesis to generate site-specific mutations in any cloned DNA segment of interest. Oligonucleotide mutagenesis is described in Reidhaar-Olson, J. F. and Sauer, R. T., Science, 241:53–57 (1988). Variants may also be created using directed evolution strategies such as those described in U.S. Pat. Nos. 6,361,974 and 6,372,497.

The variants of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, may be (i) variants in which one or more of the amino acid residues of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

Other variants are those in which one or more of the amino acid residues of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101. In other embodiments, the fragment, derivative or analogue includes a fused herterologous sequence which facilitates purification, enrichment, detection, stabilization or secretion of the polypeptide that can be enzymatically cleaved, in whole or in part, away from the fragment, derivative or analogue.

Another aspect of the present invention are polypeptides or fragments thereof which have at least 70%, at least 80%, at least 85%, at least 90%, or more than 95% homology to one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or a fragment comprising at least 5, 10, 15, 20, 25, 30, 35, 40, 50, 75, 100, or 150 consecutive amino acids thereof. Homology may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions such as those described above.

The polypeptides or fragments having homology to one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or a fragment comprising at least 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or a fragment comprising at least 5, 10, 15, 20, 25, 30, 35, 40, 50, 75, 100, or 150 consecutive amino acids thereof using a program such as BLASTP version 2.2.2 with the default parameters.

The polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments, derivatives or analogs thereof comprising at least 5, 10, 15, 20, 25, 30, 35, 40, 50, 75, 100, or 150 consecutive amino acids thereof invention may be used in a variety of application. For example, the polypeptides or fragments, derivatives or analogs thereof may be used to biocatalyze biochemical reactions. In particular, the polypeptides of the PKSE family, namely SEQ ID NOS: 1, 13, 23, 33, 43, 53, 63, 73, 83, 93 fragments, derivatives or analogs thereof; the TEBC family, namely SEQ ID NOS: 3, 5, 15, 25, 35, 45, 55, 65, 75, 85, 95 or fragments, derivatives or analogs thereof, may be used in any combination, in vitro or in vivo, to direct the synthesis or modification of an enediyne warhead or a substructure thereof. Polypeptides of the UNBL family, namely SEQ ID NOS: 7, 17, 27, 37, 47, 57, 67, 77, 87, 97 or fragments, derivatives or analogs thereof; may be used in vitro or in vivo to direct or aid the synthesis or modification of an enediyne warhead or a substructure thereof. Polypeptides of the UNBV family, namely SEQ ID NOS: 9, 19, 29, 39, 49, 59, 69, 79, 89, 99 or fragments, derivatives or analogs thereof, may be used in vitro or in vivo to direct or aid the synthesis or modification of an enediyne warhead or a substructure thereof. Polypeptides of the UNBU family, namely SEQ ID NOS: 11, 21, 31, 41, 51, 61, 71, 81, 91, 101 or fragments, derivatives or analogs thereof may be used in vitro or in vivo to direct or aid the synthesis or modification of an enediyne warhead or a substructure thereof.

The polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments, derivatives or analogues thereof comprising at least 5, 10, 15, 20, 25, 30, 35, 40, 50, 75, 100, or 150 consecutive amino acids thereof, may also be used to generate antibodies which bind specifically to the polypeptides or fragments, derivatives or analogues. The antibodies generated from SEQ ID NOS: 1, 3, 5, 7, 9, 11 may be used to determine whether a biological sample contains Streptomyces macromyceticus or a related microorganism, The antibodies generated from SEQ ID NOS: 13, 15, 17, 19, 21 may be used to determine whether a biological sample contains Micromonospora echinospora subsp. calichensis or a related microorganism. The antibodies generated from SEQ ID NOS: 23, 25, 27, 29, 31 may be used to determine whether a biological sample contains Streptomyces ghanaensis or a related microorganism. The antibodies generated from SEQ ID NOS: 33, 35, 37, 39, 41 may be used to determine whether a biological sample contains Streptomyces carzinostaticus subsp. neocarzinostaticus or a related microorganism. The antibodies generated from 43, 45, 47, 49, 51 may be used to determine whether a biological sample contains Amycolatopsis orientalis or a related microorganism. The antibodies generated from 53, 55, 57, 59, 61 may be used to determine whether a biological sample contains Kitasatosporia sp. or a related microorganism. The antibodies generated from SEQ ID NOS: 63, 65, 67, 69, 71 may be used to determine whether a biological sample contains Micromonospora megalomicea or a related microorganism The antibodies generated from SEQ ID NOS: 73, 75, 77, 79, 81 may be used to determine whether a biological sample contains Saccharothrix aerocolonigenes or a related microorganism. The antibodies generated from SEQ ID NOS: 83, 85, 87, 89, 91 may be used to determine whether a biological sample contains Streptomyces kaniharaensis or a related microorganism. The antibodies generated from SEQ ID NOS: 93, 95, 97, 99, 101 may be used to determine whether a biological sample contains Streptomyces citricolor or a related microorganism.

In such procedures, a biological sample is contacted with an antibody capable of specifically binding to one of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof. The ability of the biological sample to bind to the antibody is then determined. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. A variety of assay protocols may be used to detect the presence of Micromonospora echinospora subsp. calichensis, Streptomyces ghanaensis, Streptomyces carzinostaticus subsp. neocarzinostaticus, Amycolatopsis orientalis, Kitasatosporia sp., Micromonospora megalomicea, Saccharothrix aerocolonigenes, Streptomyces kaniharaensis, Streptomyces citricolor or the the present of polypeptides related to SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 in a sample. Particular assays include ELISA assays, sandwich assays, radioimmunoassays, and Western Blots. Alternatively, antibodies generated from SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 may be used to determine whether a biological sample contains related polypeptides that may be involved in the biosynthesis of enediyne natural products or other enediyne-like compounds.

Polyclonal antibodies generated against the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kholer and Milstein, 1975, Nature, 256:495–497), the trioma technique, the human B-cell hybridoma technique (Kozbor et al., 1983, Immunology Today 4:72), and the EBV-hybridoma technique (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments comprising at least 5, 10, 15, 20, 25, 30, 35, 40, 50, 75, 100, or 150 consecutive amino acids thereof may be used in screening for similar polypeptides from a sample containing organisms or cell-free extracts thereof. In such techniques, polypeptides from the sample is contacted with the antibodies and those polypeptides which specifically bind the antibody are detected. Any of the procedures described above may be used to detect antibody binding. One such screening assay is described in "Methods for measuring Cellulase Activities", Methods in Enzymology, Vol 160, pp. 87–116.

As used herein, the term "enediyne-specific nucleic acid codes" encompass the nucleotide sequences of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, fragments of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, nucleotide sequences homologous to SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, or homologous to fragments of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, and sequences complementary to all of the preceding sequences. The fragments include portions of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 comprising at least 10, 15, 20, 25, 30, 35, 40, 50, 75, 100, 150, 200, 300, 400 or 500 consecutive nucleotides of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102. Preferably, the fragments are novel fragments. Homologous sequences and fragments of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 refer to a sequence having at least 99%, 98%, 97%, 96%, 95%, 90%, 80%, 75% or 70% homology to these sequences. Homology may be determined using any of the computer programs and parameters described herein, including BLASTN and TBLASTX with the default parameters. Homologous sequences also include RNA sequences in which uridines replace the thymines in the nucleic acid codes of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102. The homologous sequences may be obtained using any of the procedures described herein or may result from the correction of a sequencing error. It will be appreciated that the nucleic acid codes of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102 can be represented in the traditional single character format in which G, A, T and C denote the guanine, adenine, thymine and cytosine bases of the deoxyribonucleic acid (DNA) sequence respectively, or in which G, A, U and C denote the guanine, adenine, uracil and cytosine bases of the ribonucleic acid (RNA) sequence (see the inside back cover of Stryer, *Biochemistry*, 3$^{rd}$ edition, W. H. Freeman & Co., New York) or in any other format which records the identity of the nucleotides in a sequence.

"Enediyne-specific polypeptide codes" encompass the polypeptide sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 which are encoded by the cDNAs of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101; polypeptide sequences homologous to the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, or fragments of any of the preceding sequences. Homologous polypeptide sequences refer to a polypeptide sequence having at least 99%, 98%, 97%, 96%, 95%, 90%, 85%, 80%, 75% or 70% homology to one of the polypeptide sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101. Polypeptide sequence homology may be determined using any of the computer programs and parameters described herein, including BLASTP version 2.2.2 with the default parameters or with any user-specified parameters. The homologous sequences may be obtained using any of the procedures described herein or may result from the correction of a sequencing error. The polypeptide fragments comprise at least 5, 10, 15, 20, 25, 30, 35, 40, 50, 75, 100 or 150 consecutive polypeptides of the polypeptides of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101. Preferably the fragments are novel fragments. It will be appreciated that the polypeptide codes of the SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 can be represented in the traditional single character format or three letter format (see the inside back cover of Stryer, *Biochemistry,* 3$^{rd}$ edition, W. H. Freeman & Co., New York) or in any other format which relates the identity of the polypeptides in a sequence.

A single sequence selected from enediyne-specific nucleic acid codes and enediyne-specific polypeptide codes is sometimes referred to herein as a subject sequence.

It will be readily appreciated by those skilled in the art that the enediyne-specific nucleic acid codes, a subset thereof, enediyne-specific polypeptide codes, a subset thereof, and a subject sequence can be stored, recorded and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the enediyne-specific nucleic acid codes, a subset thereof, enediyne-specific polypeptide codes, a subset thereof, and a subject sequence.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of media known to those skilled in the art.

The enediyne-specific nucleic acid codes, a subset thereof and a subject sequence may be stored and manipulated in a variety of data processor programs in a variety of formats. For example, the enediyne-specific nucleic acid codes, a subset thereof, enediyne-specific polypeptide codes, a subset thereof, and a subject sequence may be stored as ASCII or text in a word processing file, such as MicrosoftWORD or WORDPERFECT in a variety of database programs familiar to those of skill in the art, such as DB2 or ORACLE. In addition, many computer programs and databases may be used as sequence comparers, identifiers or sources of query nucleotide sequences or query polypeptide sequences to be compared to the enediyne-specific nucleic acid codes, a subset thereof, the enediyne-specific polypeptide codes, a subset thereof, and a subject sequence.

The following list is intended not to limit the invention but to provide guidance to programs and databases useful with the enediyne-specific nucleic acid codes, a subset thereof, enediyne-specific polypeptide codes, a subset thereof, and a subject sequence. The program and databases which may be used include, but are not limited to: MacPattern (EMBL), DiscoveryBase (Molecular Applications Group), GeneMine (Molecular Applications Group) Look (Molecular Applications Group), MacLook (Molecular Applications Group), BLAST and BLAST2 (NCBI), BLASTN and BLASTX (Altschul et al., *J. Mol. Biol.* 215:403 (1990)), FASTA (Person and Lipman, *Proc. Nalt. Acad. Sci. USA*, 85:2444 (1988)), FASTDB (Brutlag et al. *Comp. App. Biosci.* 6-237–245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II (Molecular Simulations Inc.), Discover (Molecular Simulations Inc.), CHARMm (Molecular Simulations Inc.), Felix (Molecular Simulations Inc.), DelPhi (Molecular Simulations Inc.), QuanteMM (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WetLab (Molecular Simulations Inc.), WetLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents' World Drug Index database, the BioByteMasterFile database, the Genbank database, and the Gensyqn database. Many other programs and databases would be apparent to one of skill in the art given the present disclosure.

Embodiments of the present invention include systems, particularly computer systems that store and manipulate the sequence information described herein. As used herein, "a computer system", refers to the hardware components, software components, and data storage components used to analyze enediyne-specific nucleic acid codes, a subset thereof, enediyne-specific polypeptide codes, a subset thereof, or a subject sequence.

Preferably, the computer system is a general purpose system that comprises a processor and one or more internal data storage components for storing data, and one or more data retrieving devices for retrieving the data stored on the data storage components. A skilled artisan can readily appreciate that any one of the currently available computer systems are suitable.

Figure 1:
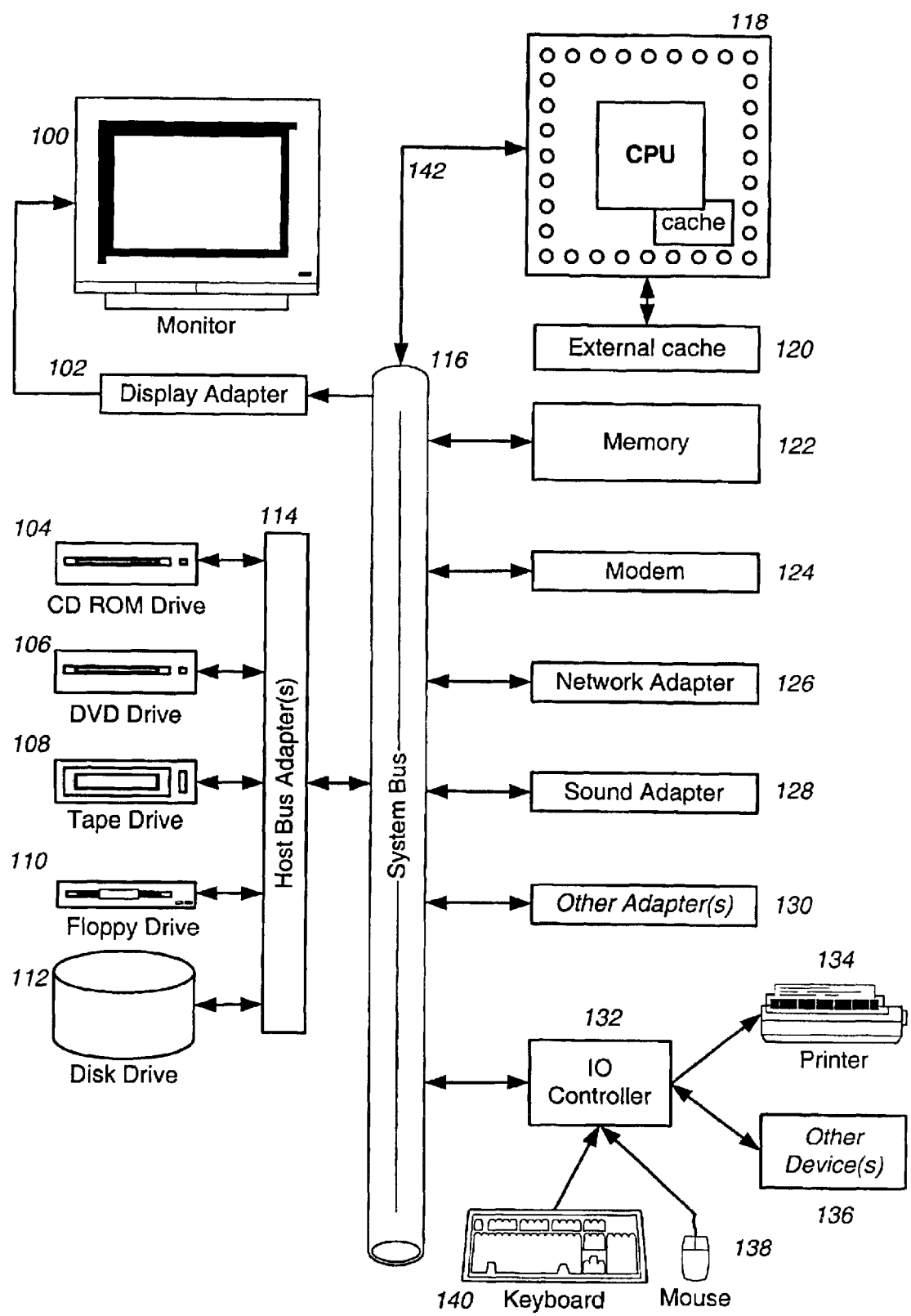
FIG. 1 is a block diagram of a computer system which implements and executes software tools for the purpose of comparing a query to a subject, wherein the subject is selected from the reference sequences of the invention.

One example of a computer system is Illustrated in FIG. 1. The computer system of FIG. 4 will includes a number of components connected to a central system bus 116, including a central processing unit 118 with internal 118 and/or external cache memory 120, system memory 122, display adapter 102 connected to a monitor 100, network adapter 126 which may also be referred to as a network interface, internal modem 124, sound adapter 128, IO controller 132 to which may be connected a keyboard 140 and mouse 138, or other suitable input device such as a trackball or tablet, as well as external printer 134, and/or any number of external devices such as external modems, tape storage drives, or disk drives. One skilled in the art will readily appreciate that not all components illustrated in FIG. 1 are required to practice the invention and, likewise, additional components not illustrated in FIG. 1 may be present in a computer system contemplated for use with the invention.

One or more host bus adapters 114 may be connected to the system bus 116. To host bus adapter 114 may optionally be connected one or more storage devices such as disk drives 112 (removable or fixed), floppy drives 110, tape drives 108, digital versatile disk DVD drives 106, and compact disk CD ROM drives 104. The storage devices may operate in read-only mode and/or in read-write mode. The computer system may optionally include multiple central processing units 118, or multiple banks of memory 122.

Arrows 142 in FIG. 1 indicate the interconnection of internal components of the computer system. The arrows are illustrative only and do not specify exact connection architecture.

Software for accessing and processing the reference sequences (such as sequence comparison software, analysis software as well as search tools, annotation tools, and modeling tools etc.) may reside in main memory 122 during execution.

In one embodiment, the computer system further comprises a sequence comparison software for comparing the nucleic acid codes of a query sequence stored on a computer readable medium to a subject sequence which is also stored on a computer readable medium; or for comparing the polypeptide code of a query sequence stored on a computer readable medium to a subject sequence which is also stored on computer readable medium A "sequence comparison software" refers to one or more programs that are implemented on the computer system to compare nucleotide sequences with other nucleotide sequences stored within the data storage means. The design of one example of a sequence comparison software is provided in FIGS. 2A, 2B, 2C and 2D.

Figure 3:
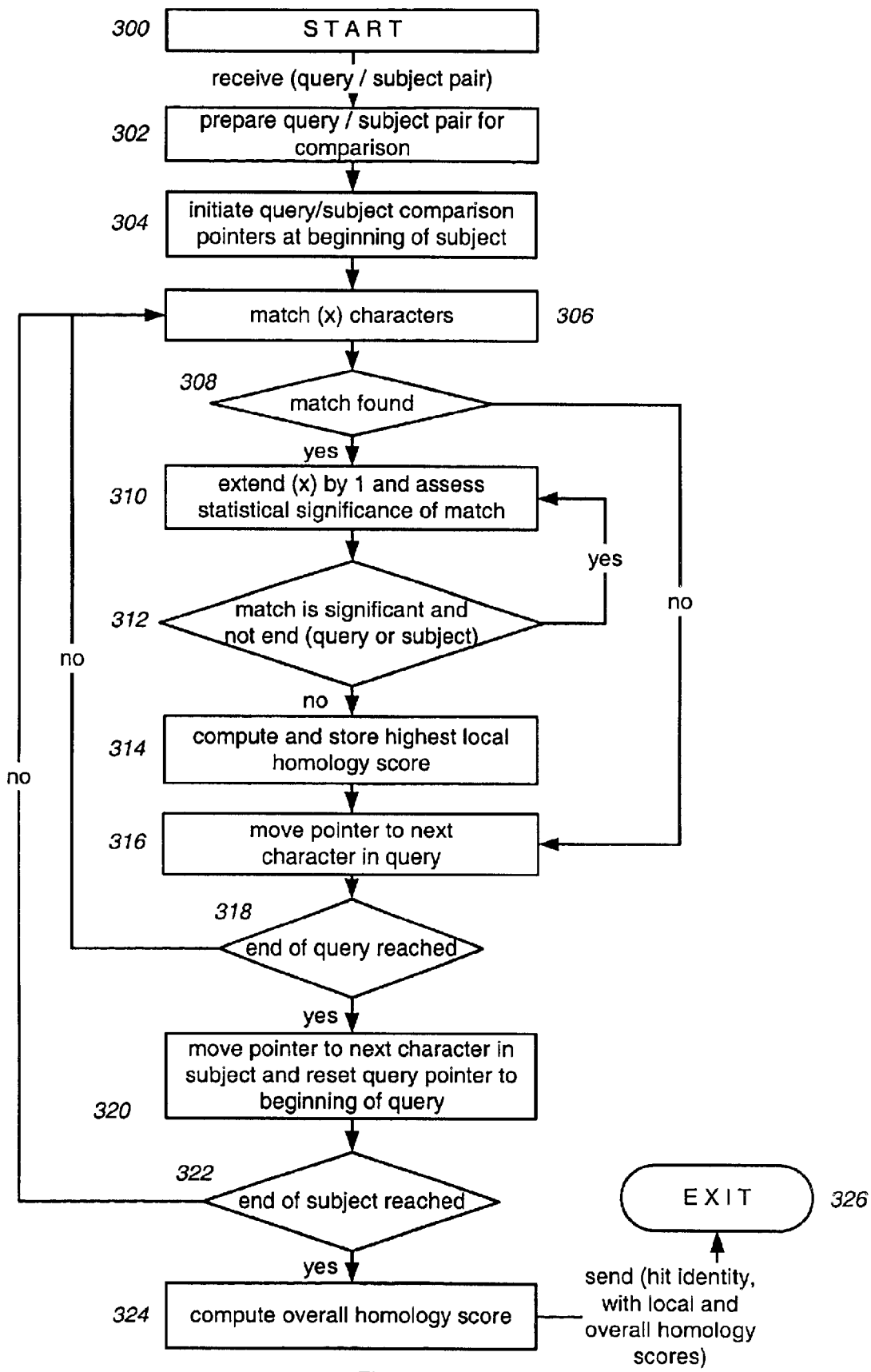
FIG. 3 is a flow diagram of the comparator algorithm (238) of FIG. 2C which is one embodiment of a comparator algorithm that can be used for pairwise determination of similarity between a query/subject pair.

The sequence comparison software will typically employ one or more specialized comparator algorithms. Protein and/or nucleic acid sequence similarities may be evaluated using any of the variety of sequence comparator algorithms and programs known in the art. Such algorithms and programs include, but are no way limited to, TBLASTN, BLASTN, BLASTP, FASTA, TFASTA, CLUSTAL, HMMER, MAST, or other suitable algorithm known to those skilled in the art. (Pearson and Lipman, 1988, *Proc. Natl. Acad. Sci. USA* 85(8): 2444–2448; Altschul et al., 1990, *J. Mol. Biol.* 215(3):403–410; Thompson et al., 1994, *Nucleic Acids Res.* 22(2):4673–4680, Higgins et al., 1996, *Methods Enzymol.* 266:383–402; Altschul et al., 1990, *J. Mol. Biol.* 215(3):403–410; Altschul et al., 1993, *Nature Genetics* 3:266–272, Eddy S. R., Bioinformatics 14:755–763, 1998; Bailey T L et al, J Steroid Biochem Mol Biol 1997 May; 62(1):29–44). One example of a comparator algorithm is illustrated in FIG. 3. Sequence comparator algorithms identified in this specification are particularly contemplated for use in this aspect of the invention.

Figure 4:
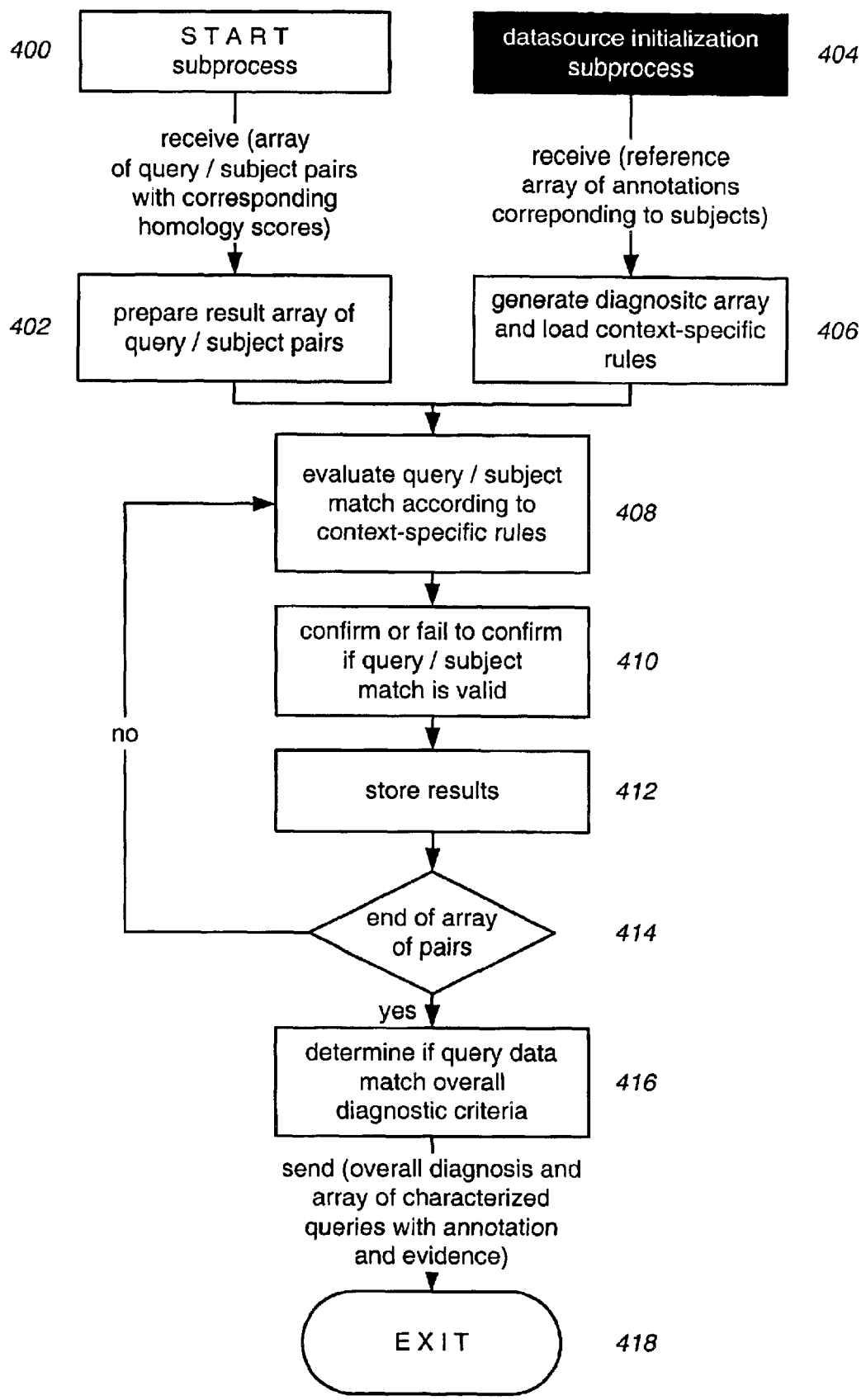
FIG. 4 is a flow diagram of the analyzer algorithm (244) of FIG. 2C which is one embodiment of an analyzer algorithm that can be used to assign identity to a query sequence, based on similarity to a subject sequence, where the subject sequence is a reference sequence of the invention.

The sequence comparison software will typically employ one or more specialized analyzer algorithms. One example of an analyzer algorithm is illustrated in FIG. 4. Any appropriate analyzer algorithm can be used to evaluate similarities, determined by the comparator algorithm, between a query sequence and a subject sequence (referred to herein as a query/subject pair). Based on context specific rules, the annotation of a subject sequence may be assigned to the query sequence. A skilled artisan can readily determine the selection of an appropriate analyzer algorithm and appropriate context specific rules. Analyzer algorithms identified elsewhere in this specification are particularly contemplated for use in this aspect of the invention.

FIGS. 2A, 2B, 2C and 2D together provide a flowchart of one example of a sequence comparison software for comparing query sequences to a subject sequence. The software determines if a gene or set of genes represented by their nucleotide sequence, polypeptide sequence or other representation (the query sequence) is significantly similar to the enediyne-specific nucleic acid codes, a subset thereof, enediyne-specific polypeptide codes, a subset thereof, of the invention (the subject sequence). The software may be implemented in the C or C++ programming language, Java, Perl or other suitable programming language known to a person skilled in the art.

Referring to FIG. 2A, the query sequence(s) may be accessed by the program by means of input from the user 210, accessing a database 208 or opening a text file 206. The "query initialization process" allows a query sequence to be accessed and loaded into computer memory 122, or under control of the program stored on a disk drive 112 or other storage device in the form of a query sequence array 216. The query array 216 is one or more query nucleotide or polypeptide sequences accompanied by some appropriate identifiers.

A dataset is accessed by the program by means of input from the user 228, accessing a database 226, or opening a text file 224. The "subject data source initialization process" of FIG. 2B refers to the method by which a reference dataset containing one or more sequence selected from the enediyne-specific nucleic acid codes, a subset thereof, enediyne-specific polypeptide codes, a subset thereof, or a subject sequence is loaded into computer memory 122, or under control of the program stored on a disk drive 112 or other storage device in the form of a subject array 234. The subject array 234 comprises one or more subject nucleotide or polypeptide sequences accompanied by some appropriate identifiers.

The "comparison subprocess" of FIG. 2C is the process by which the comparator algorithm 238 is invoked by the software for pairwise comparisons between query elements in the query sequence array 216, and subject elements in the subject array 234. The "comparator algorithm" of FIG. 2C refers to the pairwise comparisons between a query sequence and subject sequence, i.e. a query/subject pair from their respective arrays 216, 234. Comparator algorithm 238 may be any algorithm that acts on a query/subject pair, including but not limited to homology algorithms such as BLAST, Smith Waterman, Fasta, or statistical representation/probabilistic algorithms such as Markov models exemplified by HMMER, or other suitable algorithm known to one skilled in the art. Suitable algorithms would generally require a query/subject pair as input and return a score (an indication of likeness between the query and subject), usually through the use of appropriate statistical methods such as Karlin Altschul statistics used in BLAST, Forward or Viterbi algorithms used in Markov models, or other suitable statistics known to those skilled in the art.

The sequence comparison software of FIG. 2C also comprises a means of analysis of the results of the pairwise comparisons performed by the comparator algorithm 238. The "analysis subprocess" of FIG. 2C is a process by which the analyzer algorithm 244 is invoked by the software. The "analyzer algorithm" refers to a process by which annotation of a subject is assigned to the query based on query/subject similarity as determined by the comparator algorithm 238 according to context-specific rules coded into the program or dynamically loaded at runtime. Context-specific rules are what the program uses to determine if the annotation of the subject can be assigned to the query given the context of the comparison. These rules allow the software to qualify the overall meaning of the results of the comparator algorithm 238.

In one embodiment, context-specific rules may state that for a set of query sequences to be considered representative of an enediyne locus the comparator algorithm 238 must determine that the set of query sequences contain at least one query sequence that shows a statistical similarity to reference sequences corresponding to a nucleic acid sequence code for a polypeptide from two of the groups consisting of: (1) SEQ ID NOS: 1, 13, 23, 33, 43, 53, 63, 73, 83, 93 and polypeptides having at least 75% homology to a polypeptide sequence of SEQ ID NOS: 1, 13, 23, 33, 43, 53, 63, 73, 83, 93, (2) SEQ ID NOS: 3, 5, 15, 25, 35, 45, 55, 65, 75, 85, 95 and polypeptides having at least 75% homology to a polypeptide sequence of SEQ ID NOS: 3, 5, 15, 25, 35, 45, 55, 65, 75, 85, 95; (3) SEQ ID NOS: 7, 17, 27, 37, 47, 57, 67, 77, 87, 97, and polypeptides having at least 75% homology to a polypeptide sequence of SEQ ID NOS: 7, 17, 27, 37, 47, 57, 67, 77, 87, 97; (4) SEQ ID NOS: 9, 19, 29, 39, 49, 59, 69, 79, 89, 99 and polypeptides having at least 75% homology to a polypeptide sequence of SEQ ID NOS: 9, 19, 29, 39, 49, 59, 69, 79, 89, 99, (5) SEQ ID NOS: 11, 21, 31, 41, 51, 61, 71, 81, 91, 101 and polypeptides having at least 75% homology to a polypeptide sequence of SEQ ID NOS: 11, 21, 31, 41, 51, 61, 71, 81, 91, 101. Of course preferred context specific rules may specify a wide variety of thresholds for identifying enediyne-biosynthetic genes or enediyne-producing organisms without departing from the scope of the invention. Some thresholds contemplate that at least one query sequence in the set of query sequences show a statistical similarity to the nucleic acid code corresponding to 2 or 3 or 4 or 5 of the above 5 groups polypeptides diagnostic of enediyne biosynthetic genes. Other context specific rules set the level of homology required in each of the group may be set at 70%, 80%, 85%, 90%, 95% or 98% in regards to any one or more of the subject sequences.

In another embodiment context-specific rules may state that for a query sequence to be considered an enediyne polyketide synthase, the comparator algorithm 238 must determine that the query sequence shows a statistical similarity to subject sequences corresponding to a nucleic acid sequence code for a polypeptide of SEQ ID NOS: 1, 13, 23, 33, 43, 53, 63, 73, 83, 93, polypeptides having at least 75% homology to a polypeptide of SEQ ID NOS: 1, 13, 23, 33, 43, 53, 63, 73, 83, 93 and fragment comprising at least 500 consecutive amino acids of the polypeptides of SEQ ID NOS: 1, 13, 23, 33, 43, 53, 63, 73, 83, 93. Of course preferred context specific rules may specify a wide variety of thresholds for identifying enediyne polyketide synthase proteins without departing from the scope of the invention. Some context specific rules set level of homology required of the query sequence at 70%, 80%, 85%, 90%, 95% or 98% in regards to the reference sequences.

Thus, the analysis subprocess may be employed in conjunction with any other context specific rules and may be adapted to suit different embodiments. The principal function of the analyzer algorithm 244 is to assign meaning or a diagnosis to a query or set of queries based on context specific rules that are application specific and may be changed without altering the overall role of the analyzer algorithm 244.

Finally the sequence comparison software of FIG. 2 comprises a means of returning of the results of the comparisons by the comparator algorithm 238 and analyzed by the analyzer algorithm 244 to the user or process that requested the comparison or comparisons. The "display/report subprocess" of FIG. 2D is the process by which the results of the comparisons by the comparator algorithm 238 and analyses by the analyzer algorithm 244 are returned to the user or process that requested the comparison or comparisons. The results 240, 246 may be written to a file 252, displayed in some user interface such as a console, custom graphical interface, web interface, or other suitable implementation specific interface, or uploaded to some database such as a relational database, or other suitable implementation specific database.

Once the results have been returned to the user or process that requested the comparison or comparisons the program exits.

The principle of the sequence comparison software of FIG. 2 is to receive or load a query or queries, receive or load a reference dataset, then run a pairwise comparison by means of the comparator algorithm 238, then evaluate the results using an analyzer algorithm 244 to arrive at a determination if the query or queries bear significant similarity to the reference sequences, and finally return the results to the user or calling program or process.

FIG. 3 is a flow diagram illustrating one embodiment of comparator algorithm 238 process in a computer for determining whether two sequences are homologous. The comparator algorithm receives a query/subject pair for comparison, performs an appropriate comparison, and returns the pair along with a calculated degree of similarity.

Referring to FIG. 3, the comparison is initiated at the beginning of sequences 304. A match of (x) characters is attempted 306 where (x) is a user specified number. If a match is not found the query sequence is advanced 316 by one polypeptide with respect to the subject, and if the end of the query has not been reached 318 another match of (x) characters is attempted 306. Thus if no match has been found the query is incrementally advanced in entirety past the initial position of the subject, once the end of the query is reached 318, the subject pointer is advanced by 1 polypeptide and the query pointer is set to the beginning of the query 318. If the end of the subject has been reached and still no matches have been found a null homology result score is assigned 324 and the algorithm returns the pair of sequences along with a null score to the calling process or program. The algorithm then exits 326. If instead a match is found 308, an extension of the matched region is attempted 310 and the match is analyzed statistically 312. The extension may be unidirectional or bidirectional. The algorithm continues in a loop extending the matched region and computing the homology score, giving penalties for mismatches taking into consideration that given the chemical properties of the polypeptide side chains not all mismatches are equal. For example a mismatch of a lysine with an arginine both of which have basic side chains receive a lesser penalty than a mismatch between lysine and glutamate which has an acidic side chain. The extension loop stops once the accumulated penalty exceeds some user specified value, or of the end of either sequence is reached 312. The maximal score is stored 314, and the query sequence is advanced 316 by one polypeptide with respect to the subject, and if the end of the query has not been reached 318 another match of (x) characters is attempted 306. The process continues until the entire length of the subject has been evaluated for matches to the entire length of the query. All individual scores and alignments are stored 314 by the algorithm and an overall score is computed 324 and stored. The algorithm returns the pair of sequences along with local and global scores to the calling process or program. The algorithm then exits 326.

Comparator algorithm 238 algorithm may be represented in pseudocode as follows:

```
INPUT:  Q[m]: query, m is the length
        S[n]: subject, n is the length
        x:   x is the size of a segment
START:
for each i in [1,n] do
    for each j in [1,m] do
        if ( j + x - 1 ) <= m and ( i + x - 1 ) <= n then
            if Q(j, j+x-1) = S(i, i+x-1) then
                k=1;
                while Q(j, j+x-1+k ) = S(i, i+x-1+ k) do
                    k++;
                Store highest local homology
Compute overall homology score
Return local and overall homology scores
END.
```

The comparator algorithm 238 may be written for use on nucleotide sequences, in which case the scoring scheme would be implemented so as to calculate scores and apply penalties based on the chemical nature of nucleotides. The comparator algorithm 238 may also provide for the presence of gaps in the scoring method for nucleotide or polypeptide sequences.

BLAST is one implementation of the comparator algorithm 238. HMMER is another implementation of the comparator algorithm 238 based on Markov model analysis. In a HMMER implementation a query sequence would be compared to a mathematical model representative of a subject sequence or sequences rather than using sequence homology.

FIG. 4 is a flow diagram illustrating an analyzer algorithm 244 process for detecting the presence of an enediyne biosynthetic locus. The analyzer algorithm of FIG. 4 may be used in the process by which the annotation of a subject is assigned to the query based on their similarity as determined by the comparator algorithm 238 and according to context-specific rules coded into the program or dynamically loaded at runtime. Context sensitive rules are what determines if the annotation of the subject can be assigned to the query given the context of the comparison. Context specific rules set the thresholds for determining the level and quality of similarity that would be accepted in the process of evaluating matched pairs.

The analyzer algorithm 244 receives as its input an array of pairs that had been matched by the comparator algorithm 238. The array consists of at least a query identifier, a subject identifier and the associated value of the measure of their similarity. To determine if a group of query sequences includes sequences diagnostic of an enediyne biosynthetic gene cluster, a reference or diagnostic array 406 is generated by accessing a data source and retrieving enediyne specific information 404 relating to enediyne-specific nucleic acid codes and enediyne-specific polypeptide codes. Diagnostic array 406 consists at least of subject identifiers and their associated annotation. Annotation may include reference to the five protein families diagnostic of enediyne biosynthetic genes clusters, i.e. PKSE, TEBC, UNBL, UNBV and UNBU. Annotation may also include information regarding exclusive presence in loci of a specific structural class or may include previously computed matches to other databases, for example databases of motifs.

Once the algorithm has successfully generated or received the two necessary arrays 402, 406, and holds in memory any context specific rules, each matched pair as determined by the comparator algorithm 238 can be evaluated. The algorithm will perform an evaluation 408 of each matched pair and based on the context specific rules confirm or fail to confirm the match as valid 410. In cases of successful confirmation of the match 410 the annotation of the subject is assigned to the query. Results of each comparison are stored 412. The loop ends when the end of the query/subject array is reached. Once all query/subject pairs have been evaluated against enediyne-specific nucleic acid codes and enediyne-specific polypeptide codes, a final determination can be made if the query set of ORFs represents an enediyne locus 416.

The algorithm then returns the overall diagnosis and an array of characterized query/subject pairs along with supporting evidence to the calling program or process and then terminates 418.

The analyzer algorithm 244 may be configured to dynamically load different diagnostic arrays and context specific rules. It may be used for example in the comparison of query/subject pairs with diagnostic subjects for other biosynthetic pathways, such as chromoprotein enediyne-specific nucleic acid codes or non-chromoprotein enediyne-specific polypeptide codes, or other sets of annotated subjects.

The present invention will be further described with reference to the following examples; however, it is to be understood that the present invention is not limited to such examples.

EXAMPLES

Example 1

Identification and Sequencing of the Macromomycin (Auromomycin) Biosynthetic Locus Macromomycin is a chromoprotein enediyne produced by *Streptomyces macromyceticus* (NRRL B-5335) Macromomycin is believed to be a derivative of a larger chromoprotein enediyne compound referred to as auromomycin (Vandre and Montgomery (1982) Biochemistry Vol 21 pp. 3343–3352, Yamashita et al. (1979) J. Antibiot. Vol. 32 pp. 330–339). Thus, throughout the specification, reference to macromomycin is intended to encompass the molecules referred to by some authors as auromomycin. Likewise, reference to the biosynthetic locus for macromomycin is intended to encompass the biosynthetic locus that directs the synthesis of the molecules some authors have referred to as macromomycin and auromomycin.

*Streptomyces macromyceticus* (NRRL B-5335) was obtained from the Agricultural Research Service collection (National Center for Agricultural Utilization Research, 1815 N. University Street, Peoria, Ill. 61604) and cultured using standard microbiological techniques (Kieser et al., supra). The organism was propagated on oatmeal agar medium at 28 degrees Celsius for several days. For isolation of high molecular weight genomic DNA, cell mass from three freshly grown, near confluent 100 mm petri dishes was used. The cell mass was collected by gentle scraping with a plastic spatula. Residual agar medium was removed by repeated washes with STE buffer (75 mM NaCl; 20 mM Tris-HCl, pH 8.0; 25 mM EDTA). High molecular weight DNA was isolated by established protocols (Kieser et al. supra) and its integrity was verified by field inversion gel electrophoresis (FIGE) using the preset program number 6 of the FIGE MAPPER™ power supply (BIORAD). This high molecular weight genomic DNA serves for the preparation of a small size fragment genomic sampling library (GSL), i.e., the small insert library, as well as a large size fragment cluster identification library (CIL), i.e., the large insert library. Both libraries contained randomly generated *S. macromyceticus* genomic DNA fragments and, therefore, are representative of the entire genome of this organism.

For the generation of the *S. macromyceticus* GSL library, genomic DNA was randomly sheared by sonication. DNA fragments having a size range between 1.5 and 3 kb were fractionated on a agarose gel and isolated using standard molecular biology techniques (Sambrook et al., supra). The ends of the obtained DNA fragments were repaired using T4 DNA polymerase (Roche) as described by the supplier. This enzyme creates DNA fragments with blunt ends that can be subsequently cloned into an appropriate vector. The repaired DNA fragments were subcloned into a derivative of pBluescript SK+ vector (Stratagene) which does not allow transcription of cloned DNA fragments. This vector was selected as it contains a convenient polylinker region surrounded by sequences corresponding to universal sequencing primers such as T3, T7, SK, and KS (Stratagene). The unique EcoRV restriction site found in the polylinker region was used as it allows insertion of blunt-end DNA fragments. Ligation of the inserts, use of the ligation products to transform *E. coli* DH10B (Invitrogen) host and selection for recombinant clones were performed as previously described (Sambrook et al., supra). Plasmid DNA carrying the *S. macromyceticus* genomic DNA fragments was extracted by the alkaline lysis method (Sambrook et al., supra) and the insert size of 1.5 to 3 kb was confirmed by electrophoresis on agarose gels. Using this procedure, a library of small size random genomic DNA fragments is generated that covers the entire genome of the studied microorganism. The number of individual clones that can be generated is infinite but only a small number is further analyzed to sample the microorganism's genome.

A CIL library was constructed from the *S. macromyceticus* high molecular weight genomic DNA using the SuperCos-1 cosmid vector (Stratagene™). The cosmid arms were prepared as specified by the manufacturer. The high molecular weight DNA was subjected to partial digestion at 37 degrees Celsius with approximately one unit of Sau3AI restriction enzyme (New England Biolabs) per 100 micrograms of DNA in the buffer supplied by the manufacturer. This enzyme generates random fragments of DNA ranging from the initial undigested size of the DNA to short fragments of which the length is dependent upon the frequency of the enzyme DNA recognition site in the genome and the extent of the DNA digestion. At various timepoints, aliquots of the digestion were transferred to new microfuge tubes and the enzyme was inactivated by adding a final concentration of 10 mM EDTA and 0.1% SDS. Aliquots judged by FIGE analysis to contain a significant fraction of DNA in the desired size range (30–50 kb) were pooled, extracted with phenol/chloroform (1:1 vol:vol), and pelleted by ethanol precipitation.

The 5' ends of Sau3AI DNA fragments were dephosphorylated using alkaline phosphatase (Roche) according to the manufacturers specifications at 37 degrees Celcius for 30 min. The phosphatase was heat inactivated at 70 degrees Celcius for 10 min and the DNA was extracted with phenol/chloroform (1:1 vol:vol), pelletted by ethanol precipitation, and resuspended in sterile water. The dephosphorylated Sau3AI DNA fragments were then ligated overnight at room temperature to the SuperCos-1 cosmid arms in a reaction containing approximately four-fold molar excess SuperCos-1 cosmid arms.

The ligation products were packaged using Gigapack® III XL packaging extracts (Stratagene™) according to the manufacturer's specifications. The CIL library consisted of 864 isolated cosmid clones in $E$ coli DH10B (Invitrogen). These clones were picked and inoculated into nine 96-well microtiter plates containing LB broth (per liter of water: 10.0 g NaCl; 10.0 g tryptone; 5.0 g yeast extract) which were grown overnight and then adjusted to contain a final concentration of 25% glycerol. These microtiter plates were stored at −80 degrees Celcius and served as glycerol stocks of the CIL library. Duplicate microtiter plates were arrayed onto nylon membranes as follows Cultures grown on microtiter plates were concentrated by pelleting and resuspending in a small volume of LB broth. A 3×3 96-pin-grid was spotted onto nylon membranes.

The membranes, representing the complete CIL library, were then layered onto LB agar and incubated ovenight at 37 degrees Celcius to allow the colonies to grow. The membranes were layered onto filter paper pre-soaked with 0.5 N NaOH/1.5 M NaCl for 10 min to denature the DNA and then neutralized by transferring onto filter paper pre-soaked with 0.5 M Tris (pH 8)/1.5 M NaCl for 10 min. Cell debris was gently scraped off with a plastic spatula and the DNA was crosslinked onto the membranes by UV irradiation using a GS GENE LINKER™ UV Chamber (BIORAD). Considering an average size of 8 Mb for an actinomycete genome and an average size of 35 kb of genomic insert in the CIL library, this library represents roughly a 4-fold coverage of the microorganism's entire genome.

The GSL library was analyzed by sequence determination of the cloned genomic DNA inserts. The universal primers KS or T7, referred to as forward (F) primers, were used to initiate polymerization of labeled DNA. Extension of at least 700 bp from the priming site can be routinely achieved using the TF, BDT v2.0 sequencing kit as specified by the supplier (Applied Biosystems). Sequence analysis of the small genomic DNA fragments (Genomic Sequence Tags, GSTs) was performed using a 3700 ABI capillary electrophoresis DNA sequencer (Applied Biosystems). The average length of the DNA sequence reads was ~700 bp. Further analysis of the obtained GSTs was performed by sequence homology comparison to various protein sequence databases. The DNA sequences of the obtained GSTs were translated into amino acid sequences and compared to the National Center for Biotechnology Information (NCBI) nonredundant protein database and the proprietary Ecopia natural product biosynthetic gene Decipher™ database using previously described algorithms (Altschul et al., supra). Sequence similarity with known proteins of defined function in the database enables one to make predictions on the function of the partial protein that is encoded by the translated GST.

Figure 5:
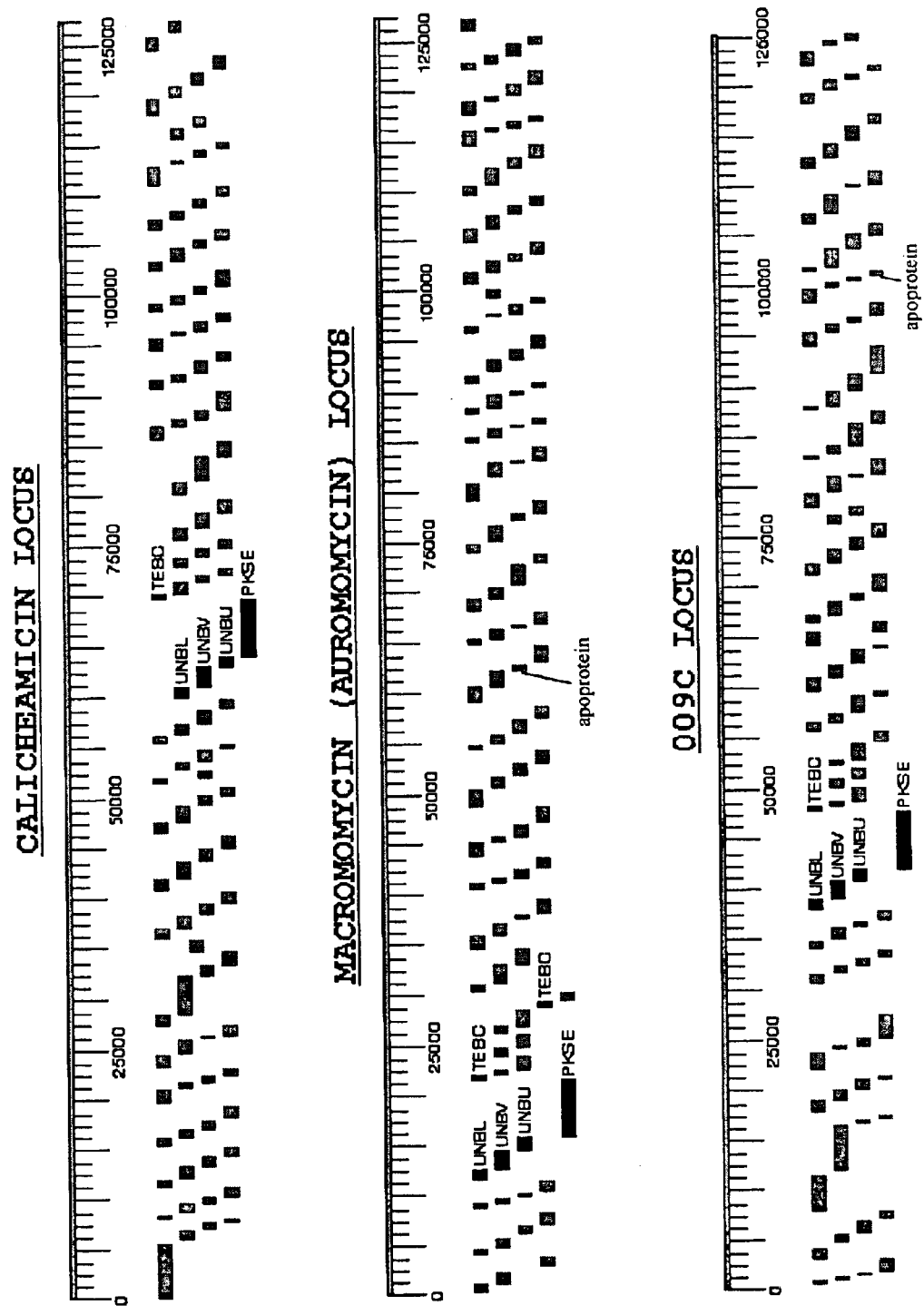
FIG. 5 is a schematic representation comparing the calicheamicin enediyne biosynthetic locus from *Micromonospora echinospora* subsp. *calichensis* (CALI), the macromomycin (auromomycin) enediyne biosynthetic locus from *Streptomyces macromycetius* (MACR), and a chromoprotein enediyne biosynthetic locus from Streptomyces ghanaensis (009C). Open reading frames in each locus are identified by boxes; gray boxes indicate ORFs that are not common to the three enediyne loci, black boxes indicate ORFs that are common to the three enediyne loci and are labeled using a four-letter protein family designation. The scale is in kilobases.

A total of 479 $S.$ macromyceticus GSTs obtained with the forward sequencing primer were analyzed by sequence comparison using the Blast algorithm (Altschul et al., supra). Sequence alignments displaying an E value of at least e-5 were considered as significantly homologous and retained for further evaluation. GSTs showing similarity to a gene of interest can be at this point selected and used to identify larger segments of genomic DNA from the CIL library that include the gene(s) of interest. Several $S.$ macromyceticus GSTs that contained genes of interest were pursued. One of these GSTs encoded a portion of an oxidoreductase based on Blast analysis of the forward read and a portion of the macromomycin apoprotein based on Blast analysis of the reverse read. Oligonucleotide probes derived from such GSTs were used to screen the CIL library and the resulting positive cosmid clones were sequenced. Overlapping cosmid clones provided in excess of 125 kb of sequence information surrounding the macromomycin apoprotein gene (FIG. 5).

Hybridization oligonucleotide probes were radiolabeled with $P^{32}$ using T4 polynucleotide kinase (New England Biolabs) in 15 microliter reactions containing 5 picomoles of oligonucleotide and 6.6 picomoles of $[\gamma-P^{32}]$ATP in the kinase reaction buffer supplied by the manufacturer. After 1 hour at 37 degrees Celcius, the kinase reaction was terminated by the addition of EDTA to a final concentration of 5 mM. The specific activity of the radiolabeled oligonucleotide probes was estimated using a Model 3 Geiger counter (Ludlum Measurements Inc., Sweetwater, Tex.) with a built-in integrator feature. The radiolabeled oligonucleotide probes were heat-denatured by incubation at 85 degrees Celcius for 10 minutes and quick-cooled in an ice bath immediately prior to use.

The $S.$ macromyceticus CIL library membranes were pretreated by incubation for at least 2 hours at 42 degrees Celcius in Prehyb Solution (6×SSC; 20 mM $NaH_2PO_4$; 5× Denhardt's; 0.4% SDS; 0.1 mg/ml sonicated, denatured salmon sperm DNA) using a hybridization oven with gentle rotation. The membranes were then placed in Hyb Solution (6×SSC; 20 mM $NaH_2PO_4$; 0.4% SDS; 0.1 mg/ml sonicated, denatured salmon sperm DNA) containing 1×10$^6$ cpm/ml of radiolabeled oligonucleotide probe and incubated overnight at 42 degrees Celcius using a hybridization oven with gentle rotation. The next day, the membranes were washed with Wash Buffer (6×SSC, 0.1% SDS) for 45 minutes each at 46, 48, and 50 degrees Celcius using a hybridization oven with gentle rotation. The *S. macromyceticus* CIL membranes were then exposed to X-ray film to visualize and identify the positive cosmid clones. Positive (FIG. 6, Table 2). Table 2 lists the results of sequence comparison using the Blast algorithm (Altschul et al., supra) for each of these enediyne-specific polypeptides from the macromomycin locus. Homology was determined using the BLASTP algorithm with the default parameters.

TABLE 2

MACR locus

| Family | #aa | GenBank homology Accession, #aa | probability | identity | similarity | proposed function of GenBank match |
|---|---|---|---|---|---|---|
| PKSE | 1936 | T37056, 2082aa | 6e-86 | 273/897 (30.43%) | 372/897 (41.47%) | multi-domain beta keto-acyl synthase, *Streptomyces coelicolor* |
|  |  | NP_485686.1, 1263aa | 5e-82 | 256/900 (28.44%) | 388/900 (43.11%) | heterocyst glycolipid synthase, *Nostoc* sp |
|  |  | AAL01060.1, 2573aa | 6e-78 | 244/884 (27.6%) | 376/884 (42.53%) | polyunsaturated fatty acid synthase, *Photobacterium profundum* |
| TEBC1 | 162 | NP_249659.1, 148aa | 4e-06 | 38/134 (28.36%) | 59/134 (44.03%) | hypothetical protein, *Pseudomonas aeruginosa* |
|  |  | CAB50777.1, 150aa | 4e-06 | 39/145 (26.9%) | 65/145 (44.83%) | hypothetical protein, *Pseudomonas putida* |
|  |  | NP_214031.1, 128aa | 2e-04 | 33/129 (25.58%) | 55/129 (42.64%) | hypothetical protein, *Aquifex aeolicus* |
| TEBC2 | 157 | NP_242865.1, 138aa | 0.27 | 31/131 (23%) | 50/131 (37%) | 4-hydroxybenzoyl-CoA thioesterase, *Bacillus halodurans* |
| UNBL | 327 | NP_422192.1, 423aa | 0.095 | 30/86 (34.88%) | 40/86 (46.51%) | peptidase, *Caulobacter creacentus* |
| UNBV | 642 | NO HOMOLOG |  |  |  |  |
| UNBU | 433 | NP_486037.1, 300aa | 1e-06 | 49/179 (27.37%) | 83/179 (46.37%) | hypothetical protein, *Nostoc* sp. |
|  |  | NP_107088.1, 503aa | 2e-04 | 72/280 (25.71%) | 126/280 (45%) | hypothetical protein, *Mesorhizobium loti* |
|  |  | NP_440874.1, 285aa | 4e-04 | 47/193 (24.35%) | 86/193 (44.56%) | hypothetical protein, *Synechocystis* sp | clones were identified, cosmid DNA was extracted from 30 ml cultures using the alkaline lysis method (Sambrook et al., supra) and the inserts were entirely sequenced using a shotgun sequencing approach (Fleischmann et al., (1995) *Science*, 269:496–512).

Sequencing reads were assembled using the Phred-Phrap™ algorithm (University of Washington, Seattle, USA) recreating the entire DNA sequence of the cosmid insert. Reiterations of hybridizations of the CIL library with probes derived from the ends of the original cosmid allow indefinite extension of sequence information on both sides of the original cosmid sequence until the complete sought-after gene cluster is obtained. The structure of macromomycin (auromomycin) has not been elucidated, however the apoprotein component has been well characterized (Van Roey and Beerman (1989) Proc Natl Acad Sci USA Vol. 86 pp. 6587–6591). An unusual polyketide synthase (PKSE) was found approximately 40 kb upstream of the macromomycin apoprotein gene (FIG. 5). No other polyketide synthase or fatty acid synthase gene cluster was found in the vicinity of the macromomycin apoprotein gene, suggesting that the PKSE may be the only polyketide synthase involved in the biosynthesis of macromomycin (auromomycin).

Four other enediyne-specific genes clustered with or in close proximity to the PKSE gene were found in the macromomycin biosynthetic locus. These genes and the polypeptides that they encode have been assigned the family designations TEBC, UNBL, UNBV, and UNBU. The macromomycin locus contains two copies of the TEBC gene The macromomycin genes listed in Table 2 are arranged as depicted in FIG. 6. The UNBL, UNBV, UNBU, PKSE, and TEBC1 genes span approximately 10.5 kb and are tandemly arranged in the order listed. Thus these five genes may constitute an operon. A second TEBC gene (TEBC2) is found approximately 6.6 kb downstream of the 5-gene enediyne-specific cassette. The macromomycin enediyne-specific cassette is composed of six functionally linked genes and polypeptides, five of which may be expressed as a single operon.

Example 2

Identification and Sequencing of the Calicheamicin Biosynthetic Locus

Calicheamicin is a non-chromoprotein enediyne produced by *Micromonospora echinospora* subsp. *calichensis* NRRL 15839. Both GSL and CIL genomic DNA libraries of *M. echinospora* genomic DNA were prepared as described in Example 1. A total of 288 GSL clones were sequenced with the forward primer and analyzed by sequence comparison using the Blast algorithm (Altschul et al., supra) to identify those clones that contained inserts related to the macromomycin (auromomycin) biosynthetic genes, particularly the PKSE. Such GST clones were identified and were used to isolate cosmid clones from the *M. echinospora* CIL library. Overlapping cosmid clones were sequenced and assembled as described in Example 1. The resulting DNA sequence information was more than 125 kb in length and included the calicheamicin genes described in WO 00/37608. The calicheamicin biosynthetic genes disclosed in WO 00/37608 span only from 37140 bp to 59774 bp in FIG. 5 and do not include the unusual PKS gene (PKSE) and four other flanking genes (UNBL, UNBV, UNBU, and TEBC) that are homologuous to those in the macromomycin biosynthetic locus. Table 3 lists the results of sequence comparison using the Blast algorithm (Altschul et al., supra) for each of these enediyne-specific polypeptides from the calicheamicin locus. Homology was determined using the BLASTP algorithm with the default parameters.

were prepared as described in Example 1. A total of 435 GSL clones were sequenced with the forward primer and analyzed by sequence comparison using the Blast algorithm (Altschul et al., supra).

Surprisingly, two GSTs from *S. ghanaensis* were identified as encoding portions of genes in the 5-gene cassette common to both the macromomycin and calicheamicin enediyne biosynthetic loci. One of these GSTs encoded a portion of a TEBC homologue and the other encoded a portion of a UNBV homologue. These *S. ghanaensis* GSTs

TABLE 3

CALI locus

| Family | #aa | GenBank homology Accession, #aa | probability | identity | similarity | proposed function of GenBank match |
|---|---|---|---|---|---|---|
| PKSE | 1919 | AAF26923.1, 2439aa | 1e-60 | 228/876 (26.03%) | 317/876 (36.19%) | polyketide synthase, *Polyangium cellulosum* |
|  |  | NP_485686.1, 1263aa | 5e-59 | 148/461 (32.1%) | 210/461 (45.55%) | heterocyst glycolipid synthase, Nostoc sp |
|  |  | T37056, 2082aa | 9e-58 | 161/466 (34.55%) | 213/466 (45.71%) | multi-domain beta keto-acyl synthase, *Streptomyces coelicolor* |
| TEBC | 148 | NP_249659.1, 148aa | 8e-06 | 41/133 (30.83%) | 62/133 (46.62%) | hypothetical protein, *Pseudomonas aeruginosa* |
|  |  | AAD49752.1, 148aa | 1e-05 | 41/138 (29.71%) | 63/138 (45.65%) | orf1, *Pseudomonas aeruginosa* |
|  |  | NP_242865.1, 138aa | 2e-04 | 32/130 (24.62%) | 56/130 (43.08%) | 4-hydroxybenzoyl-CoA thioesterase, *Bacillus halodurans* |
| UNBL | 322 | NO HOMOLOG |  |  |  |  |
| UNBV | 651 | NO HOMOLOG |  |  |  |  |
| UNBU | 321 | NP_486037.1, 300aa | 8e-09 | 61/210 (29.05%) | 99/210 (47.14%) | hypothetical protein, Nostoc sp |
|  |  | NP_107088.1, 503aa | 5e-05 | 58/208 (27.88%) | 96/208 (46.15%) | hypothetical protein, *Mesorhizobium loti* |

The calicheamicin genes listed in Table 3 are arranged as depicted in FIG. 6. The UNBL, UNBV, UNBU, PKSE, and TEBC genes span approximately 10.5 kb and are tandemly arranged in the order listed. Thus these five genes may constitute an operon. Therefore, the calicheamicin enediyne-specific cassette is composed of five functionally linked genes and polypeptides that may be expressed as a single operon.

Example 3

Identification and Sequencing of the Biosynthetic Locus for an Unknown Chromoprotein Enediyne in *Streptomyces ghanaensis*

The genomic sampling method described in Example 1 was applied to genomic DNA from *Streptomyces ghanaensis* NRRL B-12104. *S. ghanaensis* has not previously been described to produce enediyne compounds. Both GSL and CIL genomic DNA libraries of *S. ghanaensis* genomic DNA were subsequently found in a genetic locus referred to herein as 009C (FIG. 5). As in the macromomycin and calicheamicin enediyne biosynthetic loci, the UNBV and TEBC genes in 009C were found to flank a PKSE gene and adjacent to UNBL and UNBU genes. The 009C locus included a gene encoding a homologue of the macromomycin apoprotein approximately 50 kb downstream of the UNBV-UNBU-UNBL-PKSE-TEBC cassette. The presence of the 5-gene cassette in the vicinity of an apoprotein suggests that 009C represents a biosynthetic locus for an unknown chromoprotein enediyne that was not previously described to be produced by *S. ghanaensis* NRRL B-12104.

Table 4 lists the results of sequence comparison using the Blast algorithm (Altschul et al., supra) for each of these enediyne-specific polypeptides from the 009C locus. Homology was determined using the BLASTP algorithm with the default parameters.

TABLE 4

009C locus

| Family | #aa | GenBank homology Accession, #aa | probability | identity | similarity | proposed function of GenBank match |
|---|---|---|---|---|---|---|
| PKSE | 1956 | T37056, 2082aa | 1e-101 | 298/902 (33.04%) | 395/902 (43.79%) | multi-domain beta keto-acyl synthase, *Streptomyces coelicolor* |
|  |  | NP_485686.1, 1263aa | 2e-99 | 274/900 (30.44%) | 407/900 (45.22%) | heterocyst glycolipid synthase, Nostoc sp |
|  |  | BAB69208 1, 2365aa | 3e-89 | 282/880 (32.05%) | 366/880 (41.59%) | polyketide synthase, *Streptomyces avermitilis* |
| TEBC | 152 | NP_249659.1, 148aa | 5e-07 | 39/131 (29.77%) | 59/131 (45.04%) | hypothetical protein, *Pseudomonas aeruginosa* |

TABLE 4-continued 009C locus

| Family | #aa | GenBank homology Accession, #aa | probability | identity | similarity | proposed function of GenBank match |
|---|---|---|---|---|---|---|
| | | NP_231474.1, 155aa | 2e-04 | 30/129 (23.26%) | 62/129 (48.06%) | hypothetical protein, *Vibrio cholerae* |
| | | NP_214031.1, 128aa | 2e-04 | 31/128 (24.22%) | 55/128 (42.97%) | hypothetical protein, *Aquifex aeolicus* |
| UNBL | 329 | NO HOMOLOG | | | | |
| UNBV | 636 | NP_615809.1, 2275aa | 6e-05 | 72/314 (22.93%) | 114/314 (36.31%) | cell surface protein, *Methanosarcina acetivorans* |
| UNBU | 382 | NP_486037.1, 300aa | 4e-07 | 46/175 (26.29%) | 81/175 (46.29%) | hypothetical protein, Nostoc sp |
| | | NP_107088.1, 503aa | 6e-06 | 68/255 (26.67%) | 118/255 (46.27%) | hypothetical protein, *Mesorhizobium loti* |

The 009C genes listed in Table 4 are arranged as depicted in FIG. 6. The UNBL, UNBV, UNBU, PKSE, and TEBC genes span approximately 10.5 kb and are tandemly arranged In the order listed. These five genes may constitute an operon. Therefore, the 009C enediyne-specific cassette is composed of five functionally linked genes and polypeptides that may be expressed as a single operon.

Example 4

The 5-Gene Enediyne Cassette is Present in the Neocarzinostatin Biosynthetic Locus Neocarzinostatin is a chromoprotein enediyne produced by *Streptomyces carzinostaticus* subsp. *neocarzinostaticus* ATCC 15944. The neocarzinostatin biosynthetic locus was sequenced and was shown to contain, in addition to the neocarzinostatin apoprotein gene, the 5-gene cassette that is present in the macromomycin and calicheamicin enediyne biosynthetic loci. The genes and proteins involved in the biosynthesis of neocarzinostatin are disclosed in co-pending application U.S. Ser. No. 60/354,474. The presence of the 5-gene cassette in the neocarzinostatin biosynthetic locus reconfirms that it is present in all enediyne biosynthetic loci.

Table 5 lists the results of sequence comparison using the Blast algorithm (Altschul et al., supra) for each of these enediyne-specific polypeptides from the neocarzinostatin locus. Homology was determined using the BLASTP algorithm with the default parameters.

TABLE 5

NEOC locus

| Family | #aa | GenBank homology Accession, #aa | probability | identity | similarity | proposed function of GenBank match |
|---|---|---|---|---|---|---|
| PKSE | 1977 | T37056, 2082aa | 7e-93 | 285/891 (31.99%) | 384/891 (43.1%) | multi-domain beta keto-acyl synthase, *Streptomyces coelicolor* |
| | | NP_485686.1, 1283aa | 8e-88 | 261/890 (29.33%) | 397/890 (44.61%) | heterocyst glycolipid synthase, Nostoc ap |
| | | BAB69208.1, 2365aa | 2e-85 | 276/876 (31.51%) | 370/876 (42.24%) | polyketide synthase, *Streptomyces avermitilis* |
| TEBC | 153 | NP_249659.1, 148aa | 3e-06 | 37/129 (28.68%) | 56/129 (43.41%) | hypothetical protein, *Pseudomonas aeruginosa* |
| | | CAB50777.1, 150aa | 1e-04 | 32/114 (28.07%) | 53/114 (46.49%) | hypothetical protein, *Pseudomonas putida* |
| | | NP_214031.1, 128aa | 2e-04 | 34/129 (26.36%) | 55/129 (42.64%) | hypothetical protein, *Aquifex aeolicus* |
| UNBL | 328 | | | | | |
| UNBV | 636 | NP_618575.1, 1881aa | 2e-05 | 77/317 (24.29%) | 117/317 (36.91%) | cell surface protein, *Methanosarcina acetivorans* |
| UNBU | 364 | NP_107088.1, 503aa | 2e-05 | 49/158 (31.01%) | 79/158 (50%) | hypothetical protein, *Mesorhizobium loti* |
| | | NP_486037.1, 300aa | 8e-05 | 33/126 (26.19%) | 60/126 (47.62%) | hypothetical protein, Nostoc sp |

The neocarzinostatin genes listed in Table 5 are arranged as depicted in FIG. 6. The UNBL, UNBV, UNBU, PKSE, and TEBC genes span approximately 10.5 kb and are tandemly arranged in the order listed. Thus these five genes may constitute an operon. Therefore, the neocarzinostatin enediyne-specific cassette is composed of five functionally linked genes and polypeptides that may be expressed as a single operon.

Example 5

The 5-Gene Enediyne Cassette is Present in the Biosynthetic Locus of an Unknown Chromoprotein Enediyne in *Amycolatopsis orientalis*

The genomic sampling method described in Example 1 was applied to genomic DNA from *Amycolatopsis orientalis* ATCC 43491. *A. orientalis* has not previously been described to produce enediyne compounds. Both GSL and CIL genomic DNA libraries of *A. orientalis* genomic DNA were prepared as described in Example 1.

A total of 1025 GSL clones were sequenced with the forward primer and analyzed by sequence comparison using the Blast algorithm (Altschul et al., supra). Several secondary metabolism loci were identified and sequenced as described in Example 1. One of these loci (herein referred to as 007A) includes a 5-gene cassette common to all enediyne biosynthetic loci. The arrangement of the five genes of the cassette in 007A is shown in FIG. 6 Interestingly, the *A. orientalis* genome also contains an enediyne apoprotein gene that is similar to that from the macromomycin and 009C loci as well as other chromoprotein enediynes (data not shown). Therefore, *A. orientalis*, the producer of the well-known glycopeptide antibiotic vancomycin, has the genomic potential to produce a chromoprotein enediyne.

Table 6 lists the results of sequence comparison using the Blast algorithm (Altschul et al., supra) for each of the enediyne-specific polypeptides from the 007A locus. Homology was determined using the BLASTP algorithm with the default parameters.

Example 6

The 5-Gene Enediyne Cassette is Present in the Biosynthetic Locus of an Unknown Enediyne in *Kitasatosporia* sp. CECT 4991

The genomic sampling method described in Example 1 was applied to genomic DNA from *Kitasatosporia* sp. CECT 4991. This organism was not previously described to produce enediyne compounds. Both GSL and CIL genomic DNA libraries of *Kitasatosporia* sp. genomic DNA were prepared as described in Example 1.

A total of 1390 GSL clones were sequenced with the forward primer and analyzed by sequence comparison using the Blast algorithm (Altschul et al., supra). Surprisingly, two GSTs from *Kitasatosporia* sp. were identified as encoding portions of genes in the 5-gene cassette common to enediyne biosynthetic loci. One of these GSTs encoded a portion of a

TABLE 6

007A locus

| Family | #aa | GenBank homology Accession, #aa | probability | identity | similarity | proposed function of GenBank match |
|---|---|---|---|---|---|---|
| PKSE | 1939 | T37056, 2082aa | 5e-96 | 291/906 (32.12%) | 399/906 (44.04%) | multi-domain beta keto-acyl synthase, *Streptomyces coelicolor* |
|  |  | NP_485686.1, 1263aa | 9e-87 | 255/897 (28.43%) | 395/897 (44.04%) | heterocyst glycolipid synthase, Nostoc sp |
|  |  | BAB69208.1, 2365aa | 8e-86 | 285/926 (30.78%) | 393/926 (42.44%) | modular polyketide synthase, *Streptomyces avermitilis* |
| TEBC | 146 | NP_214031.1, 128aa | 0.052 | 28/124 (22.58%) | 51/124 (41.13%) | hypothetical protein, *Aquifex aeolicus* |
| UNBL | 324 | NO HOMOLOG |  |  |  |  |
| UNBV | 654 | NP_618575.1, 1881aa | 0.001 | 80/332 (24.1%) | 117/332 (35.24%) | cell surface protein, *Methanosarcina acetivorans* |
| UNBU | 329 | NP_486037.1, 300aa | 0.005 | 56/245 (22.86%) | 96/245 (39.18%) | hypothetical protein, Nostoc sp |

The 007A genes listed in Table 6 are arranged as depicted in FIG. 6. The UNBL, UNBV, and UNBU genes span approximately 4 kb and are tandemly arranged in the order listed. The PKSE and TEBC genes span approximately 6.5 kb and are tandemly arranged in the order listed. Thus these five genes may constitute two operons. The two putative operons are separated by approximately 5 kb. Although these two clusters of genes may not be transcriptionally linked to one another, they are still functionally linked. Therefore, the 007A enediyne-specific cassette is composed of five functionally linked genes and polypeptides, three of which may be expressed as a one operon and two of which may be expressed as a second operon.

PKSE homologue and the other encoded a portion of a UNBV homologue. These *Kitasatosporia* sp. GSTs were subsequently found in a genetic locus referred to herein as 028D which includes a 5-gene cassette common to all enediyne biosynthetic loci. The arrangement of the five genes of the cassette in 028D is shown in FIG. 6. Therefore, *Kitasatosporia* sp. CECT 4991 has the genomic potential to produce enediyne compound(s).

Table 7 lists the results of sequence comparison using the Blast algorithm (Altschul et al., supra) for each of the enediyne-specific polypeptides from the 028D locus. Homology was determined using the BLASTP algorithm with the default parameters

TABLE 7

028D locus

| Family | #aa | GenBank homology Accession, #aa | probability | identity | similarity | proposed function of GenBank match |
|---|---|---|---|---|---|---|
| PKSE | 1958 | BAB69208.1, 2365aa | 1e-81 | 273/926 (29.48%) | 354/926 (38.23%) | polyketide synthase, *Streptomyces avermitilis* |
|  |  | T37056, 2082aa | 3e-78 | 263/895 (29.39%) | 356/895 (39.78%) | multi-domain beta keto-acyl synthase, *Streptomyces coelicolor* |
|  |  | NP_485686.1, 1263aa | 7e-71 | 231/875 (26.4%) | 345/875 (39.43%) | heterocyst glycolipid synthase, Nostoc sp |
| TEBC | 158 | NP_249659.1, 148aa | 1e-04 | 38/133 (28.57%) | 61/133 (45.86%) | hypothetical protein, *Pseudomonas aeruginosa* |
|  |  | AAD49752.1, 148aa | 3e-04 | 38/138 (27.54%) | 62/138 (44.93%) | orf1, *Pseudomonas aeruginosa* |
|  |  | NP_231474.1, 155aa | 7e-04 | 31/127 (24.41%) | 61/127 (48.03%) | hypothetical protein, *Vibrio* |

TABLE 7-continued 028D locus

| Family | #aa | GenBank homology Accession, #aa | probability | identity | similarity | proposed function of GenBank match |
|---|---|---|---|---|---|---|
| | | | | | | cholerae |
| UNBL | 327 | NO HOMOLOG | | | | |
| UNBV | 676 | NO HOMOLOG | | | | |
| UNBU | 338 | NP_486037.1, 300aa | 5e-08 | 66/240 (27.5%) | 105/240 (43.75%) | hypothetical protein, Nostoc sp |
| | | NP_440874.1, 285aa | 2e-04 | 51/190 (26.84%) | 98/190 (51.58%) | hypothetical protein, Synechocystis sp |

The 028D genes listed in Table 7 are arranged as depicted in FIG. 6. The UNBV, UNBU, PKSE, and TEBC genes span approximately 9.5 kb and are tandemly arranged in the order listed. Thus these four genes may constitute an operon. This putative operon is separated from the UNBL gene, which is oriented in the opposite direction relative to the putative operon, by approximately 10.5 kb. Although the UNBL gene cannot be transcriptionally linked to the other genes, it is still functionally linked to the former. Therefore, the 028D enediyne-specific cassette is composed of five functionally linked genes and polypeptides, four of which may be expressed as a single operon. Although expression of functionally linked enediyne-specific genes may be under control of distinct transcriptional promoters they may, nonetheless, be expressed in a concerted fashion. As depicted in FIG. 6, the 028D biosynthetic locus is unique in that it is the only example whose enediyne-specific genes are not all oriented in the same direction.

Example 7

The 5-Gene Enediyne Cassette is Present in the Biosynthetic Locus of an Unknown Enediyne in *Micromonospora megalomicea*

The genomic sampling method described in Example 1 was applied to genomic DNA from *Micromonospora megalomicea* NRRL 3275. This organism was not previously described to produce enediyne compounds. Both GSL and CIL genomic DNA libraries of *M. megalomicea* genomic DNA were prepared as described in Example 1.

A total of 1390 GSL clones were sequenced with the forward primer and analyzed by sequence comparison using the Blast algorithm (Altschul et al., supra). Surprisingly, one GST from *M. megalomicea* was identified as encoding a portion of the PKSE gene present in the 5-gene cassette common to biosynthetic loci. The forward read of this GST encoded the C-terminal portion of the KS domain and the N-terminal portion of the AT domain of a PKSE gene. The complement of the reverse read of this GST encoded the C-terminal portion of the AT domain of a PKSE gene. This *M. megalomicea* GST was subsequently found in a genetic locus referred to herein as 054A which includes a 5-gene cassette common to all enediyne biosynthetic loci. The arrangement of the five genes of the cassette in 054A is shown in FIG. 6. Therefore, *M. megalomicea* has the genomic potential to produce enediyne compound(s).

Table 8 lists the results of sequence comparison using the Blast algorithm (Altschul et al., supra) for each of the enediyne-specific polypeptides from the 054A locus. Homology was determined using the BLASTP algorithm with the default parameters.

TABLE 8

054A locus

| Family | #aa | GenBank homology Accession, #aa | probability | identity | similarity | proposed function of GenBank match |
|---|---|---|---|---|---|---|
| PKSE | 1927 | NP_485686.1, 1263aa | 3e-76 | 247/886 (27.88%) | 365/886 (41.2%) | heterocyst glycolipid synthase, Nostoc sp |
| | | T37056, 2082aa | 3e-75 | 269/903 (29.79%) | 354/903 (39.2%) | multi-domain beta keto-acyl synthase, Streptomyces coelicolor |
| | | BAB69208.1, 2365aa | 9e-74 | 277/923 (30.01%) | 359/923 (38.89%) | polyketide synthase, Streptomyces avermitilis |
| TEBC | 154 | NP_249659.1, 148aa | 2e-06 | 43/147 (29.25%) | 66/147 (44.9%) | hypothetical protein, Pseudomonas aeruginosa |
| | | AAD49752.1, 148aa | 2e-05 | 42/147 (28.57%) | 65/147 (44.22%) | orf1, Pseudomonas aeruginosa |
| | | CAB50777.1, 150aa | 1e-04 | 40/139 (28.78%) | 61/139 (43.88%) | hypothetical protein, Pseudomonas putida |
| UNBL | 322 | NO HOMOLOG | | | | |
| UNBV | 659 | CAC44518.1, 706aa | 0.048 | 50/166 (30.12%) | 67/166 (40.36%) | putative secreted esterase, Streptomyces coelicolor |
| UNBU | 354 | NP_486037.1, 300aa | 5e-06 | 66/268 (24.63%) | 118/268 (44.03%) | hypothetical protein, Nostoc sp |

The 054A genes listed in Table 8 are arranged as depicted in FIG. 6. The UNBL, PKSE, and TEBC genes span approximately 7.5 kb and are tandemly arranged in the order listed. The UNBV and UNBU genes span approximately 3 kb and are tandemly arranged in the order listed. Thus these five genes may constitute two operons. The two putative operons are separated by approximately 2 kb. Therefore, the 054A enediyne-specific cassette is composed of five functionally linked genes and polypeptides, three of which may be expressed as a one operon and two of which may be expressed as another operon.

Example 8

The 5-Gene Enediyne Cassette is Present in the Biosynthetic Locus of an Unknown Enediyne in *Saccharothrix aerocolonigenes*

The genomic sampling method described in Example 1 was applied to genomic DNA from *Saccharothrix aerocolonigenes* ATCC 39243. This organism was not previously described to produce enediyne compounds Both GSL and CIL genomic DNA libraries of *Saccharothrix aerocolonigenes* genomic DNA were prepared as described in Example 1.

A total of 513 GSL clones were sequenced with the forward primer and analyzed by sequence comparison using the Blast algorithm (Altschul et al., supra). Several secondary metabolism loci were identified and sequenced as described in Example 1. One of these loci (herein referred to as 132H) includes a 5-gene cassette common to all enediyne biosynthetic loci. The arrangement of the five genes of the cassette in 132H is shown in FIG. 6. Therefore, *Saccharothrix aerocolonigenes* has the genomic potential to produce enediyne compound(s).

Table 9 lists the results of sequence comparison using the Blast algorithm (Altschul et al., supra) for each of these enediyne-specific polypeptides from the 132H locus. Homology was determined using the BLASTP algorithm with the default parameters.

cassette is composed of five functionally linked genes and polypeptides that may be expressed as a single operon.

Example 9

The 5-Gene Enediyne Cassette is Present in the Biosynthetic Locus of an Unknown Enediyne in *Streptomyces kaniharaensis*

The genomic sampling method described in Example 1 was applied to genomic DNA from *Streptomyces kaniharaensis* ATCC 21070 This organism was not previously described to produce enediyne compounds. Both GSL and CIL genomic DNA libraries of *S. kaniharaensis* genomic DNA were prepared as described in Example 1.

A total of 1020 GSL clones were sequenced with the forward primer and analyzed by sequence comparison using the Blast algorithm (Altschul et al., supra). Surprisingly, one GST from *S. kaniharaensis* was identified as encoding a portion of the PKSE gene present in the 5-gene cassette common to biosynthetic loci. The forward read of this GST encoded the N-terminal portion of the KS domain of a PKSE gene. The complement of the reverse read of this GST encoded the C-terminal portion of the AT domain of a PKSE gene. This *S. kaniharaensis* GST was subsequently found in a genetic locus referred to herein as 135E which includes a 5-gene cassette common to all enediyne biosynthetic loci. The arrangement of the five genes of the cassette in 135E is shown in FIG. 6 Therefore, *S. kaniharaensis* has the genomic potential to produce enediyne compound(s).

TABLE 9

132H locus

| Family | #aa | GenBank homology Accession, #aa | probability | identity | similarity | proposed function of GenBank match |
|---|---|---|---|---|---|---|
| PKSE | 1892 | BAB69208.1, 2365aa | 1e-108 | 312/872 (35.78%) | 404/872 (46.33%) | polyketide synthase, *Streptomyces avermitilis* |
|  |  | T37056, 2082aa | 1e-101 | 290/886 (32.73%) | 407/886 (45.94%) | multi-domain beta keto-acyl synthase, *Streptomyces coelicolor* |
|  |  | T30183, 2756aa | 4e-94 | 271/886 (30.59%) | 398/886 (44.92%) | hypothetical protein. *Shewanella sp* |
| TEBC | 143 | NP_442358.1, 138aa | 0.001 | 32/127 (25.2%) | 48/127 (37.8%) | hypothetical protein, *Synechocystis sp.* |
| UNBL | 313 | NO HOMOLOG |  |  |  |  |
| UNBV | 647 | AAD34550.1, 1529aa | 0.012 | 76/304 (25%) | 105/304 (34.54%) | esterase, *Aspergillus terreus* |
| UNBU | 336 | NP_486037.1, 300aa | 1e-04 | 42/1 72 (24.42%) | 79/172 (45.93%) | hypothetical protein, *Nostoc sp* |
|  |  | NP_440874.1, 285aa | 1e-04 | 48/181 (26.52%) | 90/181 (49.72%) | hypothetical protein, *Synechocystis sp* |

The 132H genes listed in Table 9 are arranged as depicted in FIG. 6. The UNBL, UNBV, UNBU, PKSE, and TEBC genes span approximately 10.5 kb and are tandemly arranged in the order listed. Thus, these five genes may constitute an operon. Therefore, the 132H enediyne-specific Table 10 lists the results of sequence comparison using the Blast algorithm (Altschul et al., supra) for each of the enediyne-specific polypeptides from the 135E locus. Homology was determined using the BLASTP algorithm with the default parameters.

TABLE 10

135E locus

| Family | #aa | GenBank homology Accession, #aa | probability | identity | similarity | proposed function of GenBank match |
|---|---|---|---|---|---|---|
| PKSE | 1933 | T37056, 2082aa | 1e-65 | 282/909 (31.02%) | 365/909 (40.15%) | multi-domain beta keto-acyl synthase, *Streptomyces coelicolor* |
| | | BAB69208.1, 2365aa | 3e-84 | 285/925 (30.81%) | 366/925 (39.57%) | polyketide synthase, *Streptomyces avermitilis* |
| | | T30937, 1053aa | 2e-69 | 246/907 (27.12%) | 356/907 (39.25%) | glycolipid synthase, *Nostoc punctiforme* |
| TEBC | 154 | NP_249659.1, 146aa | 2e-07 | 41/132 (31.06%) | 63/132 (47.73%) | hypothetical protein, *Pseudomonas aeruginosa* |
| | | AAD49752.1, 148aa | 2e-06 | 40/132 (30.3%) | 62/132 (46.97%) | orf1, *Pseudomonas aeruginosa* |
| | | NP_214031.1, 128aa | 5e-04 | 35/127 (27.56%) | 60/127 (47.24%) | hypothetical protein, *Aquifex aeolicus* |
| UNBL | 323 | NO HOMOLOG | | | | |
| UNBV | 655 | CAC44518.1, 706aa | 9e-04 | 41/135 (30.37%) | 59/135 (43.7%) | putative secreted esterase, *Streptomyces coelicolor* |
| UNBU | 346 | NP_486037.1, 300aa | 4e-09 | 52/191 (27.23%) | 87/191 (45.55%) | hypothetical protein, Nostoc sp |
| | | NP_440874.1, 285aa | 9e-06 | 47/197 (23.86%) | 89/197 (45.18%) | hypothetical protein, Synechocystis sp |

The 135E genes listed in Table 10 are arranged as depicted in FIG. 6. The UNBL, UNBV, and UNBU genes span approximately 4 kb and are tandemly arranged in the order listed. The PKSE and TEBC genes span approximately 6.5 kb and are tandemly arranged in the order listed. Thus these five genes may constitute two operons. The two putative operons are separated by approximately 6 kb. Although these two clusters of genes may not be transcriptionally linked to one another, they are still functionally linked. Therefore, the 135E enediyne-specific cassette is composed of five functionally linked genes and polypeptides, three of which may be expressed as a one operon and two of which may be expressed as another operon.

Example 10

The 5-Gene Enediyne Cassette is Present in the Biosynthetic Locus of an Unknown Enediyne in *Streptomyces citricolor*

The genomic sampling method described in Example 1 was applied to genomic DNA from *Streptomyces citricolor* IFO 13005. This organism was not previously described to produce enediyne compounds. Both GSL and CIL genomic DNA libraries of *S. citricolor* genomic DNA were prepared as described in Example 1.

A total of 1245 GSL clones were sequenced with the forward primer and analyzed by sequence comparison using the Blast algorithm (Altschul et al., supra). Several secondary metabolism loci were identified and sequenced as described in Example 1. One of these loci (herein referred to as 145B) includes a 5-gene cassette common to all enediyne biosynthetic loci. The arrangement of the five genes of the cassette in 145B is shown in FIG. 6. Therefore, *S citricolor* has the genomic potential to produce enediyne compound(s).

Table 11 lists the results of sequence comparison using the Blast algorithm (Altschul et al., supra) for each of the enediyne-specific polypeptides from the 145B locus. Homology was determined using the BLASTP algorithm with the default parameters.

TABLE 11

145B locus

| Family | #aa | GenBank homology Accession, #aa | probability | identity | similarity | proposed function of GenBank match |
|---|---|---|---|---|---|---|
| PKSE | 1958 | T37056, 2082aa | 4e-88 | 285/929 (30.68%) | 378/929 (40.69%) | multi-domain beta keto-acyl synthase, *Streptomyces coelicolor* |
| | | BAB69208.1,2365aa | 3e-82 | 284/923 (30.77%) | 375/923 (40.63%) | polyketide synthase, *Streptomyces avermitilis* |
| | | AAL01060.1,2573aa | 5e-78 | 240/855 (28.07%) | 354/855 (41.4%) | polyunsaturated fatty acid synthase, *Photobacterium profundum* |
| TEBC | 165 | NP_249659.1,148aa | 2e-07 | 39/133 (29.32%) | 60/133 (45.11%) | hypothetical protein, *Pseudomonas aeruginosa* |
| | | NP_231474.1,155aa | 3e-04 | 30/127 (23.62%) | 60/127 (47.24%) | hypothetical protein. *Vibrio choleree* |
| | | CAB50777 1,150aa | 4e-04 | 37/135 (27.41%) | 58/135 (42.96%) | hypothetical protein, *Pseudomonas pulida* |
| UNBL | 324 | NO HOMOLOG | | | | |

TABLE 11-continued 145B locus

| Family | #aa | GenBank homology Accession, #aa | probability | identity | similarity | proposed function of GenBank match |
| --- | --- | --- | --- | --- | --- | --- |
| UNBV | 659 | NP_618575.1,1881aa | 0.003 | 57/245 (23.27%) | 85/245 (34.69%) | cell surface protein, *Methanosarcina acetivorans* |
| UNBU | 337 | NP_486037.1,300aa | 0.002 | 62/267 (23.22%) | 109/267 (40.82%) | hypothetical protein, *Nostoc sp.* |

The 145B genes listed in Table 11 are arranged as depicted in FIG. 6. The UNBV, and UNBU genes span approximately 3 kb and are tandemly arranged in the order listed. The PKSE and TEBC genes span approximately 6.5 kb and are tandemly arranged In the order listed. Thus these four genes may constitute two operons. The two putative operons are separated by approximately 9.5 kb that includes the UNBL gene. Although these genes may not be transcriptionally linked to one another, they are still functionally linked. Therefore, the 145B enediyne-specific cassette is composed of five functionally linked genes and polypeptides, four of which may be expressed as two operons each containing two genes.

Example 11

Analysis of the Polypeptides Encoded by the 5-Gene Enediyne-Specific Cassette

The amino acid sequences of the PKSE, TEBC, UNBL, UNBV, and UNBU protein families from the ten enediyne biosynthetic loci described above were compared to one another by multiple sequence alignment using the Clustal algorithm (Thompson et al., 1994, *Nucleic Acids Res.* 22(2):4673–4680; Higgins et al., 1996, *Methods Enzymol.* 266:383–402, Higgins and Sharp (1988) Gene Vol. 73 pp. 237–244). The alignments are shown in FIGS. 8, 11, 12, 13, and 14, respectively. Where applicable, conserved residues or motifs important for the function are highlighted in black and additional features are indicated.

Figure 7:
FIG. 7 is a graphical depiction of the domain architecture typical of enediyne polyketide synthases (PKSE).

The PKSE family is a family of polyketide synthases that are involved in formation of enediyne warhead structures. FIG. 7 summarizes schematically the domain organization of a typical PKSE, showing the position and relative size of the putative domains based on Markov modeling of PKS domains: ketosynthase (KS), acyltransferase (AT), acyl carrier protein (ACP), ketoreductase (KR), dehydratase (DH), and 4'-phosphopantetheinyl transferase (PPTE) activities. Using the calicheamicin PKSE as an example, the full-length PKSE protein is 1919 amino acids in length As indicated in FIG. 8 for the calicheamicin PKSE, the KS domain spans positions 3 to 467 of the PKSE; the AT domain spans positions 482 to 905 of the PKSE, the ACP domain spans positions 939 to 1009 of the PKSE; a small domain of unknown function of approximately 130 amino acids (spanning positions 1025 to 1144 of the PKSE) is present between the ACP and the KR domains; the KR domain spans positions 1153 to 1414 of the PKSE; the DH domain spans positions 1421 to 1563 of the PKSE; a C-terminal 4'-phosphopantetheinyl transferase (PPTE) domain spans positions 1708 to 1914 of the PKSE; a small domain of about 110 amino acids (spanning positions 1591 to 1701 of the PKSE) is present between the DH and the PPTE domains.

The PKSE contains a conserved unusual ACP domain (FIG. 9A). This ACP domain contains several conserved residues that are also present in the well-characterized ACP of the actinorhodin type II PKS (PDBid:1AF8 in FIG. 9B). The most important conserved resudue is the serine residue to which a 4'-phosphopantetheine prosthetic group is covalently attached (corresponding to Ser-42 of 1AF8). In addition to Ser-42, several surface-exposed charged residues are conserved, namely Glu-20, Asp-37, and Glu-84 (highlighted in the alignment of FIG. 9A and highlighted and labeled in the three dimensional structure shown in FIG. 9B). Several buried uncharged or non-polar residues that may be important in stabilizing the overall fold of the ACP domain are also conserved, namely Leu-14, Val-15, Gly-57, Pro-71, Ala-83, and Ala-85 (highlighted in the alignment and three dimensional structure shown in FIG. 9). Interestingly, the conserved serine (Ser-42) is almost always immediately preceeded by another serine in the ACP domains of PKSEs. As shown in FIG. 8, nine of the ten PKSE members contain this double serine arrangement, the only exception being that from the 132H locus in which the first of the serine is replaced by a threonine. Therefore, PKSEs contain ACP domains with two potential hydroxyl-containing residues in close proximity to one another. These ACPs may carry two 4'-phosphopantetheine prosthetic groups. The positioning of the KR and DH domains after the ACP is unusual among PKSs, but is described in one of the three PKS-like components of the eicosapentaenoic acid (EPA) and docosahexaenoic acid (DHA) biosynthetic machinery (Metz et al. (2001) *Science* Vol. 293 pp. 290–293). The unusual domain organization shared by the PKSE genes of the invention and the PKS-like synthetase involved in synthesis of polyunsaturated fatty acids suggests that enediyne warhead formation involves intermediates similar to those generated during assembly of polyunsaturated fatty acids.

The presence of an unusual ACP domain in the PKSE, and the absence of any obvious 4'-phosphopantetheinyl transferase or holo-ACP synthase (involved in phosphopantetheinyl transfer onto the conserved serine of the ACP) common to enediyne biosynthetic loci led us to search for the presence of a 4'-phosphopantetheinyl transferase. We examined the conserved domains of the PKSE whose functions were unaccounted for as well as the UNBL, UNBV, and UNBU polypeptides in more detail and determined that the PPTE domain was a 4'-phosphopantetheinyl transferase.

The C-terminal domains of the PKSEs from the biosynthetic loci of three known enediynes, namely neocarzinostatin (NEOC, aa 1620-1977), calicheamicin (CALI, aa 1562-1919) and macromomycin (MACR, aa 1582-1936), were analyzed for their folding using secondary structure predictions and salvation potential information (Kelley et al. (2000) *J. Mol. Biol.* Vol. 299 pp. 499–520). Comparison searches using a database of known 3-D structures of proteins revealed similarities between the C-terminal domains of the PKSEs and Sfp, the 4'-phosphopantetheinyl transferase from the *Bacillus subtilis* surfactin biosynthetic locus (Reuter et al. (1999) EMBO Vol. 18 pp. 6823–6831).

The alignment shown in FIG. 10A indicates the predicted secondary structures of all three C-terminal PKSE domains (PPTE domains) along with the X-ray crystallography-determined secondary structure of Sfp (PDB id: 1QR0). Alpha-helices are indicated by rectangles and β-sheets by arrows.

An overall conservation of secondary structure over the entire length of the proteins is evident. All major structural constituents of Sfp, namely α-helices α1–α5 and β-sheets β2–β4 and β8 are also present in PPTE domains. Similar to Sfp, the PPTE domains are predicted to have an intramolecular 2-fold pseudosymmetry.

The loop formed between α5 and β7 in Sfp is not present in the PPTE domains. It is believed that this region of Sfp is in part responsible for ACP recognition and contributes to the broad substrate specificity observed for this enzyme. The size of this loop appears to vary among phosphopantetheinyl transferases, as the EntD enzyme, which exhibits a greater ACP substrate specificity than Sfp, has a region between α5 and β7 structures shorter than that of Sfp but longer than that found in the PPTE domains. The short α5/β7 loop region found in the PPTE domains may reflect the need for a specific interaction with the rather unusual ACP domain found in the PKSE enzymes. Residues conserved in all phosphopantetheinyl transferases and shown in Sfp to make contacts with the CoA substrate and $Mg^{++}$ cofactor are also conserved in the PPTE domains (highlighted in FIG. 10A).

Figure 10B:
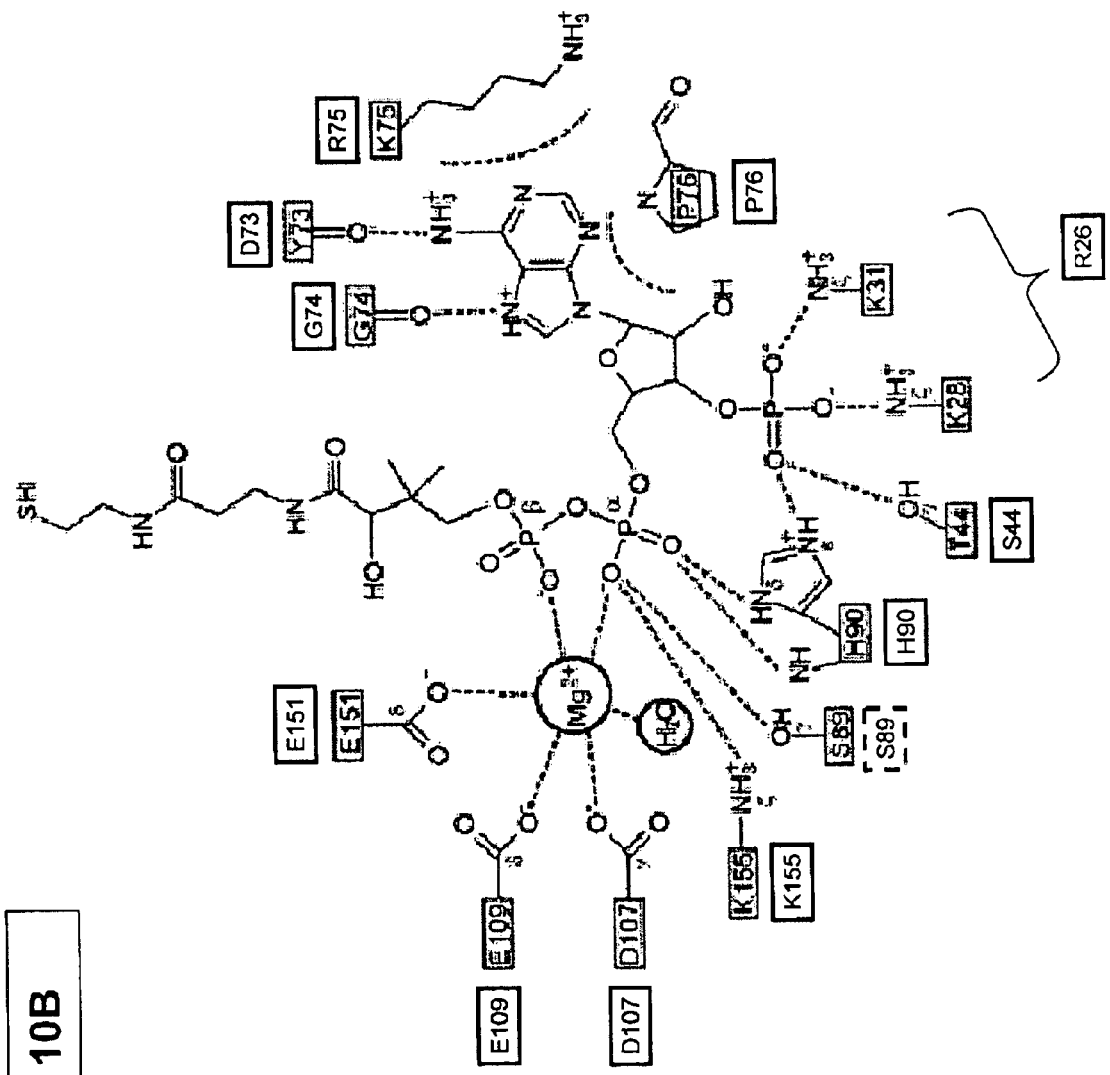
FIG. 10B shows how the conserved residues of the 4'-phosphopantetheinyl transferase Sfp co-ordinate a magnesium ion and coenzyme A; corresponding residues in the neocarzinostatin PPTE domain are shown in bold.

Referring to FIG. 10B, Sfp residues Lys-28 and Lys-31 make salt bridges with the 3'-phosphate of CoA and are not found in the PPTE domains; however, a similar interaction could be provided by the corresponding conserved residue Arg-26. Sfp Thr-44 makes a hydrogen bond and His-90 a salt bridge with the 3'-phosphate of CoA; similar hydrogen bonding potential is provided by the conserved serine found at the corresponding position 44 of the PPTE domains, while the histidine 90 residue is absolutely conserved in all three PPTE domains.

Sfp amino acid residues 73–76 hold in place the adenine base of CoA. The main chain carbonyl of Tyr-73 forms a hydrogen bond with the adenine amino group and residues Gly-74, Lys-75 and Pro-76 hold firmly in place the adenine ring. In the PPTE domains, a conserved aspartic acid that may form a salt bridge with the adenine amino group is substituted for Tyr-73 and a conserved arginine residue is substituted for Lys-75. The remaining two residues, Gly-74 and Pro-76, are also found in the PPTE domains.

Sfp residues Ser-89 and His-90 interact via hydrogen bonding and salt bridging with the α-phosphate of the CoA substrate. Similarly, Lys-155 in helix α5 interacts with the CoA α-phosphate. The His-90 and Lys-155 residues are highly conserved in the PPTE domains whereas Ser-89 is found only in the neocarzinostatin PPTE domain.

Sfp residues Asp-107, Glu-109 in the β4 sheet and Glu-151 in the α5 helix participate in the complexation of a metal ion (presumably $Mg^{++}$) together with the α and β phosphates of the CoA pyrophosphate and a water molecule. All three residues are also conserved in PPTE domains. Importantly, Asp-107 was altered by mutagenesis in Sfp and shown to be critical for catalytic activity but not for CoA binding of the protein suggesting the $Mg^{++}$ ion is important for catalysis (Quadri et al., 1998, Biochemistry, Vol. 37, 1585–1595).

In the Sfp protein, residue Glu-127 salt-bridges the amino group of Lys-150. In the PPTE domains, a Glu/Asp residue is found at the corresponding position 127, whereas Lys-150 is not conserved Since Glu-127 is highly conserved in the PPTE domains, it is conceivable that the role of Lys-150 is served by other basic residues in the vicinity, namely the conserved arginine at the corresponding position 145. Residue Trp-147, conserved in all phosphopantetheinyl transferases and shown to be critical for catalytic activity, is also present in all three PPTE domains (Quadri et al., 1998, Biochemistry, Vol. 37, 1585–1595).

The presence of a phosphopantetheinyl domain (PPTE) in the C-terminal part of the PKSE enediyne warhead PKS is reminiscent of the 4'-phosphopantetheinyl domain found in the yeast fatty acid synthase (FAS) complex, where it resides in the C-terminal region of the FAS α subunit. FAS is capable of auto-pantetheinylation resulting in a post-translational autoactivation of this enzyme (Fichtlscherer et al., 2000, Eur. J. Biochem., Vol. 267, 2666–2671). In a similar manner, the PKSE warhead PKSs are likely to be capable of auto-pantetheinylation and activation of their ACP domains before proceeding to the iterative synthesis of the polyunsaturated polyketide intermediate forming the enediyne core.

The ACP and KR domains of the PKSEs are separated by approximately 130 amino acids. The presence of a considerable number of invariable residues within this stretch of amino acids suggests that the putative domain formed by these 130 amino acids has a functional role. The putative domain may serve a structural role, for example as a protein-protein interaction domain or it may form a cleft adjacent to the ACP that acts as a "chain length factor" for the growing polyketide chain. A search of NCBI's Conserved Domain Database with Reverse Position Specific BLAST revealed several short stretches of homology to proteins that bind substrates such as ATP, AMP, NAD(P), as well as folates and double stranded RNA (adenosine deaminase). Thus, the putative domain may adopt a structure accommodating an adenosine or adenosine-like structure and serve as a cofactor-binding site. Alternatively, the domain might interact with the adenosine moiety of coenzyme A (CoA). As such, the physical proximity of the CoA to the ACP domain may facilitate the phosphopantetheinylation of the ACP. Yet another possibility is that a molecule of CoA is noncovalently-bound to the putative domain downstream of the ACP via its adenosine moiety and its phosphopantetheinyl tail protrudes out from the enzyme, as would the phosphopantetheinyl tail on the holo-ACP. Alternatively, the PPTE domain can carry a molecule of noncovalently-bound CoA. Thus, it is expected that KS carries out several iterations of condensation reactions involving the transfer of an acetyl group from an acetyl-ACP-thioester to a growing acyl-CoA chain that is non-covalently bound to the enzyme. The proposed scenario explains the presence of the TEBC, an acyl-CoA thioesterase rather than a "conventional" PKS-type thioesterase: the full-length polyketide chain generated by the PKSE is not tethered to the holo-ACP, but rather to a non-covalently bound CoA and the TEBC hydrolyzes the thioester bond of a polyketide-CoA to release the full-length polyketide and CoA. A CoA-activated thioester may render the polyketide more accessible to auxiliary enzymes involved in cyclization and acetylenation prior to or concomitant to hydrolytic release by TEBC.

FIG. 11 is a Clustal amino acid alignment showing the relationship between the TEBC family of proteins and the enzyme 4-hydroxybenzoyl-CoA thioesterase (1BVQ) of *Pseudomonas* sp. Strain CBS-3 for which the crystal structure has been previously determined (Benning et al. (1998) J. Biol. Chem. Vol. 273 pp. 33572–33579). The black bars highlight the three regions of conservation believed to play important roles in the catalysis for 4-hydroxybenzoyl-CoA thioesterase. Homology between the TEBC family of proteins and 1BVQ is concentrated in these three highlighted regions.

FIG. 12 is a Clustal amino acid alignment of the UNBL family of proteins. The UNBL family of proteins represents a novel group of conserved proteins that are unique to enediyne biosynthetic loci. The UNBL proteins are rich in basic residues and contain several conserved or invariant histidine residues. Besides the PKSE and TEBC proteins, the UNBL proteins are the only other proteins predicted by the PSORT program (Nakai et al. (1999) Trends Biochem. Sci. Vol. 24 pp. 34–36) to be cytosolic that are encoded by the enediyne warhead gene cassette and thus represent the best candidates for the acetylenase activity that is required to introduce triple bonds into the warhead structure.

FIG. 13 is a Clustal amino acid alignment of the UNBV family of proteins. PSORT analysis of the UNBV family of proteins predicts that they are secreted proteins. The approximate position of the putative cleavable N-terminal signal sequence is indicated above the alignment. The UNBV proteins display considerable amino acid conservation but do not have any known homologue. Thus, the UNBV family of proteins represents a novel group of conserved proteins of unknown function that are unique to enediyne biosynthetic loci.

FIG. 14 is a Clustal amino acid alignment of the UNBU family of proteins. PSORT analysis of the UNBU family of proteins predicts that they are integral membrane proteins with seven or eight putative membrane-spanning alpha helices (indicated by dashes in FIG. 14). The UNBU proteins display considerable amino acid conservation but do not have any known homologue. The UNBU family of proteins represents a novel group of conserved proteins that are unique to enediyne biosynthetic loci.

UNBU is likely involved in transport of the enediynes across the cell membrane. UNBU may also contribute, in part, to the biochemistry involved in the completion of the warhead. In the case of chromoprotein enediynes, the apoprotein carries its own cleavable N-terminal signal sequence and is probably exported independently of the chromoprotein by the general protein secretion machinery. Formation of the bioactive warhead, export, and binding of the chromophore and protein component must occur in and around the cell membrane to minimize damage to the producer and to maximize the stability of the natural product. UNBV is predicted to be an extracellular protein. UNBV may finalize or stabilize the warhead structure. UNBV may act in close association with the extracellularly exposed portion(s) of UNBU.

To date, we have sequenced over ten enediyne biosynthetic loci that contain the 5-gene cassette made up of PKSE, TEBC, UNBL, UNBV, and UNBU genes. In all cases, the PKSE and TEBC genes are adjacent to one another and the TEBC gene is always downstream of the PKSE gene. Moreover, these two genes are usually, if not always, translationally coupled. These observations suggest that the expression of the PKSE and TEBC genes is tightly coordinated and that their gene products, i.e, polypeptides, act together. Likewise, the UNBV and UNBU genes are always adjacent to one another and the UNBU gene is always downstream of the UNBV gene. Moreover, these two genes are usually, if not always, translationally coupled. These observations suggest that the expression of the UNBV and UNBU genes is tightly coordinated and that their gene products, i.e., polypeptides, act together.

Example 12

Common Mechanism for the Biosynthesis of Enediyne Warheads

Without intending to be limited to any particular biosynthetic scheme or mechanism of action, the genes and proteins of the present invention can explain formation of enediyne warheads in both chromoprotein enediynes and non-chromoprotein enediynes.

The PKSE is proposed to generate a highly conjugated polyunsaturated hepta/octaketide intermediate in a manner analogous to the action of polyunsaturated fatty acid synthases (PUFAs). The polyunsaturated fatty acyl intermediate is then modified by tailoring enzymes involving one or more of UNBL, UNBU and UNBV to introduce the acetylene bonds and form the ring structure(s). The conserved auxiliary proteins UNBL, UNBU and UNBV are expected to be involved in modulating iterations performed by the PKSE, or in subsequent transformations to produce the enediyne core in a manner analogous to action of lovastatin monaketide synthase, a fungal iterative type I polyketide synthase that is able to perform different oxidative/reductive chemistry at each iteration with the aid of at least one auxiliary protein (Kennedy et al., 1999, Science Vol. 284 pp. 1368–1372).

The acetate enrichment pattern of the enediyne moiety of esperamicin and dynemicin suggest that both are derived from an intact heptaketide/octaketide. There has been suggestion that esperamicin and dynemicin may share a common precursor (Lam et. al., J. Am. Chem. Soc. 1993, Vol. 115 pp. 12340). However, in the case of neocarzinostatin, representative of other chromoprotein enediynes, incorporation studies investigating carbon-carbon connectivities revealing that the final enediyne core contains uncoupled acetate atoms (Hensens et al., 1989 JACS, Vol. 111, pp. 3295–3299), and other studies regarding polyacetylene biosynthesis (Hensens et. al., supra), suggest that the chromoprotein enediyne precursors are distinct from those of the non-chromoprotein enediynes. Thus, prior art studies regarding formation of the enediyne core teach away from the present invention that genes and proteins common to both chromoprotein enediynes and non-chromoprotein enediynes are responsible for formation of the warhead in both classes of enediynes.

We propose that skeletal rearrangements may account for the distinct chromoprotein/nonchromoprotein enediyne labeling patterns. For instance, thermal electrocyclic rearrangement of an intermediate cyclobutene to a 1,3 diene could result in an isotopic labeling pattern consistent with that which has been reported.

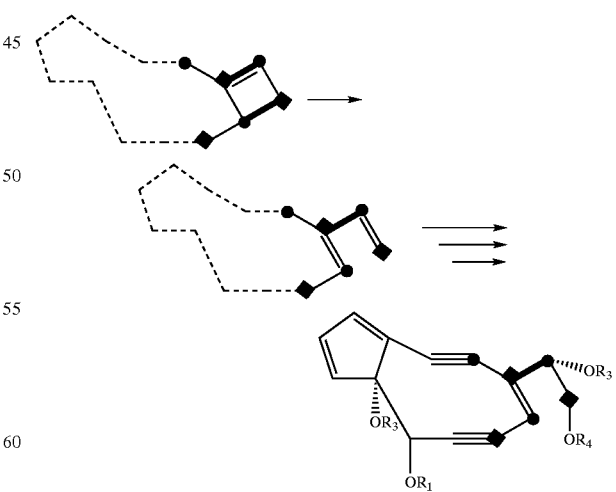

Accordingly, the warhead precursor in the formation of neocarzinostatin could be a heptaketide, similar to that proposed for the other classes of enediynes. Since calicheamicin and esperimicin do not contain any uncoupled acetates, the common unsaturated polyketidic precursor must rearrange differently from the chromoprotein class. However, the proposed biosynthetic scheme is consistent with one aspect of the present invention, namely that warhead formation in all enediynes involves common genes, proteins and common precursors.

Example 13

Heterologous Expression of Genes and Proteins of the Calicheamicin Enediyne Cassette

*Escherichia coli* was used as a general host for routine subcloning. *Streptomyces lividans* TK24 was used as a heterologous expression host. The plasmid pECO1202 was derived from plasmid pANT1202 (Desanti, C. L. 2000. The molecular biology of the *Streptomyces* snp Locus, 262 pp., Ph.D dissertation, Ohio State Univ., Columbus, Ohio) by deleting the Kpnl site in the multi-cloning site (MCS). pECO1202RBS contains a DNA sequence encoding a putative ribosome-binding site (AGGAG) introduced just upstream of the ClaI site located in the MCS of pECO1202.

*E. coli* strains carrying plasmids were grown in Luria-Bertani (LB) medium and were selected with appropriate antibiotics. *S. lividans* TK24 strains were grown on R2YE medium. (Kieser, T. et al., Practical Streptomyces Genetics, The John Innes Foundation, Norwich, United Kingdom, 2000).

Preparation of *S. lividans* TK24 protoplasts was carried out using the standard protocols. (Kieser et al., supra). Polyethylene glycol-induced protoplast transformation was carried out with 1 µg DNA per transformation. After protoplast regeneration on R5 agar medium for 16 h at 30° C., transformants were selected by overlaying each R5 plate with 50 µg/ml apramycin solutions. Transformants were grown in 50 ml flasks containing R2YE medium plus apramycin for seven days.

SDS-PAGE and Western-blotting were carried out by standard procedures (Sambrook, J. et al. 1989. Molecular cloning: a laboratory manual, $2^{nd}$ ed. Cold Spring Harbor Laboratory, Cold Spring Harbor, N.Y.). Penta-His antibody was obtained from Qiagen. Western blots were performed using the ECL detection kit from Amersham Pharmacia biotech using the manufacturer's suggested protocols. One milliliter of seven-day *S. lividans* culture was centrifuged and mycelium resuspended in cold extraction buffer (0.1M Tris-HCl, pH 7.6, 10 mM $MgCl_2$ and 1 mM PMSF). The mycelium was sonicated 4×20 sec on ice with 1 min intervals to release soluble protein. After 10 min centrifugation at 20,000 g, the supernatant and pellet fractions were diluted with sample buffer and subjected to SDS-PAGE and Western-blotting analysis.

DNA manipulations used in construction of expression plamsids were carried out using standard methods (Sambrook, J. et al., supra). The plasmid pECO1202 was used as the parent plasmid. Cosmid 061CR, carrying the calicheamicin biosynthetic gene locus was digested with Mfel, and the restriction fragments were made blunt ended by treatment with the Klenow fragment of DNA polymerase I. Upon additional digestion with Bg/II after phenol extraction and ethanol precipitation, the resulting 11.5 kb blunt-ended, Bg/II fragment was gel purified and cloned into pECO1202 (previously digested with EcoRI, made blunt ended by treatment with Klenow fragment of polymerase I, then digested with BamHI), to yield pECO1202-CALI-1, as shown in FIG. 15.

PCR was carried out on a PTC-100 programmable thermal controller (MJ research) with Pfu polymerase and buffer from Stratagene. A typical PCR mixture consisted of 10 ng of template DNA, 20 µM dNTPs, 5% dimethyl sulfoxide, 2 U of Pfu polymerase, 1 µM primers, and 1× buffer in a final volume of 50 µl. The PCR temperature program was the following: initial denaturation at 94° C. for 2 min, 30 cycles of 45 sec at 94° C., 1 min at 55° C., and 2 min at 72° C., followed by an additional 7 min at 72° C. A PCR product amplified by primer 1402, 5'-GAGTTGTATCGATGAGCAGGATCGCCGTCGTC GGC-3' [containing Cla I site (italic) and the start codon of PKSE gene (bold)], and primer 1420, 5'GTAGCCGGC-CGCCTCCGGCC (corresponding to the nucleotide sequence 940 to 959 bp of PKSE), was digested with ClaI and NheI and gel purified. This fragment was then cloned into ClaI, NheI digested pECO1202-CALI-1 to yield pECO1202-CALI-5 (FIG. 16).

PCR products were amplified by primer 1421, 5'-GACCTGCCGTACACCGTCTCC-3' (corresponding to the nucleotide sequence 5367 to 5387 bp of PKSE), and primer 1403, 5'-CCCAAGCTTCA GTGGTGGTGGTGGTGGTGCCCCTGCCCCACCGTG GCCGAC-3'[containing a His Tag (underlined), HindIII site (italic) and stop codon of TEBC (bold)], or primer 1500, 5'-CCCAAGCTTCACCCCTGCCCCACCGTGGCCGAC-3'(containing HindIII site (italic) and stop codon (bold) of TEBC). These PCR products were digested with HindIII and PstI, gel purified, and then cloned into HindIII, PstI digested pECO1205 to yield pECO1202-CALI-2 (with HisTag) and pECO1202-CALI-3 (without HisTag), respectively (FIG. 16).

The ClaI and HindIII fragments from pECO1202-CALI-2 and pECO1202-CALI-3 were cloned into pECO1202RBS to yield pECO1202-CALI-6 (with HisTag) and pECO1202-CALI-7 (without HisTag), respectively, as shown in FIG. 16.

Six transformants of *S. lividans* TK24 harboring pECO1202-CALI-2 were analyzed for expression of the His-tagged TEBC protein. Referring to FIG. 17, lane M provides molecular weight markers; lanes 1 to 6 represent crude extracts of independent transformants of *S. lividans* TK24 harboring pECO1202-CALI-2; lane 7 represents a crude extract of *S. lividans* TK24 harboring pECO1202-CALI-4; and lane 8 represents a crude extract of *S. lividans* TK24 harboring pECO1202 (control). TEBC protein expression was detected in four pECO1202-CALI-2 transformants by Western blotting using an antibody that recognizes the His-tag (lanes 2, 3, 5, 6). TEBC protein expression was also observed in the transformant of *S. lividans* TK24 harboring pECO1202-CALI-4 (lane 7).

As shown in FIG. 12, the TEBC protein was expressed as a soluble protein in *S. lividans* although the pellet fraction also contains TEBC protein, perhaps reflecting insoluble protein or incomplete lysis of *S. lividans* by the sonication procedure used. FIG. 12 provides an analysis of His-tagged TEBC protein derived from recombinant *S. lividans* TK24 by immunoblotting. The soluble and insoluble protein fractions of *S. lividans* transformants were separated by 12% SDS-polyacrylamide gel electrophoresis, blotted to PVDF membrane, and detected detection with the Penta-His antibody. Referring to FIG. 12, lane M provides molecular weight markers; lane 1 to 6 represent soluble (S) and pellet (P) protein fractions of independent transformants of *S. lividans* TK24 harboring pECO1202-CALI-2; lane C represents protein fractions of *S. lividans* TK24 harboring pECO1202 (control).

Example 14

Disruption of the PKSE Gene Abolishes Production of Enediyne

To confirm that the PKSE is critical to the biosynthesis of enediynes, the PKSE gene of the calicheamicin producer, *M.*

*echinospora*, was disrupted by introduction of an apramycin selectable marker as follows. *M. echinospora* was grown with a 1:100 fresh inoculum in 50 mL MS medium (Kieser et al., supra) supplemented with 5% PEG 8000 and 5 mM $MgCl_2$ for 24–36 h and 6 h prior to harvest, 0.5% glycine was added. The digest of the cell wall was accomplished via published procedures with the exception that 5 mg $mL^{-1}$ lysozyme and 2000 U mutanolysin were used. Under these conditions, protoplast formation was complete within 30–60 min after which the mixture was filtered twice through cotton wool. Transformation was accomplished via typical methodology (Kieser et al., supra) with a 1:1 mixture of T-buffer and PEG 2000 containing up to 10 μg of alkaline denatured DNA per transformation. The protoplasts were then plated on R2YE plates supplemented with 10 mg $L^{-1}$ $CoCl_2$ and submitted to antibiotic pressure (70 μg $mL^{-1}$ apramycin) after 3–4 days. To date, all attempts to use methods other than protoplast chemical transformation (e.g. phage transduction, conjugation and electroporation) have failed to introduce DNA into *M. echinospora*. Low transformation efficiencies were observed in all calicheamicin-producing *Micromonospora* strains tested, including those developed from strain improvement efforts. In comparison to other actinomycetes, *M. echinospora* protoplast regeneration was found to be slow (~4 weeks). Moreover, integration into the locus requires homologous fragments exceeding 3 kb in size as constructs containing PKSE fragments (or other calicheamicin gene fragments) smaller than 3 kb all failed to integrate into the chromosome (data not shown).

Nine independent apramycin-resistant PKSE disruption clones were obtained. All nine isolates mapped consistently with the expected PKSE gene disruption both by PCR fragment amplification and by Southern hybridization (data not shown). All nine PKSE disruption mutants and two parental controls were subsequently tested in parallel for calicheamicin production. Extracts from these strains were prepared as follows. Fresh *M. echinospora* cells grown in R2YE were inoculated 1:100 in 10 mL medium E (Kieser et al., supra) in stoppered 25 ml glass tubes containing a 4 cm stainless coil spring for better aeration and incubated on an orbital shaker with 230 rpm at 28° C. for one to three weeks. A 600 μl aliquot was removed at various time points, extracted with an equal volume of EtOAc and centrifuged at 10000×g for 5 min in a benchtop centrifuge. The supernatant was concentrated to dryness, the pellet redissolved in 200 μl acetonitrile, centrifuged again and the supernatant removed, concentrated to dryness and the residual material finally dissolved in 10 μl acetonitrile. One μl of this solution was utilized for the bioassays and the remaining 8 μl aliquot was utilized for analysis by HPLC (Ultrasphere-ODS chromatography, 5 μm, 4.6 mm×250 mm, 55:45 $CH_3CN$-0.2 $NH_4OAc$, pH 6.0, 1.0 mL $min^{-1}$, 280 nm detection). A typical *M. echinospora* fermentation contains a mixture of calicheamicins that are resolved by HPLC-$\gamma_1^I$ (retention time—7 min, ~60%), $\delta_1^I$ (retention time—5.7 min, ~30%), and $\alpha_3^I$ (retention time—3.8 min, ~10%)—and all of these calicheamicin components contribute to bioassay activities. The best production was found to occur during late log or early stationary phase growth. The estimate of calicheamicin production by parental *M. echinospora* is 0.78–0.85 mg $mL^{-1}$. Extracts were analyzed by i) the biological induction assay, a modified prophage induction assay used in the original discovery of the calicheamicins (Greenstein et al. (1986) *Antimicrob. Agents Chemotherap.* Vol. 29, 861); ii) the molecular break light assay, a DNA-cleavage assay based upon intramolecular fluorescence quenching optimized for DNA-cleavage by enediynes (in which fM calicheamicin concentrations are detectable) (Biggins et al. (2000) *Proc. Natl. Acad. Sci. USA* Vol. 97, 13537); and iii) high-performance liquid chromatography (HPLC) (described above). As expected, all three methods revealed that the parental *M. echinospora* fermentations produced 0.5–0.8 mg $L^{-1}$. In contrast, the PKSE gene disruption mutant strains were both devoid of any calicheamicin, known calicheamicin derivatives and/or enediyne activity by all three methods of detection. The elimination of calicheamicin production brought about by disruption of the PKSE gene indicates that it provides an essential activity for biosynthesis of calicheamicin. Based on the presence of the PKSE in all enediyne biosynthetic loci sequenced to date and on their overall conservation, it is expected that PKSEs fulfill the same, essential function in the biosynthesis of all enediyne structures.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all sizes and all molecular weight or mass values are approximate, and are provided for description.

Some open reading frames listed herein initiate with non-standard initiation codons (e.g. GTG—Valine or TTG—Leucine) rather than the standard initiation codon ATG, namely SEQ ID NOS: 2, 8, 16, 28, 30, 32, 38, 40, 42, 48, 54, 56, 70, 74, 76, 78, 80, 82, 84, 86, 88, 92, 98, 100. All ORFs are listed with M, V or L amino acids at the amino-terminal position to indicate the specificity of the first codon of the ORF. It is expected, however, that in all cases the biosynthesized protein will contain a methionine residue, and more specifically a formylmethionine residue, at the amino terminal position, in keeping with the widely accepted principle that protein synthesis in bacteria initiates with methionine (formylmethionine) even when the encoding gene specifies a non-standard initiation codon (e.g. Stryer, Biochemistry $3^{rd}$ edition, 1998, W. H. Freeman and Co., New York, pp. 752–754).

Patents, patent publications, procedures and publications cited throughout this application are incorporated herein in their entirety for all purposes.

What is claimed is:

1. A method of discovering an enediyne biosynthetic locus comprising the step of detecting, within a sample of microbial sequence information, the presence of at least one member of a protein family selected from the group consisting of PKSE, TEBC, UNBL, UNBV and UNBU.

2. The method of claim 1 wherein the step of detecting, within the sample of microbial sequence information, the presence of the at least one member of the protein family selected from the group consisting of PKSE, TEBC, UNBL, UNBV and UNBU comprises detecting a polypeptide sequence within the sample of microbial sequence information corresponding to the at least one member of the protein family.

3. The method of claim 1 wherein the step of detecting, within the sample of microbial sequence information, the presence of the at least one member of the protein family selected from the group consisting of PKSE, TEBC, UNBL, UNBV and UNBU comprises detecting a nucleic acid sequence encoding a polypeptide within the sample of microbial sequence information corresponding to the at least one member of the protein family.

4. The method of claim 1 wherein the sample of microbial sequence information is microbial sequence information sequence information stored on computer readable medium.

5. The method of claim 1 wherein the step of detecting, within the sample of microbial sequence information, the presence of the at least one member of the protein family selected from the group consisting of PKSE, TEBC, UNBL, UNBV and UNBU is computer-assisted.

6. The method of claim 1 wherein the protein family detected is PKSE.

7. The method of claim 1 wherein the protein family detected is TEBC.

8. The method of claim 1 wherein the protein family detected is UNBL.

9. The method of claim 1 wherein the protein family detected is UNBV.

10. The method of claim 1 wherein the protein family detected is UNBU.

11. The method of claim 1 wherein the step of detecting, within the sample of microbial sequence information, the presence of the at least one member of the protein family selected from the group consisting of PKSE, TEBC, UNBL, UNBV and UNBU comprises detecting the presence of at least one member from two protein families selected from the group consisting of PKSE, TEBC, UNBL, UNBV and UNBU.

12. The method of claim 1 wherein the step of detecting, within the sample of microbial sequence information, the presence of the at least one member of the protein family selected from the group consisting of PKSE, TEBC, UNBL, UNBV and UNBU comprises detecting the presence of at least one member from three protein families selected from the group consisting of PKSE, TEBC, UNBL, UNBV and UNBU.

13. The method of claim 1 wherein the step of detecting, within the sample of microbial sequence information, the presence of the at least one member of the protein family selected from the group consisting of PKSE, TEBC, UNBL, UNBV and UNBU comprises detecting the presence of at least one member from four protein families selected from the group consisting of PKSE, TEBC, UNBL, UNBV and UNBU.

14. The method of claim 1 wherein the step of detecting, within the sample of microbial sequence information, the presence of the at least one member of the protein family selected from the group consisting of PKSE, TEBC, UNBL, UNBV and UNBU comprises detecting the presence of a member of each of the protein families selected from the group consisting of PKSE, TEBC, UNBL, UNBV and UNBU.

* * * * *

SEQUENCE LISTING

<160> NUMBER OF SEQ ID NOS: 102

<210> SEQ ID NO 1
<211> LENGTH: 1936
<212> TYPE: PRT

<213> ORGANISM: Streptomyces macromyceticus

<400> SEQUENCE: 1

| Val | Thr | Arg | Ile | Ala | Ile | Val | Gly | Ile | Ala | Ala | Arg | Tyr | Pro | Asp | Ala |
|---|---|---|---|---|---|---|---|---|---|---|---|---|---|---|---|
| 1 | | | | 5 | | | | | 10 | | | | | 15 | |

| Thr | Ser | His | Arg | Glu | Leu | Trp | Glu | Asn | Ala | Val | Ala | Gly | Arg | Arg | Ala |
| | | | 20 | | | | | 25 | | | | | 30 | | |

| Phe | Arg | Arg | Leu | Pro | Asp | Val | Arg | Met | Arg | Leu | Glu | Asp | Tyr | Trp | Asp |
| | | 35 | | | | | 40 | | | | | 45 | | | |

| Ala | Asp | Pro | Thr | Thr | Pro | Asp | Arg | Phe | Tyr | Ala | Arg | Asn | Ala | Ala | Val |
| | 50 | | | | | 55 | | | | | 60 | | | | |

| Leu | Glu | Gly | Tyr | Ser | Phe | Asp | Arg | Ile | Ala | His | Arg | Ile | Ala | Gly | Ser |
| 65 | | | | | 70 | | | | | 75 | | | | | 80 |

| Thr | Tyr | Arg | Ser | Thr | Asp | Leu | Thr | His | Trp | Leu | Ala | Leu | Glu | Thr | Ala |
| | | | | 85 | | | | | 90 | | | | | 95 | |

| Ser | Ser | Ala | Leu | Ala | Asp | Ala | Gly | Phe | Ala | Ala | Gly | Glu | Gly | Leu | Pro |
| | | | 100 | | | | | 105 | | | | | 110 | | |

| Lys | Glu | Arg | Thr | Gly | Val | Ile | Val | Gly | Asn | Thr | Leu | Thr | Gly | Glu | Phe |
| | | 115 | | | | | 120 | | | | | 125 | | | |

| Ser | Arg | Ala | Asn | Val | Met | Arg | Leu | Arg | Trp | Pro | Tyr | Val | Arg | Arg | Val |
| | 130 | | | | | 135 | | | | | 140 | | | | |

| Leu | Ala | Ala | Ala | Leu | Lys | Ala | Glu | Asp | Trp | Asp | Glu | Lys | Leu | Ala |
| 145 | | | | | 150 | | | | | 155 | | | | | 160 |

| Asp | Phe | Leu | Glu | Gly | Val | Glu | Gly | Ala | Tyr | Lys | Gln | Pro | Phe | Pro | Ala |
| | | | | 165 | | | | | 170 | | | | | 175 | |

| Ile | Asp | Glu | Asp | Thr | Leu | Ala | Gly | Gly | Leu | Ser | Asn | Thr | Ile | Ala | Gly |
| | | | 180 | | | | | 185 | | | | | 190 | | |

| Arg | Ile | Cys | Asn | Tyr | Phe | Asp | Leu | Asn | Gly | Gly | Gly | Tyr | Thr | Val | Asp |
| | | 195 | | | | | 200 | | | | | 205 | | | |

| Gly | Ala | Cys | Ser | Ser | Ser | Leu | Leu | Ser | Val | Thr | Thr | Ala | Ala | Thr | Gly |
| | 210 | | | | | 215 | | | | | 220 | | | | |

| Leu | Val | Asn | Gly | Asp | Leu | Asp | Val | Ala | Val | Ala | Gly | Gly | Val | Asp | Leu |
| 225 | | | | | 230 | | | | | 235 | | | | | 240 |

| Ser | Ile | Asp | Pro | Phe | Glu | Ile | Ile | Gly | Phe | Ala | Lys | Thr | Gly | Ala | Leu |
| | | | | 245 | | | | | 250 | | | | | 255 | |

| Ala | Lys | Arg | Glu | Met | Arg | Leu | Tyr | Asp | Arg | Gly | Ser | Asn | Gly | Phe | Trp |
| | | | 260 | | | | | 265 | | | | | 270 | | |

| Pro | Gly | Glu | Gly | Cys | Gly | Met | Val | Val | Leu | Met | Arg | Glu | Glu | Asp | Ala |
| | | 275 | | | | | 280 | | | | | 285 | | | |

| Leu | Ala | Ser | Gly | His | Arg | Ile | Tyr | Ala | Ser | Val | Ala | Gly | Trp | Gly | Ile |
| | 290 | | | | | 295 | | | | | 300 | | | | |

| Ser | Ser | Asp | Gly | Gln | Gly | Gly | Ile | Thr | Arg | Pro | Glu | Val | Ser | Gly | Tyr |
| 305 | | | | | 310 | | | | | 315 | | | | | 320 |

| Gln | Leu | Ala | Met | Arg | Arg | Ala | Tyr | Glu | Arg | Ala | Gly | Phe | Gly | Ala | Asp |
| | | | | 325 | | | | | 330 | | | | | 335 | |

| Thr | Val | Pro | Leu | Phe | Glu | Gly | His | Gly | Thr | Gly | Thr | Glu | Val | Gly | Asp |
| | | | 340 | | | | | 345 | | | | | 350 | | |

| Ala | Thr | Glu | Leu | Thr | Ala | Ile | Met | Gly | Ala | Arg | Ala | Glu | Ala | Asp | Pro |
| | | 355 | | | | | 360 | | | | | 365 | | | |

| Lys | Ala | Pro | Leu | Ala | Ala | Ile | Ser | Ser | Ile | Lys | Gly | Met | Ile | Gly | His |
| | 370 | | | | | 375 | | | | | 380 | | | | |

| Thr | Lys | Ala | Ala | Ala | Gly | Val | Ala | Gly | Leu | Ile | Lys | Ala | Ala | Met | Ala |
| 385 | | | | | 390 | | | | | 395 | | | | | 400 |

-continued

```
Val Asp Ala Ala Met Leu Pro Pro Ala Ile Gly Cys Val Asp Pro His
                405                 410                 415
Asp Leu Leu Thr Gly Glu Gln Ser Asn Leu Arg Val Leu Arg Lys Ala
            420                 425                 430
Glu Ala Trp Pro Lys Asp Ala Pro Leu Arg Ala Val Thr Ala Met
            435                 440                 445
Gly Phe Gly Gly Ile Asn Thr His Val Val Asp Lys Ala Val Pro
450                 455                 460
Lys Arg Arg Pro Ala Pro Ser Arg Arg Ala Thr Thr Leu Ala Ala Ser
465                 470                 475                 480
Leu Gln Asp Ala Glu Leu Leu Leu Asp Gly Glu Ser Pro Gln Ala
                485                 490                 495
Leu Ala Ala Arg Leu Thr Glu Val Ala Ala Phe Ala Ala Gln Val Ser
            500                 505                 510
Tyr Ala Gln Val Gly Asp Leu Ala Ala Thr Leu Gln Arg Glu Leu Arg
            515                 520                 525
Asp Leu Pro Tyr Arg Ala Ala Val Val Thr Ser Pro Glu Asp Ala
530                 535                 540
Asp Leu Arg Leu Arg Gln Leu Ala Gly Thr Val Glu Ala Gly Thr Thr
545                 550                 555                 560
Ser Leu Phe Ala Pro Asp Gly Arg Thr Phe Leu Gly Arg Thr Gly Asp
                565                 570                 575
Gly Asp Ala Arg Ile Gly Phe Leu Phe Pro Gly Gln Gly Ser Gly Lys
            580                 585                 590
Gly Thr Gly Gly Gly Ala Leu Arg Arg Arg Phe Thr Glu Ala Ala Glu
            595                 600                 605
Val Tyr Asp Lys Ala Gly Leu Pro Thr Asp Gly Asp Met Val Ala Thr
            610                 615                 620
Asp Val Ala Gln Pro Arg Ile Val Thr Gly Ser Thr Ala Gly Leu Arg
625                 630                 635                 640
Val Leu Asp Ala Leu Gly Ile Glu Ala Asp Val Ala Val Gly His Ser
                645                 650                 655
Leu Gly Glu Leu Ser Ala Leu His Trp Ala Gly Ala Leu Asp Gly Pro
            660                 665                 670
Thr Val Leu Glu Ala Ala Arg Val Arg Gly Ala Ala Met Ala Glu His
            675                 680                 685
Ser Ala Ser Gly Thr Met Ala Ser Leu Ala Ala Pro Asp Ala Val
690                 695                 700
Ala Pro Leu Ile Asp Gly Leu Pro Val Val Ile Ser Gly Tyr Asn Gly
705                 710                 715                 720
Pro Gln Gln Thr Val Val Ala Gly Pro Val Asp Ala Val Glu Ser Val
                725                 730                 735
Ala Gln Arg Ala Gly Gln Ala Gly Val Lys Cys Thr Arg Leu Ala Val
            740                 745                 750
Ser His Ala Phe His Ser Pro Leu Val Ala Pro Ala Glu Ser Phe
            755                 760                 765
Gly Glu Trp Leu Ala Gly Ala Asp Phe Gly Ser Val Asp Arg Arg Ile
            770                 775                 780
Val Ser Thr Val Thr Gly Ala Asp Leu Glu Gln Asp Gly Asp Leu Ala
785                 790                 795                 800
Lys Leu Leu Arg Gln Gln Ile Thr Asp Pro Val Leu Phe Thr Gln Ala
                805                 810                 815
Leu Glu Ala Ala Ala Ala Asp Val Asp Leu Phe Ile Glu Val Gly Pro
```

-continued

```
                820                 825                830
Gly Arg Val Leu Ser Thr Leu Ala Glu Ala Gly Val Asp Val Pro Ala
        835                 840                845
Val Ala Leu Asn Thr Asp Asp Glu Ser Leu Arg Ala Leu Leu Gln Val
        850                 855                860
Val Gly Ala Ala Tyr Val Val Gly Ala Pro Leu Ile His Glu Arg Leu
865                 870                875                880
Phe Arg Asp Arg Leu Thr Arg Pro Leu Glu Ile Gly Ala Glu Phe Ser
                885                 890                895
Phe Leu Thr Ser Pro Cys Glu Gln Ala Pro Glu Ile Ser Leu Pro Ala
            900                 905                910
Gly Arg Ala Pro Arg Thr Glu Gly Ala Gly Asp Gly Asp Gly Gly Glu
            915                 920                925
Gln Ala Gly Gln Ala Gln Gly Glu Ser Ala Leu Glu Val Leu Arg Ala
        930                 935                940
Leu Val Ala Glu Arg Ala Glu Leu Pro Pro Glu Leu Val Ala Asp Asp
945                 950                955                960
Ser Ser Leu Leu Asp Asp Leu His Met Ser Ser Ile Thr Val Gly Gln
                965                 970                975
Ile Val Asn Gln Ala Ala Thr Arg Leu Gly Ile Gly Ala Ala His Val
            980                 985                990
Pro Thr Asn Phe Ala Thr Ala Thr Val Ala Gln Leu Ala Glu Ala Leu
            995                1000               1005
Glu Glu Leu Ala Gly Thr Gly Gly Gly Ala Ala Gly Ser Gly Pro
       1010                1015               1020
Leu Val Thr Gly Ser Ala Val Trp Ala Arg Pro Phe Ala Val Asp
       1025                1030               1035
Leu Asp Glu Val Pro Leu Ala Val Ala Ala Pro Gly Gly Glu Asn
       1040                1045               1050
Gly Pro Trp Glu Leu Phe Thr Ala Gly Ser Asp Pro Phe Gly Gln
       1055                1060               1065
Gln Leu Lys Ala Ala Leu Glu Gly Ala Gly Val Gly Ala Gly Val
       1070                1075               1080
Val Val Trp Leu Pro Pro Ala Cys Pro Ala Glu His Ile Ala Gln
       1085                1090               1095
Ala Leu Asp Gly Ala Lys Ala Ala Leu Ala Gly Asp Arg Glu Arg
       1100                1105               1110
Arg Phe Val Leu Val Gln His Gly Arg Gly Ala Ala Gly Leu Ala
       1115                1120               1125
Lys Thr Leu His Gln Glu Gly His Leu Arg Thr Thr Ile Val His
       1130                1135               1140
Thr Pro Arg Pro Asp Ala Asp Ala Val Arg Thr Val Val Ala Glu
       1145                1150               1155
Val Ala Ala Thr Ala Arg Phe Thr Glu Val His Tyr Asp Thr Glu
       1160                1165               1170
Gly Ala Arg Arg Val Pro Thr Leu Arg Ala Leu Pro Val Ala Pro
       1175                1180               1185
Ala Arg Lys Glu His Val Leu Gly Ser Ser Asp Val Leu Leu Val
       1190                1195               1200
Thr Gly Gly Gly Lys Gly Ile Thr Ala Glu Cys Ala Leu Ala Val
       1205                1210               1215
Ala Lys Glu Thr Gly Ala Lys Leu Ala Val Leu Gly Arg Ser Asp
       1220                1225               1230
```

```
Pro Ala Glu Asp Lys Asp Leu Gly Asp Asn Leu Ala Arg Met Ala
1235                1240                1245

Asp Ser Gly Val Thr Val Ala Tyr Ala Arg Ala Asp Val Thr Asp
1250                1255                1260

Pro Ala Arg Val Ala Ala Ala Val Ala Glu Leu Ala Glu Lys Leu
1265                1270                1275

Gly Pro Val Thr Ala Leu Leu His Gly Ala Gly Arg Asn Glu Pro
1280                1285                1290

Ala Ala Leu Thr Ala Leu Gly Ile Glu Asp Phe Arg Arg Thr Phe
1295                1300                1305

Ala Pro Lys Val Asp Gly Leu Arg Ala Val Leu Asp Ala Val Gly
1310                1315                1320

Glu Gly Ser Leu Lys Leu Leu Val Thr Phe Gly Ser Ile Ile Gly
1325                1330                1335

Arg Ala Gly Leu Arg Gly Glu Ala His Tyr Ala Thr Ala Asn Glu
1340                1345                1350

Trp Leu Ala Asp Leu Thr Glu Glu Val Ala Arg Asn His Pro Gly
1355                1360                1365

Cys Arg Ala Leu Cys Met Glu Trp Ser Val Trp Ser Gly Val Gly
1370                1375                1380

Met Gly Glu Lys Leu Ser Val Val Glu Thr Leu Ser Arg Glu Gly
1385                1390                1395

Ile Val Pro Val Ser Pro Asp His Gly Val Glu Ile Leu Leu Arg
1400                1405                1410

Leu Ile Ser Asp Pro Asp Ala Pro Val Val Thr Val Ile Ser Gly
1415                1420                1425

Arg Thr Glu Gly Ile Ala Thr Val Arg Arg Asp Leu Pro Gln Leu
1430                1435                1440

Pro Leu Leu Arg Phe Ala Gly Thr Pro Leu Val Arg Tyr His Gly
1445                1450                1455

Val Glu Leu Val Thr Glu Val Glu Leu Asn Ser Gly Thr Asp Ala
1460                1465                1470

Tyr Leu Ala Asp His Leu Leu Asp Gly Asn Leu Leu Met Pro Ala
1475                1480                1485

Val Leu Gly Met Glu Ala Met Val Gln Val Ala His Ala Ala Thr
1490                1495                1500

Gly Trp Glu Lys Val Pro Val Ile Glu Gly Ala Lys Phe Leu Arg
1505                1510                1515

Pro Ile Val Val Pro Pro Asn Gly Ala Thr Arg Ile Arg Ile Ala
1520                1525                1530

Ala Thr Val Thr Gly Pro Asp Thr Val Asp Val Ala Val His Ala
1535                1540                1545

Glu Glu Thr Gly Phe Val Ala Glu His Phe Arg Ala Arg Leu Arg
1550                1555                1560

Tyr Ala Glu Gly Ala Ile Pro Asp Gly Ala Pro Asp Gln Val Gly
1565                1570                1575

Ala Gly Val Pro Ala Ala Pro Leu Val Pro Ala Thr Asp Leu Tyr
1580                1585                1590

Gly Gly Val Leu Phe Gln Gly Asp Arg Phe Gln Arg Leu Gly Thr
1595                1600                1605

Phe His Arg Ala Ala Ala Arg His Val Asp Ala Asp Val Ala Ile
1610                1615                1620
```

-continued

| | | | | | | | | | |
|---|---|---|---|---|---|---|---|---|---|
| Gly | Ala | Pro | Thr | Gly | Trp | Phe | Ala | Pro | Tyr | Leu | Pro | Ala | Thr | Leu |
| | 1625 | | | | 1630 | | | | 1635 | | | | | |

| Leu | Met | Ala | Asp | Pro | Gly | Met | Arg | Asp | Ala | Leu | Met | His | Gly | Asn |
| | 1640 | | | | 1645 | | | | 1650 | | | | | |

| Gln | Val | Cys | Val | Pro | Asp | Ala | Thr | Leu | Leu | Pro | Ser | Gly | Ile | Glu |
| | 1655 | | | | 1660 | | | | 1665 | | | | | |

| Arg | Leu | Tyr | Pro | Met | Ala | Ala | Gly | Thr | Asp | Leu | Pro | Ala | Lys | Val |
| | 1670 | | | | 1675 | | | | 1680 | | | | | |

| Arg | Tyr | Cys | Ala | Thr | Glu | Arg | Tyr | Arg | Asp | Gly | Asp | Thr | Tyr | Val |
| | 1685 | | | | 1690 | | | | 1695 | | | | | |

| Tyr | Asp | Ile | Ala | Val | Arg | Thr | Glu | Asp | Gly | Thr | Val | Val | Glu | Arg |
| | 1700 | | | | 1705 | | | | 1710 | | | | | |

| Trp | Glu | Gly | Leu | Thr | Leu | His | Ala | Val | Arg | Lys | Thr | Asp | Gly | Ser |
| | 1715 | | | | 1720 | | | | 1725 | | | | | |

| Gly | Pro | Trp | Val | Glu | Pro | Leu | Leu | Gly | Ser | Tyr | Leu | Glu | Arg | Thr |
| | 1730 | | | | 1735 | | | | 1740 | | | | | |

| Leu | Glu | Glu | Val | Leu | Gly | Ser | His | Ile | Ala | Val | Ala | Val | Glu | Pro |
| | 1745 | | | | 1750 | | | | 1755 | | | | | |

| Asp | Ala | Pro | Asp | Ala | Asp | Gly | Ser | Gln | Gly | Ser | Arg | Arg | Ala | Gly |
| | 1760 | | | | 1765 | | | | 1770 | | | | | |

| Thr | Ala | Val | Ala | Leu | Gln | Arg | Ala | Leu | Gly | Ala | Thr | Ala | Glu | Val |
| | 1775 | | | | 1780 | | | | 1785 | | | | | |

| Arg | Tyr | Arg | Pro | Asp | Gly | Arg | Pro | Glu | Ile | Asp | Gly | Gly | Leu | Gln |
| | 1790 | | | | 1795 | | | | 1800 | | | | | |

| Val | Ser | Ala | Ala | His | Gly | Leu | Gly | Val | Thr | Leu | Gly | Val | Ala | Ala |
| | 1805 | | | | 1810 | | | | 1815 | | | | | |

| Gly | Arg | Thr | Val | Ala | Cys | Asp | Val | Glu | Ala | Val | Asn | Val | Arg | Thr |
| | 1820 | | | | 1825 | | | | 1830 | | | | | |

| Glu | Ala | Asp | Trp | Thr | Gly | Leu | Leu | Gly | Glu | His | Ala | Ala | Leu | Ala |
| | 1835 | | | | 1840 | | | | 1845 | | | | | |

| Lys | Leu | Val | Ala | Lys | Glu | Thr | Gly | Glu | Ala | Pro | Asp | Thr | Ala | Ala |
| | 1850 | | | | 1855 | | | | 1860 | | | | | |

| Thr | Arg | Val | Trp | Ser | Ala | Ala | Glu | Cys | Leu | Lys | Lys | Ala | Gly | Val |
| | 1865 | | | | 1870 | | | | 1875 | | | | | |

| Met | Ala | Gly | Ala | Pro | Leu | Thr | Leu | Ala | Pro | Arg | Thr | Arg | Asp | Asn |
| | 1880 | | | | 1885 | | | | 1890 | | | | | |

| Trp | Val | Val | Phe | Thr | Ala | Gly | Ala | Leu | Arg | Ile | Ala | Thr | Phe | Val |
| | 1895 | | | | 1900 | | | | 1905 | | | | | |

| Thr | Ser | Leu | Arg | Gly | Ala | Leu | Asp | Pro | Ala | Val | Phe | Ala | Phe | Leu |
| | 1910 | | | | 1915 | | | | 1920 | | | | | |

| Thr | Asp | Gly | Ala | Asp | Asp | Val | Pro | Gly | Val | Lys | Gly | Ala | | |
| | 1925 | | | | 1930 | | | | 1935 | | | | | |

<210> SEQ ID NO 2
<211> LENGTH: 5811
<212> TYPE: DNA
<213> ORGANISM: Streptomyces macromyceticus

<400> SEQUENCE: 2

```
gtgaccagaa tcgccatcgt cggcatagcg gcccgctacc ccgacgccac gagccaccgc      60
gagctgtggg agaacgccgt cgcgggccgc cgggccttcc gccggctgcc cgacgtgcgg     120
atgcggctgg aggactactg ggacgcggac ccgaccaccc cggaccgctt ctacgcccgc     180
aacgccgccg tcctggaggg ctactccttc gaccggatcg cccaccgcat cgccggcagc     240
```

-continued

```
acctaccgct ccaccgacct cacccactgg ctcgccctgg agaccgcctc cagcgccctg    300
gccgacgccg gcttcgcggc cggcgaggga ctgcccaagg agcgcaccgg cgtcatcgtc    360
ggcaacacgc tcaccggcga gttctcccgc gccaacgtga tgcggctgcg ctggccgtac    420
gtacggcggg tgctcgcggc cgccctcaag gcagaggact gggaggacga gaagctcgcc    480
gacttcctgg aaggcgtgga gggcgcgtac aagcagccct tccccgccat cgacgaggac    540
accctcgccg gcggcctctc caacaccatc gcgggccgga tctgcaacta cttcgacctc    600
aacggcggcg gctacaccgt cgacggcgcc tgctcctcct cgctgctgtc ggtcaccacc    660
gccgcgaccg gcctcgtcaa cggcgacctc gacgtggcgg tcgccggcgg cgtggacctg    720
tccatcgacc ccttcgagat catcgggttc gccaagaccg gcgccctggc caagcgggag    780
atgcggctct acgaccgcgg ctccaacggc ttctggccgg gcgagggctg cggcatggtc    840
gtcctgatgc gcgaagagga cgccctcgcc tccggccacc gcatctacgc ctccgtcgcc    900
ggctgggca tctcctccga cggccagggc ggcatcaccc ggcccgaggt cagcggctac    960
cagctggcca tgcggcgcgc ctacgagcgc gccgggttcg gcgccgacac cgtgccgctc    1020
ttcgagggcc acggcaccgg caccgaggtc ggcgacgcca ccgagctcac cgccatcatg    1080
ggcgcccgcg ccgaggccga cccgaaggcg ccgctcgccg cgatcagctc catcaagggc    1140
atgatcggcc acaccaaggc cgccgccggc gtcgccggac tcatcaaggc ggccatggcc    1200
gtggacgcgg cgatgctgcc ggccggccatc ggctgcgtcg acccgcacga cctgctcacc    1260
ggcgagcagt ccaacctgcg ggtgctgcgc aaggccgagg cctggcccaa ggacgccccg    1320
ctgcgcgcgg ccgtcaccgc catgggcttc ggcggcatca cacccacgt ggtcgtcgac    1380
aaggccgtgc ccaagcggcg cccggcaccc agccgccgcg ccaccaccct ggccgcctcc    1440
ctccaggacg ccgaactgct cctgctggac ggcgagtccc cgcaggcgct ggccgcccgc    1500
ctcaccgagg tggccgcctt cgccgcgcag gtctcgtacg cacaggtcgg cgacctcgcc    1560
gcgaccctcc agcgcgaact gcgcgacctg ccctaccggg ccgccgccgt cgtcacctcc    1620
ccggaggacg ccgacctgcg gctgcgccag ctcgccggca ccgtcgaggc gggcaccacc    1680
tcgctgttcg cgcccgacgg gcgcaccttc ctgggccgca ccggggacgg ggacgcccgc    1740
atcggcttcc tcttcccggg ccagggctcc ggcaagggca ccggcggagg cgcgctgcgc    1800
cgccgcttca ccgaggccgc cgaggtgtac gacaaggcgg gcctgcccac cgacggcgac    1860
atggtggcga ccgacgtggc ccagccgcgc atcgtcaccg gctccaccgc cggcctgcgg    1920
gtgctcgacg ccctcggcat cgaggccgac gtggccgtcg gccacagcct cggcgaactg    1980
tccgccctgc actgggcggg cgccctcgac ggtcccaccg tcctggaggc ggcccgggta    2040
cgcggcgcgg cgatggccga gcacagcgcc tcgggcacca tggcctcgct cgcggcagcg    2100
cccgacgcgg tcgcaccgct gatcgacggg ctccccgtcg tcatctccgg ctacaacggg    2160
ccgcagcaga cggtcgtcgc cggtcccgtg gacgccgtcg agtcggtggc gcagcgggcc    2220
gggcaggccg gtgtgaagtg cacccgcctc gccgtctcgc acgccttcca ctccccgctg    2280
gtcgccccgg cggccgagtc cttcggcgag tggctggccg cgcgggactt cgggagcgtg    2340
gaccggcgga tcgtgtccac cgtcaccggc gccgacctgg agcaggacgg cgacctcgcg    2400
aagctgctgc gccagcagat caccgacccg gtgctgttca cgcaggcact ggaggcggcc    2460
gccgcggacg tcgacctgtt catcgaggtc ggccccggcc gggtgctgag cacgctggcc    2520
gaggccggcg tcgacgtccc ggccgtcgcc ctcaacacgg acgacgaatc gctgcgcgcg    2580
ctgctccagg tggtcggcgc cgcgtacgtg gtcggcgccc cgctcatcca cgagcggctg    2640
```

```
ttccgcgacc ggctcacccg gccccctggag atcggcgccg agttcagctt cctgaccagc    2700
ccctgcgagc aggcacccga gatcagcctg cccgccggac gcgctccgcg tacggagggc    2760
gccggggacg cgcacggcgg cgagcaggcc ggccaggcgc agggcgagtc ggcgctggag    2820
gtgctgcggg cgctggtcgc cgagcgggcg gaactgccgc cggagctggt ggccgacgac    2880
agcagcctcc tggacgacct gcacatgagc tcgatcacgg tcggccagat cgtcaaccag    2940
gcggccaccc ggctcgggat cggcgcggcc cacgtgccga cgaacttcgc caccgccacg    3000
gtggcgcagc tcgccgaggc gctggaggag ctggcgggca ccggcggcgg cgcggcgggc    3060
tccggcccgc tcgtcaccgg atccgcggtc tgggcgcggc cgttcgcggt cgacctggac    3120
gaggtgcccc tggcggtcgc ggccccgggc ggcgagaacg gcccctggga gctgttcacg    3180
gccggctcgg acccattcgg gcagcagctg aaggcggccc tcgaaggcgc cggggtgggc    3240
gcgggcgtgg tggtctggct cccgccggcc tgcccggccg agcacatcgc gcaggccctc    3300
gacggggcga aggccgcgct cgcggggcgac cgggagcggc ggttcgtgct ggtgcagcac    3360
gggcggggcg cggccggcct ggccaagacc ctgcaccagg aagggcacct gcggacgacc    3420
atcgtccaca ccccgcggcc cgacgccgac gccgtacgca cggtcgtcgc ggaagtcgcg    3480
gccaccgccc ggttcaccga ggtgcactac gacaccgaag gcgcccgccg ggtcccgacc    3540
ctgcgcgcgc tgccggtggc gcccgcccgc aaggagcacg tactgggctc gtcggacgtc    3600
ctgctcgtca cgggcggcgg caagggcatc accgcagagt gcgccctggc cgtggccaag    3660
gagaccggcg cgaagctggc cgtcctgggc cgctccgacc cggccgagga caaggacctg    3720
ggcgacaacc tcgcccggat ggcggacagc ggtgtgacgg tggcctacgc gcgcgccgac    3780
gtcaccgacc ccgcccgggt cgcggccgcc gtcgccgaac tcgcggagaa gctcggaccg    3840
gtcaccgcgc tgctgcacgg cgccggccgc aacgagccgg ccgcgctgac ggcactgggc    3900
atcgaggact tccggcgcac cttcgcgccg aaggtcgacg gcctgcgggc cgtgctcgac    3960
gccgtcggcg agggcagcct caagctgctc gtcaccttcg gcagcatcat cggccgcgcg    4020
ggcctgcgcg cgcgaggcgca ctacgccacc gccaacgagt ggctggccga cctcaccgaa    4080
gaggtcgcgc gcaaccaccc cggctgccgc gccctgtgca tggagtggtc ggtgtggtcc    4140
ggcgtcggca tgggcgagaa gctctccgtc gtcgagaccc tctcccgcga gggcatcgtg    4200
ccggtctcgc ccgaccacgg cgtggagatc ctgctgcgcc tgatcagcga cccggacgcg    4260
ccggtggtca ccgtcatcag cggccgcacc gagggcatcg cgacggtccg ccgggacctg    4320
ccgcagctgc cgctgctgcg cttcgccggc accccgctgg tgcgctacca cggggtggag    4380
ctggtcaccg aggtcgagct gaactcgggt accgacgcct acctcgccga ccacctgctc    4440
gacgggaacc tgctgatgcc ggcggtgctc ggcatggagg cgatggtcca ggtcgcgcac    4500
gcggccaccg gctgggagaa ggtcccggtc atcgagggcg ccaagttcct gcggcccatc    4560
gtcgtgccgc ccaacggcgc caccccggatc cggatcgcgg ccaccgtgac cggaccggac    4620
accgtcgacg tggcggtgca cgcggaggag accggcttcg tcgccgagca cttccgggcg    4680
cgcctgcgct acgcggaggg cgccatcccc gacggagcac ccgaccaggt cggggcgggg    4740
gtgccggccg cgccgctggt gcccgcgacc gacctgtacg gcggggtcct cttccagggc    4800
gaccgcttcc agcggctggg caccttccac cgggccgccg cccggcacgt cgacgccgac    4860
gtggcgatcg gcgcgccgac ggggtggttc gccccgtacc tgccggccac gctgctgatg    4920
gccgacccgg gcatgcggga cgcgctgatg cacggcaacc aggtgtgcgt cccggacgcg    4980
```

| | | | | |
|---|---|---|---|---|
| accctgctgc | cgtcgggcat | cgagcggctg | tacccgatgg | ccgcgggcac ggacctgccg | 5040 |
| gcgaaggtgc | gctactgcgc | caccgagcgg | taccgcgacg | agacacgta cgtgtacgac | 5100 |
| atcgcggtgc | gcaccgagga | cgggaccgtc | gtcgagcggt | gggagggtct gaccctgcac | 5160 |
| gccgtgcgca | agacggacgg | ctccggaccg | tgggtggagc | cgctgctcgg ctcgtacctg | 5220 |
| gagcgcacgc | tggaggaggt | gctcggttcg | cacatcgcgg | tcgcggtgga gcccgacgcg | 5280 |
| ccggacgccg | acgggtcgca | gggcagccgc | cgggcgggta | ccgccgtcgc gctgcagcgg | 5340 |
| gccctgggcg | ccaccgccga | ggtgcgctac | cggcccgacg | gcggcccga gatcgacggc | 5400 |
| ggcctccagg | tctccgcggc | ccacgggctg | gcgtcaccc | tcgggtggc ggccgggcgg | 5460 |
| accgtcgcct | gcgacgtcga | ggcggtcaac | gtccgcaccg | aggccgactg acgggtctg | 5520 |
| ctcggcgaac | acgccgcgct | ggccaagctg | gtcgccaagg | agacgggcga ggccccggac | 5580 |
| acggcggcga | cacgggtgtg | agcgccgcc | gagtgcctga | agaaggcagg ggtgatggcg | 5640 |
| ggggcaccgc | tcacgctggc | accgcgcacc | cgggacaact | gggtggtctt cacggcgggc | 5700 |
| gcactgcgga | tcgcgacctt | cgtgacctcg | ctgcgcggcg | ccctggaccc ggcggtcttc | 5760 |
| gccttcctga | cggacggcgc | ggacgacgtc | cccggcgtga | agggggcctg a | 5811 |

<210> SEQ ID NO 3
<211> LENGTH: 162
<212> TYPE: PRT
<213> ORGANISM: Streptomyces macromyceticus

<400> SEQUENCE: 3

```
Met Ser Gly Ser Ala Asp Ser Leu Gly Tyr Phe Glu Tyr Arg His Thr
1               5                   10                  15

Val Ala Phe Ala Glu Thr Asp Leu Ala Gly Ser Ala Asp Tyr Val Asn
            20                  25                  30

Tyr Leu Gln Trp Gln Ala Arg Cys Arg Gln Leu Phe Leu Arg Gln Thr
        35                  40                  45

Ala Phe Gly Thr Val Leu Asp Asp Leu Asp Ala Gly His Ala Asp
    50                  55                  60

Leu Arg Leu Phe Thr Leu Gln Val Glu Cys Glu Leu Phe Glu Ala Val
65                  70                  75                  80

Ser Ala Leu Asp Arg Leu Ala Ile Arg Met Arg Val Ala Glu Ile Gly
                85                  90                  95

His Thr Gln Phe Asp Leu Thr Phe Asp Tyr Val Lys Gly Ala Gly Glu
            100                 105                 110

Gly Asp Val Pro Val Ala Arg Gly Arg Gln Arg Val Val Cys Leu Arg
        115                 120                 125

Gly Pro Ala Gly Ala Pro Val Pro Ala Leu Ile Pro Asp Ala Leu Ala
    130                 135                 140

Gln Ala Leu Ala Pro Tyr Ala Ala Gly Thr Arg Pro Leu Ala Gly Arg
145                 150                 155                 160

His Thr
```

<210> SEQ ID NO 4
<211> LENGTH: 489
<212> TYPE: DNA
<213> ORGANISM: Streptomyces macromyceticus

<400> SEQUENCE: 4

| | | | | |
|---|---|---|---|---|
| atgagcggca | gcgcggacag | cctcgggtac | ttcgagtacc | ggcacacggt cgccttcgcc | 60 |
| gagaccgatc | tcgcgggcag | cgccgactac | gtgaactacc | tccagtggca ggcacgttgc | 120 |

```
cggcagttgt tcctgcgcca gacggcgttc gggacggtcc tcgacgacga cctggacgcc     180
gggcacgccg acttgaggct gttcacgctg caggtcgagt gcgagctctt cgaagcggtc     240
tcggcactcg accgcctggc catccggatg cgggtggccg agatcggaca cacacagttc     300
gacttgacgt tcgactacgt caaggggggca ggggagggcg acgtaccggt ggctcgcggc     360
aggcagcgcg tcgtgtgtct gcgcgggccg gccggcgccc ccgtcccggc cctgatcccc     420
gacgcgctgg cacaagcgct ggcgccctac gcggccggga cccggccgtt ggcagggagg     480
catacatga                                                             489

<210> SEQ ID NO 5
<211> LENGTH: 157
<212> TYPE: PRT
<213> ORGANISM: Streptomyces macromyceticus

<400> SEQUENCE: 5

Met Thr Thr Thr Ala Thr Thr Asp Tyr Phe Glu Tyr Arg His Thr Val
1               5                   10                  15

Gly Phe Glu Glu Thr Asn Leu Val Gly Asn Val Tyr Tyr Val Asn Tyr
            20                  25                  30

Leu Arg Trp Gln Gly Arg Cys Arg Glu Leu Phe Leu Lys Gln Lys Ala
        35                  40                  45

Pro Ala Val Leu Ala Asp Val Gln Glu Asp Leu Lys Leu Phe Thr Leu
    50                  55                  60

Lys Val Asp Cys Glu Phe Phe Ala Glu Ile Thr Ala Phe Asp Glu Leu
65                  70                  75                  80

Ser Ile Arg Met Arg Leu Ala Glu Gln Ala Gln Thr Gln Leu Glu Phe
                85                  90                  95

Thr Phe Asp Tyr Val Lys Val Thr Glu Asp Gly Thr Glu Thr Leu Val
            100                 105                 110

Ala Arg Gly Lys Gln Arg Ile Ala Cys Met Arg Gly Pro Asn Thr Ala
        115                 120                 125

Thr Val Pro Ser Leu Ile Pro Asp Ala Leu Ala Gln Ala Leu Ala Pro
    130                 135                 140

Tyr Ala Thr Gln Asn Arg Ser Leu Val Gly Arg Ala Ala
145                 150                 155

<210> SEQ ID NO 6
<211> LENGTH: 474
<212> TYPE: DNA
<213> ORGANISM: Streptomyces macromyceticus

<400> SEQUENCE: 6
atgacgacca ccgcgacgac cgactacttc gagtaccggc acaccgttgg cttcgaggag      60
accaacctgg tgggcaacgt gtactacgtg aactacctcc ggtggcaggg acgctgccgg     120
gagctgttcc tcaagcagaa ggcacccgcg gtcctcgccg acgtccagga ggacctcaag     180
ctcttcaccc tgaaggtcga ctgcgagttc ttcgccgaga tcacggcctt cgacgagctg     240
tcgatccgga tgcggctggc cgagcaggcg cagacccagc tggagttcac cttcgactac     300
gtcaaggtga ccgaggacgg cacggagacc ctggtggccc gcggcaagca gcggatcgcc     360
tgcatgcggg gtccgaacac ggccaccgtc ccctcgctga tccccgacgc cctcgcccag     420
gcgctggcgc cgtacgccac ccagaaccgc tcgctcgtcg gccgggccgc ctga           474

<210> SEQ ID NO 7
```

```
<211> LENGTH: 327
<212> TYPE: PRT
<213> ORGANISM: Streptomyces macromyceticus

<400> SEQUENCE: 7
```

| | | | | | | | | | | | | | | |
|---|---|---|---|---|---|---|---|---|---|---|---|---|---|---|
| Val | Ser | Met | Leu | Arg | Ala | Leu | Arg | Arg | Val | Leu | Thr | Pro | Asn | Val |
| 1 | | | | 5 | | | | | 10 | | | | | 15 |
| Arg | Glu | Thr | His | Leu | Asp | Arg | Arg | Gly | Phe | His | Val | Lys | Asn | Pro | Glu |
| | | | 20 | | | | | 25 | | | | | 30 | |
| Ala | Lys | Asn | Gln | Leu | Glu | Thr | Val | Gly | Ala | Thr | Phe | Leu | Gln | Gly | Tyr |
| | | | 35 | | | | 40 | | | | | 45 | | |
| Ala | Tyr | Ala | Val | Glu | Ala | Arg | Ser | Ala | Ala | Glu | Ala | Glu | Glu | Trp | Leu |
| | 50 | | | | | 55 | | | | | 60 | | | |
| Glu | Thr | Val | Pro | Arg | Ala | Tyr | Arg | Gly | Phe | Ala | Tyr | Glu | Gly | Ala | Gly |
| 65 | | | | | 70 | | | | | 75 | | | | | 80 |
| Met | Gly | Ala | Val | Met | Leu | Asp | Ser | Leu | Thr | Gly | Ser | Lys | Arg | Leu | Ala |
| | | | | 85 | | | | | 90 | | | | | 95 | |
| Gly | Phe | Leu | Glu | Gly | Glu | Gly | Ala | Arg | His | Asp | Tyr | Met | Ile | Trp | Val |
| | | | 100 | | | | | 105 | | | | | 110 | |
| Gly | Val | Gly | Trp | Ala | Met | Ala | Arg | Leu | Pro | Lys | Phe | Leu | Trp | Pro | Asp |
| | | | 115 | | | | | 120 | | | | | 125 | |
| Val | Thr | Glu | Ile | Asp | Pro | Val | Leu | Arg | Trp | Leu | Ile | Leu | Asp | Gly | Tyr |
| | 130 | | | | | 135 | | | | | 140 | | | |
| Gly | Phe | His | Gln | Ala | Tyr | Phe | Lys | Thr | Asp | Ala | Tyr | Val | Arg | Lys | Pro |
| 145 | | | | | 150 | | | | | 155 | | | | | 160 |
| His | Leu | Thr | His | Pro | Phe | Ser | Trp | Lys | Gly | Gly | Asp | Asp | Thr | Tyr | Ser |
| | | | | 165 | | | | | 170 | | | | | 175 | |
| Gln | Arg | Val | Leu | Asp | Gln | Gly | Ile | Gly | Arg | Ala | Leu | Trp | Phe | Val | Gly |
| | | | 180 | | | | | 185 | | | | | 190 | |
| Gly | Thr | Asp | Pro | Asp | Val | Val | Ala | Gly | Leu | Ile | Ala | Ala | Tyr | Pro | Glu |
| | | | 195 | | | | | 200 | | | | | 205 | |
| His | Arg | His | Gly | Asp | Leu | Tyr | Ala | Gly | Ser | Gly | Leu | Ala | Cys | Thr | Tyr |
| | 210 | | | | | 215 | | | | | 220 | | | |
| Ala | Gly | Ser | Ala | Asp | Glu | Thr | Glu | Leu | Lys | Arg | Phe | Ala | Glu | His | Ala |
| 225 | | | | | 230 | | | | | 235 | | | | | 240 |
| Gly | Lys | His | Leu | Pro | Asn | Leu | Ala | Gln | Gly | Ser | Ala | Phe | Ala | Ser | Glu |
| | | | | 245 | | | | | 250 | | | | | 255 | |
| Ala | Arg | Val | Lys | Ala | Gly | Thr | Ile | Ile | Asp | His | Thr | Lys | Met | Ala | Ser |
| | | | 260 | | | | | 265 | | | | | 270 | |
| Arg | Val | Leu | Cys | Ala | Gly | Arg | Thr | Pro | Glu | Glu | Ala | Ser | Arg | Val | Cys |
| | | 275 | | | | | 280 | | | | | 285 | | |
| Leu | Glu | Thr | Arg | Pro | Thr | Gly | Cys | Asp | Gly | Gly | Ala | Ile | Pro | Ala | Phe |
| | 290 | | | | | 295 | | | | | 300 | | | |
| Glu | Thr | Trp | Arg | Gln | Glu | Ile | Ala | Arg | Gln | Ile | Val | Val | Pro | Ala | Tyr |
| 305 | | | | | 310 | | | | | 315 | | | | | 320 |
| Ser | Gln | Lys | Gly | Ala | Ser | Ala | | | | | | | | | |
| | | | 325 | | | | | | | | | | | | |

```
<210> SEQ ID NO 8
<211> LENGTH: 984
<212> TYPE: DNA
<213> ORGANISM: Streptomyces macromyceticus

<400> SEQUENCE: 8
gtgtccatgt tgcgtgcgct gaggcgccga gtcctcacac ccaatgtccg ggaaacgcat      60
```

```
ctggatcggc gcggtttcca cgtcaagaac ccggaagcga agaatcagct ggaaaccgtg    120
ggggccacgt tcctccaggg ttacgcctat gcggtcgagg cccgttccgc ggcggaggcc    180
gaggagtggc tggagaccgt tccccgtgcc taccgcggat tcgcgtacga gggcgccggc    240
atgggcgccg tgatgctcga ctcgctgacg ggcagcaagc ggctggccgg cttcctggag    300
ggcgagggcg cccgccacga ctacatgatc tgggtcggcg tcggctgggc gatggcccgg    360
ctgccgaagt tcctgtggcc ggacgtgacg gagatcgacc cggttctgcg ctggctgatc    420
ctcgacggat acggcttcca ccaggcgtac ttcaagacgg acgcctacgt ccgcaagccg    480
cacctcacgc acccgttcag ctggaagggc ggcgacgaca cctacagcca gcgggtcctc    540
gaccagggaa tcggccgggc cctgtggttc gtcggcggca ccgaccccga cgtggtggcc    600
ggtctgatcg ccgcgtaccc cgagcaccgg cacggcgacc tgtacgccgg ctccggcctc    660
gcctgcacct acgcgggcag cgccgacgag acggagctca agcgcttcgc cgagcacgcg    720
ggcaagcacc tgcccaacct cgcgcagggc tccgccttcg cctccgaggc ccgggtcaag    780
gccggcacca tcatcgacca caccaagatg gcgtcgcgcg tgctgtgcgc cggccgcacc    840
ccggaggagg cctcccgggt ctgcctggag acgcgcccga ccggctgcga cggcggcgcg    900
attcccgcat cgaaacctg gcggcaggag atcgcccggc aaatcgtcgt tcccgcgtac    960
tcccagaaag gagcgagcgc atga                                          984
```

<210> SEQ ID NO 9
<211> LENGTH: 642
<212> TYPE: PRT
<213> ORGANISM: Streptomyces macromyceticus

<400> SEQUENCE: 9

```
Met Thr Gln Asn Pro Val Ser Trp Leu Arg Arg Gln Ala Ala Gly Ile
1               5                   10                  15

Val Ala Leu Val Val Met Val Ser Ala Phe Tyr Ala Val Lys Pro Asp
                20                  25                  30

Glu Ser Ser Ala Ala Glu Lys Arg Glu Leu Ala Lys Ser Phe Gln Phe
            35                  40                  45

Glu Pro Met Ser Ile Ala Met Pro Ala Gly Phe Lys Gln Gln Thr Val
        50                  55                  60

Arg Lys Val Asn Lys Ala Tyr Lys His Ile Glu Ala Trp Ile Ser Ser
65                  70                  75                  80

Val Gly Ala Gly Val Ala Met Asn Asp Ile Asp Asn Asp Gly Leu Pro
                85                  90                  95

Asn Asp Leu Cys Ile Thr Asp Pro Arg Ile Asp Gln Ala Val Ile Thr
            100                 105                 110

Pro Ala Pro Val Pro Gly Arg Lys Ser Ala Thr Tyr Glu Pro Phe Ala
        115                 120                 125

Leu Asp Met Ala Pro Leu Pro Lys Ser Lys Tyr Ser Ala Pro Ile Gly
    130                 135                 140

Cys Val Pro Gly Asp Phe Asn Glu Asp Gly Ala Thr Asp Leu Leu Val
145                 150                 155                 160

Tyr Tyr Trp Gly Arg Thr Pro Val Ile Phe Gln Gln Lys Lys Met Ala
                165                 170                 175

Trp Asp Lys Lys Met Pro Pro Lys Met Glu Cys Phe Glu Pro Ile Glu
            180                 185                 190

Leu Val Pro Gly Ala Gly Gly Ile Tyr Thr Gly Pro Leu Trp Asn
        195                 200                 205
```

-continued

Ser Asn Ala Ala Ala Val Ala Asp Phe Asp Gly Asp Gly His Lys Asp
    210                 215                 220

Leu Tyr Ile Gly Asn Tyr Phe Pro Glu Ser Pro Val Leu Asp Asp Thr
225                 230                 235                 240

Lys Asp Gly Gly Val Thr Met Asn Asp Ser Met Ser His Ala Gln Asn
                245                 250                 255

Gly Gly Gly Gly His Phe Phe Leu Lys Thr Pro Gly Gly Tyr Lys Trp
            260                 265                 270

Ile Pro Ala Asp Lys Val Val Pro Glu Gly Arg Glu Lys Gly Trp Thr
        275                 280                 285

Leu Ala Ala Ser Ala Thr Asp Val Asp Gly Asp Leu Leu Pro Glu Leu
    290                 295                 300

Tyr Leu Gly Leu Asp Phe Gly Ser Thr Thr Leu Leu His Asn Arg Ser
305                 310                 315                 320

Thr Pro Gly Glu Leu Lys Phe Val Glu Val Lys Ala Ser His Asn Gly
                325                 330                 335

Ile Met Pro Lys Ser Lys Glu Ile Gly Arg Ser Ser Phe Lys Gly Met
            340                 345                 350

Gly Ile Asp Trp Ala Asp Leu Asn Gly Asp Gly Ile Leu Asp Ala Phe
        355                 360                 365

Leu Ser Asn Ile Thr Thr Ser Phe Gly Ile Gln Glu Ser Asn Tyr Thr
    370                 375                 380

Phe Ile Ser Lys Ala Lys Asn Leu Asp Asp Leu His Arg Lys Met Ser
385                 390                 395                 400

Asp Lys Lys Ala Pro Trp Lys Asp Glu Ser Ala Ser Leu Asn Thr Ala
                405                 410                 415

Trp Ser Gly Trp Gly Trp Asp Ala Lys Met Ala Asp Phe Asp Asn Asp
            420                 425                 430

Gly Arg Pro Glu Ile Thr Gln Ala Thr Gly Phe Val Lys Gly Lys Arg
        435                 440                 445

Ser Arg Trp Ala Gln Leu Gln Glu Leu Ala Thr Ala Asn Asp Leu Leu
    450                 455                 460

Val Arg His Pro Gly Ala Trp Pro Lys Val Glu Ala Gly Asp Asp Leu
465                 470                 475                 480

Ala Gly Asp Gln Tyr Leu Arg Phe Trp Thr Arg Asn Gly Gly Lys Tyr
                485                 490                 495

Asp Asn Ile Ser Pro Glu Leu Gly Leu Asp Val Pro Val Pro Thr Arg
            500                 505                 510

Gly Ile Ala Thr Gly Asp Ala Asp Gly Asp Gly Arg Leu Asp Phe Val
        515                 520                 525

Val Ala Arg Gln Trp Asp Ala Pro Val Phe Tyr Cys Asn Leu Ser Pro
    530                 535                 540

Ala Lys Asn Asp Phe Leu Gly Leu Lys Leu Val Asp Asp Lys Gly Ser
545                 550                 555                 560

Pro Val Val Gly Ala Gln Val Arg Val Asn Phe Pro Asp Gly Lys Val
                565                 570                 575

Leu Leu Gly Arg Val Asp Gly Gly Ser Gly His Ser Gly Lys Arg Ser
            580                 585                 590

Thr Asp Val His Ile Gly Leu Gly Lys Val Ser Gly Pro Val Gln Ala
        595                 600                 605

Ser Ile Ser Trp Arg Asp Thr Thr Gly Gln Val Arg Lys Gln Ala Leu
    610                 615                 620

Thr Leu Ser Pro Gly Trp His Ser Val Gln Leu Gly Thr Glu Ala Lys

```
                625                 630                 635                 640

Glu Lys

<210> SEQ ID NO 10
<211> LENGTH: 1929
<212> TYPE: DNA
<213> ORGANISM: Streptomyces macromyceticus

<400> SEQUENCE: 10
atgacgcaga atccagtctc ctggctgcgt aggcaggcag caggaattgt ggccctcgtc       60
gtcatggtga gcgctttcta tgcggtgaag ccggacgagt cgtccgcggc cgagaagcgg      120
gaactcgcca agtccttcca gttcgagccg atgtccatcg ccatgccggc cggcttcaag      180
cagcagaccg tccgcaaggt gaacaaggcg tacaagcaca tcgaggcgtg gatctcctcg      240
gtcggcgccg tgtcgcgat gaacgacatc gacaacgacg gctccccaa cgacctgtgc       300 atcaccgacc cccggatcga ccaggcggtc atcaccccgg cccccgtccc gggccgcaag      360
agcgccacgt acgagccctt cgcgctggac atggcgccgc tgcccaagag caagtacagc      420 gccccccatcg gctgtgtccc cggtgacttc aacgaggacg cgccaccga cctcctcgtc     480 tactactggg gccgcacccc ggtgatcttc cagcagaaga gatggcctg gacaagaag       540 atgccgccca agatggagtg cttcgagccg atcgagctgg tgccgggcgc cggcggcggc      600
atctacaccg gcccgctgtg gaactccaac gcggccgccg tcgcggactt cgacggtgac      660
ggccacaagg acctctacat cggcaactac ttccccgaga gccccgtcct ggacgacacc      720
aaggacggcg gggtcacgat gaacgactcc atgtcgcacg cgcagaacgg cggcggcggg      780
cacttcttcc tcaagacccc cggcggctac aagtggatcc cggcggacaa ggtcgtcccc      840
gagggccgtg aaaagggctg gacgctggcc gcctcggcca cggacgtcga cggcgacctg      900
ctgcccgagc tgtacctcgg cctcgacttc ggttccacga cgctgctgca caaccggtcc      960
accccgggcg agctcaagtt cgtcgaggtg aaggccagcc acaacgggat catgccgaag     1020
tccaaggaga tcgggcgcag ctccttcaag ggcatgggca tcgactgggc cgacctgaac     1080
ggcgacggca tcctcgacgc cttcctgtcc aacatcacga cctcgttcgg catccaggag     1140
tccaactaca ccttcatcag caaggcgaag aacctggacg acctgcaccg caagatgagc     1200
gacaagaagg cgccctggaa ggacgagagc gcttccctca acacggcctg gtccggctgg     1260
ggctgggacg ccaagatggc ggacttcgac aacgacggcc gccggagat cacccaggcc     1320 accggcttcg tgaagggcaa cgcagccgc tgggcgcagc tccaggagct cgccaccgcc      1380
aacgacctgc tggtgcgcca ccccggcgcc tggccgaagg tcgaggccgg cgacgacctc     1440 gccgcgacc agtacctgcg cttctggacc cgcaacggcg gcaagtacga caacatctcc     1500
cccgagctcg ggctcgacgt gcccgtgccc accgcggta tcgccaccgg tgacgccgac      1560
ggcgacggcc gcctggactt cgtggtggcc cggcagtggg acgccccggt cttctactgc     1620
aacctcagcc ccgcgaagaa cgacttcctg ggcctgaagc tcgtcgacga caagggatcc     1680
cccgtggtcg gcgcccaggt acgggtcaac ttccccgacg gcaaggtcct gctgggccgc     1740
gtcgacggcg gcagcggcca ctccggcaag gcagcaccg acgtccacat cggtctcggc     1800
aaggtctccg gacccgtcca ggccagcatc tcctggcggg acacgaccgg ccaggtccgc     1860
aagcaggctc tcacgctgag ccccggctgg cactcggtcc agctcggtac cgaggccaag     1920
gagaagtag                                                              1929
```

<210> SEQ ID NO 11
<211> LENGTH: 433
<212> TYPE: PRT
<213> ORGANISM: Streptomyces macromyceticus

<400> SEQUENCE: 11

| | | | | | | | | | | | | | | |
|---|---|---|---|---|---|---|---|---|---|---|---|---|---|---|
| Met | Ser | Ser | His | Thr | Ser | Ala | Val | Pro | Pro | Thr | Ala | Ala | Pro | Thr |
| 1 | | | | 5 | | | | | 10 | | | | | 15 |

| | | | | | | | | | | | | | | |
|---|---|---|---|---|---|---|---|---|---|---|---|---|---|---|
| Ala | Ala | Ala | Gly | Ser | Pro | Ala | Lys | Ser | Ala | Lys | Pro | Ala | Ala | Pro |
| | | | 20 | | | | | 25 | | | | | 30 | |

| | | | | | | | | | | | | | | |
|---|---|---|---|---|---|---|---|---|---|---|---|---|---|---|
| Arg | His | Asp | Pro | Lys | Val | Ile | Lys | Ala | Leu | Gln | Arg | Phe | Ala | Val | Ser |
| | | | 35 | | | | | 40 | | | | | 45 | |

| | | | | | | | | | | | | | | |
|---|---|---|---|---|---|---|---|---|---|---|---|---|---|---|
| Ile | Ser | Val | Leu | Asn | Val | Leu | Gly | Tyr | Thr | Val | Leu | Gly | Phe | Glu | Gln |
| 50 | | | | | 55 | | | | | 60 | | | | | |

| | | | | | | | | | | | | | | |
|---|---|---|---|---|---|---|---|---|---|---|---|---|---|---|
| Gly | Trp | Leu | Trp | Pro | Phe | Ile | Ala | Val | Ala | Thr | Gly | Tyr | Thr | Thr | Glu |
| 65 | | | | | 70 | | | | | 75 | | | | | 80 |

| | | | | | | | | | | | | | | |
|---|---|---|---|---|---|---|---|---|---|---|---|---|---|---|
| Ile | Val | Leu | Glu | Trp | Ile | Ser | Ala | Lys | Gly | Glu | Gly | Arg | Ala | Pro | Arg |
| | | | | 85 | | | | | 90 | | | | | 95 | |

| | | | | | | | | | | | | | | |
|---|---|---|---|---|---|---|---|---|---|---|---|---|---|---|
| Tyr | Ala | Gly | Gly | Gly | Arg | Lys | Gly | Leu | Met | Glu | Phe | Leu | Leu | Pro | Ala |
| | | | | 100 | | | | | 105 | | | | | 110 | |

| | | | | | | | | | | | | | | |
|---|---|---|---|---|---|---|---|---|---|---|---|---|---|---|
| His | Ile | Thr | Ser | Leu | Ala | Val | Asn | Met | Leu | Thr | Tyr | Thr | Asn | Asp | Arg |
| | | | 115 | | | | | 120 | | | | | 125 | | |

| | | | | | | | | | | | | | | |
|---|---|---|---|---|---|---|---|---|---|---|---|---|---|---|
| Trp | Trp | Val | Met | Met | Phe | Gly | Val | Ile | Val | Ala | Val | Gly | Thr | Lys | His |
| | 130 | | | | | 135 | | | | | 140 | | | | |

| | | | | | | | | | | | | | | |
|---|---|---|---|---|---|---|---|---|---|---|---|---|---|---|
| Val | Leu | Arg | Ala | Pro | Val | Lys | Gly | Arg | Met | Arg | His | Tyr | Met | Asn | Pro |
| 145 | | | | | 150 | | | | | 155 | | | | | 160 |

| | | | | | | | | | | | | | | |
|---|---|---|---|---|---|---|---|---|---|---|---|---|---|---|
| Ser | Asn | Phe | Gly | Ile | Met | Ile | Ile | Leu | Val | Leu | Phe | Pro | Trp | Ala | Ser |
| | | | | 165 | | | | | 170 | | | | | 175 | |

| | | | | | | | | | | | | | | |
|---|---|---|---|---|---|---|---|---|---|---|---|---|---|---|
| Ile | Ala | Pro | Pro | Tyr | His | Phe | Thr | Glu | Tyr | Leu | Thr | Gly | Thr | Thr | Gly |
| | | | 180 | | | | | 185 | | | | | 190 | | |

| | | | | | | | | | | | | | | |
|---|---|---|---|---|---|---|---|---|---|---|---|---|---|---|
| Pro | Gly | Asp | Trp | Ile | Leu | Pro | Ala | Val | Ile | Thr | Leu | Gly | Thr | Met |
| | | | 195 | | | | | 200 | | | | | 205 | | |

| | | | | | | | | | | | | | | |
|---|---|---|---|---|---|---|---|---|---|---|---|---|---|---|
| Leu | Asn | Ala | Lys | Leu | Thr | Asn | Arg | Met | Pro | Leu | Ile | Met | Gly | Trp | Leu |
| 210 | | | | | 215 | | | | | 220 | | | | | |

| | | | | | | | | | | | | | | |
|---|---|---|---|---|---|---|---|---|---|---|---|---|---|---|
| Val | Gly | Phe | Ala | Leu | Gln | Ala | Ile | Ile | Arg | Gly | Trp | Met | Phe | Asp | Thr |
| 225 | | | | | 230 | | | | | 235 | | | | | 240 |

| | | | | | | | | | | | | | | |
|---|---|---|---|---|---|---|---|---|---|---|---|---|---|---|
| Ser | Ile | Pro | Ala | Ala | Leu | Gly | Met | Met | Thr | Gly | Thr | Ala | Phe | Val | Leu |
| | | | | 245 | | | | | 250 | | | | | 255 | |

| | | | | | | | | | | | | | | |
|---|---|---|---|---|---|---|---|---|---|---|---|---|---|---|
| Phe | Thr | Asn | Tyr | Met | Val | Thr | Asp | Pro | Gly | Thr | Ser | Pro | Ser | Lys | Lys |
| | | | 260 | | | | | 265 | | | | | 270 | | |

| | | | | | | | | | | | | | | |
|---|---|---|---|---|---|---|---|---|---|---|---|---|---|---|
| Ser | Ser | Gln | Ile | Ala | Phe | Gly | Ala | Gly | Val | Ala | Ala | Val | Tyr | Gly | Leu |
| | | 275 | | | | | 280 | | | | | 285 | | | |

| | | | | | | | | | | | | | | |
|---|---|---|---|---|---|---|---|---|---|---|---|---|---|---|
| Leu | Met | Ala | Val | Asn | Ile | Thr | Tyr | Gly | Ile | Phe | Phe | Ala | Thr | Ala | Ile |
| | 290 | | | | | 295 | | | | | 300 | | | | |

| | | | | | | | | | | | | | | |
|---|---|---|---|---|---|---|---|---|---|---|---|---|---|---|
| Val | Cys | Gly | Ile | Arg | Gly | Leu | Phe | Leu | Trp | Phe | Leu | His | Leu | Gln | Ala |
| 305 | | | | | 310 | | | | | 315 | | | | | 320 |

| | | | | | | | | | | | | | | |
|---|---|---|---|---|---|---|---|---|---|---|---|---|---|---|
| Lys | Gln | Gln | Ala | Ala | Ala | Lys | Thr | Ala | Pro | Val | Arg | Pro | Val | Glu | Ala |
| | | | | 325 | | | | | 330 | | | | | 335 | |

| | | | | | | | | | | | | | | |
|---|---|---|---|---|---|---|---|---|---|---|---|---|---|---|
| Leu | Val | Ala | Val | Pro | Ser | Pro | Ala | Pro | Ala | Pro | Ala | Glu | Ala | Pro | Thr |
| | | | 340 | | | | | 345 | | | | | 350 | | |

| | | | | | | | | | | | | | | |
|---|---|---|---|---|---|---|---|---|---|---|---|---|---|---|
| Val | Pro | Leu | Ala | Ala | Ala | Thr | Glu | Asp | Ala | Cys | Ala | Ala | Gly | Thr | Cys |
| | | | 355 | | | | | 360 | | | | | 365 | | |

| | | | | | | | | | | | | | | |
|---|---|---|---|---|---|---|---|---|---|---|---|---|---|---|
| Gly | His | Glu | Lys | Cys | Ala | Ala | Ala | Arg | Val | Ala | Ala | Pro | Ala | Ala | Ala |
| | 370 | | | | | 375 | | | | | 380 | | | | |

Val Pro Pro Ala Ala Val Ser Pro Ala Val Pro Ala Ala Ser Ala
385                 390                 395                 400

Ala Ala Glu Asp Ala Cys Ala Ala Gly Ser Cys Gln His Gly Lys Cys
            405                 410                 415

Ala Ala Met Arg Ala Glu Ala Ala Lys Glu Lys Lys Val Ala Val Ser
        420                 425                 430

Leu

<210> SEQ ID NO 12
<211> LENGTH: 1302
<212> TYPE: DNA
<213> ORGANISM: Streptomyces macromyceticus

<400> SEQUENCE: 12
atgtcttctc acaccagcgc agtgcccccc acggccgctg cccccaccgc tgccgccggc      60
agcccagcca agtccgccaa gcccgccgcg ccccgcggc acgacccaa ggtcatcaag       120 gcgctccagc ggttcgccgt ctcgatctcc gtgctgaacg tcctcggcta caccgtgctc     180
ggtttcgagc agggctggct gtggccgttc atcgcggtgg ccaccggcta caccaccgag     240
atcgtcctcg aatggatcag tgccaagggc gagggccgtg cccgcgcta cgcgggcggc      300 ggccgcaagg gactcatgga gttcctgctc cccgcgcaca tcaccagcct cgcggtcaac     360
atgctcacct acaccaatga ccgctggtgg gtcatgatgt tcggcgtcat cgtggccgtc     420
ggcaccaagc acgtgctgcg cgccccggtg aagggccgca tgcggcacta catgaacccg     480
tcgaacttcg gcatcatgat catcctggtg ctgttcccct gggccagcat cgccccgccg     540
taccacttca ccgagtacct gacgggcacc accggccccg cgactggat cctcccggcg      600 gtcatcatca cgctcggcac gatgctcaac gccaagctca ccaaccgcat gccgctcatc     660
atgggctggc tcgtgggctt cgccctccag gcgatcatcc gaggctggat gttcgacacg     720
tccatccccg cggccctcgg catgatgacg ggcacggcct cgtgctctt caccaactac      780 atggtcaccg acccgggtac ctcgccctcg aagaagtcct cgcagatcgc gttcggcgcc     840
ggtgtcgccg ccgtctacgg cctgctgatg ccgtgaaca tcacgtacgg catcttcttc      900
gccaccgcga tcgtctgcgg gatccgcggc ctgttcctgt ggttcctgca cctgcaggcc     960
aagcagcagg cggccgccaa gaccgcgccg gtccggcccg tggaggcgct cgtcgccgtc    1020
ccgtcgcccg cccggcgcc cgccgaggcg cccacggtcc cgctcgccgc cgcgaccgag    1080
gacgcctgcg ccgccgggac ctgcgggcac gagaagtgcg ccgccgcgcg cgtcgccgcc    1140
ccggccgccg ccgtaccgcc cgccgctgta tcgcccgccg tccccgccgc ggcctccgcc    1200
gccgccgagg acgcgtgcgc cgccggcagc tgccagcacg gcaagtgcgc cgccatgcgc    1260
gccgaggccg ccaaggagaa aaaggtggcg gtgtccctgt ga                       1302

<210> SEQ ID NO 13
<211> LENGTH: 1919
<212> TYPE: PRT
<213> ORGANISM: Micromonospora echinospora calichensis

<400> SEQUENCE: 13

Met Ser Arg Ile Ala Val Val Gly Leu Ala Cys Arg Phe Pro Asp Ala
1               5                   10                  15

Ala Gly Pro Gly Gln Leu Trp Glu Asn Ala Leu Ala Gly Arg Arg Ala
            20                  25                  30

Phe Arg Arg Leu Pro Glu Glu Arg Met Arg Ala Ala Asp Tyr Trp Ser
        35                  40                  45

-continued

```
Pro Asp Pro Ala Ala Pro Asp Arg Tyr Tyr Ala Gly Asn Ala Ala Val
 50                  55                  60

Ile Glu Gly Tyr Glu Phe Asp Arg Val Gly Phe Lys Val Ser Gly Ser
 65                  70                  75                  80

Thr Tyr Arg Ser Thr Asp Leu Thr His Trp Leu Ala Leu Asp Met Ala
                 85                  90                  95

Ala Gln Ala Leu Ala Asp Ala Gly Phe Pro Glu Gly Asp Gly Leu Pro
            100                 105                 110

Arg Glu Arg Thr Ala Val Val Gly Asn Thr Leu Thr Gly Glu Phe
            115                 120                 125

Thr Arg Ala Gly Met Met Arg Leu Arg Trp Pro Tyr Val Arg Arg Val
            130                 135                 140

Val Gly Ala Ala Leu Gly Glu Gln Gly Trp Asp Asp Arg Val Ala
145                 150                 155                 160

Ala Phe Leu Ala Asp Leu Glu Arg Ser Tyr Lys Ala Pro Phe Ala Glu
                165                 170                 175

Ile Thr Glu Asp Ser Leu Ala Gly Gly Leu Ser Asn Thr Ile Ala Gly
            180                 185                 190

Arg Ile Cys Asn His Phe Asp Leu His Gly Gly Tyr Thr Val Asp
            195                 200                 205

Gly Ala Cys Ala Ser Ser Leu Leu Ser Val Val Thr Ala Cys Arg Ser
210                 215                 220

Leu Thr Asp Leu Asp Val Asp Val Ala Val Ala Gly Val Asp Leu
225                 230                 235                 240

Ser Ile Asp Pro Phe Glu Met Val Gly Phe Ala Lys Thr Gly Ala Leu
                245                 250                 255

Ala Gly Asp Glu Met Arg Val Tyr Asp Arg Arg Ser Asn Gly Phe Trp
            260                 265                 270

Pro Gly Glu Gly Cys Gly Met Val Val Leu Met Arg Glu Arg Asp Ala
            275                 280                 285

Leu Ala Gln Gly Arg Arg Ile Tyr Ala Ser Val Ala Gly Trp Gly Val
            290                 295                 300

Ser Ser Asp Gly Arg Gly Gly Ile Thr Arg Pro Glu Ala Ala Gly Tyr
305                 310                 315                 320

Arg Leu Ala Leu Arg Arg Ala Tyr Gln Arg Ala Gly Phe Gly Val Asp
                325                 330                 335

Thr Val Pro Leu Phe Glu Gly His Gly Thr Gly Thr Ala Val Gly Asp
            340                 345                 350

Gly Thr Glu Leu Arg Ala Leu Gly Glu Glu Arg Arg Ala Ala Asp Pro
            355                 360                 365

Asp Ala Asp Pro Ala Ala Ile Gly Ser Ile Lys Gly Met Ile Gly His
            370                 375                 380

Thr Lys Ala Ala Ala Gly Val Ala Gly Leu Ile Lys Ala Val Leu Ala
385                 390                 395                 400

Val His His Gln Val Val Pro Thr Val Gly Cys Val Glu Pro His
                405                 410                 415

Pro Glu Leu Ala Ala Asp Arg Pro Ala Leu Arg Ala Val Arg Arg Ala
            420                 425                 430

Glu Pro Trp Pro Ala Gly Ala Ala Gln Arg Ala Gly Val Thr Ala Met
            435                 440                 445

Gly Phe Gly Gly Ile Asn Thr His Leu Val Val Asp Gly Pro Thr Arg
450                 455                 460
```

```
Pro Arg Arg Arg Ser Leu Asp Arg Arg Thr Gln Gln Leu Ala Arg Ser
465                 470                 475                 480

Val Gln Asp Ala Glu Leu Leu Val Asp Ala Thr Arg Asp Glu
                485                 490                 495

Leu Arg Asp Arg Leu Asp Asp Leu Arg Thr Val Val Ala Gly Leu Ala
            500                 505                 510

Phe Ala Glu Leu Gly Asp Leu Ala Thr Asn Leu His Arg Ser Gln Arg
            515                 520                 525

Gly Arg Ala Tyr Arg Ala Ala Val Val Ala Arg Ser Pro Glu Glu Ala
            530                 535                 540

Asp Arg Ala Leu Gly Leu Ala Ala Arg Ala Leu Ala Pro Glu Gly Ala
545                 550                 555                 560

Gly Thr Leu Val Asp Pro Ala Arg Gly Val Phe Val Gly Arg Val Thr
                565                 570                 575

Arg Pro Ala Arg Val Gly Phe Leu Phe Pro Gly Gln Gly Ser Gly Arg
                580                 585                 590

Gly Trp Gly Gly Gly Ala Leu Arg Arg Arg Phe Thr Glu Ile Asp Asp
            595                 600                 605

Val Tyr Arg Ala Ala Gly Glu Pro Pro Gly Asp Glu Ala Ala Gly Ser
            610                 615                 620

Thr Val Phe Ala Gln Pro Arg Ile Val Thr Gly Ser Leu Ala Gly Leu
625                 630                 635                 640

Arg Ala Leu Ala Ala Leu Asp Ile Asp Ala Thr Val Val Val Gly His
                645                 650                 655

Ser Leu Gly Glu Leu Thr Thr Leu His Trp Ala Gly Cys Leu Asp Glu
            660                 665                 670

Asp Glu Leu Arg Glu Leu Val Thr Leu Arg Gly Glu Ala Met Ala Arg
            675                 680                 685

His Ala Pro Pro Gly Ala Met Leu Gly Val Thr Ala Gly Pro Glu Glu
            690                 695                 700

Thr Val Ala Leu Leu Ala Gly Thr Asn Ala Val Ile Ala Gly Tyr Asn
705                 710                 715                 720

Gly Pro Arg Gln Thr Val Val Ala Gly Ala Asp Asp Ile Val Ala Glu
                725                 730                 735

Val Ala Arg Arg Ala Ala Thr Ala Gly Val Asn Cys Thr Arg Leu Pro
                740                 745                 750

Val Pro His Ala Phe His Ser Pro Leu Met Ala Ser Ala Ala Ala
            755                 760                 765

Phe Ala Glu Arg Leu Arg Ser Arg Arg Phe Gly Pro Leu Leu Arg Arg
            770                 775                 780

Val Ala Ser Thr Val Thr Gly Ala Val Leu Pro Ser Asp Thr Asp Leu
785                 790                 795                 800

Pro Arg His Leu His Arg Gln Ile Glu Ala Pro Val Arg Phe Ala Ala
                805                 810                 815

Ala Leu Gly Arg Ala Ala Glu Val Asp Leu Phe Leu Glu Val Gly
            820                 825                 830

Pro Gly Arg Val Leu Thr Gly Leu Ala Arg Glu Gln Ala Pro Asp Val
            835                 840                 845

Pro Ala Leu Ala Val Asp Thr Asp Ala Glu Ser Leu Ser Gly Leu Leu
            850                 855                 860

Ala Ala Val Gly Ala Val Tyr Ala Leu Gly Gly Pro Ala Ala Tyr Pro
865                 870                 875                 880

Val Leu Phe Glu Asp Arg Leu Thr Arg Pro Phe Asp Pro His Arg Ala
```

-continued

```
                885             890             895
Arg Thr Phe Phe Ala Ser Pro Cys Glu Ala Ala Pro Glu Leu Ala Gly
        900                 905                 910

Pro Ala Pro Ala Ala Val Ala Pro Val Pro Ala Pro Ala Arg Ala Asp
        915                 920                 925

Asp Thr Ala Leu Pro Ala Ala Thr Gly Ala Leu Glu Leu Val Arg His
        930                 935                 940

Leu Val Ala Glu Arg Ala Glu Leu Pro Val Glu Val Leu Arg Asp Asp
945                 950                 955                 960

Ser Arg Phe Leu Asp Asp Leu His Met Ser Ser Ile Thr Val Gly Gln
        965                 970                 975

Leu Val Asn Glu Ala Ala Arg Ala Met Gly Leu Ser Ala Val Ala Met
        980                 985                 990

Pro Thr Asn Phe Ala Thr Ala Thr Val Arg Glu Met Ala Glu Ala Leu
        995                 1000                1005

Glu Ala Arg Glu Arg Glu Ala Pro His Glu Arg Ala Asp Leu Val
        1010                1015                1020

Ala Gly Val Ala Pro Trp Val Arg Thr Phe Val Val Asp Leu Val
        1025                1030                1035

Asp Glu Pro Leu Pro Ala Thr Asp Pro Thr Glu Pro Cys Gly Arg
        1040                1045                1050

Trp Gln Val Phe Ala Gly Ala Asp His Pro Leu Ala Asp Ala Leu
        1055                1060                1065

Arg Arg Ala Leu Glu Ala Ala Gly Val Gly Glu Gly Val Leu Val
        1070                1075                1080

Cys Leu Pro Asp Glu Pro Asp Glu Glu His Leu Val Thr Ala Val
        1085                1090                1095

Arg Gly Ala Gln Ala Ala Leu Arg Gln Pro Pro Gly Gly Arg Leu
        1100                1105                1110

Val Val Val Gln Pro Ala Ala Arg Ala Gly Ala Leu Ala Lys Thr
        1115                1120                1125

Ala Arg Leu Glu Gly Asp Arg Leu Arg Thr Thr Val Val Thr Thr
        1130                1135                1140

Pro Leu Asp Pro Ala Ala Val Asp Arg Val Val Ala Asp Val Ala
        1145                1150                1155

Ala Thr Asp Asp Phe Thr Glu Ala Val Tyr Asp Pro Gly Gly Arg
        1160                1165                1170

Arg Arg Val Pro Val Leu Arg Pro Leu Pro Ala Ser Asp Gly Glu
        1175                1180                1185

Pro Gly Ala Leu Pro Leu Gly Pro Ala Asp Val Leu Leu Val Thr
        1190                1195                1200

Gly Gly Gly Lys Gly Ile Thr Ala Glu Ser Ala Leu Met Leu Ala
        1205                1210                1215

Arg Glu Ser Gly Ala Arg Leu Ala Val Leu Gly Arg Ser Asp Pro
        1220                1225                1230

Thr Ala Asp Glu Ala Leu Ala Asp Asn Leu Lys Arg Leu Ala Asp
        1235                1240                1245

Ala Ala Ser Asp Leu Arg Tyr Leu Arg Val Asp Val Thr Asp Ala
        1250                1255                1260

Gly Ala Val Ala Ala Val Ala Thr Val Thr Ala Asp Trp Gly
        1265                1270                1275

Pro Val Thr Ala Val Leu His Gly Ala Gly Gln Asn Thr Pro Ala
        1280                1285                1290
```

-continued

```
Ala Leu Ala Asp Leu Asp Glu Ala Ala Leu Arg Gly Val Phe Ala
1295                1300                1305

Ala Lys Val Asp Gly Leu Arg Ala Val Leu Ala Ala Val Asp Pro
1310                1315                1320

Ala Arg Leu Arg Leu Leu Val Thr Phe Gly Ser Ile Ile Gly Arg
1325                1330                1335

Ala Gly Leu His Gly Glu Ala His Tyr Ala Ala Ala Asn Glu Ala
1340                1345                1350

Leu Ala Glu Leu Thr Arg Glu Val Ala Ala Thr Arg Pro Glu Cys
1355                1360                1365

Arg Ala Val Cys Leu Glu Trp Ser Val Trp Ser Gly Val Gly Met
1370                1375                1380

Gly Glu Arg Leu Ser Val Val Glu Ser Leu Ser Gly Ser Gly Val
1385                1390                1395

Thr Pro Ile Ser Pro Asp Asp Gly Leu Arg Val Leu Arg Glu Val
1400                1405                1410

Val Ala Asp Asp Thr Leu Pro Pro Val Val Val Thr Gly Arg
1415                1420                1425

Thr Gly Gly Val Glu Thr Leu Arg Tyr His Arg Ser Glu Leu Pro
1430                1435                1440

Leu Leu Arg Phe Thr Glu Arg Pro Leu Val Arg Tyr Asp Gly Ile
1445                1450                1455

Glu Leu Val Cys Glu Val Asp Leu Ala Arg Thr Thr Asp Pro Tyr
1460                1465                1470

Leu Glu Asp His Arg Leu Asp Gly Asp Leu Leu Phe Pro Ala Val
1475                1480                1485

Leu Gly Leu Glu Ala Met Ala Gln Val Ala Thr Ala Leu Ala Arg
1490                1495                1500

His Pro Gly Val Pro Val Ile Glu Glu Val Arg Phe Asp Arg Pro
1505                1510                1515

Val Val Val Asp Pro Asp Thr Gly Thr Thr Val Arg Val Ala Ala
1520                1525                1530

Leu Val Arg Ser Glu Gln Val Ile Asp Val Val Leu Arg Ser Ala
1535                1540                1545

Val Thr Gly Phe Ala Ala Asp His Phe Arg Ala Arg Leu Arg Phe
1550                1555                1560

Ala Pro Asp Glu Thr Tyr Pro Ala Tyr Thr Ala Ala Pro Ala Pro
1565                1570                1575

Ala Glu Leu Pro Ala Val Pro Leu Asp Pro Ala Arg Asp Leu Tyr
1580                1585                1590

Gly Asp Val Leu Phe Gln Ala Gly Arg Phe Arg Arg Ile Lys Gly
1595                1600                1605

Tyr Arg Gln Val Ala Ala Arg Val Ala Glu Ala Glu Val Val Thr
1610                1615                1620

Ser Asp Ala Ala Ser Trp Phe Ser Ala Phe Leu Pro Gly Arg Leu
1625                1630                1635

Val Leu Gly Asp Pro Gly Ala Arg Asp Ala Phe Met His Gly Ile
1640                1645                1650

Gln Val Cys Val Pro Asp Ala Thr Leu Leu Pro Glu Gly Ile Asp
1655                1660                1665

Arg Ile Trp Ser Ala Gly Pro Lys Leu Ser Ala Thr Glu Ala Val
1670                1675                1680
```

| | | | | | | | | | | |
|---|---|---|---|---|---|---|---|---|---|---|
|Thr|Met|Thr|Ala|Arg|Glu|Arg|Glu|Gln|His|Gly|Thr|Ala|Tyr|Val|
| |1685| | | |1690| | | |1695| | | | | |

| Tyr | Asp | Val | Val | Val | Arg | Asp | Ala | Thr | Gly | Ala | Val | Ile | Glu | His |
|---|---|---|---|---|---|---|---|---|---|---|---|---|---|---|
| | 1700 | | | | | 1705 | | | | 1710 | | | | |

Trp Met Gly Leu Arg Leu Arg Ala Val Arg Pro His Ala Pro Arg
    1715            1720                1725

Gly Ser Trp Pro Pro Ala Leu Leu Gly Pro Leu Leu Gln Arg Arg
    1730            1735                1740

Leu Ala Glu Val Phe Pro Gly Asp Ile Ala Val Ala Ala Ala Pro
    1745            1750                1755

Gly Gly Gly Pro Arg Asp Ser Gly Ala Leu Leu Ser Arg Ala Leu
    1760            1765                1770

Gly Gln Pro Val Val Val Arg His Arg Pro Asp Gly Arg Pro Glu
    1775            1780                1785

Val Asp Leu Pro Tyr Thr Val Ser Val Ala His Ser Ala Pro Leu
    1790            1795                1800

Asp Leu Ala Val Ala Gly Asp Gly Thr Leu Ala Cys Asp Ala Glu
    1805            1810                1815

Pro Val Ala Ala Arg Pro Ala Asp Val Arg Arg Asp Leu Val Gly
    1820            1825                1830

Arg His Gly Ala Val Ala Ala Leu Leu Val Ala Glu Val Gly Asp
    1835            1840                1845

Pro Pro Asp Val Ala Ala Thr Arg Val Trp Cys Ala Glu Glu Cys
    1850            1855                1860

Leu Gln Lys Ala Gly Arg Pro Glu Gly Arg Leu Thr Leu Leu Pro
    1865            1870                1875

Gly Ala Leu Pro Asp Gly Trp Val Val Leu Asp Ala Gly Asp Val
    1880            1885                1890

Arg Val Ala Thr Arg Val Val Ala Val Ala Gly Ala Ala Ala Pro
    1895            1900                1905

Ala Val Val Ala Val Leu Ser Gly Ala Gly Arg
    1910            1915

<210> SEQ ID NO 14
<211> LENGTH: 5760
<212> TYPE: DNA
<213> ORGANISM: Micromonospora echinospora calichensis

<400> SEQUENCE: 14

| | |
|---|---|
| atgagcagga tcgccgtcgt cggcctggcc tgccgcttcc cggacgccgc cggccccggg | 60 |
| cagctgtggg agaacgccct cgccgggcgg cgtgcgttcc gccgcctgcc cgaggagcgg | 120 |
| atgcgggccg ccgactactg gtccccggat ccggccgccc ccgaccgcta ctacgcgggc | 180 |
| aacgcggccg tcatcgaggg ctacgagttc gaccgggtcg ggttcaaggt cagcgggagc | 240 |
| acgtaccggt ccaccgacct cacccactgg ctggccctcg acatggccgc gcaggcgctc | 300 |
| gccgacgccg ggttccccga gggcgacggg ctgccgcggg aacggacggc ggtggtcgtc | 360 |
| ggcaacaccc tcaccggcga gttcacccgg gccggcatga tgcgcctgcg gtggccgtac | 420 |
| gtccggcgcg tggtgggcgc cgccctcggc gagcagggct gggacgacga ccgggtggcg | 480 |
| gccttcctcg ccgacctgga acgctcctac aaggcgccgt cgccgagat caccgaggac | 540 |
| agcctcgcgg gcggcctgtc caacaccatc gccgggcgga tctgcaacca cttcgacctg | 600 |
| cacggcggcg gtacacggt ggacggcgcc tgcgcctcct ccctgctgtc ggtggtcacc | 660 |
| gcctgccgca gcctgaccga cctcgacgtc gacgtggcgg tggccggcgg cgtggacctg | 720 |

-continued

```
tccatcgacc ccttcgagat ggtcggcttc gccaagaccg cgcgctagc cggcgacgag    780 atgcgggtct acgaccgccg ctccaacggg ttctggcccg gcgagggctg cggcatggtg    840
gtgctcatgc gggagcggga cgcgctcgcg cagggccggc gcatctacgc ctcggtcgcc    900
gggtggggcg tctcctccga cggtcggggc ggcatcaccc ggccggaggc ggccggctac    960
cggctggccc tgcggcgcgc gtaccagcgg gccggtttcg gggtggacac cgtgccgctg   1020 ttcgagggc acggcaccgg cacggccgtc ggcgacggca ccgagctgcg ggccctgggc   1080
gaggaacgcc gggcggccga cccggacgcg gaccccgccg cgatcggatc catcaagggg   1140
atgatcgggc acaccaaggc cgcggccggg gtggccggcc tgatcaaggc cgtcctggcc   1200
gtgcaccacc aggtcgtccc gccgaccgtc gggtgcgtcg agccgcaccc cgaactcgcc   1260
gcggaccggc ccgcgctgcg cgccgtacgg cgggccgagc cgtggccggc cggcgccgcg   1320
cagcgggccg cgtcaccgc gatgggcttc ggcggcatca cacccaccct cgtcgtcgac   1380
ggccccaccc gccccgccg ccggtccctg gaccggcgga cgcagcagct cgcccggtcc   1440
gtgcaggacg ccgagctgct cctggtcgac gcggacaccc gcgacgagct gcgcgaccgg   1500
ctggacgacc tgcggacggt cgtggccggg ctggccttcg ccgagctggg cgacctcgcc   1560
acgaacctgc accggagcca gcgcggccgc gcgtaccggg cggcggtcgt ggcccggtca   1620
ccggaggagg ccgaccgcgc cctcggactg gcggcccggg ccctggcgcc cgagggcgcc   1680
gggacactgg tcgacccggc gcggggcgtc ttcgtcggcc gggtcacccg gccggcccgg   1740
gtcggcttcc tgttccccgg gcaggggtcc ggtcggggct ggggcggcgg ggcgctgcgc   1800
cggcggttca ccgaaatcga cgacgtctac cgcgcggccg gggagccacc cggggacgag   1860
gcggccgggt cgaccgtgtt cgcccagccc cggatcgtca cgggctcgct ggccgggctg   1920
cgcgccctcg ccgcgctcga catcgacgcg accgtcgtcg tcgggcacag cctcggcgaa   1980
ctcaccacgc tgcactgggc gggctgcctc gacgaggacg agctgcggga gctcgtcacg   2040
ctccggggcg aggccatggc caggcacgcc ccgcccgggg cgatgctcgg cgtcaccgcc   2100
gggccggagg agaccgtcgc cctgctggcc ggcaccaacg cggtgatcgc cggctacaac   2160
gggccccggc agacggtcgt cgccggagcc gacgacatcg tggccgaggt ggcccgccgg   2220
gccgcgacgg cggggtgaa ctgcacccgg ctgccggtcc cgcacgcctt ccactcgccg   2280
ctgatggcat cggcggccgc cgccttcgcc gagcgcctgc ggtcccgccg gttcgggccg   2340
ctgctgcgcc gcgtggcctc gacggtgacc ggcgccgtcc tcccgtcgga caccgacctg   2400
ccgcggcacc tgcaccggca gatcgaggct ccggtgcgct tcgccgccgc gctgggacgc   2460
gccgccgccg aggtcgacct gttcctcgag gtcggcccg gcagggtgct caccgggctg   2520
gcccgcgagc aggcgccgga cgtgccggcg ctggcggtcg acaccgacgc cgagtcgctg   2580
tcgggcctgc tcgccgcggt cggcgcggtg tacgcgctcg gcggcccggc cgcgtacccg   2640
gtcctgttcg aggaccggct gacccgaccg ttcgacccgc accgcgcccg caccttcttc   2700
gcgagcccgt gcgaggcggc gcccgagctg gccgggccgg caccggccgc ggtcgccccg   2760
gtcccggctc cggcccgggc cgacgacacc gcgctgccgg ccgccaccgg tgcgctcgag   2820
ctggtgcggc acctcgtggc ggaacgcgcc gagctgccgg tggaggtgct tcgggacgac   2880
agccggttcc tcgacgacct gcacatgagc tcgatcaccc tcggccagct cgtcaacgag   2940 gccgccgcg ccatgggct gtccgcggtg gcgatgccga ccaacttcgc caccgccacc   3000
gtccgggaga tggccgaggc gctggaggcc cgggagcgcg aggccccgca cgagcgcgcg   3060
```

```
gacctcgtcg ccggggtcgc gccgtgggtg cgtaccttcg tcgtcgacct ggtcgacgag   3120
ccgctgccgg cgaccgaccc gacggagccg tgcggccgct ggcaggtgtt cgcgggcgcc   3180
gaccacccc tcgcggacgc cctgcgccgg gccctggagg cggcgggcgt cggcgagggc   3240
gttctcgtct gcctgcccga cgaacccgac gaggagcacc tggtcaccgc ggtgcgcggg   3300
gcccaggccg cgctgcgcca accgccggg gggcggctcg tggtggtgca gccggcggcg   3360
cgggcggggg cgctggccaa gaccgccggg ctggagggcg accggctgcg gaccaccgtc   3420
gtgaccaccc cctcgacccc ggccgcggtc gaccgggtgg tcgccgacgt ggccgccacg   3480
gacgacttca ccgaggcggt gtacgacccg gcggccgcc gtcgggtgcc cgtgctgcgc   3540
ccgctgcccg cgtccgacgg cgagccgggc gccctgccgc tgggcccggc cgacgtgctg   3600
ctggtgactg gcggcggcaa gggcatcacg gccgagtccg cgctgatgct ggcccgggag   3660
agcggtgccc gactcgccgt cctcggccgg tccgaccca ccgccgacga ggccctggcc   3720
gacaacctga gcggctcgc ggacgccgcg tccgacctgc gctacctgcg ggtcgacgtc   3780
accgacgccg gcgcggtggc cgccgcggtc gccacggtca ccgccgactg ggggcccggtg   3840
accgccgtc tccacggcgc cgggcagaac accccagccg cgctcgccga cctggacgag   3900
gcggccctgc ggggcgtgtt cgccgccaag gtcgacggcc tgcgggcggt gctcgccgcg   3960
gtcgacccca cacggctgcg cctgctggtc acgttcggca gcatcatcgg gcgggcgggg   4020
ctgcacggcg aggcgcacta cgccgcggcg aacgaggcgc tggccgagct gacccgggag   4080
gtggccgcga cgcggccgga gtgccgcgcc gtctgcctgg agtggtcggt gtggtccggg   4140
gtcggcatgg gggagcggct gtcggtggtc gagtcgttga gcggctccgg cgtcaccccg   4200
atcagcccgg acgacggcct gcgggtcctg cgccgaggtgg tcgccgacga cacgctgccc   4260
ccggtggtgg tggtcaccgg ccgtaccggc ggcgtggaga ccctgcgcta ccaccgctcc   4320
gagctgccgc tgctgcgctt caccgaacg ccgttggtgc gctacgacgg catcgagctg   4380
gtgtgcgagg tcgacctggc ccgcaccacg gatccgtacc tggaggacca ccggctcgac   4440
ggcgacctgc tgttcccggc ggtgctcggg ttggaggcca tggcccaggt ggccaccgcc   4500
ctggcccggc acccgggagt gcccgtgatc gaggaggtcc ggttcgaccg cccggtggtc   4560
gtcgacccgg acaccggcac gaccgtacgc gtcgccgcgc tggtccggtc ggagcaggtc   4620
atcgacgtcg tcctgcgtag cgcggtgacc ggcttcgcgg ccgaccactt ccgcgcccgg   4680
ctccggttcg cgccggacga gacctacccg gcgtacaccg cggcgcccgc gccggcggag   4740
ctgccggccg taccgctcga cccggcccgc gacctctacg gcgacgtgtt gttccaggcc   4800
ggtcggttcc gccggatcaa gggctaccgg caggtcgcgg cgcgggtcgc cgaggccgag   4860
gtggtcacca gcgacgccgc ctcctggttc agcgccttcc tgccggggcg gctggtgctc   4920
ggcgacccgg gcgccgggga cgcgttcatg cacgggatcc aggtgtgcgt gccggacgcg   4980
acgctgctgc cggagggcat cgaccggatc tggtcggcgg gccccaagct gtcggccacc   5040
gaggccgtga cgatgaccgc gcgggaacgc gaacagcacg gcaccgccta cgtgtacgac   5100
gtcgtcgtcc gggacgccac gggcgcgtg atcgagcact ggatgggtct gcggctgcgc   5160
gccgtgcgtc cgcacgcgcc gcgcgggtcc tggccgcccg cgctgctggg gccgctgctg   5220
caacgacggc tcgccgaggt gttccccggc gacatcgcgg tcgccgccgc acccggggc   5280
gggccccgcg actccggcgc gctgctctcc cgcgcgctgg gccagcccgt ggtggtgcgg   5340
caccggcccg acggcggcc ggaggtcgac ctgccgtaca ccgtctccgt ggcgcactcg   5400
gcgccgctcg acctcgccgt cgccggggac gggacgctcg cctgcgacgc cgagccggtg   5460
```

```
gccgcccgcc cggcggacgt gcggcgcgac ctggtgggtc ggcacggcgc ggtggcggcg    5520
ctgctcgtcg cggaggtcgg tgatccgccg gacgtggcgg ccacccgggt ctggtgcgcg    5580
gaggagtgcc tgcagaaggc cggccgcccc gagggccggc tcaccctgct gcccggggcg    5640
ctccccgacg gctgggtggt gctggacgcc ggcgacgtcc gggtcgccac ccgggtcgtc    5700
gcggtggcgg gagcggcggc gccggccgtg gtcgccgtgc tcagcggggc ggggaggtga    5760
```

<210> SEQ ID NO 15
<211> LENGTH: 148
<212> TYPE: PRT
<213> ORGANISM: Micromonospora echinospora calichensis

<400> SEQUENCE: 15

```
Val Ser Met Pro Arg Tyr Tyr Glu Tyr Arg His Val Val Gly Phe Glu
1               5                   10                  15

Glu Thr Asn Leu Val Gly Asn Val Tyr Tyr Val Asn Tyr Leu Arg Trp
            20                  25                  30

Gln Gly Arg Cys Arg Glu Met Phe Leu Tyr Glu His Ala Pro Glu Ile
        35                  40                  45

Leu Asp Glu Leu Arg Ala Asp Leu Lys Leu Phe Thr Leu Lys Ala Glu
    50                  55                  60

Cys Glu Phe Phe Ala Glu Leu Ala Pro Phe Asp Arg Leu Ala Val Arg
65                  70                  75                  80

Met Arg Leu Val Glu Leu Thr Gln Thr Gln Met Glu Leu Gly Phe Asp
                85                  90                  95

Tyr Leu Arg Leu Gly Gly Asp Asp Leu Leu Val Ala Arg Gly Arg Gln
            100                 105                 110

Arg Ile Ala Cys Met Arg Gly Pro Asn Gly Arg Thr Glu Pro Val Arg
        115                 120                 125

Val Pro Ala Gly Leu Val Arg Ala Phe Ala Pro Phe Arg Ser Ala Thr
    130                 135                 140

Val Gly Gln Gly
145
```

<210> SEQ ID NO 16
<211> LENGTH: 447
<212> TYPE: DNA
<213> ORGANISM: Micromonospora echinospora calichensis

<400> SEQUENCE: 16

```
gtgagcatgc cgcgctacta cgagtaccgg cacgtcgtcg gcttcgagga gaccaacctc     60
gtcggcaacg tgtactacgt caactacctg cgctggcagg gccggtgccg ggagatgttc    120
ctgtacgagc acgcgccgga gatcctcgac gagctgcgcg ccgacctgaa gctgttcacc    180
ctcaaggccg agtgcgagtt cttcgccgag ctggcgccgt tcgaccgcct cgcggtccgg    240
atgcggctgg tcgaactcac ccagacccag atggagctgg gcttcgacta cctgcggctc    300
ggcggcgacg atctgctggt cgcccggggg cggcagcgga tcgcgtgcat gcgcgggccg    360
aacgggcgga ccgagccggt ccgggtgccg gccggcctgg tgcgggcgtt cgccccgttc    420
cggtcggcca cggtggggca ggggtga                                        447
```

<210> SEQ ID NO 17
<211> LENGTH: 322
<212> TYPE: PRT
<213> ORGANISM: Micromonospora echinospora calichensis -continued

```
<400> SEQUENCE: 17

Met Pro Ala Asn Trp Arg Thr Ile Arg Gln Tyr Ala Leu Thr Pro Gly
1               5                   10                  15

Met Ala Gln Thr Thr Phe Ala Thr Arg Gly Phe Arg Ala Arg Asp Glu
            20                  25                  30

Pro Thr Arg Glu Arg Leu Glu Ser Val Gly Ala His Phe Leu Thr Gly
        35                  40                  45

Tyr Gly His Ala Val Gly Ala Arg Gly Pro Asp Glu Ala Val Gly Ala
    50                  55                  60

Leu Glu Thr Val Ala Pro Asp Leu Arg Gly Phe Ala Tyr Glu Gly Ala
65                  70                  75                  80

Ala Met Gly Leu Ala Val Leu Asp Gly Leu Thr Gly Gly Arg Arg Ile
                85                  90                  95

Ala Arg Phe Leu Ala Gly Pro Ala Ala Arg His Val Tyr Met Val His
            100                 105                 110

Val Gly Val Gly Trp Ala Met Ala Arg Leu Pro Arg Trp Arg Arg His
        115                 120                 125

Ala Ile Gln Pro Ala Asp Arg Leu Leu Gly Trp Leu Ala Leu Asp Gly
    130                 135                 140

Tyr Gly Phe His Gln Ala Tyr Phe His Thr Arg Arg Tyr Val Trp Ser
145                 150                 155                 160

His Arg Arg Asp Glu Val Leu Pro Trp Pro Gly Asp Pro Ile Gly Arg
                165                 170                 175

Trp Thr Gly Arg Val Val Asp Gln Gly Ile Gly Arg Ala Leu Trp Phe
            180                 185                 190

Val Glu Gly Ala Asp Thr Asp Arg Ile Ala Asp Thr Val Asp Gly Phe
        195                 200                 205

Pro Pro Asp Arg His Glu Asp Leu Tyr Ser Gly Val Ala Leu Ala Ala
    210                 215                 220

Thr Tyr Ala Gly Gly Ala Pro Pro Glu Asp Leu Arg Arg Leu Arg Glu
225                 230                 235                 240

Arg Gly Gly Ala Tyr Ala Pro Ala Met Ala Gln Gly Ser Ala Phe Ala
                245                 250                 255

Ala Glu Ala Arg Glu Arg Ala Gly Leu Thr Thr Ala His Thr Ala Val
            260                 265                 270

Ala Thr Asp Val Phe Cys Gly Ala Pro Pro Ala Glu Ala Ala Ala Val
        275                 280                 285

Thr Gln Ala Ala Leu Ala Asp Leu Asp Arg Asp Gly Pro Glu Pro Ala
    290                 295                 300

Tyr Leu Val Trp Arg Gln Arg Ile Ala Lys Gln Phe Val Thr Leu Gly
305                 310                 315                 320

Arg Cys

<210> SEQ ID NO 18
<211> LENGTH: 969
<212> TYPE: DNA
<213> ORGANISM: Micromonospora echinospora calichensis

<400> SEQUENCE: 18
atgcccgcca attggcgaac cattcgtcaa tacgccctga cgccggggat ggcccagacc    60
accttcgcga cccggggctt ccgcgcccgg gacgagccga cccgcgagcg gctggagtcg   120
gtcggcgccc acttcctcac cggctacggg cacgccgtcg cgcccggggg cccggacgag   180
gccgtcgggg cgctggagac cgtcgcgccg gacctgcgcg ggttcgcgta cgagggcgcg   240
```

-continued

```
gcgatgggcc tcgccgtcct ggacgggctg accggtggcc gccggatcgc ccggttcctg    300
gccgggccgg ccgcccggca cgtgtacatg gtccatgtcg gggtgggctg ggcgatggcc    360
cgcctgcccc gctggcgtcg gcacgcgatc caacccgccg accggctgct gggctggctg    420
gcgctggacg gctacggatt ccaccaggcg tacttccaca cccggcggta cgtgtggtcg    480
caccggcgtg acgaggtgct gccctggccc ggcgacccga tcgggcggtg gaccgggcgc    540
gtcgtggacc agggcatcgg ccgcgcgctg tggttcgtcg agggcgccga caccgaccgg    600
atcgccgaca ccgtcgacgg cttcccgccg gaccggcacg aggacctgta cagcggggtg    660
gcgctggccg ccacgtacgc cggcggggcg ccgcccgagg acctgcggcg gctgcgcgag    720
cgcggcggag cgtacgcccc ggcgatggcc cagggcagcg ccttcgcggc ggaggcccgg    780
gagcgcgccg ggctgaccac cgcgcacacc gcggtcgcca ccgacgtctt ctgcggcgcg    840
ccaccggccg aggcggcggc ggtcacccag gccgcgctgg ccgacctcga ccgggacggg    900
ccggagccgg cctacctggt gtggcggcag cggatcgcca agcagttcgt gacgctgggg    960
aggtgctga                                                            969
```

<210> SEQ ID NO 19
<211> LENGTH: 651
<212> TYPE: PRT
<213> ORGANISM: Micromonospora echinospora calichensis

<400> SEQUENCE: 19

```
Met Phe Arg Arg Gln Leu Ala Gly Leu Val Ala Leu Val Leu Leu Thr
1               5                   10                  15

Gly Met Tyr Val Leu Val Arg Gln Pro Glu Ala Asn Ala Asp Glu Arg
            20                  25                  30

Arg Ala Met Ala Glu Pro Tyr Arg Phe Thr Pro Met Ser Leu Pro Met
        35                  40                  45

Pro Gly Gly Leu Pro Gln Gln Ser Ile Arg Arg Val Asn Gly Ala Tyr
    50                  55                  60

Gln His Leu Ala Ala Trp Ile Ser Ser Val Gly Ala Gly Ala Ala Met
65                  70                  75                  80

Asn Asp Leu Asp Gly Asp Gly Leu Ala Asn Asp Leu Cys Val Thr Asp
                85                  90                  95

Pro Arg Val Asp Arg Val Val Thr Pro Ala Pro Thr Ala Gly Ala
            100                 105                 110

Asp Arg Tyr Gln Pro Phe Val Leu Asp Pro Ala Pro Leu Pro Met Asn
        115                 120                 125

Pro Tyr Val Ala Pro Met Gly Cys Leu Pro Gly Asp Leu Asn Ala Asp
    130                 135                 140

Gly Arg Thr Asp Leu Leu Val Tyr Trp Trp Gly Arg Thr Pro Val Val
145                 150                 155                 160

Phe Leu Ala Arg Ala Asp Ala Thr Gly Leu Ser Arg Ala Ala Tyr His
                165                 170                 175

Pro Val Glu Leu Val Pro Gly Ala Ala Thr Gly Gly Ser Arg Tyr Asp
            180                 185                 190

Gly Pro Lys Trp Asn Thr Asn Ala Ala Thr Leu Ala Asp Phe Asp Gly
        195                 200                 205

Asp Gly His Leu Asp Val Tyr Ile Gly Asn Tyr Phe Pro Asp Ser Ala
    210                 215                 220

Val Leu Asp Asp Thr Val His Gly Gly Val Ala Met Asn Arg Ser Met
225                 230                 235                 240
```

-continued

Ser Asn Gly Leu Asn Gly Gly Glu Asp His Val Phe Arg Trp Thr Gly
            245                 250                 255

Gly Thr Ala Gly Ala Thr Pro Ser Ala Ser Phe Ala Glu Val Pro Asp
        260                 265                 270

Val Phe Asp Thr Lys Val Ser Arg Gly Trp Thr Leu Ala Val Ala Ala
        275                 280                 285

Asn Asp Leu Asp Gly Asp Gln Leu Pro Glu Leu Tyr Val Ala Asn Asp
290                 295                 300

Phe Gly Pro Asp Arg Leu Leu His Asn Arg Ser Glu Arg Gly Arg Ile
305                 310                 315                 320

Ala Phe Ala Pro Val Glu Ser Pro Gly Leu Pro Gly Leu Thr Pro Lys
                325                 330                 335

Ser Lys Arg Leu Gly His Asp Ser Phe Lys Gly Met Gly Val Asp Phe
                340                 345                 350

Gly Asp Ile Asp Gly Asp Gly Met Phe Asp Leu Tyr Val Gly Asn Ile
            355                 360                 365

Thr Thr Ser Phe Gly Ile Gln Glu Ser Asn Phe Ala Phe Val Asn Thr
370                 375                 380

Ala Ala Asp Thr Ala Ala Leu Arg Ala Ala Leu Trp Ala Gly Glu Ala
385                 390                 395                 400

Pro Trp His Asp Arg Ser Ala Glu Leu Gly Leu Ala Trp Ser Gly Trp
                405                 410                 415

Ser Trp Asp Val Lys Phe Gly Asp Phe Thr Asn Arg Gly Asp Pro Ala
            420                 425                 430

Ile Val Gln Thr Ser Gly Phe Val Lys Gly Glu Val Asn Arg Trp Ala
            435                 440                 445

Gln Leu Gln Glu Ala Ala Thr Ala Asn Asp Asp Leu Leu Ala Asn Pro
    450                 455                 460

Arg Trp Trp Pro Lys Val Glu Gln Gly Asp Asp Ile Ala Gly Gly Gln
465                 470                 475                 480

His Leu Ala Phe His Val Arg Gly Ala Asp Gly Arg Tyr Glu Asp Leu
                485                 490                 495

Ser His Glu Leu Gly Leu Ala Asp Arg Val Pro Ser Arg Gly Ile Ala
            500                 505                 510

Thr Ala Asp Ala Asp Gly Asp Gly Arg Leu Asp Leu Val Val Ala Arg
        515                 520                 525

Gln Trp Asp Ala Pro Val Phe Tyr Arg Asn Asp Ser Pro Asp Thr Gly
    530                 535                 540

Ser Phe Leu Thr Leu Arg Leu Leu His Glu Gln Ala Pro Ala Ala Gly
545                 550                 555                 560

Pro Leu Ala Gly Ala Gly Ser Pro Val Val Gly Ala Gln Val Arg Val
                565                 570                 575

Thr Thr Pro Asp Gly Arg Val Leu Ile Asp Arg Val Asp Gly Gly Ser
            580                 585                 590

Gly His Ser Gly Arg Arg Ser Asn Glu Val Ser Leu Gly Leu Asp Asp
        595                 600                 605

Val Thr Gly Pro Val Ser Val His Leu Thr Trp Arg Asp Arg Ser Gly
    610                 615                 620

Ala Pro His Glu Gln Leu Thr Leu Ala Pro Gly Arg His Thr Leu
625                 630                 635                 640

Thr Leu Gly Ser Gln Ala Arg Glu Val Ser Arg
                645                 650

<210> SEQ ID NO 20
<211> LENGTH: 1956
<212> TYPE: DNA
<213> ORGANISM: Micromonospora echinospora calichensis

<400> SEQUENCE: 20

| | | | | | |
|---|---|---|---|---|---|
| atgttccgcc | ggcagttggc | cgggctggtc | gcgctggtgc | tgctcaccgg | catgtacgtg | 60 |
| ctggtccgga | agccggaggc | gaacgccgac | gagcggcgcg | ccatggcgga | gccgtaccgg | 120 |
| ttcacgccga | tgtcgctgcc | gatgccgggc | ggcctgccgc | agcagtcgat | ccgccgggtc | 180 |
| aacggcgcgt | accagcacct | gcggcgtgg | atctcctccg | tcggcgccgg | cgccgcgatg | 240 |
| aacgacctgg | acggtgacgg | actggccaac | gacctgtgcg | tcaccgaccc | acgcgtcgac | 300 |
| cgcgtcgtgg | tgaccccggc | cccgaccgcc | ggcgccgacc | gctaccagcc | gttcgtgctg | 360 |
| gacccggcgc | cgctgccgat | gaacccgtac | gtcgccccga | tgggctgcct | gcccggcgac | 420 |
| ctcaacgccg | acgccgcac | cgacctgctc | gtgtactggt | ggggccggac | cccggtggtc | 480 |
| ttcctggccc | gggcggacgc | gaccgggctg | tcccggggccg | cctaccaccc | cgtcgagctg | 540 |
| gtgccgggcg | cggcgaccgg | cggtagccgg | tacgacgggc | cgaagtggaa | caccaacgcc | 600 |
| gcgacgctgg | ccgacttcga | cggcgacggg | cacctggacg | tctacatcgg | caactacttc | 660 |
| cccgacagcg | ccgtcctcga | cgacaccgtc | cacggcgggg | tggcgatgaa | ccggtccatg | 720 |
| tccaacggcc | tcaacggcgg | cgaggaccac | gtgttccggt | ggaccggcgg | caccgccggc | 780 |
| gccacgccga | gcgcctcctt | cgccgaggtc | ccggacgtct | tcgacaccaa | ggtctcccgg | 840 |
| ggctggacgc | tcgccgtcgc | cgcgaacgac | ctcgacggcg | accaactgcc | cgagctgtac | 900 |
| gtggccaacg | acttcgggcc | ggaccggctg | ctgcacaacc | ggtcggagcg | ggggcggatc | 960 |
| gccttcgcgc | cggtcgagag | ccccgggctg | cccggcctga | ccccaagtc | aaagcggctc | 1020 |
| ggccacgact | cgttcaaggg | catgggcgtg | gacttcggcg | acatcgacgg | cgacggcatg | 1080 |
| ttcgacctgt | acgtcggcaa | catcaccacc | tccttcggca | tccaggagag | caacttcgcc | 1140 |
| ttcgtcaaca | ccgccgccga | caccgccgcg | ctgcgcgccg | cgctgtgggc | cggcgaggcg | 1200 |
| ccgtggcacg | accgcagcgc | cgagctgggc | ctggcctgga | gcgggtggag | ctgggacgtc | 1260 |
| aagttcggcg | acttcaccaa | ccgcggcgac | ccggcgatcg | tgcagacctc | cggcttcgtc | 1320 |
| aagggcgagg | tcaaccgctg | ggcgcagttg | caggaggcgg | ccaccgccaa | cgacgacctg | 1380 |
| ctcgccaacc | cccgctggtg | gccgaaggtc | gagcagggcg | acgacatcgc | cggcggccag | 1440 |
| cacctcgcct | tccacgtccg | gggcgccgac | ggccgctacg | aggacctcag | ccacgaactg | 1500 |
| ggcctggccg | accgggtgcc | cagccggggc | atcgccaccg | ccgacgccga | cggcgacggg | 1560 |
| cgcctcgacc | tcgtcgtcgc | ccggcagtgg | gacgcgccgc | tcttctaccg | caacgacagc | 1620 |
| ccggacaccg | gttccttcct | caccctgcgg | ctgctgcacg | agcaggcgcc | ggccgccggc | 1680 |
| cccctcgccg | ggcggggtc | gccggtcgtc | ggcgcgcagg | tccgggtgac | cacgccggac | 1740 |
| ggccgggtgc | tcatcgaccg | ggtcgacggc | ggcagcggcc | actcgggccg | cgcagcaac | 1800 |
| gaggtgtcgc | tcggtctcga | cgacgtgacc | ggcccggtgt | cggtccacct | cacctggcgg | 1860 |
| gaccggtccg | gcgccccgca | cgagcaggag | ctgacgctgg | ccccggtcg | acacaccctc | 1920 |
| accctcggtt | cgcaggctcg | ggaggtctcg | cgatga | | | 1956 |

<210> SEQ ID NO 21
<211> LENGTH: 321
<212> TYPE: PRT
<213> ORGANISM: Micromonospora echinospora calichensis

<400> SEQUENCE: 21

| | | | | | | | | | | | | | | |
|---|---|---|---|---|---|---|---|---|---|---|---|---|---|---|
|Met|Thr|Gln|Lys|Pro|Ala|Lys|Asp|Pro|Arg|Ile|Thr|Ala|Leu|Arg|Arg|
|1| | | |5| | | | |10| | | | |15| |

Phe Ala Ile Ser Ile Thr Ile Leu Asn Ile Ala Gly Tyr Thr Val Leu
            20                  25                  30

Gly Phe Glu Gln Ala Trp Ala Trp Pro Leu Ile Ala Leu Ala Thr Gly
                35                  40                  45

Tyr Ala Val Glu Leu Gly Leu Glu Ile Ile Gly Ala Arg Ala Glu Arg
         50                  55                  60

Arg Pro Pro Arg Phe Arg Gly Asn Gly Leu Arg Gly Leu Val Glu Phe
65                  70                  75                  80

Leu Tyr Pro Ala His Ile Thr Ala Leu Ala Val Asn Met Leu Leu Tyr
                85                  90                  95

Val Asn Asp Arg Val Pro Val Met Met Phe Ala Val Ala Val Ala Ile
            100                 105                 110

Ser Gly Lys Trp Leu Phe Arg Val Pro Val Asn Gly Arg Leu Arg His
            115                 120                 125

Phe Met Asn Pro Ser Asn Phe Gly Ile Ala Val Leu Leu Leu Phe
130                 135                 140

Pro Trp Ile Ser Ile Ala Pro Pro Tyr Gln Phe Thr Glu Tyr Leu Glu
145                 150                 155                 160

Gly Pro Ala Asp Trp Ile Val Pro Ala Ile Val Val Phe Gly Thr
                165                 170                 175

Met Leu Asn Ala Lys Leu Thr Gly Arg Met Trp Leu Ile Ala Gly Trp
            180                 185                 190

Leu Gly Val Phe Val Leu Gln Ser Val Val Arg Gly Leu Val Leu Asp
            195                 200                 205

Thr Ala Ile Leu Pro Ala Leu Ala Thr Met Thr Gly Val Ala Phe Val
210                 215                 220

Leu Phe Thr Asn Tyr Met Ile Thr Asp Pro Gly Thr Thr Pro Ser Arg
225                 230                 235                 240

Pro Leu Ser Gln Phe Ala Phe Gly Gly Gly Val Ala Leu Val Tyr Gly
                245                 250                 255

Val Leu Thr Gly Ala Ser Ile Val Tyr Gly Leu Phe Phe Ala Thr Ala
            260                 265                 270

Ile Val Cys Leu Ile Arg Gly Gly Phe Leu Trp Ser Leu His Ala Val
            275                 280                 285

Arg Val Ala Ala Arg Asp Gly Lys Gly Thr Pro Pro Ala Ala Pro Gly
            290                 295                 300

Thr Val Asp Gly Thr Val Pro Pro Ala Val Ala Arg Glu Met Val Arg
305                 310                 315                 320

Ala

<210> SEQ ID NO 22
<211> LENGTH: 966
<212> TYPE: DNA
<213> ORGANISM: Micromonospora echinospora calichensis

<400> SEQUENCE: 22

```
atgacgcaga agccggcgaa ggacccgcgg atcaccgcgc tgcgcaggtt cgccatctcc      60
atcaccatcc tcaacatcgc cggctacacc gtgctcggct cgagcaggc ctgggcgtgg     120 ccgctgatcg cgctcgccac cggctacgcc gtcgagctcg gctggagat catcggcgcg     180
```

-continued

```
cgggccgagc ggcgcccgcc ccggttccgc ggcaacggcc tgcgcggcct ggtcgagttc    240
ctctaccccg cgcacatcac cgccctcgcg gtgaacatgc tgctgtacgt caacgaccgc    300
gtgccggtga tgatgttcgc ggtggccgtg gcgatcagcg ggaagtggct gttccgggtg    360
ccggtcaacg gccggctgcg gcacttcatg aacccgtcga acttcggcat cgcggtggtg    420
ctgctgctgt cccgtggat ctcgatcgcc ccgccgtacc agttcaccga gtacctggag     480
ggccccgccg actggatcgt ccccgcggtc atcgtcgtct tcggcaccat gctcaacgcg    540
aagctcaccg gccggatgtg gctgatcgcc ggctggctgg gcgtcttcgt gctccagtcg    600
gtggtgcggg gactcgtgct ggacaccgcc atcctgccgg cgctggccac catgaccggg    660
gtggcgttcg tcctgttcac gaactacatg atcaccgacc cggggacgac cccgtcgcgg    720
ccgctgtccc agttcgcctt cggtggcggg gtggccctgg tgtacggcgt cctcaccggc    780
gcgtccatcg tctacggcct cttcttcgcc accgccatcg tctgtctgat ccggggcggc    840
ttcctctggt cgctgcacgc ggtacgcgtc gccgcccgcg acggcaaggg cacgccgccc    900
gccgccccgg ggaccgtcga cggcacggtg ccacccgccg tggcccgcga gatggtgcgg    960
gcatga                                                                966
```

<210> SEQ ID NO 23
<211> LENGTH: 1956
<212> TYPE: PRT
<213> ORGANISM: Streptomyces ghanaensis

<400> SEQUENCE: 23

```
Met Thr Arg Ile Ala Ile Val Gly Met Ala Cys Arg Tyr Pro Asp Ala
1               5                   10                  15

Thr Asp Pro Lys Glu Leu Trp Asp Asn Ala Val Ala Gly Arg Arg Ala
            20                  25                  30

Phe Arg Arg Leu Pro Asp Val Arg Met Asn Leu Asp Asp Tyr Trp Asp
        35                  40                  45

Ala Asp Pro Thr Thr Pro Asp Thr Phe Tyr Ala Arg Asn Ala Ala Val
    50                  55                  60

Ile Glu Gly Tyr Glu Phe Asp Arg Ile Ala Lys Ile Ala Gly Ser
65                  70                  75                  80

Thr Phe Arg Ser Thr Asp Leu Thr His Trp Leu Ala Leu Asp Thr Ala
                85                  90                  95

Gly Arg Ala Leu Ala Asp Ala Gly Phe Pro Gly Gly Glu Gly Leu Pro
            100                 105                 110

Arg Glu Arg Thr Gly Val Val Gly Asn Thr Leu Thr Gly Glu Phe
        115                 120                 125

Ser Arg Ala Asn Val Met Arg Leu Arg Trp Pro Tyr Val Arg Arg Val
    130                 135                 140

Met Ala Ala Ala Leu Lys Asp Glu Gln Asp Trp Asp Glu Asp Arg Ile
145                 150                 155                 160

Ala Arg Phe Leu Asp Asp Val Glu Thr Ala Tyr Lys Glu Pro Phe Pro
                165                 170                 175

Ala Ile Asp Glu Asp Thr Leu Ala Gly Leu Ala Asn Thr Ile Ala
            180                 185                 190

Gly Arg Ile Cys Asn His Phe Asp Leu Asn Gly Gly Tyr Thr Val
        195                 200                 205

Asp Gly Ala Cys Ser Ser Ser Leu Leu Ser Val Thr Thr Ala Gly Thr
    210                 215                 220

Ala Leu Ile Asn Gly Asp Ile Asp Val Ala Val Ala Gly Gly Val Asp
```

```
225                 230                 235                 240
Leu Ser Ile Asp Pro Phe Glu Ile Ile Gly Phe Ala Lys Thr Gly Ala
                245                 250                 255
Leu Ala Lys Gly Glu Met Arg Leu Tyr Asp Arg Gly Ser Asn Gly Phe
            260                 265                 270
Trp Pro Gly Glu Gly Cys Gly Met Ile Val Leu Met Arg Glu Glu Asp
        275                 280                 285
Ala Leu Ala Ala Gly His Arg Ile Tyr Ala Thr Ile Ala Gly Trp Gly
    290                 295                 300
Val Ser Ser Asp Gly Gln Gly Gly Ile Thr Arg Pro Glu Val Ser Gly
305                 310                 315                 320
Tyr Gln Leu Ala Leu Arg Arg Ala Tyr Glu Arg Ala Gly Phe Gly Ile
                325                 330                 335
Glu Thr Val Gly Leu Phe Glu Gly His Gly Thr Gly Thr Ala Val Gly
            340                 345                 350
Asp Thr Thr Glu Leu Thr Ala Leu Ser Asp Ala Arg Arg Arg Ala Asp
        355                 360                 365
Pro Asp Ala Pro Ala Ala Ile Thr Ser Ile Lys Gly Met Ile Gly
    370                 375                 380
His Thr Lys Ala Ala Ala Gly Val Ala Gly Leu Ile Lys Ala Ala Met
385                 390                 395                 400
Ala Val Asn His Gln Val Leu Pro Pro Ser Ile Gly Thr Ile Asp Pro
                405                 410                 415
His Ala Leu Leu Thr Asp Asp Asn Ala Thr Leu Lys Ala Leu Arg Lys
            420                 425                 430
Ala Glu Pro Trp Pro Thr Gly Ala Pro Arg Arg Ala Gly Val Thr Ala
        435                 440                 445
Met Gly Phe Gly Gly Ile Asn Thr His Val Val Leu Asp Glu Pro Ala
    450                 455                 460
Gly Arg Arg Arg Thr Ala Pro Ser Arg Arg Ser Ala Thr Leu Ala His
465                 470                 475                 480
Thr Pro Gln Asp Cys Glu Leu Leu Val Leu Asp Gly Glu Ser Pro Lys
                485                 490                 495
Ala Leu His Ala Arg Leu Thr Glu Val Ala Ala Phe Val Ala Gln Val
            500                 505                 510
Ser Tyr Gly Gln Val Ala Asp Leu Ala Ala Thr Leu Gln Arg Glu Leu
        515                 520                 525
Arg Gly Leu Ser His Arg Ala Val Val Thr Ser Pro Glu Asp
    530                 535                 540
Ala Glu Arg Arg Leu Thr His Leu Ala Asp Leu Leu Gln Thr Gly Glu
545                 550                 555                 560
Thr Ser Tyr Thr Ala Ala Asp Gly Arg Gly Phe Leu Gly Arg Ala Thr
                565                 570                 575
Arg Pro Ala Arg Ile Gly Phe Leu Phe Pro Gly Gln Gly Ser Gly His
            580                 585                 590
Gly Thr Val Gly Gly Ala Leu Cys Arg Arg Phe Pro Glu Ala Ala Glu
        595                 600                 605
Val Phe Ala Arg Ala Ala Leu Pro Ala Thr Gly Asp Met Thr Ala Thr
    610                 615                 620
Asn Val Ala Gln Pro Arg Ile Ala Thr Gly Ser Ala Ala Gly Leu Arg
625                 630                 635                 640
Val Leu Asp Ala Leu Arg Leu Glu Ala Ser Val Ala Val Gly His Ser
                645                 650                 655
```

-continued

```
Leu Gly Glu Leu Ser Ala Leu His Trp Ala Gly Ala Leu Asp Glu Glu
            660                 665                 670

Thr Leu Leu Gln Ala Ala Arg Val Arg Gly Arg Ala Met Ala Glu His
            675                 680                 685

Ser Ala Thr Gly Thr Met Ala Ser Leu Ala Ala Pro Glu Arg Ala
            690                 695                 700

Glu Glu Leu Leu Ala Asp Leu Asp Ala Val Ile Ala Gly Tyr Asn Gly
705                 710                 715                 720

Pro Glu Gln Thr Val Ile Ala Gly Ser Pro Ala Asp Ile Glu Glu Leu
                    725                 730                 735

Gln Arg Arg Ala Glu Arg Ala Glu Val Thr Cys Thr Arg Leu Asn Val
                740                 745                 750

Ser His Ala Phe His Ser Pro Leu Val Ala His Ser Ala Glu Val Phe
            755                 760                 765

Gly Ala Trp Leu Ala Glu Ala Arg Leu Gly Ser Pro Ser Gly Arg Val
            770                 775                 780

Val Ser Thr Val Thr Gly Glu Glu Leu Thr Ala Gly Thr Asp Leu Ala
785                 790                 795                 800

Ala Leu Leu Thr Glu Gln Ile Thr Gly Pro Val Arg Phe Thr Arg Ala
                805                 810                 815

Val Ser Glu Ala Ala Arg His Val Asp Leu Phe Val Glu Val Gly Pro
            820                 825                 830

Gly Arg Val Leu Ser Gly Leu Ala Arg Ala Thr Thr Gly Val Pro Ala
            835                 840                 845

Val Ala Leu Asn Thr Asp Asp Glu Ser Leu Arg Ser Ala Leu Ala Val
850                 855                 860

Ala Gly Ala Ala Phe Val Ala Gly Ala Pro Val Ala Leu Glu Arg Phe
865                 870                 875                 880

Phe Glu Asp Arg Leu Ile Arg Pro Leu Arg Val Gly Gln Glu Phe Ser
                885                 890                 895

Phe Leu Ala Asn Pro Cys Glu Gln Ala Pro Arg Glu Lys Ala Pro Ala
            900                 905                 910

Gly Arg Arg Pro Arg Pro Val Thr Pro Ala Ala Glu Thr Pro His Asp
            915                 920                 925

Ala His Pro Ala Pro Thr Pro Ala Asp Ala Thr Thr Ala Ala Glu Ala
            930                 935                 940

Pro Thr Thr Glu Glu Ala Pro Glu Asp Gly Ala Gly Ala Leu Glu Val
945                 950                 955                 960

Leu Arg Val Leu Val Ala Glu Arg Ala Glu Leu Pro Ala Glu Leu Val
                965                 970                 975

Asp Pro Asp Ser Arg Leu Leu Asp Asp Leu His Met Ser Ser Ile Thr
            980                 985                 990

Val Gly Gln Ile Val Asn Gln Ala Ala Ser Arg Leu Gly Ile Ala Ala
            995                 1000                1005

Ala Gln Val Pro Thr Asn Phe Ala Thr Ala Thr Leu Ala Glu Leu
    1010                1015                1020

Ala Glu Ala Leu Asp Thr Leu Val Asp Thr Gly Thr Thr Gly Glu
    1025                1030                1035

Pro Thr Thr Ser Ala Val Val Gly Ala Ala Pro Trp Ala Arg Pro
    1040                1045                1050

Phe Ala Val Asp Leu Asp Glu Val Ala Arg Pro His Ala Ala Ala
    1055                1060                1065
```

-continued

```
Asp Gly Ala Asp Gly Asp Trp Glu Leu Phe Ala Pro Gln Asp His
    1070            1075                1080
Pro Tyr Ala Glu Arg Leu Arg Arg Glu Leu Ala Gly Ala Gly Val
    1085            1090                1095
Gly Ala Gly Val Val Ala Val Leu Pro Lys Gly Cys Ala Arg Gln
    1100            1105                1110
Glu Val Asp Arg Val Leu Ala Ala Ala His Ser Ala Leu Ala Gly
    1115            1120                1125
Asp Arg Thr Arg Arg Phe Val Leu Val Gln Asp Gly Arg Gly Ala
    1130            1135                1140
Ala Gly Leu Ala Lys Thr Leu Tyr Leu Glu Ala Pro His Leu Arg
    1145            1150                1155
Thr Thr Val Val His Thr Pro Ala Ala Gln Asp Val Val Glu Arg
    1160            1165                1170
Val Val Ala Glu Val Ala Ala Thr Thr Arg Phe Thr Glu Val His
    1175            1180                1185
Tyr Asp Glu Ala Gly Val Arg Arg Val Pro Thr Leu Arg Ala Leu
    1190            1195                1200
Pro Val Ala Pro Gln His Thr Ala Ser Pro Leu Asp Ala Ser Asp
    1205            1210                1215
Val Leu Leu Val Thr Gly Gly Gly Lys Gly Ile Ser Ala Glu Cys
    1220            1225                1230
Ala Leu Ala Val Ala Gln Arg Thr Gly Ala Ala Leu Ala Val Leu
    1235            1240                1245
Gly Arg Ser Asp Pro Ala Ser Asp Arg Glu Leu Ala Asp Asn Ile
    1250            1255                1260
Glu Arg Met Arg Ala Gly Gly Ala Arg Val His Tyr Ala Arg Ala
    1265            1270                1275
Asp Val Thr Val Pro Glu Gln Val Thr Ala Ala Val Ala Glu Leu
    1280            1285                1290
Thr Glu Arg Leu Gly Thr Ile Thr Ala Leu Leu His Gly Ala Gly
    1295            1300                1305
Arg Asn Glu Pro Asn Ala Leu Ala Arg Leu Ala Pro Arg Asp Phe
    1310            1315                1320
Glu Arg Thr Phe Ala Pro Lys Val Asp Gly Leu Arg Thr Val Leu
    1325            1330                1335
Asp Ala Val Asp Pro Gly Asn Leu Lys Leu Leu Val Thr Phe Gly
    1340            1345                1350
Ser Ile Ile Gly Arg Ala Gly Leu Arg Gly Glu Ala His Tyr Ala
    1355            1360                1365
Thr Ala Asn Glu Trp Leu Ala Asp Leu Thr Glu Glu Val Ala Arg
    1370            1375                1380
Ala His Pro Asn Leu Arg Ala Arg Cys Met Glu Trp Ser Val Trp
    1385            1390                1395
Ser Gly Val Gly Met Gly Glu Lys Leu Ser Val Val Glu Ser Leu
    1400            1405                1410
Ser Arg Glu Gly Ile Thr Pro Val Ser Pro Asp Gln Gly Val Asp
    1415            1420                1425
Ile Leu Leu Arg Leu Ile Glu Asp Pro Asp Ala Pro Val Val Thr
    1430            1435                1440
Val Val Ser Gly Arg Thr Glu Gly Ile Asp Thr Val Arg Arg Asp
    1445            1450                1455
Leu Pro Asp Leu Pro Met Leu Arg Phe Thr Gly Asn Pro Leu Val
```

-continued

```
                1460                1465                1470
Arg Tyr His Gly Val Glu Leu Val Thr Glu Val Glu Leu Asn Ala
    1475                1480                1485
Gly Thr Asp Pro Tyr Leu Ser Asp His Leu Leu Asp Gly Asn Leu
    1490                1495                1500
Leu Leu Pro Ala Val Ile Gly Met Glu Ala Met Ala Gln Val Ala
    1505                1510                1515
Ser Ala Val Thr Gly Arg Thr Gly Val Pro Val Ile Glu Asp Ala
    1520                1525                1530
Glu Phe Leu Arg Pro Ile Val Val Pro Pro Ser Gly Ser Thr Arg
    1535                1540                1545
Ile Arg Ile Ala Ala Val Val Thr Ala Pro Asp Thr Val Asp Val
    1550                1555                1560
Ala Val His Ala Glu Asp Thr Gly Phe Val Ala Glu His Phe Arg
    1565                1570                1575
Ala Arg Leu Leu Phe Thr Gly Ala Ala Val Pro Asp Gly Pro Pro
    1580                1585                1590
Leu Gln Val Pro Asp Asp Thr Pro Val Val Pro Leu Asp Pro Ala
    1595                1600                1605
Thr Asp Leu Tyr Gly Gly Ile Leu Phe Gln Gly Ala Arg Phe Gln
    1610                1615                1620
Arg Leu His Arg Phe His Arg Ala Ala Ala Arg His Val Asp Ala
    1625                1630                1635
Glu Val Ala Val Gln Gln Arg Pro Glu Gly Trp Phe Ala Gly Phe
    1640                1645                1650
Leu Pro Gly Arg Leu Leu Leu Ala Asp Pro Gly Met Arg Asp Ala
    1655                1660                1665
Leu Met His Gly Asn Gln Val Cys Val Pro Asp Ala Thr Leu Leu
    1670                1675                1680
Pro Ser Gly Val Glu Arg Ile His Ala Leu Gly Ser Gly Glu His
    1685                1690                1695
Val Pro Asp Arg Leu Arg Tyr Thr Ala Val Glu Arg Ser Arg Asp
    1700                1705                1710
Gly Asp Thr Tyr Val Tyr Asp Ile Ala Val Arg Asp Glu Asn Gly
    1715                1720                1725
Val Val Val Glu Arg Trp Asp Gly Leu Thr Leu His Ala Val Arg
    1730                1735                1740
Lys Thr Asp Gly Ser Gly Pro Trp Val Ala Pro Leu Leu Gly Pro
    1745                1750                1755
Tyr Leu Glu Arg Ser Leu Glu Asp Val Thr Gly Ser Arg Ile Ala
    1760                1765                1770
Val Ala Val Glu Pro His Gly Asp Ala Pro Ala Gly Ser Val Ala
    1775                1780                1785
Gln Arg Arg Gly Phe Thr Ala Asp Ala Ala Arg Ala Leu Gly
    1790                1795                1800
Ser Pro Val Ala Val Arg His Arg Pro Asp Gly Arg Pro Glu Leu
    1805                1810                1815
Glu Pro Asp Arg His Leu Ser Val Ser Ala Ala His Gly Leu Gly
    1820                1825                1830
Val Thr Leu Ser Ala Val Ser Asp Thr Glu Val Ala Cys Asp Ile
    1835                1840                1845
Glu Ala Val Ser Met Arg Ser Ala His Glu Trp Arg Gly Leu Leu
    1850                1855                1860
```

```
Gly Glu  His Ala Val Ala Ala  Glu Leu Val Ala  Lys Glu Thr Gly
    1865              1870              1875

Glu Ala  Pro Asp Thr Ala Ala  Thr Arg Val Trp  Gly Ala Val Glu
    1880              1885              1890

Cys Leu  Arg Lys Ala Gly Ile  Met Ala Gly Ala  Pro Leu Thr Val
    1895              1900              1905

Leu Pro  Arg Arg Lys Asp Ala  Trp Val Phe Ala  Ala Gly Asp
    1910              1915              1920

Leu Arg  Ile Ala Thr Phe Val  Thr Ala Leu Arg  Asp Ala Leu Glu
    1925              1930              1935

Pro Ala  Val Phe Ala Phe Leu  Thr His Glu Pro  Gln Ser Ala Gln
    1940              1945              1950

Glu Arg  Gly
    1955

<210> SEQ ID NO 24
<211> LENGTH: 5871
<212> TYPE: DNA
<213> ORGANISM: Streptomyces ghanaensis

<400> SEQUENCE: 24
atgaccagaa tcgccatcgt cggcatggcc tgccgctatc ccgacgccac tgacccgaag      60
gaactgtggg acaacgccgt cgccggacga cgcgcgttcc gccgcctgcc cgacgtccgg     120
atgaacctgg acgactactg ggacgcggac ccgaccaccc ccgacacctt ctacgcccgc     180
aacgccgcgg tcatcgaggg ctacgagttc gaccggatcg cccacaagat cgcgggcagc     240
accttccggt cgaccgacct gacgcactgg ctcgccctgg acaccgccgg cgcgcactc      300 gccgacgccg gcttccccgg cggcgagggc ctgccccgcg aacgcaccgg tgtcgtcgtc     360
ggcaacaccc tcaccggcga gttctccccgc gccaacgtga tgcggctgcg ctggccgtac     420
gtacgacgcg tgatggccgc ggccctcaag gacgaacagg actgggacga ggaccgcatc     480
gcgcggttcc tcgacgacgt cgagaccgcg tacaaggagc cgttccccgc catcgacgag     540
gacaccctcg ccggtggact cgccaacacc atcgccggcc ggatctgcaa ccacttcgac     600
ctcaacggcg gcgggtacac cgtcgacggc gcctgctcct cctcgctgct gtcagtcacc     660
accgcgggaa ccgccctgat caacggggac atcgacgtcc ccgtcgccgg cgggtggac      720 ctgtcgatcg acccgttcga gatcatcggc ttcgccaaga ccggcgcgct cgccaagggc     780
gagatgcggc tgtacgaccg cggctccaac ggcttctggc cgggtgaggg ctgcggcatg     840
atcgtcctga tgcgggagga ggacgcccctt gccgcgggcc accgcatcta cgccaccatc     900
gcgggctggg gcgtgtcctc ggacggccag ggaggcatca cccgccccga ggtgagcggg     960
taccagctgg cactccggcg ggcctacgag cgagccggat cggcatcga ccgtcggg      1020 ctcttcgagg gccacggcac cggcaccgcc gtcggcgaca ccaccgagct caccgctctg    1080
tccgacgcgc gccgccgggc cgaccccgac gcgccggccg cggccatcac ctccatcaag    1140
ggcatgatcg gccacaccaa ggccgccgcc ggcgtcgccg gctgatcaa gcggccatg      1200 gccgtcaacc accaggtcct cccgccgtcc atcggcacca tcgacccgca cgccctgctc    1260
accgacgaca acgccacccct caaagccctg cgcaaggccg aaccgtggcc cacgggagca    1320
ccgcgcaggg ccggcgtcac cgccatgggc ttcggcggca tcaacaccca cgtcgtcctc    1380
gacgaacccg ccggccgacg ccgcacggcc ccagccggc gctccgccac cctcgcccac    1440
acgccgcagg actgcgaact gctcgtcctg gacggcgagt cgcccaaggc cctgcacgcc    1500
```

```
cggctcaccg aggtcgccgc cttcgtcgcc caggtctcct acggccaggt cgccgacctc   1560
gccgccacgc tccagcgcga actgcggggc ctgtcccacc gcgcggccgt cgtcgtcacc   1620
tccccggagg acgccgaacg ccggctgacc cacctggccg acctgctgca gaccggagag   1680
acctcgtaca ccgccgccga cggccgcggc ttcctgggcc gggccacccg gcccgcacgg   1740
atcggcttcc tcttcccggg ccagggctcc ggccacggca ccgtcggagg cgcgctgtgc   1800
cgccgcttcc ccgaggcggc cgaggtcttc gcccgggccg cgctgcccgc caccggcgac   1860
atgaccgcca cgaacgtggc acagccgcgc atcgccaccg gctccgccgc gggcctgcgc   1920
gtcctcgacg cgctgcgcct ggaggcgtcc gtcgccgtcg acacagtct cggcgagctg   1980 tccgccctgc actgggccgg agccctcgat gaggaaacgc ttctccaggc ggcgcgggta   2040
cgcggccggg ccatggccga gcacagcgcc acgggcacga tggcctccct cgcagccgcg   2100
cccgagcggg ccgaggaact cctcgccgac ctcgacgccg tcatcgccgg gtacaacggc   2160
ccggagcaga ccgtgatcgc cggttcgccg gcggacatcg aggaactgca gcgccgcgcc   2220
gagcgggccg aggtcacctg cacccggctg aacgtctcgc acgccttcca ctcacccctc   2280
gtcgcccact ccgccgaagt gttcggtgcc tggctggcgg aggcccgcct cggctccccg   2340
tccggccggg tcgtctccac cgtcaccggc gaggagctca cagccgggac ggacctggcc   2400
gcactgctca ccgagcagat caccggaccc gtccgcttca cccgggcggt gagcgaggcg   2460
gcccggcacg tcgacctgtt cgtcgaggtc ggacccgggc gggtgctcag cggcctcgcc   2520
cgggccacca ccggtgtccc ggccgtcgcc ctgaacaccg acgacgagtc gctgcgcagc   2580
gccctcgcgg tcgccggcgc cgcgttcgtc gcgggagcgc ccgtcgccct ggagcggttc   2640
ttcgaggacc ggctcatccg gccgctccgc gtcggtcagg agttctcctt cctcgccaac   2700
ccctgtgagc aggcaccgcg cgagaaggcg ccggccgggc gccggccgcg gcccgtcacc   2760
ccggcggccg agacccccgca cgacgcacac ccggcgccga ctcccgcgga cgcgacgacc   2820
gccgccgagg caccgaccac cgaagaggca cccgaggacg cgccggtgc gctcgaggtg   2880 ctgcgcgtcc tcgtcgccga gcgcgccgag ctgcccgccg aactcgtcga cccggacagc   2940
cggctcctgg acgacctcca catgagctcg atcaccgtcg ccagatcgt caaccaggcg   3000 gcgtcccgcc tcgggatcgc cgcggcgcag gtgccgacca acttcgccac cgccaccctg   3060
gccgaactgg ccgaggccct ggacaccctc gtcgacaccg gcaccaccgg ggagcccacc   3120
acctccgccg tcgtgggcgc ggcccccctgg gccgtccct cgccgtcga cctcgacgag   3180 gtcgcccggc cgcacgccgc cgccgacggc gccgacgggg actgggagct gttcgccccc   3240
caggaccacc cgtacgccga acggctgcgc cgggaactgg cggggccgg tgtcggcgcg   3300 ggcgtggtgg ccgtactgcc caagggctgc gcgcggcagg aggtggaccg ggtactggcc   3360
gccgcgcaca gcgcgctcgc cggtgaccgc acacgccgct tcgtcctcgt ccaggacggg   3420
cgcggcgccg ccggcctggc caagaccctg tacctggagg caccgcacct gcgcaccacc   3480
gtcgtccaca ccccggccgc gcaggacgtg gtggaacgcg tcgtggccga ggtggcggcc   3540
accacccgct tcaccgaggt ccactacgac gaagccggtg tgcgccgcgt gccgaccctg   3600
cgggccctgc ccgtggcgcc gcagcacacc gcgtccccgc tggacgcctc ggacgtgctg   3660
ctggtgacgg gcggcggaaa gggcatctcc gcggagtgcg ccctgccgt ggcccagagg   3720 accggtgccg cgctgccgt cctcggccgc tccgacccgg cgagcgaccg ggaactggcc   3780
gacaacatcg agcggatgcg cgccggtggc gcgcgcgtgc actacgcgcg cgccgacgtc   3840
```

```
accgtccccg aacaggtcac cgcggccgtc gccgaactga ccgagcgact cgggacgatc   3900
accgcgttgc tgcacggcgc cggccgcaac gaaccgaacg cgctggcgcg actggccccg   3960
cgcgacttcg aacggacctt cgccccgaag gtcgacggac tgcgcacggt cctggacgcg   4020
gtggaccccg gcaacctcaa gctgctggtg accttcggca gcatcatcgg ccgggccggt   4080
ctgcgcggcg aggcccacta cgccaccgcc aacgagtggc tggccgacct caccgaggag   4140
gtcgcccgcg cccacccgaa cctgcgcgcc cgctgcatgg agtggtcggt gtggtcgggc   4200
gtcggcatgg gcgagaagct ctccgtcgtc gagtccctct cccgcgaggg catcaccccg   4260
gtctccccgg accagggcgt ggacatcctg ctgcgcctga tcgaggaccc ggacgcgccc   4320
gtcgtgacgg tcgtcagcgg ccgcaccgag ggcatcgaca ccgtccgtcg cgacctgccc   4380
gacctgccga tgctgcgctt caccggcaac ccgctggtgc gctaccacgg cgtcgagctg   4440
gtcaccgagg tcgaactgaa cgccgggacc gacccgtacc tgtccgacca cctgctcgac   4500
ggcaacctgt tgctgcccgc cgtcatcggc atggaggcca tggcccaggt cgcctccgcg   4560
gtcaccggcc gcaccggcgt cccggtcatc gaggacgccg agttcctgcg gcccatcgtg   4620
gtaccgccga gcggcagcac ccggatcagg atcgcggcgg tcgtcaccgc tcccgacacc   4680
gtcgacgtcg ccgtccacgc cgaggacacg ggtttcgtcg ccgagcactt ccgggcccgt   4740
ctgctgttca ccggggccgc cgtgcccgac ggcccgccgc tgcaggtgcc cgacgacacc   4800
ccggtcgttc cgctggaccc cgccaccgac ctgtacggcg gcatcctgtt ccagggcgcc   4860
cgcttccagc ggctgcaccg cttccaccgg gccgccgccc ggcacgtgga cgccgaggtc   4920
gccgtccagc agcggcccga gggctggttc gccggcttcc tgcccggccg gctgctgctc   4980
gccgacccgg gcatgcgcga cgcgctcatg cacggcaacc aggtgtgcgt ccccgacgcc   5040
accctgctgc cgtccggcgt ggagcgcatc cacgcgctcg gctcgggcga gcacgtcccc   5100
gaccggctgc ggtacaccgc cgtcgagcgc agccgcgacg gggacaccta cgtctacgac   5160
atcgcggtgc gcgacgagaa cggcgtcgtc gtcgaacgct gggacgggct gaccctgcac   5220
gccgtgcgca agaccgacgg ctccggtccg tgggtcgcgc cgctgctcgg cccgtacctg   5280
gagcgctcgc tggaggacgt caccggcagc cgcatcgccg tcgccgtcga gccgcacggg   5340
gacgcaccgg ccggttccgt cgcccagcgc cgcggcttca ccgcggacgc ggcggccccg   5400
gcgctgggca gcccggtggc cgtccggcac cgcccggacg ggcggccgga gctggaaccg   5460
gaccggcacc tgtcggtgtc ggcggcgcac ggcctggggg tcaccctcag cgccgtctcc   5520
gacaccgagg tggcctgtga catcgaggcg gtcagcatgc gctcggccca tgagtggcgc   5580
ggactgctcg gggagcacgc ggtcgccgcc gagctggtcg ccaaggagac gggcgaggcg   5640
ccggacaccg ccgccacgcg cgtgtggggt gccgtggagt gcctgcgcaa ggccggcatc   5700
atggccggcg cgcccctgac ggtactgccg cgccgcaagg acgcctgggt ggtcttcgcc   5760
gcgggcgatc tgcggatcgc gaccttcgtc accgcgctgc gcgacgccct ggagcccgcc   5820
gtcttcgcgt tcctcacgca cgaaccgcaa tccgctcagg agagggcta g            5871
```

<210> SEQ ID NO 25
<211> LENGTH: 152
<212> TYPE: PRT
<213> ORGANISM: Streptomyces ghanaensis

<400> SEQUENCE: 25

```
Met Ala Glu Asp Tyr Phe Glu Tyr Arg His Thr Val Gly Phe Glu Glu
1               5                   10                  15
```

Thr Asn Leu Val Gly Asn Val Tyr Tyr Val Asn Tyr Leu Arg Trp Gln
                20                  25                  30

Gly Arg Cys Arg Glu Leu Phe Leu Gln Gln Lys Ala Pro Glu Val Leu
            35                  40                  45

Ala Glu Val Gln Asp Asp Leu Lys Leu Phe Thr Leu Lys Val Asp Cys
 50                  55                  60

Glu Phe Phe Ala Glu Ile Thr Ala Phe Asp Glu Leu Ser Ile Arg Met
 65                  70                  75                  80

Arg Leu Ser Glu Leu Gly Gln Thr Gln Leu Glu Phe Ser Phe Asp Tyr
                 85                  90                  95

Val Lys Val Thr Gly Ala Glu Leu Leu Ala Arg Gly Arg Gln
            100                 105                 110

Arg Ile Ala Cys Met Arg Gly Pro Asn Thr Asn Thr Val Pro Ser Arg
            115                 120                 125

Ile Pro Glu Ala Leu Ala His Ala Leu Glu Pro Tyr Thr Ala His Gly
        130                 135                 140

Arg Val Pro Thr Gly Arg Ala Ala
145                 150

<210> SEQ ID NO 26
<211> LENGTH: 459
<212> TYPE: DNA
<213> ORGANISM: Streptomyces ghanaensis

<400> SEQUENCE: 26
atggcggaag actacttcga gtaccggcac acgtcggtt tcgaggagac caacctggtc      60
ggcaacgtct actacgtgaa ctacctgcgc tggcagggcc ggtgccggga gctcttcctg     120
cagcagaagg cgccggaggt actggccgag gtgcaggacg acctgaagct gttcacgctg     180
aaggtggact gcgagttctt cgccgagatc accgccttcg acgagctgtc catccgcatg     240
cggctgtccg aactggggca gacacagctg gagttctcct cgactacgt caaggtgacc      300 ggcggggcgg agctcctcgt ggctcgcggg cgccagcgga tcgcgtgcat gcgcggaccc     360
aacaccaaca ccgtgccctc ccgcattccc gaggccctgg cccacgccct ggagccgtac     420
accgcccacg gccgggtgcc gacggggcgt gcggcatga                            459

<210> SEQ ID NO 27
<211> LENGTH: 329
<212> TYPE: PRT
<213> ORGANISM: Streptomyces ghanaensis

<400> SEQUENCE: 27

Val Ser Ser Val Phe Gly Ala Leu Arg Arg Arg Leu Leu Thr Pro Pro
  1               5                  10                  15

Val Ser Glu Thr Thr Met Glu Val Arg Gly Phe His Val Lys Asn Ala
                20                  25                  30

Glu Ala Lys Lys Arg Leu Glu Tyr Ile Gly Glu Val Phe Leu Arg Gly
            35                  40                  45

Tyr Ala Tyr Ala Val Glu Ala Gly Ser Pro Ala Glu Ala Gln Glu Arg
 50                  55                  60

Leu Glu Thr Val Pro Arg Asp Val Arg Gly Phe Ala Tyr Glu Gly Ala
 65                  70                  75                  80

Gly Met Gly Ala Val Val His Asp Ala Leu Pro Gly His Gly Gly Arg
                 85                  90                  95

Leu Gln Gly Leu Leu Ala Gly Gln Gly Arg His His Asp Tyr Met Ile
            100                 105                 110

```
Tyr Val Gly Ile Gly Trp Ala Met Ala Arg Leu Pro Lys Pro Leu Trp
        115                 120                 125

Pro Asp Ile Ser Ala Thr Asp Pro Leu Leu Arg Trp Leu Ala Leu Asp
        130                 135                 140

Gly Tyr Gly Phe His Gln Ala Tyr Phe Arg Thr Asp Ala Tyr Val Arg
145                 150                 155                 160

Asn Pro His Leu Gln His Pro Phe Arg Trp Gly Gly His Asn His
                165                 170                 175

Tyr Thr Ala Asn Ala Ile Asp Gln Gly Ile Gly Arg Ala Leu Trp Phe
                180                 185                 190

Val Gly Gly Thr Asp Pro Asp Val Val Ser Gly Leu Ile Arg Ala Tyr
        195                 200                 205

Pro Glu His Arg His Gly Asp Leu Tyr Ala Gly Ala Gly Leu Ala Cys
        210                 215                 220

Ala Tyr Ala Gly Gly Ala Gly Glu Asp Glu Leu Ala His Phe Ala Glu
225                 230                 235                 240

Gly Ala Gly Glu His Arg Trp Ala Leu Ala Gln Gly Ala Ala Phe Ala
                245                 250                 255

Thr Glu Ala Arg Ile Lys Ala Gly Thr Val Ile Asp His Thr His Leu
                260                 265                 270

Ala Ala Arg Val Val Cys Gly Thr Thr Ala Glu Lys Ala Ser Gln Val
        275                 280                 285

Cys Arg Asp Thr Arg Pro Gln Ala Pro Asp Val His Gly Ala Phe Pro
290                 295                 300

Ala Tyr Glu Lys Trp Arg Arg Asp Ile Ala Ala Gln Leu Ala Ser Ser
305                 310                 315                 320

Ser Leu Val Ser Lys Gly Ala Asp Gln
                325
```

<210> SEQ ID NO 28
<211> LENGTH: 990
<212> TYPE: DNA
<213> ORGANISM: Streptomyces ghanaensis

<400> SEQUENCE: 28

```
gtgtccagtg tatttggcgc actccggcgc cgattgctca cgcctcctgt ttcggaaacg      60
accatggagg tgcgcggatt ccatgtgaag aacgcggaag caaaaaagcg gctcgagtac     120
atcggcgagg tgttcctgcg gggatacgcc tacgcggtgg aggcgggctc gcccgccgag     180
gcgcaggaac ggctggagac cgtcccgcgc gacgtgcgcg gcttcgccta cgagggcgcc     240
ggcatgggcg ccgtcgtgca cgacgcgctg cccgggcacg cgggcagact gcaggggctg     300
ctcgccggcc agggccgtca ccacgactac atgatctacg tgggcatcgg ctgggcgatg     360
gcccgcctgc cgaagccgct gtggcccgac atctccgcca ccgacccgct gctgcgctgg     420
ctggcgctgg acgggtacgg attccaccag gcgtacttca ggaccgacgc gtatgtgcgc     480
aaccccacc tccagcatcc cttccgctgg cgcggcggcc acaaccacta cacggccaac     540
gccatcgacc agggcatcgg ccgcgcgctg tggttcgtcg gcggtaccga tcccgacgtc     600
gtctccggcc tgatccgcgc ctaccccgaa caccgccacg gcgacctgta cgcgggcgcc     660
gggctcgcct gcgcctacgc gggcggcgcc ggcgaggacg aactcgcgca tttcgccgag     720
ggggccggtg aacaccgctg ggcactcgcc caggggccg ccttcgcgac cgaggcccgc     780
atcaaggcgg gcacggtcat cgaccacacc catcttgcgg cccgtgtcgt gtgcggcacg     840
```

-continued

```
acggccgaaa aggcctcgca ggtgtgccgg gacacccggc cccaggcacc cgacgtccac      900
ggcgcattcc cggcctacga gaaatggcgg cgcgacatcg ccgcgcaact cgcttcttcc      960
tcgctcgtct cgaaagggc cgaccagtga                                        990
```

<210> SEQ ID NO 29
<211> LENGTH: 636
<212> TYPE: PRT
<213> ORGANISM: Streptomyces ghanaensis

<400> SEQUENCE: 29

```
Val Thr Val Ala Lys Asn Trp Ile Arg Arg Asn Ser Pro Gly Ile Val
1               5                  10                  15

Ala Leu Ala Leu Met Val Gly Thr Phe Tyr Gly Val Arg Leu Pro Glu
            20                  25                  30

Ser Ser Ala Ala Glu Ile Asp Lys Leu Ala Lys Asp Phe Ser Phe Glu
        35                  40                  45

Pro Met Ser Ile Ala Leu Pro Ala Gly Phe Glu Arg Gln Glu Val Arg
    50                  55                  60

Lys Val Asn Lys Ala Tyr Gln His Ile Glu Ala Trp Ile Ser Ser Val
65                  70                  75                  80

Gly Ala Gly Val Ala Val Asn Asp Leu Asp Gly Asp Gly Leu Ala Asn
                85                  90                  95

Asp Leu Cys Val Asn Asp Val Arg Ile Asp Gln Ala Val Val Thr Pro
            100                 105                 110

Ala Pro Thr Arg Lys Asp Ala Tyr Glu Pro Phe Ala Leu Asp Pro Ala
        115                 120                 125

Pro Leu Gly Thr Ser Lys Thr Met Ala Pro Met Gly Cys Met Pro Gly
    130                 135                 140

Asp Tyr Asn Glu Asp Gly Arg Met Asp Leu Leu Val Tyr Tyr Trp Gly
145                 150                 155                 160

Arg Thr Pro Val Leu Phe Met Asn Glu Gly Lys Gly Lys Pro Leu
                165                 170                 175

Thr Ala Asp Ser Phe Thr Pro Thr Glu Leu Leu Pro Gly Lys Pro Gly
            180                 185                 190

Arg Thr Tyr Thr Gly Pro Leu Trp Asn Ser Asn Ala Ala Ala Val Ala
        195                 200                 205

Asp Phe Asp Gly Asp Gly His Asp Ile Tyr Ile Gly Asn Tyr Phe
    210                 215                 220

Pro Asp Ser Pro Val Leu Asp Pro Ser Lys Asp Gly Asp Val Thr Met
225                 230                 235                 240

Asn Ala Ser Leu Ser His Ala Gln Asn Gly Gly Gly His Phe Phe
                245                 250                 255

Arg Trp Thr Glu Asp Gly Tyr Glu Lys Val Asp Asp Ala Ile Pro Gln
            260                 265                 270

Ser Leu Asn Lys Gly Trp Thr Leu Gly Ala Ser Ala Ala Asp Leu Asp
        275                 280                 285

Gly Asp Gly Leu Pro Glu Met Phe Leu Ala His Asp Phe Gly Thr Ser
    290                 295                 300

Ala Leu Leu His Asn Thr Ser Thr Pro Gly Arg Leu Arg Phe Ser Glu
305                 310                 315                 320

Val Lys Ser Glu His Thr Ala Thr Ile Pro Lys Ser Lys Glu Leu Gly
                325                 330                 335

Arg Ser Ser Phe Lys Gly Met Gly Val Asp Phe Gly Asp Leu Asp His
            340                 345                 350
```

```
Asp Gly Leu Tyr Asp Met Phe Val Ser Asn Ile Thr Thr Ser Phe Gly
            355                 360                 365
Ile Gln Glu Ser Asn Phe Ala Phe Ile Ser Asp Ala Gly Ser Arg Ser
        370                 375                 380
Glu Leu Gln Gly Arg Phe Ala Glu Gly Glu Ala Pro Tyr Lys Asp Lys
385                 390                 395                 400
Ser Thr Gly Leu Gly Leu Ala Trp Ser Gly Trp Gly Trp Asp Val Lys
                405                 410                 415
Met Gly Asp Phe Asp Asn Asn Gly Asp Leu Glu Ile Val Gln Ala Leu
            420                 425                 430
Gly Phe Val Lys Gly Lys Asn Asn Arg Trp Pro Gln Leu Gln Glu Leu
        435                 440                 445
Ala Thr Ala Asn Asp Ala Leu Val Pro Asn Pro Gln Trp Trp Pro Asn
    450                 455                 460
Val Glu His Gly Asp Asp Leu Ala Gly Ser Gln Arg Met Arg Phe Phe
465                 470                 475                 480
Ala Lys Asp Pro Asp Ser Gly Arg Tyr His Asn Leu Ser Val Ala Leu
                485                 490                 495
Gly Ile Gly Glu Pro Ile Pro Thr Arg Gly Ile Ala Thr Gly Asp Val
            500                 505                 510
Asp Gly Asp Gly Arg Leu Asp Leu Val Val Ala Arg Gln Trp Gly Glu
        515                 520                 525
Pro Val Phe Leu His Asn Val Ser Lys Ser Pro Gly Ala Tyr Leu Gly
    530                 535                 540
Leu Lys Leu Thr His Pro Asp Gly Ser Pro Val Val Gly Ala Glu Val
545                 550                 555                 560
Cys Val Glu Leu Pro Asp Gly Thr Lys Arg Ile Thr Arg Leu Asp Gly
                565                 570                 575
Gly Gly Gly His Ser Gly Lys Arg Ser Thr Asp Val His Ile Gly Leu
            580                 585                 590
Gly Lys Asp Val Arg Asp Pro Val Pro Ala Thr Ile Thr Trp Arg Asp
        595                 600                 605
Arg Ala Gly Glu Val His Glu Gln Lys Leu Lys Leu Thr Pro Gly Trp
    610                 615                 620
His Ser Ile Gln Leu Gly Thr Glu Ala Lys Glu Lys
625                 630                 635

<210> SEQ ID NO 30
<211> LENGTH: 1911
<212> TYPE: DNA
<213> ORGANISM: Streptomyces ghanaensis

<400> SEQUENCE: 30
gtgacggttg caaagaactg gattcgcagg aactcgccgg gaatcgtggc cctggctctg      60
atggtgggca ctttctacgg cgtgcggcta cccgagtcct cggccgctga gatcgacaag     120
ctggcgaagg acttctcctt cgaaccgatg tccatcgccc tgcccgccgg tttcgagagg     180
caggaggtcc ggaaggtcaa caaggcctac cagcacatcg aggcgtggat ctcctcggtc     240
ggcgccggcg tcgccgtcaa cgacctggac ggcgacggcc tggccaacga cctgtgcgtg     300
aacgacgtgc gcatcgacca ggccgtggtc accccgcac ccaccgcaa ggacgcgtac     360 gagccgttcg cgctggaccc ggcaccgctg gcaccagca agacgatggc gccgatgggc     420
tgcatgcccg tgactacaa cgaggacggc cgcatggacc tcctcgtcta ctactggggc     480
```

```
cgcacgcccg tgctgttcat gaacgagggg gagaagggca agccgctgac cgccgactcc    540 ttcacccca  ccgaactgct gcccggcaaa cccggccgga cctacaccgg cccgctgtgg    600
aactccaacg cggccgcggt ggccgacttc gacggcgacg ccacgacga catctacatc    660 ggcaactact  tccccgacag cccggtcctg gacccgtcca aggacggcga cgtcaccatg   720
aacgcctcgc  tgtcgcacgc ccagaacggc ggcggcggcc acttcttccg gtggaccgag   780
gacggctacg agaaggtcga cgacgccatc ccgcagagcc tgaacaaggg ctggacgctc    840
ggtgcctccg  ccgccgacct cgacggcgac ggactgcccg agatgttcct cgcccacgac   900
ttcggcacct  cggcactgct gcacaacacc tcgaccccgg gcaggctccg cttctccgag   960
gtcaagtcgg  aacacaccgc gaccatcccc aagtccaagg aactgggccg cagttccttc  1020
aagggcatgg  gcgtcgactt cggagacctg gaccacgacg gctgtacga catgttcgtc   1080 agcaacatca  ccacctcgtt cggcatccag gagtccaact tcgccttcat cagcgacgcc  1140
ggcagccgct  ccgagctgca ggggcgcttc gccgagggcg aggcgcccta caaggacaag  1200
tccaccggcc  tggggctcgc ctggtccggc tggggctggg acgtgaagat gggcgacttc  1260
gacaacaacg  cgacctgga gatcgtccag gccctcggct tcgtcaaggg caagaacaac   1320
cgctggccgc  agctgcagga gctcgccacc gccaacgacg ccctggtgcc caaccccag   1380 tggtggccga  acgtcgagca cggcgacgac ctcgccggca ccagcgcat gcgcttcttc    1440 gcgaaggacc  ccgacagcgg ccgctaccac aacctctccg tcgccctcgg catcggtgag  1500
cccattccca  cccgcggcat cgccaccggc gacgtcgacg cgacggccg cctcgacctc    1560 gtggtcgccc  gccagtgggg cgagccggtc ttcctccaca acgtcagcaa gagccccggc  1620
gcctacctgg  gcctgaagct cacccacccg gacggctccc ccgtggtcgg cgcggaggtc  1680
tgcgtcgaac  tgcccgacgg caccaagcgc atcacccggc tggacggcgg cggcgggcac  1740
tccggcaagc  gcagcaccga cgtccacatc ggcctgggca aggacgtacg cgaccccgtc  1800
cccgccacga  tcacctggcg cgaccgggcc ggcgaggtcc acgagcagaa gctgaagctc  1860
acaccgggct  ggcacagcat ccagctgggc accgaggcca aggagaagtg a           1911
```

<210> SEQ ID NO 31
<211> LENGTH: 382
<212> TYPE: PRT
<213> ORGANISM: Streptomyces ghanaensis

<400> SEQUENCE: 31

```
Val Thr Met Ser Ala Pro His Thr Ala Ala Arg His Asn Pro Lys Val
 1               5                  10                  15

Thr Thr Ala Leu Arg Arg Phe Ala Ile Ser Ile Ser Val Leu Asn Val
            20                  25                  30

Phe Gly Tyr Thr Val Leu Gly Phe Glu Gln Pro Trp Leu Trp Pro Phe
        35                  40                  45

Val Ala Leu Ala Thr Gly Tyr Thr Val Glu Ile Ala Leu Glu Leu Leu
    50                  55                  60

Gly Ala Arg Ala Glu Gly Arg Ala Pro Arg Phe Thr Gly Gly Gly Phe
65                  70                  75                  80

Lys Gly Leu Val Glu Phe Leu Phe Pro Ala His Ile Thr Ala Leu Ala
                85                  90                  95

Val Asn Met Leu Ser Tyr Val Asn Asp Lys Met Trp Val Met Val Phe
            100                 105                 110

Gly Val Ile Val Ala Val Gly Thr Lys Trp Val Leu Arg Ala Pro Val
        115                 120                 125
```

```
Lys Gly Arg Met Arg His Phe Met Asn Pro Ser Asn Phe Gly Ile Ala
    130                 135                 140

Val Ile Leu Val Leu Phe Pro Trp Ala Ser Ile Ala Pro Pro Tyr His
145                 150                 155                 160

Phe Thr Glu Tyr Leu Asp Gly Gly Phe Asp Trp Leu Val Pro Ala Ile
                165                 170                 175

Ile Ile Thr Leu Gly Thr Met Leu Asn Ala Lys Leu Thr Glu Arg Met
            180                 185                 190

Trp Leu Ile Leu Ala Trp Val Gly Phe Ala Leu Gln Ala Ile Val
        195                 200                 205

Arg Gly Leu Leu Phe Asp Thr Ser Ile Pro Ala Ala Leu Ala Met Met
    210                 215                 220

Thr Gly Val Ala Phe Val Leu Phe Thr Asn Tyr Met Ile Thr Asp Pro
225                 230                 235                 240

Gly Thr Thr Pro Ser Ser Lys Trp Gly Gln Ile Ala Phe Gly Gly Gly
                245                 250                 255

Val Ala Ala Leu Tyr Gly Val Leu Thr Ala Met Ser Ile Ala Tyr Gly
            260                 265                 270

Leu Phe Phe Ala Thr Ala Leu Ala Cys Ala Ile Arg Gly Ala Phe Leu
        275                 280                 285

Trp Thr Ala Asp Ile Val Ala Lys Lys Arg Ala Glu Glu Ala Leu Glu
    290                 295                 300

Leu Ala Ala Val Thr Arg Ser Val Ser Arg Ala Glu Ala Pro Ser Gly
305                 310                 315                 320

Ala Gln Pro Asp Ala Ala Pro Ala Gln Ala Glu Ala Pro Ala Pro Cys
                325                 330                 335

Ala Cys Pro Ala Asp Ala Cys Ser Cys Pro Ala Pro Ala Asn Thr Glu
            340                 345                 350

Ala Ala Pro Cys Ala Cys Pro Ala Asp Ala Cys Ser Cys Pro Ala Pro
        355                 360                 365

Ala Asn Thr Glu Ala Asp Pro Ala Lys Thr Pro Val Ala Ala
    370                 375                 380

<210> SEQ ID NO 32
<211> LENGTH: 1149
<212> TYPE: DNA
<213> ORGANISM: Streptomyces ghanaensis

<400> SEQUENCE: 32
gtgacgatgt ccgcacccca caccgccgca cggcacaacc cgaaggtcac gaccgcactg      60
cgccggttcg cgatctccat ctccgtgctg aacgtcttcg gctacaccgt gctcggcttc     120
gagcagccct ggctctggcc gttcgtcgcc ctggcgaccg gctacaccgt cgagatcgcc     180
ctggaactcc tcggcgcccg cgccgagggc gcgcgccac  gcttcaccgg cggcggtttc     240 aagggctgg  tggaattcct cttcccggcc cacatcaccg cgctcgccgt gaacatgctg     300
tcctacgtca cgacaagat  gtgggtcatg gtgttcggcg tcatcgtcgc cgtcggcacc     360
aagtgggtgc tgcgcgcccc ggtcaagggc cggatgcggc acttcatgaa cccgtcgaac     420
ttcggcatcg ccgtcatcct ggtgctcttc ccctgggcct cgatcgcccc gccgtaccac     480
ttcaccgagt acctcgacgg cggcttcgac tggctcgtgc cggcgatcat catcaccctc     540
ggcacgatgc tcaacgccaa gctcaccgag cgcatgtggc tgatcctcgc ctgggtcggc     600
ggcttcgccc tccaggcgat cgtgcgcggt ctgctgttcg acacctccat acccgcggcc     660
```

```
ctggcgatga tgaccggcgt ggcgttcgtg ctcttcacga actacatgat cacggacccg    720
ggtacgacac cgtcgtcgaa gtggggtcag atcgccttcg cggcggcgt cgccgccctg     780 tacggcgtgc tgaccgcgat gagcatcgcc tacggcctgt tcttcgccac cgccctggcc   840
tgcgccatcc gtggcgcctt cctgtggacc gccgacatcg tggccaagaa gcgggccgag   900
gaggccctcg agctcgccgc cgtcacccgg tccgtctccc gggccgaagc accctccggc   960
gctcagcccg acgccgcccc cgcgcaggcc gaggcccccg ccccgtgcgc ctgcccggcc   1020
gacgcctgct cctgccccgc cccggcgaac accgaggccg ccccgtgcgc ctgcccggcc   1080
gacgcctgct cctgccccgc cccggcgaac accgaggccg accctgcgaa gacaccggtg   1140
gcagcatga                                                            1149
```

<210> SEQ ID NO 33
<211> LENGTH: 1977
<212> TYPE: PRT
<213> ORGANISM: Streptomyces carzinostaticus neocarzinostaticus

<400> SEQUENCE: 33

```
Met Thr Arg Ile Ala Ile Val Gly Met Ala Cys Arg Tyr Pro Asp Ala
1               5                   10                  15

Thr Ser Pro Ala Glu Leu Trp Ala Asn Ala Ile Ala Gly Arg Arg Ala
                20                  25                  30

Phe Arg Arg Leu Pro Glu Arg Ile Arg Leu Glu Asp Tyr Trp Asp
            35                  40                  45

Ala Asp Pro Ser Thr Pro Asp Thr Phe Tyr Ala Arg Asn Ala Ala Val
    50                  55                  60

Leu Glu Gly Tyr Ser Phe Asp Arg Val Thr His Arg Ile Ala Gly Ser
65                  70                  75                  80

Thr Phe Arg Ser Thr Asp Met Thr His Trp Leu Ala Leu Asp Thr Ala
                85                  90                  95

Gly Arg Ala Leu Ala Asp Ala Gly Phe Pro Ala Gly Glu Gly Leu Pro
            100                 105                 110

His Glu Arg Thr Gly Val Val Met Gly Asn Thr Leu Thr Gly Glu Phe
        115                 120                 125

Thr Arg Ala Asn Val Met Arg Leu Arg Trp Pro Tyr Val Arg Arg Val
    130                 135                 140

Met Ala Ala Leu Ala Gly Gln Gln Asp Trp Asp Glu Ala Arg Val
145                 150                 155                 160

Thr Ala Phe Leu Glu Glu Val Glu Thr Ser Tyr Lys Ala Pro Phe Pro
                165                 170                 175

Pro Val Asp Glu Asp Thr Leu Ala Gly Gly Leu Ser Asn Thr Ile Ala
            180                 185                 190

Gly Arg Ile Cys Asn His Phe Asp Leu Asn Gly Gly Tyr Thr Val
        195                 200                 205

Asp Gly Ala Cys Ser Ser Leu Leu Ser Val Thr Thr Ala Gly Thr
    210                 215                 220

Ala Leu Val Asn Gly Asp Leu Asp Val Ala Val Ala Gly Gly Val Asp
225                 230                 235                 240

Leu Ser Ile Asp Pro Phe Glu Ile Ile Gly Phe Ala Lys Thr Gly Ala
                245                 250                 255

Leu Ala Arg Gly Glu Met Lys Leu Tyr Asp Lys Gly Ser Asn Gly Phe
            260                 265                 270

Trp Pro Gly Glu Gly Cys Gly Val Val Val Leu Met Arg Glu Glu Asp
        275                 280                 285
```

```
Ala Ile Ala Arg Gly His Arg Ile Tyr Ala Thr Val Ala Gly Trp Gly
    290                 295                 300

Val Ser Ser Asp Gly Gln Gly Gly Ile Thr Arg Pro Glu Val Asp Gly
305                 310                 315                 320

Tyr Arg Leu Ala Leu Glu Arg Ala Tyr Ala Arg Ala Gly Phe Gly Ile
                325                 330                 335

Glu Thr Val Pro Leu Phe Glu Gly His Gly Thr Gly Thr Ala Val Gly
                340                 345                 350

Asp Ala Thr Glu Leu Ala Ala Leu Ile Lys Ala Arg Ser Ala Ala Asp
                355                 360                 365

Pro Gln Ala Pro Val Ala Ala Ile Gly Ser Ile Lys Gly Met Ile Gly
            370                 375                 380

His Thr Lys Ala Ala Ala Gly Val Ala Gly Leu Ile Lys Ala Ala Leu
385                 390                 395                 400

Ala Val Asp Asn Gln Thr Leu Pro Pro Ser Ile Gly Thr Ser Asp Pro
                405                 410                 415

His Glu Leu Leu Thr Glu Pro Gly Ala Asn Leu Lys Ala Leu Arg Lys
                420                 425                 430

Ala Glu Thr Trp Pro Arg Glu Leu Pro Arg Arg Ala Gly Ile Thr Ala
                435                 440                 445

Met Gly Phe Gly Gly Ile Asn Thr His Val Val Leu Asp Glu Pro Ser
            450                 455                 460

Gly Arg Arg Arg Pro Ala Ser Val Arg Arg Leu Thr Pro Leu Ala Asp
465                 470                 475                 480

Ser Met Gln Asp Ser Glu Leu Leu Phe Glu Gly Ala Ser Ala Arg
                485                 490                 495

Glu Leu Ser His Arg Leu Ser Glu Val Ala Asp Tyr Thr Val Arg Leu
                500                 505                 510

Ser Tyr Gly Glu Ile Ala Asp Leu Ala Ala Thr Leu Gln Arg Glu Leu
            515                 520                 525

Arg Gly Leu Pro His Arg Ala Ala Ala Val Val Thr Ser Pro Asp Asp
            530                 535                 540

Ala Glu Asn Arg Leu Arg His Leu Ala Asp Leu Leu Asp Arg Gly Glu
545                 550                 555                 560

Thr Glu His Trp Ala Ala Asp Gly Arg Thr Leu Leu Gly Lys Ala Thr
                565                 570                 575

Gly Arg Lys Arg Ile Gly Leu Leu Phe Pro Gly Gln Gly Ser Gly Arg
            580                 585                 590

Gly Thr Gly Gly Gly Ala Leu Ser Arg Arg Phe Pro Glu Val Ala Glu
            595                 600                 605

Val Leu Ala Arg Ala Gly Ser Ala Ala Gly Ser Asp Thr Val Ala Thr
            610                 615                 620

Glu Val Ala Gln Pro Arg Ile Val Thr Gly Ser Ala Ala Gly Leu Arg
625                 630                 635                 640

Val Leu Asp Glu Leu Arg Val Glu Ala Ser Val Gly Ile Gly His Ser
                645                 650                 655

Leu Gly Glu Leu Ser Ala Leu Cys Trp Ala Gly Ala Leu Asp Glu Asp
                660                 665                 670

Val Leu Ile Glu Ala Ala Gly Val Arg Gly Arg Ala Met Ala Glu His
                675                 680                 685

Gly Ser Ser Gly Thr Met Ala Ser Leu Gly Ala Ala Pro Glu Gln Ala
            690                 695                 700
```

-continued

```
Glu Glu Leu Ile Gly Ala Leu Ser Val Val Ala Gly Tyr Asn Gly
705                 710                 715                 720

Pro Gln Gln Thr Val Ser Gly Pro Val His Glu Val Glu Glu Val
                725                 730                 735

Arg Arg Arg Ala Ala Arg Ser Gly Val Thr Cys Thr Pro Leu Ala Val
            740                 745                 750

Ser His Ala Phe His Ser Pro Leu Val Ala Ser Ala Ala Glu Ser Phe
        755                 760                 765

Gly Asn Trp Leu Lys Ser Val Asp Phe Arg Glu Pro Ala Gly Arg Val
    770                 775                 780

Val Ser Thr Val Thr Gly Ala Glu Leu Thr Pro Gly Thr Asp Leu Ser
785                 790                 795                 800

Ala Leu Leu Arg Glu Gln Ile Thr Ala Ala Val Arg Phe Thr Glu Ala
                805                 810                 815

Val Arg Ala Ala Ala Gln Asp Val Asp Leu Phe Ile Glu Val Gly Pro
            820                 825                 830

Gly Arg Val Leu Gly His Leu Ala Gly Thr Ala Thr Asn Ile Pro Ala
        835                 840                 845

Val Ser Leu Asp Thr Asp Glu Ser Leu Arg Ser Leu Leu Gln Val
    850                 855                 860

Val Gly Ala Ala Phe Val Val Gly Ala Pro Val Ala Pro Glu Arg Leu
865                 870                 875                 880

Phe Arg Asp Arg Leu Ile Arg Pro Leu Arg Ile Gly Gln Glu Leu Ser
                885                 890                 895

Phe Leu Ala Ser Pro Cys Glu Gln Ala Pro Ala Thr Thr Leu Pro Val
            900                 905                 910

Ser Arg Arg Ser Ala Gln Pro Pro Ala Val Pro Ala Asp Arg Glu Gln
        915                 920                 925

Glu Pro Gln Pro Ala Ala Val Ser Pro Pro Ala Ala Gln Asn Ser Pro
    930                 935                 940

Ala Ser Asn Asp Thr Ser Thr Ala Ser Thr Ala Ser Thr Ala Gly Ser
945                 950                 955                 960

Glu Arg Thr Pro Gln Glu Glu Ser Ile Gly Ala Lys Ala Leu Asp
                965                 970                 975

Val Leu Ser Ala Leu Val Val Glu Arg Ala Glu Leu Pro Ala His Leu
            980                 985                 990

Val Asp Pro Asp Ser Arg Leu Leu  Asp Asp Leu His Leu  Ser Ser Ile
        995                 1000                1005

Thr Val  Gly Gln Ile Val Asn  Gln Ala Met Ala Gln  Leu Gly Ile
    1010                1015                1020

Ala Pro  Ala Ala Gln Glu Pro  Thr Asn Phe Ala Thr  Ala Thr Leu
    1025                1030                1035

Ala Glu  Leu Ala Glu Ala Leu  Glu Ser Leu Ala Ser   Thr Gly Gly
    1040                1045                1050

Pro Ala  Asp Ala Gly Ala Ala  Ser Phe Ile Ala Gly  Ala Ala Pro
    1055                1060                1065

Trp Ala  Arg Pro Phe Ala Val  Asp Leu Asp Ala Val  Ala Arg Pro
    1070                1075                1080

Pro Ala  Arg Pro Ala Ala Val  Arg Gly Thr Trp Glu  Leu Phe Ala
    1085                1090                1095

Pro Ala  Gly Tyr Gly Ile Ala  Ala Thr Leu Arg Ala  Ala Leu Gln
    1100                1105                1110

Asp Ala  Gln Ala Gly Ser Gly  Val Leu Val Cys Leu  Pro Pro Gln
```

-continued

```
                  1115                1120                1125

Cys  Ser  Ala  Asp  Gly  Ile  Asp  Leu  Ala  Leu  Ala  Ala   Ala  Lys  Arg
     1130                1135                1140

Ala  Leu  Ala  Ala  Pro  Lys  Asp  Ser  Arg  Phe  Val  Leu   Val  Gln  His
     1145                1150                1155

Gly  Arg  Ala  Ala  Ala  Gly  Leu  Val  Lys  Thr  Leu  His   Gln  Glu  Ala
     1160                1165                1170

Ser  His  Leu  Val  Thr  Thr  Val  Val  Asp  Thr  Pro  Leu   Thr  Glu  Asp
     1175                1180                1185

Thr  Val  Asp  Arg  Val  Val  Ala  Glu  Val  Ser  Ala  Thr   Thr  Arg  Phe
     1190                1195                1200

Ser  Glu  Val  His  Tyr  Ser  Ala  Asp  Gly  Val  Arg  Arg   Val  Pro  Thr
     1205                1210                1215

Leu  Arg  Ala  Leu  Pro  Met  Ser  Pro  Glu  Gln  Gln  Asp   Lys  Pro  Leu
     1220                1225                1230

Ser  Ala  Ser  Asp  Val  Leu  Leu  Val  Thr  Gly  Gly  Gly   Lys  Gly  Ile
     1235                1240                1245

Ser  Ala  Glu  Cys  Ala  Leu  Ala  Ile  Ala  Gln  Asp  Ser   Gly  Thr  Arg
     1250                1255                1260

Leu  Ala  Val  Leu  Gly  Arg  Ser  Asp  Pro  Ala  Thr  Asp   Arg  Glu  Leu
     1265                1270                1275

Ala  Asp  Asn  Leu  Lys  Arg  Met  Glu  Asp  Ser  Gly  Val   Thr  Met  Arg
     1280                1285                1290

Tyr  Ala  Arg  Ala  Asp  Val  Thr  Asn  Pro  Glu  Gln  Val   Arg  Thr  Ala
     1295                1300                1305

Val  Ala  Glu  Leu  Arg  Gly  Glu  Leu  Gly  Pro  Ile  Thr   Gly  Val  Leu
     1310                1315                1320

His  Gly  Ala  Gly  Arg  Asn  Glu  Pro  Gly  Pro  Leu  His   Ala  Leu  Glu
     1325                1330                1335

Pro  Glu  Asp  Phe  Arg  Arg  Thr  Phe  Ala  Pro  Lys  Val   Asp  Gly  Leu
     1340                1345                1350

Arg  Thr  Val  Leu  Glu  Ala  Val  Asp  Ala  Glu  Glu  Leu   Lys  Leu  Leu
     1355                1360                1365

Val  Thr  Phe  Gly  Ser  Ile  Ile  Gly  Arg  Ala  Gly  Leu   Arg  Gly  Glu
     1370                1375                1380

Ala  His  Tyr  Ala  Thr  Ala  Asn  Glu  Trp  Leu  Ala  Asp   Leu  Thr  Glu
     1385                1390                1395

Glu  Ile  Ala  Arg  Thr  His  Pro  Gln  Val  Arg  Ala  Arg   Cys  Val  Glu
     1400                1405                1410

Trp  Ser  Val  Trp  Ser  Gly  Val  Gly  Met  Gly  Glu  Lys   Leu  Ser  Val
     1415                1420                1425

Val  Glu  Ser  Leu  Ser  Arg  Gln  Gly  Ile  Val  Pro  Val   Ser  Pro  Asp
     1430                1435                1440

Gln  Gly  Val  Glu  Ile  Leu  Leu  Arg  Leu  Ile  Arg  Asp   Pro  Asp  Ala
     1445                1450                1455

Pro  Val  Val  Thr  Val  Val  Ser  Gly  Arg  Thr  Glu  Gly   Ile  Glu  Thr
     1460                1465                1470

Val  Arg  Arg  Asp  Leu  Pro  Pro  Leu  Pro  Leu  Leu  Arg   Phe  Thr  Gly
     1475                1480                1485

Thr  Pro  Leu  Val  Arg  Tyr  His  Gly  Val  Glu  Leu  Val   Thr  Glu  Val
     1490                1495                1500

Glu  Leu  Asn  Ala  Gly  Thr  Asp  Pro  Tyr  Leu  Gly  Asp   His  Leu  Leu
     1505                1510                1515
```

-continued

```
Asp Gly Asn Leu Leu Leu Pro Ala Val Met Gly Met Glu Ala Met
1520                1525                1530

Val Gln Val Ala Ala Ala Thr Gly Trp Pro Gly Thr Pro Val
1535                1540                1545

Ile Glu Gly Ala Arg Phe Leu Arg Pro Ile Val Val Pro Pro Asp
1550                1555                1560

Gly Ser Thr Thr Ile Arg Val Ala Ala Thr Val Thr Gly Pro Asp
1565                1570                1575

Thr Val Asp Val Ala Val His Ala Ser Asp Thr Gly Phe Ala Ala
1580                1585                1590

Glu His Phe Arg Ala Arg Leu Val Tyr Ser Val Ala Gly Val Pro
1595                1600                1605

Asp Gly Pro Pro Leu Gln Thr Gly Ser Asp Thr Pro Glu Val Pro
1610                1615                1620

Leu Asp Pro Ala Ser Asp Leu Tyr Gly Gly Ile Leu Phe Gln Gly
1625                1630                1635

Ser Arg Phe Gln Arg Leu Arg Arg Phe His Arg Met Ala Ala Arg
1640                1645                1650

His Val Asp Ala Asp Val Thr Val Arg Arg Pro Glu Gly Trp Phe
1655                1660                1665

Ala Gly Phe Leu Pro Ala Glu Met Leu Leu Ala Asp Pro Gly Met
1670                1675                1680

Arg Asp Ala Leu Met His Gly Asn Gln Val Cys Val Pro Asp Ala
1685                1690                1695

Thr Leu Leu Pro Ser Gly Val Glu Arg Val His Pro Leu Gly Asn
1700                1705                1710

Ser Gly Asn Val Pro Asp Gln Leu Arg Tyr Cys Ala Val Glu Arg
1715                1720                1725

Ser Arg Asp Gly Asp Thr Tyr Val Tyr Asp Ile Ala Val Arg Asp
1730                1735                1740

Ala Glu Gly Thr Val Val Glu Arg Trp Glu Gly Leu Thr Leu His
1745                1750                1755

Ala Val Arg Lys Thr Asn Gly Ser Gly Pro Trp Val Ala Pro Leu
1760                1765                1770

Leu Gly Pro Tyr Leu Glu Arg Thr Leu Glu Glu Val Leu Gly Ala
1775                1780                1785

His Ile Ala Val Thr Val Glu Pro His Gly Asp Asn Pro Ala Gly
1790                1795                1800

Ser Val Ala Glu Arg Arg Ala Leu Thr Thr Ile Ala Ala Ser Arg
1805                1810                1815

Thr Leu Gly Ala Ala Val Thr Val Arg His Arg Pro Asp Gly Arg
1820                1825                1830

Pro Glu Val Asp Gly Gly Trp His Ile Ser Ala Ser His Gly Leu
1835                1840                1845

Glu Leu Thr Val Ser Ala Val Ala Arg Ala Glu Val Ala Cys Asp
1850                1855                1860

Ile Glu Ala Val Ser Met Arg Glu Pro Ser Glu Trp Gln Gly Leu
1865                1870                1875

Leu Gly Glu Tyr Ala Ala Val Ala Glu Leu Val Ala Arg Glu Thr
1880                1885                1890

Gly Glu Ala Pro Asp Thr Ala Ala Thr Arg Val Trp Ser Ala Val
1895                1900                1905
```

```
Glu Cys Leu Arg Lys Ala Gly Ala Met Ala Gly Thr Pro Leu Thr
    1910            1915                1920

Val Leu Pro Gln Lys Lys Glu Ala Trp Val Val Phe Thr Ala Gly
    1925            1930                1935

Asp Leu Arg Ile Ala Thr Phe Val Thr Ala Leu Arg Asp Ala Leu
    1940            1945                1950

Glu Pro Ala Val Phe Ala Phe Leu Thr Arg Thr Pro Glu Leu Leu
    1955            1960                1965

Glu Gly Arg Ser Gln Asp Tyr Val Gly
    1970            1975

<210> SEQ ID NO 34
<211> LENGTH: 5934
<212> TYPE: DNA
<213> ORGANISM: Streptomyces carzinostaticus neocarzinostaticus

<400> SEQUENCE: 34
```

| | | | | | |
|---|---|---|---|---|---|
| atgaccagaa | tcgccatcgt | cggcatggcc | tgccgctacc | ccgacgccac | cagtcccgcc | 60 |
| gaactgtggg | ccaacgccat | tgccggacgc | cgagccttcc | gacgcctccc | cgaggaacga | 120 |
| atacgtctgg | aggactactg | ggacgccgat | ccgtccacac | ccgacaccttc | ctacgcccgc | 180 |
| aacgcggccg | tgctcgaggg | gtattccttc | gaccgcgtta | cccaccggat | cgccggcagt | 240 |
| acgttcaggt | ccaccgacat | gacgcactgg | ctcgccctgg | acactgccgg | gcgggcgctg | 300 |
| gccgacgccg | ggttcccggc | gggtgagggg | ctgcctcacg | agcggaccgg | cgtcgtcatg | 360 |
| ggcaacacgc | tcaccggtga | attcacccgt | gccaacgtca | tgcggctgcg | ctggccgtac | 420 |
| gtgcggcggg | tgatggcggc | cgcgctcgcc | ggacagcagg | actgggacga | ggcccgggtc | 480 |
| accgcgttcc | tcgaggaggt | cgaaacctcc | tacaaggcgc | cgttcccgcc | cgtcgacgag | 540 |
| gacactctgg | ccggtgggct | ctccaacacc | atcgccggcc | ggatctgcaa | ccacttcgac | 600 |
| ctcaacggcg | gcggatacac | cgtcgacgga | gcctgctcct | cctcgctgct | gtcggtcacc | 660 |
| accgccggaa | cagctctggt | caacggtgac | ttggacgtcg | ccgtcgccgg | tggtgtcgac | 720 |
| ctgtccatcg | acccgttcga | gatcatcggc | ttcgccaaga | ccggtgctct | ggcccggggg | 780 |
| gagatgaagc | tgtacgacaa | gggctccaac | ggtttctggc | ccggcgaggg | ctgcggagtg | 840 |
| gtcgtgctga | tgcgggaaga | ggacgcgatc | gcacgcggcc | accgcatcta | cgcgaccgtc | 900 |
| gcaggctggg | gggtgtcctc | ggacggtcag | ggcgggatca | cccggcccga | ggtcgacggc | 960 |
| taccgcctgg | ccctcgagcg | tgcctacgcg | cgtgccgggt | tcggcatcga | gaccgtcccc | 1020 |
| ctcttcgagg | gccacggcac | gggaacggcc | gttggtgacg | cgacggagct | ggcggcgctg | 1080 |
| ataaaggccc | gctcggcagc | cgacccgcag | gcgcctgtcg | ccgccatcgg | ctccatcaag | 1140 |
| ggcatgatcg | gtcacaccaa | ggcggcagca | ggcgtggcag | gtctgatcaa | ggcggccctg | 1200 |
| gcggtggaca | accagaccct | gccgccctcc | atcggcacct | ccgatccgca | cgagctgctc | 1260 |
| accgagccag | gggccaacct | caaggcgctg | cgcaaggcgg | aaacctggcc | ccgggaactg | 1320 |
| ccgcgccgcg | cgggcatcac | cgccatgggg | ttcggcggca | tcaacacgca | cgtagtcctg | 1380 |
| gacgagccgt | ccggccggcg | ccggccggct | tccgtccgcc | ggctcacccc | cctggccgac | 1440 |
| tccatgcagg | acagcgaact | cctgctgttc | gaggggcct | cggcccgaga | gctgagccac | 1500 |
| aggttgtccg | aggtcgcgga | ctacactgtg | aggctctcgt | acgggagat | cgccgacctc | 1560 |
| gccgccactc | tccagcgcga | gctccggggc | cttccgcacc | gggcagcggc | ggtggtgacc | 1620 |
| tctccggacg | acgccgagaa | ccggctgcgc | cacctcgcgg | accttctgga | ccgggggggag | 1680 |

```
acggagcact gggccgcgga cggccggacc ctccttggaa aggccaccgg ccgcaaacgg    1740
atcggtctgc tgtttcccgg ccagggctct ggacgcggca ccggtggcgg tgcgttgagc    1800
cgccgcttcc ccgaggtcgc cgaggtgctg gctcgcgccg ggtcggcggc gggctcggac    1860
accgtggcca ccgaagtggc ccagccgcgc atcgtcactg gttcggcagc gggtctgcgt    1920
gttctggacg agctgcgggt ggaggcgtcc gtcggtatcg acacagcct cggcgagctc     1980
tccgccctgt gctgggccgg ggctctcgac gaggacgtcc tgatcgaggc ggcgggcgtg    2040
cgtggcaggg caatggcgga gcacgggtcg tcgggaacca tggcgtcact gggtgccgca    2100
ccggagcagg cggaggagct catcggcgcc ctctccgtgg tcgtggccgg ctacaacggt    2160
ccgcagcaga cggtcgtctc gggtcccgtg cacgaagtgg aggaggtgcg caggcgggcc    2220
gctcgctccg gcgtgacgtg tacgccgctt gccgtgtccc acgcgttcca ctcaccgctc    2280
gtggcgtccg ccgccgagtc gttcggcaac tggctgaaga gcgttgactt tcgcgagccc    2340
gccgacgtg tggtgtccac ggtcaccggg gccgagctga caccgggcac tgacctgtcg     2400
gcgctgctgc gggagcagat caccgctgcg gtgcgtttca ccgaagcggt cagggccgcg    2460
gcccaggacg tcgacctgtt catcgaggtg ggacccggcc gggtgctcgg ccacctggcc    2520
gggacggcga cgaacattcc cgcggtttcc ctcgacacgg acgacgagtc cctgcgatcg    2580
ctcctgcagg tggtgggcgc cgcgttcgtc gtcggcgcgc ccgtcgcccc cgaacgcctc    2640
ttccgggacc ggttgatacg cccgctccgg attggccagg agctctcctt cctggccagt    2700
ccatgcgaac aggcaccggc gacgacccta cccgtatcgc gccggtccgc ccagccgccc    2760
gccgtacctg ctgatcgcga caagagccg cagcccgcgg ccgtgtcacc tccggcagca     2820
cagaactccc cggcctcgaa cgacacctcc accgcgtcca ccgcgtccac cgccgggtcc    2880
gagcggacgc ctcaggagga ggagagcatc ggcgccaagg ccctcgatgt cctcagtgcc    2940
ctggtcgtcg agcgagccga actcccggcc cacctggtgg accggacag caggctcctg      3000
gacgacctgc acctgagctc catcaccgtc ggccagatcg tgaaccaggc catggcgcaa    3060
ctcggtatcg ccccgcagc gcaggagccg acgaacttcg ccactgccac gctggcggaa     3120
ctggccgaag cgctcgagag cctggccagt accggcggcc cggccgatgc cggtgcggct    3180
tcgttcatcg ccggagcggc gccgtgggcg cgtcccttcg cggtggacct ggacgcggtc    3240
gcccggccgc cggcgcgtcc ggcagcggtt cgcggcacct gggagctgtt cgcaccggcc    3300
gggtatggga tcgccgcgac actgcgcgcg gcgctccagg acgcccaggc gggttccgga    3360
gtgctggtct gtctgccgcc ccagtgctct gccgacggga tcgacctggc gctagcagcg    3420
gcgaagcggg cgctcgccgc cccgaaggac agccgtttcg tgctggtgca gcacggccgc    3480
gctgccgccg gcctggtcaa gaccctccac caggaggcgt cccacctggt gacgactgtc    3540
gtcgacaccc ccctcaccga ggacacggtg gaccgggtgg tcgccgaggt gtcggcgacc    3600
acccggttct ccgaggtgca ctacagcgcg gacgcagtcc gccgcgtccc cacgctgcgg    3660
gcactcccca tgagcccgga gcaacaggac aaaccgctca gcgcatccga cgtcctgctg    3720
gtcaccgggg gtggcaaggg catctccgcc gagtgcgccc tggcgatcgc ccaggacagc    3780
gggacacggc ttgcggtgct gggacgctcc gacccggcca cggaccgaga actggccgac    3840
aacctgaagc ggatggagga cagcggtgta accatgcggt acgcgcgcgc cgacgtcacc    3900
aatccggagc aggtccggac ggcagtcgcc gagctgcgcg gcgagctggg tccgatcacc    3960
ggcgtgctgc acgcgccgg acgtaacgaa cccgggccgt tgcatgcgtt ggaaccggag    4020
gacttccggc gtaccttcgc tcccaaggtg gacggcctac ggaccgtact cgaggcagtg    4080
```

```
gacgccgagg aactgaaact gctcgtcacg ttcggcagca tcatcggccg tgccggcctg    4140
cggggcgagg cgcactacgc caccgcgaac gagtggctgg ccgacctcac cgaggagatc    4200
gcacgcacgc acccgcaggt acgcgcccgc tgcgtggaat ggtcggtgtg gtccggggtc    4260
gggatgggtg agaagctctc ggtcgtcgag tcgctctccc gccaaggcat cgtcccggtc    4320
tccccggatc aggggtaga gatcctcctg cggctgatcc gggatcccga cgcgccggtg    4380
gtgacggtcg tcagcggccg taccgaaggc atcgagacgg tgcgccgtga cctgccgccc    4440
ctgccgcttc tccggttcac cggcacccccg ctggtgcgct accacggcgt ggagctcgtc    4500
accgaggtcg agctgaacgc gggcacggac ccctacctcg cgaccacct gctggacggc     4560 aatctcctgc tgcctgcggt gatggggatg gaagccatgg ttcaggtcgc ggccgcggcc    4620
accggctggc cggggacacc ggtcatcgag ggcgcgcgct tcctgcgtcc catcgtggtt    4680
ccacccgacg ggagcaccac catccgtgtc gccgcgacgg tgaccggacc ggacacggtc    4740
gacgtcgccg tccacgccag cgacaccgga ttcgccgcag agcacttccg cgcccggctg    4800
gtgtattccg tcgccggtgt cccggacggg ccgccgctgc agacgggctc cgacaccccg    4860
gaagttcctc tggacccagc aagcgacctc tacgcggca tcctcttcca gggctcccgc     4920
ttccagcggt tgcggcgatt ccaccgaatg gcggcccggc acgtggacgc cgacgtgaca    4980
gtgcgaaggc cggagggctg gttcgccggc ttcctccctg cggagatgct tctgccgac    5040 cccggcatgc gcgacgcgct gatgcacggc aaccaagtgt gcgtgcccga cgccacgctg    5100
cttccttcgg gggtcgagcg tgtccacccc ctgggcaaca gcgggaatgt acccgaccaa    5160
ctgcgttact gcgcggtcga gcgcagccgt gacggcgaca catacgtgta cgacatcgcg    5220
gtacgcgacg ccgagggcac cgtcgtcgaa cgctgggaag gtctgaccct gcacgcggtg    5280
cgcaagacca acggctccgg cccctgggtc gcgcccctgt gggaccgta cctggagcgg    5340 accctcgagg aagtgctcgg tgcgcacatc gcggtgacgg tcgaaccgca cggcgacaac    5400
ccggctgggt cggtcgccga acgtcgggcc ctgaccacca tcgcggcctc ccggacctc    5460 ggggccgccg tgaccgtgcg tcaccggccc gacgggcggc cggaggtgga tggtgggtgg    5520
cacatctcgg cctcccacgg cctggaactc accgtgagcg ctgtggcccg gcggaggtt    5580 gcctgtgaca tagaggcggt cagcatgcgg gagccgagcg agtggcaggg gctgctcggc    5640
gagtacgccg cggtcgccga actcgtcgcc cgggagaccg gcgaagctcc cgacacggcc    5700
gccaccccgg tgtggagcgc ggtcgagtgc ctgaggaagg cgggcgccat ggcgggcaca    5760
ccgctgaccg tactgccgca gaagaaggaa gcgtgggtgg tcttcaccgc cggcgacctc    5820
cggatcgcga ccttcgtcac ggccctgcgg gacgctctgg aacccgccgt cttcgcattc    5880
ttgacgcgca caccggaact gctggaagga cggtcccagg actatgtcgg atga          5934
```

<210> SEQ ID NO 35
<211> LENGTH: 153
<212> TYPE: PRT
<213> ORGANISM: Streptomyces carzinostaticus neocarzinostaticus

<400> SEQUENCE: 35

```
Met Ser Asp Asp Tyr Phe Glu Tyr Arg His Thr Val Gly Phe Glu Glu
1               5                   10                  15

Thr Asn Leu Val Gly Asn Val Tyr Tyr Val Asn Tyr Leu Arg Trp Gln
            20                  25                  30

Gly Arg Cys Arg Glu Leu Phe Leu Lys Gln Lys Ala Pro Glu Val Leu
        35                  40                  45
```

-continued

```
Ala Asp Val Gln Asp Leu Lys Leu Phe Thr Leu Lys Val Asp Cys
    50                  55                  60

Glu Phe Phe Ala Glu Ile Thr Ala Phe Asp Glu Leu Ser Ile Arg Met
65                  70                  75                  80

Arg Leu Ser Asp Phe Gly Gln Thr Gln Leu Glu Phe Thr Phe Asp Tyr
                85                  90                  95

Val Lys Val Asp Glu Asp Gly Glu Thr Leu Val Ala Arg Gly Arg
                100                 105                 110

Gln Arg Val Ala Cys Met Arg Gly Pro Asn Thr Asn Thr Val Pro Ser
            115                 120                 125

Leu Val Pro Glu Ala Leu Val Arg Ala Leu Glu Pro Tyr Gly Ala Gln
        130                 135                 140

Arg Arg Val Leu Pro Gly Arg Thr Ala
145                 150
```

<210> SEQ ID NO 36
<211> LENGTH: 462
<212> TYPE: DNA
<213> ORGANISM: Streptomyces carzinostaticus neocarzinostaticus

<400> SEQUENCE: 36

```
atgtcggatg actacttcga gtaccggcac acggtcggct tcgaggaaac caatctggtc      60
ggcaacgtct actacgtgaa ctacctacgc tggcagggac gttgccggga gctgttcctc     120
aagcagaagg caccggaggt cctcgcggac gtacaggacg acctcaagct gttcacgctc     180
aaggtggact gtgagttctt cgccgagatc accgccttcg acgagttgtc catacggatg     240
cggctctccg acttcgggca gacccagttg gagttcacct tcgactacgt caaggtggac     300
gaggacggcg gcgagaccct ggtggcccgg ggccggcagc gggtcgcctg catgcgaggg     360
cccaacacca acacagtgcc ctcactggtc cccgaggcac tggtccgagc cctcgagccg     420
tacggcgcac agaggcgggt gctgccgggg cggacggcat ga                       462
```

<210> SEQ ID NO 37
<211> LENGTH: 328
<212> TYPE: PRT
<213> ORGANISM: Streptomyces carzinostaticus neocarzinostaticus

<400> SEQUENCE: 37

```
Val Ser Thr Ala Phe Gly Ala Leu Arg Arg Arg Leu Leu Thr Pro Pro
1               5                   10                  15

Ile Ser Glu Thr Thr Met Lys Val Arg Gly Phe His Val Lys Asn Thr
                20                  25                  30

Glu Ser Lys Lys Arg Leu Glu Gln Val Gly Glu Thr Phe Leu Gln Gly
            35                  40                  45

Tyr Ala Phe Ala Val Glu Ala Gly Ser Ser Ala Glu Ala Glu Glu Leu
        50                  55                  60

Leu Glu Thr Val Pro Arg Asp Phe Arg Gly Phe Ala Tyr Glu Gly Ala
65                  70                  75                  80

Ala Met Gly Ala Val Ile His Asp Ala Leu Pro Gly His Gly Gly Arg
                85                  90                  95

Leu Ala Gly Leu Leu Ser Gly Arg Gly Arg Tyr His Asp Tyr Met Ile
            100                 105                 110

His Val Gly Ile Gly Trp Ala Met Ala Arg Leu Pro Arg Pro Leu Trp
        115                 120                 125

Pro Asp Ile Arg Thr Thr Asp Pro Leu Leu Arg Trp Leu Ala Leu Asp
```

```
            130             135             140
Gly Phe Gly Phe His Gln Ala Tyr Phe Lys Thr Ser Ala Tyr Val Arg
145                 150                 155                 160

Asp Pro Ser Pro Pro Ala Pro Phe Arg Trp Asn Gly Gly His Asn His
                165                 170                 175

Tyr Thr Ala Asn Ala Ile Asp Gln Gly Ile Gly Arg Ala Leu Trp Phe
            180                 185                 190

Val Gly Gly Thr Asp Pro Asp Thr Val Ala Gly Leu Ile Arg Ser Tyr
        195                 200                 205

Ser Glu Pro Arg His Ala Asp Leu Trp Ala Gly Ala Gly Leu Ala Cys
    210                 215                 220

Ala Tyr Ala Gly Gly Ala Thr Glu Gln Glu Leu Ala Leu Phe Ala Arg
225                 230                 235                 240

Gln Ala Gly Glu His Arg Trp Ala Leu Ala Gln Gly Ala Ala Phe Ala
                245                 250                 255

Ala Glu Ala Arg Val Arg Ala Gly Leu Val Ser Glu His Thr His Leu
                260                 265                 270

Ala Ser Arg Val Val Cys Gly Val Ser Val Glu Gln Ala Ser Arg Met
            275                 280                 285

Cys Asn Gly Leu Arg Pro Ser Val Ala Ser Arg Asn Ala Leu Pro Ala
        290                 295                 300

Tyr Glu Asn Trp Arg Arg Asp Ile Ser Ala Arg Leu Ala Ser Glu Ser
305                 310                 315                 320

Thr Leu Arg Lys Gly Ala Asp Gln
                325

<210> SEQ ID NO 38
<211> LENGTH: 987
<212> TYPE: DNA
<213> ORGANISM: Streptomyces carzinostaticus neocarzinostaticus

<400> SEQUENCE: 38
gtgtctactg cattcggtgc gcttcggcgc cggctactca cacctcccat ttctgagacg     60
acaatgaagg tgcgcggatt ccatgtgaag aacacggaat ccaagaagcg tctcgagcaa    120
gtcggcgaga catttcttca ggggtacgcc ttcgctgtcg aggcgggttc gtcggccgag    180
gccgaggaac tcctcgagac ggtgccgcgg gatttccgtg gcttcgccta cgaggggggcc   240 gccatgggcg ccgtcatcca tgacgcgctc cccggtcacg gcggccggct cgcgggcctg    300
ctgtccggcc gcggccggta ccacgactac atgatccatg tcgggatcgg ctgggcgatg    360
gctcggctgc cgcgtcccct gtggccggac atccgtacca cggaccccct cctgcgctgg    420
ctggccctgg acgggttcgg cttccaccag gcgtacttca gacctccgc atacgtgcgc     480 gaccctccc cgcccgcgcc cttccgctgg aacggcggcc acaaccacta caccgccaac    540
gccatcgacc agggcatagg gcgggcgctg tggttcgtcg gcggcacgga cccggacacg    600
gtcgccgggc tcatccgctc ctactccgaa ccccgtcacg ccgacctgtg gccggtgcg    660 ggactcgcct gcgcctacgc cggggggagcc acggagcagg aactcgcct tttcgcacgg    720 caggcgggtg aacaccgctg ggccctcgcc caggggcgg cgttcgcggc cgaggcccgg    780
gtaagggccg ggtcgtgag cgagcacact cacctggctt cccgtgtcgt atgcggcgtc    840
tccgtcgaac aggcgtcccg gatgtgcaac ggcctcaggc cctccgttgc ctcccggaat    900
gcccttccgg cctatgagaa ctggcgcaga gacatttctg cccgactcgc ttccgaatcg    960
actctccgga aaggtgccga tcagtga                                        987
```

<210> SEQ ID NO 39
<211> LENGTH: 636
<212> TYPE: PRT
<213> ORGANISM: Streptomyces carzinostaticus neocarzinostaticus

<400> SEQUENCE: 39

Val Thr Met Ala Lys Asn Trp Leu Arg Arg Asn Ser Pro Gly Ile Val
1               5                   10                  15

Ala Leu Thr Leu Met Ala Ser Val Phe Tyr Val Val Arg Leu Pro Glu
            20                  25                  30

Pro Ser Ala Ala Asp Val Arg Glu Ser Ala Ala Asp Phe Ala Phe Glu
        35                  40                  45

Pro Met Thr Ile Ala Met Pro Gly Gly Phe Pro Thr Gln Lys Ile Arg
    50                  55                  60

Gln Val Asn Lys Ala Tyr Glu His Ile Asp Ala Trp Ile Ser Ser Val
65                  70                  75                  80

Gly Ala Gly Ile Ala Leu Asn Asp Met Asp Gly Asp Gly Leu Ser Asn
                85                  90                  95

Asp Leu Cys Leu Thr Asp Pro Arg Ile Asp Gln Ala Val Val Thr Pro
            100                 105                 110

Ala Pro Ser Arg Gly Lys Ala Tyr Glu Pro Phe Ala Leu Asp Ala Ala
        115                 120                 125

Pro Leu Gly Ile Ser Asp Thr Met Ala Pro Met Gly Cys Val Pro Gly
    130                 135                 140

Asp Phe Asn Glu Asp Gly Ala Ile Asp Leu Leu Val Tyr Tyr Trp Gly
145                 150                 155                 160

Arg Thr Pro Val Ile Phe Gln Asn Glu Gly Gly Arg Gly Glu Pro Leu
                165                 170                 175

Thr Ala Ser Ser Phe Thr Pro Thr Glu Leu Leu Pro Gly Lys Pro Gly
            180                 185                 190

Pro Arg Tyr Thr Gly Pro Leu Trp Asn Ser Asn Thr Ala Ala Val Ala
        195                 200                 205

Asp Phe Asp Gly Asp Gly His Asp Asp Ile Tyr Ile Gly Asn Tyr Phe
    210                 215                 220

Pro Asp Ser Pro Val Leu Asp Pro Ser Lys Asn Gly Asp Val Thr Met
225                 230                 235                 240

Asn Asp Ser Leu Ser His Ala Gln Asn Gly Gly Gly His Phe Phe
                245                 250                 255

Arg Trp Thr Glu Ser Gly Phe Glu Lys Thr Asp Asp Ala Ile Pro Gln
            260                 265                 270

Gly Leu Asn Lys Gly Trp Ser Leu Gly Ala Ser Ala Ala Asp Leu Asp
        275                 280                 285

Gly Asp Arg Leu Pro Glu Ile Phe Leu Ala His Asp Phe Gly Thr Ser
    290                 295                 300

Ala Leu Leu His Asn Thr Ser Arg Pro Gly Arg Ile Glu Phe Arg Glu
305                 310                 315                 320

Val Lys Ala Val His Ser Gly Thr Val Pro Lys Ser Lys Glu Ile Gly
                325                 330                 335

Arg Ser Ser Phe Lys Gly Met Gly Val Asp Phe Gly Asp Leu Asp His
            340                 345                 350

Asp Gly Leu Tyr Asp Met Phe Val Ser Asn Ile Thr Thr Ser Phe Gly
        355                 360                 365

Ile Gln Glu Ser Asn Phe Ala Phe Ile Asn Lys Ala Gly Asp Lys Ala

```
                    370                 375                 380
Asp Leu Arg Ser Arg Phe Glu Asn Gly Glu Ala Pro Tyr Arg Asp Glu
385                 390                 395                 400

Ser Thr Asp Leu Gly Leu Ala Trp Ser Gly Trp Gly Trp Asp Val Lys
                405                 410                 415

Met Gly Asp Phe Asp Asn Asn Gly Asp Leu Glu Ile Thr Gln Ala Leu
            420                 425                 430

Gly Phe Val Lys Gly Lys Asn Asn Arg Trp Pro Gln Leu Gln Glu Leu
        435                 440                 445

Ala Thr Ser Asn Asp Ala Leu Val Ala Asn Pro Thr Trp Trp Pro Asn
    450                 455                 460

Val Arg Gln Gly Asp Asp Leu Ala Gly Ser Gln Arg Met Arg Phe Phe
465                 470                 475                 480

Ala Lys Asp Gln Asp Thr Gly Arg Tyr Ile Asn Leu Ser Thr Ala Leu
                485                 490                 495

Gly Leu Gly Asp Pro Val Pro Thr Arg Gly Ile Ala Thr Gly Asp Val
            500                 505                 510

Asp Gly Asp Gly Arg Leu Asp Ile Ala Val Ala Arg Gln Trp Asp Glu
        515                 520                 525

Pro Val Phe Tyr Arg Asn Thr Ala Pro Glu Pro Gly Ser Trp Leu Glu
    530                 535                 540

Leu Val Phe Thr His Pro Asp Gly Ala Pro Val Gly Ala Glu Val
545                 550                 555                 560

Arg Val Glu Leu Pro Asp Gly Ser Lys Arg Val Ala Arg Val Asp Gly
                565                 570                 575

Gly Gly Gly His Ser Gly Lys Arg Ser Thr Asp Ile His Ile Gly Leu
            580                 585                 590

Gly Glu Glu Ala Gln Gly Glu Val Ser Gly Thr Val Thr Trp Arg Asp
        595                 600                 605

Arg Glu Gly Asp Val His Glu Gln Val Arg Leu Ala Pro Gly Arg
    610                 615                 620

His Ser Phe Glu Leu Gly Ser Gln Val Lys Glu Lys
625                 630                 635

<210> SEQ ID NO 40
<211> LENGTH: 1911
<212> TYPE: DNA
<213> ORGANISM: Streptomyces carzinostaticus neocarzinostaticus

<400> SEQUENCE: 40
gtgaccatgg cgaagaactg gctacgcagg aattctccgg gaatcgtcgc gctcaccctg      60
atggcgagcg tcttctacgt cgttcgcctc cctgaaccgt ctgccgccga tgtcagggaa     120
tcggcagccg acttcgcctt cgagccgatg accatagcca tgccgggagg atttcccaca     180
cagaagatca gacaggtcaa caaggcttac gagcacatcg acgcctggat ttcatcggtc     240
ggcgccggca tcgccctcaa tgacatggac ggcgacggcc tgtccaatga tctgtgcctg     300
accgacccca ggatcgacca ggccgtggtg accccggctc cctcgcgcgg caaggcctac     360
gaaccgttcg cactcgatgc ggccccctg ggaatcagcg acaccatggc tccgatgggg     420
tgcgtacccg gtgacttcaa cgaggacggc gccatcgacc tgctcgtcta ctactggggc     480
cgcaccctg tgatcttcca gaacgaaggt ggccgtggcg agccactcac cgcttcctcg     540
ttcacgccca cggaactgct accgggtaaa cccggcccgc ggtacacggg tccgctgtgg     600
aacagcaaca cagccgccgt cgccgacttc gacggcgacg acacgacga catctacatc     660
```

| | |
|---|---|
| ggcaactact tccccgacag cccggtcctc gacccgtcca agaacggcga cgtcaccatg | 720 |
| aacgactcgc tgtcgcacgc ccagaacggc ggtggtggtc acttcttccg ctggaccgag | 780 |
| tccggtttcg agaagacgga cgatgccata ccgcagggcc tcaacaaggg atggtcactc | 840 |
| ggcgcgtcgg ccgcggacct tgacggcgac cgtcttcctg agatcttcct cgcccatgac | 900 |
| ttcgggacct cggcgctgtt gcacaacacc tcgcggccgg ccggatcga gttccgcgag | 960 |
| gtcaaagcgg tccactccgg caccgttccc aagtccaagg agatcggacg cagctccttc | 1020 |
| aaggggatgg tgtcgacttc ggtgacctg gaccacgacg gcctgtacga catgttcgtc | 1080 |
| agcaacatca cgacatcgtt cgggatccag gagtcgaact tcgccttcat caacaaggcc | 1140 |
| ggcgacaagg ccgacctgcg gtcccgcttc gagaacggcg aggcgcccta cagggacgag | 1200 |
| tcgaccgacc tcggcctggc ctggtccggc tggggctggg acgtgaagat gggcgatttc | 1260 |
| gacaacaacg cgatcttga gatcacccag gcgctcggtt tcgtcaaggg caagaacaac | 1320 |
| cgctggccgc agttgcagga actcgccacg tccaacgacg cgctggtcgc caaccccacc | 1380 |
| tggtggccga cgtcaggca gggagatgac ctcgccggca ccagcggat gcggttcttc | 1440 |
| gccaaggacc aggacaccgg ccgctacatc aacctctcca cggcgctggg cctgggggat | 1500 |
| cctgttccga cccgtggcat cgcgaccggt gacgtggacg cgacggccg cctcgacatc | 1560 |
| gcagtcgccc gccagtggga cgagcccgtc ttctaccgca acacgccccc cgagcccggc | 1620 |
| tcctggctgg aactcgtctt cacgcacccc gacggtgctc cggtggtcgg agccgaagtc | 1680 |
| cgcgtcgagc tgcccgacgg gagcaagagg gtcgcccgcg tcgacggggg cggtggccac | 1740 |
| tcgggcaaac gaagtaccga tatccacatc ggcctgggcg aggaggccca gggcgaggtc | 1800 |
| tcagggacgg tcacctggcg cgaccgcgaa ggtgacgtcc acgagcagga agtgaggctg | 1860 |
| gcgccgggca ggcacagctt cgagctcggc agccaggtca aggagaagtg a | 1911 |

<210> SEQ ID NO 41
<211> LENGTH: 364
<212> TYPE: PRT
<213> ORGANISM: Streptomyces carzinostaticus neocarzinostaticus

<400> SEQUENCE: 41

Val Thr Met Ser Ala Ala Gln Pro Leu Ser Gln Thr Ala Gly Pro Arg
1               5                   10                  15

His Asn Pro Lys Val Val Thr Ala Leu Arg Arg Phe Ala Ile Ser Ile
            20                  25                  30

Ser Val Leu Asn Ile Val Gly Tyr Thr Val Leu Gly Phe Glu Gln Pro
        35                  40                  45

Trp Leu Trp Pro Phe Ile Ala Leu Ala Thr Ala Tyr Thr Val Glu Leu
    50                  55                  60

Thr Leu Glu Ala Val Gly Ala Arg Ala Glu Lys Arg Ala Thr Arg Phe
65                  70                  75                  80

Arg Gly Gly Gly Phe Arg Gly Leu Met Glu Phe Leu Tyr Pro Ala His
                85                  90                  95

Ile Thr Ala Leu Ala Val Asn Met Leu Thr Tyr Val Asn Asp Gln Val
            100                 105                 110

Trp Val Met Val Phe Gly Val Val Ala Val Gly Ala Lys Trp Val
            115                 120                 125

Leu Arg Ala Pro Val Arg Gly Arg Met Arg His Phe Met Asn Pro Ser
    130                 135                 140

Asn Leu Gly Ile Ala Val Ile Leu Leu Leu Phe Pro Trp Ala Ser Ile

```
                145                 150                 155                 160
Ala Pro Pro Tyr His Phe Thr Glu Tyr Val Asp Gly Gly Ile Asp Trp
                    165                 170                 175
Leu Val Pro Ala Val Ile Leu Thr Leu Gly Thr Met Leu Asn Ala Lys
            180                 185                 190
Leu Thr Glu Arg Met Trp Leu Ile Val Ala Trp Val Gly Gly Phe Ala
        195                 200                 205
Ala Gln Ala Val Val Arg Gly Leu Leu Phe Gly Thr Ser Ile Pro Ala
    210                 215                 220
Ala Leu Ala Met Met Thr Gly Val Ala Phe Val Leu Phe Thr Asn Tyr
225                 230                 235                 240
Met Ile Thr Asp Pro Gly Thr Thr Pro Ser Ser Lys Trp Gly Gln Ile
                245                 250                 255
Ala Phe Gly Gly Gly Val Ala Ala Ala Tyr Gly Leu Leu Thr Ala Leu
                260                 265                 270
Ser Val Ala Tyr Gly Ile Phe Phe Ala Thr Ala Leu Val Cys Gly Val
            275                 280                 285
Arg Gly Gly Phe Leu Trp Ile Ser Asp Ile Val Ser Arg Arg Arg Thr
        290                 295                 300
Glu Glu Ala Leu Ala Val Ala Ala Val Gly Leu Thr Ser Glu Lys Pro
305                 310                 315                 320
Ser Val Glu Arg Thr Pro Ile Glu His Ala Glu Thr Leu Pro Cys Val
                325                 330                 335
Asn Gly Cys Ala Glu Gly Ala Cys Ser Cys Ser Gly Asn Pro Lys Asp
                340                 345                 350
Ser Glu Ala Asp Asp Arg Arg Ile Val Val Ser Ala
            355                 360

<210> SEQ ID NO 42
<211> LENGTH: 1095
<212> TYPE: DNA
<213> ORGANISM: Streptomyces carzinostaticus neocarzinostaticus

<400> SEQUENCE: 42
gtgaccatgt ccgcagcaca gcccctgtcc cagaccgcgg gaccgcgcca caacccgaag      60
gtcgtcaccg ccctccgccg cttcgcgatc tcgatctccg tactcaacat cgtcggctac     120
accgtactgg gcttcgaaca gccctggctc tggcccttca tcgcgctggc gacggcctac     180
accgtggagc tcacgctcga ggccgtcggt gcacgcgccg agaagcgagc gactcgcttc     240
cgcgggggcg gcttccgagg gctgatggaa ttcctctacc ccgcacacat cacggccctc     300
gcggtgaaca tgctcaccta cgtcaacgac caggtgtggg tcatggtgtt cggcgtcgtg     360
gtggcggtag gcgccaagtg ggtgctgcgg gccccggtga ggggccgcat gcgccacttc     420
atgaacccct cgaatctcgg catcgcggtc atcctgctgt tgttcccgtg ggcgtcgatc     480
gccccgccgt accacttcac cgagtacgtg gacggcggca ttgactggct cgtgccggcc     540
gtcatcctca cgctcggcac catgctcaac gcgaagctca ccgaacgcat gtggctcatc     600
gtcgcgtggg tcggcgggtt cgccgcgcag gcggtcgtgc gagggctgtt gttcggcacg     660
tcgattcctg cggccctcgc gatgatgacc ggtgtggcgt tcgtactctt cacgaactac     720
atgatcacgg accccggcac cacgccgtcc tccaagtggg gccagatcgc cttcgggggc     780
ggtgtcgccg ccgcgtacgg cctcctgacg gcgctgagtg tcgcctacgg gatcttcttc     840
gccaccgctc tggtctgcgg ggtccgcggt ggcttcctgt ggatcagcga catcgtctcc     900
```

-continued

```
cgcaggcgca ccgaggaggc cctggccgtt gccgcggtcg gcctgacctc cgagaagccc      960
tccgtcgagc gcaccccgat cgagcacgcg gaaacactcc cgtgcgtgaa cggctgcgcc     1020 gaagggcct gctcctgctc cgggaacccg aaggacagcg aggcggacga ccgcaggatc     1080
gtggtgtcgg catga                                                      1095
```

<210> SEQ ID NO 43
<211> LENGTH: 1939
<212> TYPE: PRT
<213> ORGANISM: Amycolatopsis orientalis

<400> SEQUENCE: 43

```
Met Ser Val Glu Arg Ile Ser Ile Val Gly Ile Gly Leu Arg Tyr Pro
1               5                   10                  15

Asp Ala Gly Ser Pro Glu Glu Leu Trp Glu Asn Val Leu Ala Gly Arg
            20                  25                  30

Arg Ala Phe Arg Arg Leu Pro Asp Glu Arg Met Asn Arg Glu Asp Tyr
        35                  40                  45

Tyr Ser Pro Asp Pro Lys Ala Pro Asp Arg Phe Tyr Ala Gln Lys Ala
    50                  55                  60

Ala Val Leu Arg Asp Tyr Glu Phe Asp Arg Ile Lys Tyr Lys Val Ala
65                  70                  75                  80

Gly Ser Thr Phe Arg Ser Thr Asp Thr Thr His Trp Leu Ala Leu Asp
                85                  90                  95

Val Ala Ala Gln Ala Leu Ala Asp Ala Gly Phe Pro Glu Gly Glu Gly
            100                 105                 110

Leu Pro Lys Pro Ala Thr Gly Val Val Ile Gly Asn Ser Leu Thr Gly
        115                 120                 125

Glu Phe Ser Arg Ala Asn Ile Met Arg Leu Arg Trp Pro Tyr Val Arg
    130                 135                 140

Arg Thr Val Ala Ala Leu Ala Glu Arg Gly Trp Ala Asp Gly Asp
145                 150                 155                 160

Thr Ala Glu Phe Leu His Asp Leu Glu Ala Gln Tyr Lys Ala Pro Phe
                165                 170                 175

Pro Glu Ile Asp Glu Asp Thr Leu Ala Gly Gly Leu Ala Asn Thr Ile
            180                 185                 190

Ala Gly Arg Val Cys Asn Phe Phe Asp Phe Gly Gly Gly Phe Thr
        195                 200                 205

Val Asp Gly Ala Cys Ser Ser Ser Leu Leu Ser Val Val Thr Ala Ala
    210                 215                 220

Asn Ala Leu Ser Glu Gly Asp Leu Asp Val Ala Ile Ala Gly Val
225                 230                 235                 240

Asp Leu Ser Ile Asp Pro Phe Glu Val Ile Gly Phe Ala Lys Thr Gly
                245                 250                 255

Ala Leu Ala Lys Arg Glu Met Lys Val Tyr Asp Ala Asp Ser Asn Gly
            260                 265                 270

Phe Trp Pro Gly Glu Gly Ser Gly Met Leu Val Leu Met Arg Glu Glu
        275                 280                 285

Asp Ala Ile Ala Gln Gly Lys Arg Ile Tyr Ala Thr Ile Gly Gly Trp
    290                 295                 300

Gly Val Ser Ser Asp Gly Lys Gly Gly Ile Thr Arg Pro Glu Ala Ser
305                 310                 315                 320

Gly His Arg Leu Ala Leu Lys Arg Ala Tyr Asp Lys Ala Gly Tyr Gly
                325                 330                 335
```

```
Val Glu Thr Val Ser Tyr Phe Glu Gly His Gly Thr Gly Thr Ala Leu
            340                 345                 350

Gly Asp Ala Thr Glu Ile Glu Ala Leu Ser Thr Ala Arg Arg Asp Ala
        355                 360                 365

Asp Pro Leu Ala Glu Arg Ala Ala Leu Ser Thr Ile Lys Gly Asn Ile
    370                 375                 380

Gly His Thr Lys Ala Ala Ala Gly Val Ala Gly Leu Ile Lys Ala Thr
385                 390                 395                 400

Leu Ala Val Tyr His Gln Val Ile Pro Pro Ala Thr Gly His Phe Glu
                405                 410                 415

Pro His Glu Ser Leu Val Gly Asp Ser Ala Arg Met Tyr Val Pro Ala
            420                 425                 430

Glu Ala Gly Leu Trp Pro Ser Asp Gln Pro Val Arg Ala Gly Val Ser
        435                 440                 445

Ala Met Gly Phe Gly Gly Ile Asn Ser His Val Thr Val Thr Glu Ala
    450                 455                 460

Pro Gly Ala Ala Arg Arg Lys Glu Leu Asp Glu Arg Thr Arg Ser Leu
465                 470                 475                 480

Val Ala Gly Arg Gln Asp Ser Glu Leu Leu Leu Leu Asp Ala Asp Asp
                485                 490                 495

Ala Ala Ser Leu Arg Gly Lys Val Thr Gly Leu Leu Glu Val Val Pro
            500                 505                 510

Lys Leu Ser Phe Ala Glu Leu Ala Asp Leu Ala Gly Thr Leu Ser Ala
        515                 520                 525

Glu Leu Ser Gly Lys Pro Val Arg Ala Ala Val Val Ala Ala Gly Pro
    530                 535                 540

Asp Asp Ala Glu Arg Lys Leu Ala Lys Leu Leu Asp Leu Leu Gly Glu
545                 550                 555                 560

Gly Glu Pro Glu Val Phe Ser Ala Lys Glu Gly Ile Phe Ala Gly Ser
                565                 570                 575

Arg Ser Gln Ser Pro Lys Ile Gly Phe Leu Phe Pro Gly Gln Gly Ser
            580                 585                 590

Gly Gln Gly Arg Val Gly Ala Leu Arg Lys Arg Phe Ala His Ala Asp
        595                 600                 605

Asp Ile Tyr Arg Ala Ala Asn Leu Ser Thr Gly Ala Asp Gln Val Ala
    610                 615                 620

Thr Asp Val Ala Gln Pro Arg Ile Val Thr Gly Ser Leu Ala Gly Leu
625                 630                 635                 640

Arg Val Leu Lys Ser Leu Gly Ile Glu Ala Ala Val Thr Gly His
                645                 650                 655

Ser Leu Gly Glu Leu Thr Ala Leu His Trp Gly Ala Leu Thr Glu
            660                 665                 670

Arg Glu Val Leu Lys Leu Ala Lys Ile Arg Gly Lys Val Met Ala Thr
        675                 680                 685

Ala Ser Asp Gly Asp Gly Ala Met Ala Ala Ile Ala Ala Thr Pro Ser
    690                 695                 700

Val Ala Glu Gly Leu Ala Glu Gly Glu Glu Val Ile Ala Gly Tyr
705                 710                 715                 720

Asn Ala Pro Glu Gln Thr Val Leu Ser Gly Pro Ala Glu Ala Ile Asp
                725                 730                 735

Arg Val Val Ala Arg Ala Arg Ala Glu Gly Val Thr Ala Ala Arg Ile
            740                 745                 750

Asn Val Ser His Ala Phe His Ser Pro Ala Val Val Pro Ala Ala Glu
```

```
                755                 760                 765
Ala Met Thr Gly Glu Leu Ala Ala Ile Asp Phe Ala Arg Leu Asp Arg
770                 775                 780

Pro Val Ser Thr Val Thr Gly Asp Val Leu His Ala Ala Glu Asp
785                 790                 795                 800

Leu Arg Asp Leu Leu Arg Asp Gln Val Val Leu Pro Val Arg Phe Arg
                805                 810                 815

Glu Ala Ala Ala Lys Val Ala Glu Arg Ser Asp Leu Val Ile Glu Val
                820                 825                 830

Gly Pro Gly Arg Val Leu Thr Gly Leu Leu Gly Thr Ile Ala Pro Gly
                835                 840                 845

Thr Pro Val Leu Ser Ile Asp Thr Asp Ser Leu Thr Leu Ala Pro Val
850                 855                 860

Leu Lys Val Ala Gly Ala Ala Phe Ala Phe Gly Ala Gln Leu Glu Thr
865                 870                 875                 880

Ser Thr Leu Phe Asp Gly Arg Val Val Arg Ala Leu Pro Ala Asp Gly
                885                 890                 895

Glu Phe Ser Phe Leu Ala Ser Pro Cys Glu Ala Ala Pro Ser Ile Gly
                900                 905                 910

Ala Val Leu Thr Arg Asp Arg Val Ala Glu Pro Ala Glu Ala Ala Ala
                915                 920                 925

Gly Thr Ala Ser Glu Ser Gly Gly Ser Ser Thr Leu Asp Leu Leu Arg
                930                 935                 940

Lys Leu Ala Ser Glu Arg Val Glu Leu Pro Leu Glu Ala Val Thr Ala
945                 950                 955                 960

Asp Thr His Pro Leu Asp Asp Leu His Leu Ser Ser Ile Thr Val Gly
                965                 970                 975

Gln Leu Val Asn Asp Val Thr Arg Ala Leu Gly Arg Pro Ala Leu Glu
                980                 985                 990

Gly Met Pro Asn Phe Ala Thr Val Cys Leu Gly Glu Leu Ala Glu Met
                995                 1000                1005

Ile Asp Glu Leu Ala Gln Thr Ala Lys Pro Ala Asp Ser Asn Gln
    1010                1015                1020

Ala Glu Val Ala Gly Val Gly Pro Trp Val Arg Pro Phe Ala Val
    1025                1030                1035

Glu Tyr Val Val Ala Pro Lys Pro Ser Pro Asp Leu Ala Thr Gly
    1040                1045                1050

Ile Ser Thr Ala Glu Trp Thr Ala Phe Ala Pro Ala Gly His Pro
    1055                1060                1065

Leu Ala Glu Pro Leu Arg Ala Ala Leu Ala Thr Ala Gly Val Gly
    1070                1075                1080

Asp Gly Val Leu Leu Cys Leu Asn Ala Asp Ser Ala Ser Gly Asp
    1085                1090                1095

Val Gly Leu Phe Leu Asp Ala Gly Arg Ala Val Leu Ala Ala Pro
    1100                1105                1110

Asn Gly Thr Arg Phe Val Val Gln His Gly Leu Gly Ala Ser
    1115                1120                1125

Gly Leu Ala Lys Thr Leu Arg Leu Glu Asp Pro Ser Ala Arg Thr
    1130                1135                1140

Thr Ile Val Asp Leu Ala Asp Leu Gly Pro Val Asp Pro Glu Ala
    1145                1150                1155

Leu Asp Ala Ala Val Ser Thr Val Val Thr Glu Val Ala Ala Thr
    1160                1165                1170
```

-continued

```
Thr Asp Phe Ser Glu Val Arg Tyr Asp Thr Ala Gly Val Arg Thr
1175                1180                1185

Val Pro Lys Leu Ala Ala Leu Thr Pro Ala Glu Ala Glu Gly Thr
1190                1195                1200

Pro Leu Asp Thr Gly Asp Val Leu Leu Val Thr Gly Gly Gly Lys
1205                1210                1215

Gly Ile Thr Ala Glu Ser Ala Leu Ala Leu Ala Lys Asp Ser Gly
1220                1225                1230

Ala Lys Leu Ala Leu Leu Gly Arg Ser Asp Pro Ala Asp Asp Ala
1235                1240                1245

Glu Leu Ser Glu Asn Leu Gly Arg Met Ala Ala Gly Ile Thr
1250                1255                1260

Tyr Arg Tyr Glu Arg Ala Asp Val Thr Asp Gly Arg Gln Val Ala
1265                1270                1275

Asp Ala Ile Gly Arg Val Gln Ala Glu Phe Gly Pro Val Thr Ala
1280                1285                1290

Val Leu His Gly Ala Gly Arg Asn Glu Pro Ala Ala Leu Phe Ser
1295                1300                1305

Leu Thr Glu Glu Ser Phe Arg Lys Thr Leu Ala Pro Lys Ile Gly
1310                1315                1320

Gly Leu Asn Ala Val Leu Asp Ala Val Asp Lys Asp Lys Ile Lys
1325                1330                1335

Leu Leu Val Thr Phe Gly Ser Ile Ile Gly Arg Ala Gly Leu Arg
1340                1345                1350

Gly Glu Ala His Tyr Ala Thr Ala Asn Asp Trp Met Thr Glu Leu
1355                1360                1365

Thr Val Arg Phe Gly Gln Glu His Pro Arg Ala Lys Ala Ile Ala
1370                1375                1380

Leu Glu Trp Ser Val Trp Ser Gly Thr Gly Met Gly Glu Lys Leu
1385                1390                1395

Gly Val Val Ser Ala Leu Met Arg Asp Gly Ile Thr Pro Ile Pro
1400                1405                1410

Thr Glu Glu Gly Ile Glu Ile Leu Arg Gln Val Val Gly Asp Pro
1415                1420                1425

Ala Ala Pro Ser Val Leu Val Cys Gly Arg Thr Ala Gly Leu
1430                1435                1440

Ala Thr Leu Pro Val Glu Lys Arg Glu Leu Pro Leu Thr Arg Phe
1445                1450                1455

Val Asp Arg Ala Val Val His Tyr Pro Gly Val Glu Leu Ile Thr
1460                1465                1470

Glu Ala Asp Leu Ser Ala Gly Ser Asp Pro Tyr Leu Ala Asp His
1475                1480                1485

Leu Leu Asp Gly Gln Leu Leu Phe Pro Ala Val Ile Gly Met Glu
1490                1495                1500

Ala Met Thr Gln Val Ala Lys Ala Ala Leu Ala Ala Glu Thr Leu
1505                1510                1515

Pro Ala Pro Val Phe Ser Asp Val Glu Phe Leu Arg Pro Ile Ile
1520                1525                1530

Val Ser Pro Gly Gly Ser Thr Thr Ile Arg Leu Ala Ala Leu Ala
1535                1540                1545

Arg Asp Ala Glu Thr Val Asp Val Val Leu Arg Ser Gly Glu Thr
1550                1555                1560
```

```
Gly Phe Ser Ala Asp His Phe Arg Ala Arg Leu Ser Phe Ser Arg
1565                1570                1575

Pro Asp Pro Leu Gly Asp Thr Val Ala Arg Asp Val Ala Leu Pro
    1580                1585                1590

Pro Val Pro Val Asp Pro Thr Thr Glu Leu Tyr Gly Thr Val Leu
1595                1600                1605

Phe Gln Gly Lys Arg Phe Gln Arg Val Thr Gly Tyr Arg Arg Ala
1610                1615                1620

Ser Ala Arg His Ala Val Ala Glu Val Ala Thr Gly Ala Glu Val
1625                1630                1635

Asp Trp Phe Ala Pro Phe Leu Pro Gln Glu Gln Leu Leu Ala Asp
    1640                1645                1650

Pro Gly Thr Arg Asp Ala Met Met His Ala Ile Gln Cys Cys Val
    1655                1660                1665

Pro Asp Ala Thr Leu Leu Pro Gln Gly Ile Glu Arg Leu Tyr Leu
    1670                1675                1680

Ala Glu Pro Gly Glu Gln His Pro Glu Tyr Val Leu Leu Asp Ala
    1685                1690                1695

Arg Glu Arg Ser Gln Asp Gly Asp Ser Tyr Val Tyr Asp Leu Asp
    1700                1705                1710

Val Arg Asn Pro Asp Gly Lys Leu Val Glu Arg Trp Glu Gly Leu
    1715                1720                1725

Lys Leu Arg Ala Val Arg Lys Arg Asp Gly Gly Pro Trp Val
1730                1735                1740

Pro Ser Met Leu Gly Ser Tyr Leu Glu Arg Ser Val Glu Arg Leu
    1745                1750                1755

Leu Gly Ser Ser Arg Ala Ile Val Val Glu Pro Asp Pro Val Gly
    1760                1765                1770

Val Pro Val Glu Thr Thr Pro Glu Arg Arg Ala Gln Thr Ala Leu
    1775                1780                1785

Ala Ala Gly Arg Ala Val Asp Ala Pro Leu Glu Ile Arg Tyr Arg
    1790                1795                1800

Pro Asp Gly Lys Pro Glu Ala Asp Gly Val Glu Val Ser Ala Ser
    1805                1810                1815

His Ser Ala Asp Leu Thr Leu Ala Ile Ala Gly Ala Gly Arg Ile
    1820                1825                1830

Ala Cys Asp Val Glu Thr Ala Ile Glu Arg Thr Pro Glu Asp Trp
    1835                1840                1845

Ala Gly Leu Leu Gly Glu Asp Leu Leu Ala Val Gly Glu Leu Leu
    1850                1855                1860

Ala Ala Asp Ala Arg Glu Pro Leu Ser Val Ala His Thr Arg Val
    1865                1870                1875

Trp Ser Ala Leu Glu Cys Val Arg Lys Thr Gly Asp Met Thr Gln
    1880                1885                1890

Ala Leu Thr Val His Arg Val Asp Pro Asp Gly Trp Ala Val Leu
    1895                1900                1905

Ser His Gly Gly Ala Arg Ile Ala Thr Trp Val Thr Thr Val Asn
    1910                1915                1920

Asp Arg Thr Asp Pro Val Val Phe Ala Val Leu Gln Gly Glu Glu
    1925                1930                1935

Ser

<210> SEQ ID NO 44
```

-continued

```
<211> LENGTH: 5820
<212> TYPE: DNA
<213> ORGANISM: Amycolatopsis orientalis

<400> SEQUENCE: 44
atgagcgttg agcggatttc gattgtcggt atcggtctcc gatacccgga cgccggttcc      60
ccggaagagc tgtgggagaa cgtcctcgcc ggccgccggg cgttccggag gctgcccgac     120
gagcggatga accgcgagga ttactactcg cccgacccca aggctccgga ccgtttctac     180
gcccagaagg ccgcggtcct ccgcgactac gaattcgacc ggatcaagta caaggtcgcg     240
ggcagcacgt tccgttcgac cgacaccacg cactggctgg ccctcgacgt cgccgcgcag     300
gcgctggccg acgcgggctt ccccgagggc gagggctgc cgaagcccgc caccggcgtg     360
gtcatcggca acagcctcac cggcgagttc tcccgtgcca acatcatgcg gctgcgctgg     420
ccgtacgtgc gccgcacggt ggcggcggcg ctcgccgagc gcggctgggc cgacggcgac     480
accgccgagt tcctccacga tctcgaggcg cagtacaagg cccccttccc ggagatcgac     540
gaggacacgc tcgcgggcgg gctggcgaac acgatcgccg ccgggtctg caacttcttc     600 gacttcggcg gcgcgggtt cactgtggac ggtgcctgtt cgtcgtcgct gctttccgtg     660
gtcacggcgg cgaacgcgct ttcggagggc gacctcgacg tcgccatcgc gggcggtgtc     720
gacttgtcga tcgacccgtt cgaggtgatc gggttcgcca agaccggcgc gctcgccaaa     780
cgcgagatga aggtctacga cgccgattcc aacgggttct ggcccggcga ggggtccggc     840
atgctcgtgc tgatgcgcga ggaggacgcg atcgcgcagg gcaagcggat ctacgccacc     900
atcggcggct ggggcgtctc gtccgacggc aagggcggca tcacccgccc cgaggcctcg     960
gggcaccgcc tcgcgctcaa gcgggcgtac gacaaggcgg ggtacggcgt cgagaccgtt    1020
tcctacttcg agggccacgg caccgggacc gcactgggcg acgccaccga aatcgaggcg    1080
ctctccaccg cccgccgcga cgccgatccg ctcgccgagc gggccgcgct gagcacgatc    1140
aagggcaaca tcggccacac caaggccgcg gccggggtcg ccgggctgat caaggcgacc    1200
ttggcggtgt accaccaggt catcccgccc gcgaccggcc atttcgaacc gcacgagtcg    1260
ctggtcggcg actcggcgcg gatgtacgtg cccgccgagg ccgggctgtg gccctcggac    1320
cagccggtcc gcgccggtgt ctccgcgatg gggttcggcg gcatcaactc gcacgtcacc    1380
gtcaccgaag cgccgggcgc ggcccgtcgc aaggagctcg acgagcggac caggtcgctg    1440
gtcgccggac ggcaggacag tgaactgctg ctcctcgacg ccgacgacgc cgcgtcgttg    1500
cgtggcaagg tgaccggcct gctggaggtc gtcccgaagc tctcgttcgc ggaactcgcg    1560
gacctcgcgg gcacgctttc ggccgagctg tccgggaaac cggtccgggc ggcggtcgtc    1620
gcggccggac cggacgacgc cgagcgcaaa ctggccaaac tcctcgacct tctcggtgag    1680
ggggagccgg aagtcttctc cgccaaggaa ggcatcttcg ccggatcccg ctcccagtcc    1740
ccgaagatcg ggttcctgtt ccccggccag ggttccgggc agggcagggt cggcgcgctg    1800
cgcaaacgct tcgcgcacgc cgacgacatc taccgcgccg cgaacctgtc caccggcgcc    1860
gaccaggtcg ccaccgacgt cgcccagccg cgcatcgtca ccggttcgct ggccgggctg    1920
cgggtgctga agagcctcgg catcgaggcg gccacggtca cgggccacag cctcggcgag    1980
ctcaccgccc tgcactgggg cggcgcgctc accgaacgcg aagtgctcaa actggccaag    2040
atccgcgcca aggtgatggc gaccgccagc gacggggacg gggccatggc ggcgatcgcg    2100
gccacgccga gtgtcgccga gggcctggcc gagggcgaag aggtcgtcat cgcgggctac    2160 aacgccccg agcagactgt cctttccgga ccggcggagg cgatcgaccg cgtggtcgcc    2220
```

```
cgtgcccgcg cggaaggggt caccgccgcc cgcatcaacg tctcgcacgc cttccactcg   2280
cccgcggtcg tcccggccgc cgaggcgatg accggggaac tcgccgcgat cgacttcgcg   2340
cggctcgacc ggcccgtcgt ctccacggtg accggtgacg tcctgcacgc cgccgaagac   2400
ctgcgcgatc tgctgcgcga ccaggtggtc ctgccggtcc gcttccgtga ggcggccgcg   2460
aaggtcgccg agcgcagcga cctggtgatc gaggtcggcc ccggccgcgt gctcaccggc   2520
ctgctcggca ccatcgcgcc cggtaccccg gtgctttcga tcgacaccga cagcctgacg   2580
ctcgcgccgg tgctgaaggt cgccggtgcc gcgttcgcgt tcggcgcgca gctggagacg   2640
tccacgctgt tcgacggccg ggtcgtgcgg gccctgcccg cggacggcga gttctcgttc   2700
ctcgccagcc cgtgcgaggc cgcgccgtcc atcggcgccg tgctgacccg cgaccgagtc   2760
gccgagcccg ccgaggccgc cgccggaacg gcctcggaaa gcggtggcag cagcaccctc   2820
gacctgctgc gcaagctcgc gtccgaacgg gtcgagctgc cgctcgaagc ggtcaccgcc   2880
gacacgcatc ccctcgacga tctgcaccct tcgtcgatca ccgtcggcca gctggtcaac   2940
gacgtgacca gggcgctcgg ccggccggcg ctggagggta tgccgaactt cgcgaccgtg   3000
tgcctcggcg aactcgccga gatgatcgac gagctcgcgc agaccgccaa acccgccgac   3060
agcaaccagg ccgaggtcgc cggcgtcggc ccgtgggtcc ggccgttcgc ggtggagtac   3120
gtcgtcgcgc cgaagccgtc gcccgatctc gccacgggta tctccaccgc ggagtggacg   3180
gcgttcgccc cggccggtca cccactggcg gagccgctgc gcgcggcatt ggccacggcg   3240
ggcgtcggcc acggtgtcct cctctgcctg aacgccgaca gcgcttccgg cgacgtcggc   3300
ctgttcctgg acgcgggccg cgcggtgctg gccgcgccca acggcacgcg gttcgtcgtg   3360
gtgcagcacg gtctcggcgc ctcggggctg gcgaagacgc tccggctgga ggacccgtcg   3420
gcccgcacca cgatcgtcga cctcgccgac ctcggcccgg tcgaccccga agccctcgac   3480
gccgcggtgt ccactgtggt caccgaagtg gcggcgacga ccgacttcag cgaagtccgc   3540
tacgacaccg ccggagtccg cacggtgccg aagctcgcgg cgctgacccc ggccgaggcc   3600
gaaggcaccc cgctggacac cggcgacgtc ctgctcgtca cgggcggcgg gaagggcatc   3660
accgccgaga gcgcgttggc gctggccaag gattccggcg cgaagctggc actgctcggc   3720
cggagcgacc cggccgacga cgccgaactg tcggagaacc tcggccgcat ggcggcgggg   3780
ggcatcacct accgctacga gcgtgccgac gtcaccgacg acggcaggt ggccgacgcg   3840 atcggccggg tgcaggccga attcggcccg gtcaccgcgg tgctgcacgg cgcgggccgc   3900
aacgagcccg ccgcgctgtt ctccttgacc gaagagagct tccgcaagac gctggcgccg   3960
aagatcggtg gtctcaacgc cgtcctcgac gccgtcgaca aggacaagat caagctgctg   4020
gtgaccttcg gcagcatcat cggccgggcg ggcctgcgcg gtgaggcgca ctacgccacg   4080
gccaacgact ggatgaccga actgaccgtg cggttcggcc aggaacaccc ccgggccaag   4140
gcgatcgcgc tcgaatggtc ggtctggtcc ggcaccggga tgggcgaaaa gctcggtgtg   4200
gtcagcgcgt tgatgcgcga cggcatcacc cccatcccga ccgaggaggg catcgagatc   4260
ctccgccagg tcgtcggcga cccggccgcc ccgtcggtac tggtcgtctg cggccgcacc   4320
gccgggctgg ccacccttcc ggtggagaag cgcgaactgc cgctgacccg cttcgtcgac   4380
cgcgccgtcg tgcactaccc gggggtcgag ctgatcaccg aggccgacct gtccgcgggc   4440
agcgacccgt atctggccga ccacctgctc gacggtcagc tgctgttccc ggcggtgatc   4500
ggcatggagg cgatgaccca ggtcgccaag gccgcgctgg ccgcggaaac gctgccggcg   4560
```

```
ccggtgttct ccgacgtcga gttcctgcgc ccgatcatcg tctcgccggg cgggtcgacc    4620
acgatccggc tcgccgcgct ggccagggac gccgaaacgg tggacgtggt gctgcgcagc    4680
ggggagaccg gcttcagcgc cgaccacttc cgggcccggc tgagcttctc gcggccggat    4740
ccgctcggtg acaccgtcgc ccgcgacgtc gcgctgccgc cggtgccggt ggacccgacg    4800
accgagctct acggcacggt tctgttccag ggcaagcgat ccagcgggt caccggatac     4860 cggcgggcca gcgcgcggca cgcggtcgcg gaggtcgcca ccggtgccga ggtcgactgg    4920
ttcgcgccgt tcctcccgca ggagcagctc ctggccgacc cgggcacccg cgacgcgatg    4980
atgcacgcga tccagtgctg tgtcccggac gcgaccctgc tgccgcaagg gatcgagcgg    5040
ctgtacctcg ccgaacccgg tgagcagcac ccggagtacg tgctcctcga cgcccgcgag    5100
cgttcgcagg acggtgacag ctacgtctac gacctcgacg tccgcaaccc cgacgggaag    5160
ctggtcgagc ggtgggaagg gctgaagctg cgcgcggtgc gcaagcgtga cggcgaaggg    5220
ccttgggtcc cgtcgatgct cggtcctat ttggagcgtt ccgtcgaacg gctgctcggc     5280
tcgtcccgcg cgatcgtcgt cgaaccggat ccggtgggcg ttcccgtgga gaccacgccg    5340
gagcggcggg cgcagacggc actggccgcc ggccgagccg tcgacgcgcc gctggagatc    5400
cgctaccgcc cggacgggaa accggaggcc gacggggtcg aggtgagcgc gtcgcacagc    5460
gccgacctca ccctggccat cgcgggcgcc ggacggatcg cgtgtgacgt cgaaacggcg    5520
atcgaacgga cgccggagga ctgggccggc ctgctcggcg aggatctgct cgcggtgggc    5580
gaactgctgg ccgcggacgc ccgcgagccg ctttcggtgg cgcacaccag ggtctggagc    5640
gcactggaat gcgtgcgcaa gaccggggac atgacacagg cgctcaccgt gcaccgggtc    5700
gacccggacg gctgggcggt gctttcccac ggcggtgccc gcatcgccac ctgggtgacg    5760
accgtcaacg accggaccga tcccgtcgtc ttcgcggtgc tccagggaga ggagagctga    5820
```

<210> SEQ ID NO 45
<211> LENGTH: 146
<212> TYPE: PRT
<213> ORGANISM: Amycolatopsis orientalis

<400> SEQUENCE: 45

Met Ala Asp Tyr Tyr Glu Ile Leu His Thr Val Gly Phe Glu Glu Thr
1               5                   10                  15

Asn Leu Val Gly Asn Val Tyr Tyr Val Asn Tyr Val Arg Trp Gln Gly
            20                  25                  30

Arg Cys Arg Glu Met Phe Leu Lys Glu Lys Ala Pro Ala Val Leu Glu
        35                  40                  45

Glu Val Arg His Asp Leu Lys Leu Phe Thr Leu Lys Val Asp Cys Glu
    50                  55                  60

Phe Tyr Ala Glu Ile Thr Ala Phe Asp Glu Leu Ser Ile Arg Leu Arg
65                  70                  75                  80

Leu Glu Glu Leu Thr Gln Thr Gln Ile Gln Phe Thr Phe Asp Tyr Val
                85                  90                  95

His Leu Thr Ala Glu Gly Glu Arg Leu Val Ala Arg Gly Arg Gln Arg
            100                 105                 110

Ile Ala Cys Met Arg Gly Pro Asn Thr Ala Thr Val Pro Ser Arg Val
        115                 120                 125

Pro Glu Gln Leu Arg Glu Ala Leu Ala Pro Tyr Ala Val Asp Gly Lys
    130                 135                 140

Gly Glu
145

<210> SEQ ID NO 46
<211> LENGTH: 441
<212> TYPE: DNA
<213> ORGANISM: Amycolatopsis orientalis

<400> SEQUENCE: 46

| | | | | | |
|---|---|---|---|---|---|
| atggccgact | actacgagat | cctccacacg | gtcggattcg | aagagaccaa | cctggtgggc | 60 |
| aacgtctact | acgtgaacta | cgtgcgctgg | cagggccggt | gccgcgagat | gttcctgaag | 120 |
| gagaaggcgc | cgcggtgct | cgaagaggtc | cgccacgacc | tcaagctgtt | cacgctcaag | 180 |
| gtggactgcg | agttctacgc | ggagatcacc | gcgttcgacg | agctgtccat | ccggctgcgg | 240 |
| ctggaggagc | tgacccagac | ccagatccag | ttcaccttcg | actacgtcca | cctcaccgcg | 300 |
| gaaggcgagc | ggctggtggc | ccgcggacgg | cagcggatcg | cgtgcatgcg | cggcccgaac | 360 |
| acggccacgg | tgcccagccg | ggtgcccgaa | cagctgcgtg | aggcgctggc | cccgtacgcg | 420 |
| gtcgacggca | aggggaatg | a | | | | 441 |

<210> SEQ ID NO 47
<211> LENGTH: 324
<212> TYPE: PRT
<213> ORGANISM: Amycolatopsis orientalis

<400> SEQUENCE: 47

Leu Gly Asn Gly Trp Arg Thr Ile Arg Arg Arg Met Ile Thr Pro Asp
1               5                   10                  15

Val Ser Glu Thr Ser Leu Asp Lys Arg Gly Phe His Lys Lys Ser Pro
            20                  25                  30

Ala Ala Gln Glu Leu Leu Glu Thr Val Gly Glu Lys Phe Leu Leu Gly
        35                  40                  45

Tyr Ala His Ala Val Glu Ala Arg Ser Val Glu Gln Ala Glu Glu Trp
    50                  55                  60

Leu Glu Gln Ile Pro Val Lys Tyr Arg Gly Phe Ala Tyr Glu Gly Ala
65                  70                  75                  80

Gly Met Gly Tyr Gly Met Leu Asp Gly Leu Pro Gly Gly Gly Arg Arg
                85                  90                  95

His Val Glu Arg Phe Leu Asp Gly Pro Gly Glu Lys His Asp Tyr Ile
            100                 105                 110

Ile Tyr Val Gly Val Gly Trp Ala Met Ala Arg Leu Pro Arg Phe Arg
        115                 120                 125

Trp Pro Ser Ala Glu Asp Phe Asp Pro Leu Leu Arg Trp Leu Val Leu
    130                 135                 140

Asp Gly Tyr Gly Phe His Gln Ala Tyr Phe Lys Thr Ala Lys Tyr Val
145                 150                 155                 160

Asp Gly Gln Phe Gln Asp Pro Asp Phe Ser Trp Pro Gly Asn Asp
                165                 170                 175

Gly Tyr Ala Leu Arg Ala Ile Asp Gln Gly Ile Gly Arg Ala Leu Trp
            180                 185                 190

Phe Ile Cys Gly Thr Asp Val Asp Leu Val Ala Asp Thr Val Ala Arg
        195                 200                 205

Phe Pro Glu Arg Arg His Gly Asp Leu Tyr Ala Gly Ile Gly Leu Ala
    210                 215                 220

Ser Thr Tyr Ala Cys Gly Val Thr Gly Asp Glu Leu Leu Lys Leu Ala
225                 230                 235                 240

Glu Phe Ala Gly Glu His Arg Gly Asn Leu Ala Gln Gly Ser Ala Phe

```
                245                 250                 255
Ala Ala Glu Ala Arg Val Arg Ala Gly Leu Leu Ile Pro Glu Thr Glu
                260                 265                 270

Val Ala Thr Arg Ala Ile Cys Gly Leu Pro Ala Glu Arg Ala Ala Ala
            275                 280                 285

Ile Thr Gln Glu Val Arg Pro Ala Thr Val Val Asp Gly Glu Leu Pro
        290                 295                 300

Ala Phe Glu Thr Trp Arg Gln Arg Ile Ala Glu Ala Ile Leu Ser Gly
305                 310                 315                 320

Gly Ala Gly Lys

<210> SEQ ID NO 48
<211> LENGTH: 975
<212> TYPE: DNA
<213> ORGANISM: Amycolatopsis orientalis

<400> SEQUENCE: 48
ttgggcaatg gttggcgcac gatcagacgt cgcatgatca cgccggacgt ctccgagacg        60
tcactggaca gcgcggtttt ccacaagaag agcccggccg ctcaagaatt gctggagacc       120
gtcggtgaga agttcctgct cggctacgcg cacgcggtcg aagcacggtc cgtcgaacag       180
gcggaagaat ggctcgaaca gattccggtg aaataccgcg gtttcgccta cgaaggcgcg       240
ggaatgggtt acggaatgct ggacgggctg ccgggcggcg gccgccgcca cgtcgaacgg       300
ttcctcgacg gccccggcga gaagcacgac tacatcatct acgtcggcgt cggctgggcg       360
atggcgcgcc tgccgcgctt ccgctggccg tccgccgagg acttcgaccc gttgctgcgc       420
tggctggtgc tcgacggcta cggcttccac caggcctact tcaagacggc gaaatacgtc       480
gacgggcagt tccaggaccc ggacttctcc tggccgcccg ggaacgacgg ctacgcgctg       540
cgggcgatcg accagggcat cgggcgggcg ctgtggttca tctgcggcac cgacgtcgac       600
ctggtcgccg acacggtcgc gcggttcccg gaacggcggc acggagacct gtacgccggt       660
atcgggctcg cctcgaccta cgcgtgcggt gtcaccggtg acgaactgct gaagctggcc       720
gagttcgccg gtgagcaccg cgggaacctc gcccagggca gcgctttcgc cgccgaagcc       780
cgcgtccgcg ccgggctgct gatccccgag accgaggtcg ccacgcgggc gatctgcggg       840
ctgccggccg agcgggccgc ggccatcacc caggaggtgc gccggcgac cgtggtcgac       900 ggcgaactcc cggcattcga aacctggcga cagcgcatcg ccgaagcgat tctttctgga       960
ggtgcaggga aatga                                                        975

<210> SEQ ID NO 49
<211> LENGTH: 654
<212> TYPE: PRT
<213> ORGANISM: Amycolatopsis orientalis

<400> SEQUENCE: 49

Met Thr Ala Thr Leu Gly Trp Leu Arg Lys Gln Leu Ala Gly Ile Val
1               5                   10                  15

Ala Leu Val Leu Met Ala Gly Leu Phe Val Val Ala Gln Leu Pro Thr
            20                  25                  30

Val Ser Thr Ala Glu Ala Asp Thr Met Ala Ser Lys Tyr Ala Phe Glu
        35                  40                  45

Pro Leu Thr Ile Ala Leu Pro Glu Ala Ala Lys Ser Gln Ser Ile Arg
    50                  55                  60

Thr Val Asn Lys Glu Tyr Glu His Ile Arg Ala Trp Ile Ser Ser Val
```

-continued

```
              65                  70                  75                  80
Gly Ala Ala Ile Ala Val Asn Asp Leu Asp Gly Asp Lys Leu Ala Asn
                    85                  90                  95
Asp Leu Cys Phe Val Asp Pro Arg Ser Asp Gln Val Val Ile Thr Pro
                100                 105                 110
Thr Pro Gly Lys Gly Asp Arg Tyr Ala Pro Phe Ala Leu Asp Ala
            115                 120                 125
Ala Pro Leu Pro Met Gly Lys Tyr Ile Ala Pro Met Gly Cys Val Pro
            130                 135                 140
Ala Asp Tyr Asn Glu Asp Gly Arg Val Asp Leu Leu Ala Tyr Tyr Trp
145                 150                 155                 160
Gly Arg Thr Pro Ile Leu Phe Leu Ser Lys Pro Gly Ala Thr Lys Leu
                165                 170                 175
Glu Pro Lys Ala Tyr Glu Pro Val Glu Leu Val Pro Gly Asn Asn Ser
                180                 185                 190
Lys Asn Gly Glu Tyr Ser Gly Pro Leu Trp Asn Thr Asn Ala Ala Ser
            195                 200                 205
Val Gly Asp Phe Asp Gly Asp Gly His Gln Asp Ile Phe Ile Gly Asn
        210                 215                 220
Tyr Phe Pro Asp Ser Ala Val Leu Asp Asp Arg Val Ser Gly Gly Val
225                 230                 235                 240
Glu Met Asn Lys Ser Met Ser His Ala Asp Asn Ala Gly Gly Lys Tyr
                245                 250                 255
Ile Leu Arg Phe Thr Gly Ala Thr Gln Gly Ala Lys Pro Ser Ala Thr
                260                 265                 270
Phe Ala Leu Asp Asp Lys Ala Ile Pro Ala Asp Ser Gln Gly Gly Trp
            275                 280                 285
Ser Leu Ala Ala Ser Ala Thr Asp Val Asp Gly Asp Asn Leu Pro Glu
        290                 295                 300
Leu Tyr Ile Gly Asn Asp Phe Gly His Asp Arg Leu Leu Tyr Asn Lys
305                 310                 315                 320
Ser Arg Pro Gly His Val Glu Phe Ala Glu Val Lys Gly Ile Arg Gly
                325                 330                 335
Pro Asn Glu Pro Lys Ser Lys Val Ile Gly Asn Asp Ser Phe Lys Gly
                340                 345                 350
Met Gly Val Asp Phe Ala Asp Leu Asp His Asp Gly Leu Tyr Asp Leu
            355                 360                 365
Tyr Val Ser Asn Ile Thr Thr Ser Trp Gly Ile Glu Glu Ser His Phe
        370                 375                 380
Gln Phe Met Asn Thr Ala Lys Asp Thr Ala Asp Leu Arg Gly Arg Leu
385                 390                 395                 400
Gln Gly Gly Glu Ala Pro Trp Val Asp Arg Ser Ala Gln Ala Gly Thr
                405                 410                 415
Ala Trp Ser Gly Trp Gly Trp Asp Val Lys Ile Ala Asp Tyr Asp Asn
                420                 425                 430
Ser Gly Glu Ser Val Ile Thr Gln Ala Thr Gly Phe Val Lys Gly Asp
            435                 440                 445
Val Asn Arg Trp Pro Gln Leu Gln Glu Leu Ala Thr Ser Asn Asp Glu
        450                 455                 460
Leu Leu Lys His Pro Tyr Phe Trp Pro Asn Met Val Ala Gly Asp Asp
465                 470                 475                 480
Val Gly Gly Asp His Thr Leu His Phe Trp Ala Lys Ser Ser Asp Gly
                485                 490                 495
```

```
Arg Tyr Thr Asp Leu Ala Pro Arg Leu Gly Leu Ala Val Pro Val Pro
            500                 505                 510

Thr Arg Gly Ile Ala Thr Gly Asp Ala Asp Gly Asp Gly Lys Leu Asp
        515                 520                 525

Phe Ala Val Ala Arg Gln Trp Glu Gln Pro Ile Phe Tyr Arg Asn Val
    530                 535                 540

Ser Pro Gly Thr Gly Ser Tyr Leu Asn Leu Lys Leu Val His Asp Lys
545                 550                 555                 560

Ala Ser Ala Asp Gly Pro Leu Lys Ala Gly Thr Ala Ile Gly
                565                 570                 575

Ala Gln Val Thr Val Thr Pro Asp Gly Lys Lys Tyr Met Asp Arg
        580                 585                 590

Val Asp Gly Gly Ser Gly His Ser Gly Lys Arg Ser His Glu Ile Gln
        595                 600                 605

Ile Gly Leu Gly Lys Val Thr Gly Pro Val Lys Val Cys Leu Gln Trp
    610                 615                 620

Arg Asp Leu Thr Gly Gln Ile Arg Thr Gln Glu Val Gln Leu Thr Pro
625                 630                 635                 640

Gly Asp His Thr Phe Gln Leu Gly Ala Gln Ala Lys Glu Lys
                645                 650

<210> SEQ ID NO 50
<211> LENGTH: 1965
<212> TYPE: DNA
<213> ORGANISM: Amycolatopsis orientalis

<400> SEQUENCE: 50
atgaccgcga ccttgggctg gctccgcaag cagcttgcgg gcatcgtggc gctggtgctg      60
atggcgggac tgttcgtggt ggcgcagctg cccaccgtct cgaccgccga agccgacacc     120
atggcttcga agtacgcgtt cgagccgctg acgatcgcct gccggaagc ggcgaagagc      180 cagtcgatcc ggacggtgaa caaggagtac gagcacatcc gcgcctggat ctcctcggtc     240
ggcgccgcga tcgcggtgaa cgacctcgac ggcgacaagc tcgcgaacga cctgtgcttc     300
gtcgatccgc gcagcgacca ggtcgtcatc accccgacgc cgggcaaggg cggcgaccgc     360
tacgcgccgt tcgcgctcga cgcggcaccg ttgccgatgg gcaagtacat cgcgcccatg     420
ggctgtgtcc ccgcggacta caacgaggac ggccgggtcg acctgctggc ctactactgg     480
ggccgcacgc cgatcctgtt cctctcgaag ccgggcgcca cgaagctgga ccgaaggcc      540 tacgagccgg tggaactggt gccgggcaac aactccaaga cggcgagta ctccggtcca      600 ctgtgaaca ccaacgccgc ctccgtcggt gacttcgacg cgacggcca ccaggacatc      660 ttcatcggca actacttccc cgacagcgcg gtgctggacg accgcgtctc cggcggggtc     720
gagatgaaca agtcgatgtc gcacgccgac aacgccggcg gcaagtacat cctgaggttc     780
accggcgcca cgcagggcgc gaagccgagc gcgacgttcg ccctcgacga caaggccatc     840
ccggccgact cccagggcgg ctggtcgctg gcggccagcg ccaccgacgt cgacggggac     900
aacctgcccg agctctacat cggcaacgac ttcggccacg accgcctgct gtacaacaag     960
tcccgccccg gtcacgtcga attcgccgag gtgaagggca tccgcgggcc caacgagccg    1020
aagtccaagg tgatcggcaa cgactccttc aagggcatgg gcgtcgactt cgccgacctc    1080
gaccacgacg tctctacga cctgtacgtc agcaacatca cgacctcctg ggtatcgag     1140 gaaagccact tccagttcat gaacaccgcc aaggacaccg cggatctgcg tggccgtctg    1200
```

```
cagggcggcg aggcgccgtg ggtggaccgc agcgcgcagg ccggcaccgc ctggtccggc    1260
tggggctggg acgtcaagat cgccgactac gacaacagcg cgaatcggt gatcacccag    1320 gcgaccgggt tcgtcaaggg cgacgtcaac cgctggccgc agctgcagga gctggcgacg    1380
tcgaacgacg aactgctgaa gcacccgtac ttctggccga acatggtcgc cggtgacgac    1440
gtcggtggcg accacacgct gcacttctgg gccaagagct ccgacggccg ctacaccgac    1500
ctggccccgc gcctcggtct cgcggtcccg gtgcccaccc gcggtatcgc caccggtgac    1560
gccgacggcg acggcaagct cgacttcgcc gtggcccgcc agtgggaaca gccgatcttc    1620
taccgcaacg tcagccccgg caccgggtcc tacctgaacc tgaagctggt acacgacaag    1680
gcttcggcgg acggtccgct caaggcggcc ggtaccgcgg cgatcggcgc gcaggtcacc    1740
gtcgtcaccc ccgacggcaa gaagtacatg gaccgcgtcg acggcggcag cggccactcc    1800
ggcaagcgca gccacgagat ccagatcggg ctgggcaagg tcaccgggcc ggtgaaggtc    1860
tgcctgcagt ggcgcgacct gaccgggcag atccgcacgc aggaagtcca gctgaccccg    1920
ggcgaccaca cgttccagct cggcgctcag gctaaggaga aatga                    1965
```

<210> SEQ ID NO 51
<211> LENGTH: 329
<212> TYPE: PRT
<213> ORGANISM: Amycolatopsis orientalis

<400> SEQUENCE: 51

```
Met Thr Val Met Ala Glu Gln Thr Leu Thr Ala Pro Lys Ser Asn Lys
1               5                   10                  15

Thr Ile Thr Ala Leu Arg Arg Phe Ala Ile Ser Ile Thr Ile Phe Asn
            20                  25                  30

Ile Ile Gly Tyr Thr Val Leu Gly Phe Glu Gln Pro Tyr Thr Tyr Pro
        35                  40                  45

Phe Ile Ala Leu Ala Thr Ala Tyr Ala Thr Glu Ile Leu Leu Glu Ile
    50                  55                  60

Ile Gly Ala Arg Ala Gln Gly Arg Gly Val Arg Phe Arg Gly Asn Gly
65                  70                  75                  80

Phe Lys Gly Leu Val Glu Phe Leu Phe Pro Ala His Ile Thr Gly Leu
                85                  90                  95

Ala Leu Asn Met Leu Thr Tyr Val Asn Asp Gln Val Leu Val Met Met
            100                 105                 110

Phe Gly Val Val Ala Val Gly Ala Lys Trp Val Leu Gln Ala Pro
        115                 120                 125

Val Arg Gly Arg Leu Arg His Tyr Met Asn Pro Ser Asn Phe Gly Ile
    130                 135                 140

Thr Ile Ile Leu Leu Val Phe Pro Trp Ala Ser Ile Ala Pro Pro Tyr
145                 150                 155                 160

His Phe Thr Glu Gln Val Asp Ser Trp Val Gly Trp Leu Ile Val Gly
                165                 170                 175

Ile Ile Ile Val Ser Gly Thr Val Leu Asn Ala Met Leu Thr Gln Arg
            180                 185                 190

Met Trp Leu Ile Gly Ala Trp Leu Ile Thr Phe Ala Leu Gln Ala Ile
        195                 200                 205

Ile Arg Gly Leu Val Phe Asp Thr Ala Ile Pro Gly Ala Leu Gly Met
    210                 215                 220

Met Thr Gly Val Ala Phe Val Leu Tyr Thr Asn Tyr Met Val Thr Asp
225                 230                 235                 240
```

```
Pro Gly Thr Thr Pro Ser Lys Pro Ala Ser Gln Ile Leu Phe Gly Ser
            245                 250                 255

Gly Val Ala Leu Ala Tyr Gly Phe Phe Met Val Val His Val Ala Tyr
        260                 265                 270

Gly Leu Phe Leu Ala Thr Ala Leu Val Cys Leu Ile Arg Gly Met Phe
        275                 280                 285

Leu Trp Gly Leu His Phe Ser Lys Lys Ala Thr Glu Lys Trp Glu Ala
290                 295                 300

Glu Gln Ala Lys Ser Ala Glu Ile Thr Ser Leu Pro Lys Pro Ala Glu
305                 310                 315                 320

Lys Pro Glu Thr Gly Ala Val Ala Ala
            325

<210> SEQ ID NO 52
<211> LENGTH: 990
<212> TYPE: DNA
<213> ORGANISM: Amycolatopsis orientalis

<400> SEQUENCE: 52
atgaccgtca tggctgagca gacactcacc gcaccgaaga gcaacaagac gatcacggcg      60
ctgcgccggt tcgcgatctc gatcaccatc ttcaacatca tcggctacac cgtgctcggt     120
ttcgagcagc cctacactta tccgttcatc gcgctggcca cggcgtacgc cacggaaatc     180
ctgctggaga tcatcggggc ccgcgcacag gggcgcggcg tccgcttccg gggcaacggg     240
ttcaagggac tggtggagtt cctcttcccc gcgcatatca ccggtctcgc gctgaacatg     300
ctcacctacg tcaacgacca ggtgctggtc atgatgttcg gcgtcgtggt cgccgtcggc     360
gccaagtggg tcctgcaggc cccggtgcgc ggcaggctcc gccactacat gaacccgtcg     420
aacttcggca tcacgatcat cctgctggtg ttcccctggg cgagcatcgc cccgccgtat     480
cacttcaccg agcaggtcga ctcgtgggtc ggctggctga tcgtcggcat catcatcgtc     540
tccggcaccg tgctcaacgc gatgctgacc cagcgcatgt ggctgatcgg cgcctggctg     600
atcaccttcg cgctccaggc gatcatccgt ggcctggtgt tcgacaccgc gatcccgggc     660
gcgctcggga tgatgaccgg tgtggcgttc gtgctctaca cgaactacat ggtcaccgac     720
ccggggacga ccccgtccaa gcccgcgtcg cagatcctgt tcggctcggg agtggcgctg     780
gcgtacgggt tcttcatggt cgtgcacgtg gcttacggtc tgttcctcgc caccgcgctg     840
gtctgcctca tccgcgggat gttcctgtgg ggcctgcact ctccaagaa ggccaccgag     900 aaatgggagg ccgagcaggc gaagtcggcc gagatcacct ccttgccgaa gccggccgag     960
aagccggaaa ccggggccgt ggcggcatga                                      990

<210> SEQ ID NO 53
<211> LENGTH: 1958
<212> TYPE: PRT
<213> ORGANISM: Kitasatosporia sp.

<400> SEQUENCE: 53

Val Ser Asp Gly Ala Gly Arg Pro Ala Arg Asp Gly Gly Gln Pro Thr
1               5                  10                  15

Gly Arg Gly Arg Ile Ala Val Val Gly Met Ala Cys Arg Tyr Pro Asp
            20                  25                  30

Ala Asp Ser Pro Glu Gln Leu Trp Gln Asn Val Leu Ala Gly Arg Arg
        35                  40                  45

Ala Phe Arg Arg Leu Pro Asp Val Arg Met Arg Ala Glu Asp Tyr Tyr
    50                  55                  60
```

```
Ser Pro Asp Pro Ala Ala Pro Asp Arg Phe Tyr Ser Ala Lys Ala Ala
 65                  70                  75                  80

Val Ile Glu Gly Phe Glu Phe Asp Arg Val Arg His Arg Val Ala Gly
                 85                  90                  95

Ser Thr Phe Arg Ala Thr Asp Met Thr His Trp Leu Ala Leu Asp Thr
            100                 105                 110

Ala Ala Arg Ala Leu Glu Asp Ala Gly Phe Pro Phe Gly Glu Gly Leu
        115                 120                 125

Ala Asp Ala Asn Thr Gly Val Val Ile Gly Asn Thr Leu Thr Gly Glu
    130                 135                 140

Phe Ser Arg Ala Asn Leu Met Arg Leu Arg Trp Pro Tyr Val Arg Arg
145                 150                 155                 160

Thr Val Gly Ala Ala Leu Arg Glu Gln Gly Trp Gly Asp Thr Glu Leu
                165                 170                 175

Gly Ala Phe Leu Asp Gly Leu Glu Gly Arg Tyr Lys Ser Ala Phe Pro
            180                 185                 190

Pro Ile Gly Glu Asp Thr Leu Ala Gly Gly Leu Ala Asn Thr Ile Ala
        195                 200                 205

Gly Arg Ile Cys Asn His Phe Asp Phe Lys Gly Gly Gly Phe Thr Val
    210                 215                 220

Asp Gly Ala Cys Ser Ser Leu Leu Ser Val Ser Thr Ala Cys Asp
225                 230                 235                 240

Ala Leu Leu Gly Gly Arg Met Asp Val Ala Val Ala Gly Gly Val Asp
                245                 250                 255

Leu Ser Ile Asp Pro Phe Glu Val Ile Gly Phe Ala Lys Thr Gly Ala
            260                 265                 270

Leu Ala Thr Ala Glu Met Arg Val Tyr Asp Lys Gly Ser Asn Gly Phe
        275                 280                 285

Trp Pro Gly Glu Gly Cys Gly Met Val Val Leu Met Arg Asp Glu Asp
290                 295                 300

Ala Arg Ala Gln Gly Arg Phe Arg Tyr Ala Thr Ile Pro Gly Trp Gly
305                 310                 315                 320

Tyr Ser Ser Asp Gly Arg Gly Ile Thr Arg Pro Glu Ala Ser Gly
                325                 330                 335

His Arg Leu Ala Leu Thr Arg Ala Tyr Arg Ala Ala Gly Phe Gly Ile
            340                 345                 350

Glu Thr Val Gly Tyr Phe Glu Gly His Gly Thr Gly Thr Ala Val Gly
        355                 360                 365

Asp Ala Thr Glu Leu Arg Ala Phe Ser Glu Ala Arg Arg Ala Ala Gly
    370                 375                 380

Ala Thr Ala Pro Ala Ala Leu Ser Thr Val Lys Gly Asn Phe Gly His
385                 390                 395                 400

Thr Lys Ala Ala Ala Gly Val Ala Gly Leu Leu Lys Ala Ile Leu Ala
                405                 410                 415

Val Arg His Gln Val Ile Pro Pro Ala Thr Ser His Val Asp Pro His
            420                 425                 430

Pro Glu Leu Thr Gly Pro Ala Pro Ala Leu Arg Val Pro Asp Arg Ala
        435                 440                 445

Glu Leu Trp Pro Ala Gly Ala Pro Ile Arg Ala Gly Ile Ser Ser Met
    450                 455                 460

Gly Phe Gly Gly Ile Asn Ala His Val Val Glu His Ala Asp Gly
465                 470                 475                 480
```

-continued

Val Arg Arg Thr Ala Val Pro Ala Val Ala His Arg Leu Val Ala Ser
            485                 490                 495

Arg Gln Asp Ala Glu Leu Leu Leu Asp Gly Ala Asp Pro Ala Glu
        500                 505                 510

Leu His Ala Lys Ala Thr Arg Leu Ala Ala Phe Ala Ala Gln Leu Ser
            515                 520                 525

Tyr Ala Glu Ile Gly Asp Leu Ala Ala Leu Gln Arg Asp Leu Ala
        530                 535                 540

Asp Arg Pro Leu Arg Ala Ala Val Leu Ala Asp Ser Pro Glu Gln Ala
545                 550                 555                 560

Ala Gln Arg Phe Thr Gly Leu Ala Gln Leu Leu Asp Ser Gly Ala Arg
            565                 570                 575

Ser Leu Leu Ser Pro Ala Gln Gly Val Phe Leu Gly Ser Ala Gly Arg
            580                 585                 590

Ala Pro Arg Ile Gly Phe Leu Phe Pro Gly Gln Gly Ala Gly Arg Arg
            595                 600                 605

Gly Asp Gly Gly Ala Leu Arg Arg Phe Thr Ala Val Arg Asp Leu
        610                 615                 620

Tyr Ala His Leu Asp Leu Pro Ala Asp Gly Asp Gln Val Ala Thr Asp
625                 630                 635                 640

Val Ala Gln Pro Arg Ile Val Ala Ala Ser Val Ala Gly Leu Arg Val
            645                 650                 655

Leu Asp Leu Leu Gly Val Gln Ala Asp Leu Ala Thr Gly His Ser Leu
            660                 665                 670

Gly Glu Leu Thr Ala Leu His Trp Ala Gly Ala Met Asp Glu Asp Thr
            675                 680                 685

Val Leu Arg Ala Ala Ala Arg Gly Arg Ile Met Ala Ala Ala Gly
            690                 695                 700

Asp Gly Gly Thr Met Ala Ala Leu Ala Thr Thr Pro Ala Leu Ala
705                 710                 715                 720

Glu Ala Leu Ile Val Gly Glu Pro Val Val Ala Gly Leu Asn Ser
            725                 730                 735

Pro Thr Gln Thr Val Val Ser Gly Pro Val Asp Ala Val Asp Arg Val
            740                 745                 750

Cys Ala Leu Ala Ala Arg Gln Gly Ile Gly Val Gly Arg Val Asn Val
            755                 760                 765

Ser His Ala Phe His Ser Pro Ala Val Ala Pro Ala Ala Gly Leu
770                 775                 780

Ala Glu His Leu Ala Gly Glu Arg Phe Gly Pro Val Gly Pro Gly Leu
785                 790                 795                 800

Val Ser Thr Val Thr Gly Ala Pro Leu Pro Ala Asp Thr Asp Val Val
            805                 810                 815

Asp Leu Leu Thr Arg Gln Val Val Gln Pro Val Arg Phe Thr Asp Ala
            820                 825                 830

Leu Arg Ala Met Asp Gly Gln Val Asp Leu Leu Ile Glu Val Gly Pro
            835                 840                 845

Gly Gln Ile Leu Arg Thr Leu Ala Ala Glu Val Leu Pro Ala Val Pro
            850                 855                 860

Ala Val Ala Thr Glu Ala Asp Ala Leu Ser Leu Ala Gly Leu Leu Ala
865                 870                 875                 880

Thr Val Ala Thr Ala Trp Thr Met Gly Ala Pro Val Arg His Glu Arg
            885                 890                 895

Leu Phe Ala Asp Arg Phe Thr Arg Pro Leu Pro Leu Asp Lys Glu Phe

-continued

```
              900              905              910
Arg Phe Phe Ala Ser Pro Cys Glu Thr Gly Gly Glu Asp Phe Val Leu
        915              920              925
Glu His Ala Gly Ala Thr Pro Ala Thr Ala Ala Ala Pro Arg Pro Ala
        930              935              940
Ala Ala Ala Ala Pro Ala Ala Gly Glu Ala Thr Ser Leu Glu Val Leu
945              950              955              960
Ile Arg Leu Ala Ala Ala Arg Ala Glu Leu Pro Ala Glu Thr Val Asp
                965              970              975
Pro Ala Ala Asn Pro Leu Asp Glu Leu His Leu Ser Ser Ile Thr Val
        980              985              990
Gly Gln Ile Met Asn Gln Ala Ala  Gln Glu Leu Gly Ile  Ser Ala Pro
        995              1000             1005
Met Val  Thr Thr Ala Phe Ala  Thr Ser Thr Leu Ser  Gln Leu Ala
    1010             1015             1020
Asp Leu  Leu Asp Glu Leu Ala  Gln Gln Ser Pro Gln  Asp Thr Arg
    1025             1030             1035
Pro Gly  Ala Ala Ala Gly Val  Ala Pro Trp Val Arg  Pro Phe Arg
    1040             1045             1050
Ile Asp  Leu Thr Glu Thr Pro  Pro Pro Ala Pro Ala  Ala Gly Pro
    1055             1060             1065
Gly Gly  Arg Trp Glu Val Phe  Ala Thr Asp Arg His  Pro Leu Ala
    1070             1075             1080
Gly Pro  Leu Ala Glu Arg Leu  Thr Ala Thr Ala Pro  Gly Gly Gly
    1085             1090             1095
Val Leu  Leu Ala Leu Pro Arg  Asp Cys Asp Gln Arg  His Leu Gly
    1100             1105             1110
Leu Met  Leu Ala Ala Ala Arg  Ala Ala Leu Asp Pro  Ala Arg Arg
    1115             1120             1125
Ala Ala  Gly Thr Arg Leu Val  Ala Val Gly Asp His  Arg Gly Ala
    1130             1135             1140
Ala Gly  Leu Ala Lys Thr Leu  His Leu Glu Ala Pro  Asp Ile Pro
    1145             1150             1155
Val Thr  Val Val Thr Leu Pro  Leu Asp Gln Glu Leu  Pro Ala Pro
    1160             1165             1170
Ala Ala  Glu Gln Ala Ala Ala  Arg Ile Ala Ala Asp  Thr Ala Ala
    1175             1180             1185
Thr Thr  Gly Phe Ser Glu Val  His Tyr Asp Ala Asp  Gly Thr Arg
    1190             1195             1200
Arg Val  Pro Val Leu Arg Pro  Val Pro Leu Glu Pro  Asp Pro Gly
    1205             1210             1215
Arg Gln  Ala Leu Gly Pro Arg  Asp Val Leu Leu Val  Thr Gly Gly
    1220             1225             1230
Gly Lys  Gly Ile Thr Ala Glu  Cys Ala Leu Ala Leu  Ala Gly Gly
    1235             1240             1245
Asn Gly  Ala Ala Ile Gly Leu  Ile Gly Arg Ser Asp  Pro Ala Arg
    1250             1255             1260
Asp Thr  Glu Leu Ala Asp Asn  Leu Ala Arg Met Ala  Ala Ala Gly
    1265             1270             1275
Met Arg  Val His Tyr Ala Arg  Ala Asp Val Thr Ser  Ala Asp Gln
    1280             1285             1290
Val Lys  Ala Ala Val Thr Glu  Ile Thr Arg Glu Leu  Gly Pro Val
    1295             1300             1305
```

-continued

```
Thr Gly Leu Leu His Gly Ala Gly Arg Asn Glu Pro Gln Ser Leu
    1310            1315                1320
Ala Thr Leu Asp Glu Asp Ser Phe Arg Arg Thr Leu Ala Thr Lys
    1325            1330                1335
Ile Asp Gly Val Glu Ala Val Leu Ala Ala Val Asp Thr Ala Ala
    1340            1345                1350
Leu Arg Leu Phe Val Thr Phe Gly Ser Ile Ile Gly Arg Ala Gly
    1355            1360                1365
Leu Arg Gly Glu Ala Asp Tyr Ala Thr Ala Asn Asp Trp Leu Thr
    1370            1375                1380
Asp Leu Thr Val Arg Phe Gln Gln Asp His Pro His Cys Arg Cys
    1385            1390                1395
Leu Ala Leu Glu Trp Ser Val Trp Ser Gly Ser Gly Met Gly Glu
    1400            1405                1410
Arg Leu Gly Val Leu Glu Ala Leu Val Arg Glu Gly Ile Glu Pro
    1415            1420                1425
Ile Pro Thr Glu Asp Gly Val Ala Leu Leu Gly Arg Leu Leu Ala
    1430            1435                1440
Thr Pro Gly Thr Asp Thr Ala Leu Val Val Met Gly Arg Ala Gly
    1445            1450                1455
Gly Leu Pro Thr Leu Thr Leu Glu Gln Arg Glu Leu Pro Leu Leu
    1460            1465                1470
Arg Phe Leu Glu Arg Pro Gln Val His Tyr Pro Gly Ile Glu Leu
    1475            1480                1485
Val Ala Asp Ala Glu Leu Thr Gly Gly Gly Asp Arg Tyr Leu Pro
    1490            1495                1500
Asp His Leu Leu Asp Gly Asp Leu Leu Phe Pro Ala Val Leu Gly
    1505            1510                1515
Met Glu Ala Met Thr Gln Ala Ala Thr Ala Leu Thr Gly Arg Arg
    1520            1525                1530
Asp Thr Pro Val Leu Glu Gly Met Glu Phe Leu Arg Pro Ile Val
    1535            1540                1545
Val Pro Val Thr Gly Ala Thr Thr Leu Arg Thr Ala Val Leu Ala
    1550            1555                1560
Thr Gly Pro Asp Thr Val Gln Ala Val Leu Arg Ser Gly Glu Thr
    1565            1570                1575
Gly Phe Gln Ala Asp His Phe Arg Ala Thr Leu Arg Tyr Gly Ala
    1580            1585                1590
Ala Arg Pro Glu Asp Glu Pro Ala Pro Val Thr Asp Glu Val Pro
    1595            1600                1605
Arg Val Pro Leu Thr Pro Ala Gln Leu Tyr Gly Pro Val Leu Phe
    1610            1615                1620
Gln Gly Asp Arg Phe Arg Arg Leu Leu Ala Tyr Arg Asp Leu Ala
    1625            1630                1635
Ala Thr His Cys Leu Ala Glu Ile Asp Asp Thr Pro Arg Thr Asp
    1640            1645                1650
Trp Phe Ala Gly Tyr His Pro Gly Glu Leu Leu Leu Ala Asp Pro
    1655            1660                1665
Gly Thr Arg Asp Ala Leu Met His Ser Ile Gln Ala Cys Val Pro
    1670            1675                1680
Asp Ala Thr Leu Leu Pro Val Ser Val Glu Arg Leu His Leu Ala
    1685            1690                1695
```

-continued

| | | | | | | | | | |
|---|---|---|---|---|---|---|---|---|---|
| Glu | Ala | Ala | Ala | Arg | Thr | Gly | Arg | Leu | Leu | Phe | Leu | Asp | Ala |
| | 1700 | | | | 1705 | | | | 1710 | | | | |
| Arg | Glu | Arg | Ser | Arg | Asp | Gly | Asp | Ser | Tyr | Leu | Tyr | Asp | Leu | Asp |
| | 1715 | | | | 1720 | | | | 1725 | | | | |
| Val | Arg | Asp | Ala | Ala | Gly | Ser | Pro | Val | Glu | Gln | Trp | Glu | Gly | Leu |
| | 1730 | | | | 1735 | | | | 1740 | | | | |
| Leu | Leu | Arg | Ala | Val | Arg | Lys | Gln | Asp | Gly | Ser | Gly | Pro | Trp | Leu |
| | 1745 | | | | 1750 | | | | 1755 | | | | |
| Pro | Ala | Leu | Leu | Gly | Pro | Phe | Leu | Glu | Arg | Arg | Val | Glu | Ala | Ala |
| | 1760 | | | | 1765 | | | | 1770 | | | | |
| Leu | Gly | His | Arg | Val | Arg | Cys | Val | Val | Leu | Pro | Gly | Gly | Glu | Asp |
| | 1775 | | | | 1780 | | | | 1785 | | | | |
| Ala | Asp | Gly | Ser | Val | Ala | Asp | Arg | Arg | Arg | Arg | Thr | Ala | Glu | Ala |
| | 1790 | | | | 1795 | | | | 1800 | | | | |
| Ala | Ser | Trp | Ala | Leu | Gly | Arg | Thr | Thr | Glu | Val | His | His | Arg | Pro |
| | 1805 | | | | 1810 | | | | 1815 | | | | |
| Asp | Gly | Arg | Pro | Glu | Leu | Ala | Asp | Gly | Arg | Arg | Ile | Ser | Ser | Ser |
| | 1820 | | | | 1825 | | | | 1830 | | | | |
| His | Ala | Ala | Gly | Val | Thr | Phe | Thr | Val | Val | Ala | Asp | Ala | Gly | Arg |
| | 1835 | | | | 1840 | | | | 1845 | | | | |
| Pro | Leu | Ala | Cys | Asp | Val | Glu | Gln | Val | Ala | Glu | Arg | Thr | Ala | Glu |
| | 1850 | | | | 1855 | | | | 1860 | | | | |
| Gln | Trp | Ala | Gly | Leu | Leu | Gly | Pro | Asp | Ala | Glu | Arg | Leu | Ala | His |
| | 1865 | | | | 1870 | | | | 1875 | | | | |
| Leu | Leu | Ala | Ala | Glu | Arg | Gly | Glu | Pro | Leu | Ser | Thr | Ala | Ala | Thr |
| | 1880 | | | | 1885 | | | | 1890 | | | | |
| Arg | Val | Trp | Gly | Ala | Val | Glu | Thr | Leu | Arg | Lys | Ala | Gly | His | Ala |
| | 1895 | | | | 1900 | | | | 1905 | | | | |
| Val | Ala | Ala | Leu | Ser | Leu | Ala | Asp | Gly | Ser | Gly | Leu | Pro | Pro | Gly |
| | 1910 | | | | 1915 | | | | 1920 | | | | |
| Trp | Val | Ala | Leu | Arg | Gly | Gly | Ala | His | Arg | Ile | Val | Ser | Phe | Val |
| | 1925 | | | | 1930 | | | | 1935 | | | | |
| Thr | Ala | Leu | Asp | Gly | Ala | Ala | Asp | Pro | Val | Ala | Phe | Thr | Val | Leu |
| | 1940 | | | | 1945 | | | | 1950 | | | | |
| Thr | Gly | Gly | Ala | Arg | | | | | | | | | | |
| | 1955 | | | | | | | | | | | | | |

<210> SEQ ID NO 54
<211> LENGTH: 5877
<212> TYPE: DNA
<213> ORGANISM: Kitasatosporia sp.

<400> SEQUENCE: 54

```
gtgagcgacg gcgcaggacg accggcccgg gacggcgggc agccgaccgg ccggggacgg      60
atcgcggtgg tcggcatggc ctgccgctac cccgacgcgg acagccccga acagctctgg     120
cagaacgtgc tcgccggccg ccgggccttc cgccggctgc ccgacgtgcg gatgcgcgcc     180
gaggactact actcgcccga ccccgccgcg cccgaccgct tctacagcgc caaggccgcc     240
gtcatcgagg gcttcgagtt cgaccgggtc cgccaccgcg tcgcgggcag caccttccgc     300
gccaccgaca tgacccactg gctcgccctg gacaccgccg cccgcgccct ggaggacgcc     360
ggcttcccgt tcggcgaggg cctggccgac gccaacaccg gcgtcgtcat cggcaacacc     420
ctcaccggcg agttcagccg cgccaacctg atgcgcctgc gctggcccta cgtgcgccgc     480
accgtcggcg ccgcgctgcg cgaacagggc tggggcgaca ccgagttggg cgccttcctg     540
```

```
gacggcctgg agggccgcta caagagcgcc ttcccgccga tcggcgagga caccctggcc    600
ggcggcctgg ccaacaccat cgccggccgg atctgcaacc acttcgactt caagggcggc    660
ggcttcaccg tcgacggcgc ctgctcctcc tcgctgctgt ccgtctccac cgcctgcgac    720
gccctgctcg gcggccggat ggacgtcgcc gtggccggcg gcgtcgacct cagcatcgac    780
ccgttcgagg tgatcggctt cgccaagacc ggcgcgctcg ccaccgccga gatgcgggtc    840
tacgacaagg gctccaacgg cttctggccc ggcgagggct gcggcatggt cgtcctgatg    900
cgcgacgagg acgcccgcgc ccagggccgg ttccgctacg ccaccatccc cggctggggc    960
tactcctccg acggccgggg cggcatcacc cgccccgagg ccagcggcca ccggctcgcc   1020
ctgacccgcg cctaccgggc ggccggcttc ggcatcgaga cggtcggcta cttcgagggc   1080
cacggcaccg gcaccgccgt cggcgacgcc accgaactgc gcgccttctc cgaggcccgc   1140
cggggccgccg gcgccaccgc gcccgccgcg ctcagcaccg tcaagggcaa cttcgggcac   1200
accaaggccg ccgccggcgt cgccggactg ctcaaggcga tcctggccgt ccgccaccag   1260
gtcatcccgc cgccaccagc cacgtcgac ccgcaccccg aactcaccgg ccccgcaccg    1320
gcgctgcgcg tccccgaccg ggccgaactg tggcccgcgg gcgcgccgat ccgggccggg   1380
atctcctcga tgggcttcgg cggcatcaac gcgcacgtcg tcgtcgaaca cgccgacggc   1440
gtccggcgca ccgccgtgcc cgccgtcgcc caccggctgg tcgcctcccg gcaggacgcc   1500
gaactgctcc tgctggacgg cgccgacccg gccgaactgc acgccaaggc gaccggctg    1560
gccgcgttcg ccgcccagct gtcgtacgcc gaaatcggcg acctgccgcc cgccctgcaa   1620
cgcgacctgg ccgaccggcc gctgcgcgcc gccgtactgg ccgactcgcc cgaacaggcc   1680
gcccagcggt tcaccggact ggcccagctg ctcgactccg ggcccgctc gctgctcagc    1740
ccgcccagg gcgtcttcct cggcagcgcc ggccgcgccc ccggatcgg cttcctcttc    1800
ccggccagg gcgccggccg gcgcggcgac ggcggagcac tgcgccgccg cttcaccgcc    1860
gtccgcgacc tgtacgcgca cctggacctg cccgccgacg gcgaccaggt cgccaccgac   1920
gtcgcccagc cccggatcgt cgccgcctcg gtggccggcc tgcgggtgct ggacctactg   1980
ggcgtccagg ccgacctcgc caccggccac agcctcggcg aactcaccgc cctgcactgg   2040
gcgggcgcca tggacgagga caccgtgctg cgcgccgccg ccgcccgcgg ccggatcatg   2100
gccgccgccg gcgacggcgg cggcaccatg gccgccctgg ccaccacccc cgccctcgcc   2160
gaggcgctga tcgtcggcga accggtcgtc gtcgcgggcc tcaacagccc cacccagacc   2220
gtcgtctccg gacccgtcga cgccgtggac cgggtctgcg cgctggccgc ccggcagggc   2280
atcggcgtcg gccgggtcaa cgtctcgcac gccttccact ccccgccgt cgccccggcc   2340
gccgccggac tcgccgaaca cctcgccggg gagcgcttcg gccggtcgg ccccggcctg    2400
gtctccaccg tcaccggcgc gccgctgccc gccgacaccg acgtggtgga cctgctcacc   2460
cgccaggtcg tccagccggt gcgcttcacc gacgcgctgc gcgccatgga cgggcaggtc   2520
gacctgctga tcgaggtcgg ccccggccag atcctgcgga cgctggccgc cgaggtgctg   2580
cccgccgtgc ccgcggtcgc caccgaggcc gacgcgctct cgctggccgg gctgctcgcc   2640
accgtcgcca ccgcctggac gatgggcgcg ccggtccgcc acgagcggct gttcgccgac   2700
cggttcaccc ggccgctgcc gctcgacaag gagttccggt tcttcgccag cccctgcgag   2760
acgggcggcg aggacttcgt cctggagcac gccggagcga ccccgccac cgccgccgcg    2820
ccccggccgg ccgccgccgc ggcgcccgcc gccggagagg ccaccagcct ggaggtgctg   2880
```

```
atccggctcg ccgccgcgcg ggccgaactg cccgccgaga cggtcgaccc ggccgccaat   2940
ccgctcgacg aactgcacct cagctccatc accgtcggcc agatcatgaa ccaggccgcc   3000
caggaactgg gcatctccgc ccccatggtc accaccgcgt tcgccacctc cacgctcagc   3060
caactcgcca acctgctgga cgagttggcc cagcagtcac cgcaggacac ccgcccnggc   3120
gccgccgccg gcgtcgcccc ctgggtgcgg cccttccgga tcgacctcac cgagaccccg   3180
ccgcccgccc ccgccgccgg acccggcggc cgctgggagg tcttcgccac cgaccggcac   3240
ccgctggccg gaccgctcgc cgagcggctc accgccaccg cccccggcgg cggcgtcctg   3300
ctcgccctgc cccgcgactg cgaccagcgc cacctcggcc tgatgctcgc cgccgcccgc   3360
gccgccctcg acccggcccg ccgcgcggcc ggcacccggc tcgtcgccgt cggcgaccac   3420
cgcggcgccg ccgcctcgc caagacgctc cacctggagg ccccgacat cccggtcacc    3480
gtcgtcaccc tgcccctcga ccaggaactg cccgcccgg ccgccgagca ggccgccgcc   3540
cggatcgccc ccgacaccgc cgccaccacc ggcttcagcg aggtccacta cgacgccgac   3600
ggcacccgcc gggtccccgt gctgcgcccc gtcccgctcg aacccgaccc cggacggcag   3660
gccctcggcc cgcgggacgt cctgctggtc accggcggcg gcaagggcat caccgccgag   3720
tgcgccctcg ccctggccgg cggcaacggc gccgcgatcg gcctgatcgg ccgctccgac   3780
cccgcccggg acaccgaact cgccgacaac ctcgcccgga tggcggccgc cggcatgcgg   3840
gtacactacg cccgcgccga cgtcacctcc gccgaccagg tcaaggccgc cgtcaccgag   3900
atcacccgcg aactcggccc cgtcaccggc ctgctgcacg cgccggccg caacgaaccg   3960
cagtcgctgg ccaccctcga cgaggactcc ttccggcgca ccctcgccac caagatcgac   4020
ggcgtggagg ccgtcctggc cgccgtcgac accgccgcgc tgcgcctgtt cgtcaccttc   4080
ggcagcatca tcggccgggc cggcctgcgc ggcgaggccg actacgccac cgccaacgac   4140
tggctcaccg acctcaccgt ccgcttccag caggaccacc gcactgccg ctgcctggcc    4200
ctggagtggt cggtctggtc cggctccggc atgggcgagc ggctcggcgt cctggaggcg   4260
ctggtccgcg agggcatcga accgatcccc accgaggacg cgtcgccct gctcggccgg   4320
ctgctcgcca ccccggcac cgacaccgcc ctggtggtga tgggccgcgc cggcggcctg   4380
cccaccctca ccctcgaaca gcgcgaactg ccgctgctgc gcttcctgga gcgcccgcag   4440
gtccactacc ccggcatcga actggtggcg gacgccgaac tcaccggcgg cggcgaccgc   4500
tacctgcccg accacctgct cgacggcgac ctgctcttcc ccgccgtcct cggcatggag   4560
gccatgaccc aaggccgccac cgcgctgacc ggccgccggg acacccccggt gctggagggc   4620
atggagttcc tgcgcccat cgtcgtcccc gtcaccggcg ccaccaccct gcgcaccgcc   4680
gtcctcgcca ccgcccccga caccgtccag gcggtgctgc gcagcggcga accggcttc    4740
caggccgacc acttccgggc caccctgcgc tacggcgccg cccggcccga ggacgagccc   4800
gccccgtca ccgacgaggt gccccgggtg ccgttgacgc ccgcccagct gtacgggccg    4860
gtgctgttcc agggcgaccg cttccggcgg ctgctcgcct accgcgacct cgccgccacg   4920
cactgcctgg ccgagatcga cgacacccc gcaccgact ggttcgccgg ctaccacccc    4980
ggcgaactgc tgctcgccga ccccggcacc cgcgacgcgc tgatgcactc catccaggcg   5040
tgcgtccccg acgccaccct gctgccggtc agcgtcgaac gcctgcacct ggccgaggcc   5100
gccgccgccc gcaccggacg gctgctgttc ctcgacgccc gcgagcgctc ccgcgacggc   5160
gacagctacc tgtacgacct ggacgtccgc gacgcggcgg gctccccggt cgagcagtgg   5220
gagggcctgc tgctgcgggc cgtccgcaag caggacggct ccggcccgtg gctgcccgcg   5280
```

```
ctgctcggcc ccttcctgga acggcgggtc gaggcggcgc tcggccaccg cgtgcgctgc    5340
gtggtcctgc ccggcggcga ggacgccgac ggctccgtcg ccgaccggcg ccggcgcacc    5400
gccgaggccg ccagctgggc cctgggccgg accaccgagg tgcaccaccg ccccgacgga    5460
cgacccgaac tcgccgacgg gcggcggatc tcctcctcgc acgcggcggg cgtcaccttc    5520
accgtcgtcg ccgacgccgg ccggccgctg gcctgcgacg tcgaacaggt cgccgaacgg    5580
accgccgaac agtgggcggg cctgctcggc cccgacgccg aacggctggc ccacctgctg    5640
gccgccgagc gcggcgagcc gctgagcacc gccgcgaccc gggtctgggg cgcggtggag    5700
accctgcgca aggccggcca cgcggtggcc gcgctcagcc tcgcggacgg ctccggcctg    5760
ccgcccggct gggtggccct ccggggcggc gcgcaccgga tcgtgagctt cgtgacggcc    5820
ctggacggcg ccgccgaccc ggtggccttc accgtcctga cgggaggcgc ccggtga      5877
```

<210> SEQ ID NO 55
<211> LENGTH: 158
<212> TYPE: PRT
<213> ORGANISM: Kitasatosporia sp.

<400> SEQUENCE: 55

```
Val Thr Gly Pro Asp Tyr Tyr Glu Tyr Arg His Leu Val Gly Phe Glu
1               5                   10                  15

Glu Thr Asn Leu Val Gly Asn Val Tyr Tyr Val Asn Tyr Leu Arg Trp
            20                  25                  30

Gln Gly Arg Cys Arg Glu Met Phe Leu Leu Glu Lys Ala Pro Glu Val
        35                  40                  45

Leu Ala Asp Ile Arg Ala Asp Leu Lys Leu Phe Thr Leu Lys Val Asp
    50                  55                  60

Cys Glu Phe Phe Ala Glu Ile Thr Ala Phe Asp Glu Leu Ser Ile Arg
65                  70                  75                  80

Met Arg Leu Ala Asp Leu Thr Gln Thr Gln Val Ala Phe Thr Phe Asp
                85                  90                  95

Tyr Val Lys Leu Gly Pro Asp Gly Thr Glu Tyr Leu Val Ala Arg Gly
            100                 105                 110

Gln Gln Arg Val Ala Cys Met Arg Gly Pro Asn Thr Asp Thr Arg Pro
        115                 120                 125

Thr Arg Val Pro Glu Pro Leu Arg Leu Ala Leu Glu Pro Tyr Ala Val
    130                 135                 140

Pro Ala Thr Ala Pro Ser Leu Thr Gly Thr Thr Thr Val Gly
145                 150                 155
```

<210> SEQ ID NO 56
<211> LENGTH: 477
<212> TYPE: DNA
<213> ORGANISM: Kitasatosporia sp.

<400> SEQUENCE: 56

```
gtgaccgggc ccgactacta cgagtaccgc cacctggtgg gcttcgagga gaccaacctg      60
gtcggcaacg tctactacgt caactacctg cgctggcagg gacgttgccg ggagatgttc     120
ctgctggaga aggcccccga ggtgctcgcc gacatccgcg ccgacctcaa gctgttcacc     180
ctcaaggtgg actgcgagtt cttcgccgag atcaccgcct tcgacgagct gtccatccgg     240
atgcgcctcg ccgacctcac ccagacccag gtcgccttca ccttcgacta cgtcaagctc     300
ggccccgacg gcaccgagta cctggtcgcc cgcgggcagc agcgggtcgc ctgcatgcgc     360
```

-continued

```
ggccccaaca ccgacacccg cccgacccgg gtgcccgaac cgctgcggct cgccctggag    420
ccctacgccg tccccgcgac ggcaccctcc ctgaccggca ccaccaccgt ggggtga       477
```

<210> SEQ ID NO 57
<211> LENGTH: 327
<212> TYPE: PRT
<213> ORGANISM: Kitasatosporia sp.

<400> SEQUENCE: 57

```
Met Ser Gly Gly Trp Arg Ala Val Arg Arg Leu Leu Thr Pro Ser
1               5                   10                  15

His Asn Glu Thr Lys Leu Ser Thr Arg Gly Phe His Leu Lys Asp Asp
                20                  25                  30

Ala Ala Arg Thr Asn Leu Glu Thr Val Gly Gly Thr Phe Leu Asp Gly
            35                  40                  45

Tyr Ala Ile Ala Val Glu Ala Arg Asp Gln Asp Glu Ala His Glu Arg
        50                  55                  60

Leu Glu Arg Ile Pro Val Arg Tyr Arg Gly Phe Ala Tyr Glu Gly Ala
65                  70                  75                  80

Ala Met Gly Leu Ala Met Leu Asp Gly Leu Pro Leu Pro Gly Asn Asp
                85                  90                  95

Arg Val Ala Arg Phe Leu Ala Gly His Gly Ala Pro His Asp Tyr Met
            100                 105                 110

Val His Val Gly Val Gly Trp Ala Met Ala Arg Leu Pro Arg Phe Arg
        115                 120                 125

Trp Ala Ser Ile Ala Pro Pro Asp Pro Leu Leu Arg Trp Leu Ala Leu
    130                 135                 140

Asp Gly Tyr Gly Phe His Gln Ala Tyr Phe Arg Thr Ala Arg Tyr Val
145                 150                 155                 160

His Gln His His Arg Glu Ser Asp Phe Pro Trp Pro Gly Asp Gly Thr
                165                 170                 175

Gly Arg Tyr Ala Gly His Ala Ile Asp Gln Gly Val Gly Arg Ala Leu
            180                 185                 190

Trp Phe Ile Gly Gly Thr Asp Pro Ala Val Val Ala Asp Leu Val Asp
        195                 200                 205

Gly Tyr Gln Ala Asp Arg His Ala Asp Leu Trp Ala Gly Val Gly Leu
    210                 215                 220

Ala Ala Cys Tyr Ala Ala Gly Ala Thr Asp Ala Glu Leu Arg Leu Leu
225                 230                 235                 240

Leu Asp Arg Ala Gly Pro His Arg Pro Gln Leu Ala Gln Gly Ala Ala
                245                 250                 255

Phe Ala Ala Thr Ala Arg Ile Glu Ala Gly Leu Leu Thr Glu His Ala
            260                 265                 270

Glu Ala Ala Thr Ala Val Leu Cys Gly Leu Thr Pro Gln Gln Ala Ala
        275                 280                 285

Gly Val Cys Thr Arg Ala Arg Pro Arg Pro Ala Val Asp Gly Pro Val
    290                 295                 300

Pro Ala Tyr Glu Val Trp Arg Gln Glu Ile Ala Asp Arg Ile Thr Asp
305                 310                 315                 320

Leu Ala Ala Gly Ala His Arg
                325
```

<210> SEQ ID NO 58
<211> LENGTH: 984
<212> TYPE: DNA

<213> ORGANISM: Kitasatosporia sp.

<400> SEQUENCE: 58

```
atgagcggag gctggcgggc ggtccgacga cgcctgttga caccgagtca caacgagacg      60
aagttgtcca ccagggtttt ccacctcaag gacgacgcgg cgcggaccaa cctggagacc     120
gtcggcggga ccttcctcga cggttacgcg atcgccgtcg aggcgcgcga ccaggacgag     180
gcgcacgagc ggctggagcg gataccggtg cgctaccggg gcttcgccta cgaggcgcg      240
gcgatgggcc tggccatgct ggacggcctg ccgctgcccg caacgaccg gtcgcccgg       300
ttcctggccg gccacggcgc gccgcacgac tacatggtgc acgtcggggt cggctgggcg     360
atggcccggc tgccccgctt ccgctgggcc tcgatcgcgc cgcccgaccc gctgctgcgc     420
tggctcgccc tggacgggta cggcttccac caggcgtact ccgcaccgc gcggtacgtg      480
caccagcacc accgggagag cgacttcccg tggcccggcg acgggaccgg cgctacgcg      540
gggcacgcca tcgaccaggg cgtcggccgg gccctgtggt tcatcggcgg caccgacccg     600
gccgtggtcg ccgacctggt cgacggctac caggccgacc ggcacgccga cctgtgggcc    660
ggggtcgggc tggccgcctg ctacgcggcc ggggccaccg acgccgaact gcgcctgctg    720
ctcgaccggg ccggcccgca ccggccccaa ctcgcccagg gcgcggcctt cgccgccacc    780
gcccggatcg aggccggcct gctcaccgaa cacgccgaag ccgccaccgc ggtgctctgc    840
gggctcaccc cgcagcaggc cgccggggtg tgcacccggg cccggccgcg cccggcggtc    900
gacgccccgg tccccgcgta cgaggtgtgg cggcaggaga tcgccgaccg gatcaccgac    960
ctggccgccg gagcccaccg gtga                                            984
```

<210> SEQ ID NO 59
<211> LENGTH: 676
<212> TYPE: PRT
<213> ORGANISM: Kitasatosporia sp.

<400> SEQUENCE: 59

```
Met Ser Pro Arg Arg Phe Arg Arg Leu Val Pro Gly Leu Val Thr
1               5                   10                  15

Val Leu Val Ala Ala Ser Met Phe Phe Val Ile Arg Ser Ser Val Ala
                20                  25                  30

Val Ala Gly Gly Asp Asp Ala Ala Ala Tyr Arg Phe Lys Glu Leu
            35                  40                  45

Pro Ile Ala Met Pro Pro Gly Tyr Glu Ser Arg Pro Met Asn Thr Ile
    50                  55                  60

Arg Lys Val Asn Pro Ala Tyr Glu Lys Ile Arg Ala Trp Ile Ser Ser
65                  70                  75                  80

Val Gly Ala Ser Ile Ala Ile Asn Asp Val Thr Gly His Gly Leu Ala
                85                  90                  95

Asp Gly Met Cys Ile Val Asp Thr Arg Thr Asp Ser Val Val Thr
                100                 105                 110

Trp Thr Pro Thr Ala Pro Glu Ala Asp Arg Phe Thr Pro Phe Val Leu
            115                 120                 125

Asp Gly Arg Pro Leu Pro Met Asp Asp Thr Met Ala Pro Thr Gly Cys
    130                 135                 140

Thr Pro Gly Asp Phe Asn Gly Asp Gly Arg Asn Asp Phe Leu Val Thr
145                 150                 155                 160

Tyr Trp Gly Arg Thr Pro Val Leu Phe Met Ala Arg Ala Asp Ala Ala
                165                 170                 175
```

-continued

```
Ala Pro Ala Ala Glu Ser Tyr Val Pro Arg Glu Leu Val Ala Ser Glu
            180                 185                 190

Ser Leu Asp Gly Arg Tyr His Gly Pro Arg Trp Asn Thr Asp Ala Ala
            195                 200             205

Tyr Val Gly Asp Leu Asp Gly Ser Gly His Pro Ser Ile Ile Ile Gly
            210                 215                 220

Asn Tyr Phe Pro Asp Ser Asp Val Leu Asp Pro Gln Gly Ile Arg Asn
225                 230                 235                 240

Val Gln Met Asn Asp Ser Leu Ser Ser Ala Lys Asn Ala Gly Gly Asp
                245                 250                 255

His Val Leu Arg Phe His Ser Ser Thr Ala Gly Ala Ala Pro Asp Ala
            260                 265                 270

Arg Phe Val Glu Glu Lys Asp Ala Ile Ala Phe Asp Ala Ser Thr Gly
            275                 280                 285

Trp Thr Leu Ala Ile Ala Gly Ala Asp Leu Thr Gly Asp Ala Leu Pro
            290                 295                 300

Glu Val Tyr Ile Ala Asn Asp Phe Gly His Ala His Leu Leu His Asn
305                 310                 315                 320

Val Ser Thr Pro Gly Arg Ile Arg Phe Glu Glu Ala Thr Gly Glu Arg
                325                 330                 335

Thr Pro Thr Thr Pro Lys Ser Phe Val Leu Gly Lys Gly Ser Phe Lys
            340                 345                 350

Gly Met Gly Val Asp Phe Gly Asp Val Asp Gly Asn Gly Ser Phe Asp
            355                 360                 365

Met Met Val Ser Asn Ile Thr Val Ala Trp Gly Leu Glu Glu Ser Asn
            370                 375             380

Phe Leu Trp Ile Asn Gln Ala Lys Asp Pro Ala Glu Met Lys Arg Lys
385                 390                 395                 400

Leu Thr Asp Arg Ile Ala Pro Phe Thr Gln Glu Ala Ala Asp His Gly
                405                 410                 415

Val Ala Trp Thr Gly Trp Gly Trp Asp Ala Lys Met Gly Asp Phe Arg
            420                 425                 430

Asn Ser Gly Gln Gln Asp Ile Leu Gln Ala Asp Gly Phe Val Lys Gly
            435                 440                 445

Asn Ile Asp Arg Trp Pro Trp Leu Gln Glu Met Ala Met Thr Asn Asp
450                 455                 460

Asp Leu Leu Ser Asn Pro Lys Leu Trp Pro Asn Val Gly Pro Gly Asp
465                 470                 475                 480

Asp Leu Ala Gly Asp Glu Thr Met Ala Phe Tyr Ala Arg Thr Asp Ser
                485                 490                 495

Gly Lys Phe Ala Asn Ile Ser Lys Gln Leu Gly Leu Asp Val Pro Ile
            500                 505                 510

Pro Thr Arg Gly Ile Ala Thr Ala Asp Thr Thr Gly Thr Gly Ala Leu
            515                 520                 525

Asp Phe Ala Ile Ala Arg Gln Trp Gly Pro Pro Ala Phe Tyr Ala Asn
            530                 535                 540

Gln Ser Ala Asn Leu Gly His Asp Leu Thr Leu Arg Leu Tyr Arg Pro
545                 550                 555                 560

Ala Thr Asp Thr Ala Thr Thr Gly Thr Thr Gly Ala Gly Ala Thr Ala
                565                 570                 575

Ala Thr Asp Ala Thr Ala Gly Pro Gly Leu Ala Thr Thr Gly Thr Pro
            580                 585                 590

Ala Tyr Gly Ala Thr Val Cys Val Thr Thr Pro Asp Gly Arg Lys Gln
```

```
              595                 600                 605
Ile Gly Gln Leu Asp Gly Gly Gly His Gly Phe Arg Ser Phe
    610                 615                 620

Asp Val Arg Phe Gly Leu Gly Thr Gln Ser Gly Pro Val Thr Val Asp
625                 630                 635                 640

Leu Ala Trp Arg Asp Asn Ala Gly Gly Leu His Thr Glu Thr Arg Gln
                645                 650                 655

Leu Ser Ala Gly Ser His Thr Leu Met Leu Thr Asp Asp Ile Gln Glu
                660                 665                 670

Val Ala Ala Arg
        675

<210> SEQ ID NO 60
<211> LENGTH: 2031
<212> TYPE: DNA
<213> ORGANISM: Kitasatosporia sp.

<400> SEQUENCE: 60
atgtcgccac gacgacgatt ccgcagactc gtacccgggt tggtcaccgt actggtggcc      60
gcctcgatgt tcttcgtcat ccggtcctcg gtggcggtcg ccggtggtga tgacgcggca     120
gcggcctaca ggttcaagga actcccgatc gcgatgccgc cgggctacga gtcgcggccg     180
atgaacacca tccgcaaggt caatccggcg tacgagaaga tccgggcctg gatctcctcg     240
gtcggcgcca gcatcgccat caacgacgtc accggccacg gcctggccga cggcatgtgc     300
atcgtcgaca cccgcaccga ctccgtcgtg gtcacctgga ccccgaccgc ccccgaggcc     360
gaccggttca ccccgttcgt gctcgacggc aggccgctgc cgatggacga caccatggcg     420
cccaccggct gcaccccgg cgacttcaac ggcgacggcc gcaacgactt cctggtcacc      480
tactggggcc gcacgcccgt cctgttcatg gcccgggccg acgccgccgc acccgccgcc     540
gagtcgtacg tgccgcgcga actggtcgcc tcggagagcc tggacggccg ctaccacggc     600
ccgcgctgga acaccgacgc gcgtacgtc ggcgacctgg acggcagcgg ccacccgtcg      660
atcatcatcg caactactt ccccgactcc gacgtgctcg acccgcaggg catccgcaac      720
gtccagatga acgactcgct gtccagcgcg aagaacgccg gcggcgacca cgtgctgcgc     780
ttccactcct cgaccgccgg cgccgcaccg gacgcccggt tcgtcgagga gaaggacgcc     840
atcgccttcg acgcctccac cggctggacg ctggccatcg ccggcgccga cctgaccggc     900
gacgccctgc ccgaggtcta catcgccaac gacttcggcc acgcccacct gctgcacaac     960
gtctccaccc cgggccgcat ccggttcgag gaggccaccg gcgagcgcac cccgaccacc    1020
ccgaagtcct tcgtgctcgg caagggctcc ttcaagggca tgggcgtcga cttcggcgac    1080
gtcgacggca acggcagctt cgacatgatg gtcagcaaca tcaccgtcgc ctggggcctg    1140
gaggagagca acttcctctg gatcaaccag gccaaggacc cggccgagat gaagcgcaag    1200
ctcaccgacc ggatcgcccc gttcacccag gaggccgccg accacggcgt cgcctggacc    1260 ggctgggct gggacgccaa gatgggcgac ttccgcaaca gcggacagca ggacatcctg     1320
caggccgacg gcttcgtcaa ggggaacatc gaccgctggc cctggctgca ggagatggcc    1380
atgaccaacg acgacctgct ctccaacccg aagctctggc cgaacgtcgg ccccggcgac    1440
gacctggccg gcgacgagac gatggccttc tacgcccgca ccgacagcgg caagttcgcc    1500
aacatcagca gcagctcgg cctcgacgtg ccgatcccga cccgcggcat cgccaccgcc     1560
gacaccaccg gcaccggcgc cctggacttc gccatcgccc ccagtggggg cccgccggcc    1620
```

```
ttctacgcca accagtccgc gaacctcggc cacgacctga ccctgcgcct gtaccgcccg    1680
gccaccgaca ccgcgaccac cggcaccacc ggcgccggtg cgaccgccgc gaccgacgcc    1740
accgccggcc cgggcctggc caccaccggc acccccgcct acggcgccac cgtctgcgtc    1800 accaccccg acggcaggaa gcagatcggc caactggacg gcggcggcgg ccacggcggc      1860
ttccgcagct cgacgtccg cttcggcctc ggcacccaga gcggccccgt caccgtcgac      1920
ctcgcctggc gcgacaacgc cggcggcctg cacaccgaga cccggcagct cagcgccggg    1980
agccacactc tcatgctgac cgacgacatc caggaggtgg cggcccgatg a              2031
```

<210> SEQ ID NO 61
<211> LENGTH: 338
<212> TYPE: PRT
<213> ORGANISM: Kitasatosporia sp.

<400> SEQUENCE: 61

```
Met Thr Ala Thr Asp Ile Ser Gly Val Ala Thr Arg Ala Val Arg Pro
  1               5                  10                  15

His Ala Ala Lys Lys Gln Pro Asn Arg Asp Pro Arg Tyr Leu Ala Leu
                 20                  25                  30

Arg Asn Phe Ala Leu Ser Met Ser Val Phe Asn Ile Phe Gly Tyr Thr
             35                  40                  45

Leu Leu Gly Phe Glu Gln Pro Trp Leu Trp Pro Leu Ile Cys Ala Pro
 50                  55                  60

Phe Gly Tyr Val Val Glu Ile Val Leu Glu Leu Ile Ser Ala Trp Ala
 65                  70                  75                  80

Gln Gln Arg Thr Pro Arg Phe Arg Gly Asn Gly Pro Arg Gly Leu Tyr
                 85                  90                  95

Glu Phe Leu Leu Pro Ser His Ile Thr Ala Leu Ala Ala Asn Met Leu
            100                 105                 110

Leu Tyr Ala Asn Asp Arg Leu Leu Pro Ile Leu Leu Ala Val Phe Ile
            115                 120                 125

Gly Val Ala Ala Lys His Val Leu Gln Ala Pro Val Tyr Gly Arg Met
        130                 135                 140

Arg His Phe Met Asn Pro Ser Asn Phe Gly Ile Thr Met Ala Leu Val
145                 150                 155                 160

Leu Phe Gly Ser Trp Ile Ser Ile Ala Pro Pro Tyr Glu Phe Thr Glu
                165                 170                 175

Asn Ala Asn Thr Phe Phe Arg Ile Gly Ile Pro Leu Ile Ile Thr Thr
            180                 185                 190

Ala Gly Thr Val Ile Asn Ala Met Leu Thr Lys Arg Val Pro Leu Ile
        195                 200                 205

Val Gly Trp Leu Gly Gly Phe Val Ile Gln Ala Leu Leu Arg His Trp
    210                 215                 220

Ile Trp Asp Val Ala Ile Phe Ser Ala Leu Gly Pro Met Ser Gly Val
225                 230                 235                 240

Ala Phe Val Leu Tyr Thr Asn Tyr Met Ile Thr Asp Pro Gly Thr Thr
                245                 250                 255

Pro Ser Lys Gly Arg Asn Gln Phe Met Phe Gly Ser Ser Val Ala Met
            260                 265                 270

Val Tyr Gly Val Leu Met Leu Phe Asn Val Val Tyr Thr Leu Phe Phe
        275                 280                 285

Ala Thr Thr Ile Val Cys Gly Leu Arg Gly Ala Gly Trp Trp Val Ala
    290                 295                 300
```

-continued

His Phe Arg Asn Arg Arg Lys Gln Gly Gly Gly Pro Val Glu Val Pro
305                 310                 315                 320

Ser Gly Gln Ser Gly Ala Pro Glu Arg Pro Met Gly Asn Glu Ala Val
                325                 330                 335

Ala Ala

<210> SEQ ID NO 62
<211> LENGTH: 1017
<212> TYPE: DNA
<213> ORGANISM: Kitasatosporia sp.

<400> SEQUENCE: 62

| | | | | | |
|---|---|---|---|---|---|
| atgaccgcga | ccgacatctc | cggcgtggcc | acccgcgccg | tgcgccccca | cgccgccaag | 60 |
| aagcagccca | accgcgaccc | gcgctacctc | gccctgcgca | acttcgccct | ctcgatgagc | 120 |
| gtcttcaaca | tcttcggcta | caccctgctc | ggcttcgaac | agccctggct | ctggccgctg | 180 |
| atctgcgccc | cgttcggcta | cgtggtcgag | atcgtgctgg | agctgatcag | cgcctgggcg | 240 |
| cagcagcgca | ccccgcgctt | ccgcggcaac | ggcccgcgcg | gcctgtacga | gttcctgctg | 300 |
| ccctcgcaca | tcaccgcgct | cgccgcgaac | atgctgctct | acgccaacga | ccggctgctg | 360 |
| ccgatcctgc | tcgccgtgtt | catcggcgtc | gccgccaagc | acgtcctcca | ggccccggtg | 420 |
| tacgccgga | tgcggcactt | catgaacccg | tcgaacttcg | gcatcaccat | ggcgctggtg | 480 |
| ctgttcggct | cctggatcag | catcgccccg | ccgtacgagt | tcaccgagaa | cgccaacacc | 540 |
| ttcttccgga | tcggcatccc | gctgatcatc | accaccgccg | gcaccgtcat | caacgccatg | 600 |
| ctcaccaagc | gcgtcccgct | gatcgtcggc | tggctcggcg | gcttcgtcat | ccaggccctg | 660 |
| ctgcggcact | ggatctggga | cgtggcgatc | ttctccgcgc | tcggcccgat | gagcggcgtc | 720 |
| gccttcgtcc | tctacaccaa | ctacatgatc | accgacccgg | gcaccacccc | gtccaagggc | 780 |
| cgcaaccagt | tcatgttcgg | ctcctcggtg | gccatggtct | acggcgtgct | gatgctcttc | 840 |
| aacgtcgtct | acacgctgtt | cttcgccacc | accatcgtct | gcggcctgcg | cggcgccggc | 900 |
| tggtgggtgg | cgcacttccg | gaacaggcgc | aagcaggggg | gcgggccggt | cgaggtcccc | 960 |
| tccggtcagt | cgggcgcgcc | cgagcggccc | atgggcaacg | aggcggtggc | ggcgtga | 1017 |

<210> SEQ ID NO 63
<211> LENGTH: 1927
<212> TYPE: PRT
<213> ORGANISM: Micromonospora megalomicea

<400> SEQUENCE: 63

Met Thr Arg Ile Ala Val Val Gly Met Ala Cys Arg Tyr Pro Asp Ala
1               5                   10                  15

Thr Ser Pro Arg Glu Leu Trp Glu Asn Ala Leu Ala Gly Arg Arg Ala
            20                  25                  30

Phe Arg Arg Leu Pro Asp Val Arg Met Arg Leu Asp Asp Tyr Trp Asp
        35                  40                  45

Ala Asp Pro Ala Pro Asp Lys Phe Tyr Ala Arg Asn Ala Ala Val
    50                  55                  60

Ile Glu Gly Tyr Glu Phe Asp Arg Ile Ala Tyr Lys Ile Ala Gly Ser
65              70                  75                  80

Thr Phe Arg Ser Thr Asp Met Thr His Trp Leu Ala Leu Asp Val Ala
            85                  90                  95

Ala Ser Ala Leu Ala Asp Ala Gly Phe Pro Met Gly Asp Gly Leu Pro
            100                 105                 110

-continued

```
Arg Glu Arg Thr Gly Val Val Gly Asn Ser Leu Thr Gly Glu Phe
    115                 120                 125
Ser Arg Ala Asn Gln Leu Arg Leu Arg Trp Pro Tyr Val Arg Arg Met
    130                 135                 140
Val Ala Ala Ala Leu Lys Glu Gln Asp Trp Asp Asp Gln Leu Gly
145                 150                 155                 160
Thr Phe Leu Asp Glu Phe Glu Ala Thr Phe Lys Ser Pro Phe Pro Gln
                165                 170                 175
Val Asp Glu Asp Thr Leu Ala Gly Ala Leu Ser Asn Thr Ile Ala Gly
            180                 185                 190
Arg Ile Cys Asn His Phe Asp Phe Lys Gly Gly Tyr Thr Val Asp
        195                 200                 205
Gly Ala Cys Ser Ser Ser Leu Leu Ser Val Ala Thr Ala Gly Lys Thr
    210                 215                 220
Leu Ile Asp Gly Asp Val Asp Val Ala Val Ala Gly Gly Val Asp Leu
225                 230                 235                 240
Ser Ile Asp Pro Phe Glu Ile Ile Gly Phe Ala Lys Thr Gly Ala Leu
                245                 250                 255
Ala Arg Gly Glu Met Arg Val Tyr Asp Arg Ser Ala Asn Gly Phe Trp
            260                 265                 270
Pro Gly Glu Gly Cys Gly Met Val Val Leu Met Arg Glu Val Asp Ala
        275                 280                 285
Val Ala Ala Gly His Arg Ile Tyr Ala Thr Leu Thr Gly Trp Gly Ile
    290                 295                 300
Ser Ser Asp Gly Lys Gly Gly Ile Thr Arg Pro Glu Val Gly Gly Tyr
305                 310                 315                 320
Arg Leu Ala Leu Arg Arg Ala Tyr Gln Arg Ser Gly Phe Gly Ile Glu
                325                 330                 335
Thr Val Gly Leu Phe Glu Gly His Gly Thr Gly Thr Ser Val Gly Asp
            340                 345                 350
Thr Thr Glu Leu Thr Ala Leu Ser Ala Ala Arg Thr Ala Ala Gly Gly
        355                 360                 365
Ala Gly Leu Pro Ala Ala Val Gly Ser Ile Lys Ala Met Ile Gly His
    370                 375                 380
Thr Lys Ala Ala Ala Gly Val Ala Gly Leu Ile Lys Ala Ala Met Ala
385                 390                 395                 400
Val His Gln Glu Val Leu Pro Pro Ala Val Gly Cys Val Asp Pro His
                405                 410                 415
Glu Val Leu Thr Gly Thr Ser Pro Ala Leu Arg Val Leu Arg Lys Ala
            420                 425                 430
Glu Ala Trp Pro Thr Asp Val Pro Val Arg Ala Gly Val Thr Ala Met
        435                 440                 445
Gly Phe Gly Gly Ile Asn Thr His Ile Val Leu Glu Asn Pro Arg Pro
    450                 455                 460
Arg Arg Arg Val Pro Leu Asp Thr Arg Thr Arg Ala Leu Ala Ala Ser
465                 470                 475                 480
Ile Gln Asp Ala Glu Leu Leu Ala Val Asp Ala Ser Ala Pro Glu
                485                 490                 495
Leu Val Gln Arg Leu Thr Arg Leu Val Asp Phe Val Gly Ser Val Ser
            500                 505                 510
Tyr Ala Gln Leu Ala Asp Leu Gly Ala Thr Leu His Gly Glu Leu Arg
        515                 520                 525
Asp Leu Pro Tyr Arg Ala Ala Val Val Ala Thr Ser Pro Glu Asp Ala
```

-continued

```
            530                 535                 540
Glu Arg Arg Leu Arg Gln Leu Arg Thr Ala Val Glu Ala Gly Glu Thr
545                 550                 555                 560

Arg Gln Phe Ser Ser Asp Gly Arg Ser Leu Leu Gly His Val Asn Gly
                    565                 570                 575

Pro Gly Arg Ile Gly Leu Leu Phe Pro Gly Gln Gly Ser Gly Arg Gly
                    580                 585                 590

Thr Ser Gly Gly Ala Leu Arg Arg Phe Thr Glu Val Glu Glu Thr
                595                 600                 605

Tyr Leu Arg Ala Asp Leu Pro Thr Gly Asp Val Val Ala Thr Glu
610                 615                 620

Val Ala Gln Pro Arg Ile Val Thr Gly Ser Thr Ala Gly Leu Arg Val
625                 630                 635                 640

Leu His Thr Leu Gly Ile Glu Ser Ser Ile Ala Val Gly His Ser Leu
                    645                 650                 655

Gly Glu Leu Ser Ala Leu His Trp Ala Gly Val Leu Asp Glu Ala Asp
                660                 665                 670

Leu Leu Arg Ile Ala Ser Leu Arg Gly Ala Ala Met Ala Arg His Ser
                675                 680                 685

Ser Ser Gly Met Met Ala Ser Leu Ala Ala Asp Pro Glu Ala Leu Asp
690                 695                 700

Pro Leu Leu Ala Asp Leu Pro Val Val Ala Ala Tyr Asn Gly Pro
705                 710                 715                 720

Gly Asn Thr Val Val Ala Gly Thr Asp Glu Ala Val Arg Ala Ala Cys
                    725                 730                 735

Gln Arg Ala Gly Asp Ala Gly Phe Thr Ala Thr Val Leu Pro Val Ser
                740                 745                 750

His Ala Phe His Ser Pro Leu Val Pro Ala Ala Asp Glu Phe Gly
            755                 760                 765

Ala Ala Leu Ala Asp Arg Gln Trp His Pro Leu Ala Gly Arg Val Ile
                770                 775                 780

Ser Thr Val Thr Gly Asp Leu Leu Pro Pro His Thr Asp Val Pro Ala
785                 790                 795                 800

Leu Leu Arg Arg Gln Ile Thr Asp Pro Val Leu Phe Thr Gln Ala Val
                805                 810                 815

Gly Leu Ala Ala Lys Ser Val Asp Leu Phe Val Glu Val Gly Pro Gly
                820                 825                 830

Arg Val Leu Ala Gly Leu Ala Gly Arg Ala Thr Asp Val Pro Ala Val
                835                 840                 845

Ser Leu Asp Thr Asp Asp Glu Ser Ile Ala Ser Leu Leu Thr Val Val
                850                 855                 860

Gly Ser Ala Tyr Val Val Gly Ala Ala Arg Ile Glu Ala Ala Leu Phe
865                 870                 875                 880

His Gly Arg Leu Ile Arg Pro Leu Ala Val Gly Ala Glu Phe Ser Phe
                    885                 890                 895

Phe Ala Asn Pro Cys Glu Gln Ala Pro Ser Val Asp Leu Pro Val Arg
                900                 905                 910

Ala Ala Gly Pro Val Pro Val Ala Glu Ala Asp Ala Gln Ser Ala Ala
                915                 920                 925

Val Val Pro Gly Glu Thr Thr Val Asp Leu Leu Arg Arg Ile Ala Ala
                930                 935                 940

Glu Arg Ala Glu Leu Pro Pro Glu Thr Val Arg Pro Asp Ser Arg Leu
945                 950                 955                 960
```

-continued

```
Leu Asp Asp Leu His Leu Ser Ser Ile Thr Val Gly Gln Val Val Asn
        965                 970                 975

Gln Leu Ala Gln Arg Leu Asn Val Pro Pro Ala Ala Val Pro Thr Asn
        980                 985                 990

Phe Ala Val Ala Thr Val Gln Glu Leu Ala Glu Ala Leu Asp Thr Leu
        995                1000                1005

Ala Ala Thr Ala Ser Ala Asp Ala Val Ala Ala Pro Val Val
        1010                1015                1020

Ala Gly Ala Ala Pro Trp Ala Arg Ala Trp Arg Ile Asp Leu Asp
        1025                1030                1035

Val Ala Glu Pro Pro Thr Arg Ala Asp Ala Pro Glu Asp Gly Thr
        1040                1045                1050

Trp Gln Leu Phe Ala Ala Asp Asp His Pro Leu Ala Thr Glu Leu
        1055                1060                1065

Leu Ala Glu Leu His Arg Ala Arg Leu Gly Gly Gly Val Leu Val
        1070                1075                1080

Trp Leu Pro Gln Asp Cys Pro Glu Glu Ala Leu Glu His Ala Leu
        1085                1090                1095

Arg Gly Ala Gln Gln Ala Ala Arg Gly Gly Pro Gly Thr Arg Phe
        1100                1105                1110

Val Leu Val Asp His Gly Arg Gly Gly Ala Gly Leu Ala Lys Thr
        1115                1120                1125

Leu Arg Leu Glu Ala Pro His Leu Arg Val Thr Val Val His Leu
        1130                1135                1140

Ser Asp Ala Ser Gly Ala Val Glu Arg Val Thr Ala Glu Val Ala
        1145                1150                1155

Gly Thr Val Gly Phe Val Glu Val Asp Tyr Asp Ala Asp Gly Thr
        1160                1165                1170

Arg Arg Val Pro Val Leu Arg Ala Met Ser Val Arg Pro Gln Ile
        1175                1180                1185

Ser Arg Pro Ala Leu Asp Asp Thr Asp Val Leu Leu Val Thr Gly
        1190                1195                1200

Gly Gly Lys Gly Ile Thr Ala Glu Cys Ala Leu Ala Met Ala Thr
        1205                1210                1215

Asp Ser Gly Ala Ser Leu Ala Leu Leu Gly Arg Ser Ala Pro Ala
        1220                1225                1230

Glu Asp Pro Glu Leu Ala Ala Asn Leu Ser Arg Met Thr Ala Ala
        1235                1240                1245

Gly Val Thr Val Arg Tyr Ala Arg Ala Asp Val Thr Asp Pro Asp
        1250                1255                1260

Gln Val Arg Arg Ala Val Ala Glu Leu Thr Ala Asp Leu Gly Pro
        1265                1270                1275

Val Thr Ala Val Leu His Gly Ala Gly Arg Asn Glu Pro Ala Ala
        1280                1285                1290

Leu Ala Asn Leu Asp Met Gly Ala Val Arg Arg Thr Phe Ala Pro
        1295                1300                1305

Lys Leu Asp Gly Leu Ser Ala Thr Leu Ala Ala Val Asp Pro Asp
        1310                1315                1320

Arg Leu Arg Leu Leu Val Thr Leu Gly Ser Ile Ile Gly Arg Ala
        1325                1330                1335

Gly Leu Arg Gly Glu Ala His Tyr Ala Thr Ala Asn Asp Trp Leu
        1340                1345                1350
```

-continued

| | | | | | | | | | | |
|---|---|---|---|---|---|---|---|---|---|---|
| Ala | Glu | Ala | Thr | Thr | Ala | Phe | Gly | Arg | Arg | His | Arg | His | Cys | Arg |
| 1355 | | | | 1360 | | | | | 1365 | | | | | |
| Ser | Leu | Cys | Leu | Glu | Trp | Ser | Val | Trp | Ser | Gly | Val | Gly | Met | Gly |
| 1370 | | | | | 1375 | | | | | 1380 | | | | |
| Glu | Arg | Leu | Ser | Val | Val | Glu | Ser | Leu | His | Arg | Glu | Gly | Val | Ala |
| 1385 | | | | | 1390 | | | | | 1395 | | | | |
| Ala | Leu | Thr | Pro | Asp | Gln | Gly | Val | Ala | Val | Leu | Arg | Arg | Leu | Leu |
| 1400 | | | | | 1405 | | | | | 1410 | | | | |
| Ala | Asp | Pro | Glu | Ala | Thr | Gly | Thr | Val | Val | Ser | Gly | Arg | Thr |
| 1415 | | | | | 1420 | | | | | 1425 | | | | |
| Gln | Gly | Ile | Asp | Thr | Ile | Gly | Tyr | Asp | Arg | Pro | Glu | Leu | Pro | Leu |
| 1430 | | | | | 1435 | | | | | 1440 | | | | |
| Arg | Arg | Phe | Leu | Glu | Lys | Pro | Leu | Val | His | Tyr | Pro | Gly | Val | Glu |
| 1445 | | | | | 1450 | | | | | 1455 | | | | |
| Leu | Val | Ala | Glu | Thr | Glu | Leu | Asn | Val | Gly | Thr | Asp | Leu | Tyr | Leu |
| 1460 | | | | | 1465 | | | | | 1470 | | | | |
| Ala | Asp | His | Leu | Leu | Asp | Gly | Asn | Leu | Leu | Phe | Pro | Ala | Val | Phe |
| 1475 | | | | | 1480 | | | | | 1485 | | | | |
| Gly | Met | Glu | Ala | Met | Ala | Gln | Val | Ala | Ala | Ala | Val | Arg | Gly | Thr |
| 1490 | | | | | 1495 | | | | | 1500 | | | | |
| Asp | Asp | Val | Pro | Val | Ile | Glu | Arg | Ala | Glu | Phe | Leu | Arg | Pro | Ile |
| 1505 | | | | | 1510 | | | | | 1515 | | | | |
| Ile | Val | Pro | Pro | Tyr | Gly | Arg | Gly | Arg | Ile | Arg | Val | Gly | Ala | Val |
| 1520 | | | | | 1525 | | | | | 1530 | | | | |
| Ala | Thr | Asp | Asp | Asp | Thr | Val | Glu | Val | Ala | Val | Arg | Ser | Glu | Asp |
| 1535 | | | | | 1540 | | | | | 1545 | | | | |
| Thr | Asp | Phe | Val | Ala | Asp | His | Phe | Thr | Ala | Arg | Leu | Arg | Tyr | Gly |
| 1550 | | | | | 1555 | | | | | 1560 | | | | |
| Val | Gly | Pro | Ala | Pro | Glu | Gly | Pro | Pro | Glu | Gln | Leu | Ser | Asp | Asp |
| 1565 | | | | | 1570 | | | | | 1575 | | | | |
| Leu | Gly | Pro | Val | Ser | Leu | Ala | Pro | Asp | Ala | Asp | Leu | Tyr | Gly | Gly |
| 1580 | | | | | 1585 | | | | | 1590 | | | | |
| Leu | Leu | Phe | Gln | Gly | Ser | Arg | Phe | Gln | Arg | Leu | Arg | Gly | Tyr | Arg |
| 1595 | | | | | 1600 | | | | | 1605 | | | | |
| Arg | Ala | Ala | Ala | Lys | Cys | Val | Asp | Ala | Glu | Val | Ala | Ala | Leu | Asp |
| 1610 | | | | | 1615 | | | | | 1620 | | | | |
| Gly | Val | Asp | Trp | Phe | Ala | Pro | Phe | Val | Pro | Asp | Glu | Leu | Leu | Leu |
| 1625 | | | | | 1630 | | | | | 1635 | | | | |
| Gly | Asp | Pro | Gly | Val | Arg | Asp | Ala | Leu | Met | His | Gly | Asn | Gln | Val |
| 1640 | | | | | 1645 | | | | | 1650 | | | | |
| Cys | Val | Pro | Asp | Ala | Thr | Leu | Leu | Pro | Met | Gly | Val | Asp | Arg | Ile |
| 1655 | | | | | 1660 | | | | | 1665 | | | | |
| His | Pro | Gly | Ala | Ala | Ala | Leu | Ser | Gly | Arg | Arg | Asp | Leu | Arg | Phe |
| 1670 | | | | | 1675 | | | | | 1680 | | | | |
| Cys | Ala | Val | Glu | Arg | Ser | Arg | Asp | Gly | Asp | Thr | Tyr | Val | Tyr | Asp |
| 1685 | | | | | 1690 | | | | | 1695 | | | | |
| Val | Ala | Leu | Arg | Asp | Pro | Asp | Gly | Arg | Thr | Val | Glu | Arg | Trp | Glu |
| 1700 | | | | | 1705 | | | | | 1710 | | | | |
| Gly | Leu | Arg | Leu | Arg | Ala | Val | Arg | Arg | Gln | Asp | Gly | Ser | Gly | Pro |
| 1715 | | | | | 1720 | | | | | 1725 | | | | |
| Trp | Val | Ala | Pro | Leu | Leu | Gly | Ala | Tyr | Leu | Glu | Arg | Thr | Leu | Asp |
| 1730 | | | | | 1735 | | | | | 1740 | | | | |
| Asp | Leu | Val | Gly | Thr | Pro | Val | Ala | Val | Thr | Val | Gln | Pro | Asp | Gly |

```
                    1745                1750                1755
Pro Asp Asp Gly Pro Asp Asp His Val Ala Arg Arg Ala Arg
    1760                1765                1770

Thr Arg Ser Ala Ala Gly Gln Val Phe Gly Arg Pro Val Glu Val
    1775                1780                1785

Arg Tyr Arg Pro Asp Gly Arg Pro Glu Val Pro Gly Gly Gln Asn
    1790                1795                1800

Leu Ser Val Ala His Gly Ala Gly Leu Thr Leu Cys Val Ser Ser
    1805                1810                1815

Ala Glu Thr Val Gly Cys Asp Val Glu Pro Val Thr Gly Arg Ser
    1820                1825                1830

Ala Gln Thr Trp Thr Gly Leu Leu Gly Arg His Thr Asp Leu Ala
    1835                1840                1845

Arg Leu Leu Ala Ala Glu Ala Gly Glu Glu Ile Asp Val Ala Ala
    1850                1855                1860

Thr Arg Val Trp Thr Ala Leu Glu Cys Leu Gln Lys Ala Gly Arg
    1865                1870                1875

Arg Ser Gly Asp Pro Leu Val Leu His Pro Val Thr Arg Ser Gly
    1880                1885                1890

Trp Ser Val Leu Val Ser Gly Asp Val Arg Val Ala Thr Phe Ala
    1895                1900                1905

Thr Thr Val Arg Asp Val Thr Glu Pro Val Val Phe Ala Val Leu
    1910                1915                1920

Thr Glu Gly Arg
    1925

<210> SEQ ID NO 64
<211> LENGTH: 5784
<212> TYPE: DNA
<213> ORGANISM: Micromonospora megalomicea

<400> SEQUENCE: 64
atgacgagaa ttgccgtcgt cggcatggcg tgccggtacc cggacgccac ctcgccgagg      60
gagttgtggg agaacgcgct cgccggccgg cgggcgttcc gccggctgcc ggacgtccgg     120
atgcgcctcg acgactactg ggacgccgac ccggcggctc cagacaagtt ctacgcgcgc     180
aatgccgccg tcatcgaggg atacgagttc gaccggatcg cctacaagat tgccggcagc     240
acgtttcgtt ccacggacat gacccactgg ctggcgctcg acgtggctgc gagcgcactg     300
gccgacgcgg ggttcccgat gggggacggg ctgccgcgcg agcgcaccgg ggtggtggtc     360
ggcaacagcc tcaccggtga gttctcccgc gccaaccaac tgcgcctgcg gtggccgtac     420
gtgcggcgca tggtggcggc ggcgctcaag gagcaggact gggacgacga tcagctgggc     480
acgttcctcg acgagttcga ggcgaccttc aagagcccgt tcccgcaggt cgacgaggac     540
actctggccg ggcgctgtc caatacgatc gccgggcgga tctgcaacca cttcgacttc     600
aagggcggcg ggtacaccgt ggacggggct tgttcgtcct cgctgctgtc ggtcgccacg     660
gcgggtaaga cgctgatcga cggcgacgtg acgtggcgg tcgccggtgg tgtggacctg     720
tcgatcgatc ccttcgagat catcgggttc gccaagacgg tgcgctggc gcgcggcgag     780 atgcgcgtgt acgaccgctc cgcgaacggg ttctggcccg gcgagggctg cgggatggtg     840
gtgttgatgc gcgaggtcga gcggtcgcc gccggccacc gcatctacgc cacgctcacc     900
ggttggggca tcctcgga cggcaagggc ggcatcaccc ggccgaggt cggcgggtac     960 cgcctggcgc tgcggcgggc ctaccagcgc agcgggttcg gcatcgagac ggtcggcctg    1020
```

-continued

```
ttcgagggc  acggtaccgg  caccagcgtc  ggggacacca  ccgagctgac  ggcgctgtcc   1080
gcggcccgca  cggccgccgg  tggcgcgggc  ctgccggcgg  cggtcgggtc  gatcaaggcc   1140
atgatcggac  acaccaaggc  cgcggccgga  gtggcgggtc  tgatcaaagc  ggcgatggcg   1200
gtccaccagg  aggtcctgcc  cccggccgtg  gggtgcgtcg  acccgcacga  ggtgctcacc   1260
ggcacgtcac  cagcgctacg  cgtgctgcgc  aaggccgagg  cgtggcccac  cgacgttccg   1320
gtccgggcgg  gtgtcacggc  gatgggcttc  ggcggcatca  acacccacat  cgtgttggag   1380
aacccgcgtc  ctcgccgccg  ggtgccgctg  acacccgga   cccgcgccct  ggccgcctcg   1440
atccaggacg  ccgaactgct  ggccgtcgac  gccgcctccg  caccggaact  ggtccaacgg   1500
ctgacccggc  tggtcgactt  cgtgggttcg  gtgtcgtacg  cgcagttggc  ggacctcggt   1560
gccacgctgc  acggcgagct  acgcgacctg  ccgtaccggg  cggcggtcgt  ggcgacgtcg   1620
ccggaggacg  cggagcggcg  gttgcggcag  ctcgtacgg   cggtcgaggc  cggcgagacc   1680
cggcagttct  cctccgacgg  ccgcagcctg  ctgggccacg  tcaacggtcc  tggccgcatc   1740
gggctgctgt  ttcccgggca  gggctccggg  cgcggcacca  gcggtggcgc  actgcgtcgg   1800
cgcttcaccg  aggtcgagga  gacgtacctg  cgcgccgacc  tgcccaccgg  tggggacgtc   1860
gtcgccaccg  aggtcgccca  gccccgcatc  gtcaccgggt  ccaccgccgg  cctgcgggtg   1920
ctgcacacgt  tgggcatcga  aagctcgatc  gccgtcggac  acagcctcgg  tgagctgtcc   1980
gccctgcact  gggccggtgt  gctcgacgag  gccgacctgc  tgcgcatcgc  cagtcttcgc   2040
ggagccgcca  tgcccggca   cagctcgtcg  ggcatgatgg  ccagcctcgc  cgcggatccc   2100
gaggccctcg  atccgctcct  ggccgaccta  ccggtcgtgg  tggcggccta  caacggcccg   2160
ggcaacaccg  tcgtcgccgg  caccgacgag  gcggtacggg  cggcctgcca  gcgggccggc   2220
gacgcgggct  tcaccgccac  cgtgttgccg  gtgtcacacg  ccttccactc  gcccctggtg   2280
gcccccgccg  ccgacgagtt  cggtgccgcg  ctggccgacc  ggcaatggca  tccgttggcc   2340
ggtcgggtga  tctccaccgt  gaccggtgac  ctgctgccgc  cgcacaccga  cgtgccggcc   2400
ctgctgcgtc  ggcagatcac  cgacccgtg   ctgttcaccc  aggcggtggg  gctcgccgcg   2460
aagtccgtcg  acctcttcgt  cgaggtgggg  cccggtcggg  tgctcgccgg  cctggccggt   2520
cgggcgaccg  acgtacctgc  ggtgtcgttg  gacaccgacg  acgagtccat  cgccagcctg   2580
ctcacggtgg  tcgggtcggc  ctacgtcgtc  ggagcggccc  ggatcgaggc  ggcgttgttc   2640
cacggcggcg  tgatccgacc  gctggcggtc  ggtgccgagt  tctccttctt  cgccaacccg   2700
tgcgagcagg  caccttcggt  ggacctaccg  gtgcgggccg  ccggtccggt  gccggtggcg   2760
gaggcggacg  cccagtcggc  cgccgtggtg  ccgggcgaga  ccaccgtcga  cctgttgcgt   2820
cggatcgccg  ccgagcgggc  cgaactgccc  ccggagaccg  tccggccgga  cagtcgcctc   2880
ctcgacgacc  tgcacctgag  ttcgatcacc  gtcggccagg  tggtcaatca  gctgcccag   2940 cggctgaacg  tgccgccggc  agcggtgccg  acgaacttcg  cggtggccac  ggtccaggag   3000
ctggccgagg  cgctggacac  cctcgccgcc  accgcctccg  ctgacgacgc  cgtcgcggca   3060
ccggtggtcg  ccggcgccgc  cccgtgggcg  cgggcgtggc  ggatcgacct  cgacgtggcc   3120
gaaccaccca  cccgtgccga  cgcgccggag  acggcacct   gcagctctt  cgccgccgac   3180 gaccacccac  tggcgacgga  gctgctcgcc  gagctgcacc  gagcccgcct  cggtggcggg   3240
gtgctcgtgt  ggctgccgca  ggactgtccc  gaggaggcgc  tggaacacgc  gctgcgcggt   3300
gcccagcagg  ctgcgcgggg  tggaccgggc  acccggttcg  tcctggtcga  ccacggtcgt   3360
```

```
ggcggggccg gactggccaa gacgttgcgc ctggaagcac cgcacctgcg ggtcacagtg    3420
gtgcacctgt cggacgcctc cggcgctgtc gagcgggtga ccgccgaggt ggcgggcaca    3480
gtcgggttcg tcgaggtcga ctacgacgcc gacggcaccc gccggtgcc cgtcctgcgg    3540
gccatgtccg tgcgtccgca gatcagccgc ccggcgctgg acgacaccga cgtgctgctg    3600
gtgaccggcg gcggcaaggg catcaccgcc gagtgcgcct tggccatggc caccgactcg    3660
ggcgcgagcc tggcactgct cggccggtcg gccccgccc aggatccgga gctggccgcg    3720
aacctgtccc ggatgacggc ggccggtgtc acagtcaggt acgcccgggc cgacgtcacc    3780
gatcccgacc aggtccggcg ggcggtcgcc gagctgacgg ccgacctcgg tccggtgacc    3840
gccgtcctgc acggtgccgg acgcaacgag ccggcggcgt tggccaacct ggacatgggg    3900
gccgtgcgcc gcaccttcgc gcccaagctg acggtctctc cggccaccct ggcggcagtg    3960
gatccggacc ggctgcggct gctggtcacc ctgggcagca tcatcggccg gccgggctg    4020
cgcggcgagg cgcactacgc cacggccaac gactggctgg ccgaggccac caccgccttc    4080
ggtcgccgtc accgtcactg ccgcagcctc tgcctggagt ggtcggtgtg gtcgggcgtc    4140
gggatggggg agcggttgtc ggtggtcgag tcgctgcacc gggagggcgt cgccgcgctc    4200
accccggacc agggcgtggc cgtcctgcgg cggttgctgg ccgaccccga ggccaccggt    4260
acggtcgtcg tctccggccg cacccagggc atcgacacca tcgggtacga ccggccggag    4320
ctgccgttgc gacggttcct ggagaagccg ctggtgcact acccgggggt ggagctggtc    4380
gccgagacga aactgaacgt cggcaccgat ctctatctgg cagaccacct cctcgacggc    4440
aacctgctct tcccggcggt cttcggcatg gaggccatgg cccaggtcgc cgcagcggtg    4500
aggggcaccg acgacgtgcc ggtcatcgag cgggccgagt cctgcggcc gatcatcgtg    4560
ccgccgtacg gtcgtggtcg aatcaggggtc ggggcggtcg ccaccgacga cgacaccgtc    4620
gaggtggccg tccgcagcga ggacaccgac ttcgtcgccg accacttcac cgcgcgcgttg    4680
cgatacggtg tcggaccggc gcccgagggg ccaccggagc agttgtcgga cgacctgggt    4740
ccggtgtcgt tggccccgga cgcggacctc tacggcggtc tgctcttcca gggttcccgg    4800
ttccagcgtc tccgcggcta ccggcgggcc gctgccaaat gcgtcgacgc cgaggtcgcc    4860
gccctggacg gggtcgactg gttcgccccc ttcgtgccgg acgagctgct gctcggtgat    4920
cccggtgtcc gggatgcgtt gatgcacgga accaggtgt gtgtccccga cgcgaccctg    4980
ctgccgatgg gcgtggaccg gatccacccc ggcgcagcgg ccctgtcggg ccggcgggac    5040
ctgcgcttct gcgccgtgga acgcagccgc gacggcgaca cctacgtcta cgacgtggcg    5100
ttgcgcgacc cggacgggcg gaccgtggag cggtgggagg gacttcggct gcgggcggtt    5160
cgcagacagg acggcagcgg gccgtggtg gcgccgttgc tcggcgccta tctggaacgc    5220
accctcgacg acctggtcgg tacgccggtg gcggtgacgg tccagcccga cggcccggac    5280
gacggcccgg acgaccacgt ggcccgtcgg cgcgcccgga cccggtcggc ggccgggcag    5340
gtgttcggca ggccggtcga ggtcggtat cggcccgacg tcgcccgga ggtacccggc    5400
gggcagaacc tgtcggtggc ccacggcgca gggctgaccc tctgcgtctc cagcgcggag    5460
acggtgggct gcgacgtcga accggtcacc ggacggtcgg cgcagacgtg gaccgggttg    5520
ctcggtcggc acaccgacct ggcccggctt ctcgccgccg aggcgggcga ggagatcgac    5580
gtcgccgcca cccgggtgtg gacggcgttg gagtgtctac agaaggccgg ccgtcgcagt    5640
ggcgacccgc tggtcctgca tccggtcacc cgctcgggct ggagcgtgct ggtctccggc    5700
gacgtacggg tggccacctt cgccactacc gtccgcgacg tcaccgaacc ggtggtcttc    5760
```

```
gcggtgctga ccgagggacg gtga                                            5784
```

<210> SEQ ID NO 65
<211> LENGTH: 154
<212> TYPE: PRT
<213> ORGANISM: Micromonospora megalomicea

<400> SEQUENCE: 65

```
Met Glu Gln Tyr Tyr Glu Tyr Arg His Val Gly Phe Glu Glu Thr
1               5                   10                  15
Asn Ile Val Gly Asn Val Tyr Tyr Val Asn Tyr Leu Arg Trp Gln Gly
            20                  25                  30
Arg Cys Arg Glu Met Phe Leu Arg Glu Arg Ala Pro Gln Val Leu Ala
        35                  40                  45
Asp Leu Gln Asp Asp Leu Lys Leu Phe Thr Leu Arg Val Asp Cys Glu
    50                  55                  60
Phe Phe Ala Glu Ile Thr Ala Phe Asp Glu Leu Ala Ile Arg Met Arg
65                  70                  75                  80
Leu Leu Glu Leu Ala Gln Thr Gln Val Glu Phe Gly Phe Asp Tyr Val
                85                  90                  95
Arg Leu Gly Val Ala Gly Val Glu Thr Leu Val Ala Arg Gly Thr Gln
            100                 105                 110
Arg Val Ala Cys Met Arg Gly Pro Asn Asn Arg Thr Val Pro Ala Arg
        115                 120                 125
Val Pro Glu Ala Leu Gly Arg Ala Leu Ala Pro Tyr Ala Thr Gly Ala
    130                 135                 140
Pro Val Thr Val Ala Ala Gly Arg Pro Leu
145                 150
```

<210> SEQ ID NO 66
<211> LENGTH: 465
<212> TYPE: DNA
<213> ORGANISM: Micromonospora megalomicea

<400> SEQUENCE: 66

```
atggagcagt actacgagta ccggcatgtc gtcgggttcg aggagacgaa catcgtcggc    60
aacgtctact acgtcaacta cctgcgatgg cagggccgct gccggagat gttcctccgg    120
gagcgggccc cgcaggtgct ggccgacctg caggacgacc tcaagttgtt cactctgcgg    180
gtcgactgcg agttcttcgc cgagatcacc gccttcgacg aactggcgat ccggatgagg    240
ctgttggagc tggcccagac ccaggtcgag ttcggcttcg actacgtccg gctcggcgtc    300
gccggtgtcg agacgctcgt cgcccggggc acgcagcggg tcgcctgcat gcggggggccg    360
aacaaccgta cggtgcccgc ccgggtgccg gaggcgctcg gccgtgcact cgcgccgtac    420
gccaccggcg cacccgtcac cgtcgcggca gggaggccac tgtga                    465
```

<210> SEQ ID NO 67
<211> LENGTH: 322
<212> TYPE: PRT
<213> ORGANISM: Micromonospora megalomicea

<400> SEQUENCE: 67

```
Met Lys Ala Trp Arg Thr Leu Arg Arg Arg Val Leu Thr Pro Asp Val
1               5                   10                  15
Ser Gln Thr Leu Met Ser Val Arg Gly Phe His Val Lys Asp Gln Ala
            20                  25                  30
```

-continued

```
Gly Arg Glu Arg Leu Glu Asn Val Gly Arg Tyr Phe Leu Thr Gly Tyr
            35                  40                  45
Ala Ala Ala Glu Ala Arg Thr Ala Ala Glu Ala Glu Val Pro Leu
        50                  55                  60
Glu Ala Val Ala Ala Pro Tyr Arg Gly Phe Ala Tyr Glu Gly Ala Ala
65                  70                  75                  80
Met Ala Ser Ala Val Arg Asp Ala Leu Pro Gly Gly Arg His Val
                85                  90                  95
Arg Asp Leu Leu Ala Gly Arg Gly Asp Arg His Val Tyr Met Ala Tyr
                100                 105                 110
Val Gly Val Gly Trp Ala Met Ala Arg Leu Pro Arg Pro Leu Trp Gly
            115                 120                 125
Arg Leu His Ala Pro Asp Pro Leu Leu Arg Trp Leu Val Leu Asp Gly
        130                 135                 140
Tyr Gly Phe His Gln Ala Tyr Phe Lys Thr Ser Arg Tyr Val Asp Gly
145                 150                 155                 160
Gln Tyr Arg His Asp Arg Phe Pro Trp Pro Val Glu Gly Pro Ala Asp
                165                 170                 175
Tyr Ala Ala Arg Val Val Asp Gln Gly Val Gly Arg Ala Thr Trp Phe
                180                 185                 190
Val Cys Gly Thr Asp Ala Arg Arg Val Val Gln Thr Phe Asp Arg Phe
            195                 200                 205
Ala Ala Asp Arg Arg Pro Asp Leu Tyr Ala Gly Ala Gly Leu Ala Ala
        210                 215                 220
Thr Tyr Ala Gly Gly Ala Gly Ala Gln Glu Leu Thr Trp Leu Arg Asp
225                 230                 235                 240
Ala Ala Gly Pro Tyr Ala Ala Asp Leu Ala Gln Gly Ala Ala Phe Ala
                245                 250                 255
Ala Gly Ala Arg Val Arg Ala Gly Leu Val Val Pro His Asn Glu Val
                260                 265                 270
Ala Thr Arg Ile Leu Cys Gly Leu Pro Thr Gln Ala Ala Ala Ala Val
            275                 280                 285
Thr Asp Glu Ala Arg Ile Asp Leu Ala Ala Val Gly Ala Thr Pro Val
        290                 295                 300
Tyr Glu Val Trp Arg Gln Arg Ile Lys Ser Thr Phe Ala Ser Thr Arg
305                 310                 315                 320
Arg Ala
```

<210> SEQ ID NO 68
<211> LENGTH: 969
<212> TYPE: DNA
<213> ORGANISM: Micromonospora megalomicea

<400> SEQUENCE: 68

| | | | | | |
|---|---|---|---|---|---|
| atgaaagctt | ggcggacgct | tcggcgtcga | gtcctcaccc | ctgacgtctc | gcagaccctg | 60 |
| atgtccgtac | gtggcttcca | cgtcaaggac | caggccgggc | gggaacgtct | ggagaacgtc | 120 |
| ggtcggtact | tcctgaccgg | ctacgcggcc | gcggccgagg | cgcgtaccgc | cgccgaggcg | 180 |
| gaggtccctc | tggaggccgt | ggcggcaccg | taccggggct | cgcctacga | gggcgcggcg | 240 |
| atggcctcag | ccgtccgcga | cgccctcccc | ggtggtggtc | ggcacgtgcg | cgacctgctg | 300 |
| gccggtcggg | gcgaccggca | cgtgtacatg | gcctacgtgg | gggtcggctg | gcgatggct | 360 |
| cggctgcccc | gtccgctctg | ggggcggctg | cacgccccgg | acccactgct | gcgctggctg | 420 |
| gtcctcgacg | ggtacgggtt | ccaccaggcg | tacttcaaga | ccagccggta | cgtcgacggc | 480 |

-continued

```
cagtaccgtc acgaccggtt cccgtggccg gtcgaggggc cggccgacta cgccgccagg    540
gtcgtcgacc aggggtcgg ccgggccacc tggttcgtct gtggcaccga cgcgcgccgg    600
gtcgtgcaga ccttcgaccg cttcgccgcc gaccgccggc ccgacctgta cgccggcgcc    660
ggcctggccg ccacctacgc gggcggtgcc ggggcgcagg agttgacctg gctgcgtgac    720
gctgccggcc cgtacgccgc cgacctcgcc cagggcgcgg ccttcgcggc tggtgcgcgg    780
gtgcgggccg ggctggtggt gccgcacaac gaggtggcca cccggatcct gtgcgggctg    840
ccgacccagg cggcggcggc ggtgaccgac gaggcccgca tcgacctcgc cgccgtcggt    900
gccacccccg tgtacgaggt gtggcgccaa cgcatcaaga gcacgttcgc gtctacccgg    960
cgcgcctga                                                          969
```

```
<210> SEQ ID NO 69
<211> LENGTH: 659
<212> TYPE: PRT
<213> ORGANISM: Micromonospora megalomicea

<400> SEQUENCE: 69

Leu Pro Ser Gln Pro Val Ser Pro Leu Arg Arg Leu Met Ala Pro Ile
1               5                  10                  15

Leu Val Leu Val Leu Ala Ala Thr Met Phe Leu Val Ala Arg Leu Pro
            20                  25                  30

Ser Ala Ser Ala Asp Thr Arg Ala Glu Ile Ala Gly Arg Phe Ala Phe
        35                  40                  45

Thr Glu Leu Pro Ile Glu Leu Pro Pro Gly Leu Pro Glu Arg Ser Ile
    50                  55                  60

Arg Thr Val Asn Pro Lys Tyr Glu His Ile Arg Ser Trp Ile Ser Ser
65                  70                  75                  80

Val Gly Ala Ser Ile Ala Val Asn Asp Leu Asp Gly Gln Gly Val Ala
                85                  90                  95

Asn Asp Met Cys Leu Val Asp Thr Arg Ser Asp Ala Val Ile Val Thr
            100                 105                 110

Pro Val Pro Asp Thr Gly Ala Thr Tyr Gln Pro Phe Val Val Asp Pro
        115                 120                 125

Ala Pro Leu Pro Met Gly Ser Thr Ile Ala Pro Met Gly Cys Thr Pro
    130                 135                 140

Gly Asp Phe Asn Leu Asp Gly Arg Met Asp Leu Leu Val Ile Tyr Trp
145                 150                 155                 160

Gly Arg Thr Pro Val Val Phe Leu Gln Lys Glu Gly Ala Thr Ala Leu
                165                 170                 175

Ser Asn Asp Thr Tyr Gln Pro Val Glu Leu Val Pro Gln Gln Arg Thr
            180                 185                 190

Asp Asp Gly Val Tyr Arg Gly Pro Leu Trp Asn Thr Asn Ala Val Thr
        195                 200                 205

Val Ala Asp Phe Asp Gly Asp Gly Arg Pro Asp Ile Ala Leu Phe Asn
    210                 215                 220

Tyr Phe Pro Asp Ser Gln Val Leu Asp Pro Glu Gly Leu Pro Asn Val
225                 230                 235                 240

Gln Met Asn His Ser Met Ser His Gly His Asn Ala Gly Gly Ala His
                245                 250                 255

Val Leu Arg Trp Ser Gly Ala Thr Ser Gly Asp Asp Pro Thr Val Thr
            260                 265                 270

Tyr Glu Glu Gln Val Ala Leu Asp Pro Arg Tyr Ala Thr Gly Trp Thr
```

```
                275                 280                 285
Leu Gly Ala Ala Ser Ala Asp Leu Asp Gly Asp Leu Leu Pro Glu Leu
    290                 295                 300

Tyr Leu Ala Asn Asp Phe Gly Gln Asp Arg Phe Phe His Asn Val Ser
305                 310                 315                 320

Thr Pro Gly Arg Ile Arg Phe Asn Leu Ala Glu Gly Val Arg Thr Pro
                325                 330                 335

Leu Thr Pro Lys Ser Leu Val Leu Gly His Asp Ser Phe Lys Gly Met
                340                 345                 350

Gly Val Asp Phe Ala Asp Leu His Ser Arg Gly Arg Phe Asp Met Phe
    355                 360                 365

Val Ser Asn Ile Thr Glu Ser Trp Gly Leu Glu Glu Ser Asn Phe Val
370                 375                 380

Trp His Asn Thr Ala Ala Ser Pro Glu Ala Ala Arg Glu Gln Leu Ser
385                 390                 395                 400

Arg Gly Ile Ala Pro Phe Glu Asn Arg Ala Ala Arg Arg Asn Leu Ala
                405                 410                 415

Trp Val Gly Trp Gly Trp Asp Val Lys Met Ala Asp Phe Asp Asn Ser
                420                 425                 430

Gly Gly Leu Glu Val Val Gln Ala Ala Gly Phe Ile Lys Gly Asp Ile
                435                 440                 445

Asn Arg Phe Asn Trp Leu Gln Glu Leu Ala Met Ala Asn Asp Leu Met
    450                 455                 460

Leu Arg Glu Pro Ala Met Trp Pro Asn Ala Lys Pro Gly Asp Asp Ile
465                 470                 475                 480

Ser Gly Gly Asn Pro Val Ala Phe Trp Val Arg Glu Asp Asn Gly Arg
                485                 490                 495

Tyr Val Asn Leu Ser Pro Glu Leu Gly Leu Asp Glu Asp Thr Pro Ser
                500                 505                 510

Arg Gly Ile Ser Val Ala Asp Pro Asp Gly Asp Gly Ala Gln Asp Ile
                515                 520                 525

Ala Val Ala Arg Gln Trp Gly Ala Pro Ala Tyr Phe Arg Asn Thr Arg
530                 535                 540

Gly Asp Ser Asp Asn His Leu Ser Leu Arg Leu Ser Arg Pro Ala Leu
545                 550                 555                 560

Ala Ala Asp Gly Arg Thr Pro Ser Thr Thr Gly Thr Ser Pro Ala Tyr
                565                 570                 575

Gly Ala His Val Thr Ile Thr Thr Ala Asp Gly Arg Thr Gln Val Gly
                580                 585                 590

Gln Leu Asp Gly Gly Gly His Ser Gly Arg Arg Ser Phe Asp Val
                595                 600                 605

Phe Phe Gly Leu Gly Asp Ala Ala Asp Arg Pro Val Ser Val Gln Leu
    610                 615                 620

Cys Trp Arg Asp Leu Asn Gly Gln Thr His Arg Gln Thr Ile Asp Leu
625                 630                 635                 640

Thr Ala Gly Arg His Asp Leu Leu Leu Thr Asp Arg Ala Glu Glu Leu
                645                 650                 655

Asn Arg Arg

<210> SEQ ID NO 70
<211> LENGTH: 1980
<212> TYPE: DNA
<213> ORGANISM: Micromonospora megalomicea
```

```
<400> SEQUENCE: 70
ttgccatcgc aaccagtaag cccactgcgt cgtctcatgg cacccatcct ggtgctcgtg      60
ctggcggcca cgatgttcct cgtcgcacgc ctgccgagcg cctcggcgga cacccgtgcc     120
gagatcgccg gccgattcgc gttcacggag ttgccgatcg agctgccacc cggtctgccg     180
gagcgcagca tccgtaccgt caatcccaag tacgagcaca tccgctcctg gatctcgtcg     240
gtcggcgcgt ccatcgccgt caacgacctc gacggccagg tgtcgccaa cgacatgtgc     300
ctggtcgaca cccgcagcga cgcggtgatc gtcacgccgg taccggacac cggtgcgacg     360
taccaaccgt tcgtggtgga cccggcgccg ctgccgatgg gctcgaccat cgccccgatg     420
ggctgcacac ccggtgactt caacctcgac ggccggatgg acctgttggt catctactgg     480
ggtcgcaccc ccgtggtctt cctgcagaag gagggtgcca cggcactgag taacgacacg     540
taccaacctg tcgagctcgt tccgcagcag cgcaccgacg acggtgtcta ccgagggccg     600
ctgtggaaca ccaacgcggt caccgtggcc gacttcgacg gagacggcag acccgacatc     660
gctctgttca actacttccc ggacagtcag gtgctcgacc ccgaaggtct gcccaacgtg     720
cagatgaacc actccatgtc gcacggccac aacgccggcg gcgcacacgt cctgcgttgg     780
agcggtgcga cgtcggggga cgacccgacg gtgacctacg aggaacaggt cgccctcgac     840
ccgcggtacg ccaccggctg gaccctcggt gcggcctccg ccgacctcga cggggacctg     900
ctgccggagc tgtacctcgc caacgacttc ggccaggacc ggttcttcca acgtctcc      960
actcccggcc ggatccggtt caacctggcc gagggcgtcc gcacgcccct gacgcccaag    1020
tcgctggtgc tcgggcacga ctccttcaag ggcatgggcg tcgacttcgc cgacctgcac    1080
agtcggggac ggttcgacat gttcgtcagc aacatcaccg agtcctgggg gctggaggag    1140
agcaacttcg tctggcacaa caccgccgcg tccccggagg ccgcccggga gcagttgagt    1200
cgggggatcg ctcccttcga gaaccgggcg gcccggcgca acctcgcgtg ggtcggctgg    1260
ggttgggacg tgaagatggc ggacttcgac aacagcggcg gcctggaggt cgtgcaggcc    1320
gcaggattca tcaagggcga catcaaccgg ttcaactggc ttcaggaact ggccatggcc    1380
aacgacctga tgctgcggga gcccgccatg tggcccaacg ccaagcccgg cgacgacatc    1440
tccgggggca acccgtggcc cttctgggtc cgcgaggaca atggtcgata cgtgaacctg    1500
agcccggaac tggggctgga cgaggacacg ccgtcgcggg ggatctccgt cgccgatccc    1560
gacggcgacg cgcgcagga catcgcggtc gcccgacagt ggggcgcacc cgcctacttc    1620
cgtaacaccc gcggtgacag cgacaaccat ctgtcgctgc ggctgagccg gccggccctc    1680
gccgccgacg gacgtacccc gtcgaccacc ggcacgtcac ccgcctacgg cgcgcacgtc    1740
accatcacga ccgccgacgg tcggacccag gtcgacaaac tcgacggtgg tggcgggcac    1800
tccggacggc gcagcttcga cgtcttcttc ggtctcggcg acgcggccga ccgtccggtc    1860
tcggtgcagc tgtgctggcg agacctcaac ggccagacac accgacagac gatcgacctg    1920
accgccggcc ggcacgacct gctgctgacc gaccgagccg aggagttgaa ccgccgatga    1980
```

<210> SEQ ID NO 71
<211> LENGTH: 354
<212> TYPE: PRT
<213> ORGANISM: Micromonospora megalomicea

<400> SEQUENCE: 71

```
Met Thr Asp Val Lys Pro Val Glu Asp Ala Arg Gly Val Leu Thr Thr
1               5                   10                  15
```

```
Ala Ser Pro Asp Thr Ala Gly Arg Asn Gly Gly Asn Pro Val Pro Arg
        20                  25                  30

Gln Gln Ala Gly Gly Asp Arg Pro Gly Val Pro Arg Val Asp Ser
    35                  40                  45

Arg Asp Pro Arg Tyr Met Ala Leu Arg Asn Phe Ala Met Ser Met Thr
50                      55                  60

Val Phe Asn Ile Leu Gly Tyr Thr Val Leu Gly Phe Glu Gln Pro Trp
65                  70                  75                  80

Thr Trp Pro Phe Phe Ala Leu Ala Ile Gly Tyr Ala Thr Glu Ile Leu
                85                  90                  95

Val Glu Thr Val Ala Ala Arg Ala Thr Gly Arg Ser Ala Ala Tyr Ser
                100                 105                 110

Gly Asn Gly Met Trp Gly Met Tyr Thr Phe Leu Leu Pro Thr His Ile
            115                 120                 125

Thr Ala Leu Ala Ala Asn Met Leu Leu Tyr Ala Asn Asp Asn Phe Trp
130                 135                 140

Pro Ile Gly Phe Ala Val Val Ala Val Gly Gln Lys Ala Leu Leu
145                 150                 155                 160

Gln Ala Pro Ile Arg Gly Arg Met Arg His Phe Met Asn Pro Ser Asn
                165                 170                 175

Phe Gly Ile Thr Ala Thr Leu Leu Val Phe Ser Trp Val Asn Val Ala
                180                 185                 190

Pro Pro Tyr His Phe Thr Glu Asn Val Pro Asp Met Ile Ser Ile Leu
            195                 200                 205

Ile Pro Ile Val Ile Val Thr Ala Gly Thr Val Leu Asn Ala Met Leu
210                 215                 220

Thr Lys Lys Val Pro Leu Ile Val Gly Trp Leu Gly Ala Phe Ile Ile
225                 230                 235                 240

Gln Ala Leu Val Arg His Trp Ile Trp Asp Val Ser Leu Trp Gly Ala
                245                 250                 255

Leu Val Pro Ile Thr Gly Val Ala Phe Val Leu Phe Thr Asn Tyr Met
            260                 265                 270

Ile Thr Asp Pro Gly Thr Thr Pro Thr Ala Gly Trp Met Gln Phe Met
            275                 280                 285

Phe Gly Ala Ser Val Gly Met Val Tyr Gly Val Leu Met Val Phe Asn
290                 295                 300

Ile Val Tyr Thr Thr Phe Phe Ala Val Thr Ile Val Cys Leu Leu Arg
305                 310                 315                 320

Gly Leu Phe Trp Trp Gly Lys Trp Leu Leu Glu Arg Lys His Arg Asp
                325                 330                 335

Val Ser Leu Asp Pro Ala Pro Pro Ala Ala Val Ala Leu Pro Thr
            340                 345                 350

Ala Arg

<210> SEQ ID NO 72
<211> LENGTH: 1065
<212> TYPE: DNA
<213> ORGANISM: Micromonospora megalomicea

<400> SEQUENCE: 72
atgacggacg tcaaacccgt cgaggacgcc cgcggcgtcc tcaccacggc aagcccggac    60
accgccgggc gtaacggcgg caaccccgtg ccgcggcagc aggccggtgg cgaccggccg   120
ggcgtaccgc ccgggtggaa cagccgcgac ccgcgctaca tggcgctgcg caacttcgcg   180
```

-continued

```
atgtccatga ccgtcttcaa catcctgggc tacaccgtcc tcggcttcga gcagccctgg      240 acctggcccct tcttcgccct ggcgatcggc tatgccaccg agatcctggt ggagacggtc     300
gccgcgcggg cgacgggccg gtcggccgcc tacagcggaa acggcatgtg gggcatgtac     360
accttcctgc tgcccaccca catcaccgcg ctcgcggcca acatgctgct ctacgccaac     420
gacaacttct ggccgatcgg cttcgcggtc gtcgtggcgg tggggcagaa ggcgctgctg     480
caggcaccga tccggggtcg gatgcggcac ttcatgaacc cgtcgaactt cggcatcacg     540
gcaaccctgt tggtcttctc ctgggtcaac gtcgcgccgc cgtaccactt caccgagaac     600
gtgccggaca tgatcagcat cctgatcccg atcgtgatcg tgaccgccgg cacggtcctc     660
aacgcgatgc tgaccaagaa ggtcccctg atcgtcggct ggctgggcgc cttcatcatc     720
caggcgttgg ttcggcactg gatctgggac gtgtcgttgt ggggcgcgct ggtgccgatc     780
accggcgtgg cgttcgtgct gttcaccaac tacatgatca ccgaccccgg tacgaccccg     840
acagccggtt ggatgcagtt catgttcggg gcgagtgtgg gcatggtgta cggcgtgctg     900
atggtcttca acatcgtcta ccaccacttc ttcgccgtca cgatcgtctg tctgctgcgc     960
ggactgttct ggtgggggaa gtggctcctg gagcgcaaac accgggacgt ctccctggac    1020
ccggctccac cgccggccgc ggtggccctg ccgaccgccc gctga                    1065
```

<210> SEQ ID NO 73
<211> LENGTH: 1892
<212> TYPE: PRT
<213> ORGANISM: Saccharothrix aerocolonigenes

<400> SEQUENCE: 73

```
Val Arg His Gly Asp Asp Ala Asp Pro Ile Ala Ile Val Gly Met Ala
1               5                  10                  15

Cys Arg Tyr Pro Asp Ala Asp Pro Gln Gln Leu Trp Gln Met Val
                20                  25                  30

Leu Asp Gln Arg Gln Ala Phe Arg Ile Pro Pro Glu Arg Leu Asp
            35                  40                  45

Leu Ala Asp Tyr Phe Asp Ala Asp Arg Thr Ala Ala Asp Arg Ile Tyr
        50                  55                  60

Ser Ser Met Ala Ala Leu Ile Glu Gly Trp Glu Phe Asp Arg Ala Ala
65                  70                  75                  80

Phe Arg Ile Pro Gly Pro Ser Tyr Arg Ala Thr Asp Pro Ala His Trp
                85                  90                  95

Leu Ala Leu Glu Thr Ala Gly Arg Ala Leu Ser Asp Ala Gly Trp Pro
            100                 105                 110

Gly Ala Asp Gly Leu Ala Arg Asp Lys Val Ala Val Phe Gly Asn
        115                 120                 125

Ser Leu Thr Gly Glu Val Thr Arg Ala Thr Thr Met Arg Leu Arg Trp
130                 135                 140

Pro Tyr Val Arg His Ala Leu Thr Ala Ala Leu Ala Glu Ala Glu Ile
145                 150                 155                 160

Ser Thr Glu Gln Ala Gly Leu Leu Gly Arg Ala Glu Ala His Tyr
                165                 170                 175

Leu Ala Pro Phe Pro Ala Val Gly Asp Glu Thr Leu Ala Gly Ala Leu
            180                 185                 190

Ser Asn Thr Ile Ala Gly Arg Ile Cys Asn Tyr Phe Asp Leu His Gly
        195                 200                 205

Gly Gly Tyr Thr Val Asp Gly Ala Cys Ser Ser Ala Leu Leu Ala Val
    210                 215                 220
```

```
Val Thr Ala Cys Arg Ser Leu Arg Asp Gly Ser Ala Asp Val Val Leu
225                 230                 235                 240

Ala Gly Gly Val Asp Leu Ser Val Asp Pro Phe Glu Leu Val Gly Phe
                245                 250                 255

Ala Lys Thr Gly Ala Leu Thr Ala Gly Pro Met Arg Val Tyr Asp Glu
                260                 265                 270

Arg Ser Asp Gly Phe Ile Pro Gly Glu Gly Cys Gly Val Val Val Leu
                275                 280                 285

Met Arg Ala Ser Asp Ala Arg Ala Ala Gly Ala Arg Val Tyr Ala Glu
        290                 295                 300

Ile Thr Gly Trp Gly Leu Ser Ser Asp Gly Asn Gly Gly Ile Thr Arg
305                 310                 315                 320

Pro Glu Lys Gln Gly Gln Leu Leu Ala Leu Arg Arg Ala Tyr Ala Met
                325                 330                 335

Ala Gly Val Asp Pro Ala Glu Val Arg Leu Ile Glu Gly His Gly Thr
                340                 345                 350

Gly Thr Ala Val Gly Asp Glu Thr Glu Leu Ser Ala Leu Ala Glu Leu
            355                 360                 365

Arg Gly Gly Ala Arg Glu Gln Ala Val Val Gly Ser Ile Lys Ala Asn
        370                 375                 380

Ile Gly His Thr Lys Ala Ala Ser Gly Val Ala Gly Leu Ile Lys Ala
385                 390                 395                 400

Val Leu Ser Ile Ala Ser Gly Val Leu Pro Pro Val Thr Gly Cys Glu
                405                 410                 415

Arg Pro His His Val Leu Thr Ala Arg Glu Thr Pro Leu Arg Val Leu
                420                 425                 430

Thr Glu Ala Gln Pro Trp Pro Ala Gly Pro Arg Leu Ala Gly Val Ser
            435                 440                 445

Ser Phe Gly Phe Gly Gly Ile Asn Ala His Val Ala Leu Arg Asp Pro
        450                 455                 460

Val Thr Ala Leu Pro Arg Thr Val Ser Thr Pro Ile Arg Pro His His
465                 470                 475                 480

Arg Pro Ala Pro Arg Thr Asp Ala Phe Val Leu Ala Gly Ser Asp Ala
                485                 490                 495

Ala Glu Leu Arg Ala Thr Leu Glu Arg Ile Ala Glu Leu Ala Pro Arg
                500                 505                 510

Leu Ser Glu Ala Glu Leu His Asp Leu Ala Cys Gln Trp Gly Arg Asp
            515                 520                 525

Val Ala Pro Gly Glu His Arg Val Ala Leu Val Ala Ser Thr Pro Arg
        530                 535                 540

Gln Leu Ala Glu Arg Ala Val Val Ala Ala Arg Ser Leu Glu Ser Ala
545                 550                 555                 560

Pro Arg Gly Arg Leu Val Val Glu Asp Gly Val Phe Leu Gly Thr Ala
                565                 570                 575

Val Ala Gly Arg Val Thr Val Leu Leu Pro Gly Gln Gly Ala Pro Val
                580                 585                 590

Arg Ala Glu Leu Gly Ala Leu Gly Arg Asp Leu Ala Leu Thr Gly Gly
            595                 600                 605

Glu Leu Arg Leu Asp Glu Glu Leu Ala Gly Thr Arg Gly Thr Ala Thr
        610                 615                 620

Ala Gln Pro Ser Ile Phe Arg Ala Ser Leu Ala Ala Leu Arg Trp Leu
625                 630                 635                 640
```

-continued

```
Asp Arg Leu Gly Val Ala Gly Ala Ala Val Gly His Ser Leu Gly
            645                 650                 655
Glu Ile Ala Ala Leu Val Trp Ala Gly Cys Leu Ser Thr Glu Asp Ala
            660                 665                 670
Asp Arg Leu Val Arg Glu Arg Gly Arg Val Met Glu Asp Phe Gly Pro
            675                 680                 685
Arg Ala Thr Gly Met Val Gly Ile Val Ala Asp Val Pro Thr Ala His
            690                 695                 700
Gly Leu Cys Glu Gly Thr Gly Met Val Ala Cys Tyr Asn Gly Pro
705                 710                 715                 720
Arg Ser Gln Val Leu Ala Gly Ala Arg Thr Ala Ile Asp Glu Val Val
                725                 730                 735
Ala Arg Ala Ala Arg Leu Gly Val Gln Thr Val Val Leu Pro Val Thr
            740                 745                 750
His Gly Phe His Ser Pro Ala Met Ala Asp Gly Ala Thr Glu Phe Lys
            755                 760                 765
Pro Tyr Leu Gln Ser Val Gly Phe Arg Ala Pro Ala Ala Arg Leu Val
            770                 775                 780
Ser Thr Val Leu Gly Arg Thr Leu Ser Ala Gln Asp Asp Ile Gly Glu
785                 790                 795                 800
Leu Leu Gly Gln Gln Phe Thr Ala Pro Val Arg Phe Trp Gln Ala Met
                805                 810                 815
Asp Glu Val Leu Pro Asp Thr Asp Leu Phe Cys Glu Ala Gly Pro Gly
            820                 825                 830
Arg Thr Leu Ser Ala Leu Val Ala Ala Gly Cys Pro Val Pro Val Val
            835                 840                 845
Gly Val Asp Ala Gly Ala Leu Asp Asp Arg Pro Leu Ala Glu Thr Val
            850                 855                 860
Ala Ala Leu Phe Ala Ala Gly Ala Leu His Asp Leu Ser Pro Val Phe
865                 870                 875                 880
Thr Gly Arg Pro Ala Arg Pro Ile Asp Ile Trp Arg Asp Arg Arg Phe
                885                 890                 895
Leu Ala Asn Pro Cys Ser Ser Val Pro Asn Ala Lys Pro Ile Glu Val
            900                 905                 910
Val Pro Ile Glu Val Val Thr Pro Gly Glu Val Ala Pro Pro Ala Glu
            915                 920                 925
Glu Ile Arg Asp Pro Arg Thr Val Val Leu Glu Leu Ala Glu Ala
            930                 935                 940
Ser Glu Leu Asp Val Ala Ser Leu Asp Pro Arg Ala Arg Leu Leu Gly
945                 950                 955                 960
Asp Leu His Leu Thr Ser Leu Ala Val Thr Gln Leu Val Leu Ala Ala
                965                 970                 975
Val Asp Ala Ala Gly Arg Glu Arg Pro Ala Ala Pro Leu Ala Leu Ala
            980                 985                 990
Asp Ala Ser Ile Ala Glu Leu Ile Glu Thr Ile Glu Asn Leu Pro Ala
            995                 1000                1005
Ala Glu  Ala Ile Gly Glu Asn  Glu Pro Val Ala Gly  Val Ala Ser
    1010                1015                 1020
Trp Ile Arg Cys Phe Ala Glu  Val Pro Gly Pro Val  Val Glu Pro
        1025                1030                1035
Gly Pro  Pro Gly Gly Thr Arg  Arg Trp Arg Ile His  Ile His Ser
    1040                1045                1050
Gly Gln  Arg Pro Asp Val Ala  Asp Glu Ile Arg Leu  Leu Phe Gly
```

-continued

```
         1055                1060                1065
Gly Ser  Asp Ala Gly Ser Gly  Asp Val Ala Asp  Leu Leu Tyr Leu
         1070                1075                1080
Pro Asp  Pro Ser Ala Gln Glu  Ala Val Gly Thr  Leu Leu Ser Ala
         1085                1090                1095
Val Ser  Ser Ala Leu Gly Ser  Gly Arg Leu Val  Ile Thr His
         1100                1105                1110
Gly Ser  Gly Leu Ser Gly Phe  Leu Arg Ser Leu  Arg Met Glu His
         1115                1120                1125
Pro Arg  Leu Gly Val Thr Leu  Leu Arg Val Pro  Pro Gly Val Asp
         1130                1135                1140
Gly Val  Arg Ala Ala Ala Arg  His Ala Val Val  Ala Ala Gly Glu
         1145                1150                1155
Trp Arg  Glu Leu Val Val Gly  Ala Glu Gly Val  Ala Thr Glu Pro
         1160                1165                1170
Ala His  Arg Pro Val Trp His  Leu Ser Asp Gly  Glu Pro Pro Leu
         1175                1180                1185
Gly Glu  Arg Asp Val Leu Leu  Val Thr Gly Gly  Gly Lys Gly Ile
         1190                1195                1200
Gly Tyr  Glu Cys Ala Ala Ala  Leu Ala Arg Arg  Ser Gly Ala Ala
         1205                1210                1215
Leu Ala  Leu Val Gly Arg Ala  Asp Pro His Ala  Asp Glu Leu Leu
         1220                1225                1230
Arg Ser  Asn Val Asp Asn Leu  Ser Ala Ala Gly  Leu Arg Val Ala
         1235                1240                1245
Tyr Glu  Ser Val Asp Val Ala  Asp Pro Ala Ala  Val Glu Ala Gly
         1250                1255                1260
Val Arg  Arg Leu Glu Gln Arg  Leu Gly Pro Ile  Thr Ala Leu Met
         1265                1270                1275
His Ala  Ser Gly Val Asn Glu  Pro Thr Arg Phe  Asp Pro Leu Asp
         1280                1285                1290
Asp Thr  Arg Phe Thr Thr His  Leu Ala Pro Lys  Thr Ile Gly Leu
         1295                1300                1305
Arg Asn  Leu Leu Ala Ala Leu  Glu Pro Arg Arg  Leu Arg Leu Leu
         1310                1315                1320
Val Thr  Phe Gly Ser Val Ile  Gly Arg His Gly  Leu Thr Gly Glu
         1325                1330                1335
Cys His  Tyr Ala Phe Ala Asn  Gly Ala Leu Arg  Ala Glu Ala Glu
         1340                1345                1350
Arg Leu  Ala Ala Glu Leu Pro  Asp Cys Arg Val  Leu Asn Leu Asp
         1355                1360                1365
Trp Ser  Val Trp Ser Gly Ala  Gly Met Gly Glu  Ser Leu Gly Val
         1370                1375                1380
Leu Asp  Thr Leu Leu Arg Leu  Asp Val Thr Pro  Ile Pro Val Pro
         1385                1390                1395
Glu Gly  Val Glu Leu Phe Leu  Arg Leu Leu Gly  Thr His Asp Leu
         1400                1405                1410
Pro Thr  Thr Val Ala Val His  Gly Arg Leu Gly  Gly Leu Phe Thr
         1415                1420                1425
Val Gly  Lys Pro Leu Phe Gly  Gly Arg Phe Leu  Glu Thr Val Pro
         1430                1435                1440
Ala Tyr  Cys Pro Glu Val Glu  Leu Val Ala Asp  Ser Arg Leu Asp
         1445                1450                1455
```

-continued

```
Leu Asp Arg Asp Ala Tyr Leu Arg Asp His Arg Ile Asp Gly Leu
    1460                1465                1470

Ala Val Leu Pro Ala Val Val Gly Met Glu Ala Met Ala Gln Val
    1475                1480                1485

Ala Ser Ala Leu Ala Gly Arg Pro Leu Arg Glu Met Thr Asp Val
    1490                1495                1500

Thr Leu Glu Arg Pro Val Ile Val Pro Glu Asp Gly Asp Arg Met
    1505                1510                1515

Val Arg Val Cys Ala Leu Arg Gln Asp Asp Ala Val Leu Val Val
    1520                1525                1530

Leu Arg Ser Asp Glu Thr Arg Cys Gln Val Asp His Phe Arg Ala
    1535                1540                1545

Arg Phe Pro Leu Thr Pro Val Ser Gly Ala Thr Pro Ser Glu Glu
    1550                1555                1560

Asp Phe Pro Glu Gly Glu Ala Gly Leu Asn Gly Asp Glu Leu Tyr
    1565                1570                1575

Gly Pro Leu Phe Phe His Thr Gly Arg Phe Arg Leu Val Arg Arg
    1580                1585                1590

Phe Ser Ala Leu Ala Ala Arg His Cys Arg Val Arg Leu His Ala
    1595                1600                1605

Ser Glu His Ala Pro Asp Gly Leu Ala Leu Leu Gly Asp Pro Ser
    1610                1615                1620

Leu Leu Gly Asp Leu Ala Ser Asn Asp Ala Thr Val His Ala Leu
    1625                1630                1635

Gln Ala Cys Val Pro His Arg Arg Leu Leu Pro Val Gly Cys Glu
    1640                1645                1650

Arg Phe Ala Val Glu Pro Asp Ala Gly Ala Ala Val Glu Val Leu
    1655                1660                1665

Ala Ser Glu Arg His Ala Gly Gly Gly Glu Tyr Val Trp Asp Val
    1670                1675                1680

Val Ala Leu Asp Arg Asp Gly Arg Arg Arg Ala Ser Trp Ser Gly
    1685                1690                1695

Leu Arg Leu Arg Asp Thr Gly Ser Leu Pro Ala Ser Gly Pro Trp
    1700                1705                1710

Ala Ala Ala Leu Leu Ser Val Tyr Leu Glu Arg Ser Val Leu Ala
    1715                1720                1725

Leu Val Pro Ala Pro Arg Leu Thr Val Arg Ile Gly Ala Gly Glu
    1730                1735                1740

Arg Phe Gly Gly Ser Arg Ser Arg His Ala Gly Pro Ala Asp Leu
    1745                1750                1755

Ser Gly Arg Glu Cys Arg Ser Tyr Gln Asn Gly Met Val Leu Ser
    1760                1765                1770

Val Ser Ala Ala Ala Arg Val Ala Cys Asp Trp Glu Ala Val Gly
    1775                1780                1785

Arg Arg Thr Asp Asp Glu Trp Leu Leu Leu Val Gly Ser Arg Phe
    1790                1795                1800

Glu Pro Leu Ile Gly Gln Leu Arg Thr Met Leu Thr Glu Pro Val
    1805                1810                1815

Thr His Thr Ala Ala Arg Val Trp Thr Ala Val Glu Cys Leu Ser
    1820                1825                1830

Lys Ile Gly Tyr Pro Pro Gly Val Pro Leu Val Leu Gly Gly Val
    1835                1840                1845
```

```
Tyr Asp Glu Gly Trp Val Val Leu Arg Thr Gly Ser Val Thr Leu
    1850                1855                1860

Val Ser Thr Val Val Pro Ile Ser Gly Ala Asp Ser Pro Val Ala
    1865                1870                1875

Val Ala Val Leu Val Ala Ala Pro Glu Gly Gly Asp Arg Gly
    1880                1885                1890

<210> SEQ ID NO 74
<211> LENGTH: 5679
<212> TYPE: DNA
<213> ORGANISM: Saccharothrix aerocolonigenes

<400> SEQUENCE: 74
gtgaggcacg cgacgacgc ggacccgatc gcgatcgtgg gaatggcctg ccgctacccg      60
gacgcggacg atccgcagca gctgtggcag atggtgctgg accagcgcca ggcgttccgg     120
cgtatcccgc cggaacgcct ggatctcgct gactacttcg acgccgaccg caccgcggcc     180
gaccggatct acagctcgat ggcggcgttg atcgagggct gggagttcga ccgcgccgcg     240
ttccggattc ccggaccgtc gtaccgcgcg accgacccgg cgcactggct cgcactggag     300
acggcaggtc gtgcgctgtc cgacgccggc tggcccggtg cggatggcct ggcacgcgac     360
aaggtcgcgg tcgtgttcgg caacagcctg accggcgagg tgaccagggc gacaacgatg     420
cggctgcgct ggccttatgt gcggcacgcg ctcacgcccg cgctcgcgga ggcggagatc     480
tccaccgagc aggccgggtt gctgctcggc cgggccgagg cgcactacct cgcgccgttt     540
cccgccgtcg gggacgagac cctcgcgggt gcgctgtcca acacgatcgc gggccggatc     600
tgcaactact tcgacctcca cggcggtggg tacacagtgg acggtgcctg ctcctcggcg     660
ctgctcgcgg tcgtcaccgc ctgccggtcg ttgcgggacg gcagtgccga cgtggttctc     720
gccggcggcg tcgacctcag cgtcgacccg ttcgagctgg tcggtttcgc caagaccgga     780
gcgctgaccg cggggccgat gcgggtgtac gacgagcgat cggacggctt catccccggc     840
gagggctgcg gcgtcgtggt gctgatgcgt gcctcggacg cgcgtgccgc ggggcgcgg      900 gtctacgccg agatcaccgg atggggcctg tcgtccgacg gaacggggg gatcaccaga     960 cccgagaagc agggccagtt gctcgcgttg cgccgtgcct acgccatggc gggcgtcgac    1020
cccgccgaag tgcggttgat cgaaggcaca ggcaccggaa ccgcggtggg cgacgaaacc    1080
gagctgagcg ccctcgccga actgcgcggc ggagcccgtg agcaggcggt ggtcggctcg    1140
atcaaggcca acatcggcca caccaaagcc gcgtccggtg tcgccgggct gatcaaggcc    1200
gtgctgagca tcgcgtcggg tgtgctgccg cctgtcactg gatgtgaacg gccccaccac    1260
gtgctcaccg cgagggagac accgctgcgc gtgctgaccg aggcccagcc gtggccggcc    1320
ggaccgaggc tggccggggt gagctccttc gggttcggtg gcatcaacgc gcacgtcgcg    1380
ttgcgcgatc ctgtcacggc actgccacgt accgtctcga cgccgatcag gccgcaccac    1440
cgtccggcgc cacgcaccga cgcgttcgtc ctcgcgggca gcgatgccgc cgagctgcgc    1500
gccacgctcg agcggatcgc ggagctggct ccccggctct ccgaggcgga gctgcacgac    1560
ctggcctgcc agtggggccg cgacgtcgct cccggtgagc atcgggtcgc cctggtggcg    1620
agcacgccgc ggcaactggc cgaacgggcg gtggtcgcgg gcggagcct cgaatccgca    1680 ccgcgaggca ggctggtcgt cgaggacggg gtcttcctcg gcacgccgt cgcgggcagg    1740 gtcacggtgc tgctgcccgg tcagggcgcg cccgtccgag cggaactggg cgcgctcggc    1800
cgggacctcg cgctgaccgg cggcgagctc cggctgacga ggaactggc ggggacgcgg    1860
```

```
ggaaccgcca ccgcgcagcc gtcgatcttc cgggcgagcc tggccgcact gcgctggctc    1920
gaccggctgg gtgtcgtcgc cggtgccgcc gtcggccaca gcctcggtga gatcgccgcg    1980
ctggtgtggg cgggctgtct gtccactgag gacgcggacc ggctggtgcg ggagcgtggc    2040
agggtgatgg aggacttcgg tccccgtgcc accggcatgg tcggaatcgt cgcggacgtg    2100
ccgaccgcgc acgggttgtg cgagggcacc gggatggtcg tggcctgcta caacggaccg    2160
cgctcgcagg tgctcgccgg tgcgcggacc gccatcgacg aggtcgtcgc acgcgcggca    2220
cgactgggtg tgcagaccgt cgtcctgccg gtcacgcacg ggttccactc gcccgcgatg    2280
gccgacggtg ccaccgagtt caagccgtac ctgcagtcgg tcggcttccg cgccccggcc    2340
gccaggctgg tctcgacggt gctcggacgc acgctcagcg cacaggacga catcggtgag    2400
ttgctggggc agcagttcac cgcaccggtg cggttctggc aggcgatgga cgaggtgctg    2460
cccgacaccg acctcttctg cgaggccggt cctggacgca cgttgtcggc tctggtcgcg    2520
gccggttgcc cggttcccgt ggtcggcgtc gacgccggcg cgctggacga ccggcctctc    2580
gccgagacgg tcgcggccct cttcgccgcc ggtgcgctgc acgacctgag ccctgtcttc    2640 accggcggc ccgcacgccc gatcgacatc tggcgtgacc gccggttcct ggccaacccc    2700
tgctcgtccg tgccgaacgc caagccgatc gaggtcgtgc ccatcgaggt ggtcaccccc    2760
ggcgaggtcg cccctccggc ggaggagatc agggacccgc ggacggtcgt gctcgaactg    2820
ctcgccgagg cgagtgagct ggacgtggca tcgctcgacc cgcgggctcg cctgctcggt    2880
gacctgcacc tgacctcgct cgcggtcacc cagctcgtcc tcgccgcggt cgacgcggcg    2940
ggcagggagc gtcccgcggc gccgctggcg ctggccgacg cgtcgatcgc cgagctgatc    3000
gagacgatcg agaacctgcc cgcggccgag gcgatcgggg agaacgagcc cgttgccggg    3060
gtggcgtcct ggatccggtg cttcgccgag gttccggggc cggtcgtcga gcccgggcca    3120
ccgggtggaa cccggcgctg gcgcatccac atccacagtg gacagaggcc cgatgtggcc    3180
gacgagatcc ggctgctgtt cggcggatcg gatgccggct ccggagatgt cgccgacctg    3240
ttgtacctgc ccgacccgtc ggctcaggag gcggtcggca cactgctctc gcggtcagc    3300 tcggcgctcg gttcgggccg gctggtcgtc atcacccacg ggtccggcct gagcggattc    3360
ctgcgcagcc tgcggatgga acatcccagg ctgggcgtca cgctcctgcg cgttccgccc    3420
ggtgtcgacg gagtacgcgc ggcggcccgc cacgccgtcg tggcggcggg agagtggcgg    3480
gaactggtcg tcggcgccga gggcgttgcc accgaaccgg cgcatcggcc ggtgtggcac    3540
ctgtccgacg gcgaaccgcc gctggggag cgggacgtcc tcctggtcac cggtggcggc    3600
aagggcatcg gctacgagtg cgcggcggcg ctcgcccggc ggtccggtgc cgcgctggcc    3660
ctggtcggcc gagccgaccc gcacgccgac gagctcctgc ggtccaatgt ggacaatctg    3720
agtgcggcgg gactgcgggt cgcctacgag tcggtggacg tcgcggaccc cgcggcggtg    3780
gaggcgggcg tgcgtcgcct ggagcagcgc ctcggcccga tcacgccct gatgcacgcg    3840 agcggggtca acgaaccgac gaggttcgac ccgctggacg acacccggtt caccacccac    3900
ctggcaccca agacgatcgg gctgcgcaac ctcctggccg cgctcgaacc ccggcggctc    3960
cggttgctgg tgacgttcgg ctcggtgatc ggccgccacg ggctcacggg cgagtgccac    4020
tacgccttcg ccaacggggc gttgcgggcg gaggcggaac ggctggcggc tgaactcccct   4080 gactgccgcg tgctcaacct ggactggtcg gtgtggtccg gtgcgggaat gggggagtcg    4140
ctgggtgtgc tcgacacccct gctgcgcctg gacgtgaccc cgatcccggt gccggaaggc    4200
gtggagctct tcctcaggtt gctgggcaca cacgatctgc cgaccacggt cgcggtacac    4260
```

-continued

```
ggccggctcg gtgggctgtt caccgtcggg aaacccecttt tcggcggccg tttcctggaa    4320
acggtgcccg cgtactgccc cgaggtcgaa ctggtcgccg actcccggtt ggatctcgat    4380
cgcgacgcgt acctgcgcga ccaccgcatc gacgggctgg ccgtgttgcc cgccgtggtg    4440
gggatggagg cgatggcgca ggtggcctcc gcgctggccg ccgtccgct gcgggagatg     4500
accgacgtga cgctggaacg gcccgtgatc gtccccgagg acggcgaccg gatggtccgg    4560
gtatgcgcgt tgcgtcagga cgacgccgtc ctggtggtgc tgcgcagcga cgagacccgt    4620
tgtcaggtgg accacttccg cgccaggttt cctctcacgc cggtcagcgg tgccactccg    4680
tccgaagagg acttcccgga aggcgaagcc ggtctgaacg gtgacgagct gtacgggcca    4740
ctgttcttcc acaccggcag gttccggctg gtgcggaggt tctcggcgtt ggccgcacga    4800
cactgccggg tccggctgca cgcatcggag cacgcgcccg acggtctggc cctgctgggt    4860
gacccgagcc tgttgggtga tctggcgagc aacgacgcga ccgtcacgc gttgcaggcc     4920
tgcgtgccgc accggcggct gctgccggtc ggttgtgagc gtttcgccgt cgaacccgat    4980
gcgggcgccg cggtggaggt gctcgcgtcc gaacggcacg ccggtggcgg tgagtacgtc    5040
tgggacgtcg tggcactgga ccgcgatggc aggcgacggg cgagctggtc ggggctgcga    5100
ctgcgcgaca cgggttcgtt gccggcgtcc gggccgtggg ctgccgcgct actctccgtc    5160
tacttggaac ggtcggtgct cgcgctggtt cccgctcccc ggttgaccgt gcggatcggt    5220
gcgggcgaga ggttcggcgg tagcaggtca cgtcacgccg gtcccgcgga cctgtcagga   5280
cgggaatgcc gcagctacca gaacgggatg gtgctgagcg tctccgccgc cgcccgcgtc    5340
gcgtgcgact gggaagcggt cggacggaga accgacgacg agtggctgct gctggtcggc    5400
tcgcggttcg agccgctcat cgggcagctc cgcacgatgc tgaccgaacc ggtcacacac    5460
accgcggcca gggtctggac cgccgtcgag tgcctctcca agatcggcta tccgcccggt    5520
gtgccgctcg tcctcggcgg tgtctacgac gagggctggg tggtgctgcg caccggatcc    5580
gtgacgctcg tttccacggt ggtgcccatc agcggcgccg actcaccggt agccgtcgcc    5640
gtgctggtcg cagcaccgga aggcggtgac cgtggctag                           5679
```

<210> SEQ ID NO 75
<211> LENGTH: 143
<212> TYPE: PRT
<213> ORGANISM: Saccharothrix aerocolonigenes

<400> SEQUENCE: 75

```
Val Thr Val Ala Arg Thr Phe Asp Tyr Arg His Val Ile Thr Leu Glu
1               5                   10                  15
Glu Thr Asn Leu Val Gly Asn Val Tyr Phe Thr Asn Tyr Leu Arg Trp
            20                  25                  30
Gln Gly His Cys Arg Glu Arg Phe Leu Met Glu His Ala Pro Gly Val
        35                  40                  45
Leu Arg Ala Leu Arg Gly Ala Leu Ala Leu Val Thr Val Ser Cys Gln
    50                  55                  60
Cys Asp Phe Phe Asp Glu Leu Phe Ala Ser Asp Thr Val Glu Leu Arg
65                  70                  75                  80
Met Ala Leu Gln Gly Thr Ser Asp Asn Arg Val Thr Met Ala Phe Asp
                85                  90                  95
Tyr Tyr Arg Thr Ser Gly Ser Val Ala Gln Leu Val Ala Arg Gly Ser
            100                 105                 110
Gln Thr Ile Ala Cys Met Ser Arg Thr Glu Glu Gly Thr Val Pro Val
```

```
                115                 120                 125
Ser Val Pro Ala Glu Leu Arg Asp Ala Leu Ser His Tyr Ala Glu
    130                 135                 140

<210> SEQ ID NO 76
<211> LENGTH: 432
<212> TYPE: DNA
<213> ORGANISM: Saccharothrix aerocolonigenes

<400> SEQUENCE: 76
gtgaccgtgg ctaggacgtt cgactaccgg cacgtgatca ccctcgagga gacgaacctg      60
gtcgggaacg tctacttcac gaactacctg cgctggcagg gacattgccg tgaacgtttc     120
ctgatggagc acgcgccgg tgtgctccgc gcgttgcgag gggcactcgc cctggtcacg      180
gtctcctgcc agtgcgactt cttcgacgag ctcttcgcgt cggacacggt cgaactccgc     240
atggcgttgc agggcaccag cgacaacagg gtcacgatgg cgttcgacta ctaccggacc     300
tcgggttcgg tggcgcagct ggtggccagg ggcagtcaga ccatcgcgtg catgagcagg     360
accgaggagg ggaccgtgcc ggtgagcgtg cccgccgaac tgcgggacgc gttgtcgcac     420
tacgccgagt ga                                                         432

<210> SEQ ID NO 77
<211> LENGTH: 313
<212> TYPE: PRT
<213> ORGANISM: Saccharothrix aerocolonigenes

<400> SEQUENCE: 77

Val Ala Ala Leu Gly Gln Glu Leu Asp Gln Val Asp Phe Gly Arg Arg
1               5                   10                  15

Arg Phe Arg Leu Arg Thr Gly Pro Ala Arg Glu Thr Leu Glu Arg Ala
            20                  25                  30

Gly Arg Ser Phe Leu Glu Gly Phe Asn Ala Ala Val Ala Tyr Pro Ala
        35                  40                  45

Asp Asp Arg Leu Ala Ser Glu Ile Glu Arg Ile Asp Val Pro Leu Arg
    50                  55                  60

Gly Phe Ala Tyr Glu Gly Ala Gly Met Ala Cys Ala Val Leu Asp Ile
65                  70                  75                  80

Leu Thr Leu Ser Gly Gly Arg Asn Thr Arg Ala Leu Leu Arg Gly Pro
                85                  90                  95

Ala Ser Asp Tyr Pro His Leu Val His Val Gly Val Gly Trp Ala Phe
            100                 105                 110

Ala Arg Leu Arg Leu Arg Pro Gly Trp Gly Arg Ala Val Val Arg Asp
        115                 120                 125

Pro Leu Leu Arg Trp Leu Ala Trp Asp Gly Tyr Gly Phe His Gln Gly
    130                 135                 140

Phe Phe His Thr Asp Arg Val Ile Gly Gly Lys Val Val Glu His Gly
145                 150                 155                 160

Leu Thr Glu Asp Gln Arg Ala Ile Arg Asp Gln Gly Val Gly Arg Ser
                165                 170                 175

Leu Trp Phe Gln Glu Cys Ala Asp Pro Glu Ala Val Ala Leu Arg Ile
            180                 185                 190

Asp Asp Phe Pro Arg Asn Arg Arg Pro Asp Leu Trp Ser Gly Val Gly
        195                 200                 205

Leu Ala Ala Thr Tyr Ala Gly Gly Val Arg Ala Asp Glu Leu Glu Ser
    210                 215                 220
```

```
Leu Ala Leu Ala Gly Glu Tyr Arg Ala Asp Leu Ala Gln Gly Cys
225                 230                 235                 240

Ser Phe Ala Cys Glu Ala Arg Arg Val Ser Gly Val Val Pro Glu His
            245                 250                 255

Thr Arg Leu Ala Ala Pro Ile Leu Ala Gly Val Thr Ala Asp Val Ala
        260                 265                 270

Gly Ser Trp Ala Asn Arg Ala Gln His Ala Leu Gly Pro Ala Asp Gly
    275                 280                 285

Thr Ser Ala Gln Tyr Gln Gln Trp Arg Ala Gly Ile Arg Asn Leu Trp
    290                 295                 300

Ala Asp Asn Met Glu Gly Gln Pro Ser
305                 310
```

<210> SEQ ID NO 78
<211> LENGTH: 942
<212> TYPE: DNA
<213> ORGANISM: Saccharothrix aerocolonigenes

<400> SEQUENCE: 78

```
gtggcggcac tcggtcagga actcgaccag gtcgacttcg ggaggcgccg gttccggctg    60
cggaccggcc cggcgcgcga acgctggaaa cgtgcgggcc ggtcgttcct cgaagggttc   120
aacgcggccg tggcgtatcc ggccgacgac cgtctggcca gtgagatcga gcgcatcgac   180
gttccactgc gcgggttcgc ctacgagggc gccggtatgg cctgcgcggt cctcgacatt   240
ctgacgctgt ccggcggcag gaacacgcgc gcgctgctgc gcggcccggc gagcgactat   300
ccgcacctgg tgcacgtggg agtcggctgg gcgttcgcga ggctgcggct gcgcccgggc   360
tgggggcgcg cggtcgtgag ggatccgttg ctgcgctggc tcgcctggga cggctacggg   420
ttccaccagg gcttcttcca caccgatcgg gtcatcggcg gcaaggtcgt cgagcacgga   480
ctgaccgagg accagcgggc catccgcgac caggggtcg gcaggtcgct gtggttccag   540
gagtgcgcgg accccgaggc ggtggccctg cgtatcgacg acttcccccg gaaccgccgg   600
cctgacctgt ggagtggcgt cggcctggcc gcgacctacg cgggtggcgt gcgagcggac   660
gaactcgagt cgctggctct gctcgccggg gagtaccgcg ccgacctcgc gcagggatgt   720
tccttcgcct gcgaggcacg ccgggtctcc ggtgtcgtgc ccgaacacac caggctggcc   780
gcgccgatcc tcgccggtgt gaccgccgat gtcgccggat cgtgggcgaa ccgggcgcag   840
cacgccctcg gtcccgcgga cggcacgtcc gcgcagtacc agcagtggcg cgccgggatc   900
cggaatctgt gggccgacaa catggaaggg cagccgtcgt ga                      942
```

<210> SEQ ID NO 79
<211> LENGTH: 647
<212> TYPE: PRT
<213> ORGANISM: Saccharothrix aerocolonigenes

<400> SEQUENCE: 79

```
Val Leu Ser Ala Pro Gly Phe Arg Arg Phe Val Pro Lys Ile Ala Ala
1               5                   10                  15

Ala Leu Cys Cys Val Leu Ala Trp Val Leu Ala Gln Pro Pro Ser Val
            20                  25                  30

Ala Ala Glu Asp Arg Ala Arg Leu Ala Thr Arg Phe Gly Phe Asp His
        35                  40                  45

His Ala Ile Ser Pro Ala Asp Arg Asp Gly Asp Arg Arg Met Arg Ala
    50                  55                  60

Val Ala Pro Val Tyr Glu Arg Ile Arg Asn Trp Val Ser Ser Val Gly
```

-continued

```
             65                  70                  75                  80
Ala Gly Ala Gly Leu Phe Ala Val Asp Gly Gly Val Val Ser His Asp
                     85                  90                  95
Ile Cys Leu Val Asp Pro Arg Thr Asp Thr Val Thr Val Glu Pro Ala
                    100                 105                 110
Pro Thr Thr Gly Glu Arg Tyr Ala Ala Phe Thr Leu Lys Pro Ala Thr
                    115                 120                 125
Leu Pro Tyr Ala Gly Tyr Val Ala Pro Met Gly Cys Leu Pro Ala Asp
            130                 135                 140
Leu Asn Glu Asp Gly Trp Gln Asp Val Val Tyr Tyr Trp Gly Arg
145                 150                 155                 160
Ser Pro Val Leu Phe Leu Arg Thr Pro Gly Ser Ala Pro Ala Ala
                    165                 170                 175
Gly Phe Ser Glu Arg Glu Leu Val Ser Pro Pro Gln Val Trp Asn Thr
                    180                 185                 190
Asn Ala Ala Thr Thr Ala Asp Leu Asp Gly Asp Gly His Leu Asp Leu
            195                 200                 205
Phe Phe Gly Asn Tyr Phe Pro Asp Gly Ala Arg Val Leu Asp Pro Thr
    210                 215                 220
Ala Gln Gln Pro Glu Leu Val Met Thr Asp Ser Leu Ser Asp Gly His
225                 230                 235                 240
Asn Gly Gly Thr His Arg Tyr Phe Arg Phe Ala Ser Ala Thr Gly Gly
                    245                 250                 255
Ser Thr Pro Asp Val Arg Tyr Ala Glu Ala Val Asp Pro Val Glu Gly
                    260                 265                 270
Asp Ser Arg Thr Thr Gly Trp Thr Leu Ala Ala Ala Gln Asp Val
            275                 280                 285
Asp Gln Asp Gly Leu Pro Glu Leu Tyr Val Ala Asn Asp Phe Ser Pro
    290                 295                 300
Asp Gln Leu Leu Val Asn Val Ser Thr Pro Gly Gln Ile Arg Phe Arg
305                 310                 315                 320
Glu Ala His Gly Glu Arg His Ala Leu Thr Pro Lys Ser Lys Val Val
                    325                 330                 335
Gly Asn Asp Ser Phe Lys Gly Met Gly Ala Ser Phe Ala Asp Leu Asn
                    340                 345                 350
Asn Asp Gly Met Pro Asp Ile Leu Val Ser Asn Ile Thr Glu Pro Tyr
            355                 360                 365
Ala Leu Gln Glu Ser Asn Phe Ala Phe Ile Ser Thr Gly Asp Arg Asp
    370                 375                 380
Ala Leu Arg Arg Gly Val Ala Pro Phe Asp Asp Arg Ser Glu Glu Leu
385                 390                 395                 400
Gly Leu Ser Arg Ser Gly Trp Ser Trp Asp Val Lys Ala Ala Asp Phe
                    405                 410                 415
Asp Asn Asp Gly Ala Ala Glu Val Met His Ala Thr Gly Phe Ile Arg
            420                 425                 430
Gly Thr Thr Asn Arg Trp Pro Gln Met Gln Glu Ala Ala Met Ser Asn
    435                 440                 445
Asp Leu Ile Leu Gly Asn Pro Ala Leu Trp Pro Arg Phe Thr Glu Glu
    450                 455                 460
Asp Gly Leu Ser Gly His Asp Arg Asn Thr Phe Phe Thr Arg Asp Gly
465                 470                 475                 480
Ala Gly Arg Phe Ala Asp Val Ala Asp Leu Val Gly Val Gly Thr Asp
                    485                 490                 495
```

```
Ala Val Ser Arg Ala Phe Ala Val Gly Asp Val Asp Gly Asp Gly Arg
            500                 505                 510

Leu Asp Phe Val Val Ala Asn Gln Trp Ala Gln Ser Thr Leu Tyr Arg
            515                 520                 525

Asn Thr Ser Gln Ser Ser Ala Glu Phe Val Gly Leu Arg Leu Arg Gln
            530                 535                 540

Pro Ala Asp Val Gly Thr Cys Ala Gly Asn Ser Glu Gly Ala Asp Arg
545                 550                 555                 560

Pro Ala Ile Gly Ala Thr Ala Val Val Thr Thr Pro Asp Gly Thr Lys
                565                 570                 575

His Ser Gln Gln Val Tyr Pro Ala Asn Gly His Asn Gly Val Asn Ala
            580                 585                 590

Pro Asp Leu Val Phe Gly Leu Gly Asp Val Arg Asp Gly Pro Leu Pro
            595                 600                 605

Val Glu Leu Ser Trp Arg Asp Gly Cys Gly Arg Arg His Thr Ala Thr
            610                 615                 620

Val Asn Val Ala Pro Gly Trp His Arg Ile Leu Leu His Ala Asp Gly
625                 630                 635                 640

Thr Thr Met Val Glu Asp Lys
                645

<210> SEQ ID NO 80
<211> LENGTH: 1944
<212> TYPE: DNA
<213> ORGANISM: Saccharothrix aerocolonigenes

<400> SEQUENCE: 80
gtgctttccg ctccggggtt ccgccggttc gtgccgaaga tcgccgcggc gctgtgctgc     60
gtgctggcgt gggtcctggc ccagccgccg tcggtcgccg ccgaggaccg cgcccgtctc    120
gccacccgct tcgggttcga ccaccacgcg atcagtcccg ccgaccgtga cggcgaccgg    180
cggatgcggg cggtggcgcc cgtctacgaa cggatccgca actgggtgtc ctccgtcggc    240
gccggggccg gtctgttcgc tgtggacggt ggcgtcgtct cgcacgacat ctgcctcgtc    300
gatccacgca ccgacacggt gaccgtcgaa ccggcgccca ccaccggtga gaggtacgcg    360
gccttcaccc tcaagccggc caccctgccc tatgccggct acgtcgcccc gatgggatgc    420
ctgcccgccg acctcaacga ggacggctgg caggacgtgg tcgtctacta ctggggccgg    480
tcgccggtgt tgttcctgcg cacgccgggc agtgcgcccg cggccgccgg gttctccgaa    540
cgcgagctcg tcagcccgcc gcaggtctgg aacaccaacg ccgccacgac cgccgacctg    600
gacggggacg gccacctgga cctgttcttc ggcaactact ccccgacggg ggcgcgggtg    660
ctcgatccca cggcgcagca gccggaactg gtcatgaccg actcgttgtc cgacggccac    720
aacggtggta cccaccgcta cttccgcttc gcgagcgcga cgggtgggag cacgcccgac    780
gtgcggtacg cggaggcggt cgacccggtc gaagggggact cccgcaccac cggctggacg    840
ctcgcggcag cggcccagga cgtcgaccag gacggcctgc cgagctcta cgtcgccaac    900 gacttcagtc cggaccagtt gctggtcaat gtgtccacgc ccggtcagat caggttccgg    960
gaggcgcacg gcgagcgaca cgcgctgacg ccgaagtcca agtggtcgg caacgactcc   1020 ttcaagggca tgggagcgag cttcgccgac ctcaacaacg acggcatgcc ggacatcctg   1080
gtcagcaaca tcaccgagcc ctacgcgttg caggagagca acttcgcctt catcagcacg   1140
ggcgatcggg atgcgctcag gcgaggtgtc gccccccttcg acgaccgcag cgaggaactc   1200
```

-continued

```
gggctgtccc gttccggctg gagctgggac gtcaaggcgg ccgacttcga caacgacggt    1260
gcggccgagg tcatgcacgc caccggcttc atccgcggca ccacgaaccg gtggccgcag    1320
atgcaggagg cggccatgtc gaacgacctc atcctcggca atcccgcgct gtggccccgg    1380
ttcaccgagg aggacggcct gtccggtcac gaccggaaca cgttcttcac cagggacggt    1440
gccgggcggt tcgcggacgt cgcggacctg gtcggcgtcg gcaccgacgc ggtcagccgc    1500
gccttcgcgg tcggtgacgt ggacggcgac ggccgcctgg acttcgtcgt ggccaaccag    1560
tgggcccagt cgacgctgta ccgcaacact tcgcagtcgt cggccgagtt cgtcggactg    1620
aggttgcgcc aaccggcgga tgtcggcacc tgcgcgggaa acagcgaagg cgcggaccgg    1680
ccggcgatcg gcgccaccgc cgtcgtgacg actccggacg gcacgaagca ctcccagcag    1740
gtctacccgg ccaacgggca caacggcgtc aacgcgcccg acctggtctt cggtctcggt    1800
gacgtgcggg acggcccgct gccggtcgag ctgtcctggc gggacggctg cggccggcgg    1860
cacacggcga cggtgaacgt cgctcccggc tggcaccgga tcctgctgca cgcggacggc    1920
acgaccatgg tggaggacaa gtga                                          1944
```

<210> SEQ ID NO 81
<211> LENGTH: 336
<212> TYPE: PRT
<213> ORGANISM: Saccharothrix aerocolonigenes

<400> SEQUENCE: 81

```
Val Lys Thr Leu Pro Arg Lys Thr Lys Asp Gln Gly Asp Ser Ala Gly
1               5                   10                  15

His Arg Lys Pro Lys Asp Pro Arg Ser Ala Ala Leu Arg Arg Phe Gly
            20                  25                  30

Leu Ser Ile Ser Val Leu Thr Ile Val Gly His Thr Leu Leu Gly Phe
        35                  40                  45

Glu Gln Ala Tyr Leu Thr Pro Val Val Val Leu Val Ala Leu Gly
    50                  55                  60

Thr Glu Val Leu Leu Glu Ser Val Glu Ala Ala Ser Leu Gly Arg Arg
65                  70                  75                  80

Pro Arg Tyr Leu Gly Gln Ala Gly Ala Val Val Asp Phe Leu Leu Pro
                85                  90                  95

Ser Tyr Ile Gly Gly Leu Ala Cys Ala Met Leu Leu Tyr Ala Asn Asp
            100                 105                 110

Arg Leu Met Pro Thr Val Leu Ala Val Val Ile Ala Val Ala Ser Lys
        115                 120                 125

Tyr Leu Ile Arg Val Lys Val Asn Gly Arg Leu Arg His Val Leu Asn
    130                 135                 140

Pro Ser Asn Thr Gly Ile Val Val Val Leu Leu Val Phe Pro Trp Val
145                 150                 155                 160

Ser Ile Ala Pro Pro Tyr Gln Phe Thr Glu Trp Thr Ser Gly Val Val
                165                 170                 175

Asp Ala Leu Ile Pro Val Leu Leu Ala Ala Gly Thr Met Leu Asn
            180                 185                 190

Ala Lys Leu Thr Lys Lys Ile Pro Leu Ile Leu Gly Trp Val Gly Gly
        195                 200                 205

Phe Val Leu Gln Ala Val Leu Arg Ser Ala Phe Thr Asp Leu Ser Ile
    210                 215                 220

Val Ser Ala Val Leu Pro Ile Thr Gly Thr Ala Phe Ile Leu Phe Thr
225                 230                 235                 240
```

-continued

```
Asn Tyr Met Ile Thr Asp Pro Ser Thr Ser Pro Ser Lys Pro Arg Asn
            245                 250                 255
Gln Val Leu Phe Gly Leu Ala Thr Ala Ala Tyr Ala Val Leu Val
        260                 265                 270
Gln Leu His Val Val Phe Gly Leu Phe Ala Leu Val Ala Val Cys
        275                 280                 285
Ala Leu Arg Gly Val Gly Leu Ala Ile Leu Ser Trp Arg Gln Ser Val
        290                 295                 300
Glu Val Pro Ala Gln Val Ala Gln Lys His Asp Ala Val Arg Asp
305                 310                 315                 320
Arg Ile Glu Glu Val Gly Val Pro Val Phe Gly Ala Asn Gly Arg Val
                325                 330                 335
```

<210> SEQ ID NO 82
<211> LENGTH: 1011
<212> TYPE: DNA
<213> ORGANISM: Saccharothrix aerocolonigenes

<400> SEQUENCE: 82

```
gtgaaaacgc tgcctcggaa gacgaaggac cagggcgact ccgcgggtca ccgcaaaccg      60
aaggatcctc gcagcgccgc actgcgccgg ttcgggctgt cgatctcggt gctcacgatc     120
gtgggccaca cgctgctcgg cttcgagcag gcgtacctga cgccggtcgt cgcggtgctg     180
gtcgcgctcg gcaccgaggt cctgctggag tccgtcgagg cggcgtcgct cgggcggcga     240
ccgcggtacc tcggtcaggc gggcgcggtg gtcgacttcc tgctgccctc ctacatcgga     300
ggcctggcgt gcgcgatgtt gttgtacgcc aacgacaggc tgatgcccac cgtgctggcc     360
gtggtgatcg cggtggcgag caagtacctg atccgggtga aggtcaacgg ccgcctgcgg     420
cacgtgctca accccagcaa caccggcatc gtcgtggtgc tgctggtgtt ccctgggtg      480
agcatcgccc cgccctacca gttcacggag tggaccagcg cgtcgtcga cgcgctgatc      540
cccgtcctcc tgctcgcggc cggcacgatg ctcaacgcga agctgacgaa gaagatcccg     600
ctgatcctgg gctgggtggg tgggttcgtc ctgcaggccg tgctgcgttc ggccttcacc     660
gacctgtcga tcgtcagtgc ggtcctgccg atcaccggaa cagcgttcat cctgttcacc     720
aactacatga tcaccgaccc gtccacgtcg ccttccaagc cccgcaacca ggtgttgttc     780
ggtcttgcca cggctgcggc ctacgccgtg ctggtgcaac tgcacgtggt gttcggtctg     840
ttcttcgcct tggtcgcggt gtgcgcgttg cgcggtgtgg ggcttgccat cctctcgtgg     900
cggcagtccg tggaggtgcc cgcgcaggtg gcgcagaagc acgatgcggt cgtgcgcgac     960
cgcatcgagg aagtcggtgt gccggtcttc ggcgcgaatg gccgggtatg a             1011
```

<210> SEQ ID NO 83
<211> LENGTH: 1933
<212> TYPE: PRT
<213> ORGANISM: Streptomyces kaniharaensis

<400> SEQUENCE: 83

```
Val Ser Gly Gln Arg Val Ala Ile Val Gly Ile Gly Leu Arg Tyr Pro
1               5                   10                  15
Asp Ala Asn Ser Pro Ile Glu Leu Trp Glu Asn Val Leu Ser Gly Arg
            20                  25                  30
Arg Ala Phe Arg Arg Leu Pro Asp Glu Arg Met Asn His Ala Asp Tyr
        35                  40                  45
Trp Ser Pro Asp Arg Ala Ala Pro Asp Arg Phe Tyr Ala Thr Lys Ala
    50                  55                  60
```

-continued

```
Ala Val Leu Arg Asp Phe Glu Phe Asp Arg Ile Ala Tyr Ser Val Ala
 65                  70                  75                  80

Gly Ser Thr Tyr Arg Ser Thr Asp Leu Thr His Trp Leu Ala Leu Asp
                 85                  90                  95

Thr Ala Ala Arg Ala Leu Ala Asp Ala Gly Phe Pro Gly Gly Ser Gly
            100                 105                 110

Leu Pro Gly Gln Thr Thr Gly Val Val Val Gly Asn Ser Leu Thr Gly
        115                 120                 125

Glu Phe Ser Arg Ala Asn Ile Met Arg Leu Arg Trp Pro Tyr Val Arg
130                 135                 140

Arg Thr Val Ala Ala Ala Leu Ala Gly Lys Gly Trp Ser Glu Ser Ala
145                 150                 155                 160

Ala Ala Glu Phe Leu Glu Glu Leu Glu Gln Ala Tyr Lys Ala Pro Phe
                165                 170                 175

Pro Pro Ile Asp Glu Asp Ser Leu Ala Gly Leu Ala Asn Thr Ile
            180                 185                 190

Ala Gly Arg Ile Cys Asn His Phe Asp Leu Arg Gly Gly Tyr Thr
        195                 200                 205

Val Asp Gly Ala Cys Ser Ser Ser Leu Leu Ser Val Ile Thr Ala Ala
    210                 215                 220

Arg Ser Leu Ala Asp Gly Asp Leu Asp Val Ala Leu Ala Gly Gly Val
225                 230                 235                 240

Asp Leu Ser Ile Asp Pro Phe Glu Val Ile Gly Phe Ala Lys Thr Gly
                245                 250                 255

Ala Leu Ala Thr Gly Glu Met Lys Val Tyr Asp Arg Asp Ser Asn Gly
            260                 265                 270

Phe Trp Pro Gly Glu Gly Ser Gly Met Leu Val Leu Met Arg Glu Glu
        275                 280                 285

Asp Ala Leu Ala Ala Ser Arg Arg Ile Tyr Ala Ser Ile Ala Gly Trp
290                 295                 300

Gly Val Ser Ser Asp Gly Lys Gly Gly Ile Thr Arg Pro Glu Ala Gly
305                 310                 315                 320

Gly His Arg Leu Ala Leu Ala Arg Ala Tyr Arg Gln Ala Gly Tyr Gly
                325                 330                 335

Val Glu Thr Val Ser Tyr Phe Glu Gly His Gly Thr Gly Thr Ala Leu
            340                 345                 350

Gly Asp Ala Thr Glu Ile Glu Ala Leu Ser Ser Ala Arg Arg Ala Ala
        355                 360                 365

Asp Pro Val Ala Arg Pro Ala Ala Leu Gly Thr Val Lys Gly Asn Phe
370                 375                 380

Gly His Thr Lys Ala Ala Ala Gly Val Ala Gly Leu Ile Lys Ala Ala
385                 390                 395                 400

Leu Ala Val His His Gln Val Ile Pro Pro Gly Thr Gly His His Asp
                405                 410                 415

Pro His Pro Gly Leu Leu Gly Asp Asp Ala Ala Leu Tyr Val Pro Gly
            420                 425                 430

Arg Ala Glu Leu Trp Pro Ala Asp Ser Pro Val Arg Ala Gly Val Ser
        435                 440                 445

Ala Met Gly Phe Gly Gly Ile Asn Thr His Val Ala Val Thr Ala Ala
    450                 455                 460

Pro Ala Ala Pro Arg Arg Thr Ala Leu Asp Ala Asp Thr Gly Arg Leu
465                 470                 475                 480
```

-continued

```
Val Ala Gly Arg Gln Asp Ala Glu Leu Leu Leu Glu Ala Arg Asp
                485                 490                 495

Arg Asp Gly Leu Arg Ala Glu Ala Ala Arg Leu Leu Asp Leu Val Pro
            500                 505                 510

Arg Leu Ala Gln Ala Glu Leu Ala Asp Leu Ala Ala Gly Leu Ala Ala
            515                 520                 525

Gly Leu Ala Asp Gly Leu Thr Gly Ala Pro Val Arg Ala Ala Val Val
    530                 535                 540

Ala Thr Ser Pro Asp Ala Ala Arg Ala Leu Glu Arg Leu Leu Gly
545                 550                 555                 560

Leu Leu Ala Ser Gly Ala Thr Arg Ala Leu Cys Ser Gly Glu Gly Val
                565                 570                 575

Phe Leu Gly Thr Gly Arg Thr Glu Pro Thr Ile Ala Tyr Leu Phe Pro
            580                 585                 590

Gly Gln Gly Ser Gly Arg Gly Ala Val Gly Ala Ile Arg Arg Arg Phe
        595                 600                 605

Ala Gln Ala Asp Glu Val Tyr Arg Arg Ala Gly Leu Pro Thr Gly Ala
    610                 615                 620

Asp Gln Val Asp Thr Arg Val Ala Gln Pro Arg Ile Val Thr Gly Ser
625                 630                 635                 640

Leu Ala Ala Leu Arg Val Leu Asp Gly Leu Gly Ile Arg Ala Ala Ala
                645                 650                 655

Ala Val Gly His Ser Leu Gly Glu Leu Thr Ala Leu His Trp Ala Gly
            660                 665                 670

Ala Leu Thr Glu Asp Gln Val Leu Arg Leu Ala Thr Val Arg Gly Gln
        675                 680                 685

Val Met Ala Glu Val Gly Ser Gly Gly Ala Met Ala Gly Leu Ala
    690                 695                 700

Ala Thr Pro Glu Asp Gly Thr Arg Leu Cys Ala Gly Leu Asp Val Val
705                 710                 715                 720

Ile Ala Gly Tyr Asn Gly Pro Arg Gln Thr Val Ser Gly Pro Ala
                725                 730                 735

Ala Ala Val Asp Glu Val Cys Arg Arg Ala Val Ala Glu Gly Val Thr
            740                 745                 750

Ala Thr Arg Leu Asn Val Ser His Ala Phe His Ser Pro Leu Val Ala
        755                 760                 765

Pro Ala His Ala Met Ala Glu Arg Leu Gly Glu Phe Asp Phe Ala
    770                 775                 780

Arg Pro Val Arg Pro Val Ala Ser Thr Val Thr Gly Ala Leu Leu Asp
785                 790                 795                 800

Pro Ala Ala Asp Leu Arg Thr Leu Leu Arg Asp Gln Val Ala Arg Pro
                805                 810                 815

Val Arg Phe His Glu Ala Ala Ala Ala Thr Ala Asp Ala Asp Leu
            820                 825                 830

Val Val Glu Val Gly Pro Gly Arg Val Leu Ser Gly Leu Leu Ala Glu
        835                 840                 845

Ile Ala Pro Asp Arg Pro Ala Leu Ala Val Asp Thr Asp Ser Ser Ser
    850                 855                 860

Leu Gly Pro Leu Leu Arg Val Ala Ala Ala Phe Val Leu Gly Ser
865                 870                 875                 880

Pro Val Arg Ala Ala Gly Leu Phe Glu Gly Arg Leu Val Arg Pro Leu
                885                 890                 895

Pro Ala Asp Gly Ala Met Thr Phe Leu Ala Ser Pro Cys Glu Ser Ala
```

-continued

```
                900             905             910
Pro Ala Ile Asp Ala Ala Arg Leu Thr Pro Ala Arg Pro Ala Val Glu
            915                 920                 925
Ala Ala Thr Gly Thr Ala Thr Ala Pro Ala Glu Ala Gly Gly Glu Ser
    930                 935                 940
Thr Leu Asp Leu Leu Arg Arg Leu Ala Ala Glu Arg Val Glu Leu Pro
945                 950                 955                 960
Leu Glu Ser Val Thr Ala Ala His Pro Met Asp Asp Leu His Leu
                965                 970                 975
Ser Ser Ile Thr Val Gly Gln Ile Val Asn Asp Val Thr Arg Ala Leu
            980                 985                 990
Gly Leu Pro Ala Leu Glu Ala Thr  Thr Ser Phe Ala Thr  Val Gly Leu
            995                 1000                1005
Gly Glu  Leu Ala Glu Leu Ile  Asp Arg Leu Ala Gln  Thr Ala Glu
            1010                1015                1020
Asp Gly  Pro Ala Pro Ala Ser  Glu Val Pro Gly Val  Ala Pro Trp
            1025                1030                1035
Val Arg  Pro Phe Ala Val Glu  His Val Glu Ala Ala  Leu Pro Ala
            1040                1045                1050
Arg Thr  Ala Ala Pro Ala Ala  Ala Thr Gly Ser Trp  Thr Val Tyr
            1055                1060                1065
Ser Thr  Pro Gly His Pro Leu  Ala Glu Pro Leu Arg  Thr Ala Leu
            1070                1075                1080
Ala Glu  Ala Gly Ile Gly Asp  Gly Val Leu Leu Cys  Leu Pro Ala
            1085                1090                1095
Glu Cys  Gly Ala Gly Asp Thr  Glu Leu Phe Leu Ala  Ala Gly Arg
            1100                1105                1110
Ala Ala  Ala Thr Ala Pro Gly  Gly Thr Arg Leu Val  Val Val Gln
            1115                1120                1125
His Arg  Leu Gly Ala Thr Gly  Leu Ala Lys Thr Leu  His Leu Glu
            1130                1135                1140
His Pro  Ser Val Pro Thr Thr  Val Val Glu Leu Pro  Asp Pro Leu
            1145                1150                1155
Ala Pro  Glu Ala Val Gly Leu  Val Val Ala Glu Ala  Ala Ala Thr
            1160                1165                1170
Thr Gly  Phe Thr Glu Val Arg  Tyr Gly Pro Asp Gly  Arg Arg Thr
            1175                1180                1185
Val Pro  Val Leu Arg Pro Leu  Thr Pro Thr Glu Ala  Pro Ala Gly
            1190                1195                1200
Ala Ser  Pro Leu Asp Glu Ala  Asp Val Leu Leu Val  Thr Gly Gly
            1205                1210                1215
Gly Lys  Gly Ile Thr Ala Glu  Cys Ala Leu Ala Met  Ala Arg Asp
            1220                1225                1230
Ser Gly  Ala Ala Leu Ala Leu  Ile Gly Arg Ala Asp  Pro Ala Glu
            1235                1240                1245
Asp Ala  Glu Leu Ala Ala Asn  Leu Ala Arg Met Thr  Ala Ala Gly
            1250                1255                1260
Leu Arg  Leu Arg Tyr Glu Arg  Ala Asp Val Thr Ser  Ala Ala Gln
            1265                1270                1275
Thr Ala  Glu Ala Val Glu Arg  Leu Glu His Ala Leu  Gly Pro Val
            1280                1285                1290
Thr Ala  Val Leu His Gly Ala  Gly Arg Asn Glu Pro  Ala Ala Val
            1295                1300                1305
```

-continued

```
Thr Ser Leu Thr Pro Asp Asp Phe Arg Arg Thr Leu Ala Pro Lys
1310                1315                1320

Thr Asp Gly Leu Ala Ala Val Leu Asp Ala Val Ala Pro Glu Arg
1325                1330                1335

Leu Lys Leu Leu Ile Thr Phe Gly Ser Ile Ile Gly Arg Ala Gly
1340                1345                1350

Leu Arg Gly Glu Ala His Tyr Ala Thr Ala Asn Asp Trp Met Thr
1355                1360                1365

Glu Leu Thr Leu Arg Phe Ala Glu Lys His Pro Gln Ala Arg Val
1370                1375                1380

Leu Ala Ile Glu Trp Ser Val Trp Ser Gly Ala Gly Met Gly Glu
1385                1390                1395

Arg Leu Gly Val Val Glu Ala Leu Met Arg Glu Gly Ile Thr Pro
1400                1405                1410

Ile Ser Thr Glu Glu Gly Ile Arg Val Leu Arg Glu Leu Leu Ala
1415                1420                1425

Asp Pro Ser Ala Gly Pro Val Leu Val Val Ser Gly Arg Ala Ala
1430                1435                1440

Gly Leu Pro Thr Leu Ala Leu Glu Gln Arg Asp Leu Pro Leu Ala
1445                1450                1455

Arg Phe Leu Glu Arg Val Val Thr His Tyr Pro Gly Val Glu Leu
1460                1465                1470

Val Thr Glu Ala Glu Leu Ser Glu Gly Ser Asp Pro Tyr Leu Thr
1475                1480                1485

Asp His Gln Leu Asp Gly Asp Leu Leu Phe Pro Ala Val Leu Gly
1490                1495                1500

Met Glu Ala Met Ala Gln Ala Ala Ala Val Ser Gly His Gln
1505                1510                1515

Gly Pro Pro Met Leu Glu Ala Val Glu Phe Leu Arg Pro Ile Ala
1520                1525                1530

Val Arg Pro Gly Gly Ser Thr Thr Leu Arg Thr Ala Ala Leu Val
1535                1540                1545

Gln Asp Thr Gly Thr Val Asp Val Val Leu Arg Thr Ser Asp Thr
1550                1555                1560

Gly Phe Ala Ala Asp His Phe Arg Ala Arg Leu Arg Tyr Leu Arg
1565                1570                1575

Pro Ala Leu Pro Asp Ser Pro Arg Pro Ala Ala Leu Asp Leu Pro
1580                1585                1590

Ala Val Pro Val Asp Pro Val Thr Glu Leu Tyr Gly Ser Val Leu
1595                1600                1605

Phe Gln Gly Lys Arg Phe Gln Arg Leu Leu Asp Tyr Arg Arg Ala
1610                1615                1620

Gly Ala Arg His Ala Val Ala Glu Val Ser Thr Thr Thr Pro Ala
1625                1630                1635

Pro Trp Phe Ala Ala Tyr Leu Pro Gln Glu Gln Leu Leu Ala Asp
1640                1645                1650

Pro Gly Thr Arg Asp Thr Met Met His Ala Ile Gln Cys Cys Val
1655                1660                1665

Pro Asp Ala Thr Leu Leu Pro Arg Gly Ile Glu Arg Leu His Leu
1670                1675                1680

Ala Glu Arg Ala Asp Gln Asp Ser Glu Phe Ile Val Leu Asp Ala
1685                1690                1695
```

-continued

| | | | | | | | | | | |
|---|---|---|---|---|---|---|---|---|---|---|
|Arg|Glu|Arg|Ser|Gln|Asp|Gly|Asp|Thr|Tyr|Val|Tyr|Asp|Val|Asp|
| |1700| | | |1705| | | |1710| | | | | |

Val Arg Thr Pro Asp Gly Arg Val Val Glu Arg Trp Glu Gly Leu
    1715                1720                1725

Ala Leu Val Ala Val Arg Lys Arg Asp Gly Ala Gly Pro Trp Val
    1730                1735                1740

Pro Ala Met Leu Gly Ser Tyr Leu Glu Arg Gly Leu Glu Arg Val
    1745                1750                1755

Leu Gly Gly Ser Arg Ala Val Val Val Glu Ala Ala Gly Ala Glu
    1760                1765                1770

Ala Asp Arg Arg Ala Arg Thr Ala Asp Ala Val Ala Arg Ala Leu
    1775                1780                1785

Gly Ala Pro Ala Glu Leu Arg His Arg Pro Asp Gly Arg Pro Glu
    1790                1795                1800

Leu Asp Gly His Thr Val Ser Ala Ala His Ser Asp Gly Leu Thr
    1805                1810                1815

Leu Ala Val Val Gly Gln Gly Arg Leu Ala Cys Asp Ala Glu Thr
    1820                1825                1830

Val Arg Pro Arg Arg Ala Glu Asp Trp Ala Ala Leu Leu Gly Glu
    1835                1840                1845

Ala Gln Leu Pro Val Arg Asp Leu Leu Val Ala Glu Ala Gly Asp
    1850                1855                1860

Asp Pro Ala Val Ala Ala Thr Arg Val Trp Cys Ala Leu Glu Cys
    1865                1870                1875

Leu Arg Lys Ser Ala Ala Thr Gly Gln Ala Leu Ala Leu Asp Arg
    1880                1885                1890

Val Asp Gly Ser Gly Trp Ala Val Leu Ser Ala Gly Asp Ala Ala
    1895                1900                1905

Ile Ala Thr Trp Val Thr Thr Val Thr Asp Arg Glu Asp Pro Val
    1910                1915                1920

Val Phe Ala Phe Leu Ala Gly Lys Glu Arg
    1925                1930

<210> SEQ ID NO 84
<211> LENGTH: 5802
<212> TYPE: DNA
<213> ORGANISM: Streptomyces kaniharaensis

<400> SEQUENCE: 84

| | |
|---|---|
|gtgagcggtc agcgggtcgc catcgtggga atagggctcc gataccccgga cgccaattcc|60|
|ccgatcgaac tctgggagaa cgtactgagc ggccggcggg ccttccggcg gctgcccgac|120|
|gagcggatga accacgccga ctactggtcg cccgaccggg cggcaccgga ccggttctac|180|
|gccaccaagg ccgccgtgct gcgggacttc gagttcgaca ggatcgccta cagcgtggcc|240|
|ggaagcacct accgctcgac cgacctgacc cactggctgg cgctcgacac ggccgcccgc|300|
|gcgctcgccg acgccggatt cccgggcggt tccggactgc ccggacaaac caccggtgtg|360|
|gtcgtcggaa acagcctcac cggggaattc tcgcgggcca acatcatgcg cctgcggtgg|420|
|ccctacgtgc gccggacggt ggccgccgca ctcgccggaa aaggctggtc cgagagcgcc|480|
|gccgcagagt ttctcgaaga actcgaacag gcctacaaag cgccttttcc cgcccatcgac|540|
|gaggactcgc tggccggcgg cctcgccaac accatcgccg gcggatctg caaccacttc|600|
|gacctccgcg gcggcggata caccgtggac ggcgcctgct cctcctcccct gctgtccgtc|660|
|atcaccgccg cccgctccct cgccgacggc gacctcgacg tcgccctcgc cggaggcgtc|720|

```
gacctgtcca tcgacccgtt cgaggtgatc ggcttcgcca agaccggcgc gctggccacc      780
ggcgagatga aggtctacga ccgcgactcc aacggcttct ggcccggcga gggctccggc      840
atgctcgtgc tcatgcgcga ggaggacgcg ctggcggcca gccggcggat ctacgccagc      900
atcgccggct ggggcgtctc ctccgacggc aagggcggga tcacccgccc ggaggcgggc      960
ggtcaccgcc tcgccctggc ccgcgcctac cggcaggccg gctacggcgt cgagaccgtc     1020
tcctacttcg aggggcacgg caccggcacc gcgctgggcg acgccaccga gatcgaggcg     1080
ctgtcctccg cccgcgggc cgccgatccg gtcgcccggc ccgccgcgct cggcaccgtc      1140
aagggcaact tcgggcacac caaggccgcg gcgggcgtcg ccggcctgat caaggccgcc     1200
ctcgcggtgc accatcaggt gatcccgccg ggcaccggcc accacgaccc gcaccccggt     1260
ctgctcggcg acgacgccgc gctgtacgtg cccggccggg ccgaactctg gcccgccgac     1320
tctcccgtcc gggccggcgt ctcggccatg ggcttcggcg gcatcaacac ccacgtcgcc     1380
gtcaccgcgg ccccgcggc gccgcgtcgc accgccctcg acgccgacac cggacggctc      1440
gtcgccgggc gccaggacgc cgagctcctg ctgctggagg cccggaccg cgacggcctg      1500
cgcgccgagg ccgcccggct gctcgacctc gtgcccggc tcgcccaggc cgaactggcc      1560
gacctggcag ccgggttggc cgccgggttg gccgacgggt tgaccggggc gccggtccgc     1620
gcggctgtcg tcgcgacgtc ccccgacgac gccgcccgcg ccctggaacg gctgctcggc     1680
ctgctcgcgt ccggcgccac ccgggcgctc tgctccggcg agggcgtctt cctcggcacc     1740
ggccgcaccg aacccacgat cgcctacctc ttccccggcc agggctccgg ccgcggcgcg     1800
gtcggtgcga tccgccgccg cttcgcccag gccgacgagg tgtaccgccg agccggcctg     1860
ccgacggggg ccgaccaggt cgacacccgc gtcgcccagc cgcgcatcgt caccggctcg     1920
ctcgccgccc tgcgcgtcct cgacgggctc ggcatccggg ccgcggccgc cgtcggccac     1980
agcctcggtg agctcaccgc gctgcactgg gccggcgcgc tgaccgagga ccaggtgctg     2040
cgcctggcca ccgtccgcgg ccaggtgatg gccgaggtcg gtagcggcgg cggcgcgatg     2100
gccggcctcg ccgcgacgcc cgaggacggc accggctct gcgcgggcct ggacgtcgtc      2160
atcgccggct acaacggccc ccggcagacg gtcgtctccg gccccgccgc cgccgtcgac     2220
gaggtctgcc gccgggccgt cgccgagggc gtcaccgcca cccggctcaa cgtctcgcac     2280
gccttccact ccccgctggt cgcacccgcc gcccacgcga tggccgagcg gctcggggag     2340
ttcgacttcg cccgccccgt ccgcccggtc gcctccaccg tcaccggcgc cctgctcgat     2400
ccggccgccg acctgcggac cctgctgcgc gaccaggtgg cccggccggt ccgcttccac     2460
gaggccgcgg ccgccgccac cgccgacgcc gacctggtcg tcgaggtcgg ccccggccgg     2520
gtgctctccg gcctgctcgc cgagatcgca cccgaccggc cggctctggc cgtcgacacc     2580
gacagctcct ccctcggccc gctgctgcgc gtcgccgccg ccgccttcgt gctcggctcg     2640
cctgtccgcg ccgccggtct gttcgaggga cggctggtcc ggccgctgcc ggcggacggc     2700
gcgatgacct tcctcgccag cccgtgcgag tccgccccgg ccatcgacgc cgcccggctc     2760
acgccggccc ggcccgctgt cgaagccgcg accgggaccg cgaccgcgcc ggccgaggcg     2820
ggcggcgagt ccaccctgga cctgctgcgc cgcctcgccg ccgaacgcgt cgaactgccg     2880
ctggagtccg tcaccgccgc cacccacccg atggacgacc tgcacctcag ctccatcacc     2940
gtcggccaga tcgtcaacga cgtcacccgg ccctgggcc tgcccgccct ggaggccacc      3000
accagcttcg ccaccgtcgg cctcggcgaa ctggccgagc tgatcgaccg gttggcgcag     3060
```

-continued

```
accgccgagg acggccccgc cccggcgtcg gaggtgcccg gagtcgcccc ctgggtccgc    3120
ccgttcgccg tcgagcacgt cgaggcggcc ctccccgcgc gaaccgccgc cccggccgcc    3180
gccaccggca gctggacggt gtacagcacc cccggccacc cgctggccga accgctgcgc    3240
accgctctcg ccgaggccgg catcggcgac ggcgtcctgc tctgccttcc tgccgagtgc    3300
ggcgcgggcg acaccgagct gttcctcgcc gccggacgcg ccgcggccac cgccccgggc    3360
ggcacccggc tggtcgtggt ccagcaccgc ctcggcgcga ccggcctcgc caagaccctc    3420
cacctggaac acccgtccgt ccccaccacc gtcgtcgaac tgcccgaccc gctcgccccc    3480
gaggccgtcg gcctggtcgt cgccgaggcc gcggccacca ccggcttcac cgaggtccgc    3540
tacgggcccg acggccgccg gacagtacca gtgctgcgcc cgctgacgcc cacggaggcc    3600
ccggcgggtg cgtccccgct ggacgaggcg gacgtcctgc tggtcaccgg cggcggcaag    3660
ggcatcaccg ccgagtgcgc cctggccatg gcccgggact ccggcgccgc cctcgccctg    3720
atcggccgcg cggaccccgg cgaggacgcc gaactcgccg ccaacctcgc ccggatgacc    3780
gccgccggac tgcgcctgcg ctacgagcgc gccgacgtca cctccgcggc gcagaccgcc    3840
gaggccgtcg aacgactgga gcacgccctc ggcccggtca ccgccgtgct ccacggcgcc    3900
ggccgcaacg agcccgcggc cgtgacctca ctgaccccg acgacttccg gcgcacccctc    3960 gccccgaaga ccgacggcct ggccgccgtc ctcgacgccg tcgcaccgga gcgcctcaag    4020
ctcctgatca ccttcggctc catcatcggc cgcgccggcc tgcgcgggga ggcgcactac    4080
gccaccgcca acgactggat gaccgaactc accctccgct tcgcggagaa gcacccgcag    4140
gccagggtgc tggcgatcga atggtccgtc tggtccggcg ccggcatggg cgaacggctc    4200
ggtgtcgtcg aggcgctgat gcgcgagggc atcaccccga tctccaccga ggagggcatc    4260
cgggtgctcc gcgagctgct ccgcgacccc tccgccgggc ccgtcctggt cgtcagcgga    4320
cgcgccgcgg gcctgcccac cctcgccctg gaacagcgcg acctgcccct cgcccgcttc    4380
ctcgaacgcg tggtcacgca ctacccgggc gtcgaactgg tcaccgaggc cgagctgagc    4440
gagggcagcg acccgtacct gaccgaccac cagctcgacg gcgacctgct cttccccgcc    4500
gtcctcggca tggaggcgat ggcccaggcc gcggccgccg tcagcgggca ccaggggccg    4560
ccgatgctgg aggccgtcga gttcctgcgg cccatcgccg tccggcccgg aggtcgacc    4620 accctgcgca ccgccgccct cgtccaggac accggcaccg tcgacgtcgt cctgcgcacc    4680
tcggacaccg gcttcgccgc cgaccacttc cgggcccgcc tgcgctacct ccgccccgcc    4740
ctgcccgaca gccccggcc cgccgcctc gacctgcccg ccgtccccgt cgaccggtg    4800 accgagctgt acggcagcgt cctgttccag ggcaagcgct tccagcgcct gctcgactac    4860
cgcagggccg gcgcccggca cgccgtcgcc gaggtctcca ccaccacgcc cgcccctgg    4920 ttcgcggcct acctcccgca ggagcagctg ctcgccgacc cgggcacccg cgacacgatg    4980
atgcacgcca tccagtgctg cgtccccgac gccaccctgc tgccgcgcgg catcgagcgg    5040
ctccacctcg ccgaacgggc cgaccaggac tccgagttca tcgtcctcga cgcccgcgaa    5100
cgctcccagg acgcgacac ctacgtctac gactcgacg tccgcacccc ggacggccgg    5160
gtcgtcgaac gctgggaggg gctggccctg gtcgccgtcc gcaagcgcga cggcgccggg    5220
ccgtgggtcc ccgcgatgct cggctcctac ctggaacgcg gcctggagcg cgtcctcggc    5280
ggcagccgcg ccgtcgtggt cgaggccgcg ggcgccgaag ccgaccggcg ggcccgcacc    5340
gccgacgccg tcgcccgggc cctcggcgca ccgccgaac tgcgccaccg cccggacggt    5400
cggcccgaac tcgacggcca caccgtctcc gccgcgcaca gcgacgggct gaccctcgcc    5460
```

```
gtggtcgggc agggccgtct cgcctgcgac gccgagacgg tccgcccgcg ccgggccgag    5520
gactgggccg cactcctcgg cgaggcccaa ctccccgtcc gcgacctgct ggtggccgag    5580
gccggcgacg acccggcggt ggcggccacc cgggtctggt cgccctgga gtgcctgcgc     5640 aagtccgccg ccaccggcca gcccctcgcc ctcgaccggg tcgacggctc cggctgggcg    5700
gtgctctccg ccggcgacgc ggcgatcgcc acctgggtga ccaccgtcac cgaccgcgag    5760
gacccggtgg tcttcgcctt cctcgccggc aaggagcggt ga                       5802
```

<210> SEQ ID NO 85
<211> LENGTH: 154
<212> TYPE: PRT
<213> ORGANISM: Streptomyces kaniharaensis

<400> SEQUENCE: 85

```
Val Met Ala Gly Tyr Tyr Glu Ile Arg His Thr Val Gly Phe Glu Glu
1               5                   10                  15

Thr Asn Leu Val Gly Asn Val Tyr Tyr Val Asn Tyr Leu Arg Trp Gln
            20                  25                  30

Gly Arg Cys Arg Glu Met Phe Leu Lys Glu Lys Ala Pro Gly Val Leu
        35                  40                  45

Ala Glu Leu Arg Asp Asp Leu Lys Leu Phe Thr Leu Arg Val Asp Cys
    50                  55                  60

Glu Phe Phe Ala Glu Ile Thr Ala Phe Asp Glu Leu Ala Val Arg Met
65                  70                  75                  80

Arg Leu Glu Glu Ile Ala Gln Thr Gln Leu Gln Phe Ser Phe Asp Tyr
                85                  90                  95

Leu Arg Leu Asp Gly Ala Gly Glu His Leu Val Ala Arg Gly Arg Gln
            100                 105                 110

Arg Ile Ala Cys Met Arg Gly Pro Asn Thr Asp Thr Val Pro Ala Arg
        115                 120                 125

Val Pro Glu Glu Leu Arg Arg Ala Leu Ala Pro Tyr Ala Thr Gly Pro
    130                 135                 140

Val Gly Ala Ala Ala Ala Gly Arg Pro Arg
145                 150
```

<210> SEQ ID NO 86
<211> LENGTH: 465
<212> TYPE: DNA
<213> ORGANISM: Streptomyces kaniharaensis

<400> SEQUENCE: 86

```
gtgatggccg gctactacga gatccggcac accgtcggct cgaggagac caacctcgtc      60 ggcaacgtct actacgtcaa ctacctacgc tggcaaggtc gttgccggga gatgttcctc    120
aaggagaagg cgcccgggt gctcgccgaa ctgcgggacg acctgaagct gttcaccctc     180
cgggtggact gcgagttctt cgccgagatc accgcgttcg acgaactcgc cgtccggatg    240
cggctggagg agatcgccca gacgcagctc cagttcagct cgactacct gcgcctcgac     300 ggcgccggcg agcacctcgt cgcccgcggg cggcagcgga tcgcctgcat gcgcggcccc    360
aacaccgaca ccgtgccggc ccgggtgccc gaggaactgc ggcgggccct ggctccgtac    420
gcgacggggc cggtcgggggc ggccgcgcc gggaggcccc ggtga                    465
```

<210> SEQ ID NO 87
<211> LENGTH: 323
<212> TYPE: PRT

<213> ORGANISM: Streptomyces kaniharaensis

<400> SEQUENCE: 87

| | | | | | | | | | | | | | | |
|---|---|---|---|---|---|---|---|---|---|---|---|---|---|---|
| Val | Pro | Ser | Pro | Leu | Arg | Met | Leu | Arg | Arg | Ile | Leu | Thr | Pro | Asn |
| 1 | | | | 5 | | | | | 10 | | | | | 15 |
| Val | Ala | Glu | Thr | Gln | Leu | Ala | Arg | Arg | Gly | Phe | His | Val | Lys | Thr | Pro |
| | | | 20 | | | | | 25 | | | | | 30 | | |
| Asp | Ala | Arg | Glu | Leu | Leu | Glu | Thr | Val | Gly | Ser | Arg | Phe | Leu | Glu | Gly |
| | | 35 | | | | | 40 | | | | | 45 | | | |
| Tyr | Ala | Tyr | Ala | Met | Glu | Ala | Gly | Thr | Pro | Ala | Glu | Ala | Glu | Thr | Arg |
| | 50 | | | | | 55 | | | | | 60 | | | | |
| Leu | Glu | Thr | Val | Pro | Ala | Arg | Phe | Arg | Gly | Phe | Ala | Tyr | Glu | Gly | Ala |
| 65 | | | | | 70 | | | | | 75 | | | | | 80 |
| Gly | Met | Gly | Phe | Ala | Met | Leu | Asp | Gly | Leu | Pro | Leu | Pro | Gly | Arg | Gly |
| | | | | 85 | | | | | 90 | | | | | 95 | |
| Arg | Val | Gly | Glu | Phe | Leu | Ala | Gly | Arg | Gly | Ala | Arg | His | Asn | Tyr | Met |
| | | | 100 | | | | | 105 | | | | | 110 | | |
| Val | Tyr | Val | Gly | Ile | Gly | Trp | Ala | Met | Ala | Arg | Leu | Pro | Arg | Phe | Arg |
| | | 115 | | | | | 120 | | | | | 125 | | | |
| Trp | Pro | Asp | Ile | Thr | Gly | Leu | Asp | Pro | Leu | Leu | Arg | Trp | Leu | Val | Leu |
| | 130 | | | | | 135 | | | | | 140 | | | | |
| Asp | Gly | Tyr | Gly | Phe | His | Gln | Ala | Tyr | Phe | Arg | Thr | Glu | Gln | Tyr | Val |
| 145 | | | | | 150 | | | | | 155 | | | | | 160 |
| His | Gly | Arg | His | Arg | Glu | Arg | Ser | Phe | Pro | Trp | Pro | Ala | Asp | Asp | Ser |
| | | | | 165 | | | | | 170 | | | | | 175 | |
| Pro | Gly | Tyr | Val | Ser | Arg | Ala | Ile | Asp | Gln | Gly | Val | Gly | Arg | Ala | Leu |
| | | | 180 | | | | | 185 | | | | | 190 | | |
| Trp | Phe | Val | Gly | Gly | Thr | Asp | Pro | Asp | Val | Val | Ala | Thr | Leu | Ile | Glu |
| | | 195 | | | | | 200 | | | | | 205 | | | |
| Lys | Phe | Pro | Glu | Arg | Arg | His | Ser | Asp | Leu | Tyr | Gly | Gly | Ala | Gly | Leu |
| | 210 | | | | | 215 | | | | | 220 | | | | |
| Ala | Ala | Ala | Tyr | Ala | Gly | Gly | Val | Asp | Glu | Ala | Glu | Leu | Arg | Ala | Phe |
| 225 | | | | | 230 | | | | | 235 | | | | | 240 |
| Gln | Asp | Arg | Ala | Gly | Ile | His | Arg | Ala | Ile | Val | Ala | Gln | Gly | Ala | Ala |
| | | | | 245 | | | | | 250 | | | | | 255 | |
| Phe | Ala | Cys | Glu | Ala | Arg | Ile | Arg | Ala | Gly | Leu | Leu | Gly | Pro | His | Thr |
| | | | 260 | | | | | 265 | | | | | 270 | | |
| Glu | Leu | Ala | Ala | Gln | Val | Leu | Cys | Gly | Thr | Asp | Ala | Ala | Ala | Ala | Ala |
| | | 275 | | | | | 280 | | | | | 285 | | | |
| Lys | Val | Thr | Gln | Asp | Leu | Arg | Pro | Thr | Gly | Arg | Ser | Thr | Gly | Pro | Val |
| | 290 | | | | | 295 | | | | | 300 | | | | |
| Pro | Ser | Tyr | Glu | Thr | Trp | Arg | Gln | Ala | Ile | Ala | Asp | Thr | Phe | Thr | Ala |
| 305 | | | | | 310 | | | | | 315 | | | | | 320 |
| Ala | Arg | Ser | | | | | | | | | | | | | |

<210> SEQ ID NO 88
<211> LENGTH: 972
<212> TYPE: DNA
<213> ORGANISM: Streptomyces kaniharaensis

<400> SEQUENCE: 88

```
gtgccaagcc cgttgcggat gttgcgtcgg cgcatcctga ccccgaacgt cgccgagacc      60
cagctggccc gacgtggttt ccacgtgaag acaccggacg cccgggagct cctggagacc     120
gtcgggagcc gctttctcga aggctatgcg tacgcgatgg aggccggtac gcccgccgag     180
```

-continued

```
gcggagaccc ggctggaaac cgtccccgcc cggttccgcg gtttcgccta cgagggggcc      240
ggcatgggtt tcgccatgct ggacggactg ccgctgccgg tcgtggaag ggtgggggaa       300 ttcctcgccg gcggggggc ccgccacaac tacatggtct acgtgggaat cggctgggcg      360
atggcgcgac tgccccggtt ccgctggccc gacatcaccg gactggaccc gctgctgcgc    420
tggctggtgc tggacggcta cgggttccac caggcgtact tccgcaccga gcagtacgtg    480
cacgggcggc accgggagcg gtcgttcccc tggccggccg acgactcgcc cgggtacgtg    540
agccgcgcga tcgaccaggg cgtcggccgc gcgctgtggt tcgtcggcgg caccgacccc    600
gacgtcgtcg ccacgctgat cgagaagttc cccgagcggc ggcactccga cctgtacggc    660
ggggcgggcc tggccgcggc ctacgcgggc ggcgtggacg aggcggagct gagggccttc    720
caggaccggg cggcatcca ccgcgccatc gtcgcccagg gggccgcctt cgcctgcgag     780
gcccgcatcc gggccgggct gctcggcccg cacaccgagc tcgccgcgca ggtcctctgc    840
gggacggacg ccgccgcggc cgccaaggtc acccaggacc tgcgccccac cgggcggtcg    900
accggcccgg tgccgtccta cgagacctgg cgccaggcca tcgccgacac gttcaccgcc    960
gcgaggagct ga                                                         972
```

<210> SEQ ID NO 89
<211> LENGTH: 655
<212> TYPE: PRT
<213> ORGANISM: Streptomyces kaniharaensis

<400> SEQUENCE: 89

```
Met Pro Thr Val Leu Gly Arg Ile Arg Leu Gln Leu Pro Gly Ile Ile
1               5                   10                  15

Ala Val Leu Ala Ile Val Thr Gly Tyr Phe Leu Val Leu Pro Pro Thr
                20                  25                  30

Thr Ser Ala Ala Glu Gln Asp Arg Met Ala Ser Arg Phe His Phe Thr
            35                  40                  45

Ala Leu Pro Ile Glu Leu Pro Pro Ala Ser Lys His Gln Thr Ile Arg
        50                  55                  60

Thr Val Asn Gln Asp Tyr Glu His Ile Arg Ala Trp Ile Ser Ser Val
65                  70                  75                  80

Gly Ala Ala Ile Thr Met Thr Asp Leu Arg Gly Thr Gly Lys Ser Gly
                85                  90                  95

Asp Leu Cys Leu Val Asp Thr Arg Thr Asp Gln Val Val Val Thr Pro
            100                 105                 110

Val Pro Gly Ser Asp Gly Thr Arg Tyr Ala Pro Phe Ala Leu Asp Ala
        115                 120                 125

Ala Pro Leu Pro Met Asn Glu Tyr Ile Ala Pro Met Gly Cys Val Ala
    130                 135                 140

Gly Asp Phe Asn Glu Asp Gly Arg Thr Asp Leu Leu Val Tyr Tyr Trp
145                 150                 155                 160

Gly Arg Thr Pro Val Leu Phe Leu Gly Arg Pro Asp Ala Thr Thr Leu
                165                 170                 175

Asp Ala His Ala Phe Gln Pro Val Glu Leu Val Pro Gly Pro Asn Glu
            180                 185                 190

Thr Asp Gly Lys Tyr Thr Gly Ala Gln Trp Asn Thr Asn Thr Ala Thr
        195                 200                 205

Val Ala Asp Phe Asp Gly Asp Gly His Gln Asp Ile Phe Ile Gly Asn
    210                 215                 220
```

-continued

```
Tyr Phe Pro Asn Gly Pro Val Leu Asn Asp Gln Val Ser Gly Gly Val
225                 230                 235                 240

Val Met Asn His Ser Met Ser His Ala Gln Asn Ser Gly Gly Lys Tyr
                245                 250                 255

Ile Leu Arg Arg Thr Gly Gly Asn Val Gly Asp Lys Leu Ser Ala Gly
            260                 265                 270

Phe Glu Cys Ser Asp Asp Ala Phe Pro Asp Glu Ala Lys His Gly Trp
        275                 280                 285

Ser Leu Ala Ser Ser Ala Ile Asp Leu Asp Gly Asp Gln Leu Pro Glu
    290                 295                 300

Leu Tyr Val Ala Asn Asp Phe Gly Asn Asp Arg Met Leu His Asn Val
305                 310                 315                 320

Ser Ser Pro Gly His Pro Lys Phe Val Thr Val Thr Gly Pro Arg Asp
                325                 330                 335

Ala Thr Thr Pro Lys Ser Lys Ile Leu Gly Asn Asp Ser Phe Lys Gly
            340                 345                 350

Met Gly Val Asp Phe Gly Asp Leu Asp Arg Lys Gly Leu Tyr Asp Leu
        355                 360                 365

Phe Val Ser Asn Ile Thr Ala Ser Phe Gly Ile Glu Glu Ser Asn Phe
    370                 375                 380

Gln Phe Met Asn Thr Ala Arg Asp Lys Ala Asp Leu Arg Ala Gln Met
385                 390                 395                 400

Asp Asp Gly Thr Ala Pro Phe Glu Asp Arg Ser Ala Ala Ala Gly Thr
                405                 410                 415

Ala Trp Ser Gly Trp Gly Trp Asp Val Lys Met Gly Asp Phe Asp Asn
            420                 425                 430

Ser Gly Gln Leu Ala Ile Val Gln Ala Thr Gly Phe Val Lys Gly Gly
        435                 440                 445

Thr Asn Arg Trp Pro Gln Leu Gln Glu Leu Ala Thr Ala Asn Asp Ala
    450                 455                 460

Leu Leu Asp Asn Pro Trp Trp Pro Asn Val Lys Ala Gly Asp Asp
465                 470                 475                 480

Leu Ala Gly Asp Gln Thr Leu Arg Phe Val Lys Gly Thr Asp Gly
                485                 490                 495

His Tyr Ser Asn Leu Ala Gly Arg Leu Gly Leu Ala Val Pro Val Pro
            500                 505                 510

Thr Arg Gly Ile Ala Thr Gly Asp Ala Tyr Gly Asn Gly Arg Leu Asp
        515                 520                 525

Phe Ala Val Ala Arg Gln Trp Asp Ala Pro Val Phe Tyr Arg Asn Asp
    530                 535                 540

Ser Pro Asp Pro Gly Ala Tyr Leu Gly Leu Arg Leu Thr Tyr Asp Thr
545                 550                 555                 560

Pro Asp Ala Ala Gly Pro Leu Pro Ala Pro Gly Ser Pro Val Ile Gly
                565                 570                 575

Ala Gln Ile Glu Val Thr Thr Pro Asp Gly Arg Lys Leu Ile Asp Arg
            580                 585                 590

Val Asp Gly Gly Ser Gly His Ser Gly Lys Arg Ser His Tyr Val His
        595                 600                 605

Ile Gly Leu Gly Gln Gly Val Ser Gly Pro Leu Pro Val Lys Leu Gln
    610                 615                 620

Trp Arg Asp Arg Thr Gly Gln Val His Thr Gln Thr Val Thr Leu Ser
625                 630                 635                 640

Pro Gly Trp His Ser Leu Gln Leu Gly Ser Gln Ala Lys Glu Lys
```

<210> SEQ ID NO 90
<211> LENGTH: 1968
<212> TYPE: DNA
<213> ORGANISM: Streptomyces kaniharaensis

<400> SEQUENCE: 90

```
atgcccaccg tccttggccg gatccgcctg caactgcccg gcatcatcgc cgtgctcgcc     60
atcgtgaccg gctacttcct ggtcctcccg ccgaccacgt ccgccgccga gcaggaccgg    120
atggcgagcc gcttccactt cacgcgctg cccatcgaac tgccgcccgc gagcaagcac    180
cagaccatcc gcaccgtcaa ccaggactac gagcacatcc gcgcgtggat ctcctcggtc    240
ggcgcggcca tcaccatgac ggacctgcgc ggcaccggca gtccggggga cctctgcctc    300
gtcgacaccc ggaccgacca ggtcgtggtc accccggtcc ccggctcgga cggcacccgc    360
tacgcgccgt cgcgctcga cgcggcaccc ctgccgatga cgagtacat cgccccgatg    420
ggctgcgtgg cgggcgactt caacgaggac ggccgcaccg acctgctggt ctactactgg    480
ggccgcacgc cggtcctctt cctcggcagg cccgacgcca ccgcacgcga cgcacacgcc    540
ttccagccgg tcgagctggt ccccggaccc aacgagaccg acggcaagta caccggcgcg    600
cagtggaaca ccaacaccgc caccgtcgcc gacttcgacg cgacggcca ccaggacatc    660
ttcatcggca actacttccc caacggcccg gtcctcaacg accaggtcag cggcggcgtg    720
gtgatgaacc actcgatgtc ccacgcgcag aacagcggcg gcaagtacat cctgcgccgg    780
accggcggca acgtcggcga caagctgtcc gccggcttcg agtgctccga cgacgccttc    840
cccgacgagg cgaagcacgg ctggtcgctc gcctccagcg cgatcgacct ggacggcgac    900
cagctgcccg agctctacgt cgccaacgac ttcggcaacg accggatgct ccacaacgtc    960
tccagcccg gccacccgaa gttcgtcacc gtcaccggcc gcgcgacgc caccacgccc   1020
aagtccaaga tcctcggcaa cgactccttc aagggcatgg gcgtcgactt cggcgacctc   1080
gaccgcaagg gcctctacga cctgttcgtc agcaacatca ccgcctcctt cggcatcgag   1140
gagagcaact tccagttcat gaacaccgcg cgggacaagg ccgacctgcg cgcccaaatg   1200
gacgacggca ccgccccgtt cgaggaccgc agcgccgcgg ccggcaccgc ctggtccggc   1260
tggggctggg acgtgaagat gggcgacttc gacaacagcg gacagctggc gatcgtccag   1320
gcgaccggct tcgtcaaggg cgggaccaac cgctggcccc agctccagga actcgccacc   1380
gccaacgacg ccctgctcga caacccgtgg tggtggccca acgtcaaggc gggcgacgat   1440
ctcgccggcg accagacgct gcgcttcttc gtcaagggca cggacggcca ctacagcaac   1500
ctggccggcc ggctcggcct cgccgtcccg gtgccgaccc gcggcatcgc caccggcgac   1560
gcgtacggca acggacggct cgacttcgcg gtggcccgcc agtgggacgc cccggtcttc   1620
taccgcaacg acagccccga ccccggcgcc tacctcggcc tgcggctcac ctacgacacc   1680
ccggacgcgg ccggcccgct gcccgccccc ggatccccg tgatcggcgc ccagatcgag   1740
gtcaccacac ccgacgggcg caagctcatc gaccgggtgg acggcggcag cggccactcc   1800
ggcaagcgca gccactacgt gcacatcgga ctcgccagg agtctccgg cccgctgccg   1860
gtgaagctgc agtggcggga ccgcaccggc caggtgcaca cgcagaccgt gacgctcagc   1920
cccgggtggc actcgctcca actcggcagc caggccaagg agaagtga              1968
```

<210> SEQ ID NO 91
<211> LENGTH: 346

```
<212> TYPE: PRT
<213> ORGANISM: Streptomyces kaniharaensis

<400> SEQUENCE: 91

Val Thr Asp Met Ala Asp Lys Ala Pro Thr Thr Lys Gln Thr Ala His
1               5                   10                  15

Gln Pro Ala Pro Glu Ala Ala Arg Pro Ala Thr Ala Ser Arg
            20                  25                  30

His Glu Pro Lys Val Val Ile Ala Leu Arg Arg Phe Ala Ile Ser Ile
            35                  40                  45

Thr Val Phe Asn Ile Leu Gly Tyr Thr Val Leu Gly Phe Glu Gln Pro
        50                  55                  60

Trp Thr Trp Pro Leu Ile Ala Leu Ala Thr Ala Tyr Thr Thr Glu Thr
65                  70                  75                  80

Ala Leu Glu Leu Val Gly Ala Lys Val Glu Gly Arg Arg Pro Arg Phe
                85                  90                  95

Leu Gly Asn Gly Leu Pro Gly Met Leu Glu Phe Leu Tyr Pro Ser His
            100                 105                 110

Ile Thr Gly Leu Ala Leu Asn Met Leu Thr Tyr Val Asn Asp Arg Leu
        115                 120                 125

Pro Val Met Met Phe Gly Val Val Phe Ala Val Ser Ala Lys Trp Val
130                 135                 140

Leu Arg Val Pro Val Arg Gly Arg Leu Arg His Tyr Met Asn Pro Ser
145                 150                 155                 160

Asn Phe Gly Ile Ala Ala Ile Leu Val Leu Phe Pro Trp Ala Ser Ile
                165                 170                 175

Ala Pro Pro Tyr His Phe Thr Glu His Val Asn Thr Pro Phe Gly Trp
            180                 185                 190

Leu Ile Val Leu Gly Ile Leu Met Ser Gly Thr Ile Leu Asn Ala Lys
        195                 200                 205

Leu Thr Gly Arg Met Trp Leu Ile Ala Gly Trp Leu Gly Thr Phe Ala
210                 215                 220

Leu Gln Ala Val Leu Arg Gly Leu Val Phe Gly Thr Ser Ile Pro Ala
225                 230                 235                 240

Ala Leu Gly Met Met Thr Gly Val Ala Phe Val Leu Phe Thr Asn Tyr
                245                 250                 255

Met Ile Thr Asp Pro Gly Thr Thr Pro Ser Lys Pro Ala Asn Gln Val
            260                 265                 270

Ala Phe Gly Ala Gly Val Ala Leu Leu Tyr Ala Leu Phe Met Ile Ala
        275                 280                 285

His Ile Ala Tyr Gly Ile Phe Phe Ala Thr Ala Leu Thr Cys Leu Ile
        290                 295                 300

Arg Gly Leu Tyr Leu Trp Tyr Val His Phe Arg Asp Arg Gly His Asp
305                 310                 315                 320

Glu Arg Gln Ala Thr Val Leu Arg Ala Ala Ala Ser Ala Pro Ala
                325                 330                 335

Ala Glu Ala Ser Gly Lys Val Ala Ala Val
            340                 345

<210> SEQ ID NO 92
<211> LENGTH: 1041
<212> TYPE: DNA
<213> ORGANISM: Streptomyces kaniharaensis

<400> SEQUENCE: 92
```

-continued

```
gtgacggaca tggcagacaa ggccccgacc acgaagcaga cggcccacca accagcgccg    60
cccgaagcgg ccgccaggcc ggccaccgcc tcccggcacg agccgaaggt cgtcatcgcg   120
ctgcgccgct tcgcgatctc gatcaccgtc ttcaacatcc tcggctacac ggtgctcggc   180
ttcgaacagc cgtggacctg gccgctgatc gccctcgcca ccgcctacac caccgagacc   240
gcgctggaac tggtcggcgc caaggtggag ggccgccgcc cgcgcttcct cggcaacggc   300
ctgcccggga tgctggagtt cctctacccg tcgcacatca ccggcctggc cctcaacatg   360
ctgacctacg tcaacgaccg gctccccgtg atgatgttcg gcgtggtctt cgcggtgagc   420
gccaagtggg tgctgcgggt gccggtgcgc ggcaggctgc ggcactacat gaacccgtcg   480
aacttcggca tcgccgcgat cctggtgctc ttcccgtggg ccagcatcgc gccgccgtac   540
cacttcaccg agcacgtcaa cacccccgttc ggctggctga tcgtgctggg catcctgatg   600
tcgggcacca tcctcaacgc gaagctcacc ggccggatgt ggctgatcgc cgggtggctc   660
ggcacgttcg ccctccaggc cgtgctgcgc gggctggtct tcggcacgtc gatcccccgct   720
gcgctcggca tgatgaccgg cgtggcgttc gtgctcttca ccaactacat gatcacggac   780
cccggtacga cgccctcgaa gcccgccaac caggtcgcct tcggcgccgg ggtcgcgctg   840
ctgtacgccc tcttcatgat cgcgcacatc gcgtacggca tcttcttcgc caccgccctc   900
acgtgcctga tccgggggtct ctacctctgg tacgtgcact tccggaccg cgggcacgac   960
gagcggcagg ccaccgtgct gcgggcggcc gcagcgagcg ccccggcggc cgaggcgagc  1020
ggcaaggtcg cggcggtatg a                                             1041
```

<210> SEQ ID NO 93
<211> LENGTH: 1958
<212> TYPE: PRT
<213> ORGANISM: Streptomyces citricolor
<400> SEQUENCE: 93

```
Met Gly Gly Glu Tyr Met Ser Ser Glu Arg Ile Ala Ile Val Gly Ile
  1               5                  10                  15
Gly Leu Arg Tyr Pro Asp Ala Asn Ser Ala Ser Glu Leu Trp Asp Asn
             20                  25                  30
Val Leu Ser Gly Arg Arg Ala Phe Arg Arg Leu Pro Asp Glu Arg Met
         35                  40                  45
Asn Gln Ala Asp Tyr Trp Ser Ala Asp Arg Ser Ala Pro Asp Arg Tyr
     50                  55                  60
Tyr Ala Thr Lys Ala Ala Val Leu Arg Asp Tyr Ser Phe Asp Arg Ile
 65                  70                  75                  80
Arg Tyr Ser Val Ala Gly Ser Thr Tyr Arg Ala Thr Asp Leu Thr His
                 85                  90                  95
Trp Leu Ala Leu Asp Val Ala Ala Glu Ala Leu Ala Asp Ala Gly Phe
            100                 105                 110
Pro Asp Gly Ser Gly Leu Pro Arg Gln Thr Thr Gly Val Val Val Gly
        115                 120                 125
Asn Ser Leu Thr Gly Glu Phe Ser Arg Ala Asn Val Met Arg Leu Arg
    130                 135                 140
Trp Pro Tyr Val Arg Arg Thr Val Ala Ala Leu Val Gly Gln Gly
145                 150                 155                 160
Trp Ser Gln Gly Asp Ile Ala Val Phe Leu Gln Asp Leu Glu Pro Gln
                165                 170                 175
Tyr Lys Ala Pro Phe Pro Pro Ile Asp Glu Asp Ser Leu Ala Gly Gly
            180                 185                 190
```

```
Leu Ala Asn Thr Ile Ala Gly Arg Ile Cys Asn His Phe Asp Leu Arg
            195                 200                 205

Gly Gly Gly Tyr Thr Val Asp Gly Ala Cys Ser Ser Ser Leu Leu Ser
        210                 215                 220

Val Val Thr Ala Ala Lys Ala Leu Ala Asp Gly Glu Leu Glu Val Ala
225                 230                 235                 240

Val Ala Gly Gly Val Asp Leu Ser Ile Asp Pro Phe Glu Val Ile Gly
                245                 250                 255

Phe Ala Lys Thr Gly Ala Leu Ala Thr Gly Glu Met Lys Val Tyr Asp
            260                 265                 270

Arg Asp Ser Asn Gly Phe Trp Pro Glu Gly Ser Gly Met Leu Val
        275                 280                 285

Leu Met Arg Glu Glu Asp Ala Leu Ala Gln Gly Arg Arg Ile Tyr Ala
    290                 295                 300

Ser Ile Thr Gly Trp Gly Val Ser Ser Asp Gly Lys Gly Gly Ile Thr
305                 310                 315                 320

Arg Pro Glu Ala Gly Gly His Arg Leu Ala Leu Asp Arg Ala Tyr Arg
                325                 330                 335

Arg Ala Gly Tyr Gly Val Glu Thr Val Ser Tyr Phe Glu Gly His Gly
            340                 345                 350

Thr Gly Thr Ala Leu Gly Asp Ala Thr Glu Ile Glu Ala Leu Ser Ser
        355                 360                 365

Ala Arg Arg Ala Ala Asp Pro Thr Ala Arg Pro Ala Ala Leu Gly Thr
    370                 375                 380

Val Lys Gly Asn Phe Gly His Thr Lys Ala Ala Gly Val Ala Gly
385                 390                 395                 400

Leu Ile Lys Ala Ala Leu Ala Val His His Gln Val Ile Pro Pro Ala
                405                 410                 415

Thr Gly His Tyr Asp Pro His Pro Gly Leu Leu Gly Glu Thr Ala Ala
            420                 425                 430

Met Tyr Val Pro Arg Gln Ala Gly Leu Trp Pro Ala Asp Gln Pro Val
        435                 440                 445

Arg Ala Gly Val Ser Ala Met Gly Phe Gly Gly Ile Asn Thr His Ile
    450                 455                 460

Ala Leu Thr Gln Ala Pro Gly Thr Ala Arg Arg Glu Ala Leu Asp Glu
465                 470                 475                 480

Arg Ile Thr Arg Leu Val Ala Gly Arg Gln Asp Ala Glu Leu Leu Leu
                485                 490                 495

Leu Asp Gly Ala Asp Gln Ala Ala Leu Arg Ala Glu Leu Val Arg Leu
            500                 505                 510

Leu Asp Leu Val Pro Arg Leu Ala Gln Ala Glu Leu Ala Asp Leu Ala
        515                 520                 525

Gly Thr Leu Ala Asp Arg Leu Ser Asp Gly Pro Val Arg Ala Val
    530                 535                 540

Val Ala Ser Ser Pro Asp Asp Ala Val Arg Ala Leu Glu Arg Leu Val
545                 550                 555                 560

Ala Leu Leu Asp Ser Gly Thr Arg Glu Ala Phe Ser Ala Gly Glu Gly
                565                 570                 575

Ile Phe Leu Gly Arg Ala Arg Ser Ala Pro Arg Ile Ala Tyr Leu Phe
            580                 585                 590

Pro Gly Gln Gly Ser Gly Arg Gly Val Gly Ala Ile Arg Arg Arg
        595                 600                 605
```

-continued

```
Phe Ala Thr Ala Glu Arg Val Phe His Asp Phe Gly Pro Pro Thr Gly
    610                 615                 620
Asp Asp Gln Val Ala Thr Gln Val Ala Gln Pro Arg Ile Val Thr Gly
625                 630                 635                 640
Ser Leu Ala Ala Leu Arg Val Leu Asp Gly Leu Gly Ile Arg Ala Asp
                645                 650                 655
Thr Ala Val Gly His Ser Leu Gly Glu Leu Thr Ala Leu His Trp Ala
                660                 665                 670
Gly Ala Met Ser Glu Glu Gln Leu Val Arg Leu Ala Thr Ile Arg Gly
                675                 680                 685
Arg Val Met Ala Arg Ala Ser His Gly Gly Ala Met Ala Gly Leu
690                 695                 700
Ala Ala Thr Pro Glu Arg Thr Thr Arg Leu Ser Ala Gly Gln Asp Val
705                 710                 715                 720
Val Val Ala Gly Tyr Asn Gly Pro Arg Gln Thr Val Val Ser Gly Pro
                725                 730                 735
Ala Glu Ala Val Asp Glu Val Cys Arg Arg Ala Ala Glu Gly Val
                740                 745                 750
Thr Ala Thr Arg Leu Asn Val Ser His Ala Phe His Ser Pro Leu Val
                755                 760                 765
Glu Pro Ala Ala Val Ala Met Ala Ala Glu Leu Ala Gly Phe Asp Phe
770                 775                 780
Arg Glu Pro Val Arg Pro Ile Ala Ser Thr Val Thr Gly Glu Leu Leu
785                 790                 795                 800
Asp Pro Ala Ala Asp Leu Arg Glu Leu Leu Arg Asp Gln Val Leu Arg
                805                 810                 815
Pro Val Arg Phe His Glu Ala Ala Gly Val Ala Ala Val Gly Ala Asp
                820                 825                 830
Leu Val Val Glu Val Gly Pro Gly Arg Val Leu Ser Gly Leu Leu Ala
                835                 840                 845
Glu Ile Ala Pro Asp Pro Thr Val Leu Ala Leu Asp Thr Asp Ser Ala
850                 855                 860
Ser Leu Gly Ala Leu Leu Arg Val Val Gly Ala Ala Tyr Val Leu Gly
865                 870                 875                 880
Ala Pro Val Arg Thr Gly Ala Leu Phe Gly Asp Arg Leu Ile Arg Pro
                885                 890                 895
Leu Pro Ala Asp Gly Val Met Ser Phe Leu Ala Asn Pro Cys Glu Ala
                900                 905                 910
Ala Pro Pro Ile Gly Ala Gly Leu Val Pro Gln Asp Gly Asp Arg
                915                 920                 925
Gly Asp Gly Ala Ala Gly Arg Asp Glu Gly Thr Thr Pro Ala Arg Ile
                930                 935                 940
Ala Asp Ser Gly Ala Cys Pro Asp Ser Thr Leu Glu Leu Leu Arg Arg
945                 950                 955                 960
Leu Ala Ala Glu Arg Val Glu Leu Pro Leu Asp Ser Val Thr Ala Arg
                965                 970                 975
Thr His Pro Met Asp Asp Leu His Leu Ser Ser Ile Thr Val Gly Gln
                980                 985                 990
Ile Val Asn Asp Val Thr Arg Ala Leu Gly Gln Pro Val Leu Thr Ala
                995                 1000                1005
Thr Pro Ser Phe Ala Thr Val Ser Leu Gly Glu Leu Ala Asp Leu
        1010                1015                1020
Ile Asp Gly Leu Ala Asp Thr Ser Gln Asp Gly Ala Ala Ala Ala
```

-continued

```
                1025                1030                1035
Asp Glu Val Pro Gly Val Ala Pro Trp Val Arg Pro Phe Ala Val
    1040                1045                1050
Glu Tyr Met Glu Ala Ala Leu Val Pro Arg Pro Leu Pro Gly Pro
    1055                1060                1065
Gln Ala Ala Ala Gly Asp Trp Ala Val Tyr Ser Thr Pro Gly His
    1070                1075                1080
Pro Leu Ala Glu Pro Leu Arg Ala Leu Ala Arg Ala Gly Ile
    1085                1090                1095
Gly Asp Gly Val Leu Leu Cys Leu Pro Ala Glu Cys Gly Ala Gly
    1100                1105                1110
Glu Ala Asp Leu Phe Leu Ala Ala Gly Arg Ala Val Leu Ala Ala
    1115                1120                1125
Pro Glu Gly Thr Arg Leu Val Val Val Gln His Arg Phe Gly Ala
    1130                1135                1140
Gly Gly Met Ala Lys Thr Leu His Leu Glu His Pro Ser Val Leu
    1145                1150                1155
Thr Thr Val Val Glu Leu Ala Asp Pro Ala Pro Lys Gly Ala Ala
    1160                1165                1170
Leu Asp Glu Ala Val Ala Arg Val Val Ala Glu Ala Ala Ala Thr
    1175                1180                1185
Ala Gly Phe Ala Glu Val Arg Tyr Arg Gln Asp Gly Arg Arg Thr
    1190                1195                1200
Val Pro Val Leu Arg Pro Leu Gln Leu Ser Pro Ala Pro Ala Gly
    1205                1210                1215
Glu Ser Pro Leu Asp Ala Arg Asp Val Leu Leu Val Thr Gly Gly
    1220                1225                1230
Gly Lys Gly Ile Thr Ala Glu Cys Ala Leu Ala Ile Ala Lys Asp
    1235                1240                1245
Ser Gly Ala Gly Leu Ala Leu Ile Gly Arg Ala Asp Pro Ala Ala
    1250                1255                1260
Asp Thr Glu Leu Ala Glu Asn Leu Ala Arg Met Asp Ala Ala Gly
    1265                1270                1275
Leu Arg Tyr Arg Tyr Ala Arg Ala Asp Val Thr Ser Ala Asp Gln
    1280                1285                1290
Val Ala Ala Val Asp Leu Leu Glu Ala Glu Leu Gly Pro Val
    1295                1300                1305
Thr Ala Val Leu His Gly Ala Gly Arg Asn Glu Pro Ala Ala Leu
    1310                1315                1320
Glu Thr Leu Ser Ala Glu Asp Phe Arg Arg Thr Leu Ala Pro Lys
    1325                1330                1335
Thr Asp Gly Leu Glu Ala Val Leu Ala Ala Val Glu Pro Glu Arg
    1340                1345                1350
Leu Lys Leu Leu Ile Thr Phe Gly Ser Ile Ile Gly Arg Ala Gly
    1355                1360                1365
Leu Arg Gly Glu Ala His Tyr Ala Thr Ala Asn Asp Trp Met Thr
    1370                1375                1380
Glu Leu Thr Leu Arg Phe Arg Arg His Pro Gln Ala Arg Ala
    1385                1390                1395
Ile Ala Leu Glu Trp Ser Val Trp Ser Gly Ala Gly Met Gly Glu
    1400                1405                1410
Arg Leu Gly Val Val Glu Ala Leu Ile Arg Glu Gly Ile Thr Pro
    1415                1420                1425
```

-continued

```
Ile Ser Thr Glu Asn Gly Ile Gln Val Leu Arg Glu Val Leu Ala
    1430                1435                1440

Asp Pro Ser Ala Gly Pro Val Leu Val Val Ser Gly Arg Val Gly
    1445                1450                1455

Gly Leu Pro Thr Leu Thr Thr Ala His Arg Glu Leu Pro Leu Thr
    1460                1465                1470

Arg Phe Val Glu Arg Val Val Val His His Pro Asp Ile Glu Leu
    1475                1480                1485

Ile Thr Glu Ala Glu Leu Thr Glu Gly Ser Asp Pro Tyr Leu Thr
    1490                1495                1500

Asp His Arg Leu Gln Gly Asp Leu Leu Phe Pro Ala Val Leu Gly
    1505                1510                1515

Met Glu Ala Met Ala Gln Val Ala Ala Ala Val Ser Gly His Gln
    1520                1525                1530

Gly Pro Pro Leu Leu Glu Asp Val Glu Phe Arg Arg Pro Val Val
    1535                1540                1545

Val Arg Pro Gly Gly Ser Thr Thr Ile Arg Ile Ala Ala Leu Val
    1550                1555                1560

Arg Ala Pro Gly Thr Val Asp Val Val Leu Arg Ser Ala Asp Thr
    1565                1570                1575

Asp Phe Ala Ala Asp His Phe Arg Ala Arg Leu Arg Tyr Pro Arg
    1580                1585                1590

Pro Gly Val Pro Thr Thr Pro Val Pro Val Ala Phe Gly Leu Pro
    1595                1600                1605

Thr Val Pro Val Asp Pro Val Thr Glu Leu Tyr Gly Ser Val Leu
    1610                1615                1620

Phe Gln Gly Lys Arg Phe Gln Arg Leu Leu Glu Tyr Arg Arg Ala
    1625                1630                1635

Gly Ala Arg His Ala Leu Ala Glu Ile Ser Thr Thr Ala Gln Ala
    1640                1645                1650

Pro Trp Phe Ala Ala Phe Leu Pro Gln Asp Gln Leu Leu Ala Asp
    1655                1660                1665

Pro Gly Thr Arg Asp Ala Met Met His Ala Ile Gln Cys Cys Val
    1670                1675                1680

Pro Asp Ala Thr Leu Leu Pro Gln Ser Ile Glu Arg Leu Trp Leu
    1685                1690                1695

Ala Asp Arg Ala Asp Gln Asp Ser Glu Tyr Val Val Leu Asp Ala
    1700                1705                1710

Arg Glu Arg Ser Gln Asp Gly Asp Thr Tyr Val Tyr Asp Leu Asp
    1715                1720                1725

Val Arg Thr Pro Ser Gly Thr Val Val Glu Arg Trp Glu Gly Leu
    1730                1735                1740

Ala Leu Val Ala Val Arg Lys Arg Gly Ala Gly Pro Trp Val
    1745                1750                1755

Pro Ala Met Leu Gly Ser Tyr Leu Glu Arg Gly Leu Glu Arg Val
    1760                1765                1770

Leu Gly Gly Ser Arg Ala Val Val Glu Pro Ala Pro Asp Ala
    1775                1780                1785

Ala Thr Ala Asp Gln Asp Arg Arg Ser Arg Thr Glu Thr Ala Val
    1790                1795                1800

Gly Arg Ala Leu Gly Arg Pro Val Lys Leu Arg His Arg Pro Asp
    1805                1810                1815
```

-continued

| | | | | | | | | | | |
|---|---|---|---|---|---|---|---|---|---|---|
| Gly | Arg | Pro | Glu | Leu | Asp | Gly | Gly | Pro | Gly | Leu | Glu | Gly | Arg | Thr |
| | 1820 | | | | | 1825 | | | | 1830 | | | | |
| Val | Ser | Ala | Ser | His | Asp | Ala | Gly | Leu | Thr | Leu | Ala | Val | Val | Gly |
| | 1835 | | | | | 1840 | | | | 1845 | | | | |
| Ala | Gly | Arg | Leu | Ala | Cys | Asp | Val | Glu | Ser | Val | Arg | Glu | Arg | Thr |
| | 1850 | | | | | 1855 | | | | 1860 | | | | |
| Ala | Glu | Asp | Trp | Asp | Gly | Leu | Leu | Gly | Ala | Gly | Arg | Leu | Ala | Leu |
| | 1865 | | | | | 1870 | | | | 1875 | | | | |
| Arg | Asn | Leu | Leu | Ala | Thr | Glu | Ala | Gly | Glu | Asp | Arg | Ala | Val | Ala |
| | 1880 | | | | | 1885 | | | | 1890 | | | | |
| Gly | Thr | Arg | Val | Trp | Ser | Ala | Leu | Glu | Cys | Leu | Arg | Lys | Ala | Gly |
| | 1895 | | | | | 1900 | | | | 1905 | | | | |
| Ala | Thr | Thr | Gln | Ala | Leu | Thr | Leu | Asp | Arg | Val | His | Pro | Asp | Gly |
| | 1910 | | | | | 1915 | | | | 1920 | | | | |
| Trp | Ala | Val | Leu | Ser | Ala | Gly | Asp | Ala | Thr | Val | Ala | Thr | Trp | Val |
| | 1925 | | | | | 1930 | | | | 1935 | | | | |
| Thr | Thr | Val | Asn | Gly | Arg | Thr | Asp | Pro | Val | Val | Phe | Ala | Val | Leu |
| | 1940 | | | | | 1945 | | | | 1950 | | | | |
| Ala | Gly | Lys | Glu | Asn | | | | | | | | | | |
| | 1955 | | | | | | | | | | | | | |

<210> SEQ ID NO 94
<211> LENGTH: 5877
<212> TYPE: DNA
<213> ORGANISM: Streptomyces citricolor

<400> SEQUENCE: 94

```
atgggtggtg aatacatgag cagtgagcgg atcgctatcg tggggatcgg cctccgctac      60
ccggatgcca attcggcgag tgagctctgg acaacgtac tgagtggccg cagggccttc     120
cgaaggctgc cggacgagcg gatgaaccag gcggactact ggtcggcgga ccgcagtgca     180
cccgaccggt actacgcgac aaaggccgcc gtcctgaggg actacagctt cgaccgcatc     240
aggtacagcg tcgccggaag cacgtaccga gcgaccgatc tgacgcactg gctggctctt     300
gacgtcgctg ccgaggcgct ggccgacgcc ggattcccgg acggttccgg attgcccagg     360
caaaccactg gtgtggtggt cggaaacagt ctcaccgggg aattctcgcg ggccaacgtc     420
atgcggctgc ggtggcctta cgtgcgtcgg acggtggccg ccgcgctggt cggccagggc     480
tggtcccagg gggacatcgc ggtgttcctc caggacctgg agccccagta caaggcgccc     540
ttcccgccca tcgacgagga ctcgctggcc ggcggtctcg ccaacaccat cgccggccgg     600
atctgcaacc acttcgatct cgcgcggcgg ggatacacgg tcgacggcgc ctgctcctcc     660
tccctgctgt ccgtggtcac cgcggcgaag gcgctgccg acggtgagct ggaggtggcc     720
gtcgccggcg ggtcgacct gtccatcgac ccgttcgagg tgatcggctt cgccaagacc     780
ggcgcactgg ccaccggtga gatgaaggtc tacgaccggg actccaacgg cttctggccc     840
ggcgagggct ccggaatgct ggtgctgatg cgcgaggagg acgcgctggc gcaggggcgg     900
cggatctatg cgagcatcac cggctggggg gtctcctcgg acggcaaggg cggcatcacc     960
cggccggagg cgggcggcca ccgactggcg ctggaccgcg cctaccggcg ggcgggctac    1020
ggtgtcgaga cggtctcgta cttcgagggc acggcaccg gcacgccct cggcgacgcg    1080
accgagatcg aggcactgtc ttccgcgcgc gcgccgcgg atccgacggc cgtccggcc    1140
gcgctcggga cggtcaaggg gaacttcggg cacaccaagg ccgcggcggg tgtggccggt    1200
ctgatcaagg cggccctcgc cgtgcaccac caggtgatcc ccccggcgac cggccactac    1260
```

-continued

```
gacccgcacc ccggactgct cggcgagacg gcggccatgt acgtgccgcg ccaggccggg    1320
ctctggccgg ccgaccagcc cgtccgggcc ggagtgtcgg ccatgggctt cggcgggatc    1380
aacacccaca tcgccctcac ccaggcgccc ggtaccgccc ggcgcgaggc gctcgacgag    1440
cgcatcaccc ggctggtcgc cggccgccag gacgccgaac tgctgctgct ggacggagcg    1500
gaccaggccg cgctgcgggc ggagctggtc cggctgctgg acctggtgcc caggctggcc    1560
caggccgaac tggccgacct ggccggaacg ctggccgacc ggctctcgga cggtccggtc    1620
cgtgccgccg tcgtcgcgtc ctccccggac gacgccgtac gcgccctcga acggctggtc    1680
gcactgctcg actcggggac acgcgaggcg ttctcggccg gtgaggggat cttcctcggc    1740
cgggccagga gcgcccccg gatcgcctac ctcttcccgg ggcagggctc cggccgcggc    1800
ggggtcggcg ccatcaggcg ccggttcgcc acggcggagc gggtgttcca cgacttcggc    1860
ccgcccaccg gcgacgacca ggtcgccacc caggtggccc agccgcgcat cgtcaccggc    1920
tcactggccg ccctgcgagt actggacggg ctcggcatcc gggccgacac cgccgtcgga    1980
cacagcctgg gcgaactgac cgcgctgcac tgggccgggg cgatgagcga ggaacagctc    2040
gtgcgcctcg ccacgatccg cggccgggtg atggcacggg cgagccacgg cggcggcgcc    2100
atggccggcc tggcggcgac gccggagcgg accacccggc tgtccgccgg gcaggacgtc    2160
gtcgtcgcgg ggtacaacgg ccccggcag acggtggtct cgggccccgc cgaggcggtc    2220
gacgaggtct gccgccgggc ggcggccgag ggcgtcacgg cgacccggct gaacgtgtcg    2280
cacgccttcc actcgccgct ggtcgagccc gccgcggtcg cgatggcggc cgaactggcc    2340
ggattcgact ccgcgagcc ggtccgcccg atcgcctcca cggtcaccgg cgaactgctg    2400
gacccggccg ccgacctgcg tgagctgctg cgcgaccagg tgctgcgccc ggtacggttc    2460
cacgaggccg ccggtgtggc ggcggtgggc gccgacctgg tggtggaggt cggcccggga    2520
cgggtgctgt ccggtctgct ggcggagatc gcgccggacc ccaccgtgct ggccctcgac    2580
accgacagcg cctcgctcgg tgcgctgctc agggtcgtcg gcgccgcgta cgtgctcggc    2640
gcgcccgtgc ggaccggtgc cctgttcggc gaccgcctga tcaggccgct gccggcggac    2700
ggcgtgatga gcttcctggc caacccctgc gaggcggctc gcccatcgg cgcgggcctg    2760 gtgccgcagg acggcgggga ccgcggggac ggcgcggcgg gccgggacga ggggaccacg    2820
ccggcccgga tcgcggacag cggcgcgtgc ccggactcca ccctggagct gctgcgcagg    2880
ctcgcggccc agcgggtcga gctgccgctg gactcggtca ccgcccggac ccacccgatg    2940
gacgacctgc acctgagctc catcacggtc ggtcagatcg tcaacgacgt cacccgggca    3000
ctggggcagc ccgtgctcac cgcgacaccc agcttcgcga ccgtgagcct gggcgaactc    3060
gccgacctga tcgacgggtt ggcggacacc tcgcaggacg gcgccgccgc cgcggacgag    3120
gtccccggcg tggcccgtg ggtgaggccc ttcgcggtcg agtacatgga ggccgccctg    3180
gtgccacggc cgctgcccgg ccccaggcg gcggccggcg actggcggt gtacagcaca    3240 cccgccacc cgctggccga ccgctgcgc gccgcactcg cccggcggg gatcggggac    3300 ggcgtgctgc tctgcctccc ggccgagtgc ggcgcgggcg aggccgacct gttcctggcc    3360 gccgccgcg cggtcctggc cgcgcccgaa ggcaccggc tggtcgtggt ccagcaccgc    3420
ttcggggccg gcgggatggc gaagaccctg cacctggagc accgtcggt cttgaccacg    3480 gtggtcgagc tggccgatcc cgctcccaag ggggcggccc tcgacgaggc ggtggcccgc    3540
gtcgtcgccg aggccgccgc gacggccggg ttcgcggagg tgcgctaccg gcaggacggg    3600
```

-continued

```
cgccgcaccg tcccggtgct ccgtcccctg cagctgagtc cggccccggc cggtgagtca    3660
ccgctcgacg cgcgggacgt tctcctggtc accggcggcg gaaagggcat cacggccgag    3720
tgcgccctgg cgatcgccaa ggactccggg gcgggcctgg ccctgatcgg ccgcgccgac    3780
ccggccgccg acaccgaact cgccgagaac ctcgccagga tggacgccgc gggcctgcgc    3840
taccgctacg cccgggccga tgtgacctcg gccgaccagg tcgccgccgc ggtggacctg    3900
ctggaggccg aactcggccc ggtcaccgcg gtgttgcacg gtgccggccg caatgagccg    3960
gccgctctcg agacactcag cgccgaggac ttccggcgga ccctggcgcc caagaccgac    4020
ggcctggagg cggtcctggc ggccgtcgaa ccggaacgcc tgaagctgct gatcaccttc    4080
ggttcgatca tcggccgggc cggactccgc ggtgaggcgc actacgccac cgccaacgac    4140
tggatgaccg agctgaccct ccgcttccgg cgccgccacc gcaggcccg gccatcgcc     4200
ctggagtggt cggtctggtc gggcgcgggc atgggcgaac ggctcggagt cgtcgaggcg    4260
ttgatccgcg agggcatcac gccgatctcc accgagaacg ggatccaggt gctccgcgag    4320
gtgctcgccg accctcggc cggtcccgtc ctggtggtca gcggacgggt cggcggcctg    4380
cccacgctca ccacggccca ccgcgagctg ccgctgacca ggttcgtgga acgggtggtc    4440
gtgcaccacc cggacatcga gctgatcacc gaggccgagc tgaccgaggg cagcgacccc    4500
tatctgaccg accaccggct ccagggcgac ctgctgttcc ccgcagtgct gggcatggag    4560
gcgatggccc aggtcgccgc cgcggtgagc ggccaccagg gcccgccgct gctggaggac    4620
gtcgagttcc gccgtcccgt ggtggtgagg ccgggcggct cgaccaccat caggatcgcg    4680
gcgctggtcc gggccccggg gacggtggac gtggtgctgc gcagcgccga caccgacttc    4740
gcggccgacc acttcagggc caggctgcgc tacccccaggc ccggggtgcc caccacgccg    4800
gtgccggtcg cgttcggcct gccgacggtg ccggtggatc cggtgaccga gctgtacggc    4860
agtgtgctgt tccagggcaa gcggttccag cgcctgctgg agtaccgcg ggccggcgcc     4920
cggcacgccc tggcggagat ctccaccacc gcccaggcac cgtggttcgc ggccttcctg    4980
ccgcaggacc agctgctggc cgaccccggc acccggacg cgatgatgca cgccatccag    5040
tgctgcgtgc cggacgccac gctgctgccg cagagcatcg agcggctctg gctggccgac    5100
cgggcggacc aggactccga gtacgtcgtt ctcgacgccc gggagcgctc gcaggacggg    5160
gacacctacg tctacgacct cgacgtccgc accccctcgg gaacggtggt cgaacgctgg    5220
gaggggctgg ccctggtcgc cgtccgcaaa cgcggcgggg ccggcccgtg ggtgcccgcc    5280
atgctcggtt cgtacctgga gcgcggcctg gaacgggtac tgggcggcag ccgcgcggtg    5340
gtcgtcgaac ccgccccgga cgccgccacc gcggaccagg accgccgctc ccgtaccgag    5400
accgccgtcg gccgggcgct gggccggccg gtgaagctgc gccaccggcc ggacggcagg    5460
cccgaactcg acggcgggcc gggcctggag ggacggacgg tgtcggcctc gcacgacgcc    5520
ggactgaccc tcgcggtggt gggcgcggga cggctcgcct gcgatgtcga gtcggtccgg    5580
gagcggaccg ccgaggactg ggacgggctg ctgggcgccg tcggctcgc cctgcggaac     5640
ctgctggcaa ccgaggcggg cgaggaccgg cggtcgccg caccagggt gtggagcgcg     5700
ctggagtgcc tgcgcaaggc cggtgcgacc acgcaggcgc tgacgctgga ccgcgtccac    5760
ccggacggct gggccgtact gtccgccggc gacgcgaccg tcgccacctg ggtgaccacc    5820
gtcaacggcc ggaccgatcc ggtggtcttc gcggtactcg ccgggaagga gaactga      5877
```

<210> SEQ ID NO 95
<211> LENGTH: 165

```
<212> TYPE: PRT
<213> ORGANISM: Streptomyces citricolor

<400> SEQUENCE: 95

Met Ser Gly Tyr Tyr Glu Ile Arg His Thr Val Gly Phe Glu Thr
1               5                   10                  15

Asn Leu Val Gly Asn Val Tyr Tyr Val Asn Tyr Leu Arg Trp Gln Gly
            20                  25                  30

Arg Cys Arg Glu Met Phe Leu Lys Glu Lys Ala Pro Gly Val Leu Ala
        35                  40                  45

Glu Leu Arg Asp Asp Leu Lys Leu Phe Thr Leu Lys Val Asp Cys Asp
50                  55                  60

Phe Phe Ala Glu Ile Thr Ala Phe Asp Glu Leu Ser Ile Arg Met Arg
65                  70                  75                  80

Leu Glu Glu Leu Thr Gln Thr Gln Ile Gln Phe Ser Phe Asp Tyr Leu
                85                  90                  95

Arg Leu Asp Gly Gly Gln Glu Asn Leu Val Ala Arg Gly Arg Gln Arg
            100                 105                 110

Ile Ala Cys Met Arg Gly Pro Asn Thr Ala Thr Val Pro Ala Arg Val
        115                 120                 125

Pro Glu Glu Leu Arg Leu Ala Leu Ala Pro Tyr Ala Glu Gly Pro Val
130                 135                 140

Ala Ala Arg Leu Pro Ala Ala Pro Thr Ser Pro Gly Gly Pro Val Arg
145                 150                 155                 160

Thr Gly Arg Gly Arg
                165

<210> SEQ ID NO 96
<211> LENGTH: 498
<212> TYPE: DNA
<213> ORGANISM: Streptomyces citricolor

<400> SEQUENCE: 96
atgtcgggct actacgagat ccgccacacc gtgggttttg aggagaccaa cctcgtcggc      60
aacgtctact acgtgaacta cctgcgctgg caggggcgtt gccgggagat gttcctcaag     120
gagaaggcgc ccggggtgct cgccgagctg cgggacgacc tgaagctgtt caccctcaag     180
gtggactgcg acttcttcgc cgagatcacc gcgttcgacg agctgtcgat ccggatgcgg     240
ctggaggagc tgacgcagac ccagatccag ttcagcttcg actacctgcg gctcgacggc     300
gggcaggaga acctggtcgc ccgtggccgt cagcggatcg cgtgcatgcg cgggccgaac     360
acggcgacgg tccccgccag ggtgcccgag gagctgcgcc tcgccctggc gccctacgcc     420
gagggcccgg tggccgcccg actgccggcg cgccgacgt cgcccggcgg gccggtgagg      480
acggggaggg ggcggtga                                                   498

<210> SEQ ID NO 97
<211> LENGTH: 324
<212> TYPE: PRT
<213> ORGANISM: Streptomyces citricolor

<400> SEQUENCE: 97

Val Pro Ser Ala Trp Arg Lys Leu Arg Arg Ile Leu Thr Pro Ser
1               5                   10                  15

Thr Ser Glu Thr Leu Leu Glu Lys Arg Gly Phe His Arg Lys Thr Pro
            20                  25                  30

Ala Ala Gln Gln Leu Leu Glu Thr Val Gly Glu Arg Phe Leu Glu Gly
```

```
                35                  40                  45
Tyr Gly Tyr Ala Met Glu Ala Arg Asp Thr Gly Ser Ala Glu Asn Leu
             50                  55                  60
Leu Glu Gly Val Pro Ile Arg Phe Arg Gly Phe Ala Tyr Glu Gly Ala
 65                  70                  75                  80
Gly Met Gly Phe Ala Met Leu Asp Gly Leu Pro Leu Ser Gly Ser Gly
                 85                  90                  95
Ser Val Ala Arg Phe Leu Ala Gly Arg Gly Ala Asp His Val Tyr Met
                100                 105                 110
Val Tyr Ile Gly Val Gly Trp Ala Met Ala Arg Leu Pro Arg Phe Arg
            115                 120                 125
Trp Pro Asp Ile Asp Ala Leu Asp Pro Leu Leu Arg Trp Leu Val Leu
130                 135                 140
Asp Gly Tyr Gly Phe His Gln Ala Tyr Phe Arg Thr Ala Arg Tyr Val
145                 150                 155                 160
His Glu Gln Tyr Arg Asp Pro Ala Phe Pro Trp Pro Ala His Asp Ser
                165                 170                 175
Pro Ser Tyr Ala Gly Arg Ala Ile Asp Gln Gly Ile Gly Arg Ala Leu
            180                 185                 190
Trp Phe Val Gly Gly Thr Asp Ala Asp Leu Val Ala Thr Met Ile Glu
            195                 200                 205
Lys Phe Pro Glu Ser Arg Arg Ser Asp Leu Tyr Ser Gly Ala Gly Leu
210                 215                 220
Ala Ala Thr Tyr Ala Gly Gly Val Asp Glu Ala Glu Leu Arg Ala Phe
225                 230                 235                 240
Trp Glu Arg Ala Gly Ser His Arg Ala Met Val Ala Gln Gly Ser Ala
                245                 250                 255
Phe Ala Ala Glu Ala Arg Glu Arg Ala Gly Leu Pro Val Val His Thr
            260                 265                 270
Glu Leu Ala Thr Arg Val Phe Cys Gly Met Thr Pro Ala Gln Ala Ala
            275                 280                 285
Arg Val Thr Gln Glu Val Arg Pro Ala Gly Pro Val Pro Gly Ala Leu
290                 295                 300
Pro Ala Tyr Glu Val Trp Arg Gln Ala Ile Ala Asp Arg Phe Thr Asn
305                 310                 315                 320
Val Gly Gly Cys

<210> SEQ ID NO 98
<211> LENGTH: 975
<212> TYPE: DNA
<213> ORGANISM: Streptomyces citricolor

<400> SEQUENCE: 98
gtgcccagcg catggcggaa actccgacgt cgtattctca ctccgagcac ctctgaaacg    60
ctactggaga agcgtggttt ccaccggaag acgccggccg cccagcaact cctggagacg   120
gtcggcgagc ggtttctgga gggctacggc tacgccatgg aggcccggga tacgggatcg   180
gcggagaacc tcctggaggg cgtcccgatc cgattccgcg gcttcgccta cgaaggtgcc   240
ggaatgggct cgccatgct cgacggcctg ccgctgtccg gctccggctc ggtggcccga   300
tttctcgccg gaaggggcgc ggaccacgtc tacatggtct acatcggagt cggctgggcg   360
atggccaggc tgccgaggtt ccgctggccc gacatcgacg cgctcgaccc gctgctgcgc   420
tggctggtgc tcgacggata cggattccac caggcgtact ccgtaccgc ccgatatgtt    480
```

-continued

```
cacgaacagt atcgggaccc ggctttcccc tggccggccc atgactcgcc gtcgtacgcc      540
ggccgtgcga tcgaccaggg aatcggccgg gcgctgtggt tcgtcggcgg caccgacgcc      600
gacctggtcg ccaccatgat cgagaagttt ccggagtcca ggcggtccga cctctacagc      660
ggggccggac tggcggccac ctacgccggt ggcgtggacg aggcggagct gcgggcgttc      720
tgggaacggg caggctccca ccgggccatg gtcgcgcagg gcagcgcgtt cgcggccgag      780
gcccgggagc gggccggact gccggttgtg cacacgagc tcgcgacacg ggtcttctgc       840
ggcatgacgc ccgctcaggc ggcccgggtc acccaggagg tacggccggc cgggccggtg      900
ccgggtgcac ttcccgcgta cgaggtgtgg cgccaggcca tcgccgaccg tttcaccaac      960 gtcgggggt gctag                                                        975
```

<210> SEQ ID NO 99
<211> LENGTH: 659
<212> TYPE: PRT
<213> ORGANISM: Streptomyces citricolor

<400> SEQUENCE: 99

```
Val Ala Tyr Arg Glu Arg Phe Arg Arg Leu Ile Pro Gly Leu Val Val
  1               5                  10                  15

Ile Val Val Ala Thr Ser Leu Phe Phe Ala Val Arg Thr Ser Val Ala
             20                  25                  30

Val Ala Gly Gly Glu Gln Val Ala Lys Gln Tyr Gly Phe Lys Glu Met
         35                  40                  45

Pro Ile Ala Met Pro Pro Gly Tyr Asp Arg Gln Pro Met Asn Thr Val
     50                  55                  60

Arg Thr Val Asn Pro Ala Tyr Gln Lys Ile Arg Ser Trp Ile Ser Ser
 65                  70                  75                  80

Val Gly Ala Ser Ile Ala Ile Asn Asp Leu Thr Gly His Gly Val Ala
                 85                  90                  95

Asp Gly Met Cys Ile Val Asp Thr Arg Thr Asn Ser Val Ile Val Thr
            100                 105                 110

Tyr Thr Pro Thr Ala Arg Pro Ala Asp Arg Phe Thr Pro Phe Val Leu
        115                 120                 125

Asp Ala Ala Pro Leu Pro Met Asp Asp Thr Met Ala Pro Thr Gly Cys
    130                 135                 140

Thr Pro Gly Asp Phe Asn Gly Asp Gly Arg Met Asp Leu Leu Val Thr
145                 150                 155                 160

Tyr Trp Gly Arg Thr Pro Ile Leu Phe Met Ala Lys Ser Asp Ala Thr
                165                 170                 175

Thr Pro Ser Ala Ser Ser Tyr Val Pro Arg Glu Leu Val Pro Ser Gln
            180                 185                 190

Ser Leu Asp Gly Lys Tyr His Gly Pro Arg Trp Asn Thr Asp Ala Asp
        195                 200                 205

Tyr Val Ala Asp Leu Asp Gly Ser Gly His Pro Ser Ile Val Ile Gly
    210                 215                 220

Asn Tyr Phe Pro Asp Ser Asp Val Leu Asp Pro His Gly Leu Asn Asn
225                 230                 235                 240

Val Val Met Asn Asn Ser Leu Ser Ser Ala Arg Asn Ala Gly Gly Asp
                245                 250                 255

His Val Leu Arg Trp Tyr Arg Ser Thr Ser Gly Pro Glu Pro Thr Val
            260                 265                 270

Ser Tyr Val Glu Glu Lys Asp Ala Ile Pro Tyr Ser Ala Ser Thr Gly
        275                 280                 285
```

```
Trp Thr Leu Ala Ile Ser Gly Ala Asp Leu Thr Gly Glu Gly Leu Pro
    290                 295                 300

Asp Leu Tyr Ile Ala Asn Asp Phe Gly His Ala His Leu Leu Tyr Asn
305                 310                 315                 320

Arg Ser Thr Pro Gly His Ile Ser Phe Thr Glu Ala Lys Gly Glu Arg
                325                 330                 335

Thr Pro Thr Pro Lys Ser Phe Val Leu Gly Asn Gly Ser Phe Lys
            340                 345                 350

Gly Met Gly Val Asp Phe Gly Asp Leu Gly His Asp Gly Arg Phe Asp
            355                 360                 365

Met Val Val Ser Asn Ile Thr Val Pro Trp Gly Leu Glu Ser Asn
    370                 375                 380

Phe Val Trp Ile Asn Gln Ala Lys Asp Asn Ala Asp Met Arg Arg Lys
385                 390                 395                 400

Leu Ser Ser Gly Val Ala Pro Phe Thr Gln Glu Ala Gln Gln Tyr Gly
                405                 410                 415

Met Ala Trp Thr Gly Trp Gly Trp Asp Ala Lys Met Gly Asp Phe Leu
            420                 425                 430

Asn Ser Gly Asp Leu Ser Val Leu Gln Ala Asp Gly Phe Val Lys Gly
            435                 440                 445

Asn Ile Asp Arg Trp Pro Trp Leu Gln Glu Met Ala Met Thr Asn Asp
    450                 455                 460

Asp Leu Leu Ser Asn Pro Ala Met Trp Pro Asn Val Gln Pro Gly Asp
465                 470                 475                 480

Asp Ile Ala Gly Asp Glu Ala Ile Ala Phe Tyr Ala Lys Thr Pro Asp
                485                 490                 495

Gly Arg Tyr Val Asn Ile Ser Ser Gln Leu Gly Ile Ala Val Lys Thr
                500                 505                 510

Pro Thr Arg Gly Ile Ala Thr Gly Asp Thr Thr Gly Thr Gly Ala Leu
            515                 520                 525

Asp Phe Ala Val Ala Arg Gln Trp Gly Pro Pro Ala Phe Tyr Ala Asn
530                 535                 540

Thr Ser Pro Asn Leu Gly Asp Tyr Leu Asn Leu Arg Leu Tyr Arg Pro
545                 550                 555                 560

Ala Gly Ala Gly Gly Ala Gly Gln Gly Leu Val Asn Thr Gly Ser Pro
                565                 570                 575

Ala Tyr Gly Ala Thr Val Arg Ile Thr Thr Pro Ala Gly Thr Gln Ile
            580                 585                 590

Ser Gln Leu Asp Gly Gly Gly His Gly Gly Phe Arg Ser Phe Asp
    595                 600                 605

Val Arg Phe Gly Leu Gly Thr Tyr His Gly Pro Val Thr Ala Asp Leu
    610                 615                 620

Thr Trp Arg Asp Ala Gly Gly Thr Leu His Gln Thr Lys Gln Leu
625                 630                 635                 640

Ser Pro Gly Thr His Ser Leu Met Leu Thr Ser Asp Val Gln Glu Val
                645                 650                 655

Pro Ser Arg

<210> SEQ ID NO 100
<211> LENGTH: 1980
<212> TYPE: DNA
<213> ORGANISM: Streptomyces citricolor

<400> SEQUENCE: 100
```

```
gtggcgtacc gtgagcggtt ccgcagactg ataccaggcc tggtggtgat agtggtggcc      60
acctcgttgt tcttcgcggt acggacctcg gtcgcggtcg ccggggggga acaggtcgcg     120
aagcagtacg gcttcaagga gatgcccata gccatgccgc ccggttacga ccggcagccg     180
atgaacaccg tccggaccgt gaacccggcc taccagaaga tccgttcgtg gatctcctcg     240
gtcggtgcca gcatcgcgat caacgacctc accgggcacg cgtggccga cggcatgtgc      300
atcgtcgaca ccaggaccaa cagcgtgatc gtgacgtaca cgccgaccgc ccgcccggcc     360
gaccgcttca cgcccttcgt gctcgacgcc gcgccgctcc cgatgacga caccatggcg      420
cccaccggct gcacgcccgg cgacttcaac ggggacggcc ggatggacct cctggtgacg     480
tactgggggc gcacgccgat cctgttcatg gccaagtcgg atgccaccac cccgtccgcg     540
agttcctacg taccgcggga actggtgccg tcgcagtcgc tggacggcaa gtaccacggc     600
ccgcggtgga cacccgacgc ggactacgtc gccgacctcg acggcagcgg ccacccgtcc     660
atcgtgatcg gcaactactt ccccgactcc gacgtgctcg atccgcacgg gctgaacaac    720
gtggtgatga caactcgct gtccagcgca aggaacgccg gcggcgacca cgtgctgcgc     780
tggtaccgga gcacctcggg gcccgagccc acggtgtcgt acgtggagga aaggacgcc     840
atcccctaca cgcgtcgac cggatggacg ctggccatct cgggtgccga tctgaccggc    900
gagggcctgc cggacctgta catcgccaac gacttcggac acgcgcacct gctgtacaac    960
aggtcgacgc ccgggcacat cagcttcacc gaggccaagg gcgagcgcac gccgaccaca   1020
cccaagtcct tcgtgctcgg caacggttcg ttcaagggca tgggcgtcga cttcggtgac   1080
ctcggccacg acggcaggtt cgacatggtg gtcagcaaca tcaccgtccc ctggggcctg   1140
gaggagagca acttcgtctg gatcaaccag gccaaggaca acgccgacat gcggcgcaaa   1200
ctgagcagcg gcgtcgcgcc gttcacccag gaggcccagc agtacggcat ggcctggacc   1260
gggtggggct gggacgccaa gatgggcgac ttcctcaaca gcggtgacct gtcggtcctc   1320
caggccgacg gcttcgtgaa ggggaacatc gaccggtggc cctggctgca ggagatggcc   1380
atgaccaacg acgacctgct gtccaacccc gcgatgtggc caacgtaca gccgggtgac    1440
gacatcgccg agacgaggc catcgccttc tacgcgaaga ccccgacgg ccggtacgtg     1500
aacatcagct cgcagctggg catcgcggtg aagacgccga cccgcggcat cgccaccggt   1560
gacaccacgg ggaccggcgc gctggacttc gccgtcgccc gtcagtgggg gccgccggcc   1620
ttctacgcca acacgtcgcc gaacctgggc gactacctga acctgcggct ctaccggccg   1680
gccggggccg gcggagcggg ccagggcctg gtgaacaccg ggtcgccggc gtacggcgcc   1740
acggtccgga tcaccacccc ggccggcacc cagatctccc agctcgacgg cggcggcggc   1800
cacggcggct ccgcagcttc cgacgtgcgc ttcgggctcg gcacctacca cgggccggtc   1860
accgccgacc tgacgtggcg ggacgcgggc ggcaccctgc accagacgac gaagcagctc   1920
agcccgggca cgcactccct catgctgacc agcgacgtcc aggaggttcc gagccgatga   1980
```

<210> SEQ ID NO 101
<211> LENGTH: 337
<212> TYPE: PRT
<213> ORGANISM: Streptomyces citricolor

<400> SEQUENCE: 101

```
Met Ser Thr Thr Ala Gln Pro Arg Pro Lys Gly Val Ala Ala Ala Ala
1               5                   10                  15

Thr Ala Gly Pro Ala Lys Pro Lys Asp Pro Arg Tyr Leu Ala Leu Arg
```

```
                20              25                  30
Asn Phe Ala Ile Ser Ile Ser Val Phe Asn Ile Phe Gly Tyr Thr Leu
            35                  40                  45
Leu Gly Phe Glu Gln Pro Trp Leu Trp Pro Ile Ile Ala Val Leu Thr
50                  55                  60
Ala Tyr Ala Cys Glu Ile Cys Phe Glu Leu Ile Ser Ala Trp Ala Gln
65                  70                  75                  80
Arg Arg Ala Pro Arg Phe Arg Gly Asn Gly Val Arg Gly Val Tyr Glu
                85                  90                  95
Phe Leu Leu Pro Ala His Ile Thr Ala Leu Ala Val Asn Met Leu Thr
            100                 105                 110
Tyr Gly Asn Asn Gln Leu Leu Pro Val Phe Gly Val Val Gly
            115                 120                 125
Val Gly Gly Lys His Ala Leu Gln Ala Pro Ile Ala Gly Arg Met Arg
130                 135                 140
His Phe Met Asn Pro Ser Asn Phe Gly Ile Thr Met Ser Leu Leu Cys
145                 150                 155                 160
Phe Gly Ser Trp Phe Ser Ile Ala Pro Pro Tyr Glu Phe Thr Glu Asn
                165                 170                 175
Ala Asn Thr Tyr Phe Arg Val Met Ile Pro Leu Ile Ile Ala Thr Ala
            180                 185                 190
Gly Thr Val Ile Asn Ala Leu Leu Thr Lys Arg Thr Pro Leu Ile Val
            195                 200                 205
Gly Trp Leu Gly Ala Phe Ala Ile Gln Ala Phe Ile Arg His Trp Ile
210                 215                 220
Trp His Val Ala Leu Phe Ser Ala Leu Gly Val Met Thr Gly Val Ala
225                 230                 235                 240
Phe Val Leu Phe Thr Asn Tyr Met Ile Ser Asp Pro Gly Thr Thr Pro
                245                 250                 255
Met Lys Gly Arg Ala Gln Phe Val Phe Gly Ser Ser Val Ala Phe Val
                260                 265                 270
Tyr Gly Ile Leu Met Val Phe Asn Val Val Tyr Thr Leu Phe Phe Ala
            275                 280                 285
Thr Thr Ile Val Cys Gly Leu Arg Gly Leu Gly Trp Trp Ala Ala His
            290                 295                 300
Leu Ile Lys Arg Ala Arg Gln Ala Asp Ala Thr Gly Ala Glu Ser Ser
305                 310                 315                 320
Gly Gly Thr Ala Ala Gln Pro Gln Gln Ser Gln Val Gly Ala Val Ala
                325                 330                 335
Ala

<210> SEQ ID NO 102
<211> LENGTH: 1014
<212> TYPE: DNA
<213> ORGANISM: Streptomyces citricolor

<400> SEQUENCE: 102
atgagcacga ccgcgcaacc ccgacccaaa ggcgtggcgg cggccgcgac ggccggcccc      60
gcgaagccga aagacccgcg gtacctcgcc ctgcggaact tcgcgatctc gatcagtgtg     120
ttcaacatct tcggctacac cctgctcggc ttcgagcagc cctggctgtg gccgatcatc     180
gcggtgctca ccgcctacgc ctgcgagatc tgcttcgagc tgatcagcgc ctgggcccag     240
cggcgcgcgc cccgcttccg cgggaacggg gtgcgcgggg tgtacgagtt cctgctgccg     300
```

```
gcccacatca cggcgctggc ggtcaacatg ctgacctacg ggaacaacca gctgctgccg    360
gtgttcttcg gcgtcgtcgt cggggtcggc ggcaagcacg cgctgcaggc gccgatcgcg    420
ggccggatgc ggcacttcat gaacccgtcc aacttcggga tcacgatgtc gctgctgtgc    480
ttcggctcct ggttcagcat cgcgccgccc tacgagttca cggagaacgc gaacacctac    540
ttccgggtga tgatcccgct gatcatcgcc accgcgggaa cggtgatcaa cgccctgctc    600
accaagcgga ccccgctgat cgtcggctgg ctcggcgcct tcgccatcca ggcgttcatc    660
cggcactgga tctggcacgt cgcgctgttc tccgcgctcg gcgtgatgac cggtgtcgcc    720
ttcgtgctgt tcaccaacta catgatcagc gacccgggaa cgacaccgat gaagggccgg    780
gcccagttcg tgttcggctc ctcggtcgcc ttcgtgtacg ggatcctgat ggtgttcaac    840
gtcgtctaca ccctgttctt cgccaccacg atcgtctgcg gtctgcgcgg gctcggctgg    900
tgggccgcgc acctgatcaa gcgggctcgg caggcggacg ccaccggggc ggagtcctcc    960
ggcgggacgg ccgcgcagcc gcagcagagc caggtcgggg cggtcgcggc gtga         1014
```